US010626424B2

(12) United States Patent
Zhu et al.

(10) Patent No.: US 10,626,424 B2
(45) Date of Patent: Apr. 21, 2020

(54) HIGH LEVEL PRODUCTION OF LONG-CHAIN DICARBOXYLIC ACIDS WITH MICROBES

(71) Applicant: E I DU PONT DE NEMOURS AND COMPANY, Wilmington, DE (US)

(72) Inventors: Quinn Qun Zhu, West Chester, PA (US); Xiaochun Fan, West Chester, PA (US); Seung-Pyo Hong, Hockessin, DE (US); Despina Boughioukou, Wilmington, DE (US); Dongming Xie, Newark, DE (US); Himanshu H. Dhamankar, Greenville, DE (US)

(73) Assignee: DUPONT INDUSTRIAL BIOSCIENCES USA, LLC, Wilmington, DE (US)

( * ) Notice: Subject to any disclaimer, the term of this patent is extended or adjusted under 35 U.S.C. 154(b) by 3 days.

(21) Appl. No.: 15/746,094

(22) PCT Filed: Jul. 20, 2016

(86) PCT No.: PCT/US2016/043133

§ 371 (c)(1),
(2) Date: Jan. 19, 2018

(87) PCT Pub. No.: WO2017/015368

PCT Pub. Date: Jan. 26, 2017

(65) Prior Publication Data

US 2019/0144897 A1 May 16, 2019

Related U.S. Application Data

(60) Provisional application No. 62/195,340, filed on Jul. 22, 2015, provisional application No. 62/195,338, filed on Jul. 22, 2015.

(51) Int. Cl.

| | |
|---|---|
| ***C12N 1/15*** | (2006.01) |
| ***C12P 7/64*** | (2006.01) |
| ***C12N 9/00*** | (2006.01) |

(52) U.S. Cl.

CPC .............. *C12P 7/6409* (2013.01); *C12N 9/93* (2013.01); *C12Y 602/01003* (2013.01)

(58) Field of Classification Search

None

See application file for complete search history.

(56) References Cited

U.S. PATENT DOCUMENTS

| | | | | |
|---|---|---|---|---|
| 2010/0041115 | A1 | 2/2010 | Nicaud et al. | |
| 2014/0228586 | A1* | 8/2014 | Beardslee ................ | C12N 1/16 554/121 |

FOREIGN PATENT DOCUMENTS

| | | | |
|---|---|---|---|
| WO | 2006/064131 | A1 | 6/2006 |
| WO | 2013/006730 | A2 | 1/2013 |
| WO | 2013/006733 | A2 | 1/2013 |
| WO | 2014/100461 | A2 | 6/2014 |

OTHER PUBLICATIONS

D.R. Johnson et al. "*Saccharomyces cerevisiae* contains four fatty acid activation (FAA) genes: an assessment of their role in regulating protein N-myristoylation and cellular lipid metabolism", J.Cell Biology 127(3):751-762 (Year: 1994).*

Tenagy et al. "Involvement of acyl-CoA synthetase genes in n-alkane assimilation and fatty acid utilization in yeast *Yarrowia lipolytica*", FEMS Yeast Research, 15: 1-12. May 2015 (Year: 2015).*

GenBank Accession No. CAG79455. Feb. 2015 (Year: 2015).*

Choi, Jae-Yeon et al., The *Saccharomyces cerevisiae* FAT1 Gene Encodes an Acyl-CoA Synthetase That Is Required for Maintenance of Very Long Chain Fatty Acid Levels*, The Journal of Biological Chemistry, Feb. 19, 1999, pp. 4671-4683, vol. 274, No. 8.

Dulermo, Remi et al., Unraveling fatty acid transport and activation mechanisms in Yarrowia lipolytica, Biochimica et Biophysica Acta, 2015, pp. 1202-1217, vol. 1851, No. 9.

Huf, Sabine et al. Biotechnological synthesis of long-chain dicarboxylic acids as building blocks for polymers, EurJLipidSciTechnol, 2011, pp. 548-561, vol. 113.

Johnson, D. Russell et al., *Saccharomyces cerevisiae* Contains Four Fatty Acid Activation (FAA) Genes: An Assessment of Their Role in Regulating Protein N-Mydstoylation and Cellular Lipid Metabolism, the Journal of Cell Biology, 1994, pp. 751-762, vol. 127, No. 3.

Smit, Martha S. et al., α,ω-Dicarboxylic acid accumulation by acyl-CoA oxidase deficient mutants of Yarrowia lipolytica, Biotechnology Letters, 2005, pp. 859-864, vol. 27.

International Search Report and Written Opinion, PCT/US2016/043133, dated Oct. 21, 2016.

* cited by examiner

*Primary Examiner* — Rebecca E Prouty

(57) ABSTRACT

Recombinant microbial cells comprising an engineered LCDA production pathway that comprises at least one up-regulated long-chain acyl-CoA synthetase (ACoS) are disclosed. These recombinant microbial cells are capable of producing one or more long-chain dicarboxylic acid (LCDA) products from a long-chain fatty acid-comprising substrate. Methods of using recombinant microbial cells to produce LCDAs are also disclosed.

15 Claims, 20 Drawing Sheets

Figure 1:
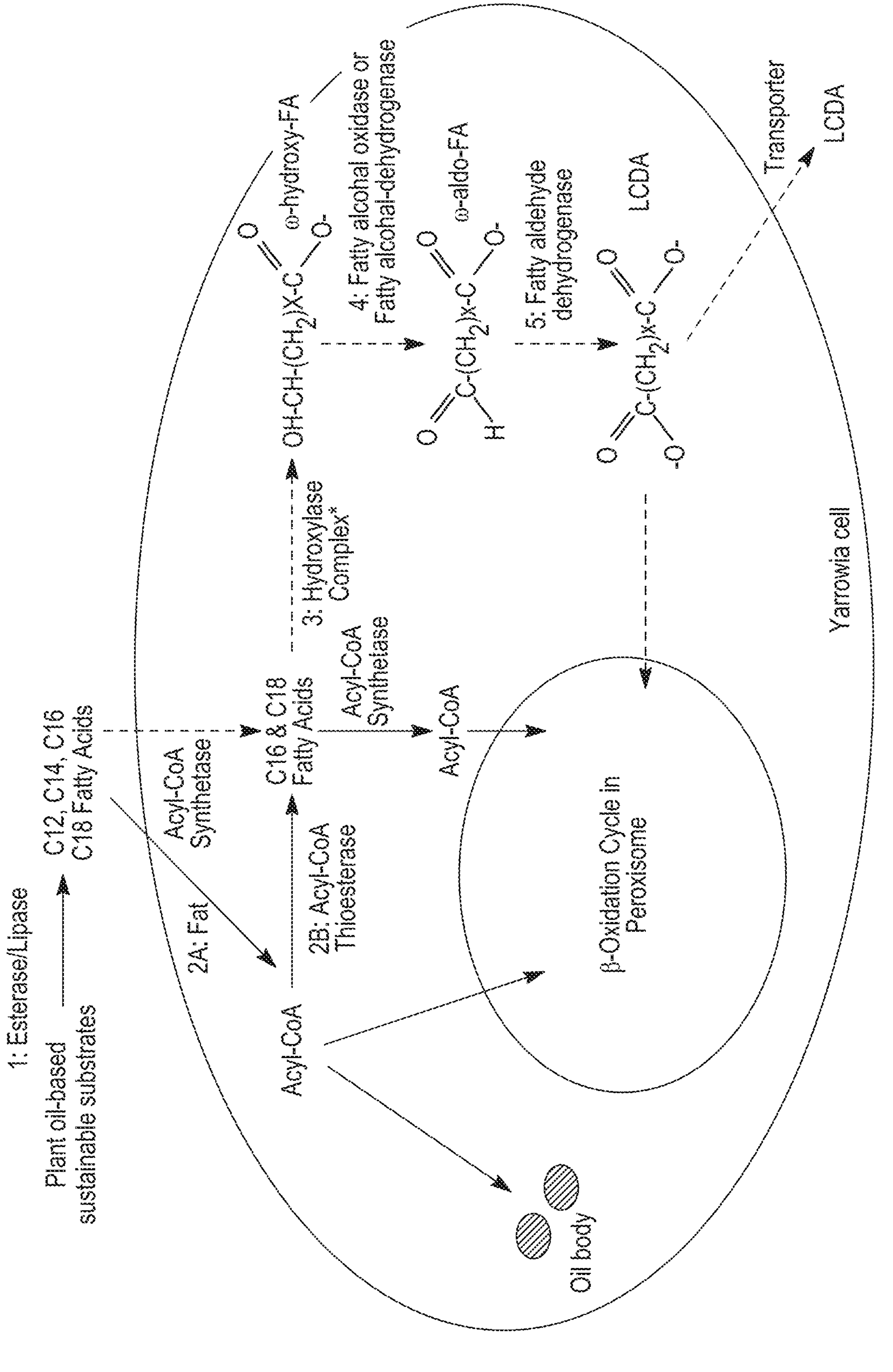

Specification includes a Sequence Listing.

SEQUENCE LISTING

```
<160> NUMBER OF SEQ ID NOS: 115

<210> SEQ ID NO 1
<211> LENGTH: 21
<212> TYPE: DNA
<213> ORGANISM: artificial sequence
<220> FEATURE:
<223> OTHER INFORMATION: primer 17864-900F

<400> SEQUENCE: 1

cacagaccgg cttctcaact t                                              21


<210> SEQ ID NO 2
<211> LENGTH: 22
<212> TYPE: DNA
<213> ORGANISM: artificial sequence
<220> FEATURE:
<223> OTHER INFORMATION: primer17864-967R
```

<400> SEQUENCE: 2
aggtgaccat ctcgaacaca aa 22

<210> SEQ ID NO 3
<211> LENGTH: 21
<212> TYPE: DNA
<213> ORGANISM: artificial sequence
<220> FEATURE:
<223> OTHER INFORMATION: primer 5885-1034F

<400> SEQUENCE: 3
cttctccctg cgtcactctg t 21

<210> SEQ ID NO 4
<211> LENGTH: 20
<212> TYPE: DNA
<213> ORGANISM: artificial sequence
<220> FEATURE:
<223> OTHER INFORMATION: primer 5885-1097R

<400> SEQUENCE: 4
ttgccacaag ccttgatgtg 20

<210> SEQ ID NO 5
<211> LENGTH: 18
<212> TYPE: DNA
<213> ORGANISM: artificial sequence
<220> FEATURE:
<223> OTHER INFORMATION: primer 14234-1341F

<400> SEQUENCE: 5
ggctccggct gagattga 18

<210> SEQ ID NO 6
<211> LENGTH: 23
<212> TYPE: DNA
<213> ORGANISM: artificial sequence
<220> FEATURE:
<223> OTHER INFORMATION: primer 14234-1404R

<400> SEQUENCE: 6
aatgacagcg acatccttta cca 23

<210> SEQ ID NO 7
<211> LENGTH: 22
<212> TYPE: DNA
<213> ORGANISM: artificial sequence
<220> FEATURE:
<223> OTHER INFORMATION: primer 11979-1248F

<400> SEQUENCE: 7
tcagctcaaa ctcgacgact tg 22

<210> SEQ ID NO 8
<211> LENGTH: 20
<212> TYPE: DNA
<213> ORGANISM: artificial sequence
<220> FEATURE:
<223> OTHER INFORMATION: primer 11979-1315R

<400> SEQUENCE: 8
ccacaggcag aggctcatct 20

<210> SEQ ID NO 9
<211> LENGTH: 21

<212> TYPE: DNA
<213> ORGANISM: artificial sequence
<220> FEATURE:
<223> OTHER INFORMATION: primer 7755-282F

<400> SEQUENCE: 9
ttacagctcg ttgccctacc a 21

<210> SEQ ID NO 10
<211> LENGTH: 15
<212> TYPE: DNA
<213> ORGANISM: artificial sequence
<220> FEATURE:
<223> OTHER INFORMATION: primer 7755-343R

<400> SEQUENCE: 10
tggcgggcga aatgg 15

<210> SEQ ID NO 11
<211> LENGTH: 18
<212> TYPE: DNA
<213> ORGANISM: artificial sequence
<220> FEATURE:
<223> OTHER INFORMATION: primer 12419-1677F

<400> SEQUENCE: 11
tgctggcatc gtggtgat 18

<210> SEQ ID NO 12
<211> LENGTH: 21
<212> TYPE: DNA
<213> ORGANISM: artificial sequence
<220> FEATURE:
<223> OTHER INFORMATION: primer 12419-1744R

<400> SEQUENCE: 12
gcaacaatcg tcgcagaatc t 21

<210> SEQ ID NO 13
<211> LENGTH: 18
<212> TYPE: DNA
<213> ORGANISM: artificial sequence
<220> FEATURE:
<223> OTHER INFORMATION: primer 20405-626F

<400> SEQUENCE: 13
ccgtggagct cacccatt 18

<210> SEQ ID NO 14
<211> LENGTH: 24
<212> TYPE: DNA
<213> ORGANISM: artificial sequence
<220> FEATURE:
<223> OTHER INFORMATION: primer 20405-691R

<400> SEQUENCE: 14
ggttaggtgc attctttgct gtct 24

<210> SEQ ID NO 15
<211> LENGTH: 22
<212> TYPE: DNA
<213> ORGANISM: artificial sequence
<220> FEATURE:
<223> OTHER INFORMATION: primer 5456-1758F

<400> SEQUENCE: 15
ctctgctgct atggttgtcg at 22

<210> SEQ ID NO 16
<211> LENGTH: 21
<212> TYPE: DNA
<213> ORGANISM: artificial sequence
<220> FEATURE:
<223> OTHER INFORMATION: primer 5456-1825R

<400> SEQUENCE: 16
tgcaaccctc atcaccagtt c 21

<210> SEQ ID NO 17
<211> LENGTH: 17
<212> TYPE: DNA
<213> ORGANISM: artificial sequence
<220> FEATURE:
<223> OTHER INFORMATION: primer 15103-516F

<400> SEQUENCE: 17
caaggccgtg cgtgtca 17

<210> SEQ ID NO 18
<211> LENGTH: 20
<212> TYPE: DNA
<213> ORGANISM: artificial sequence
<220> FEATURE:
<223> OTHER INFORMATION: primer 15103-588R

<400> SEQUENCE: 18
gagatcggga gccacaattg 20

<210> SEQ ID NO 19
<211> LENGTH: 19
<212> TYPE: DNA
<213> ORGANISM: artificial sequence
<220> FEATURE:
<223> OTHER INFORMATION: primer 5951-327F

<400> SEQUENCE: 19
gcattttgcc gcacttgat 19

<210> SEQ ID NO 20
<211> LENGTH: 18
<212> TYPE: DNA
<213> ORGANISM: artificial sequence
<220> FEATURE:
<223> OTHER INFORMATION: primer 5951-399R

<400> SEQUENCE: 20
gacgagctcc gccacagt 18

<210> SEQ ID NO 21
<211> LENGTH: 20
<212> TYPE: DNA
<213> ORGANISM: artificial sequence
<220> FEATURE:
<223> OTHER INFORMATION: primer 17314-47F

<400> SEQUENCE: 21
tgttctgtgg caacattgca 20

<210> SEQ ID NO 22
<211> LENGTH: 22
<212> TYPE: DNA
<213> ORGANISM: artificial sequence
<220> FEATURE:
<223> OTHER INFORMATION: primer 17314-112R

<400> SEQUENCE: 22
cacttgtttt ggagctcttg ga 22

<210> SEQ ID NO 23
<211> LENGTH: 20
<212> TYPE: DNA
<213> ORGANISM: artificial sequence
<220> FEATURE:
<223> OTHER INFORMATION: primer 6556-1321F

<400> SEQUENCE: 23
gcgttcgaag aggcttctga 20

<210> SEQ ID NO 24
<211> LENGTH: 20
<212> TYPE: DNA
<213> ORGANISM: artificial sequence
<220> FEATURE:
<223> OTHER INFORMATION: primer 6556-1384R

<400> SEQUENCE: 24
ttcgcaacca tcgtttcttg 20

<210> SEQ ID NO 25
<211> LENGTH: 23
<212> TYPE: DNA
<213> ORGANISM: artificial sequence
<220> FEATURE:
<223> OTHER INFORMATION: primer 12859-1002

<400> SEQUENCE: 25
ccagattctg ctgaacacaa aga 23

<210> SEQ ID NO 26
<211> LENGTH: 20
<212> TYPE: DNA
<213> ORGANISM: artificial sequence
<220> FEATURE:
<223> OTHER INFORMATION: primer 12859-1071

<400> SEQUENCE: 26
cgaagagcac gatcgaatga 20

<210> SEQ ID NO 27
<211> LENGTH: 21
<212> TYPE: DNA
<213> ORGANISM: artificial sequence
<220> FEATURE:
<223> OTHER INFORMATION: primer 9284-924F

<400> SEQUENCE: 27
tctgcttgtt gacgaccgaa t 21

<210> SEQ ID NO 28
<211> LENGTH: 21
<212> TYPE: DNA
<213> ORGANISM: artificial sequence
<220> FEATURE:
<223> OTHER INFORMATION: primer 9284-995R

<400> SEQUENCE: 28
gggttgttca ccagcatgtt g 21

-continued

<210> SEQ ID NO 29
<211> LENGTH: 20
<212> TYPE: DNA
<213> ORGANISM: artificial sequence
<220> FEATURE:
<223> OTHER INFORMATION: primer 16016-1393F

<400> SEQUENCE: 29
atgggccgat acggtaagct 20

<210> SEQ ID NO 30
<211> LENGTH: 22
<212> TYPE: DNA
<213> ORGANISM: artificial sequence
<220> FEATURE:
<223> OTHER INFORMATION: primer/probe 16016-1422T

<400> SEQUENCE: 30
catcctggcc acccgacaga cc 22

<210> SEQ ID NO 31
<211> LENGTH: 22
<212> TYPE: DNA
<213> ORGANISM: artificial sequence
<220> FEATURE:
<223> OTHER INFORMATION: primer YL-18S-329F

<400> SEQUENCE: 31
cctgagaaac ggctaccaca tc 22

<210> SEQ ID NO 32
<211> LENGTH: 21
<212> TYPE: DNA
<213> ORGANISM: artificial sequence
<220> FEATURE:
<223> OTHER INFORMATION: primer YL-18S-395R

<400> SEQUENCE: 32
ccctgtgtca ggattgggta a 21

<210> SEQ ID NO 33
<211> LENGTH: 700
<212> TYPE: PRT
<213> ORGANISM: Saccharomyces cerevisiae

<400> SEQUENCE: 33

```
Met Val Ala Gln Tyr Thr Val Pro Val Gly Lys Ala Ala Asn Glu His
1               5                   10                  15

Glu Thr Ala Pro Arg Arg Asn Tyr Gln Cys Arg Glu Lys Pro Leu Val
            20                  25                  30

Arg Pro Pro Asn Thr Lys Cys Ser Thr Val Tyr Glu Phe Val Leu Glu
        35                  40                  45

Cys Phe Gln Lys Asn Lys Asn Ser Asn Ala Met Gly Trp Arg Asp Val
    50                  55                  60

Lys Glu Ile His Glu Glu Ser Lys Ser Val Met Lys Lys Val Asp Gly
65                  70                  75                  80

Lys Glu Thr Ser Val Glu Lys Lys Trp Met Tyr Tyr Glu Leu Ser His
                85                  90                  95

Tyr His Tyr Asn Ser Phe Asp Gln Leu Thr Asp Ile Met His Glu Ile
            100                 105                 110

Gly Arg Gly Leu Val Lys Ile Gly Leu Lys Pro Asn Asp Asp Asp Lys
        115                 120                 125
```

-continued

```
Leu His Leu Tyr Ala Ala Thr Ser His Lys Trp Met Lys Met Phe Leu
    130                 135                 140

Gly Ala Gln Ser Gln Gly Ile Pro Val Val Thr Ala Tyr Asp Thr Leu
145                 150                 155                 160

Gly Glu Lys Gly Leu Ile His Ser Leu Val Gln Thr Gly Ser Lys Ala
                165                 170                 175

Ile Phe Thr Asp Asn Ser Leu Leu Pro Ser Leu Ile Lys Pro Val Gln
            180                 185                 190

Ala Ala Gln Asp Val Lys Tyr Ile Ile His Phe Asp Ser Ile Ser Ser
        195                 200                 205

Glu Asp Arg Arg Gln Ser Gly Lys Ile Tyr Gln Ser Ala His Asp Ala
    210                 215                 220

Ile Asn Arg Ile Lys Glu Val Arg Pro Asp Ile Lys Thr Phe Ser Phe
225                 230                 235                 240

Asp Asp Ile Leu Lys Leu Gly Lys Glu Ser Cys Asn Glu Ile Asp Val
                245                 250                 255

His Pro Pro Gly Lys Asp Asp Leu Cys Cys Ile Met Tyr Thr Ser Gly
            260                 265                 270

Ser Thr Gly Glu Pro Lys Gly Val Val Leu Lys His Ser Asn Val Val
        275                 280                 285

Ala Gly Val Gly Gly Ala Ser Leu Asn Val Leu Lys Phe Val Gly Asn
    290                 295                 300

Thr Asp Arg Val Ile Cys Phe Leu Pro Leu Ala His Ile Phe Glu Leu
305                 310                 315                 320

Val Phe Glu Leu Leu Ser Phe Tyr Trp Gly Ala Cys Ile Gly Tyr Ala
                325                 330                 335

Thr Val Lys Thr Leu Thr Ser Ser Ser Val Arg Asn Cys Gln Gly Asp
            340                 345                 350

Leu Gln Glu Phe Lys Pro Thr Ile Met Val Gly Val Ala Ala Val Trp
        355                 360                 365

Glu Thr Val Arg Lys Gly Ile Leu Asn Gln Ile Asp Asn Leu Pro Phe
    370                 375                 380

Leu Thr Lys Lys Ile Phe Trp Thr Ala Tyr Asn Thr Lys Leu Asn Met
385                 390                 395                 400

Gln Arg Leu His Ile Pro Gly Gly Gly Ala Leu Gly Asn Leu Val Phe
                405                 410                 415

Lys Lys Ile Arg Thr Ala Thr Gly Gly Gln Leu Arg Tyr Leu Leu Asn
            420                 425                 430

Gly Gly Ser Pro Ile Ser Arg Asp Ala Gln Glu Phe Ile Thr Asn Leu
        435                 440                 445

Ile Cys Pro Met Leu Ile Gly Tyr Gly Leu Thr Glu Thr Cys Ala Ser
    450                 455                 460

Thr Thr Ile Leu Asp Pro Ala Asn Phe Glu Leu Gly Val Ala Gly Asp
465                 470                 475                 480

Leu Thr Gly Cys Val Thr Val Lys Leu Val Asp Val Glu Glu Leu Gly
                485                 490                 495

Tyr Phe Ala Lys Asn Asn Gln Gly Glu Val Trp Ile Thr Gly Ala Asn
            500                 505                 510

Val Thr Pro Glu Tyr Tyr Lys Asn Glu Glu Glu Thr Ser Gln Ala Leu
        515                 520                 525

Thr Ser Asp Gly Trp Phe Lys Thr Gly Asp Ile Gly Glu Trp Glu Ala
    530                 535                 540
```

```
Asn Gly His Leu Lys Ile Ile Asp Arg Lys Lys Asn Leu Val Lys Thr
545                 550                 555                 560

Met Asn Gly Glu Tyr Ile Ala Leu Glu Lys Leu Glu Ser Val Tyr Arg
                565                 570                 575

Ser Asn Glu Tyr Val Ala Asn Ile Cys Val Tyr Ala Asp Gln Ser Lys
            580                 585                 590

Thr Lys Pro Val Gly Ile Ile Val Pro Asn His Ala Pro Leu Thr Lys
        595                 600                 605

Leu Ala Lys Lys Leu Gly Ile Met Glu Gln Lys Asp Ser Ser Ile Asn
    610                 615                 620

Ile Glu Asn Tyr Leu Glu Asp Ala Lys Leu Ile Lys Ala Val Tyr Ser
625                 630                 635                 640

Asp Leu Leu Lys Thr Gly Lys Asp Gln Gly Leu Val Gly Ile Glu Leu
                645                 650                 655

Leu Ala Gly Ile Val Phe Phe Asp Gly Glu Trp Thr Pro Gln Asn Gly
            660                 665                 670

Phe Val Thr Ser Ala Gln Lys Leu Lys Arg Lys Asp Ile Leu Asn Ala
        675                 680                 685

Val Lys Asp Lys Val Asp Ala Val Tyr Ser Ser Ser
    690                 695                 700


<210> SEQ ID NO 34
<211> LENGTH: 744
<212> TYPE: PRT
<213> ORGANISM: Saccharomyces cerevisiae

<400> SEQUENCE: 34

Met Ala Ala Pro Asp Tyr Ala Leu Thr Asp Leu Ile Glu Ser Asp Pro
1               5                   10                  15

Arg Phe Glu Ser Leu Lys Thr Arg Leu Ala Gly Tyr Thr Lys Gly Ser
            20                  25                  30

Asp Glu Tyr Ile Glu Glu Leu Tyr Ser Gln Leu Pro Leu Thr Ser Tyr
        35                  40                  45

Pro Arg Tyr Lys Thr Phe Leu Lys Lys Gln Ala Val Ala Ile Ser Asn
    50                  55                  60

Pro Asp Asn Glu Ala Gly Phe Ser Ser Ile Tyr Arg Ser Ser Leu Ser
65                  70                  75                  80

Ser Glu Asn Leu Val Ser Cys Val Asp Lys Asn Leu Arg Thr Ala Tyr
                85                  90                  95

Asp His Phe Met Phe Ser Ala Arg Arg Trp Pro Gln Arg Asp Cys Leu
            100                 105                 110

Gly Ser Arg Pro Ile Asp Lys Ala Thr Gly Thr Trp Glu Glu Thr Phe
        115                 120                 125

Arg Phe Glu Ser Tyr Ser Thr Val Ser Lys Arg Cys His Asn Ile Gly
    130                 135                 140

Ser Gly Ile Leu Ser Leu Val Asn Thr Lys Arg Lys Arg Pro Leu Glu
145                 150                 155                 160

Ala Asn Asp Phe Val Val Ala Ile Leu Ser His Asn Asn Pro Glu Trp
                165                 170                 175

Ile Leu Thr Asp Leu Ala Cys Gln Ala Tyr Ser Leu Thr Asn Thr Ala
            180                 185                 190

Leu Tyr Glu Thr Leu Gly Pro Asn Thr Ser Glu Tyr Ile Leu Asn Leu
        195                 200                 205

Thr Glu Ala Pro Ile Leu Ile Phe Ala Lys Ser Asn Met Tyr His Val
    210                 215                 220
```

-continued

```
Leu Lys Met Val Pro Asp Met Lys Phe Val Asn Thr Leu Val Cys Met
225                 230                 235                 240

Asp Glu Leu Thr His Asp Glu Leu Arg Met Leu Asn Glu Ser Leu Leu
                245                 250                 255

Pro Val Lys Cys Asn Ser Leu Asn Glu Lys Ile Thr Phe Phe Ser Leu
            260                 265                 270

Glu Gln Val Glu Gln Val Gly Cys Phe Asn Lys Ile Pro Ala Ile Pro
        275                 280                 285

Pro Thr Pro Asp Ser Leu Tyr Thr Ile Ser Phe Thr Ser Gly Thr Thr
    290                 295                 300

Gly Leu Pro Lys Gly Val Glu Met Ser His Arg Asn Ile Ala Ser Gly
305                 310                 315                 320

Ile Ala Phe Ala Phe Ser Thr Phe Arg Ile Pro Pro Asp Lys Arg Asn
                325                 330                 335

Gln Gln Leu Tyr Asp Met Cys Phe Leu Pro Leu Ala His Ile Phe Glu
            340                 345                 350

Arg Met Val Ile Ala Tyr Asp Leu Ala Ile Gly Phe Gly Ile Gly Phe
        355                 360                 365

Leu His Lys Pro Asp Pro Thr Val Leu Val Glu Asp Leu Lys Ile Leu
    370                 375                 380

Lys Pro Tyr Ala Val Ala Leu Val Pro Arg Ile Leu Thr Arg Phe Glu
385                 390                 395                 400

Ala Gly Ile Lys Asn Ala Leu Asp Lys Ser Thr Val Gln Arg Asn Val
                405                 410                 415

Ala Asn Thr Ile Leu Asp Ser Lys Ser Ala Arg Phe Thr Ala Arg Gly
            420                 425                 430

Gly Pro Asp Lys Ser Ile Met Asn Phe Leu Val Tyr His Arg Val Leu
        435                 440                 445

Ile Asp Lys Ile Arg Asp Ser Leu Gly Leu Ser Asn Asn Ser Phe Ile
    450                 455                 460

Ile Thr Gly Ser Ala Pro Ile Ser Lys Asp Thr Leu Leu Phe Leu Arg
465                 470                 475                 480

Ser Ala Leu Asp Ile Gly Ile Arg Gln Gly Tyr Gly Leu Thr Glu Thr
                485                 490                 495

Phe Ala Gly Val Cys Leu Ser Glu Pro Phe Glu Lys Asp Val Gly Ser
            500                 505                 510

Cys Gly Ala Ile Gly Ile Ser Ala Glu Cys Arg Leu Lys Ser Val Pro
        515                 520                 525

Glu Met Gly Tyr His Ala Asp Lys Asp Leu Lys Gly Glu Leu Gln Ile
    530                 535                 540

Arg Gly Pro Gln Val Phe Glu Arg Tyr Phe Lys Asn Pro Asn Glu Thr
545                 550                 555                 560

Ser Lys Ala Val Asp Gln Asp Gly Trp Phe Ser Thr Gly Asp Val Ala
                565                 570                 575

Phe Ile Asp Gly Lys Gly Arg Ile Ser Val Ile Asp Arg Val Lys Asn
            580                 585                 590

Phe Phe Lys Leu Ala His Gly Glu Tyr Ile Ala Pro Glu Lys Ile Glu
        595                 600                 605

Asn Ile Tyr Leu Ser Ser Cys Pro Tyr Ile Thr Gln Ile Phe Val Phe
    610                 615                 620

Gly Asp Pro Leu Lys Thr Phe Leu Val Gly Ile Val Gly Val Asp Val
625                 630                 635                 640
```

-continued

```
Asp Ala Ala Gln Pro Ile Leu Ala Ala Lys His Pro Glu Val Lys Thr
                645                 650                 655

Trp Thr Lys Glu Val Leu Val Glu Asn Leu Asn Arg Asn Lys Lys Leu
            660                 665                 670

Arg Lys Glu Phe Leu Asn Lys Ile Asn Lys Cys Thr Asp Gly Leu Gln
        675                 680                 685

Gly Phe Glu Lys Leu His Asn Ile Lys Val Gly Leu Glu Pro Leu Thr
    690                 695                 700

Leu Glu Asp Asp Val Val Thr Pro Thr Phe Lys Ile Lys Arg Ala Lys
705                 710                 715                 720

Ala Ser Lys Phe Phe Lys Asp Thr Leu Asp Gln Leu Tyr Ala Glu Gly
                725                 730                 735

Ser Leu Val Lys Thr Glu Lys Leu
            740


<210> SEQ ID NO 35
<211> LENGTH: 2076
<212> TYPE: DNA
<213> ORGANISM: artificial sequence
<220> FEATURE:
<223> OTHER INFORMATION: YlFaa1

<400> SEQUENCE: 35

atggtcggat acaccatctc ctcgaagccc gtgtccgtcg aggttggccc cgccaagcct      60

ggcgagactg ctccccgacg gaacgtcatt gccaaggacg ctcctgtggt cttccccgac     120

aacgattcgt ccctcaccac tgtctacaag ctgttcaaaa agtacgccga gatcaactcc     180

gaacgaaagg ctatgggatg gcgagacacc atcgacattc acgtggagac caagcaggtc     240

acaaaggtgg tcgacggcgt ggagaagaaa gtgcccaagg aatggaagta cttcgagatg     300

ggtccttaca agtggctgtc ctacaaggag gccctcaagc tggttcacga ttatggagct     360

ggtcttcgac atctcggcat caagcccaaa gagaagatgc acatttacgc acagacctct     420

caccgatgga tgctttccgg actggcctct ctctcgcagg gcattcccat cgtcactgcc     480

tacgacaccc ttggagagga aggtctcaca cgatctctgc aggagaccaa ctccgtcatc     540

atgttcacgg acaaggctct tctgtcgtct ctcaaggtgt ccctcaaaaa gggcaccgat     600

ctgcgaatca ttatctacgg aggcgacctg actcccgatg acaagaaagc cggaaacacc     660

gagatcgacg ccatcaagga gattgttcca gacatgaaga tctacactat ggacgaggtt     720

gtcgctctcg gtcgagagca tcctcacccc gtggaagagg tcgactacga ggatctggcc     780

ttcatcatgt acacctctgg ctccacagga gttcccaagg gtgtcgtgct gcagcacaag     840

cagatcctcg cctctgtggc cggtgtcacc aagattatcg acagatccat tatcggcaat     900

acagatcgac tgctcaactt tcttcccctc gcacacatct tcgagtttgt gttcgagatg     960

gtcaccttct ggtggggtgc ctctctgggc tacggaactg tcaagaccat ttccgacctg    1020

tcgatgaaga actgcaaggg agacatccga gagctcaagc ccaccatcat ggtcggcgtt    1080

ccagctgtct gggaacccat gcggaagggt attcttggca aaatcaagga gctgtctcct    1140

ctcatgcagc gagtcttctg ggcctccttt gctgccaagc aacgtctcga cgagaacgga    1200

cttcccggtg gctctattct ggattcgctc atcttcaaga aagtcaagga cgccactgga    1260

ggctgtctcc gatacgtgtg caacggaggt gctccagttt ccgtcgacac ccagaagttc    1320

attactaccc ttatctgtcc catgctcatt ggatgcggtc tgaccgagac tacagccaac    1380

accactatca tgtctcccaa gtcctatgcc tttggcacca ttggagagcc tactgcagcc    1440
```

-continued gtcaccctca agcttatcga cgtgcccgaa gctggctact tcgccgagaa caatcaggga 1500
gagctgtgca tcaagggcaa cgtggtcatg aaggagtatt acaagaacga ggaagagacc 1560
aagaaagcgt tctccgacga tggctacttt ctcaccggag acattgccga gtggactgcc 1620
aatggtcagc ttcgaattat cgacagacga aagaacctcg tcaagaccca gaacggagag 1680
tacattgctc tggagaagct cgaaacacag taccgatcgt cttcctacgt tgccaacctg 1740
tgcgtctacg ccgaccagaa ccgagtcaag cccatcgctc tggtcattcc caacgagggt 1800
cctaccaaaa agcttgccca gagcttgggc gtggattccg acgactggga tgccgtctgt 1860
tccaacaaga aagtggtcaa ggctgttctc aaggacatgc tggataccgg acgatctctc 1920
ggtctgtccg gcatcgagct gctgcaagga atcgtgttgc tgcctggcga gtggactccc 1980
cagaacagct acctcaccgc tgcccagaag ctcaaccgaa agaagattgt cgatgacaac 2040
aaaaaggaga tcgacgagtg ctacgagcag tcctaa 2076

<210> SEQ ID NO 36
<211> LENGTH: 691
<212> TYPE: PRT
<213> ORGANISM: Yarrowia lipolytica

<400> SEQUENCE: 36

Met Val Gly Tyr Thr Ile Ser Ser Lys Pro Val Ser Val Glu Val Gly
1 5 10 15

Pro Ala Lys Pro Gly Glu Thr Ala Pro Arg Arg Asn Val Ile Ala Lys
20 25 30

Asp Ala Pro Val Val Phe Pro Asp Asn Asp Ser Ser Leu Thr Thr Val
35 40 45

Tyr Lys Leu Phe Lys Lys Tyr Ala Glu Ile Asn Ser Glu Arg Lys Ala
50 55 60

Met Gly Trp Arg Asp Thr Ile Asp Ile His Val Glu Thr Lys Gln Val
65 70 75 80

Thr Lys Val Val Asp Gly Val Glu Lys Lys Val Pro Lys Glu Trp Lys
85 90 95

Tyr Phe Glu Met Gly Pro Tyr Lys Trp Leu Ser Tyr Lys Glu Ala Leu
100 105 110

Lys Leu Val His Asp Tyr Gly Ala Gly Leu Arg His Leu Gly Ile Lys
115 120 125

Pro Lys Glu Lys Met His Ile Tyr Ala Gln Thr Ser His Arg Trp Met
130 135 140

Leu Ser Gly Leu Ala Ser Leu Ser Gln Gly Ile Pro Ile Val Thr Ala
145 150 155 160

Tyr Asp Thr Leu Gly Glu Glu Gly Leu Thr Arg Ser Leu Gln Glu Thr
165 170 175

Asn Ser Val Ile Met Phe Thr Asp Lys Ala Leu Leu Ser Ser Leu Lys
180 185 190

Val Ser Leu Lys Lys Gly Thr Asp Leu Arg Ile Ile Ile Tyr Gly Gly
195 200 205

Asp Leu Thr Pro Asp Asp Lys Lys Ala Gly Asn Thr Glu Ile Asp Ala
210 215 220

Ile Lys Glu Ile Val Pro Asp Met Lys Ile Tyr Thr Met Asp Glu Val
225 230 235 240

Val Ala Leu Gly Arg Glu His Pro His Pro Val Glu Glu Val Asp Tyr
245 250 255

Glu Asp Leu Ala Phe Ile Met Tyr Thr Ser Gly Ser Thr Gly Val Pro

```
            260                 265                 270

Lys Gly Val Val Leu Gln His Lys Gln Ile Leu Ala Ser Val Ala Gly
        275                 280                 285

Val Thr Lys Ile Ile Asp Arg Ser Ile Ile Gly Asn Thr Asp Arg Leu
    290                 295                 300

Leu Asn Phe Leu Pro Leu Ala His Ile Phe Glu Phe Val Phe Glu Met
305                 310                 315                 320

Val Thr Phe Trp Trp Gly Ala Ser Leu Gly Tyr Gly Thr Val Lys Thr
                325                 330                 335

Ile Ser Asp Leu Ser Met Lys Asn Cys Lys Gly Asp Ile Arg Glu Leu
            340                 345                 350

Lys Pro Thr Ile Met Val Gly Val Pro Ala Val Trp Glu Pro Met Arg
        355                 360                 365

Lys Gly Ile Leu Gly Lys Ile Lys Glu Leu Ser Pro Leu Met Gln Arg
    370                 375                 380

Val Phe Trp Ala Ser Phe Ala Ala Lys Gln Arg Leu Asp Glu Asn Gly
385                 390                 395                 400

Leu Pro Gly Gly Ser Ile Leu Asp Ser Leu Ile Phe Lys Lys Val Lys
                405                 410                 415

Asp Ala Thr Gly Gly Cys Leu Arg Tyr Val Cys Asn Gly Gly Ala Pro
            420                 425                 430

Val Ser Val Asp Thr Gln Lys Phe Ile Thr Thr Leu Ile Cys Pro Met
        435                 440                 445

Leu Ile Gly Cys Gly Leu Thr Glu Thr Thr Ala Asn Thr Thr Ile Met
    450                 455                 460

Ser Pro Lys Ser Tyr Ala Phe Gly Thr Ile Gly Glu Pro Thr Ala Ala
465                 470                 475                 480

Val Thr Leu Lys Leu Ile Asp Val Pro Glu Ala Gly Tyr Phe Ala Glu
                485                 490                 495

Asn Asn Gln Gly Glu Leu Cys Ile Lys Gly Asn Val Val Met Lys Glu
            500                 505                 510

Tyr Tyr Lys Asn Glu Glu Glu Thr Lys Lys Ala Phe Ser Asp Asp Gly
        515                 520                 525

Tyr Phe Leu Thr Gly Asp Ile Ala Glu Trp Thr Ala Asn Gly Gln Leu
    530                 535                 540

Arg Ile Ile Asp Arg Arg Lys Asn Leu Val Lys Thr Gln Asn Gly Glu
545                 550                 555                 560

Tyr Ile Ala Leu Glu Lys Leu Glu Thr Gln Tyr Arg Ser Ser Ser Tyr
                565                 570                 575

Val Ala Asn Leu Cys Val Tyr Ala Asp Gln Asn Arg Val Lys Pro Ile
            580                 585                 590

Ala Leu Val Ile Pro Asn Glu Gly Pro Thr Lys Lys Leu Ala Gln Ser
        595                 600                 605

Leu Gly Val Asp Ser Asp Asp Trp Asp Ala Val Cys Ser Asn Lys Lys
    610                 615                 620

Val Val Lys Ala Val Leu Lys Asp Met Leu Asp Thr Gly Arg Ser Leu
625                 630                 635                 640

Gly Leu Ser Gly Ile Glu Leu Leu Gln Gly Ile Val Leu Leu Pro Gly
                645                 650                 655

Glu Trp Thr Pro Gln Asn Ser Tyr Leu Thr Ala Ala Gln Lys Leu Asn
            660                 665                 670

Arg Lys Lys Ile Val Asp Asp Asn Lys Lys Glu Ile Asp Glu Cys Tyr
        675                 680                 685
```

```
Glu Gln Ser
    690


<210> SEQ ID NO 37
<211> LENGTH: 574
<212> TYPE: PRT
<213> ORGANISM: Yarrowia lipolytica

<400> SEQUENCE: 37

Met Thr Thr Ile Ile His Lys Ser Thr Phe Pro Asp Ile Glu Leu Phe
1               5                   10                  15

Gln Gly Ser Ile Thr Asp Phe Ile Arg Thr Gly Ala Tyr Ala Glu Asp
            20                  25                  30

Asp Tyr Lys Pro Cys Met Ile Asp Ala Glu Thr Gly Glu Gln Leu Thr
        35                  40                  45

Gln Lys Gln Ile Leu Asp Cys Ala Asp Gln Phe Arg Ser Leu Leu Tyr
    50                  55                  60

Gln His Gly Val Gln Lys Thr Pro Asn Arg Asp Glu Arg Ile Gly Asp
65                  70                  75                  80

Val Val Ile Pro Phe Ile Asp Asn Asn Ile Tyr Leu Pro Ala Ile His
                85                  90                  95

Tyr Ala Cys Leu Glu Leu Gly Cys Cys Met Asn Pro Ala Ser Thr Gln
            100                 105                 110

Gln Thr Pro Leu Glu Leu Ser Lys Gln Ile Arg Val Thr Asp Pro Lys
        115                 120                 125

Val Ile Ile Tyr Gln Arg Lys Tyr Arg Lys Thr Val Met His Ala Ile
    130                 135                 140

Asp Leu Val Cys Tyr Thr Asn Phe Pro Ile Val Ile Glu Phe Glu Thr
145                 150                 155                 160

Met Leu Phe Leu Arg Asn Ser Val Pro Pro Pro Pro Lys Lys Ala Lys
                165                 170                 175

Phe His Ile Thr Ser Thr Glu Gln Ala Arg Lys Arg Ile Ala Tyr Leu
            180                 185                 190

Gly Met Ser Ser Gly Thr Ser Gly Lys Ser Lys Ala Val Arg Leu Ser
        195                 200                 205

His His Asn Ile Val Ala Cys Ser Gln Val Ser Gln Val Thr Phe Pro
    210                 215                 220

Ala Leu Tyr Lys Ala Ser Asn Val Cys Val Ala Val Leu Pro Ser Cys
225                 230                 235                 240

His Val Phe Gly Leu Tyr Ile Phe Phe Met Val Leu Pro Arg Ser Gly
                245                 250                 255

Gly Thr Thr Ile Met His Thr Lys Phe Asp Leu Lys Gln Leu Leu Glu
            260                 265                 270

Ser Gln Lys Lys Tyr Lys Ala Asn Phe Leu Pro Leu Val Pro Pro Ile
        275                 280                 285

Ala Val Gln Leu Ala Lys Asn Pro Met Val Lys Asn Tyr Ala Asp Ser
    290                 295                 300

Leu Lys Gln Val Lys Leu Ile Met Ser Ala Ala Ala Pro Leu Gly Ala
305                 310                 315                 320

Glu Val Thr Gln Ser Leu Ile Lys Ala Ile Gly Pro Gln Val Arg Val
                325                 330                 335

Val Gln Gly Tyr Gly Met Thr Glu Thr Ser Pro Cys Val Thr Leu Phe
            340                 345                 350

Asp Pro Ala Asp Pro His Leu His Ile Lys Ala Cys Gly Lys Leu Val
```

```
        355                 360                 365

Pro Asn Cys Glu Val Arg Ile Val Ala Asp Gly Val Asp Gln Pro Ala
    370                 375                 380

Tyr Ser Gly Ser Val Ser Asp Val Ala Lys Asn Lys Thr Asp Asn Leu
385                 390                 395                 400

Pro Val Gly Glu Ile Trp Val Arg Gly Pro Gln Val Met Asp Gly Tyr
                405                 410                 415

His Lys Asn Lys Ser Ala Thr Ser Glu Ala Phe Val Glu Ala Asn Asp
            420                 425                 430

Ser Ser Val Cys Tyr Asn Thr Lys Trp Leu Arg Thr Gly Asp Val Gly
        435                 440                 445

Leu Val Asp Ser Leu Gly Arg Phe Met Ile Val Asp Arg Thr Lys Glu
    450                 455                 460

Met Ile Lys Ser Met Ser Lys Gln Val Ala Pro Ala Glu Leu Glu Asp
465                 470                 475                 480

Met Leu Leu Ala His Ala Asp Val Ser Asp Ala Ala Val Ile Gly Val
                485                 490                 495

Glu Asn Glu Ala Lys Gly Thr Glu Gln Ile Arg Ala Phe Leu Val Leu
            500                 505                 510

Lys Lys Gly Gly Asp Ala Leu Glu Val Lys Lys Trp Met Asp Ser Lys
        515                 520                 525

Leu Pro Lys Tyr Lys Gln Leu His Gly Gly Val Val Val Ile Asp Gln
    530                 535                 540

Ile Pro Lys Ser Gln Ala Gly Lys Ile Leu Arg Arg Met Leu Arg Leu
545                 550                 555                 560

Arg Gln Asp Asp Val Val Leu Gly Thr Asp Gln Ala Lys Leu
                565                 570


<210> SEQ ID NO 38
<211> LENGTH: 1647
<212> TYPE: DNA
<213> ORGANISM: artificial sequence
<220> FEATURE:
<223> OTHER INFORMATION: YlACoS-3P

<400> SEQUENCE: 38

atggccatca tccactccac cggaactctg cccatcttca acggtaccgt caccgattac     60

ctgcgaacaa agccttctta ctcgtccaca gatccagcct acatcgacgt ggttacaggc    120

aactctatca gctactccga ggtctggaag cttgccgacc gactctcctc tgctctgtac    180

aacgactacg gactcaccga cgccaagccc gacgagaatg tgggtcctgt tgtcatgctg    240

cacgctgtca attcgcctct cctggcatct gttcactacg ctcttctgga tctgggcgtc    300

acaatcactc ccgcagctgc cacctacgag gctggcgatc tcgcacatca aatcaaggtg    360

tgctctccgt ccctggtcat ttgcaaccag cagttcgaac ccaaggtcaa atctgcctcc    420

agcaacacca agctcatttt catcgaggat ctgctcaaaa cccagtcgtc tgctccctgg    480

aaaaagttca ctacctccaa ccccaaccga gttgcctacc tgggcatgtc cagtggaacc    540

tctggtctcc ccaaggcggt tcaacagacc cacatcaaca tgtcgtcttc caccgaagcc    600

gtcatttcct ctcagaccat cttcagcgct cgaaagaacg tcaccgcagc cattgtgccc    660

atgactcatg tctacggact caccaagttt gttttccact ctgtcgcagg ctcaatgacc    720

accgttgtgt tccccaagtt ctccctggtc gacctcctgg aggcccagat caagtacaag    780

atcaacattc tgtatctggt tcctccagtg gtcttggctc tggccaagga ctctcgtgta    840
```

```
cagccctaca tcaagtccat ttgcgagctc accactctga ttgccactgg tgcggctccc    900

cttcctccca ctgcaggcga cgcccttctg gagcgactta cgggcaacaa agagggaaac    960

agagacaacg gtatggatcc cttggttctc atccagggct acggactcac agagactctc   1020

caggtgtctg tcttcaagcc agaggatccc gaacgagatc tcaagaccgt gggcaaactg   1080

cttcccaaca ccgaggttcg aattgtcggc gagaagggag atgttccgcg ttccaaatgg   1140

tcgtttgtca ctcctccaac cggcgaaatc tacattcgag gtccccacgt gactcctggt   1200

tacttcaaca acgactctgc caactctgag tcctttgacg gcgagtggct caagaccggc   1260

gatatcggat acatggacct ggaaggtcga ctcaccattg tggaccgaaa caaggagatg   1320

atcaaggtca acggacgtca ggttgctcct gccgagatcg aatctgtgct gctgggtcat   1380

cctatggtca aggatgtggc cgtcattgga gtcaccaatc ccgacagagg cacggagtct   1440

gctcgggcgt ttcttgttac tgaagctcga gctctccctg tcatcaagca gtggtttgac   1500

cgtcgagttc cctcctacaa gcgactttac ggaggcattg tggttgtcga tgccattccc   1560

aagtctgcct cgggcaagat tctgcgacgg gtcctcagag agcgaaaggg cgactccgtg   1620

tttggagagt atgtcgagga agtctaa                                       1647
```

```
<210> SEQ ID NO 39
<211> LENGTH: 548
<212> TYPE: PRT
<213> ORGANISM: artificial sequence
<220> FEATURE:
<223> OTHER INFORMATION: YlACoS-3P protein

<400> SEQUENCE: 39

Met Ala Ile Ile His Ser Thr Gly Thr Leu Pro Ile Phe Asn Gly Thr
1               5                   10                  15

Val Thr Asp Tyr Leu Arg Thr Lys Pro Ser Tyr Ser Ser Thr Asp Pro
            20                  25                  30

Ala Tyr Ile Asp Val Val Thr Gly Asn Ser Ile Ser Tyr Ser Glu Val
        35                  40                  45

Trp Lys Leu Ala Asp Arg Leu Ser Ser Ala Leu Tyr Asn Asp Tyr Gly
    50                  55                  60

Leu Thr Asp Ala Lys Pro Asp Glu Asn Val Gly Pro Val Val Met Leu
65                  70                  75                  80

His Ala Val Asn Ser Pro Leu Leu Ala Ser Val His Tyr Ala Leu Leu
                85                  90                  95

Asp Leu Gly Val Thr Ile Thr Pro Ala Ala Ala Thr Tyr Glu Ala Gly
            100                 105                 110

Asp Leu Ala His Gln Ile Lys Val Cys Ser Pro Ser Leu Val Ile Cys
        115                 120                 125

Asn Gln Gln Phe Glu Pro Lys Val Lys Ser Ala Ser Ser Asn Thr Lys
    130                 135                 140

Leu Ile Phe Ile Glu Asp Leu Leu Lys Thr Gln Ser Ser Ala Pro Trp
145                 150                 155                 160

Lys Lys Phe Thr Thr Ser Asn Pro Asn Arg Val Ala Tyr Leu Gly Met
                165                 170                 175

Ser Ser Gly Thr Ser Gly Leu Pro Lys Ala Val Gln Gln Thr His Ile
            180                 185                 190

Asn Met Ser Ser Ser Thr Glu Ala Val Ile Ser Ser Gln Thr Ile Phe
        195                 200                 205

Ser Ala Arg Lys Asn Val Thr Ala Ala Ile Val Pro Met Thr His Val
    210                 215                 220
```

Tyr Gly Leu Thr Lys Phe Val Phe His Ser Val Ala Gly Ser Met Thr
225 230 235 240

Thr Val Val Phe Pro Lys Phe Ser Leu Val Asp Leu Leu Glu Ala Gln
245 250 255

Ile Lys Tyr Lys Ile Asn Ile Leu Tyr Leu Val Pro Pro Val Val Leu
260 265 270

Ala Leu Ala Lys Asp Ser Arg Val Gln Pro Tyr Ile Lys Ser Ile Cys
275 280 285

Glu Leu Thr Thr Leu Ile Ala Thr Gly Ala Ala Pro Leu Pro Pro Thr
290 295 300

Ala Gly Asp Ala Leu Leu Glu Arg Leu Thr Gly Asn Lys Glu Gly Asn
305 310 315 320

Arg Asp Asn Gly Met Asp Pro Leu Val Leu Ile Gln Gly Tyr Gly Leu
325 330 335

Thr Glu Thr Leu Gln Val Ser Val Phe Lys Pro Glu Asp Pro Glu Arg
340 345 350

Asp Leu Lys Thr Val Gly Lys Leu Leu Pro Asn Thr Glu Val Arg Ile
355 360 365

Val Gly Glu Lys Gly Asp Val Pro Arg Ser Lys Trp Ser Phe Val Thr
370 375 380

Pro Pro Thr Gly Glu Ile Tyr Ile Arg Gly Pro His Val Thr Pro Gly
385 390 395 400

Tyr Phe Asn Asn Asp Ser Ala Asn Ser Glu Ser Phe Asp Gly Glu Trp
405 410 415

Leu Lys Thr Gly Asp Ile Gly Tyr Met Asp Leu Glu Gly Arg Leu Thr
420 425 430

Ile Val Asp Arg Asn Lys Glu Met Ile Lys Val Asn Gly Arg Gln Val
435 440 445

Ala Pro Ala Glu Ile Glu Ser Val Leu Leu Gly His Pro Met Val Lys
450 455 460

Asp Val Ala Val Ile Gly Val Thr Asn Pro Asp Arg Gly Thr Glu Ser
465 470 475 480

Ala Arg Ala Phe Leu Val Thr Glu Ala Arg Ala Leu Pro Val Ile Lys
485 490 495

Gln Trp Phe Asp Arg Arg Val Pro Ser Tyr Lys Arg Leu Tyr Gly Gly
500 505 510

Ile Val Val Val Asp Ala Ile Pro Lys Ser Ala Ser Gly Lys Ile Leu
515 520 525

Arg Arg Val Leu Arg Glu Arg Lys Gly Asp Ser Val Phe Gly Glu Tyr
530 535 540

Val Glu Glu Val
545

<210> SEQ ID NO 40
<211> LENGTH: 616
<212> TYPE: PRT
<213> ORGANISM: Yarrowia lipolytica

<400> SEQUENCE: 40

Met Pro Gln Ile Ile His Lys Ser Ala Trp Gly Asp Ile Pro Leu Ser
1 5 10 15

Thr Phe Phe Tyr Gly Asn Val Thr Asp Tyr Leu Arg Ser Lys Lys Ser
20 25 30

Phe Gly Ser Asp Lys Ile Gly Tyr Ile Asp Ala Glu Thr Gly Glu Gly

-continued

```
        35                  40                  45

Ile Thr Tyr Lys Gln Leu Trp Lys Leu Ala Asn Gly Ile Ser Ala Val
    50                  55                  60

Leu Tyr His His Tyr Gly Ile Gly His Ala Arg Ala Pro Val Ala Ser
65                  70                  75                  80

Asp His Thr Leu Gly Asp Val Val Met Leu His Ala Pro Asn Ser Arg
                85                  90                  95

Phe Phe Pro Ser Leu His Tyr Gly Met Leu Asp Met Gly Cys Thr Ile
            100                 105                 110

Thr Ser Ala Ser Val Ser Tyr Asp Val Ala Asp Leu Ala His Gln Leu
        115                 120                 125

Arg Val Thr Asp Ala Ser Leu Val Leu Cys Tyr Gln Glu Lys Glu Asn
    130                 135                 140

Asn Val Arg Gln Ala Ile Lys Glu Ala Gln Lys Asp Ala Ala Phe Pro
145                 150                 155                 160

Gly Ile Thr His Pro Val Arg Ile Leu Leu Ile Glu Asn Leu Leu Thr
                165                 170                 175

Met Ala Cys Asn Ile Ser Glu Glu Lys Ile Asn Ser Ala Met Ala Arg
            180                 185                 190

Lys Phe Glu Tyr Ser Pro Gln Glu Cys Thr Lys Arg Ile Ala Tyr Leu
        195                 200                 205

Ser Met Ser Ser Gly Thr Thr Gly Gly Ile Pro Lys Ala Val Arg Leu
    210                 215                 220

Thr His Phe Asn Met Ser Ser Cys Asp Thr Leu Gly Thr Leu Ser Thr
225                 230                 235                 240

Pro Ser Phe Ser Thr Gly Asp Asp Ile Arg Val Ala Ala Ile Val Pro
                245                 250                 255

Met Thr His Gln Tyr Gly Leu Thr Lys Phe Ile Phe Asn Met Cys Ser
            260                 265                 270

Ser His Ala Thr Thr Val Val His Arg Gln Phe Asp Leu Val Lys Leu
        275                 280                 285

Leu Glu Ser Gln Lys Lys Tyr Lys Leu Asn Arg Leu Met Leu Val Pro
    290                 295                 300

Pro Val Ile Val Lys Met Ala Lys Asp Pro Ala Val Glu Pro Tyr Ile
305                 310                 315                 320

Pro Ser Leu Tyr Glu His Val Asp Phe Ile Thr Thr Gly Ala Ala Pro
                325                 330                 335

Leu Pro Gly Ser Ala Val Thr Asn Leu Leu Thr Arg Ile Thr Gly Asn
            340                 345                 350

Pro Gln Gly Ile Arg His Ser Gln Ser Gly Arg Pro Pro Leu Thr Ile
        355                 360                 365

Ser Gln Gly Tyr Gly Leu Thr Glu Thr Ser Pro Leu Cys Ala Val Phe
    370                 375                 380

Asp Pro Leu Asp Pro Asp Val Asp Phe Arg Ser Ala Gly Lys Ala Thr
385                 390                 395                 400

Ser His Val Glu Ile Arg Ile Val Ser Glu Asp Gly Val Asp Gln Pro
                405                 410                 415

Gln Leu Lys Leu Asp Asp Leu Ser His Leu Asp Gly Met Leu Lys Arg
            420                 425                 430

Asp Glu Pro Leu Pro Val Gly Glu Val Leu Ile Arg Gly Pro Met Ile
        435                 440                 445

Met Asp Gly Tyr His Lys Asn Arg Gln Ser Ser Glu Glu Ser Phe Asp
    450                 455                 460
```

-continued

```
Arg Ser Gln Glu Asp Pro Lys Thr Leu Ile His Trp Gln Asp Lys Trp
465                 470                 475                 480

Leu Lys Thr Gly Asp Ile Gly Met Val Asp Gln Lys Gly Arg Leu Met
                485                 490                 495

Ile Val Asp Arg Asn Lys Glu Met Ile Lys Ser Met Ser Lys Gln Val
            500                 505                 510

Ala Pro Ala Glu Leu Glu Ser Leu Leu Leu Asn His Asp Gln Val Ile
        515                 520                 525

Asp Cys Ala Val Ile Gly Val Asn Ser Glu Ala Lys Ala Thr Glu Ser
    530                 535                 540

Ala Arg Ala Phe Leu Val Leu Lys Asp Pro Ser Tyr Asp Ala Val Lys
545                 550                 555                 560

Ile Lys Ala Trp Leu Asp Gly Gln Val Pro Ser Tyr Lys Arg Leu Tyr
                565                 570                 575

Gly Gly Val Val Val Leu Lys Asn Glu Gln Ile Pro Lys Asn Pro Ser
            580                 585                 590

Gly Lys Ile Leu Arg Arg Ile Leu Arg Thr Arg Lys Asp Asp Phe Ile
        595                 600                 605

Gln Gly Ile Asp Val Ser Lys Leu
    610                 615
```

<210> SEQ ID NO 41
<211> LENGTH: 1800
<212> TYPE: DNA
<213> ORGANISM: artificial sequence
<220> FEATURE:
<223> OTHER INFORMATION: YlACoS-5P

<400> SEQUENCE: 41

```
atggcctcaa tcattcacaa gtctcctgtg cccgacgttc agctgttcta cggttcctgg      60

ccagatctca tgcgaacctc tcctcatgcc cacaacgact ccaaacccgt ggtctttgac     120

ttcgatacca agcagcaact tacttggaag caggtctggc aactcagcgc tcgactcaga     180

gcccagctgt accacaagta cggaatcggc aaacccggtg ctcttgcacc tttccacaac     240

gatccctctc tcggagacgt ggtcatcttc tacactccca acacctacag ctcgttgccc     300

tatcatctgg ctcttcacga tctcggagcc accatttctc ctgcctccac atcttacgac     360

gtcaaggaca tttgccatca gatcgttact accgatgcgg tcgtggttgt cgctgcagcc     420

gagaaatccg agattgctcg agaggccgtt cagctgtctg gtcgagacgt cagagttgtg     480

gtcatggagg acctcatcaa caatgctccc accgttgcgc agaacgatat cgactcggca     540

cctcatgtgt ccctgtctcg ggaccaggct cgagccaaga ttgcatacct gggcatgtct     600

tccggtacgt ctggcggact tcccaaggct gttcgtctca ctcacttcaa cgttacctcg     660

aactgtctgc aggtctccgc tgccgcaccc aaccttgccc agaacgtggt tgccagcgcc     720

gtcattccaa ccactcacat ctacggtctc accatgtttc tgtcggttct tccctacaac     780

ggttccgtgg tcattcatca caagcaattc aacttgcgag atctgctcga ggctcagaag     840

acatacaagg tctctctgtg gattctcgtt cctcccgtca tcgtgcagct tgccaagaac     900

cctatggtcg acgagtacct ggactccatt cgagcccatg tgcggtgcat cgtctctgga     960

gctgctcctc tcggtggcaa tgtcgtggat caggtttcgg ttcgtcttac cggcaacaag    1020

gaaggcattc tgcccaacgg agacaagctc gtcattcatc aagcctacgg tcttaccgag    1080

tcctctccca tcgttggaat gctcgatcct ctgtcggacc acatcgacgt catgactgtg    1140
```

-continued

```
ggctgtctca tgcccaatac cgaggctcga attgtcgacg aagagggaaa cgatcagcca   1200

gcagtccacg ttaccgacac acgaggcatc ggtgccgctg tcaagcgagg cgagaagatt   1260

ccctccggag aactctggat tcgaggtcct cagatcatgg acggatacca caagaacccc   1320

gagtcgtctc gtgagtccct ggaacccagc acagagacct acggtctgca acatttccag   1380

gacagatggc ttcgaactgg agacgttgct gtcatcgaca ccttcggacg agtcatggtt   1440

gtggatcgaa ccaaggagct catcaagtcc atgtctcgac aggttgctcc tgccgagctc   1500

gaagctcttc tgctcaacca tccttccgtc aacgatgtgg ctgtcgttgg cgtccacaac   1560

gacgataatg gcacagagtc agcacgagcg tttgtcgttc ttcaaccagg cgacgcctgt   1620

gatcctacta ccatcaagca ctggatggac cagcaagttc cctcctacaa gcggctgtac   1680

ggaggcattg tggtcatcga cactgttccc aagaatgcct ctggcaagat tctgcgaaga   1740

ctgcttcgac agcggagaga cgatcgagtc tggggtctgg ccaaggttgc caagctctaa   1800
```

<210> SEQ ID NO 42
<211> LENGTH: 599
<212> TYPE: PRT
<213> ORGANISM: artificial sequence
<220> FEATURE:
<223> OTHER INFORMATION: YlACoS-5P protein

<400> SEQUENCE: 42

```
Met Ala Ser Ile Ile His Lys Ser Pro Val Pro Asp Val Gln Leu Phe
1               5                   10                  15

Tyr Gly Ser Trp Pro Asp Leu Met Arg Thr Ser Pro His Ala His Asn
            20                  25                  30

Asp Ser Lys Pro Val Val Phe Asp Phe Asp Thr Lys Gln Gln Leu Thr
        35                  40                  45

Trp Lys Gln Val Trp Gln Leu Ser Ala Arg Leu Arg Ala Gln Leu Tyr
    50                  55                  60

His Lys Tyr Gly Ile Gly Lys Pro Gly Ala Leu Ala Pro Phe His Asn
65                  70                  75                  80

Asp Pro Ser Leu Gly Asp Val Val Ile Phe Tyr Thr Pro Asn Thr Tyr
                85                  90                  95

Ser Ser Leu Pro Tyr His Leu Ala Leu His Asp Leu Gly Ala Thr Ile
            100                 105                 110

Ser Pro Ala Ser Thr Ser Tyr Asp Val Lys Asp Ile Cys His Gln Ile
        115                 120                 125

Val Thr Thr Asp Ala Val Val Val Val Ala Ala Ala Glu Lys Ser Glu
    130                 135                 140

Ile Ala Arg Glu Ala Val Gln Leu Ser Gly Arg Asp Val Arg Val Val
145                 150                 155                 160

Val Met Glu Asp Leu Ile Asn Asn Ala Pro Thr Val Ala Gln Asn Asp
                165                 170                 175

Ile Asp Ser Ala Pro His Val Ser Leu Ser Arg Asp Gln Ala Arg Ala
            180                 185                 190

Lys Ile Ala Tyr Leu Gly Met Ser Ser Gly Thr Ser Gly Gly Leu Pro
        195                 200                 205

Lys Ala Val Arg Leu Thr His Phe Asn Val Thr Ser Asn Cys Leu Gln
    210                 215                 220

Val Ser Ala Ala Ala Pro Asn Leu Ala Gln Asn Val Val Ala Ser Ala
225                 230                 235                 240

Val Ile Pro Thr Thr His Ile Tyr Gly Leu Thr Met Phe Leu Ser Val
                245                 250                 255
```

```
Leu Pro Tyr Asn Gly Ser Val Val Ile His His Lys Gln Phe Asn Leu
            260                 265                 270

Arg Asp Leu Leu Glu Ala Gln Lys Thr Tyr Lys Val Ser Leu Trp Ile
        275                 280                 285

Leu Val Pro Pro Val Ile Val Gln Leu Ala Lys Asn Pro Met Val Asp
    290                 295                 300

Glu Tyr Leu Asp Ser Ile Arg Ala His Val Arg Cys Ile Val Ser Gly
305                 310                 315                 320

Ala Ala Pro Leu Gly Gly Asn Val Val Asp Gln Val Ser Val Arg Leu
                325                 330                 335

Thr Gly Asn Lys Glu Gly Ile Leu Pro Asn Gly Asp Lys Leu Val Ile
            340                 345                 350

His Gln Ala Tyr Gly Leu Thr Glu Ser Ser Pro Ile Val Gly Met Leu
        355                 360                 365

Asp Pro Leu Ser Asp His Ile Asp Val Met Thr Val Gly Cys Leu Met
    370                 375                 380

Pro Asn Thr Glu Ala Arg Ile Val Asp Glu Glu Gly Asn Asp Gln Pro
385                 390                 395                 400

Ala Val His Val Thr Asp Thr Arg Gly Ile Gly Ala Ala Val Lys Arg
                405                 410                 415

Gly Glu Lys Ile Pro Ser Gly Glu Leu Trp Ile Arg Gly Pro Gln Ile
            420                 425                 430

Met Asp Gly Tyr His Lys Asn Pro Glu Ser Ser Arg Glu Ser Leu Glu
        435                 440                 445

Pro Ser Thr Glu Thr Tyr Gly Leu Gln His Phe Gln Asp Arg Trp Leu
    450                 455                 460

Arg Thr Gly Asp Val Ala Val Ile Asp Thr Phe Gly Arg Val Met Val
465                 470                 475                 480

Val Asp Arg Thr Lys Glu Leu Ile Lys Ser Met Ser Arg Gln Val Ala
                485                 490                 495

Pro Ala Glu Leu Glu Ala Leu Leu Leu Asn His Pro Ser Val Asn Asp
            500                 505                 510

Val Ala Val Val Gly Val His Asn Asp Asp Asn Gly Thr Glu Ser Ala
        515                 520                 525

Arg Ala Phe Val Val Leu Gln Pro Gly Asp Ala Cys Asp Pro Thr Thr
    530                 535                 540

Ile Lys His Trp Met Asp Gln Gln Val Pro Ser Tyr Lys Arg Leu Tyr
545                 550                 555                 560

Gly Gly Ile Val Val Ile Asp Thr Val Pro Lys Asn Ala Ser Gly Lys
                565                 570                 575

Ile Leu Arg Arg Leu Leu Arg Gln Arg Arg Asp Asp Arg Val Trp Gly
            580                 585                 590

Leu Ala Lys Val Ala Lys Leu
        595
```

<210> SEQ ID NO 43
<211> LENGTH: 1788
<212> TYPE: DNA
<213> ORGANISM: artificial sequence
<220> FEATURE:
<223> OTHER INFORMATION: YlACoS-6P

<400> SEQUENCE: 43

```
atggccacac agattatcca caacgccacc atccccaata tccccgtcga ccagctctac      60
```

-continued

```
gacggcaaga tcaccgactt cattcgatcc ggaggccact ccaacgaaac caagccttct    120

gtcatcgacg ccaagacagg ccagactctc tcccaggcgg aaatgtggca gctgtcggac    180

aagtacgcgg cacttctcag ctctcagtac ggtctgtgcc gacacagaga caacgagctg    240

gacccatcta tgggagatgt gctcatcacc ttctttggaa acgttatcct cgctcctgtg    300

gtccattggg ctgccctcga cctcggagca accatttctc ctggatccac aggctactct    360

gcccaggatc tcgctcacca gttccgagtc accactccca aggtcgttgt gtacgccaag    420

gcgttcaagg atgtggtgga cgaggctacg aagctgtaca actccccaaa ccctccagca    480

cttgtcgagc tcgaggcgct ggacaagcag gcccgaatgg ttggaaacca caaggtcgaa    540

cacacccgaa agatcaagct ggctcctcac gagtcccgaa ctcggatcgc gtaccttggc    600

atgtcttcag gtacctccgg tggagtttca aaggctgtcc gactcaccca ttccaatctc    660

acgtcgtgtt ccgaaatctc gaacaaagcc tccgagtctc tcgcaactga ccagcagatc    720

gctgccgcca tcattcccgt gagtcatctg tttggactgt ccaagttcct cattggcaac    780

cctcacgccg gagccaccac tgtctatcac aatggcttcg atctgatcga ggtgctggag    840

gcacagaaga aatacaaagt caactcgtgg accctggttc ctcccatcat tgtcctgctc    900

accaaacacc ccattgtcga gaagtacatt ccttctctcc gtgcccacat gcgagccatc    960

ctctccggag ctgctcctct gggtgccaat gtcacagagg ctcttctcac ccgagtcact   1020

ggcaacaagt ttggcgagtc tcccgagggc ggtctgcgaa tcgttcaggg ctacggactt   1080

acagagacgt ctcccgttgc cactctgttt gaccccgaag acaaggaacg acacattcgg   1140

tcgtgtggaa agctcgtgcc caactctcag gttcgaattg tcaacgaaga cggcgtggat   1200

cagcctgcct acgatgtgga ccccaacgag ctggacgagg ccatcaaaca gggcactctg   1260

ccagtcggag agctttggat cagaggtccc caggttatgg acggctacca taacaacccc   1320

gaggccaacg aagcctgttt cgtcaaggct gacgatgctg aagcagatac tgcctactac   1380

aacagacact ggttccgaac cggagacgtt gctctggtcg acaagcaggg cagatacatg   1440

attgtggacc gaaccaagga gatgatcaag agtcagggta agcaggttgc tcctgccgag   1500

ctcgaagaca tgctcctggg acacgcacag gtggcagata ccgcagtcat cggtattcag   1560

gacgtggaga agggtaacga ggctcctcga gcttttgttg tgctcaagga cccgaagtac   1620

gacgctgtgg agatcaagac atggctggac aagcagcttc ccaagtacaa gcagcttcat   1680

gctggcatcg tggtcattga tgccattccc aagaacgcca gtggcaagat tctgcgacgt   1740

ctgttgcgtg ctagaaagga cgatgttgtt ctgggtctca acaagtaa                1788
```

```
<210> SEQ ID NO 44
<211> LENGTH: 595
<212> TYPE: PRT
<213> ORGANISM: artificial sequence
<220> FEATURE:
<223> OTHER INFORMATION: YlACoS-6P protein

<400> SEQUENCE: 44

Met Ala Thr Gln Ile Ile His Asn Ala Thr Ile Pro Asn Ile Pro Val
1               5                   10                  15

Asp Gln Leu Tyr Asp Gly Lys Ile Thr Asp Phe Ile Arg Ser Gly Gly
            20                  25                  30

His Ser Asn Glu Thr Lys Pro Ser Val Ile Asp Ala Lys Thr Gly Gln
        35                  40                  45

Thr Leu Ser Gln Ala Glu Met Trp Gln Leu Ser Asp Lys Tyr Ala Ala
    50                  55                  60
```

-continued

```
Leu Leu Ser Ser Gln Tyr Gly Leu Cys Arg His Arg Asp Asn Glu Leu
65                  70                  75                  80

Asp Pro Ser Met Gly Asp Val Leu Ile Thr Phe Phe Gly Asn Val Ile
                85                  90                  95

Leu Ala Pro Val Val His Trp Ala Ala Leu Asp Leu Gly Ala Thr Ile
            100                 105                 110

Ser Pro Gly Ser Thr Gly Tyr Ser Ala Gln Asp Leu Ala His Gln Phe
        115                 120                 125

Arg Val Thr Thr Pro Lys Val Val Val Tyr Ala Lys Ala Phe Lys Asp
    130                 135                 140

Val Val Asp Glu Ala Thr Lys Leu Tyr Asn Ser Pro Asn Pro Pro Ala
145                 150                 155                 160

Leu Val Glu Leu Glu Ala Leu Asp Lys Gln Ala Arg Met Val Gly Asn
                165                 170                 175

His Lys Val Glu His Thr Arg Lys Ile Lys Leu Ala Pro His Glu Ser
            180                 185                 190

Arg Thr Arg Ile Ala Tyr Leu Gly Met Ser Ser Gly Thr Ser Gly Gly
        195                 200                 205

Val Ser Lys Ala Val Arg Leu Thr His Ser Asn Leu Thr Ser Cys Ser
    210                 215                 220

Glu Ile Ser Asn Lys Ala Ser Glu Ser Leu Ala Thr Asp Gln Gln Ile
225                 230                 235                 240

Ala Ala Ala Ile Ile Pro Val Ser His Leu Phe Gly Leu Ser Lys Phe
                245                 250                 255

Leu Ile Gly Asn Pro His Ala Gly Ala Thr Thr Val Tyr His Asn Gly
            260                 265                 270

Phe Asp Leu Ile Glu Val Leu Glu Ala Gln Lys Lys Tyr Lys Val Asn
        275                 280                 285

Ser Trp Thr Leu Val Pro Pro Ile Ile Val Leu Leu Thr Lys His Pro
    290                 295                 300

Ile Val Glu Lys Tyr Ile Pro Ser Leu Arg Ala His Met Arg Ala Ile
305                 310                 315                 320

Leu Ser Gly Ala Ala Pro Leu Gly Ala Asn Val Thr Glu Ala Leu Leu
                325                 330                 335

Thr Arg Val Thr Gly Asn Lys Phe Gly Glu Ser Pro Glu Gly Gly Leu
            340                 345                 350

Arg Ile Val Gln Gly Tyr Gly Leu Thr Glu Thr Ser Pro Val Ala Thr
        355                 360                 365

Leu Phe Asp Pro Glu Asp Lys Glu Arg His Ile Arg Ser Cys Gly Lys
    370                 375                 380

Leu Val Pro Asn Ser Gln Val Arg Ile Val Asn Glu Asp Gly Val Asp
385                 390                 395                 400

Gln Pro Ala Tyr Asp Val Asp Pro Asn Glu Leu Asp Glu Ala Ile Lys
                405                 410                 415

Gln Gly Thr Leu Pro Val Gly Glu Leu Trp Ile Arg Gly Pro Gln Val
            420                 425                 430

Met Asp Gly Tyr His Asn Asn Pro Glu Ala Asn Glu Ala Cys Phe Val
        435                 440                 445

Lys Ala Asp Asp Ala Glu Ala Asp Thr Ala Tyr Tyr Asn Arg His Trp
    450                 455                 460

Phe Arg Thr Gly Asp Val Ala Leu Val Asp Lys Gln Gly Arg Tyr Met
465                 470                 475                 480
```

```
Ile Val Asp Arg Thr Lys Glu Met Ile Lys Ser Gln Gly Lys Gln Val
            485                 490                 495

Ala Pro Ala Glu Leu Glu Asp Met Leu Leu Gly His Ala Gln Val Ala
            500                 505                 510

Asp Thr Ala Val Ile Gly Ile Gln Asp Val Glu Lys Gly Asn Glu Ala
        515                 520                 525

Pro Arg Ala Phe Val Val Leu Lys Asp Pro Lys Tyr Asp Ala Val Glu
    530                 535                 540

Ile Lys Thr Trp Leu Asp Lys Gln Leu Pro Lys Tyr Lys Gln Leu His
545                 550                 555                 560

Ala Gly Ile Val Val Ile Asp Ala Ile Pro Lys Asn Ala Ser Gly Lys
                565                 570                 575

Ile Leu Arg Arg Leu Leu Arg Ala Arg Lys Asp Asp Val Val Leu Gly
            580                 585                 590

Leu Asn Lys
        595


<210> SEQ ID NO 45
<211> LENGTH: 598
<212> TYPE: PRT
<213> ORGANISM: Yarrowia lipolytica

<400> SEQUENCE: 45

Met Val Gln Ile Ile His Lys Ala Pro Leu Gly Asp Met Ala Glu Ser
1               5                   10                  15

Glu Leu Phe Tyr Gly Ser Ile Pro Asp Phe Met Arg Ser Ser Arg Phe
            20                  25                  30

Ala Asp Asp Asp Thr Arg Ile Ser Val Val Asp Tyr Asp Thr Asp Lys
        35                  40                  45

Ala Met Thr Leu Ala Arg Val Phe Lys Val Ser Gly Met Leu Arg Ala
    50                  55                  60

Gln Phe Phe His Thr Tyr Asp Val Gly Lys Lys Lys Asp Gly Asp Ala
65                  70                  75                  80

Asn Pro Lys Val Ile Phe Tyr Val Gly Asn Thr Ala Asp Asn Leu Ala
                85                  90                  95

Cys His Ile Ala Leu His Asp Leu Gly Ala Ile Ile Ser Pro Ala Ser
            100                 105                 110

Thr Ala Tyr Asp Val Asn Asp Leu Leu His Gln Ile Asn Val Val Asp
        115                 120                 125

Ala Ala Leu Ile Val Ala Glu Ala Ala Arg Ala Asp Val Ala Arg Glu
    130                 135                 140

Ala Val Ala Lys Ala Gly Asp Lys Phe Lys His Val Lys Val Val Val
145                 150                 155                 160

Phe Glu Glu Leu Leu Glu Gln Asn Arg Arg Val Arg Pro Asn Leu Ile
                165                 170                 175

Arg Val Ala Pro Ile Val His Leu Ser Lys Glu Gln Ala Tyr Thr Thr
            180                 185                 190

Leu Ala Tyr Leu Gly Met Ser Ser Gly Thr Ser Gly Gly Val Pro Lys
        195                 200                 205

Ala Val Glu Leu Thr His Phe Ala Met Thr Ser Asn Val Gln Gln Thr
    210                 215                 220

Ala Lys Asn Ala Pro Asn Leu Val Asp Asp Asp Thr Val Cys Ser Ala
225                 230                 235                 240

Val Ile Pro Thr Ser His Ile Tyr Gly Leu Ala Leu Phe Met Leu His
                245                 250                 255
```

Met Pro Phe Leu Gly Ala Lys Val Val Tyr His Lys Lys Phe Asp Leu
260 265 270

Val Glu Met Leu Glu Gly Gln Lys Lys His Gly Val Asn Tyr Trp Val
275 280 285

Leu Val Pro Pro Ile Ile Val Ala Leu Ala Lys His Pro Ile Ile Asp
290 295 300

Arg Tyr Leu Asp Ser Ile Arg Ala Asn Leu Lys Thr Ile Thr Ser Gly
305 310 315 320

Ala Ala Pro Leu Gly Gly Asn Val Val Asp Ala Val Gln Thr Arg Phe
325 330 335

Thr Gly Asn Thr Arg Gly Thr Leu Pro Asn Asn Arg Arg Ile Val Ile
340 345 350

Tyr Gln Gly Tyr Gly Leu Thr Glu Thr Ala Pro Ile Ala Cys Leu Cys
355 360 365

Asp Pro Leu Trp Asp Asn Leu Asn Val Val Thr Val Gly Thr Leu Val
370 375 380

Pro Asn Thr Glu Ala Arg Ile Val Asp Glu Asn Gly Asp Asp Gln Pro
385 390 395 400

Ala Phe Glu Val Thr Asp Ala Arg Ala Leu Gly Asp Ala Val Arg Arg
405 410 415

Gly Asp Lys Ile Pro Ser Gly Glu Leu Tyr Leu Arg Gly Pro Gln Ile
420 425 430

Met Ser Gly Tyr His Lys Asn Pro Lys Ser Thr Glu Glu Ser Phe Glu
435 440 445

Tyr Val Asp Tyr Lys Ala Glu Gly Leu Arg His Tyr Gln Asp Arg Trp
450 455 460

Leu Lys Thr Gly Asp Val Ala Val Ile Asp Asn Phe Gly Arg Ile Gln
465 470 475 480

Ile Val Asp Arg Thr Lys Glu Leu Ile Lys Ser Met Ser Lys Gln Val
485 490 495

Ala Pro Ala Glu Leu Glu Ala Leu Leu Leu Ser His Pro Asp Val Val
500 505 510

Asp Val Ala Val Ile Gly Val Trp Gln Glu Glu Lys Ala Thr Glu Ser
515 520 525

Ala Arg Ala Phe Leu Val Val Arg Asp Pro Lys Val Asp Val Val Ala
530 535 540

Ile Lys Lys Trp Met Asp Glu Gln Val Pro Ser Tyr Lys Arg Leu Tyr
545 550 555 560

Gly Gly Val Val Val Ile Asp Ala Ile Pro Lys Asn Pro Ser Gly Lys
565 570 575

Ile Leu Arg Arg Leu Leu Arg Gln Arg Lys Asp Asp Val Val Gln Gly
580 585 590

Leu Asp Gln Ala Lys Leu
595

<210> SEQ ID NO 46
<211> LENGTH: 741
<212> TYPE: PRT
<213> ORGANISM: Yarrowia lipolytica

<400> SEQUENCE: 46

Met Leu Arg Pro Arg Ala Pro Ser Thr Leu Arg Arg Ala Ser Thr Gln
1 5 10 15

Leu Ser Ala Arg Pro Gln Gly Ile Thr Gly Pro Gln Arg Ser Phe His

-continued

```
            20                  25                  30

Leu Ala Cys Ser Arg Pro Thr Arg Ser Thr Thr Ser Glu Glu Asp Arg
        35                  40                  45

Pro Lys Trp Leu Thr Pro Arg Asn Val Arg Leu Gly Ser Leu Pro Phe
    50                  55                  60

Ser Arg Leu Leu Gln Gly His Ser Gln Arg Leu Tyr Ser Gly Leu Ser
65                  70                  75                  80

Thr Pro Gly Ile Ser Glu Val Thr Gly Cys Ser Ser Pro Ala Leu Ile
                85                  90                  95

Glu Ser His Ser Trp Asp Tyr Tyr Thr Thr Pro Ala Gln Arg Glu Leu
            100                 105                 110

Trp Gly Ser Lys Gly Glu Tyr Pro Ala Leu Ile Ser Ala Tyr Gln Gln
        115                 120                 125

Pro Asp Ile Ala Asn Ala Ile Leu Asp Arg Thr Ser Asp Tyr Thr Asn
    130                 135                 140

Glu Thr His Leu Ser Phe Ser Glu Leu Leu Lys Leu Ser Asn Leu Phe
145                 150                 155                 160

Ala Asp Ser Leu Tyr Ala His Ala Arg Glu Gln Gly Leu Val Phe Lys
                165                 170                 175

Ser Gly Asp Ser Val Ala Val Cys Gly Gly Asn Val Trp Glu Tyr Thr
            180                 185                 190

Ala Leu Gln Met Gly Leu Ser Lys Leu Gly Leu Val Leu Val Pro Leu
        195                 200                 205

Asn Pro Ala Phe Thr Ala Asn Gln Phe Ala Ala Ala Leu Ala Ala Thr
    210                 215                 220

Glu Ala Lys Ala Leu Ile Met Thr Ser His Leu Pro Gly Gly Lys Asp
225                 230                 235                 240

Lys Ala Thr Gly Lys Met Thr Leu Lys Ser Ala Ala Pro Ile Cys Gln
                245                 250                 255

Glu Val Ile Asp Asn Leu Asn Ala Ser Gly Lys Ser Lys Leu Lys Leu
            260                 265                 270

Leu Ile Asn Leu Ala Ser Gly Glu Thr Pro Gly Ala Asp Thr Ile Lys
        275                 280                 285

Asp Val Lys Phe Gln Gly Ser Gln Ser Asp Met His Glu Ile Val Phe
    290                 295                 300

Gln His Lys Lys Ala Val Ala Asn Gly Thr Leu Pro Ala Ser Val Pro
305                 310                 315                 320

Thr Glu Ile Arg Arg Leu Thr Ala Thr Val Asn Pro Asp Asp Ile Thr
                325                 330                 335

Asn Met Gln Phe Thr Ser Gly Thr Thr Ser Gln Pro Lys Val Ser Cys
            340                 345                 350

Leu Thr His Arg Asn Leu Leu Asn Asn Gly His Leu Ile Gly Thr Arg
        355                 360                 365

Met Gly Leu Lys Pro Ala Thr Gly Pro Ala Val Asn Gly Ile Ala Pro
    370                 375                 380

Asn Gln Asp Arg Leu Cys Ile Pro Val Pro Met Phe His Cys Phe Gly
385                 390                 395                 400

Leu Val Leu Ser Asn Leu Ala Ala Leu Thr Thr Gly Ala Ala Leu Val
                405                 410                 415

Tyr Pro Ser Glu Trp Phe Cys Ala Arg Ser Ala Ile Asp Asn Val Arg
            420                 425                 430

Lys Tyr Lys Cys Thr Gly Leu His Gly Val Pro Thr Met Tyr Val Ala
        435                 440                 445
```

```
Glu Leu Glu Tyr Leu Lys Asp Leu Glu Leu Lys Glu Ala Lys Ala Pro
    450                 455                 460

Gly Gln Asn Phe Leu Pro Gly Phe Glu Leu Leu Arg Thr Gly Ile Ala
465                 470                 475                 480

Ala Gly Ser Ala Val Pro Gly Glu Leu Met Thr Lys Leu Gly Gln Ser
                485                 490                 495

Met Asn Leu Lys Ala Leu Thr Ile Cys Tyr Gly Met Thr Glu Thr Ala
            500                 505                 510

Pro Val Thr Phe Met Thr Arg Pro Asp Asp Pro Val Glu Lys Arg Val
        515                 520                 525

Glu Thr Val Gly Gln Ile Met Pro His Thr Ser Cys Arg Ile Ile Lys
    530                 535                 540

Ser Gln Gln Glu Asp Leu Ser Glu Ser Glu Leu Asp Phe Thr Pro Leu
545                 550                 555                 560

Ala Thr Gly Gln Lys Gly Glu Ile Ile Thr Ser Gly Tyr Ala Leu Gln
                565                 570                 575

Lys Tyr Tyr Lys Asp Asp Pro Lys Lys Thr Ser Ala Ala Met Val Val
            580                 585                 590

Asp Pro Ala Thr Gly Val Arg Trp Met Arg Thr Gly Asp Glu Gly Cys
        595                 600                 605

Met Asp Asn Glu Gly Phe Leu Lys Val Thr Gly Arg Leu Lys Asp Leu
    610                 615                 620

Ile Ile Arg Gly Gly Glu Asn Ile His Pro Leu Glu Ile Glu Asn Val
625                 630                 635                 640

Leu Phe Ala His Asp Lys Ile Ala Gln Ala Ser Val Val Gly Val Lys
                645                 650                 655

Asp Pro Lys Tyr Gly Glu Ala Val Cys Ala Phe Val Thr Pro His Ala
            660                 665                 670

Phe Phe His Lys Gly His Gln His Val Lys His Asp Asp Ser Asp Lys
        675                 680                 685

Leu Thr Ile Glu Gln Val Gln Glu Trp Val Arg Asn Lys Leu Gly His
    690                 695                 700

Tyr Met Val Pro Lys Tyr Val Phe Phe Val Gly Asp Tyr Pro Lys Thr
705                 710                 715                 720

Ala Ser Gly Lys Ile Arg Lys Val Asp Leu Arg Lys Thr Ala Glu Ser
                725                 730                 735

Gln Leu Gly Leu Cys
            740


<210> SEQ ID NO 47
<211> LENGTH: 554
<212> TYPE: PRT
<213> ORGANISM: Yarrowia lipolytica

<400> SEQUENCE: 47

Met Ala Pro Ser Gln Gly Asp Lys Lys Met Phe Ile Ser Ala Glu Thr
1               5                   10                  15

Gly Glu Ser Leu Thr Thr Ala Gln Gln Trp Ala Thr Val Glu Leu Phe
            20                  25                  30

Ala Ser Lys Leu Tyr Gln Leu Gly Ile Gly His Ser Leu Arg Pro Asn
        35                  40                  45

Ser Asp Ala His Leu Gly Asp Val Val Leu Leu Tyr Val Lys Asn Ser
    50                  55                  60

Ile Tyr Ile Pro Ala Ala His Trp Ala Leu Leu Asp Leu Gly Ala Thr
```

-continued

```
65                  70                  75                  80

Val Ala Pro Ala Ala Ala Val Tyr Lys Ala Arg Asp Leu Val His Gln
                85                  90                  95

Ile Glu Leu Val Lys Pro Lys Leu Ile Val Cys Asp Ala Asp Leu Lys
            100                 105                 110

Ser Glu Ala Val Glu Ala Leu Lys Ile Leu Ser Lys Lys Met Pro Ile
        115                 120                 125

Val Thr Met Glu Glu Leu Arg Gln Pro Val Lys Lys Leu Lys Gln Arg
    130                 135                 140

Gln Arg Phe Arg Leu Ser Arg Pro Glu Ala Ala Lys Arg Val Ala Ala
145                 150                 155                 160

Leu Val Met Ser Ser Gly Thr Ser Gly Gly Leu Pro Lys Ala Val Arg
                165                 170                 175

Val Thr His His Val Val Thr Ser Asn Ala Gln Cys Ser Ala Ile Val
            180                 185                 190

Ala Pro Asp Leu Phe Asp Asp Pro Thr Asn Val Ile Ser Ala Val Leu
        195                 200                 205

Pro Met Ser His Ile Tyr Gly Tyr Phe Lys Phe Leu Phe Ala Cys Phe
    210                 215                 220

Tyr Thr Gly Glu Thr Cys Val Val His Gln Ser Phe Asp Leu Lys Ala
225                 230                 235                 240

Val Leu Asp Ala Gln Gln Lys Tyr Gly Ile Thr Ser Phe Phe Met Val
                245                 250                 255

Pro Pro Ile Ile Ile Ala Leu Ala Lys Ser Pro Ile Val Asp Glu Tyr
            260                 265                 270

Ile Pro Ser Leu Gln Lys Leu Arg Phe Ile Thr Ser Gly Ala Ala Pro
        275                 280                 285

Leu Gly Gly Asn Val Ile Glu Asp Val Lys Arg Arg Leu Gly Ser His
    290                 295                 300

Ile Ala Val Thr Gln Met Tyr Gly Met Thr Glu Ser Ile Leu Ser Thr
305                 310                 315                 320

Cys Phe Asn Pro Ser Asp Ala Asp Val Ala Ser Arg Ser Val Gly Lys
                325                 330                 335

Leu Cys Gly Asn Ile Glu Ala Arg Ile Val Gly His Asp Gly Val Asp
            340                 345                 350

Gln Pro Ala Tyr Asn Glu Thr Asp Pro Asp Lys Ile Asp Ala Ala Phe
        355                 360                 365

Lys Arg Gly Asp Ala Leu Pro Ser Gly Glu Leu Trp Leu Arg Gly Pro
    370                 375                 380

Ala Ile Met Ala Gly Tyr His Gly Asn Cys Leu Ala Asn Glu Glu Ser
385                 390                 395                 400

Phe Val Asp Ala Ser Asp Ala Ala Thr Val Pro His Tyr His Arg Lys
                405                 410                 415

Trp Leu Arg Thr Gly Asp Val Ala Val Ile Asp Val Lys Gly Arg Ile
            420                 425                 430

Val Ile Val Asp Arg Thr Lys Glu Met Ile Lys Ser Met Gly Arg Ala
        435                 440                 445

Val Ala Pro Ala Glu Ile Glu Ala Leu Leu Leu Ser His Pro Gln Val
    450                 455                 460

Met Asp Cys Ala Val Ile Gly Val His Val Pro Glu Lys Gly Thr Glu
465                 470                 475                 480

Ala Ala Arg Ala Phe Leu Val Leu Arg Asp Ala Gln Ala Ser Val Ala
                485                 490                 495
```

Arg Asp Val Ala Ala Trp Leu Asn Asp Gln Val Pro Ser Tyr Lys Arg
500 505 510

Leu His Gly Gly Val Val Val Phe Arg Gly Glu Val Ile Pro Lys Asn
515 520 525

Ala Ser Gly Lys Ile Leu Arg Arg Leu Leu Arg Gln Arg Lys Gly Asp
530 535 540

Glu Val Val Phe Pro Glu Arg Ala Lys Leu
545 550

<210> SEQ ID NO 48
<211> LENGTH: 1812
<212> TYPE: DNA
<213> ORGANISM: artificial sequence
<220> FEATURE:
<223> OTHER INFORMATION: YlACoS-10P

<400> SEQUENCE: 48
atggcctccg tcgctccatc ttccaacccc aatccgatcc accatctgtc gcgagtcgaa 60
gacgttcctc tctcccagac gttccgaggc aacattaccg actttgtgcg atctggaggc 120
tttgccgacg acgactccaa gccctgttgc atcgacgcga agactggcca acaacttaca 180
cagaagcaag tctgggacta cgccgacaag ttcagagcac tgctccatca cgacaacaat 240
ctgtgtcctt tcaatgccaa caccaccgat ccagctcttg gagacgtcat gatcaccctc 300
gtgcccaacc atctgttcat tacgtcgctg cactttgccg cactcgatct gggtgcgaca 360
gtttctcctg gctcggctgg atacactgtg gccgagctcg tcaaccagat caatcttacc 420
ggagcttctc tcatcgtgta cactcgaccc gtcttcaagg ttgtgcgaga ggcgcttgct 480
cagatcgtgg taccagtcaa gatcgtggag ttcgagggtc tcatcgaacg agccgagttt 540
gttcagagcc acaagattca gtccacaaag aaagtcacac tttctcctga ggagtcctac 600
tcgagaatcg cctacctggg catgtcttca ggcacctccg gaggtcttcc taaggccgtt 660
cgattgtcgc acttcaacat ggcgagttct gccgagctct ccaagcgagc tgcaccttcg 720
attgccggat ccgagcagat cgcaggtgcc attatccctg tcaaccatgt gtatggtctg 780
gccaagttcc tcattgccat gccaaagtcc ggagccacca cagtcttcca ctccaagttc 840
gacctcatcg agatcctcga ggctcaacag aagtacaagg tcaacatgta cgcccttgtt 900
cctcccatca ttgtcgttct ggccaagcat cctgctgttg agaagtacat cccttcgctg 960
cgagaacacc ttcgatacgt gtcctctgga gctgcacccc tgggtgccaa cgtcatcgag 1020
gcttgcaaca agcgtcttgc cggaactgct tctggcgaga acgagtttgg aggtctcaag 1080
attgttcagg gctacggtct cactgaaacc tcccctgtgg tctccacttt cgatcccaac 1140
gatcctgagc gacacgctcg gtcctgtggc aagctggttc ccaacaccca ggcacgaatc 1200
gtgtcggagg acggagtcga tcagcctgcc tacgagctca aggacctgtc tcagttggag 1260
gccgagctca aaaagggcaa ccttcccacc ggtgagttgt ggcttcgagg tccccagatc 1320
atggatggct accacaagaa cgacgaggcc aacgctgagt cgtttgtcga cgccactgac 1380
tacacttcca acatgccctt ctacatgaag cggtggttcc gaactggcga tgttgctctc 1440
gtcgatactc tgggcagata catgattgtc gatcgaacca aagagatgat caagagcatg 1500
agtaagcagg ttgctcctgc cgagctggag gacatcctgc ttggccatcc ccaggtagcc 1560
gatgctgctg tcatcggtgt tcagcaggtg gagaagggca ctgaggctcc ccgagcgttc 1620
gtggtgcttc gagatcccaa gttcgatgca gtggagatca aaaagtggat ggacgcccag 1680

```
gtgcccaagt acaaacaact tcatggaggt gtcgtggttc tggatgctgt tcccaagaat   1740

gccagcggca agattctcag acgactgctc cgtcagcgag agaatgacgt cgttcttgga   1800

ctcgacaagt aa                                                        1812


<210> SEQ ID NO 49
<211> LENGTH: 603
<212> TYPE: PRT
<213> ORGANISM: artificial sequence
<220> FEATURE:
<223> OTHER INFORMATION: YlACoS-10P protein

<400> SEQUENCE: 49

Met Ala Ser Val Ala Pro Ser Ser Asn Pro Asn Pro Ile His His Leu
1               5                   10                  15

Ser Arg Val Glu Asp Val Pro Leu Ser Gln Thr Phe Arg Gly Asn Ile
            20                  25                  30

Thr Asp Phe Val Arg Ser Gly Gly Phe Ala Asp Asp Asp Ser Lys Pro
        35                  40                  45

Cys Cys Ile Asp Ala Lys Thr Gly Gln Gln Leu Thr Gln Lys Gln Val
    50                  55                  60

Trp Asp Tyr Ala Asp Lys Phe Arg Ala Leu Leu His His Asp Asn Asn
65                  70                  75                  80

Leu Cys Pro Phe Asn Ala Asn Thr Thr Asp Pro Ala Leu Gly Asp Val
                85                  90                  95

Met Ile Thr Leu Val Pro Asn His Leu Phe Ile Thr Ser Leu His Phe
            100                 105                 110

Ala Ala Leu Asp Leu Gly Ala Thr Val Ser Pro Gly Ser Ala Gly Tyr
        115                 120                 125

Thr Val Ala Glu Leu Val Asn Gln Ile Asn Leu Thr Gly Ala Ser Leu
    130                 135                 140

Ile Val Tyr Thr Arg Pro Val Phe Lys Val Val Arg Glu Ala Leu Ala
145                 150                 155                 160

Gln Ile Val Val Pro Val Lys Ile Val Glu Phe Glu Gly Leu Ile Glu
                165                 170                 175

Arg Ala Glu Phe Val Gln Ser His Lys Ile Gln Ser Thr Lys Lys Val
            180                 185                 190

Thr Leu Ser Pro Glu Glu Ser Tyr Ser Arg Ile Ala Tyr Leu Gly Met
        195                 200                 205

Ser Ser Gly Thr Ser Gly Gly Leu Pro Lys Ala Val Arg Leu Ser His
    210                 215                 220

Phe Asn Met Ala Ser Ser Ala Glu Leu Ser Lys Arg Ala Ala Pro Ser
225                 230                 235                 240

Ile Ala Gly Ser Glu Gln Ile Ala Gly Ala Ile Ile Pro Val Asn His
                245                 250                 255

Val Tyr Gly Leu Ala Lys Phe Leu Ile Ala Met Pro Lys Ser Gly Ala
            260                 265                 270

Thr Thr Val Phe His Ser Lys Phe Asp Leu Ile Glu Ile Leu Glu Ala
        275                 280                 285

Gln Gln Lys Tyr Lys Val Asn Met Tyr Ala Leu Val Pro Pro Ile Ile
    290                 295                 300

Val Val Leu Ala Lys His Pro Ala Val Glu Lys Tyr Ile Pro Ser Leu
305                 310                 315                 320

Arg Glu His Leu Arg Tyr Val Ser Ser Gly Ala Ala Pro Leu Gly Ala
                325                 330                 335
```

```
Asn Val Ile Glu Ala Cys Asn Lys Arg Leu Ala Gly Thr Ala Ser Gly
            340                 345                 350

Glu Asn Glu Phe Gly Gly Leu Lys Ile Val Gln Gly Tyr Gly Leu Thr
        355                 360                 365

Glu Thr Ser Pro Val Val Ser Thr Phe Asp Pro Asn Asp Pro Glu Arg
    370                 375                 380

His Ala Arg Ser Cys Gly Lys Leu Val Pro Asn Thr Gln Ala Arg Ile
385                 390                 395                 400

Val Ser Glu Asp Gly Val Asp Gln Pro Ala Tyr Glu Leu Lys Asp Leu
                405                 410                 415

Ser Gln Leu Glu Ala Glu Leu Lys Lys Gly Asn Leu Pro Thr Gly Glu
            420                 425                 430

Leu Trp Leu Arg Gly Pro Gln Ile Met Asp Gly Tyr His Lys Asn Asp
        435                 440                 445

Glu Ala Asn Ala Glu Ser Phe Val Asp Ala Thr Asp Tyr Thr Ser Asn
    450                 455                 460

Met Pro Phe Tyr Met Lys Arg Trp Phe Arg Thr Gly Asp Val Ala Leu
465                 470                 475                 480

Val Asp Thr Leu Gly Arg Tyr Met Ile Val Asp Arg Thr Lys Glu Met
                485                 490                 495

Ile Lys Ser Met Ser Lys Gln Val Ala Pro Ala Glu Leu Glu Asp Ile
            500                 505                 510

Leu Leu Gly His Pro Gln Val Ala Asp Ala Ala Val Ile Gly Val Gln
        515                 520                 525

Gln Val Glu Lys Gly Thr Glu Ala Pro Arg Ala Phe Val Val Leu Arg
    530                 535                 540

Asp Pro Lys Phe Asp Ala Val Glu Ile Lys Lys Trp Met Asp Ala Gln
545                 550                 555                 560

Val Pro Lys Tyr Lys Gln Leu His Gly Gly Val Val Val Leu Asp Ala
                565                 570                 575

Val Pro Lys Asn Ala Ser Gly Lys Ile Leu Arg Arg Leu Leu Arg Gln
            580                 585                 590

Arg Glu Asn Asp Val Val Leu Gly Leu Asp Lys
        595                 600


<210> SEQ ID NO 50
<211> LENGTH: 627
<212> TYPE: PRT
<213> ORGANISM: Yarrowia lipolytica

<400> SEQUENCE: 50

Met Ile Ile His Thr Ser Asp Thr Ser Ser Ile Arg Val Asn Asp Leu
1               5                   10                  15

Phe Cys Gly Asn Ile Ala Asp Phe Ile Val Lys Gly Gly His Ser Lys
            20                  25                  30

Ser Ser Lys Thr Ser Ala Ile Asp Ala Ala Thr Gly Glu Ser Leu Ser
        35                  40                  45

His Val Asn Gln His Ile Leu Ser Arg Gln Ile Ala Ser Ile Leu Thr
    50                  55                  60

Glu Ser Gly Tyr Glu Pro Asn Phe Asp Pro Lys Ser His Ile Gly Asp
65                  70                  75                  80

Val Leu Val Thr Leu Phe Pro Asn Ser Ile Tyr Ser Ser Pro Val His
                85                  90                  95

Trp Ala Ala Leu Ile Arg Gly Gly Thr Val Ser Pro Ala Ser Val Ser
            100                 105                 110
```

-continued

```
Tyr Thr Leu Asn Glu Leu Ala His Gln Val Arg Thr Val Arg Pro Lys
        115                 120                 125

Val Ile Val Ala Cys Lys Ser Lys Val Ser Leu Ala Lys Lys Ala Val
    130                 135                 140

Leu Met Ala Arg Val Lys Thr Ala Val Leu Glu Leu Glu His Val Ile
145                 150                 155                 160

Ser Asn Ala Pro Lys Tyr Pro Glu Ser Asp Ser Val Lys Phe Asn Lys
                165                 170                 175

Asn Ser Gly Tyr Arg Arg Val Ala Tyr Leu Ala Met Ser Ser Gly Thr
            180                 185                 190

Ser Gly Gly Ile Phe Lys Ala Val Lys Ile Thr His Phe Asn Ile Thr
        195                 200                 205

Ser Cys Ile Gln Val Cys Gln Lys Ser Ala Pro Asn Arg Asp Thr Ala
    210                 215                 220

Ser Gln Ile Ala Ser Ala Val Ile Pro Val Ser His Leu Tyr Gly Leu
225                 230                 235                 240

Ser Lys Phe Leu Ile Met Ala Pro Tyr Val Gly Ser Thr Thr Val Phe
                245                 250                 255

His Glu Lys Phe Glu Ile Lys Glu Phe Leu Glu Ala Gln Lys Gln Phe
            260                 265                 270

Gln Val Asn Ser Trp Pro Ile Val Pro Pro Leu Val Val Leu Leu Thr
        275                 280                 285

Asn His Pro Leu Val Lys Glu Phe Ser Glu Ser Leu Arg Ala His Leu
    290                 295                 300

Arg Ile Val Cys Cys Gly Ala Ala Pro Leu Gly Glu Lys Ala Ala Arg
305                 310                 315                 320

Asp Phe Leu Thr Ala Ile Thr Gly Ser Pro Asp Gly Ile Ile Gln Pro
                325                 330                 335

Thr Ile Thr Ser Arg Asp Lys Ser Lys Ser Arg Asp Ser Gly Phe Phe
            340                 345                 350

Ser Ser Ile Arg Ala His Val Ala Asp Pro Ala Ala Ala Gly Ile Thr
        355                 360                 365

Ser Ala Asn Thr Ala Glu Ser Ala Gly Gln Ser Arg Asp Ala Pro Arg
    370                 375                 380

Leu Gln Ile Ile Gln Gly Trp Gly Leu Thr Glu Thr Ser Pro Thr Cys
385                 390                 395                 400

Thr Thr Phe Asp Pro Leu Asp Pro Asp Leu His Ile Lys Ala Cys Gly
                405                 410                 415

Lys Ile Val Ala Asn Thr Glu Ile Arg Ile Arg Gly Gln Gly Gln Asp
            420                 425                 430

Leu Gln Lys Ala Pro Ile Leu Ile Glu Asn Tyr Asp Ala Tyr Pro Ser
        435                 440                 445

Lys Glu Thr Leu Pro Ile Gly Asp Ile Tyr Val Arg Gly Pro Gln Val
    450                 455                 460

Thr Leu Gly Tyr Leu Asn Asp Asp His Ala Asp Ser Val Ser Phe Glu
465                 470                 475                 480

Gln Cys Tyr Asp Pro His Val Pro Trp Phe His Leu Lys Trp Phe Lys
                485                 490                 495

Thr Gly Asp Val Gly Phe Ile Asp Ala Lys Gly Arg Val Met Val Val
            500                 505                 510

Asp Arg Thr Lys Glu Met Ile Lys Ser Met Gly Lys Gln Val Ala Pro
        515                 520                 525
```

```
Ala Glu Ile Glu Asp Leu Leu Leu Ser His Glu Leu Val Ala Asp Ala
    530                 535                 540

Ala Val Ile Gly Val Ser Asn Glu Lys Leu Gly Thr Glu Ser Pro Arg
545                 550                 555                 560

Ala Phe Val Val Pro Lys Ser Gly Phe Lys Ala Ala Glu Leu Arg Ser
                565                 570                 575

Trp Thr Asp Ser Gln Leu Pro Lys His Lys Gln Leu His Gly Gly Ile
            580                 585                 590

Val Leu Val Asp Lys Val Pro Lys Asn Ala Ser Gly Lys Ile Leu Arg
        595                 600                 605

Arg Val Leu Arg Glu Arg Arg Gly Asp Leu Val Glu Gly Val Lys Leu
    610                 615                 620

Ser Lys Leu
625


<210> SEQ ID NO 51
<211> LENGTH: 593
<212> TYPE: PRT
<213> ORGANISM: Yarrowia lipolytica

<400> SEQUENCE: 51

Met Ile Ile His Thr Ser Leu Asn Gln Pro Ile Asp Asp Arg Glu Phe
1               5                   10                  15

Phe Asp Gly Thr Ile Pro Asp Phe Ile Arg Thr Ser Pro Phe Val Asn
            20                  25                  30

Asp Thr Thr Pro Phe Phe Ile Asp Ala Ala Thr Gly Glu Gln Leu Ser
        35                  40                  45

Gln Arg Gln Leu Trp Lys Met Ser Asn Asp Phe Leu Thr Ile Phe Arg
    50                  55                  60

Gln His Gly Leu Gly Asn Ala Arg Asp Asn Val Ser Asp Pro Ser Met
65                  70                  75                  80

Gly Asp Val Phe Ile Thr Leu Phe Pro Asn Cys Ile Trp Ala Gly Pro
                85                  90                  95

Val His Trp Ala Ala Leu Asp Ala Gly Ala Thr Leu Ser Pro Ala Ser
            100                 105                 110

Cys Ser Tyr Thr Val Gln Glu Phe Ala His Gln Leu Gln Leu Val Val
        115                 120                 125

Pro Lys Met Val Val Tyr Ser Glu Pro Phe Lys Gln Leu Leu Glu Asp
    130                 135                 140

Ala Ile Ile Val Ser Lys Thr Asn Pro Thr Ile Leu Ser Leu Glu Gln
145                 150                 155                 160

Leu Ile Glu Asp Ser Glu Arg Val Pro Leu Ala Gln Ala Asn Phe Gln
                165                 170                 175

Phe Ala Asn Arg Leu Gln Leu Arg Pro Lys Glu Ser Ile Thr Arg Val
            180                 185                 190

Ala Tyr Leu Ala Met Ser Ser Gly Thr Ser Gly Gly Leu Phe Lys Ala
        195                 200                 205

Val Arg Ile Thr His Gly Asn Ile Thr Ser Asn Ala Ile Met Ser Thr
    210                 215                 220

Lys Ser Ser Asn Ala Leu Leu Lys Thr Asn Gln Val Ala Ser Ala Ile
225                 230                 235                 240

Ile Pro Val Ser His Leu Tyr Gly Leu Ala Gln Phe Leu Val Phe Gly
                245                 250                 255

Val His Arg Gly Thr Ala Ala Val Phe His Lys Gly Phe Asp Phe Ile
            260                 265                 270
```

```
Glu Phe Leu Asp Ala Ala Val Lys Tyr Lys Val Asn Ile Phe Pro Leu
        275                 280                 285

Val Pro Pro Ile Ile Ile Leu Leu Ala Lys His Pro Phe Thr Gln Lys
    290                 295                 300

Tyr Val Pro Asp Leu Lys Arg Asn Leu Thr Thr Val Leu Ser Gly Ala
305                 310                 315                 320

Ala Pro Leu Gly Val Lys Ala Thr Glu Glu Phe Leu Glu Arg Ile Thr
                325                 330                 335

Gly Arg Lys Asp Gly Val Ser Glu Tyr Gly Thr Leu Arg Val Ile Gln
            340                 345                 350

Gly Trp Gly Met Thr Glu Thr Ser Pro Val Cys Thr Leu Phe Asp Pro
        355                 360                 365

Glu Val Pro Val Ala His Ile Arg Ser Val Gly Lys Leu Val Ser Asn
    370                 375                 380

Thr Glu Ala Arg Val Val Ser Glu Gly Val Asp Gln Pro Ala Cys Asp
385                 390                 395                 400

Val Asp Pro Ala Ser Leu Asp Ala Ala Ile Lys Ala Gly Gly Leu Pro
                405                 410                 415

Thr Gly Glu Ile Leu Ile Arg Gly Pro His Val Met Asp Gly Tyr His
            420                 425                 430

Lys Asn Pro Ser Ala Asn Ala Asp Ala Phe Glu Glu Ala Ser Asp Trp
        435                 440                 445

Thr Pro Asp Met Pro Trp Tyr Lys Lys Arg Trp Leu Arg Thr Gly Asp
    450                 455                 460

Val Gly Phe Phe Asp Leu Gln Gly Arg Val Met Ile Val Asp Arg Thr
465                 470                 475                 480

Lys Glu Leu Ile Lys Ser Met Gly Lys Gln Val Ala Pro Ala Glu Leu
                485                 490                 495

Glu Asp Ala Leu Leu Ala Asn Pro Leu Val Ala Asp Cys Ala Val Ile
            500                 505                 510

Gly Val Met Asp Val Asp Lys Gly Thr Glu Ser Pro Arg Ala Phe Val
        515                 520                 525

Val Leu Arg Asp Pro Lys Ala Asp Ala Val Gly Ile Leu Lys Ser Leu
    530                 535                 540

Asn Ser Gln Met Pro Lys Tyr Lys Asn Leu His Gly Gly Ile Val Val
545                 550                 555                 560

Val Glu Ala Val Pro Arg Asn Pro Ser Gly Lys Val Leu Arg Arg Leu
                565                 570                 575

Leu Arg Asp Arg Lys Asp Asp Val Val Leu Gly Leu Asp Val Ser Lys
            580                 585                 590

Leu
```

<210> SEQ ID NO 52
<211> LENGTH: 583
<212> TYPE: PRT
<213> ORGANISM: Yarrowia lipolytica

<400> SEQUENCE: 52

```
Met His Arg Arg Pro Asn Cys Pro Val Leu Phe Tyr Thr Ser Ser Ala
1               5                   10                  15

Ser Tyr Asp Ile Ala Leu Leu Val Leu Asn Thr Leu Ala Leu Pro Leu
            20                  25                  30

Phe Leu Pro Gly Arg Thr Pro Leu Arg Cys Ile Val Phe Arg Leu Pro
        35                  40                  45
```

```
Arg Asn Arg Ser Ala Phe Ile Thr His Leu Tyr Ile Thr Pro Leu Ser
    50                  55                  60

Thr Pro Ser Ser His Asp Thr Thr Ser Ile His Thr Met Ala Thr Leu
65                  70                  75                  80

Gln Lys Thr Ile Ser Lys Thr Gly Ala Gly Ile Phe Ile Pro Gly Ala
                85                  90                  95

Gln Glu Leu Thr Tyr Ser Gln Phe Phe Asp Leu Ile Gly Asp Phe Gln
            100                 105                 110

Lys Gln Leu Ala Gln Val Gly Leu Pro Pro Gln Ser Ala Val Ser Ile
        115                 120                 125

Ala Ile Pro Asn Ser Leu Glu Phe Ala Val Thr Phe Leu Ala Val Thr
    130                 135                 140

Phe Ser Arg Tyr Ile Ala Ala Pro Leu Asn Ser Ala Tyr Lys Lys Ser
145                 150                 155                 160

Glu Phe Glu Phe Tyr Ile Asp Asp Leu Lys Ser Lys Leu Val Leu Val
                165                 170                 175

Pro Lys Gly Ala Val Ala Gln Asn Leu Ala Ser Val Gln Ala Ala Arg
            180                 185                 190

Thr Phe Asn Ala Ala Ile Ala Glu Val Tyr Trp Asp Asp Gln Lys Lys
        195                 200                 205

Arg Ile Val Met Asp Ile Lys Glu Gly Pro Thr Asn Pro Pro Val Ala
    210                 215                 220

Val Pro Thr Pro Asp Glu Val Ser Pro Glu Asp Val Ala Leu Val Leu
225                 230                 235                 240

His Thr Ser Gly Thr Thr Gly Arg Pro Lys Ala Val Pro Leu Thr Gln
                245                 250                 255

Arg Asn Leu Cys Arg Thr Met His Asn Ile Val Asp Thr Tyr Lys Leu
            260                 265                 270

Thr Ser Lys Asp Thr Thr Tyr Leu Val Met Pro Leu Phe His Val His
        275                 280                 285

Gly Leu Leu Cys Ala Phe Leu Ala Pro Leu Ala Ser Gly Gly Gly Ile
    290                 295                 300

Val Ile Pro Ser Lys Phe Ser Ala Ser Gln Phe Trp Asp Asp Phe Val
305                 310                 315                 320

Lys Tyr Lys Cys Asn Trp Tyr Thr Ala Val Pro Thr Ile His Gln Ile
                325                 330                 335

Leu Leu Asn Thr Lys Ile Pro Gln Pro Leu Pro Glu Ile Arg Phe Ile
            340                 345                 350

Arg Ser Cys Ser Ser Ala Leu Ala Pro Ala Thr Phe His Gln Ile Glu
        355                 360                 365

Lys Ala Phe Lys Ala Pro Val Leu Glu Ala Tyr Ala Met Thr Glu Ala
    370                 375                 380

Ala His Gln Met Thr Ser Asn Asn Leu Pro Pro Gly Gln Arg Lys Pro
385                 390                 395                 400

Gly Thr Val Gly Val Gly Gln Gly Val Glu Val Ala Ile Leu Asp Asp
                405                 410                 415

Asn Gly Asp Glu Val Pro Gln Gly Lys Ile Ala Glu Ile Cys Ile Arg
            420                 425                 430

Gly Glu Asn Val Thr Lys Gly Tyr Ile Asn Asn Pro Glu Ala Asn Lys
        435                 440                 445

Ser Ser Phe Thr Lys Ser Gly Phe Phe Arg Thr Gly Asp Gln Gly Phe
    450                 455                 460
```

-continued

Leu Asp Lys Asp Gly Phe Val Asn Ile Thr Gly Arg Ile Lys Glu Leu
465 470 475 480

Ile Asn Arg Gly Gly Glu Lys Ile Ser Pro Ile Glu Leu Asp Gly Val
485 490 495

Met Leu Glu His Pro Ala Val Ala Glu Ala Val Cys Phe Gly Ala Pro
500 505 510

Asp Glu Met Tyr Gly Gln Gln Val Asn Ala Ala Ile Val Leu Lys Lys
515 520 525

Asp Ala Lys Ala Thr Glu Gln Asp Ile Lys Asp Phe Met Ala Asp Lys
530 535 540

Val Ala Lys Phe Lys Ile Pro Ala Arg Val Phe Phe Thr Asp Ile Met
545 550 555 560

Pro Lys Thr Ala Thr Gly Lys Ile Gln Arg Arg Phe Val Ala Gln Lys
565 570 575

Phe Leu Asp Lys Ala Lys Leu
580

<210> SEQ ID NO 53
<211> LENGTH: 585
<212> TYPE: PRT
<213> ORGANISM: Yarrowia lipolytica

<400> SEQUENCE: 53

Met Ala Lys Gly Lys Leu Ser Ser Gly Gly Val Lys Ser Ser Val Ala
1 5 10 15

Asp Lys Thr Thr Ala Ala Ala Ile His Thr Leu Pro Arg Ile Gln Gly
20 25 30

Asp Asp Thr Val Tyr Val Pro Asp Lys Val Asn Arg His Asn Met Asn
35 40 45

Pro Thr Tyr Phe Leu Pro Arg Ala Ala Glu Ile Glu Pro Asn Ala Lys
50 55 60

Ala Tyr Ile His Lys Gly Ala Asp Gly Val Arg Val Glu Arg Thr Tyr
65 70 75 80

Gly Glu Met Ala Asp Arg Val Leu Gly Leu Ala Thr Tyr Phe Lys Ser
85 90 95

Lys Glu Phe Lys Arg Val Ala Ile Cys Gly Pro Asn Thr Pro Ala His
100 105 110

Leu Glu Thr Met Phe Gly Ala Val Ala Ala Gly Ala Tyr Val Leu Gly
115 120 125

Leu Asn Tyr Arg Leu Thr Met Gly Glu Ile Thr Tyr Lys Met Glu Leu
130 135 140

Gly Asp Ala Asp Cys Val Val Val Asp Arg Glu Phe Val His Leu Ile
145 150 155 160

Ser Pro Glu Ile Arg Ala Lys Cys Gln Val Ile Val Asp Asp Asp Val
165 170 175

Ser Gly Ala Ser Lys Pro Gln Gln Pro Gly Glu Ile Leu Tyr Ser Asn
180 185 190

Val Val Gln Gln Gly Met Gln Leu Ala Lys Glu Gln Lys Thr Thr Trp
195 200 205

Asp Asn Leu His Val Gln Asn Glu Asp Glu Asp Glu Ile Leu Gly Leu
210 215 220

Phe Tyr Thr Ser Gly Thr Thr Gly Lys Pro Lys Ala Val Glu Tyr Thr
225 230 235 240

His Arg Ser Val Tyr Leu Cys Ala Met Ser Asn Ile Ile Glu Ala Gly
245 250 255

```
Leu Asn Cys Glu Thr Val Asp Gly His Asn Arg Cys His Tyr Leu Trp
            260                 265                 270

Thr Leu Pro Leu Phe His Ala Ala Gly Trp Thr Phe Pro Tyr Ser Val
        275                 280                 285

Thr Ala Val Arg Gly Thr His Val Leu Leu Arg Lys Ile Glu Pro Asp
    290                 295                 300

Tyr Ile Trp Asp Leu Leu Val Asp Asp Arg Ile Thr His Phe Asn Ala
305                 310                 315                 320

Ala Pro Thr Val Asn Asn Met Leu Val Asn Asn Pro Lys Ala Arg Arg
                325                 330                 335

Leu Pro Gln Thr Val Arg Val Thr Val Ala Ala Ser Pro Pro Ser Ala
            340                 345                 350

Ala Leu Phe Asn Lys Met Phe Asp Met Asn Leu His Pro Val His Met
        355                 360                 365

Tyr Gly Leu Thr Glu Ser Tyr Gly Pro Phe Val Arg Asn Tyr Phe Leu
    370                 375                 380

Gln Asp Trp His Gly Ala Thr Gly Asp Glu Arg Tyr Ala Leu Met Ala
385                 390                 395                 400

Arg Gln Gly Phe Ala Phe Val Gly Ser Gln Ser Val Gln Val Ile Ala
                405                 410                 415

Asn Asn Asp Ile Asn Gln Pro Val Pro Arg Asn Gly Gln Glu Ile Gly
            420                 425                 430

Glu Ile Val Cys Arg Gly Asn Ala Val Met Ala Arg Tyr His Lys Asp
        435                 440                 445

Pro Glu Ala Thr Ala Lys Ala Phe Glu Gln Gly Trp Phe His Thr Gly
    450                 455                 460

Asp Leu Ala Val Val Asn Pro Asp Gly Ser Ile Lys Ile Leu Asp Arg
465                 470                 475                 480

Lys Lys Asp Ile Ile Ile Ser Gly Gly Glu Asn Ile Ser Ser Val Ala
                485                 490                 495

Val Glu Gly Ile Ile Cys Lys Tyr Asp Asn Val Leu Glu Val Ala Val
            500                 505                 510

Val Gly Ile Pro Asp Glu Lys Tyr Gly Glu Val Pro Lys Ala Phe Leu
        515                 520                 525

Ile Leu Lys Asp Lys Ser Lys Pro Phe Asp Thr Asp Lys Met Ile Ala
    530                 535                 540

Trp Met Arg Glu Arg Met Gly Ala Tyr Gln Ile Pro Arg Gln Val Ser
545                 550                 555                 560

Val Val Asp Asp Leu Pro Arg Thr Ser Thr Gly Lys Ile Lys Lys Asn
                565                 570                 575

Val Leu Arg Asp Ser Val Gln Ala Ala
            580                 585


<210> SEQ ID NO 54
<211> LENGTH: 712
<212> TYPE: PRT
<213> ORGANISM: Yarrowia lipolytica

<400> SEQUENCE: 54

Met Lys Thr Ile Leu Lys Ile Thr Lys Ser Glu Asn Gln Asn Ala Leu
1               5                   10                  15

Phe Lys Asn Pro Ile Ser Pro Pro His Pro Pro Gln Thr Arg Thr Pro
            20                  25                  30

Ser Leu Lys Ile Lys Val Gln Pro Gln Ile Pro His Phe Phe His Ala
```

-continued

```
        35                  40                  45

Gly Pro Tyr Ile Asn Arg Gly Cys Pro Phe Leu Ser Pro Leu Leu His
    50                  55                  60

Tyr His Leu Val Glu Ile Pro Thr Thr Met Thr Ala Gly Leu Val Ala
65                  70                  75                  80

Ala Ala Ala Ile Gly Ala Ala Tyr Leu Glu Ala Lys Thr Leu Ile Ser
                85                  90                  95

Glu Asp Ala Tyr Met Ile Arg Gly Ala Met Thr Asn Gly Leu Asp Phe
            100                 105                 110

Phe Tyr Asn Ala Trp Lys Gly Arg Val Gln Tyr Trp Tyr Ala Phe Glu
        115                 120                 125

Asp Ala Val Lys Lys Tyr Pro Asn Asn Pro Ala Ile Val Tyr Pro Lys
    130                 135                 140

Pro Ile Glu Gly Lys Lys Pro Ser Gly Asp Ser Tyr Asp Asp Leu Phe
145                 150                 155                 160

Asp Val Glu Thr Phe Thr Tyr Gln Gln Leu Tyr Asp Glu Val Leu Lys
                165                 170                 175

Met Ser His Leu Leu Arg Asn Lys Tyr Gly Val Thr Ala Asn Asp Thr
            180                 185                 190

Ile Ala Leu Asn Ala Met Asn Ser Pro Leu Phe Ile Ile Val Trp Phe
        195                 200                 205

Ala Ile Trp Asn Leu Gly Ala Thr Pro Ala Phe Ile Asn Tyr Asn Leu
    210                 215                 220

Ala Asp Lys Ser Leu Leu His Cys Leu Lys Val Gly His Ala Ser Ile
225                 230                 235                 240

Met Phe Val Asp Thr Glu Val Glu Gly Asn Val Arg Pro Ser Leu Ala
                245                 250                 255

Glu Ile Lys Ser Glu Ala Lys Cys Asp Thr Val Phe Met Asp Asp Asp
            260                 265                 270

Phe Leu Ala Ala Tyr Ala Ala Ser Pro Ala Tyr Arg Ala Pro Asp Tyr
        275                 280                 285

Glu Arg His Pro Glu Gln Lys Asp Tyr Asp Thr Ala Val Leu Ile Tyr
    290                 295                 300

Thr Ser Gly Thr Thr Gly Leu Pro Lys Pro Ala Ile Met Ser Trp Lys
305                 310                 315                 320

Lys Ala Lys Leu Met Ser Ser Leu Tyr Gly His Ser Ile Arg Leu Lys
                325                 330                 335

Asn Asn Gly Val Val Tyr Ser Ala Met Pro Leu Tyr His Ser Thr Ala
            340                 345                 350

Ala Ile Leu Gly Cys Leu Pro Cys Leu Asn Arg Gly Ala Ala Tyr Ala
        355                 360                 365

Pro Gly Arg Lys Phe Ser Thr Thr Thr Phe Trp Thr Gln Ala Lys Leu
    370                 375                 380

Thr Asn Ala Thr His Ile Gln Tyr Val Gly Glu Thr Cys Arg Tyr Leu
385                 390                 395                 400

Ile Asn Ala Pro Pro Ser Pro Asp Glu Lys Ser His Gln Ile Lys Val
                405                 410                 415

Ala Phe Gly Asn Gly Met Arg Arg Asp Ile Trp Val Lys Phe Lys Glu
            420                 425                 430

Arg Phe Asn Ile Pro Ala Ile Gly Glu Phe Tyr Ala Ala Thr Glu Gly
        435                 440                 445

Pro Leu Gly Thr Asn Asn Phe Gln Gln Gly Glu Ile Gly Ile Gly Ala
    450                 455                 460
```

```
Met Gly Arg Tyr Gly Lys Leu Leu Ala Ala Ile Leu Ala Thr Arg Gln
465                 470                 475                 480

Thr Ile Val Pro Val Asp Pro Glu Asp Glu Thr Glu Leu Trp Arg Asp
                485                 490                 495

Pro Glu Thr Gly Phe Cys Arg Val Ala Gln Ser Asp Glu Pro Gly Glu
            500                 505                 510

Phe Ile Gln Lys Ile Pro Asn Pro Glu Lys Val His Glu Thr Phe Gln
        515                 520                 525

Gly Tyr Leu Gly Asn Asp Lys Ala Thr Asn Ser Lys Ile Met Arg Asp
    530                 535                 540

Val Phe Lys Lys Gly Asp Ala Tyr Tyr Arg Thr Gly Asp Leu Val Arg
545                 550                 555                 560

Leu Asn Asp Glu Gln Cys Tyr Tyr Phe Val Asp Arg Leu Gly Asp Thr
                565                 570                 575

Phe Arg Trp Lys Ser Glu Asn Val Ser Thr Ser Glu Val Glu Glu His
            580                 585                 590

Val Gly Ala Ser Asp Pro Asn Ile Glu Gln Val Val Cys Val Gly Val
        595                 600                 605

Lys Val Pro Glu His Glu Gly Arg Ala Gly Phe Ala Val Val Lys Leu
    610                 615                 620

Lys Asp Ala Ser Val Lys Pro Asn Leu Asp Gln Ile Ala Glu Tyr Ser
625                 630                 635                 640

Leu Lys Gln Leu Pro Lys Tyr Ala Val Pro Leu Phe Ile Lys Phe Val
                645                 650                 655

Asp Glu Ile Glu Arg Thr Gly Asn Asn Lys Val Gln Lys Val Lys Tyr
            660                 665                 670

Lys Asn Gln Lys Met Pro His Glu Glu Gly Glu Ser Pro Ile Tyr Trp
        675                 680                 685

Leu Lys Gly Asn Lys Tyr Val Glu Leu Asp Ala Gly Asp Trp Ala Ser
    690                 695                 700

Leu Gly Ser Gly Lys Ile Lys Leu
705                 710


<210> SEQ ID NO 55
<211> LENGTH: 1782
<212> TYPE: DNA
<213> ORGANISM: artificial sequence
<220> FEATURE:
<223> OTHER INFORMATION: YlACoS-5PS3

<400> SEQUENCE: 55

atggcctcaa tcattcacaa gtctcctgtg cccgacgttc agctgttcta cggttcctgg      60

ccagatctca tgcgaacctc tcctcatgcc cacaacgact ccaaacccgt ggtctttgac     120

ttcgatacca agcagcaact tacttggaag caggtctggc aactcagcgc tcgactcaga     180

gcccagctgt accacaagta cggaatcggc aaacccggtg ctcttgcacc tttccacaac     240

gatccctctc tcggagacgt ggtcatcttc tacactccca acacctacag ctcgttgccc     300

tatcatctgg ctcttcacga tctcggagcc accatttctc ctgcctccac atcttacgac     360

gtcaaggaca tttgccatca gatcgttact accgatgcgg tcgtggttgt cgctgcagcc     420

gagaaatccg agattgctcg agaggccgtt cagctgtctg gtcgagacgt cagagttgtg     480

gtcatggagg acctcatcaa caatgctccc accgttgcgc agaacgatat cgactcggca     540

cctcatgtgt ccctgtctcg ggaccaggct cgagccaaga ttgcatacct gggcatgtct     600
```

```
tccggtacgt ctggcggact tcccaaggct gttcgtctca ctcacttcaa cgttacctcg    660

aactgtctgc aggtctccgc tgccgcaccc aaccttgccc agaacgtggt tgccagcgcc    720

gtcattccaa ccactcacat ctacggtctc accatgtttc tgtcggttct tccctacaac    780

ggttccgtgg tcattcatca caagcaattc aacttgcgag atctgctcga ggctcagaag    840

acatacaagg tctctctgtg gattctcgtt cctcccgtca tcgtgcagct tgccaagaac    900

cctatggtcg acgagtacct ggactccatt cgagcccatg tgcggtgcat cgtctctgga    960

gctgctcctc tcggtggcaa tgtcgtggat caggtttcgg ttcgtcttac cggcaacaag   1020

gaaggcattc tgcccaacgg agacaagctc gtcattcatc aagcctacgg tcttaccgag   1080

tcctctccca tcgttggaat gctcgatcct ctgtcggacc acatcgacgt catgactgtg   1140

ggctgtctca tgcccaatac cgaggctcga attgtcgacg aagagggaaa cgatcagcca   1200

gcagtccacg ttaccgacac acgaggcatc ggtgccgctg tcaagcgagg cgagaagatt   1260

ccctccggag aactctggat tcgaggtcct cagatcatgg acggatacca caagaacccc   1320

gagtcgtctc gtgagtccct ggaacccagc acagagacct acggtctgca acatttccag   1380

gacagatggc ttcgaactgg agacgttgct gtcatcgaca ccttcggacg agtcatggtt   1440

gtggatcgaa ccaaggagct catcaagtcc atgtctcgac aggttgctcc tgccgagctc   1500

gaagctcttc tgctcaacca tccttccgtc aacgatgtgg ctgtcgttgg cgtccacaac   1560

gacgataatg gcacagagtc agcacgagcg tttgtcgttc ttcaaccagg cgacgcctgt   1620

gatcctacta ccatcaagca ctggatggac cagcaagttc cctcctacaa gcggctgtac   1680

ggaggcattg tggtcatcga cactgttccc aagaatgcct ctggcaagat tctgcgaaga   1740

ctgcttcgac agcggagaga cgatcgagtc tggggtctgt aa                      1782
```

<210> SEQ ID NO 56
<211> LENGTH: 593
<212> TYPE: PRT
<213> ORGANISM: artificial sequence
<220> FEATURE:
<223> OTHER INFORMATION: YlACoS-5PS3 protein

<400> SEQUENCE: 56

```
Met Ala Ser Ile Ile His Lys Ser Pro Val Pro Asp Val Gln Leu Phe
1               5                   10                  15

Tyr Gly Ser Trp Pro Asp Leu Met Arg Thr Ser Pro His Ala His Asn
            20                  25                  30

Asp Ser Lys Pro Val Val Phe Asp Phe Asp Thr Lys Gln Gln Leu Thr
        35                  40                  45

Trp Lys Gln Val Trp Gln Leu Ser Ala Arg Leu Arg Ala Gln Leu Tyr
    50                  55                  60

His Lys Tyr Gly Ile Gly Lys Pro Gly Ala Leu Ala Pro Phe His Asn
65                  70                  75                  80

Asp Pro Ser Leu Gly Asp Val Val Ile Phe Tyr Thr Pro Asn Thr Tyr
                85                  90                  95

Ser Ser Leu Pro Tyr His Leu Ala Leu His Asp Leu Gly Ala Thr Ile
            100                 105                 110

Ser Pro Ala Ser Thr Ser Tyr Asp Val Lys Asp Ile Cys His Gln Ile
        115                 120                 125

Val Thr Thr Asp Ala Val Val Val Val Ala Ala Ala Glu Lys Ser Glu
    130                 135                 140

Ile Ala Arg Glu Ala Val Gln Leu Ser Gly Arg Asp Val Arg Val Val
145                 150                 155                 160
```

-continued

```
Val Met Glu Asp Leu Ile Asn Asn Ala Pro Thr Val Ala Gln Asn Asp
                165                 170                 175

Ile Asp Ser Ala Pro His Val Ser Leu Ser Arg Asp Gln Ala Arg Ala
            180                 185                 190

Lys Ile Ala Tyr Leu Gly Met Ser Ser Gly Thr Ser Gly Gly Leu Pro
        195                 200                 205

Lys Ala Val Arg Leu Thr His Phe Asn Val Thr Ser Asn Cys Leu Gln
    210                 215                 220

Val Ser Ala Ala Ala Pro Asn Leu Ala Gln Asn Val Val Ala Ser Ala
225                 230                 235                 240

Val Ile Pro Thr Thr His Ile Tyr Gly Leu Thr Met Phe Leu Ser Val
                245                 250                 255

Leu Pro Tyr Asn Gly Ser Val Val Ile His His Lys Gln Phe Asn Leu
            260                 265                 270

Arg Asp Leu Leu Glu Ala Gln Lys Thr Tyr Lys Val Ser Leu Trp Ile
        275                 280                 285

Leu Val Pro Pro Val Ile Val Gln Leu Ala Lys Asn Pro Met Val Asp
    290                 295                 300

Glu Tyr Leu Asp Ser Ile Arg Ala His Val Arg Cys Ile Val Ser Gly
305                 310                 315                 320

Ala Ala Pro Leu Gly Gly Asn Val Val Asp Gln Val Ser Val Arg Leu
                325                 330                 335

Thr Gly Asn Lys Glu Gly Ile Leu Pro Asn Gly Asp Lys Leu Val Ile
            340                 345                 350

His Gln Ala Tyr Gly Leu Thr Glu Ser Ser Pro Ile Val Gly Met Leu
        355                 360                 365

Asp Pro Leu Ser Asp His Ile Asp Val Met Thr Val Gly Cys Leu Met
    370                 375                 380

Pro Asn Thr Glu Ala Arg Ile Val Asp Glu Glu Gly Asn Asp Gln Pro
385                 390                 395                 400

Ala Val His Val Thr Asp Thr Arg Gly Ile Gly Ala Ala Val Lys Arg
                405                 410                 415

Gly Glu Lys Ile Pro Ser Gly Glu Leu Trp Ile Arg Gly Pro Gln Ile
            420                 425                 430

Met Asp Gly Tyr His Lys Asn Pro Glu Ser Ser Arg Glu Ser Leu Glu
        435                 440                 445

Pro Ser Thr Glu Thr Tyr Gly Leu Gln His Phe Gln Asp Arg Trp Leu
    450                 455                 460

Arg Thr Gly Asp Val Ala Val Ile Asp Thr Phe Gly Arg Val Met Val
465                 470                 475                 480

Val Asp Arg Thr Lys Glu Leu Ile Lys Ser Met Ser Arg Gln Val Ala
                485                 490                 495

Pro Ala Glu Leu Glu Ala Leu Leu Leu Asn His Pro Ser Val Asn Asp
            500                 505                 510

Val Ala Val Val Gly Val His Asn Asp Asp Asn Gly Thr Glu Ser Ala
        515                 520                 525

Arg Ala Phe Val Val Leu Gln Pro Gly Asp Ala Cys Asp Pro Thr Thr
    530                 535                 540

Ile Lys His Trp Met Asp Gln Gln Val Pro Ser Tyr Lys Arg Leu Tyr
545                 550                 555                 560

Gly Gly Ile Val Val Ile Asp Thr Val Pro Lys Asn Ala Ser Gly Lys
                565                 570                 575
```

-continued

```
Ile Leu Arg Arg Leu Leu Arg Gln Arg Arg Asp Asp Arg Val Trp Gly
            580                 585                 590

Leu


<210> SEQ ID NO 57
<211> LENGTH: 696
<212> TYPE: PRT
<213> ORGANISM: Candida tropicalis

<400> SEQUENCE: 57

Met Gly Ala Pro Leu Thr Val Ala Val Gly Glu Ala Lys Pro Gly Glu
1               5                   10                  15

Thr Ala Pro Arg Arg Lys Ala Ser Gln Lys Leu Ala Pro Val Glu Arg
            20                  25                  30

Pro Thr Asp Ser Lys Ala Thr Thr Leu Pro Glu Phe Ile Glu Glu Cys
        35                  40                  45

Phe Thr Arg Asn Gly Asn Arg Asp Ala Met Ala Trp Arg Asp Leu Leu
    50                  55                  60

Glu Val His Val Glu Thr Lys Lys Val Thr Lys Ile Ile Asp Gly Glu
65                  70                  75                  80

Gln Lys Lys Val Asp Lys Glu Trp Ile Tyr Tyr Glu Met Gly Pro Tyr
                85                  90                  95

Asn Tyr Ile Ser Tyr Pro Lys Leu Leu Gln Leu Val Lys Asn Tyr Ser
            100                 105                 110

Lys Gly Leu Leu Glu Leu Gly Leu Leu Pro Asp Gln Gln Ser Lys Leu
        115                 120                 125

Met Ile Phe Ala Ser Thr Ser His Lys Trp Met Gln Thr Phe Leu Ala
    130                 135                 140

Ser Ser Phe Gln Gly Ile Pro Val Val Thr Ala Tyr Asp Thr Leu Gly
145                 150                 155                 160

Glu Ser Gly Leu Thr His Ser Leu Val Gln Thr Glu Ser Asp Ala Ile
                165                 170                 175

Phe Thr Asp Asn Gln Leu Leu Gly Ser Leu Ile Arg Pro Leu Glu Lys
            180                 185                 190

Ala Thr Ala Ile Lys Tyr Ile Ile His Gly Glu Lys Ile Asp Pro Asn
        195                 200                 205

Asp Lys Arg Gln Gly Gly Lys Ile Tyr Gln Asp Ala Glu Lys Ala Lys
    210                 215                 220

Glu Lys Ile Leu Gln Ile Arg Pro Asp Ile Lys Phe Ile Ser Tyr Asn
225                 230                 235                 240

Glu Val Ile Ala Leu Gly Glu Lys Ser Ser Lys Glu Leu His Tyr Pro
                245                 250                 255

Lys Pro Glu Asp Ser Ile Cys Ile Met Tyr Thr Ser Gly Ser Thr Gly
            260                 265                 270

Asp Pro Lys Gly Val Val Ile Thr Asn His Asn Ile Val Ala Ala Val
        275                 280                 285

Gly Gly Ile Ser Thr Asn Ala Thr Arg Asp Leu Val Arg Pro Ser Asp
    290                 295                 300

Lys Val Val Ala Phe Leu Pro Leu Ala His Ile Phe Glu Leu Ala Phe
305                 310                 315                 320

Glu Leu Ile Thr Phe Trp Trp Gly Ala Pro Leu Gly Tyr Ala Asn Val
                325                 330                 335

Lys Thr Leu Thr Asp Ala Ser Cys Arg Asn Cys Gln Pro Asp Leu Ile
            340                 345                 350
```

-continued

```
Glu Phe Lys Pro Thr Ile Met Val Gly Val Ala Ala Val Trp Glu Ser
        355                 360                 365

Val Arg Lys Gly Val Leu Ser Lys Leu Lys Gln Ala Ser Pro Leu Gln
    370                 375                 380

Gln Lys Ile Phe Trp Ala Ala Phe Lys Ala Lys Ser Thr Leu Asn His
385                 390                 395                 400

Phe Gly Leu Pro Gly Gly Gly Met Phe Asp Val Ile Phe Lys Lys Val
                405                 410                 415

Lys Ala Ala Thr Gly Gly Gln Leu Arg Tyr Val Leu Asn Gly Gly Ser
            420                 425                 430

Pro Ile Ser Ile Asp Ala Gln Val Phe Ile Ser Thr Leu Leu Ala Pro
        435                 440                 445

Met Leu Leu Gly Tyr Gly Leu Thr Glu Thr Cys Ala Asn Thr Thr Ile
    450                 455                 460

Thr Glu His Thr Arg Phe Gln Ile Gly Thr Leu Gly Ala Leu Val Gly
465                 470                 475                 480

Ser Val Thr Ala Lys Leu Val Asp Val Ala Asp Ala Gly Tyr Phe Ala
                485                 490                 495

Lys Asn Asn Gln Gly Glu Ile Trp Leu Lys Gly Gly Pro Val Val Lys
            500                 505                 510

Glu Tyr Tyr Lys Asn Glu Glu Glu Thr Lys Ala Ala Phe Thr Asp Asp
        515                 520                 525

Gly Trp Phe Lys Thr Gly Asp Ile Gly Glu Trp Thr Ser Glu Gly Gly
    530                 535                 540

Leu Asn Ile Ile Asp Arg Lys Lys Asn Leu Val Lys Thr Leu Asn Gly
545                 550                 555                 560

Glu Tyr Ile Ala Leu Glu Lys Leu Glu Ser Val Tyr Arg Ser Asn His
                565                 570                 575

Leu Val Met Asn Leu Cys Val Tyr Ala Asp Gln Thr Lys Val Lys Pro
            580                 585                 590

Ile Ala Ile Val Leu Pro Ile Glu Ala Asn Leu Lys Thr Met Leu Lys
        595                 600                 605

Asp Glu Lys Val Val Pro Asp Ala Asp Thr Gln Glu Leu Ser His Leu
    610                 615                 620

Val His Asn Lys Lys Val Val Gln Ala Val Leu Arg His Leu Leu Gln
625                 630                 635                 640

Thr Gly Lys Gln Gln Gly Leu Lys Gly Ile Glu Leu Leu Gln Asn Ile
                645                 650                 655

Val Leu Leu Asp Glu Glu Trp Thr Pro Gln Asn Gly Phe Val Thr Ser
            660                 665                 670

Ala Gln Lys Leu Gln Arg Lys Lys Ile Leu Glu Ser Cys Arg Lys Glu
        675                 680                 685

Val Asp Glu Ala Tyr Lys Ser Ser
    690                 695
```

<210> SEQ ID NO 58
<211> LENGTH: 718
<212> TYPE: PRT
<213> ORGANISM: Candida tropicalis

<400> SEQUENCE: 58

```
Met Pro Ala Leu Phe Lys Glu Ser Ala Lys His Ile Leu Asp Thr Ile
1               5                   10                  15

Ala Ala Asp Leu Pro Leu Asp Gln Lys Leu Ala Ser Ile Ala Val Pro
            20                  25                  30
```

-continued

```
Leu Glu Asn Ser Glu Glu Pro Gly Phe Ser Ala Ile Tyr Arg Asn Lys
        35                  40                  45

Tyr Ser Leu Asp Lys Leu Ile Asp Thr Pro Tyr Pro Gly Val Asp Thr
    50                  55                  60

Leu Tyr Lys Leu Phe Glu Val Ala Thr Glu Ala Tyr Gly Asp Lys Pro
65                  70                  75                  80

Cys Leu Gly Ala Arg Val Lys Asn Gln Asp Gly Thr Phe Gly Glu Tyr
                85                  90                  95

Lys Phe Gln Asp Tyr Asn Thr Ile Arg Gln Arg Arg Asn Asn Leu Gly
            100                 105                 110

Ser Gly Ile Phe Phe Val Leu Gln Asn Asn Pro Tyr Lys Thr Ser Ser
        115                 120                 125

Glu Ala His Ser Lys Leu Lys Tyr Asp Pro Ala Ser Lys Asp Ser Phe
    130                 135                 140

Ile Leu Thr Ile Phe Ser His Asn Arg Pro Glu Trp Glu Leu Cys Asp
145                 150                 155                 160

Leu Thr Ser Val Ala Tyr Ser Ile Thr Asn Thr Ala Leu Tyr Asp Thr
                165                 170                 175

Leu Gly Pro Asp Thr Ser Lys Tyr Ile Leu Gly Leu Thr Glu Ser Pro
            180                 185                 190

Ile Val Ile Cys Ser Lys Asp Lys Ile Lys Gly Leu Ile Asp Leu Lys
        195                 200                 205

Lys Ser Asn Pro Glu Glu Leu Ser Asn Leu Ile Val Leu Val Ser Met
    210                 215                 220

Asp Asp Leu Thr Thr Ala Asp Ser Ser Leu Lys Asn Tyr Gly His Glu
225                 230                 235                 240

His Asn Val Thr Val Phe Asp Met Lys Gln Val Glu Lys Leu Gly Glu
                245                 250                 255

Ile Asn Pro Leu Asp Pro Ile Glu Pro Thr Pro Asp Thr Asp Phe Thr
            260                 265                 270

Ile Thr Phe Thr Ser Gly Thr Thr Gly Ala Asn Pro Lys Gly Val Val
        275                 280                 285

Leu Asn His Arg Asn Ala Val Ala Gly Val Thr Phe Ile Leu Ser Arg
    290                 295                 300

Tyr Asp Gly Lys Phe Asn Pro Arg Ala Tyr Ser Phe Leu Pro Leu Ala
305                 310                 315                 320

His Ile Tyr Glu Arg Ala Ser Ile Gln Phe Ala Leu Ser Ile Gly Ser
                325                 330                 335

Ala Ile Gly Phe Pro Gln Gly Pro Ser Pro Leu Thr Leu Leu Glu Asp
            340                 345                 350

Val Lys Val Leu Gln Pro Asp Gly Leu Ala Leu Val Pro Arg Val Leu
        355                 360                 365

Thr Lys Leu Glu Ala Ala Ile Arg Ser Gln Thr Ile Asn Asn Asp Glu
    370                 375                 380

Lys Pro Leu Val Lys Ser Val Phe Ser Thr Val Ile Asn Ala Lys Met
385                 390                 395                 400

Asp Leu Gln Thr Lys Asp Glu Asn Glu Asn Val Asn Pro Ser Leu Leu
                405                 410                 415

Val Tyr Asp Arg Leu Leu Asn Met Leu Arg Lys Lys Ile Gly Met Gln
            420                 425                 430

Asn Val Gln Tyr Ile Ser Thr Gly Ser Ala Pro Ile Ala Pro Ser Thr
        435                 440                 445
```

-continued

```
Ile Gln Phe Leu Lys Ala Ala Leu Asn Val Gly Ile Met Gln Gly Tyr
    450                 455                 460

Gly Leu Ser Glu Ser Phe Ala Gly Cys Met Ala Ser Ser Lys Phe Glu
465                 470                 475                 480

Pro Glu Ala Ala Thr Cys Gly Ala Thr Ser Ile Thr Thr Glu Val Lys
                485                 490                 495

Leu Lys Asp Leu Val Glu Met Gly Tyr Thr Ser Lys Asp Glu Gly Gly
            500                 505                 510

Pro Arg Gly Glu Leu Leu Leu Arg Gly Pro Gln Ile Phe Arg Glu Tyr
        515                 520                 525

Tyr Lys Asn Pro Glu Glu Thr Ala Lys Ala Ile Asp Glu Asp Gly Trp
    530                 535                 540

Phe His Thr Gly Asp Val Ala Lys Ile Asn Ser Lys Gly Arg Ile Ser
545                 550                 555                 560

Ile Ile Asp Arg Ala Lys Asn Phe Phe Lys Leu Ala Gln Gly Glu Tyr
                565                 570                 575

Val Thr Pro Glu Lys Ile Glu Gly Leu Tyr Leu Ser Lys Phe Pro Tyr
            580                 585                 590

Ile Ala Gln Leu Phe Val His Gly Asp Ser Lys Glu Ser Phe Leu Val
        595                 600                 605

Ala Val Val Gly Leu Asp Pro Ile Ala Ala Lys Gln Tyr Met Glu His
    610                 615                 620

Arg Phe His Asp Lys Ile Val Lys Glu Asp Asp Ile Val Glu Phe Phe
625                 630                 635                 640

Lys Ser Pro Arg Asn Arg Lys Ile Leu Leu Gln Asp Met Asn Lys Ser
                645                 650                 655

Ile Ala Asp Gln Leu Gln Gly Phe Glu Lys Leu His Asn Ile Tyr Val
            660                 665                 670

Asp Phe Glu Pro Leu Thr Val Asp Arg Gly Val Ile Thr Pro Thr Met
        675                 680                 685

Lys Ile Arg Arg Pro Ile Ala Val Lys Phe Phe Gln Asp Gln Ile Asp
    690                 695                 700

Gly Met Tyr Asn Glu Gly Ser Leu Val Lys Asn Gly Ser Leu
705                 710                 715
```

<210> SEQ ID NO 59
<211> LENGTH: 718
<212> TYPE: PRT
<213> ORGANISM: Candida tropicalis

<400> SEQUENCE: 59

```
Met Pro Ala Leu Phe Lys Glu Ser Pro Gln Gln Ile Ser Gln Ser Leu
1               5                   10                  15

Lys Ala Lys Phe Ser Asp Pro Tyr Gln Phe Ala Thr Ser Val Pro Leu
            20                  25                  30

Ser Asp Thr Lys Glu Pro Gly Tyr Ser His Ile Tyr Arg Asn Ser Tyr
        35                  40                  45

Asp Pro Thr Thr Leu Ala Thr Cys Pro His Pro Glu Leu Asp Thr Leu
    50                  55                  60

His Lys Ile Phe Glu Phe Ser Asn Thr Ile Tyr Ser Asp Ser Pro Phe
65                  70                  75                  80

Leu Gly His Arg Val Lys Asn Pro Asp Gly Thr Phe Gly Glu Tyr Lys
                85                  90                  95

Phe Gln Thr Tyr Arg Gln Ile Tyr Lys Arg Arg Asn Asp Phe Gly Ser
            100                 105                 110
```

```
Gly Ile Tyr Tyr Val Leu Glu Asn Asn Pro Tyr Lys Thr Ser Ser Glu
        115                 120                 125

Ala His Ser Lys Leu Lys Tyr Asp Pro Thr Asn Lys Asp Pro Phe Ile
    130                 135                 140

Leu Ala Val Phe Ser His Asn Arg Pro Glu Trp Ala Leu Cys Asp Leu
145                 150                 155                 160

Thr Thr Asn Ser Phe Gly Ile Ile Asn Thr Ala Leu Tyr Ser Thr Leu
                165                 170                 175

Gly Pro Asp Thr Ser Arg Tyr Ile Leu Gly Val Thr Asp Cys Pro Ile
            180                 185                 190

Val Val Thr Thr Lys Asp Lys Val Lys Gly Ile Ile Ser Leu Lys Asn
        195                 200                 205

Ser Asn Gln Lys Glu Leu Ala Ser Leu Ile Thr Ile Val Ser Met Asp
    210                 215                 220

Glu Leu Thr Glu Glu Asp Lys Glu Leu Arg Ser Phe Gly His Glu Asn
225                 230                 235                 240

Asn Ile Thr Val Tyr Asp Ile Lys Glu Val Glu Asn Phe Gly Glu Lys
                245                 250                 255

Asn Pro Leu Lys Pro Ile Glu Pro Thr Pro Asp Thr Ile Phe Thr Ile
            260                 265                 270

Ser Phe Thr Ser Gly Thr Thr Gly Ala Ala Pro Lys Gly Val Val Leu
        275                 280                 285

Thr Asn Arg Ile Leu Val Ser Gly Ile Thr Thr His Cys Thr Ile Leu
    290                 295                 300

Ser Phe Gly Pro Glu Arg Val His Tyr Ser Phe Leu Pro Leu Ala His
305                 310                 315                 320

Ile Tyr Glu Arg Met Leu Leu Gln Phe Gly Ile Leu Ala Gly Val Lys
                325                 330                 335

Ile Gly Tyr Pro Gln Gly Pro Leu Pro Thr Thr Leu Phe Asp Asp Val
            340                 345                 350

Lys Tyr Leu Gln Pro Thr Phe Leu Cys Leu Val Pro Arg Val Phe Thr
        355                 360                 365

Lys Ile Glu Ala Ala Ile Lys Ala Gln Thr Val Glu Asn Asp Ala Asn
    370                 375                 380

Pro Lys Ile Lys Thr Leu Phe Gln Asn Ile Val Asp Lys Lys Leu Lys
385                 390                 395                 400

Leu Gln Gln Gln Glu Asp Phe Thr Asn Pro Ser Phe Pro Glu Gly Asp
                405                 410                 415

Lys Val Leu Leu Gln Leu Arg Glu Lys Leu Gly Phe Gly Lys Ile Ala
            420                 425                 430

Phe Met Asn Thr Gly Ser Ala Pro Leu Ser Glu Glu Thr Tyr Arg Phe
        435                 440                 445

Leu Gln Ala Ile Leu Asn Leu Pro Asp Gly Phe Arg Ser Gly Tyr Gly
    450                 455                 460

Leu Thr Glu Ser Ala Ser Gly Val Cys Ile Ser Pro Ala Tyr Ala Asn
465                 470                 475                 480

Glu Phe Ser Cys Gly Pro Ile Ser Val Thr Thr Glu Phe Lys Leu Arg
                485                 490                 495

Asp Ile Glu Glu Met Gly Tyr Thr Ser Ser Asp Lys Asp Gly Pro Arg
            500                 505                 510

Gly Glu Leu Leu Leu Arg Gly Pro Gln Ile Phe Pro Tyr Tyr Tyr Lys
        515                 520                 525
```

```
Asn Pro Glu Glu Thr Ala Lys Val Ile Asp Lys Asp Gly Trp Phe Tyr
    530                 535                 540

Thr Gly Asp Val Ala Val Val Ser Pro Gln His Gly Asn Arg Leu Gln
545                 550                 555                 560

Ile Ile Asp Arg Val Lys Asn Phe Phe Lys Leu Ser Gln Gly Glu Tyr
                565                 570                 575

Val Ser Pro Glu Lys Ile Glu Asn Val Tyr Leu Ser Gln Phe Pro Tyr
            580                 585                 590

Ile Ser Gln Leu Phe Ala His Gly Asp Ser Thr Glu Ser Tyr Leu Val
        595                 600                 605

Gly Val Val Gly Ile Asp Lys Ala Ser Ile Asp Pro Tyr Leu Lys Lys
    610                 615                 620

Arg Phe Asn Val Ser Ile Glu Lys Gln Ala Asp Ile Val Lys Tyr Phe
625                 630                 635                 640

Glu Asn Pro Lys Asn Arg Arg Ala Leu Leu His Asp Met Asn Glu Ala
                645                 650                 655

Ile Glu Gly Gln Leu Gln Gly Phe Glu Lys Leu His Asn Val Phe Val
            660                 665                 670

Asp Phe Glu Pro Leu Thr Leu Glu Arg Glu Val Ile Thr Pro Thr Ile
        675                 680                 685

Lys Ile Arg Arg Pro Val Ala Val Lys Phe Phe Lys Glu Gln Ile Glu
    690                 695                 700

Asn Met Tyr Arg Glu Gly Ser Leu Ile Lys Gly Ser Asn Leu
705                 710                 715


<210> SEQ ID NO 60
<211> LENGTH: 741
<212> TYPE: PRT
<213> ORGANISM: Candida tropicalis

<400> SEQUENCE: 60

Met Thr Thr Leu Pro Ser Ile Ser Glu Thr Asp Ile Val Tyr Ala Thr
1               5                   10                  15

Asp Asp Lys Pro Tyr Val Phe Glu Asn Pro Asn Asp Leu Pro Val Glu
            20                  25                  30

Thr Leu Val Asn His Ile Leu Pro Phe Pro Gln Glu Val Ala Gly Glu
        35                  40                  45

Ser Ile Lys Ile Pro Gly Thr Ala Val Glu Gly Phe Ser Glu Ile Tyr
    50                  55                  60

Arg Asn Ala Ala Thr Pro Asn Gly Ile Lys Ala Ser Leu Ile Lys Gly
65                  70                  75                  80

Leu Asp Thr Tyr His Asp Ile Phe Glu Arg Ser Ala Asp Cys Tyr Ala
                85                  90                  95

Asp Glu Pro Cys Leu Ala Phe His Glu Tyr Asp Tyr Glu Asn Ser Gln
            100                 105                 110

His Leu Glu Arg Tyr Ala Thr Ile Ser Tyr Lys Glu Val Arg Gln Arg
        115                 120                 125

Lys Asp Asp Phe Ala Ala Gly Leu Phe Phe Leu Leu Lys Ser Asn Pro
    130                 135                 140

Phe Lys Asn Asn Ser Leu Glu Ser His Gln Lys Ile Asp Asn His Glu
145                 150                 155                 160

Ala Asn Tyr Lys Ser Tyr Asn Ser Asp Asp Met Ser Phe Ile Ala Thr
                165                 170                 175

Phe Tyr Ala Gly Asn Arg Val Glu Trp Ile Leu Ser Asp Leu Ala Cys
            180                 185                 190
```

-continued

```
Ser Ser Asn Ser Ile Thr Ser Thr Ala Leu Tyr Asp Thr Leu Gly Pro
        195                 200                 205

Glu Thr Ser Lys Tyr Ile Leu Glu Thr Thr Gln Ser Pro Val Ile Ile
    210                 215                 220

Ser Ser Lys Asp His Ile Arg Gly Leu Ile Glu Leu Lys Arg Lys Tyr
225                 230                 235                 240

Pro Glu Ala Leu Glu Ser Ile Ile Leu Ile Ile Ser Met Asp Pro Leu
                245                 250                 255

Thr Lys Ser Asp Val Gly Leu Val Gln Leu Ala Glu Lys Ser Asn Ile
            260                 265                 270

Lys Leu Tyr Asp Phe Ser Gln Val Glu Arg Thr Gly Ala Ile Phe Pro
        275                 280                 285

His Glu Thr Asn Pro Pro Asn Ser Glu Thr Val Phe Thr Ile Thr Phe
    290                 295                 300

Thr Ser Gly Thr Thr Gly Ala Asn Pro Lys Gly Val Val Leu Pro Gln
305                 310                 315                 320

Arg Cys Ala Ala Ser Ala Met Leu Ala Tyr Ser Leu Leu Met Pro His
                325                 330                 335

His Arg Gly Thr Arg Glu Phe Ala Phe Leu Pro Leu Ala His Ile Phe
            340                 345                 350

Glu Arg Gln Met Val Ala Ser Met Phe Leu Phe Gly Gly Ser Ser Ala
        355                 360                 365

Phe Pro Arg Leu Gly Gly Thr Pro Leu Thr Leu Val Glu Asp Leu Lys
    370                 375                 380

Leu Trp Lys Pro Asn Phe Met Ala Asn Val Pro Arg Ile Phe Thr Lys
385                 390                 395                 400

Ile Glu Ala Gly Ile Lys Ala Ser Thr Ile Asp Ser Thr Ser Gly Leu
                405                 410                 415

Thr Arg Ser Leu Tyr Gly Arg Ala Ile Glu Ala Lys Arg Val Lys Gln
            420                 425                 430

Ile Lys Asn Asp Asp Ser Gly Asp His Phe Ile Tyr Asp Lys Leu Leu
        435                 440                 445

Ile Gln Lys Leu Arg Asn Ala Ile Gly Tyr Asp Lys Leu Glu Phe Cys
    450                 455                 460

Val Thr Gly Ser Ala Pro Ile Ala Pro Glu Thr Ile Lys Phe Leu Lys
465                 470                 475                 480

Ala Ser Leu Gly Ile Gly Phe Ala Gln Gly Tyr Gly Ser Ser Glu Ser
                485                 490                 495

Phe Ala Gly Met Leu Phe Ala Leu Pro Phe Lys Thr Ser Ser Val Gly
            500                 505                 510

Thr Cys Gly Val Ile Ala Pro Thr Met Glu Ala Arg Leu Arg Glu Leu
        515                 520                 525

Pro Asp Met Gly Tyr Met Leu Asp Asp Ala Asn Gly Pro Arg Gly Glu
    530                 535                 540

Leu Gln Ile Arg Gly Ala Gln Leu Phe Thr Lys Tyr Phe Lys Asn Asp
545                 550                 555                 560

Glu Glu Thr Ala Lys Ser Ile Asp Glu Asp Gly Trp Phe Ser Thr Gly
                565                 570                 575

Asp Val Ala Glu Ile Gly Ala Lys Asp Gly Tyr Phe Arg Ile Ile Asp
            580                 585                 590

Arg Val Lys Asn Phe Tyr Lys Leu Ala Gln Gly Glu Tyr Val Ser Pro
        595                 600                 605
```

```
Glu Lys Ile Glu Ser Leu Tyr Leu Ser Leu Asn Ser Thr Ile Ser Gln
    610                 615                 620

Leu Phe Val His Gly Asp Ser Thr Lys Ser Tyr Leu Val Gly Val Val
625                 630                 635                 640

Gly Leu Gln Pro Asp Val Ala Ser Lys Tyr Val Asp Leu Ser Ser Gly
                645                 650                 655

Asp Lys Val Val Gln Glu Leu Asn Lys Pro Glu Leu Arg Lys Gln Ile
            660                 665                 670

Leu Ser Asp Leu Asn Gly Lys Val Asn Gly Lys Leu Gln Gly Phe Glu
        675                 680                 685

Lys Leu His Asn Ile Phe Ile Asp Ile Glu Pro Leu Thr Leu Glu Arg
    690                 695                 700

Asn Val Val Thr Pro Thr Met Lys Leu Lys Arg His Phe Ala Ala Lys
705                 710                 715                 720

Phe Phe Arg Ala Gln Ile Asp Ser Met Tyr Glu Glu Gly Ser Ile Val
                725                 730                 735

Ala Asp Tyr Lys Leu
            740


<210> SEQ ID NO 61
<211> LENGTH: 741
<212> TYPE: PRT
<213> ORGANISM: Candida tropicalis

<400> SEQUENCE: 61

Met Thr Thr Leu Pro Ser Ile Ser Glu Thr Asp Ile Val Tyr Ala Thr
1               5                   10                  15

Asp Asp Lys Pro Tyr Val Phe Glu Asn Pro Asn Asp Leu Pro Val Glu
            20                  25                  30

Thr Leu Val Asn His Ile Leu Pro Phe Pro Gln Glu Val Ala Gly Glu
        35                  40                  45

Ser Ile Lys Ile Pro Gly Thr Ala Val Glu Gly Phe Ser Glu Ile Tyr
    50                  55                  60

Arg Asn Ala Ala Thr Pro Asn Gly Ile Lys Ala Ser Leu Ile Lys Gly
65                  70                  75                  80

Leu Asp Thr Tyr His Asp Ile Phe Glu Arg Ser Ala Asp Cys Tyr Ala
                85                  90                  95

Asp Glu Pro Cys Leu Ala Phe His Glu Tyr Asp Tyr Glu Asn Ser Gln
            100                 105                 110

His Leu Glu Arg Tyr Ala Thr Ile Ser Tyr Lys Glu Val Arg Gln Arg
        115                 120                 125

Lys Asp Asp Phe Ala Ala Gly Leu Phe Phe Leu Leu Lys Ser Asn Pro
    130                 135                 140

Phe Lys Asn Asn Ser Leu Glu Ser His Gln Lys Ile Asp Asn His Glu
145                 150                 155                 160

Ala Asn Tyr Lys Ser Tyr Asn Ser Asp Asp Met Ser Phe Ile Ala Thr
                165                 170                 175

Phe Tyr Ala Gly Asn Arg Val Glu Trp Ile Leu Ser Asp Leu Ala Cys
            180                 185                 190

Ser Ser Asn Ser Ile Thr Ser Thr Ala Leu Tyr Asp Thr Leu Gly Pro
        195                 200                 205

Gly Thr Ser Lys Tyr Ile Leu Glu Ala Thr Gln Ser Pro Val Ile Ile
    210                 215                 220

Thr Ser Lys Asp His Ile Lys Gly Leu Ile Glu Leu Lys Arg Lys Tyr
225                 230                 235                 240
```

-continued

```
Pro Glu Ala Leu Glu Ser Ile Ile Leu Ile Ile Ser Met Asp Pro Leu
                245                 250                 255

Thr Lys Ser Asp Val Gly Leu Val Gln Leu Ala Glu Asn Ser Asn Ile
            260                 265                 270

Lys Leu Tyr Asp Phe Ser Gln Val Glu Arg Ala Gly Ala Ile Phe Pro
        275                 280                 285

His Glu Thr Asn Pro Pro Asn Arg Glu Thr Val Phe Thr Ile Thr Phe
    290                 295                 300

Thr Ser Gly Thr Thr Gly Ala Asn Pro Lys Gly Val Val Leu Ser Gln
305                 310                 315                 320

Gly Ser Ala Ala Ser Ala Ser Phe Val Tyr Ser Leu Leu Met Pro His
                325                 330                 335

Arg Arg Gly Ala Arg Asp Phe Ala Phe Leu Pro Leu Ala His Ile Phe
            340                 345                 350

Gln Arg Gln Met Val Ala Ser Thr Leu Phe Phe Gly Gly Ser Ser Ala
        355                 360                 365

Phe Pro Arg Leu Gly Gly Thr Pro Leu Thr Leu Val Glu Asp Leu Lys
    370                 375                 380

Leu Trp Lys Pro Asn Phe Met Ala Asn Val Pro Arg Ile Phe Thr Lys
385                 390                 395                 400

Ile Glu Ala Gly Ile Lys Ala Ser Thr Ile Asp Ser Thr Ser Gly Leu
                405                 410                 415

Thr Arg Ser Leu Tyr Gly Arg Ala Ile Glu Ala Lys Arg Val Lys Gln
            420                 425                 430

Ile Lys Asn Asp Asp Ser Gly Asp His Phe Ile Tyr Asp Lys Leu Leu
        435                 440                 445

Ile Gln Lys Leu Arg Asn Ala Ile Gly Tyr Asp Lys Leu Glu Phe Leu
    450                 455                 460

Leu Thr Gly Ser Ala Pro Ile Ser Pro Glu Thr Ile Lys Phe Leu Lys
465                 470                 475                 480

Ser Ser Leu Gly Ile Gly Phe Gly Gln Gly Tyr Gly Ser Ser Glu Ser
                485                 490                 495

Phe Gly Gly Ile Leu Phe Ala Leu Pro Phe Lys Asn Ser Ser Leu Gly
            500                 505                 510

Thr Cys Gly Val Ile Ala Pro Thr Met Glu Ala Arg Leu Arg Glu Leu
        515                 520                 525

Pro Asp Met Gly Tyr Met Leu Asp Asp Ala Asn Gly Pro Arg Gly Glu
    530                 535                 540

Leu Gln Ile Arg Gly Ala Gln Leu Phe Ala Lys Tyr Phe Lys Asn Asp
545                 550                 555                 560

Glu Glu Thr Ala Lys Ser Ile Asp Glu Asp Gly Trp Phe Ser Thr Gly
                565                 570                 575

Asp Val Ala Glu Ile Gly Ala Lys Asp Gly Tyr Phe Arg Ile Ile Asp
            580                 585                 590

Arg Val Lys Asn Phe Tyr Lys Leu Ala Gln Gly Glu Tyr Val Ser Pro
        595                 600                 605

Glu Lys Ile Glu Asn Leu Tyr Leu Ser Leu Asn Ser Thr Ile Ser Gln
    610                 615                 620

Leu Phe Ile His Gly Asp Ser Thr Lys Ser Tyr Leu Val Gly Val Val
625                 630                 635                 640

Gly Leu Gln Pro Asp Val Ala Ser Lys Tyr Val Asp Leu Ser Ser Gly
                645                 650                 655
```

-continued

```
Asp Lys Val Val Gln Glu Leu Asn Lys Pro Glu Leu Arg Lys Gln Ile
            660                 665                 670

Leu Leu Asp Leu Asn Gly Lys Val Asn Gly Lys Leu Gln Gly Phe Glu
        675                 680                 685

Lys Leu His Asn Ile Phe Ile Asp Ile Glu Pro Leu Thr Leu Glu Arg
    690                 695                 700

Asn Val Val Thr Pro Thr Met Lys Leu Lys Arg His Phe Ala Ala Lys
705                 710                 715                 720

Phe Phe Arg Ala Gln Ile Asp Ser Met Tyr Glu Glu Gly Ser Ile Ile
                725                 730                 735

Ala Asp Tyr Lys Leu
            740


<210> SEQ ID NO 62
<211> LENGTH: 749
<212> TYPE: PRT
<213> ORGANISM: Candida tropicalis

<400> SEQUENCE: 62

Met Ile Glu Ser Lys Ser Ile Phe Ser Gly Glu Lys Tyr Thr Lys Gln
1               5                   10                  15

Glu Ala Leu Ser Gln Leu Pro Phe Gly Ser Asp Val Glu Asn Ala Val
            20                  25                  30

Met Ile Asp Glu Pro Val Thr Asn Val Lys Tyr Ser Pro Ile Phe Arg
        35                  40                  45

Asn Lys Ala His Leu Asp Gly Leu Ile Gln Asn Val His Pro Asp Leu
    50                  55                  60

Asn Thr His Tyr Lys Leu Phe Asn Asn Ala Ala Glu Met Tyr His Asp
65                  70                  75                  80

Arg Pro Cys Leu Gly Lys Arg Pro Tyr Asn Tyr Thr Thr His Gln Ser
                85                  90                  95

Asp Asp Tyr Phe Ser His Trp Thr Tyr Gly Glu Val Phe Thr Lys Lys
            100                 105                 110

Asn Asn Leu Gly Ala Gly Phe Ile Arg Ala Leu Leu Glu Asn Pro Phe
        115                 120                 125

Leu Asp Val Gln Leu Glu Ser His Arg Lys Val Val Asn His Leu Arg
    130                 135                 140

Asp Trp Ser Asn Phe Gly Ile Asn Lys Leu Pro Arg Asp Asn Leu Asn
145                 150                 155                 160

Cys Glu Ile Glu Lys Asn Cys Ser Phe Ile Leu Thr Ile Phe Ala Val
                165                 170                 175

Asn Arg Ala Glu Trp Ile Leu Thr Asp Leu Ala Cys Ser Ser Tyr Gly
            180                 185                 190

Ile Thr Asn Thr Ala Leu Tyr Asp Thr Leu Gly Pro Asp Val Ser Gln
        195                 200                 205

Tyr Ile Leu Asn Leu Thr Glu Ser Pro Ile Val Val Cys Thr His Asp
    210                 215                 220

Lys Ile Gln Val Leu Ile Asn Leu Lys Lys Lys Tyr Pro Gln Gln Thr
225                 230                 235                 240

Lys Asn Leu Ile Ser Ile Val Ser Met Asp Pro Ile Asp Leu Val Thr
                245                 250                 255

Gln Gly Thr Ile Glu Asp Ala Tyr Glu Leu Gly Ile Thr Ile Gln Gly
            260                 265                 270

Leu Asn Gln Ile Glu Lys Ile Gly Ala Lys Asn Pro Ile His Gln Leu
        275                 280                 285
```

-continued

```
Glu Thr Asn Pro Glu Ala Leu Phe Thr Ile Ser Phe Thr Ser Gly Thr
    290                 295                 300

Thr Gly Ser Lys Pro Lys Gly Val Met Ile Ser Gln Gly Gly Ala Ala
305                 310                 315                 320

Ala Tyr Ile Thr Tyr Leu Leu Cys Cys Glu Pro Gln Ala Lys Pro Gly
                325                 330                 335

Asp Lys Ala Phe Ile Phe Leu Pro Leu Thr His Leu Tyr Glu Arg Gln
            340                 345                 350

Thr Cys Gly Phe Ala Phe Ser Ser Gly Tyr Tyr Leu Gly Phe Pro Gln
        355                 360                 365

Val Asn Leu Gly Lys Lys Lys Ile Asn Pro Phe Glu Asn Leu Leu Ala
    370                 375                 380

Asp Leu Arg Ile Phe Lys Pro Thr Tyr Met Ser Met Val Pro Arg Leu
385                 390                 395                 400

Leu Thr Arg Leu Glu Ala Leu Ile Lys Ser Lys Ile Lys Glu Leu Pro
                405                 410                 415

Val Gln Glu Gln Glu Lys Val Asn Ser Ile Ile Glu Ala Lys Ile Lys
            420                 425                 430

Lys Gln Ser Lys Gln Asp Gly Ser Thr Gly Phe Asp Ala Thr Leu Asp
        435                 440                 445

Asn Asp Pro Thr Tyr Lys Ser Leu Ala Gln Phe Val Gly Tyr Asp Asn
    450                 455                 460

Met Arg Trp Val Gln Thr Ala Ser Ala Pro Ile Ala Pro Thr Thr Leu
465                 470                 475                 480

Ile Tyr Leu Lys Ala Ser Leu Asn Ile Gly Thr Arg Gln Gln Tyr Gly
                485                 490                 495

Leu Thr Glu Ser Gly Ala Ala Ile Thr Ser Thr Gly Glu Tyr Glu Ala
            500                 505                 510

Ser Pro Gly Ser Cys Gly Val Ile Leu Pro Thr Gly Gln Tyr Arg Leu
        515                 520                 525

Tyr Ser Val Ser Glu Met Gly Tyr Asp Leu Asn Lys Leu Glu Gly Glu
    530                 535                 540

Val Met Leu Gln Gly Pro Gln Met Phe Lys Gly Tyr Tyr Tyr Asn Tyr
545                 550                 555                 560

Glu Glu Thr Ile Asn Ala Val Thr Glu Asp Gly Trp Phe His Ser Gly
                565                 570                 575

Asp Ile Ala Arg Val Asp Ser Lys Thr Gly Arg Val Thr Ile Ile Asp
            580                 585                 590

Arg Val Lys His Phe Phe Lys Leu Ala Gln Gly Glu Tyr Ile Ser Pro
        595                 600                 605

Glu Arg Ile Glu Asn Arg Tyr Leu Ser Ser Asn Pro Asp Ile Cys Gln
    610                 615                 620

Leu Trp Val His Gly Asp Ser Lys Glu His Tyr Leu Ile Gly Ile Val
625                 630                 635                 640

Gly Val Glu Tyr Glu Lys Gly Leu Lys Phe Ile Asn Thr Glu Phe Gly
                645                 650                 655

Tyr Asn Lys Ile Asp Met Pro Pro Gly Asp Leu Leu Asp Ile Leu Asn
            660                 665                 670

Ser Pro Glu Val Lys Ser Lys Phe Leu Thr Lys Met Asn Gln Ser Val
        675                 680                 685

Arg Asp Lys Leu Asn Gly Phe Glu Ile Leu His Asn Ile Phe Ile Glu
    690                 695                 700
```

-continued

```
Phe Glu Pro Leu Thr Val Gln Arg Glu Val Val Thr Pro Thr Phe Lys
705                 710                 715                 720

Ile Arg Arg Pro Ile Cys Arg Lys Phe Phe Lys Ser Gln Leu Asp Ala
                725                 730                 735

Met Tyr Asn Glu Gly Ser Leu Ile Asn Asn Ala Lys Leu
            740                 745


<210> SEQ ID NO 63
<211> LENGTH: 8902
<212> TYPE: DNA
<213> ORGANISM: artificial sequence
<220> FEATURE:
<223> OTHER INFORMATION: Plasmid pZP2-YlACoS-3Ps

<400> SEQUENCE: 63

ggccgcaagt gtggatgggg aagtgagtgc ccggttctgt gtgcacaatt ggcaatccaa     60

gatggatgga ttcaacacag ggatatagcg agctacgtgg tggtgcgagg atatagcaac    120

ggatatttat gtttgacact tgagaatgta cgatacaagc actgtccaag tacaatacta    180

aacatactgt acatactcat actcgtaccc gggcaacggt ttcacttgag tgcagtggct    240

agtgctctta ctcgtacagt gtgcaatact gcgtatcata gtctttgatg tatatcgtat    300

tcattcatgt tagttgcgta cgggcgtcgt tgcttgtgtg atttttgagg acccatccct    360

ttggtatata agtatactct ggggttaagg ttgcccgtgt agtctaggtt atagttttca    420

tgtgaaatac cgagagccga gggagaataa acgggggtat ttggacttgt ttttttcgcg    480

gaaaagcgtc gaatcaaccc tgcgggcctt gcaccatgtc cacgacgtgt ttctcgcccc    540

aattcgcccc ttgcacgtca aaattaggcc tccatctaga cccctccata acatgtgact    600

gtggggaaaa gtataaggga aaccatgcaa ccatagacga cgtgaaagac ggggaggaac    660

caatggaggc caaagaaatg gggtagcaac agtccaggag acagacaagg agacaaggag    720

agggcgcccg aaagatcgga aaaacaaaca tgtccaattg gggcagtgac ggaaacgaca    780

cggacacttc agtacaatgg accgaccatc tccaagccag ggttattccg gtatcacctt    840

ggccgtaacc tcccgctggt acctgatatt gtacacgttc acattcaata tactttcagc    900

tacaataaga gaggctgttt gtcgggcatg tgtgtccgtc gtatggggtg atgtccgagg    960

gcgaaattcg ctacaagctt aactctggcg cttgtccagt atgaatagac aagtcaagac   1020

cagtggtgcc atgattgaca gggaggtaca agacttcgat actcgagcat tactcggact   1080

tgtggcgatt gaacagacgg gcgatcgctt ctcccccgta ttgccggcgc gccagctgca   1140

ttaatgaatc ggccaacgcg cggggagagg cggtttgcgt attgggcgct cttccgcttc   1200

ctcgctcact gactcgctgc gctcggtcgt tcggctgcgg cgagcggtat cagctcactc   1260

aaaggcggta atacggttat ccacagaatc aggggataac gcaggaaaga acatgtgagc   1320

aaaaggccag caaaaggcca ggaaccgtaa aaaggccgcg ttgctggcgt ttttccatag   1380

gctccgcccc cctgacgagc atcacaaaaa tcgacgctca agtcagaggt ggcgaaaccc   1440

gacaggacta taaagatacc aggcgtttcc ccctggaagc tccctcgtgc gctctcctgt   1500

tccgaccctg ccgcttaccg gatacctgtc cgcctttctc ccttcgggaa gcgtggcgct   1560

ttctcatagc tcacgctgta ggtatctcag ttcggtgtag gtcgttcgct ccaagctggg   1620

ctgtgtgcac gaaccccccg ttcagcccga ccgctgcgcc ttatccggta actatcgtct   1680

tgagtccaac ccggtaagac acgacttatc gccactggca gcagccactg gtaacaggat   1740

tagcagagcg aggtatgtag gcggtgctac agagttcttg aagtggtggc ctaactacgg   1800
```

-continued

```
ctacactaga agaacagtat ttggtatctg cgctctgctg aagccagtta ccttcggaaa   1860
aagagttggt agctcttgat ccggcaaaca aaccaccgct ggtagcggtg gtttttttgt   1920
ttgcaagcag cagattacgc gcagaaaaaa aggatctcaa gaagatcctt tgatcttttc   1980
tacggggtct gacgctcagt ggaacgaaaa ctcacgttaa gggattttgg tcatgagatt   2040
atcaaaaagg atcttcacct agatcctttt aaattaaaaa tgaagtttta aatcaatcta   2100
aagtatatat gagtaaactt ggtctgacag ttaccaatgc ttaatcagtg aggcacctat   2160
ctcagcgatc tgtctatttc gttcatccat agttgcctga ctccccgtcg tgtagataac   2220
tacgatacgg gagggcttac catctggccc cagtgctgca atgataccgc gagacccacg   2280
ctcaccggct ccagatttat cagcaataaa ccagccagcc ggaagggccg agcgcagaag   2340
tggtcctgca actttatccg cctccatcca gtctattaat tgttgccggg aagctagagt   2400
aagtagttcg ccagttaata gtttgcgcaa cgttgttgcc attgctacag gcatcgtggt   2460
gtcacgctcg tcgtttggta tggcttcatt cagctccggt tcccaacgat caaggcgagt   2520
tacatgatcc cccatgttgt gcaaaaaagc ggttagctcc ttcggtcctc cgatcgttgt   2580
cagaagtaag ttggccgcag tgttatcact catggttatg gcagcactgc ataattctct   2640
tactgtcatg ccatccgtaa gatgcttttc tgtgactggt gagtactcaa ccaagtcatt   2700
ctgagaatag tgtatgcggc gaccgagttg ctcttgcccg gcgtcaatac gggataatac   2760
cgcgccacat agcagaactt taaaagtgct catcattgga aaacgttctt cggggcgaaa   2820
actctcaagg atcttaccgc tgttgagatc cagttcgatg taacccactc gtgcacccaa   2880
ctgatcttca gcatctttta ctttcaccag cgtttctggg tgagcaaaaa caggaaggca   2940
aaatgccgca aaaaagggaa taagggcgac acggaaatgt tgaatactca tactcttcct   3000
ttttcaatat tattgaagca tttatcaggg ttattgtctc atgagcggat acatatttga   3060
atgtatttag aaaaataaac aaataggggt tccgcgcaca tttccccgaa aagtgccacc   3120
tgatgcggtg tgaaataccg cacagatgcg taaggagaaa ataccgcatc aggaaattgt   3180
aagcgttaat attttgttaa aattcgcgtt aaatttttgt taaatcagct cattttttaa   3240
ccaataggcc gaaatcggca aaatccctta taaatcaaaa gaatagaccg agatagggtt   3300
gagtgttgtt ccagtttgga acaagagtcc actattaaag aacgtggact ccaacgtcaa   3360
agggcgaaaa accgtctatc agggcgatgg cccactacgt gaaccatcac cctaatcaag   3420
ttttttgggg tcgaggtgcc gtaaagcact aaatcggaac cctaaaggga gcccccgatt   3480
tagagcttga cggggaaagc cggcgaacgt ggcgagaaag gaagggaaga aagcgaaagg   3540
agcgggcgct agggcgctgg caagtgtagc ggtcacgctg cgcgtaacca ccacacccgc   3600
cgcgcttaat gcgccgctac agggcgcgtc cattcgccat tcaggctgcg caactgttgg   3660
gaagggcgat cggtgcgggc ctcttcgcta ttacgccagc tggcgaaagg gggatgtgct   3720
gcaaggcgat taagttgggt aacgccaggg ttttcccagt cacgacgttg taaaacgacg   3780
gccagtgaat tgtaatacga ctcactatag ggcgaattgg gcccgacgtc gcatgcgctg   3840
atgacacttt ggtctgaaag agatgcattt tgaatcccaa acttgcagtg cccaagtgac   3900
atacatctcc gcgttttgga aaatgttcag aaacagttga ttgtgttgga atggggaatg   3960
gggaatggaa aaatgactca agtatcaatt ccaaaaactt ctctggctgg cagtacctac   4020
tgtccatact actgcatttt ctccagtcag gccactctat actcgacgac acagtagtaa   4080
aacccagata atttcgacat aaacaagaaa acagacccaa taatatttat atatagtcag   4140
ccgtttgtcc agttcagact gtaatagccg aaaaaaaatc caaagtttct attctaggaa   4200
```

-continued

```
aatatattcc aatattttta attcttaatc tcatttattt tattctagcg aaatacattt   4260
cagctacttg agacatgtga tacccacaaa tcggattcgg actcggttgt tcagaagagc   4320
atatggcatt cgtgctcgct tgttcacgta ttcttcctgt tccatctctt ggccgacaat   4380
cacacaaaaa tggggttttt tttttaattc taatgattca ttacagcaaa attgagatat   4440
agcagaccac gtattccata atcaccaagg aagttcttgg gcgtcttaat taagtcatac   4500
acaagtcagc tttcttcgag cctcatataa gtataagtag ttcaacgtat tagcactgta   4560
cccagcatct ccgtatcgag aaacacaaca acatgcccca ttggacagat catgcggata   4620
cacaggttgt gcagtatcat acatactcga tcagacaggt cgtctgacca tcatacaagc   4680
tgaacaagcg ctccatactt gcacgctctc tatatacaca gttaaattac atatccatag   4740
tctaacctct aacagttaat cttctggtaa gcctcccagc cagccttctg gtatcgcttg   4800
gcctcctcaa taggatctcg gttctggccg tacagacctc ggccgacaat tatgatatcc   4860
gttccggtag acatgacatc ctcaacagtt cggtactgct gtccgagagc gtctcccttg   4920
tcgtcaagac ccaccccggg ggtcagaata agccagtcct cagagtcgcc cttaggtcgg   4980
ttctgggcaa tgaagccaac cacaaactcg gggtcggatc gggcaagctc aatggtctgc   5040
ttggagtact cgccagtggc cagagagccc ttgcaagaca gctcggccag catgagcaga   5100
cctctggcca gcttctcgtt gggagagggg actaggaact ccttgtactg ggagttctcg   5160
tagtcagaga cgtcctcctt cttctgttca gagacagttt cctcggcacc agctcgcagg   5220
ccagcaatga ttccggttcc gggtacaccg tgggcgttgg tgatatcgga ccactcggcg   5280
attcggtgac accggtactg gtgcttgaca gtgttgccaa tatctgcgaa ctttctgtcc   5340
tcgaacagga agaaaccgtg cttaagagca agttccttga gggggagcac agtgccggcg   5400
taggtgaagt cgtcaatgat gtcgatatgg gttttgatca tgcacacata aggtccgacc   5460
ttatcggcaa gctcaatgag ctccttggtg gtggtaacat ccagagaagc acacaggttg   5520
gttttcttgg ctgccacgag cttgagcact cgagcggcaa aggcggactt gtggacgtta   5580
gctcgagctt cgtaggaggg cattttggtg gtgaagagga gactgaaata aatttagtct   5640
gcagaacttt ttatcggaac cttatctggg gcagtgaagt atatgttatg gtaatagtta   5700
cgagttagtt gaacttatag atagactgga ctatacggct atcggtccaa attagaaaga   5760
acgtcaatgg ctctctgggc gtcgcctttg ccgacaaaaa tgtgatcatg atgaaagcca   5820
gcaatgacgt tgcagctgat attgttgtcg gccaaccgcg ccgaaaacgc agctgtcaga   5880
cccacagcct ccaacgaaga atgtatcgtc aaagtgatcc aagcacactc atagttggag   5940
tcgtactcca aaggcggcaa tgacgagtca gacagatact cgtcaaacgg taggttagtg   6000
cttggtatat gagttgtagg catgacaatt tggaaagggg tggactttgg gaatattgtg   6060
ggatttcaat accttagttt gtacagggta attgttacaa atgatacaaa gaactgtatt   6120
tcttttcatt tgttttaatt ggttgtatat caagtccgtt agacgagctc agtgccttgg   6180
cttttggcac tgtatttcat ttttagaggt acactacatt cagtgaggta tggtaaggtt   6240
gagggcataa tgaaggcacc ttgtactgac agtcacagac ctctcaccga gaattttatg   6300
agatatactc gggttcattt taggctcatc gattgccccg gagaagacgg ccaggccgcc   6360
tagatgacaa attcaacaac tcacagctga ctttctgcca ttgccactag gggggggcct   6420
ttttatatgg ccaagccaag ctctccacgt cggttgggct gcacccaaca ataaatgggt   6480
agggttgcac caacaaaggg atgggatggg gggtagaaga tacgaggata acggggctca   6540
```

-continued

```
atggcacaaa taagaacgaa tactgccatt aagactcgtg atccagcgac tgacaccatt   6600
gcatcatcta agggcctcaa aactacctcg gaactgctgc gctgatctgg acaccacaga   6660
ggttccgagc actttaggtt gcaccaaatg tcccaccagg tgcaggcaga aaacgctgga   6720
acagcgtgta cagtttgtct taacaaaaag tgagggcgct gaggtcgagc agggtggtgt   6780
gacttgttat agcctttaga gctgcgaaag cgcgtatgga tttggctcat caggccagat   6840
tgagggtctg tggacacatg tcatgttagt gtacttcaat cgccccctgg atatagcccc   6900
gacaataggc cgtggcctca ttttttttgcc ttccgcacat ttccattgct cggtacccac   6960
accttgcttc tcctgcactt gccaacctta atactggttt acattgacca acatcttaca   7020
agcgggggc ttgtctaggg tatatataaa cagtggctct cccaatcggt tgccagtctc   7080
tttttccctt tctttcccca cagattcgaa atctaaacta cacatcacag aattccgagc   7140
cgtgagtatc cacgacaaga tcagtgtcga gacgacgcgt tttgtgtaat gacacaatcc   7200
gaaagtcgct agcaacacac actctctaca caaactaacc cagctctggt accatggcca   7260
tcatccactc caccggaact ctgcccatct tcaacggtac cgtcaccgat tacctgcgaa   7320
caaagccttc ttactcgtcc acagatccag cctacatcga cgtggttaca ggcaactcta   7380
tcagctactc cgaggtctgg aagcttgccg accgactctc ctctgctctg tacaacgact   7440
acggactcac cgacgccaag cccgacgaga atgtgggtcc tgttgtcatg ctgcacgctg   7500
tcaattcgcc tctcctggca tctgttcact acgctcttct ggatctgggc gtcacaatca   7560
ctcccgcagc tgccacctac gaggctggcg atctcgcaca tcaaatcaag gtgtgctctc   7620
cgtccctggt catttgcaac cagcagttcg aacccaaggt caaatctgcc tccagcaaca   7680
ccaagctcat tttcatcgag gatctgctca aaacccagtc gtctgctccc tggaaaaagt   7740
tcactacctc caaccccaac cgagttgcct acctgggcat gtccagtgga acctctggtc   7800
tccccaaggc ggttcaacag acccacatca acatgtcgtc ttccaccgaa gccgtcattt   7860
cctctcagac catcttcagc gctcgaaaga acgtcaccgc agccattgtg cccatgactc   7920
atgtctacgg actcaccaag tttgttttcc actctgtcgc aggctcaatg accaccgttg   7980
tgttccccaa gttctccctg gtcgacctcc tggaggccca gatcaagtac aagatcaaca   8040
ttctgtatct ggttcctcca gtggtcttgg ctctggccaa ggactctcgt gtacagccct   8100
acatcaagtc catttgcgag ctcaccactc tgattgccac tggtgcggct ccccttcctc   8160
ccactgcagg cgacgccctt ctggagcgac ttacgggcaa caaagaggga aacagagaca   8220
acggtatgga tcccttggtt ctcatccagg gctacggact cacagagact ctccaggtgt   8280
ctgtcttcaa gccagaggat cccgaacgag atctcaagac cgtgggcaaa ctgcttccca   8340
acaccgaggt tcgaattgtc ggcgagaagg gagatgttcc gcgttccaaa tggtcgtttg   8400
tcactcctcc aaccggcgaa atctacattc gaggtcccca cgtgactcct ggttacttca   8460
acaacgactc tgccaactct gagtcctttg acggcgagtg gctcaagacc ggcgatatcg   8520
gatacatgga cctggaaggt cgactcacca ttgtggaccg aaacaaggag atgatcaagg   8580
tcaacggacg tcaggttgct cctgccgaga tcgaatctgt gctgctgggt catcctatgg   8640
tcaaggatgt ggccgtcatt ggagtcacca atcccgacag aggcacggag tctgctcggg   8700
cgtttcttgt tactgaagct cgagctctcc ctgtcatcaa gcagtggttt gaccgtcgag   8760
ttccctccta caagcgactt tacggaggca ttgtggttgt cgatgccatt cccaagtctg   8820
cctcgggcaa gattctgcga cgggtcctca gagagcgaaa gggcgactcc gtgtttggag   8880
agtatgtcga ggaagtctaa gc                                             8902
```

<210> SEQ ID NO 64
<211> LENGTH: 9055
<212> TYPE: DNA
<213> ORGANISM: artificial sequence
<220> FEATURE:
<223> OTHER INFORMATION: Plasmid pZP2-YlACoS-5Ps

<400> SEQUENCE: 64
ggccgcaagt gtggatgggg aagtgagtgc ccggttctgt gtgcacaatt ggcaatccaa 60
gatggatgga ttcaacacag ggatatagcg agctacgtgg tggtgcgagg atatagcaac 120
ggatatttat gtttgacact tgagaatgta cgatacaagc actgtccaag tacaatacta 180
aacatactgt acatactcat actcgtaccc gggcaacggt ttcacttgag tgcagtggct 240
agtgctctta ctcgtacagt gtgcaatact gcgtatcata gtctttgatg tatatcgtat 300
tcattcatgt tagttgcgta cgggcgtcgt tgcttgtgtg atttttgagg acccatccct 360
ttggtatata agtatactct ggggttaagg ttgcccgtgt agtctaggtt atagttttca 420
tgtgaaatac cgagagccga gggagaataa acgggggtat ttggacttgt ttttttcgcg 480
gaaaagcgtc gaatcaaccc tgcgggcctt gcaccatgtc cacgacgtgt ttctcgcccc 540
aattcgcccc ttgcacgtca aaattaggcc tccatctaga cccctccata acatgtgact 600
gtggggaaaa gtataaggga aaccatgcaa ccatagacga cgtgaaagac ggggaggaac 660
caatggaggc caaagaaatg gggtagcaac agtccaggag acagacaagg agacaaggag 720
agggcgcccg aaagatcgga aaaacaaaca tgtccaattg gggcagtgac ggaaacgaca 780
cggacacttc agtacaatgg accgaccatc tccaagccag ggttattccg gtatcacctt 840
ggccgtaacc tcccgctggt acctgatatt gtacacgttc acattcaata tactttcagc 900
tacaataaga gaggctgttt gtcgggcatg tgtgtccgtc gtatggggtg atgtccgagg 960
gcgaaattcg ctacaagctt aactctggcg cttgtccagt atgaatagac aagtcaagac 1020
cagtggtgcc atgattgaca gggaggtaca agacttcgat actcgagcat tactcggact 1080
tgtggcgatt gaacagacgg gcgatcgctt ctcccccgta ttgccggcgc gccagctgca 1140
ttaatgaatc ggccaacgcg cggggagagg cggtttgcgt attgggcgct cttccgcttc 1200
ctcgctcact gactcgctgc gctcggtcgt tcggctgcgg cgagcggtat cagctcactc 1260
aaaggcggta atacggttat ccacagaatc aggggataac gcaggaaaga acatgtgagc 1320
aaaaggccag caaaaggcca ggaaccgtaa aaaggccgcg ttgctggcgt ttttccatag 1380
gctccgcccc cctgacgagc atcacaaaaa tcgacgctca agtcagaggt ggcgaaaccc 1440
gacaggacta taaagatacc aggcgtttcc ccctggaagc tccctcgtgc gctctcctgt 1500
tccgaccctg ccgcttaccg gatacctgtc cgcctttctc ccttcgggaa gcgtggcgct 1560
ttctcatagc tcacgctgta ggtatctcag ttcggtgtag gtcgttcgct ccaagctggg 1620
ctgtgtgcac gaaccccccg ttcagcccga ccgctgcgcc ttatccggta actatcgtct 1680
tgagtccaac ccggtaagac acgacttatc gccactggca gcagccactg gtaacaggat 1740
tagcagagcg aggtatgtag gcggtgctac agagttcttg aagtggtggc ctaactacgg 1800
ctacactaga agaacagtat ttggtatctg cgctctgctg aagccagtta ccttcggaaa 1860
aagagttggt agctcttgat ccggcaaaca aaccaccgct ggtagcggtg gtttttttgt 1920
ttgcaagcag cagattacgc gcagaaaaaa aggatctcaa gaagatcctt tgatcttttc 1980
tacggggtct gacgctcagt ggaacgaaaa ctcacgttaa gggattttgg tcatgagatt 2040

-continued

```
atcaaaaagg atcttcacct agatcctttt aaattaaaaa tgaagtttta aatcaatcta   2100
aagtatatat gagtaaactt ggtctgacag ttaccaatgc ttaatcagtg aggcacctat   2160
ctcagcgatc tgtctatttc gttcatccat agttgcctga ctccccgtcg tgtagataac   2220
tacgatacgg gagggcttac catctggccc cagtgctgca atgataccgc gagacccacg   2280
ctcaccggct ccagatttat cagcaataaa ccagccagcc ggaagggccg agcgcagaag   2340
tggtcctgca actttatccg cctccatcca gtctattaat tgttgccggg aagctagagt   2400
aagtagttcg ccagttaata gtttgcgcaa cgttgttgcc attgctacag gcatcgtggt   2460
gtcacgctcg tcgtttggta tggcttcatt cagctccggt tcccaacgat caaggcgagt   2520
tacatgatcc cccatgttgt gcaaaaaagc ggttagctcc ttcggtcctc cgatcgttgt   2580
cagaagtaag ttggccgcag tgttatcact catggttatg gcagcactgc ataattctct   2640
tactgtcatg ccatccgtaa gatgcttttc tgtgactggt gagtactcaa ccaagtcatt   2700
ctgagaatag tgtatgcggc gaccgagttg ctcttgcccg gcgtcaatac gggataatac   2760
cgcgccacat agcagaactt taaaagtgct catcattgga aaacgttctt cggggcgaaa   2820
actctcaagg atcttaccgc tgttgagatc cagttcgatg taacccactc gtgcacccaa   2880
ctgatcttca gcatctttta ctttcaccag cgtttctggg tgagcaaaaa caggaaggca   2940
aaatgccgca aaaaagggaa taagggcgac acggaaatgt tgaatactca tactcttcct   3000
ttttcaatat tattgaagca tttatcaggg ttattgtctc atgagcggat acatatttga   3060
atgtatttag aaaaataaac aaataggggt tccgcgcaca tttccccgaa aagtgccacc   3120
tgatgcggtg tgaaataccg cacagatgcg taaggagaaa ataccgcatc aggaaattgt   3180
aagcgttaat attttgttaa aattcgcgtt aaatttttgt taaatcagct cattttttaa   3240
ccaataggcc gaaatcggca aaatccctta taaatcaaaa gaatagaccg agatagggtt   3300
gagtgttgtt ccagtttgga acaagagtcc actattaaag aacgtggact ccaacgtcaa   3360
agggcgaaaa accgtctatc agggcgatgg cccactacgt gaaccatcac cctaatcaag   3420
ttttttgggg tcgaggtgcc gtaaagcact aaatcggaac cctaaaggga gcccccgatt   3480
tagagcttga cggggaaagc cggcgaacgt ggcgagaaag gaagggaaga aagcgaaagg   3540
agcgggcgct agggcgctgg caagtgtagc ggtcacgctg cgcgtaacca ccacacccgc   3600
cgcgcttaat gcgccgctac agggcgcgtc cattcgccat tcaggctgcg caactgttgg   3660
gaagggcgat cggtgcgggc ctcttcgcta ttacgccagc tggcgaaagg gggatgtgct   3720
gcaaggcgat taagttgggt aacgccaggg ttttcccagt cacgacgttg taaaacgacg   3780
gccagtgaat tgtaatacga ctcactatag ggcgaattgg gcccgacgtc gcatgcgctg   3840
atgacacttt ggtctgaaag agatgcattt tgaatcccaa acttgcagtg cccaagtgac   3900
atacatctcc gcgttttgga aaatgttcag aaacagttga ttgtgttgga atggggaatg   3960
gggaatggaa aaatgactca agtatcaatt ccaaaaactt ctctggctgg cagtacctac   4020
tgtccatact actgcatttt ctccagtcag gccactctat actcgacgac acagtagtaa   4080
aacccagata atttcgacat aaacaagaaa acagacccaa taatatttat atatagtcag   4140
ccgtttgtcc agttcagact gtaatagccg aaaaaaaatc caaagtttct attctaggaa   4200
aatatattcc aatattttta attcttaatc tcatttattt tattctagcg aaatacattt   4260
cagctacttg agacatgtga tacccacaaa tcggattcgg actcggttgt tcagaagagc   4320
atatggcatt cgtgctcgct tgttcacgta ttcttcctgt tccatctctt ggccgacaat   4380
cacacaaaaa tggggttttt tttttaattc taatgattca ttacagcaaa attgagatat   4440
```

-continued

```
agcagaccac gtattccata atcaccaagg aagttcttgg gcgtcttaat taagtcatac   4500
acaagtcagc tttcttcgag cctcatataa gtataagtag ttcaacgtat tagcactgta   4560
cccagcatct ccgtatcgag aaacacaaca acatgcccca ttggacagat catgcggata   4620
cacaggttgt gcagtatcat acatactcga tcagacaggt cgtctgacca tcatacaagc   4680
tgaacaagcg ctccatactt gcacgctctc tatatacaca gttaaattac atatccatag   4740
tctaacctct aacagttaat cttctggtaa gcctcccagc cagccttctg gtatcgcttg   4800
gcctcctcaa taggatctcg gttctggccg tacagacctc ggccgacaat tatgatatcc   4860
gttccggtag acatgacatc ctcaacagtt cggtactgct gtccgagagc gtctcccttg   4920
tcgtcaagac ccaccccggg ggtcagaata agccagtcct cagagtcgcc cttaggtcgg   4980
ttctgggcaa tgaagccaac cacaaactcg gggtcggatc gggcaagctc aatggtctgc   5040
ttggagtact cgccagtggc cagagagccc ttgcaagaca gctcggccag catgagcaga   5100
cctctggcca gcttctcgtt gggagagggg actaggaact ccttgtactg ggagttctcg   5160
tagtcagaga cgtcctcctt cttctgttca gagacagttt cctcggcacc agctcgcagg   5220
ccagcaatga ttccggttcc gggtacaccg tgggcgttgg tgatatcgga ccactcggcg   5280
attcggtgac accggtactg gtgcttgaca gtgttgccaa tatctgcgaa ctttctgtcc   5340
tcgaacagga agaaaccgtg cttaagagca agttccttga gggggagcac agtgccggcg   5400
taggtgaagt cgtcaatgat gtcgatatgg gttttgatca tgcacacata aggtccgacc   5460
ttatcggcaa gctcaatgag ctccttggtg gtggtaacat ccagagaagc acacaggttg   5520
gttttcttgg ctgccacgag cttgagcact cgagcggcaa aggcggactt gtggacgtta   5580
gctcgagctt cgtaggaggg cattttggtg gtgaagagga gactgaaata aatttagtct   5640
gcagaacttt ttatcggaac cttatctggg gcagtgaagt atatgttatg gtaatagtta   5700
cgagttagtt gaacttatag atagactgga ctatacggct atcggtccaa attagaaaga   5760
acgtcaatgg ctctctgggc gtcgcctttg ccgacaaaaa tgtgatcatg atgaaagcca   5820
gcaatgacgt tgcagctgat attgttgtcg gccaaccgcg ccgaaaacgc agctgtcaga   5880
cccacagcct ccaacgaaga atgtatcgtc aaagtgatcc aagcacactc atagttggag   5940
tcgtactcca aaggcggcaa tgacgagtca gacagatact cgtcaaacgg taggttagtg   6000
cttggtatat gagttgtagg catgacaatt tggaaagggg tggactttgg gaatattgtg   6060
ggatttcaat accttagttt gtacagggta attgttacaa atgatacaaa gaactgtatt   6120
tcttttcatt tgttttaatt ggttgtatat caagtccgtt agacgagctc agtgccttgg   6180
cttttggcac tgtatttcat ttttagaggt acactacatt cagtgaggta tggtaaggtt   6240
gagggcataa tgaaggcacc ttgtactgac agtcacagac ctctcaccga gaattttatg   6300
agatatactc gggttcattt taggctcatc gattgccccg gagaagacgg ccaggccgcc   6360
tagatgacaa attcaacaac tcacagctga ctttctgcca ttgccactag gggggggcct   6420
ttttatatgg ccaagccaag ctctccacgt cggttgggct gcacccaaca ataaatgggt   6480
agggttgcac caacaaaggg atgggatggg gggtagaaga tacgaggata acggggctca   6540
atggcacaaa taagaacgaa tactgccatt aagactcgtg atccagcgac tgacaccatt   6600
gcatcatcta agggcctcaa aactacctcg gaactgctgc gctgatctgg acaccacaga   6660
ggttccgagc actttaggtt gcaccaaatg tcccaccagg tgcaggcaga aaacgctgga   6720
acagcgtgta cagtttgtct taacaaaaag tgagggcgct gaggtcgagc agggtggtgt   6780
```

```
gacttgttat agcctttaga gctgcgaaag cgcgtatgga tttggctcat caggccagat   6840
tgagggtctg tggacacatg tcatgttagt gtacttcaat cgccccctgg atatagcccc   6900
gacaataggc cgtggcctca tttttttgcc ttccgcacat ttccattgct cggtacccac   6960
accttgcttc tcctgcactt gccaacctta atactggttt acattgacca acatcttaca   7020
agcgggggc ttgtctaggg tatatataaa cagtggctct cccaatcggt tgccagtctc   7080
tttttccttt tctttcccca cagattcgaa atctaaacta cacatcacag aattccgagc   7140
cgtgagtatc cacgacaaga tcagtgtcga gacgacgcgt tttgtgtaat gacacaatcc   7200
gaaagtcgct agcaacacac actctctaca caaactaacc cagctctggt accatggcct   7260
caatcattca caagtctcct gtgcccgacg ttcagctgtt ctacggttcc tggccagatc   7320
tcatgcgaac ctctcctcat gcccacaacg actccaaacc cgtggtcttt gacttcgata   7380
ccaagcagca acttacttgg aagcaggtct ggcaactcag cgctcgactc agagcccagc   7440
tgtaccacaa gtacggaatc ggcaaacccg gtgctcttgc acctttccac aacgatccct   7500
ctctcggaga cgtggtcatc ttctacactc ccaacaccta cagctcgttg ccctatcatc   7560
tggctcttca cgatctcgga gccaccattt ctcctgcctc cacatcttac gacgtcaagg   7620
acatttgcca tcagatcgtt actaccgatg cggtcgtggt tgtcgctgca gccgagaaat   7680
ccgagattgc tcgagaggcc gttcagctgt ctggtcgaga cgtcagagtt gtggtcatgg   7740
aggacctcat caacaatgct cccaccgttg cgcagaacga tatcgactcg gcacctcatg   7800
tgtccctgtc tcgggaccag gctcgagcca agattgcata cctgggcatg tcttccggta   7860
cgtctggcgg acttcccaag gctgttcgtc tcactcactt caacgttacc tcgaactgtc   7920
tgcaggtctc cgctgccgca cccaaccttg cccagaacgt ggttgccagc gccgtcattc   7980
caaccactca catctacggt ctcaccatgt ttctgtcggt tcttccctac aacggttccg   8040
tggtcattca tcacaagcaa ttcaacttgc gagatctgct cgaggctcag aagacataca   8100
aggtctctct gtggattctc gttcctcccg tcatcgtgca gcttgccaag aaccctatgg   8160
tcgacgagta cctggactcc attcgagccc atgtgcggtg catcgtctct ggagctgctc   8220
ctctcggtgg caatgtcgtg gatcaggttt cggttcgtct taccggcaac aaggaaggca   8280
ttctgcccaa cggagacaag ctcgtcattc atcaagccta cggtcttacc gagtcctctc   8340
ccatcgttgg aatgctcgat cctctgtcgg accacatcga cgtcatgact gtgggctgtc   8400
tcatgcccaa taccgaggct cgaattgtcg acgaagaggg aaacgatcag ccagcagtcc   8460
acgttaccga cacacgaggc atcggtgccg ctgtcaagcg aggcgagaag attccctccg   8520
gagaactctg gattcgaggt cctcagatca tggacggata ccacaagaac cccgagtcgt   8580
ctcgtgagtc cctggaaccc agcacagaga cctacggtct gcaacatttc caggacagat   8640
ggcttcgaac tggagacgtt gctgtcatcg acaccttcgg acgagtcatg gttgtggatc   8700
gaaccaagga gctcatcaag tccatgtctc gacaggttgc tcctgccgag ctcgaagctc   8760
ttctgctcaa ccatccttcc gtcaacgatg tggctgtcgt tggcgtccac aacgacgata   8820
atggcacaga gtcagcacga gcgtttgtcg ttcttcaacc aggcgacgcc tgtgatccta   8880
ctaccatcaa gcactggatg gaccagcaag ttccctccta caagcggctg tacggaggca   8940
ttgtggtcat cgacactgtt cccaagaatg cctctggcaa gattctgcga agactgcttc   9000
gacagcggag agacgatcga gtctggggtc tggccaaggt tgccaagctc taagc        9055
```

<210> SEQ ID NO 65
<211> LENGTH: 9043

```
<212> TYPE: DNA
<213> ORGANISM: artificial sequence
<220> FEATURE:
<223> OTHER INFORMATION: Plasmid pZP2-YlACoS-6Ps

<400> SEQUENCE: 65

ggccgcaagt gtggatgggg aagtgagtgc ccggttctgt gtgcacaatt ggcaatccaa     60

gatggatgga ttcaacacag ggatatagcg agctacgtgg tggtgcgagg atatagcaac    120

ggatatttat gtttgacact tgagaatgta cgatacaagc actgtccaag tacaatacta    180

aacatactgt acatactcat actcgtaccc gggcaacggt ttcacttgag tgcagtggct    240

agtgctctta ctcgtacagt gtgcaatact gcgtatcata gtctttgatg tatatcgtat    300

tcattcatgt tagttgcgta cgggcgtcgt tgcttgtgtg atttttgagg acccatccct    360

ttggtatata agtatactct ggggttaagg ttgcccgtgt agtctaggtt atagttttca    420

tgtgaaatac cgagagccga gggagaataa acgggggtat ttggacttgt ttttttcgcg    480

gaaaagcgtc gaatcaaccc tgcgggcctt gcaccatgtc cacgacgtgt ttctcgcccc    540

aattcgcccc ttgcacgtca aaattaggcc tccatctaga cccctccata acatgtgact    600

gtggggaaaa gtataaggga aaccatgcaa ccatagacga cgtgaaagac ggggaggaac    660

caatggaggc caaagaaatg gggtagcaac agtccaggag acagacaagg agacaaggag    720

agggcgcccg aaagatcgga aaaacaaaca tgtccaattg gggcagtgac ggaaacgaca    780

cggacacttc agtacaatgg accgaccatc tccaagccag ggttattccg gtatcacctt    840

ggccgtaacc tcccgctggt acctgatatt gtacacgttc acattcaata tactttcagc    900

tacaataaga gaggctgttt gtcgggcatg tgtgtccgtc gtatggggtg atgtccgagg    960

gcgaaattcg ctacaagctt aactctggcg cttgtccagt atgaatagac aagtcaagac   1020

cagtggtgcc atgattgaca gggaggtaca agacttcgat actcgagcat tactcggact   1080

tgtggcgatt gaacagacgg gcgatcgctt ctcccccgta ttgccggcgc gccagctgca   1140

ttaatgaatc ggccaacgcg cggggagagg cggtttgcgt attgggcgct cttccgcttc   1200

ctcgctcact gactcgctgc gctcggtcgt tcggctgcgg cgagcggtat cagctcactc   1260

aaaggcggta atacggttat ccacagaatc aggggataac gcaggaaaga acatgtgagc   1320

aaaaggccag caaaaggcca ggaaccgtaa aaaggccgcg ttgctggcgt ttttccatag   1380

gctccgcccc cctgacgagc atcacaaaaa tcgacgctca agtcagaggt ggcgaaaccc   1440

gacaggacta taaagatacc aggcgtttcc ccctggaagc tccctcgtgc gctctcctgt   1500

tccgaccctg ccgcttaccg gatacctgtc cgcctttctc ccttcgggaa gcgtggcgct   1560

ttctcatagc tcacgctgta ggtatctcag ttcggtgtag gtcgttcgct ccaagctggg   1620

ctgtgtgcac gaaccccccg ttcagcccga ccgctgcgcc ttatccggta actatcgtct   1680

tgagtccaac ccggtaagac acgacttatc gccactggca gcagccactg gtaacaggat   1740

tagcagagcg aggtatgtag gcggtgctac agagttcttg aagtggtggc ctaactacgg   1800

ctacactaga agaacagtat ttggtatctg cgctctgctg aagccagtta ccttcggaaa   1860

aagagttggt agctcttgat ccggcaaaca aaccaccgct ggtagcggtg gtttttttgt   1920

ttgcaagcag cagattacgc gcagaaaaaa aggatctcaa gaagatcctt tgatcttttc   1980

tacggggtct gacgctcagt ggaacgaaaa ctcacgttaa gggattttgg tcatgagatt   2040

atcaaaaagg atcttcacct agatcctttt aaattaaaaa tgaagtttta aatcaatcta   2100

aagtatatat gagtaaactt ggtctgacag ttaccaatgc ttaatcagtg aggcacctat   2160
```

-continued

```
ctcagcgatc tgtctatttc gttcatccat agttgcctga ctccccgtcg tgtagataac   2220
tacgatacgg gagggcttac catctggccc cagtgctgca atgataccgc gagacccacg   2280
ctcaccggct ccagatttat cagcaataaa ccagccagcc ggaagggccg agcgcagaag   2340
tggtcctgca actttatccg cctccatcca gtctattaat tgttgccggg aagctagagt   2400
aagtagttcg ccagttaata gtttgcgcaa cgttgttgcc attgctacag gcatcgtggt   2460
gtcacgctcg tcgtttggta tggcttcatt cagctccggt tcccaacgat caaggcgagt   2520
tacatgatcc cccatgttgt gcaaaaaagc ggttagctcc ttcggtcctc cgatcgttgt   2580
cagaagtaag ttggccgcag tgttatcact catggttatg gcagcactgc ataattctct   2640
tactgtcatg ccatccgtaa gatgcttttc tgtgactggt gagtactcaa ccaagtcatt   2700
ctgagaatag tgtatgcggc gaccgagttg ctcttgcccg gcgtcaatac gggataatac   2760
cgcgccacat agcagaactt taaaagtgct catcattgga aaacgttctt cggggcgaaa   2820
actctcaagg atcttaccgc tgttgagatc cagttcgatg taacccactc gtgcacccaa   2880
ctgatcttca gcatctttta ctttcaccag cgtttctggg tgagcaaaaa caggaaggca   2940
aaatgccgca aaaaagggaa taagggcgac acggaaatgt tgaatactca tactcttcct   3000
ttttcaatat tattgaagca tttatcaggg ttattgtctc atgagcggat acatatttga   3060
atgtatttag aaaaataaac aaataggggt tccgcgcaca tttccccgaa aagtgccacc   3120
tgatgcggtg tgaaataccg cacagatgcg taaggagaaa ataccgcatc aggaaattgt   3180
aagcgttaat attttgttaa aattcgcgtt aaatttttgt taaatcagct cattttttaa   3240
ccaataggcc gaaatcggca aaatccctta taaatcaaaa gaatagaccg agatagggtt   3300
gagtgttgtt ccagtttgga acaagagtcc actattaaag aacgtggact ccaacgtcaa   3360
agggcgaaaa accgtctatc agggcgatgg cccactacgt gaaccatcac cctaatcaag   3420
ttttttgggg tcgaggtgcc gtaaagcact aaatcggaac cctaaaggga gcccccgatt   3480
tagagcttga cggggaaagc cggcgaacgt ggcgagaaag gaagggaaga aagcgaaagg   3540
agcgggcgct agggcgctgg caagtgtagc ggtcacgctg cgcgtaacca ccacacccgc   3600
cgcgcttaat gcgccgctac agggcgcgtc cattcgccat tcaggctgcg caactgttgg   3660
gaagggcgat cggtgcgggc ctcttcgcta ttacgccagc tggcgaaagg gggatgtgct   3720
gcaaggcgat taagttgggt aacgccaggg ttttcccagt cacgacgttg taaaacgacg   3780
gccagtgaat tgtaatacga ctcactatag ggcgaattgg gcccgacgtc gcatgcgctg   3840
atgacacttt ggtctgaaag agatgcattt tgaatcccaa acttgcagtg cccaagtgac   3900
atacatctcc gcgttttgga aaatgttcag aaacagttga ttgtgttgga atggggaatg   3960
gggaatggaa aaatgactca agtatcaatt ccaaaaactt ctctggctgg cagtacctac   4020
tgtccatact actgcatttt ctccagtcag gccactctat actcgacgac acagtagtaa   4080
aacccagata atttcgacat aaacaagaaa acagacccaa taatatttat atatagtcag   4140
ccgtttgtcc agttcagact gtaatagccg aaaaaaaatc caaagtttct attctaggaa   4200
aatatattcc aatattttta attcttaatc tcatttattt tattctagcg aaatacattt   4260
cagctacttg agacatgtga tacccacaaa tcggattcgg actcggttgt tcagaagagc   4320
atatggcatt cgtgctcgct tgttcacgta ttcttcctgt tccatctctt ggccgacaat   4380
cacacaaaaa tggggttttt tttttaattc taatgattca ttacagcaaa attgagatat   4440
agcagaccac gtattccata atcaccaagg aagttcttgg gcgtcttaat taagtcatac   4500
acaagtcagc tttcttcgag cctcatataa gtataagtag ttcaacgtat tagcactgta   4560
```

-continued

```
cccagcatct ccgtatcgag aaacacaaca acatgcccca ttggacagat catgcggata   4620
cacaggttgt gcagtatcat acatactcga tcagacaggt cgtctgacca tcatacaagc   4680
tgaacaagcg ctccatactt gcacgctctc tatatacaca gttaaattac atatccatag   4740
tctaacctct aacagttaat cttctggtaa gcctcccagc cagccttctg gtatcgcttg   4800
gcctcctcaa taggatctcg gttctggccg tacagacctc ggccgacaat tatgatatcc   4860
gttccggtag acatgacatc ctcaacagtt cggtactgct gtccgagagc gtctcccttg   4920
tcgtcaagac ccaccccggg ggtcagaata agccagtcct cagagtcgcc cttaggtcgg   4980
ttctgggcaa tgaagccaac cacaaactcg gggtcggatc gggcaagctc aatggtctgc   5040
ttggagtact cgccagtggc cagagagccc ttgcaagaca gctcggccag catgagcaga   5100
cctctggcca gcttctcgtt gggagagggg actaggaact ccttgtactg ggagttctcg   5160
tagtcagaga cgtcctcctt cttctgttca gagacagttt cctcggcacc agctcgcagg   5220
ccagcaatga ttccggttcc gggtacaccg tgggcgttgg tgatatcgga ccactcggcg   5280
attcggtgac accggtactg gtgcttgaca gtgttgccaa tatctgcgaa ctttctgtcc   5340
tcgaacagga agaaaccgtg cttaagagca agttccttga gggggagcac agtgccggcg   5400
taggtgaagt cgtcaatgat gtcgatatgg gttttgatca tgcacacata aggtccgacc   5460
ttatcggcaa gctcaatgag ctccttggtg gtggtaacat ccagagaagc acacaggttg   5520
gttttcttgg ctgccacgag cttgagcact cgagcggcaa aggcggactt gtggacgtta   5580
gctcgagctt cgtaggaggg cattttggtg gtgaagagga gactgaaata aatttagtct   5640
gcagaacttt ttatcggaac cttatctggg gcagtgaagt atatgttatg gtaatagtta   5700
cgagttagtt gaacttatag atagactgga ctatacggct atcggtccaa attagaaaga   5760
acgtcaatgg ctctctgggc gtcgcctttg ccgacaaaaa tgtgatcatg atgaaagcca   5820
gcaatgacgt tgcagctgat attgttgtcg gccaaccgcg ccgaaaacgc agctgtcaga   5880
cccacagcct ccaacgaaga atgtatcgtc aaagtgatcc aagcacactc atagttggag   5940
tcgtactcca aaggcggcaa tgacgagtca gacagatact cgtcaaacgg taggttagtg   6000
cttggtatat gagttgtagg catgacaatt tggaaagggg tggactttgg gaatattgtg   6060
ggatttcaat accttagttt gtacagggta attgttacaa atgatacaaa gaactgtatt   6120
tcttttcatt tgttttaatt ggttgtatat caagtccgtt agacgagctc agtgccttgg   6180
cttttggcac tgtatttcat ttttagaggt acactacatt cagtgaggta tggtaaggtt   6240
gagggcataa tgaaggcacc ttgtactgac agtcacagac ctctcaccga gaattttatg   6300
agatatactc gggttcattt taggctcatc gattgccccg gagaagacgg ccaggccgcc   6360
tagatgacaa attcaacaac tcacagctga ctttctgcca ttgccactag gggggggcct   6420
ttttatatgg ccaagccaag ctctccacgt cggttgggct gcacccaaca ataaatgggt   6480
agggttgcac caacaaaggg atgggatggg gggtagaaga tacgaggata acggggctca   6540
atggcacaaa taagaacgaa tactgccatt aagactcgtg atccagcgac tgacaccatt   6600
gcatcatcta agggcctcaa aactacctcg gaactgctgc gctgatctgg acaccacaga   6660
ggttccgagc actttaggtt gcaccaaatg tcccaccagg tgcaggcaga aaacgctgga   6720
acagcgtgta cagtttgtct taacaaaaag tgagggcgct gaggtcgagc agggtggtgt   6780
gacttgttat agcctttaga gctgcgaaag cgcgtatgga tttggctcat caggccagat   6840
tgagggtctg tggacacatg tcatgttagt gtacttcaat cgccccctgg atatagcccc   6900
```

```
gacaataggc cgtggcctca ttttttttgcc ttccgcacat ttccattgct cggtacccac   6960
accttgcttc tcctgcactt gccaacctta atactggttt acattgacca acatcttaca   7020
agcgggggc ttgtctaggg tatatataaa cagtggctct cccaatcggt tgccagtctc   7080
tttttttcctt tctttcccca cagattcgaa atctaaacta cacatcacag aattccgagc   7140
cgtgagtatc cacgacaaga tcagtgtcga gacgacgcgt tttgtgtaat gacacaatcc   7200
gaaagtcgct agcaacacac actctctaca caaactaacc cagctctggt accatggcca   7260
cacagattat ccacaacgcc accatcccca atatccccgt cgaccagctc tacgacggca   7320
agatcaccga cttcattcga tccggaggcc actccaacga aaccaagcct tctgtcatcg   7380
acgccaagac aggccagact ctctcccagg cggaaatgtg gcagctgtcg gacaagtacg   7440
cggcacttct cagctctcag tacggtctgt gccgacacag agacaacgag ctggacccat   7500
ctatgggaga tgtgctcatc accttctttg gaaacgttat cctcgctcct gtggtccatt   7560
gggctgccct cgacctcgga gcaaccattt ctcctggatc cacaggctac tctgcccagg   7620
atctcgctca ccagttccga gtcaccactc ccaaggtcgt tgtgtacgcc aaggcgttca   7680
aggatgtggt ggacgaggct acgaagctgt acaactcccc aaaccctcca gcacttgtcg   7740
agctcgaggc gctggacaag caggcccgaa tggttggaaa ccacaaggtc gaacacaccc   7800
gaaagatcaa gctggctcct cacgagtccc gaactcggat cgcgtacctt ggcatgtctt   7860
caggtacctc cggtggagtt tcaaaggctg tccgactcac ccattccaat ctcacgtcgt   7920
gttccgaaat ctcgaacaaa gcctccgagt ctctcgcaac tgaccagcag atcgctgccg   7980
ccatcattcc cgtgagtcat ctgtttggac tgtccaagtt cctcattggc aaccctcacg   8040
ccggagccac cactgtctat cacaatggct tcgatctgat cgaggtgctg gaggcacaga   8100
agaaatacaa agtcaactcg tggaccctgg ttcctcccat cattgtcctg ctcaccaaac   8160
accccattgt cgagaagtac attccttctc tccgtgccca catgcgagcc atcctctccg   8220
gagctgctcc tctgggtgcc aatgtcacag aggctcttct cacccgagtc actggcaaca   8280
agtttggcga gtctcccgag ggcggtctgc gaatcgttca gggctacgga cttacagaga   8340
cgtctcccgt tgccactctg tttgaccccg aagacaagga acgacacatt cggtcgtgtg   8400
gaaagctcgt gcccaactct caggttcgaa ttgtcaacga agacggcgtg gatcagcctg   8460
cctacgatgt ggaccccaac gagctggacg aggccatcaa acagggcact ctgccagtcg   8520
gagagctttg gatcagaggt ccccaggtta tggacggcta ccataacaac cccgaggcca   8580
acgaagcctg tttcgtcaag gctgacgatg ctgaagcaga tactgcctac tacaacagac   8640
actggttccg aaccggagac gttgctctgg tcgacaagca gggcagatac atgattgtgg   8700
accgaaccaa ggagatgatc aagagtcagg gtaagcaggt tgctcctgcc gagctcgaag   8760
acatgctcct gggacacgca caggtggcag ataccgcagt catcggtatt caggacgtgg   8820
agaagggtaa cgaggctcct cgagcttttg ttgtgctcaa ggacccgaag tacgacgctg   8880
tggagatcaa gacatggctg gacaagcagc ttcccaagta caagcagctt catgctggca   8940
tcgtggtcat tgatgccatt cccaagaacg ccagtggcaa gattctgcga cgtctgttgc   9000
gtgctagaaa ggacgatgtt gttctgggtc tcaacaagta agc                     9043
```

<210> SEQ ID NO 66
<211> LENGTH: 9067
<212> TYPE: DNA
<213> ORGANISM: artificial sequence
<220> FEATURE:
<223> OTHER INFORMATION: Plasmid pZP2-YlACoS-10Ps

<400> SEQUENCE: 66
ggccgcaagt gtggatgggg aagtgagtgc ccggttctgt gtgcacaatt ggcaatccaa 60
gatggatgga ttcaacacag ggatatagcg agctacgtgg tggtgcgagg atatagcaac 120
ggatatttat gtttgacact tgagaatgta cgatacaagc actgtccaag tacaatacta 180
aacatactgt acatactcat actcgtaccc gggcaacggt ttcacttgag tgcagtggct 240
agtgctctta ctcgtacagt gtgcaatact gcgtatcata gtctttgatg tatatcgtat 300
tcattcatgt tagttgcgta cgggcgtcgt tgcttgtgtg atttttgagg acccatccct 360
ttggtatata agtatactct ggggttaagg ttgcccgtgt agtctaggtt atagttttca 420
tgtgaaatac cgagagccga gggagaataa acgggggtat ttggacttgt ttttttcgcg 480
gaaaagcgtc gaatcaaccc tgcgggcctt gcaccatgtc cacgacgtgt ttctcgcccc 540
aattcgcccc ttgcacgtca aaattaggcc tccatctaga cccctccata acatgtgact 600
gtggggaaaa gtataaggga aaccatgcaa ccatagacga cgtgaaagac ggggaggaac 660
caatggaggc caaagaaatg ggtagcaac agtccaggag acagacaagg agacaaggag 720
agggcgcccg aaagatcgga aaaacaaaca tgtccaattg gggcagtgac ggaaacgaca 780
cggacacttc agtacaatgg accgaccatc tccaagccag ggttattccg gtatcacctt 840
ggccgtaacc tcccgctggt acctgatatt gtacacgttc acattcaata tactttcagc 900
tacaataaga gaggctgttt gtcgggcatg tgtgtccgtc gtatggggtg atgtccgagg 960
gcgaaattcg ctacaagctt aactctggcg cttgtccagt atgaatagac aagtcaagac 1020
cagtggtgcc atgattgaca gggaggtaca agacttcgat actcgagcat tactcggact 1080
tgtggcgatt gaacagacgg gcgatcgctt ctcccccgta ttgccggcgc gccagctgca 1140
ttaatgaatc ggccaacgcg cggggagagg cggtttgcgt attgggcgct cttccgcttc 1200
ctcgctcact gactcgctgc gctcggtcgt tcggctgcgg cgagcggtat cagctcactc 1260
aaaggcggta atacggttat ccacagaatc aggggataac gcaggaaaga acatgtgagc 1320
aaaaggccag caaaaggcca ggaaccgtaa aaaggccgcg ttgctggcgt ttttccatag 1380
gctccgcccc cctgacgagc atcacaaaaa tcgacgctca agtcagaggt ggcgaaaccc 1440
gacaggacta taaagatacc aggcgtttcc ccctggaagc tccctcgtgc gctctcctgt 1500
tccgaccctg ccgcttaccg gatacctgtc cgcctttctc ccttcgggaa gcgtggcgct 1560
ttctcatagc tcacgctgta ggtatctcag ttcggtgtag gtcgttcgct ccaagctggg 1620
ctgtgtgcac gaaccccccg ttcagcccga ccgctgcgcc ttatccggta actatcgtct 1680
tgagtccaac ccggtaagac acgacttatc gccactggca gcagccactg gtaacaggat 1740
tagcagagcg aggtatgtag gcggtgctac agagttcttg aagtggtggc ctaactacgg 1800
ctacactaga agaacagtat ttggtatctg cgctctgctg aagccagtta ccttcggaaa 1860
aagagttggt agctcttgat ccggcaaaca aaccaccgct ggtagcggtg gtttttttgt 1920
ttgcaagcag cagattacgc gcagaaaaaa aggatctcaa gaagatcctt tgatcttttc 1980
tacggggtct gacgctcagt ggaacgaaaa ctcacgttaa gggattttgg tcatgagatt 2040
atcaaaaagg atcttcacct agatcctttt aaattaaaaa tgaagtttta aatcaatcta 2100
aagtatatat gagtaaactt ggtctgacag ttaccaatgc ttaatcagtg aggcacctat 2160
ctcagcgatc tgtctatttc gttcatccat agttgcctga ctccccgtcg tgtagataac 2220
tacgatacgg gagggcttac catctggccc cagtgctgca atgataccgc gagacccacg 2280

```
ctcaccggct ccagatttat cagcaataaa ccagccagcc ggaagggccg agcgcagaag   2340
tggtcctgca actttatccg cctccatcca gtctattaat tgttgccggg aagctagagt   2400
aagtagttcg ccagttaata gtttgcgcaa cgttgttgcc attgctacag gcatcgtggt   2460
gtcacgctcg tcgtttggta tggcttcatt cagctccggt tcccaacgat caaggcgagt   2520
tacatgatcc cccatgttgt gcaaaaaagc ggttagctcc ttcggtcctc cgatcgttgt   2580
cagaagtaag ttggccgcag tgttatcact catggttatg gcagcactgc ataattctct   2640
tactgtcatg ccatccgtaa gatgcttttc tgtgactggt gagtactcaa ccaagtcatt   2700
ctgagaatag tgtatgcggc gaccgagttg ctcttgcccg gcgtcaatac gggataatac   2760
cgcgccacat agcagaactt taaaagtgct catcattgga aaacgttctt cggggcgaaa   2820
actctcaagg atcttaccgc tgttgagatc cagttcgatg taacccactc gtgcacccaa   2880
ctgatcttca gcatctttta ctttcaccag cgtttctggg tgagcaaaaa caggaaggca   2940
aaatgccgca aaaaagggaa taagggcgac acggaaatgt tgaatactca tactcttcct   3000
ttttcaatat tattgaagca tttatcaggg ttattgtctc atgagcggat acatatttga   3060
atgtatttag aaaaataaac aaataggggt tccgcgcaca tttccccgaa aagtgccacc   3120
tgatgcggtg tgaaataccg cacagatgcg taaggagaaa ataccgcatc aggaaattgt   3180
aagcgttaat attttgttaa aattcgcgtt aaatttttgt taaatcagct cattttttaa   3240
ccaataggcc gaaatcggca aaatccctta taaatcaaaa gaatagaccg agatagggtt   3300
gagtgttgtt ccagtttgga acaagagtcc actattaaag aacgtggact ccaacgtcaa   3360
agggcgaaaa accgtctatc agggcgatgg cccactacgt gaaccatcac cctaatcaag   3420
tttttggggg tcgaggtgcc gtaaagcact aaatcggaac cctaaaggga gcccccgatt   3480
tagagcttga cggggaaagc cggcgaacgt ggcgagaaag gaagggaaga aagcgaaagg   3540
agcgggcgct agggcgctgg caagtgtagc ggtcacgctg cgcgtaacca ccacacccgc   3600
cgcgcttaat gcgccgctac agggcgcgtc cattcgccat tcaggctgcg caactgttgg   3660
gaagggcgat cggtgcgggc ctcttcgcta ttacgccagc tggcgaaagg gggatgtgct   3720
gcaaggcgat taagttgggt aacgccaggg ttttcccagt cacgacgttg taaaacgacg   3780
gccagtgaat tgtaatacga ctcactatag ggcgaattgg gcccgacgtc gcatgcgctg   3840
atgacacttt ggtctgaaag agatgcattt tgaatcccaa acttgcagtg cccaagtgac   3900
atacatctcc gcgttttgga aaatgttcag aaacagttga ttgtgttgga atggggaatg   3960
gggaatggaa aaatgactca agtatcaatt ccaaaaactt ctctggctgg cagtacctac   4020
tgtccatact actgcatttt ctccagtcag gccactctat actcgacgac acagtagtaa   4080
aacccagata atttcgacat aaacaagaaa acagacccaa taatatttat atatagtcag   4140
ccgtttgtcc agttcagact gtaatagccg aaaaaaaatc caaagtttct attctaggaa   4200
aatatattcc aatattttta attcttaatc tcatttattt tattctagcg aaatacattt   4260
cagctacttg agacatgtga tacccacaaa tcggattcgg actcggttgt tcagaagagc   4320
atatggcatt cgtgctcgct tgttcacgta ttcttcctgt tccatctctt ggccgacaat   4380
cacacaaaaa tggggttttt tttttaattc taatgattca ttacagcaaa attgagatat   4440
agcagaccac gtattccata atcaccaagg aagttcttgg gcgtcttaat taagtcatac   4500
acaagtcagc tttcttcgag cctcatataa gtataagtag ttcaacgtat tagcactgta   4560
cccagcatct ccgtatcgag aaacacaaca acatgcccca ttggacagat catgcggata   4620
cacaggttgt gcagtatcat acatactcga tcagacaggt cgtctgacca tcatacaagc   4680
```

-continued

```
tgaacaagcg ctccatactt gcacgctctc tatatacaca gttaaattac atatccatag   4740
tctaacctct aacagttaat cttctggtaa gcctcccagc cagccttctg gtatcgcttg   4800
gcctcctcaa taggatctcg gttctggccg tacagacctc ggccgacaat tatgatatcc   4860
gttccggtag acatgacatc ctcaacagtt cggtactgct gtccgagagc gtctcccttg   4920
tcgtcaagac ccaccccggg ggtcagaata agccagtcct cagagtcgcc cttaggtcgg   4980
ttctgggcaa tgaagccaac cacaaactcg ggtcggatc gggcaagctc aatggtctgc   5040
ttggagtact cgccagtggc cagagagccc ttgcaagaca gctcggccag catgagcaga   5100
cctctggcca gcttctcgtt gggagagggg actaggaact ccttgtactg ggagttctcg   5160
tagtcagaga cgtcctcctt cttctgttca gagacagttt cctcggcacc agctcgcagg   5220
ccagcaatga ttccggttcc gggtacaccg tgggcgttgg tgatatcgga ccactcggcg   5280
attcggtgac accggtactg gtgcttgaca gtgttgccaa tatctgcgaa ctttctgtcc   5340
tcgaacagga agaaaccgtg cttaagagca agttccttga gggggagcac agtgccggcg   5400
taggtgaagt cgtcaatgat gtcgatatgg gttttgatca tgcacacata aggtccgacc   5460
ttatcggcaa gctcaatgag ctccttggtg gtggtaacat ccagagaagc acacaggttg   5520
gttttcttgg ctgccacgag cttgagcact cgagcggcaa aggcggactt gtggacgtta   5580
gctcgagctt cgtaggaggg cattttggtg gtgaagagga gactgaaata aatttagtct   5640
gcagaacttt ttatcggaac cttatctggg gcagtgaagt atatgttatg gtaatagtta   5700
cgagttagtt gaacttatag atagactgga ctatacggct atcggtccaa attagaaaga   5760
acgtcaatgg ctctctgggc gtcgcctttg ccgacaaaaa tgtgatcatg atgaaagcca   5820
gcaatgacgt tgcagctgat attgttgtcg gccaaccgcg ccgaaaacgc agctgtcaga   5880
cccacagcct ccaacgaaga atgtatcgtc aaagtgatcc aagcacactc atagttggag   5940
tcgtactcca aaggcggcaa tgacgagtca gacagatact cgtcaaacgg taggttagtg   6000
cttggtatat gagttgtagg catgacaatt tggaaagggg tggactttgg gaatattgtg   6060
ggatttcaat accttagttt gtacagggta attgttacaa atgatacaaa gaactgtatt   6120
tcttttcatt tgttttaatt ggttgtatat caagtccgtt agacgagctc agtgccttgg   6180
cttttggcac tgtatttcat ttttagaggt acactacatt cagtgaggta tggtaaggtt   6240
gagggcataa tgaaggcacc ttgtactgac agtcacagac ctctcaccga gaattttatg   6300
agatatactc gggttcattt taggctcatc gattgccccg gagaagacgg ccaggccgcc   6360
tagatgacaa attcaacaac tcacagctga ctttctgcca ttgccactag gggggggcct   6420
ttttatatgg ccaagccaag ctctccacgt cggttgggct gcacccaaca ataaatgggt   6480
agggttgcac caacaaaggg atgggatggg gggtagaaga tacgaggata acggggctca   6540
atggcacaaa taagaacgaa tactgccatt aagactcgtg atccagcgac tgacaccatt   6600
gcatcatcta agggcctcaa aactacctcg gaactgctgc gctgatctgg acaccacaga   6660
ggttccgagc actttaggtt gcaccaaatg tcccaccagg tgcaggcaga aaacgctgga   6720
acagcgtgta cagtttgtct taacaaaaag tgagggcgct gaggtcgagc agggtggtgt   6780
gacttgttat agcctttaga gctgcgaaag cgcgtatgga tttggctcat caggccagat   6840
tgagggtctg tggacacatg tcatgttagt gtacttcaat cgccccctgg atatagcccc   6900
gacaataggc cgtggcctca tttttttgcc ttccgcacat ttccattgct cggtacccac   6960
accttgcttc tcctgcactt gccaacctta atactggttt acattgacca acatcttaca   7020
```

-continued

```
agcggggggc ttgtctaggg tatatataaa cagtggctct cccaatcggt tgccagtctc   7080
tttttttcctt tctttcccca cagattcgaa atctaaacta cacatcacag aattccgagc   7140
cgtgagtatc cacgacaaga tcagtgtcga gacgacgcgt tttgtgtaat gacacaatcc   7200
gaaagtcgct agcaacacac actctctaca caaactaacc cagctctggt accatggcct   7260
ccgtcgctcc atcttccaac cccaatccga tccaccatct gtcgcgagtc gaagacgttc   7320
ctctctccca gacgttccga ggcaacatta ccgactttgt gcgatctgga ggctttgccg   7380
acgacgactc caagccctgt tgcatcgacg cgaagactgg ccaacaactt acacagaagc   7440
aagtctggga ctacgccgac aagttcagag cactgctcca tcacgacaac aatctgtgtc   7500
ctttcaatgc caacaccacc gatccagctc ttggagacgt catgatcacc ctcgtgccca   7560
accatctgtt cattacgtcg ctgcactttg ccgcactcga tctgggtgcg acagtttctc   7620
ctggctcggc tggatacact gtggccgagc tcgtcaacca gatcaatctt accggagctt   7680
ctctcatcgt gtacactcga cccgtcttca aggttgtgcg agaggcgctt gctcagatcg   7740
tggtaccagt caagatcgtg gagttcgagg gtctcatcga acgagccgag tttgttcaga   7800
gccacaagat tcagtccaca aagaaagtca cactttctcc tgaggagtcc tactcgagaa   7860
tcgcctacct gggcatgtct tcaggcacct ccggaggtct tcctaaggcc gttcgattgt   7920
cgcacttcaa catggcgagt tctgccgagc tctccaagcg agctgcacct tcgattgccg   7980
gatccgagca gatcgcaggt gccattatcc ctgtcaacca tgtgtatggt ctggccaagt   8040
tcctcattgc catgccaaag tccggagcca ccacagtctt ccactccaag ttcgacctca   8100
tcgagatcct cgaggctcaa cagaagtaca aggtcaacat gtacgccctt gttcctccca   8160
tcattgtcgt tctggccaag catcctgctg ttgagaagta catcccttcg ctgcgagaac   8220
accttcgata cgtgtcctct ggagctgcac ccctgggtgc caacgtcatc gaggcttgca   8280
acaagcgtct tgccggaact gcttctggcg agaacgagtt tggaggtctc aagattgttc   8340
agggctacgg tctcactgaa acctcccctg tggtctccac tttcgatccc aacgatcctg   8400
agcgacacgc tcggtcctgt ggcaagctgg ttcccaacac ccaggcacga atcgtgtcgg   8460
aggacggagt cgatcagcct gcctacgagc tcaaggacct gtctcagttg gaggccgagc   8520
tcaaaaaggg caaccttccc accggtgagt tgtggcttcg aggtccccag atcatggatg   8580
gctaccacaa gaacgacgag gccaacgctg agtcgtttgt cgacgccact gactacactt   8640
ccaacatgcc cttctacatg aagcggtggt tccgaactgg cgatgttgct ctcgtcgata   8700
ctctgggcag atacatgatt gtcgatcgaa ccaaagagat gatcaagagc atgagtaagc   8760
aggttgctcc tgccgagctg gaggacatcc tgcttggcca tccccaggta gccgatgctg   8820
ctgtcatcgg tgttcagcag gtggagaagg gcactgaggc tccccgagcg ttcgtggtgc   8880
ttcgagatcc caagttcgat gcagtggaga tcaaaaagtg gatggacgcc caggtgccca   8940
agtacaaaca acttcatgga ggtgtcgtgg ttctggatgc tgttcccaag aatgccagcg   9000
gcaagattct cagacgactg ctccgtcagc gagagaatga cgtcgttctt ggactcgaca   9060
agtaagc                                                             9067
```

<210> SEQ ID NO 67
<211> LENGTH: 10109
<212> TYPE: DNA
<213> ORGANISM: artificial sequence
<220> FEATURE:
<223> OTHER INFORMATION: Plasmid pZKL7A-FYlFAAs

<400> SEQUENCE: 67

-continued

```
ggccgcaagt gtggatgggg aagtgagtgc ccggttctgt gtgcacaatt ggcaatccaa     60
gatggatgga ttcaacacag ggatatagcg agctacgtgg tggtgcgagg atatagcaac    120
ggatatttat gtttgacact tgagaatgta cgatacaagc actgtccaag tacaatacta    180
aacatactgt acatactcat actcgtaccc gggcaacggt ttcacttgag tgcagtggct    240
agtgctctta ctcgtacagt gtgcaatact gcgtatcata gtctttgatg tatatcgtat    300
tcattcatgt tagttgattt aaatgtaacg aaactgaaca caagcttcca cacaacgtac    360
gatgtattta tacttgacag tgcgggtcgg aggaagttcg gttcgggcca ggtctgccaa    420
gttgactgtt actacgctaa tgcaatcata aggagaactg tagctaattc accgttgcag    480
ttagatctct cgaaggtgtc acgaaccatt atcatgtatg ctattgtaca ctgccctctg    540
tcctggtaag tgtgttattc caagtaagag ctcttcaatc atcctggaaa tgttcaaaga    600
agaaaaaacc ccgatatatt caactattct tgaaaggaaa tcatgaggga ggcaatgccc    660
actcgatttt gtgcttaaat gacagtgtcg tgcatcagtg tgatcctaac catatacagt    720
aattgtgtca agtgtcaggc ccctttcgtg cttgtacaag cctccaacag aagtaccgag    780
tcgcaaaatg gggtcaattg atgttctcac atgttggtcc tatgactctc ggtttcttca    840
acgagactac cctaagaagc gttacatgtg tggtcagggt ggtgtgtcat gtatagatac    900
agagcgagca cgactcacat ggagaacaac ttctgtaaga gcagagaaac cttaacagga    960
taataataaa taaatcgact cttcttgtga tgtcttttcg cttgttgtac cccacatttg   1020
tgatctgacg taaaagtggg cctgtgcttt gttatcgaga atcacatttc acactaatta   1080
gtgcacgact agtagcacgc agagttgcat gtcagtagtt attgtggatc ccgactactg   1140
tacggtatgt agttatgagc gacttatcat gaactagttt gctcgttatg gcgcgccagc   1200
tgcattaatg aatcggccaa cgcgcgggga gaggcggttt gcgtattggg cgctcttccg   1260
cttcctcgct cactgactcg ctgcgctcgg tcgttcggct gcggcgagcg gtatcagctc   1320
actcaaaggc ggtaatacgg ttatccacag aatcagggga taacgcagga aagaacatgt   1380
gagcaaaagg ccagcaaaag gccaggaacc gtaaaaaggc cgcgttgctg gcgtttttcc   1440
ataggctccg cccccctgac gagcatcaca aaaatcgacg ctcaagtcag aggtggcgaa   1500
acccgacagg actataaaga taccaggcgt ttccccctgg aagctccctc gtgcgctctc   1560
ctgttccgac cctgccgctt accggatacc tgtccgcctt tctcccttcg ggaagcgtgg   1620
cgctttctca tagctcacgc tgtaggtatc tcagttcggt gtaggtcgtt cgctccaagc   1680
tgggctgtgt gcacgaaccc cccgttcagc ccgaccgctg cgccttatcc ggtaactatc   1740
gtcttgagtc caacccggta agacacgact tatcgccact ggcagcagcc actggtaaca   1800
ggattagcag agcgaggtat gtaggcggtg ctacagagtt cttgaagtgg tggcctaact   1860
acggctacac tagaagaaca gtatttggta tctgcgctct gctgaagcca gttaccttcg   1920
gaaaaagagt tggtagctct tgatccggca aacaaaccac cgctggtagc ggtggttttt   1980
ttgtttgcaa gcagcagatt acgcgcagaa aaaaaggatc tcaagaagat cctttgatct   2040
tttctacggg gtctgacgct cagtggaacg aaaactcacg ttaagggatt ttggtcatga   2100
gattatcaaa aaggatcttc acctagatcc ttttaaatta aaaatgaagt tttaaatcaa   2160
tctaaagtat atatgagtaa acttggtctg acagttacca atgcttaatc agtgaggcac   2220
ctatctcagc gatctgtcta tttcgttcat ccatagttgc ctgactcccc gtcgtgtaga   2280
taactacgat acgggagggc ttaccatctg gccccagtgc tgcaatgata ccgcgagacc   2340
```

-continued

```
cacgctcacc ggctccagat ttatcagcaa taaaccagcc agccggaagg gccgagcgca   2400
gaagtggtcc tgcaacttta tccgcctcca tccagtctat taattgttgc cgggaagcta   2460
gagtaagtag ttcgccagtt aatagtttgc gcaacgttgt tgccattgct acaggcatcg   2520
tggtgtcacg ctcgtcgttt ggtatggctt cattcagctc cggttcccaa cgatcaaggc   2580
gagttacatg atcccccatg ttgtgcaaaa aagcggttag ctccttcggt cctccgatcg   2640
ttgtcagaag taagttggcc gcagtgttat cactcatggt tatggcagca ctgcataatt   2700
ctcttactgt catgccatcc gtaagatgct tttctgtgac tggtgagtac tcaaccaagt   2760
cattctgaga atagtgtatg cggcgaccga gttgctcttg cccggcgtca atacgggata   2820
ataccgcgcc acatagcaga actttaaaag tgctcatcat tggaaaacgt tcttcggggc   2880
gaaaactctc aaggatctta ccgctgttga gatccagttc gatgtaaccc actcgtgcac   2940
ccaactgatc ttcagcatct tttactttca ccagcgtttc tgggtgagca aaaacaggaa   3000
ggcaaaatgc cgcaaaaaag ggaataaggg cgacacggaa atgttgaata ctcatactct   3060
tcctttttca atattattga agcatttatc agggttattg tctcatgagc ggatacatat   3120
ttgaatgtat ttagaaaaat aaacaaatag gggttccgcg cacatttccc cgaaaagtgc   3180
cacctgatgc ggtgtgaaat accgcacaga tgcgtaagga gaaaataccg catcaggaaa   3240
ttgtaagcgt taatattttg ttaaaattcg cgttaaattt ttgttaaatc agctcatttt   3300
ttaaccaata ggccgaaatc ggcaaaatcc cttataaatc aaaagaatag accgagatag   3360
ggttgagtgt tgttccagtt tggaacaaga gtccactatt aaagaacgtg gactccaacg   3420
tcaaagggcg aaaaaccgtc tatcagggcg atggcccact acgtgaacca tcaccctaat   3480
caagtttttt ggggtcgagg tgccgtaaag cactaaatcg gaaccctaaa gggagccccc   3540
gatttagagc ttgacgggga aagccggcga acgtggcgag aaaggaaggg aagaaagcga   3600
aaggagcggg cgctagggcg ctggcaagtg tagcggtcac gctgcgcgta accaccacac   3660
ccgccgcgct taatgcgccg ctacagggcg cgtccattcg ccattcaggc tgcgcaactg   3720
ttgggaaggg cgatcggtgc gggcctcttc gctattacgc cagctggcga aggggggatg   3780
tgctgcaagg cgattaagtt gggtaacgcc agggttttcc cagtcacgac gttgtaaaac   3840
gacggccagt gaattgtaat acgactcact atagggcgaa ttgggcccga cgtcgcatgc   3900
tcaaatttca agactcatat cgagtctagt cggaacaggc gcgccagagt tgggttgggg   3960
acgatgtatg tccaggtacc ctgctcatac aagtacagta tatcctaggt gcaaaaaaag   4020
aaggtatttg tcttatatac cggtactagc acatgtgaat ctatgtttag tctcaagtat   4080
attcattaac atgccctcaa tcgtttctgt ttactttcag atactccttt ggtgcctatg   4140
gttccacaga atccacaatg atactgtaga aggggactac gtgaagtaga ataaaaccag   4200
cttttctgga aacttgtctg ttctatcacc tgttggtcat gtcagtttcc gcgttcttca   4260
cacccacccc cctaataata caacacaata aaatcattga aacaagagcg atgcgaccct   4320
cagtccagca aaccactctg gaaatattga gaaacaaaag acctacagta atacaattgt   4380
ggcatctata gaataggaaa tttaatatgt gcaactgtcc attctctcga cctgtacttc   4440
tacacgattg tcaaaagata ttatcatagt ctacagtaat ttatacagat tgaaagaggg   4500
tcattcaaat atggaagctg gtggtcaaag atcatcccca gtcactctct tctaccttct   4560
aaaagatggt ggaaccgttg gcaagacctc cgtagagcca agtaccttca aacttgcgcc   4620
ctctctccag atctcgacgt ccaatattga gagtgcataa agagatccag tcaaagtagg   4680
ccaggtggtt cttgacaatg tctaaccgag caagagcgtt aaagtccttt ctgtaacagc   4740
```

-continued

```
tcatactctt aattaagttg cgacacatgt cttgatagta tcttgaattc tctctcttga   4800
gcttttccat aacaagttct tctgcctcca ggaagtccat cggtggtttg atcatggttt   4860
tggtgtagtg gtagtgcagt ggtggtattg tgactgggga tgtagttgag aataagtcat   4920
acacaagtca gctttcttcg agcctcatat aagtataagt agttcaacgt attagcactg   4980
tacccagcat ctccgtatcg agaaacacaa caacatgccc cattggacag atcatgcgga   5040
tacacaggtt gtgcagtatc atacatactc gatcagacag gtcgtctgac catcatacaa   5100
gctgaacaag cgctccatac ttgcacgctc tctatataca cagttaaatt acatatccat   5160
agtctaacct ctaacagtta atcttctggt aagcctccca gccagccttc tggtatcgct   5220
tggcctcctc aataggatct cggttctggc cgtacagacc tcggccgaca attatgatat   5280
ccgttccggt agacatgaca tcctcaacag ttcggtactg ctgtccgaga gcgtctccct   5340
tgtcgtcaag acccaccccg ggggtcagaa taagccagtc ctcagagtcg cccttaggtc   5400
ggttctgggc aatgaagcca accacaaact cggggtcgga tcgggcaagc tcaatggtct   5460
gcttggagta ctcgccagtg gccagagagc ccttgcaaga cagctcggcc agcatgagca   5520
gacctctggc cagcttctcg ttgggagagg ggactaggaa ctccttgtac tgggagttct   5580
cgtagtcaga gacgtcctcc ttcttctgtt cagagacagt ttcctcggca ccagctcgca   5640
ggccagcaat gattccggtt ccgggtacac cgtgggcgtt ggtgatatcg gaccactcgg   5700
cgattcggtg acaccggtac tggtgcttga cagtgttgcc aatatctgcg aactttctgt   5760
cctcgaacag gaagaaaccg tgcttaagag caagttcctt gagggggagc acagtgccgg   5820
cgtaggtgaa gtcgtcaatg atgtcgatat gggttttgat catgcacaca taaggtccga   5880
ccttatcggc aagctcaatg agctccttgg tggtggtaac atccagagaa gcacacaggt   5940
tggttttctt ggctgccacg agcttgagca ctcgagcggc aaaggcggac ttgtggacgt   6000
tagctcgagc ttcgtaggag ggcattttgg tggtgaagag gagactgaaa taaatttagt   6060
ctgcagaact ttttatcgga accttatctg gggcagtgaa gtatatgtta tggtaatagt   6120
tacgagttag ttgaacttat agatagactg gactatacgg ctatcggtcc aaattagaaa   6180
gaacgtcaat ggctctctgg gcgtcgcctt tgccgacaaa aatgtgatca tgatgaaagc   6240
cagcaatgac gttgcagctg atattgttgt cggccaaccg cgccgaaaac gcagctgtca   6300
gacccacagc ctccaacgaa gaatgtatcg tcaaagtgat ccaagcacac tcatagttgg   6360
agtcgtactc caaaggcggc aatgacgagt cagacagata ctcgtcgacc ttttccttgg   6420
gaaccaccac cgtcagccct tctgactcac gtattgtagc caccgacaca ggcaacagtc   6480
cgtggatagc agaatatgtc ttgtcggtcc atttctcacc aactttaggc gtcaagtgaa   6540
tgttgcagaa gaagtatgtg ccttcattga gaatcggtgt tgctgatttc aataaagtct   6600
tgagatcagt ttggccagtc atgttgtggg gggtaattgg attgagttat cgcctacagt   6660
ctgtacaggt atactcgctg cccactttat actttttgat tccgctgcac ttgaagcaat   6720
gtcgtttacc aaaagtgaga atgctccaca gaacacaccc cagggtatgg ttgagcaaaa   6780
aataaacact ccgatacggg gaatcgaacc ccggtctcca cggttctcaa gaagtattct   6840
tgatgagagc gtatcgatga gcctaaaatg aacccgagta tatctcataa aattctcggt   6900
gagaggtctg tgactgtcag tacaaggtgc cttcattatg ccctcaacct taccatacct   6960
cactgaatgt agtgtacctc taaaaatgaa atacagtgcc aaaagccaag gcactgagct   7020
cgtctaacgg acttgatata caaccaatta aaacaaatga aaagaaatac agttctttgt   7080
```

-continued

```
atcatttgta acaattaccc tgtacaaact aaggtattga aatcccacaa tattcccaaa   7140
gtccacccct ttccaaattg tcatgcctac aactcatata ccaagcacta acctaccgtt   7200
taaacagtgt acgcagtact atagaggaac aattgccccg gagaagacgg ccaggccgcc   7260
tagatgacaa attcaacaac tcacagctga ctttctgcca ttgccactag gggggggcct   7320
ttttatatgg ccaagccaag ctctccacgt cggttgggct gcacccaaca ataaatgggt   7380
agggttgcac caacaaaggg atgggatggg gggtagaaga tacgaggata acggggctca   7440
atggcacaaa taagaacgaa tactgccatt aagactcgtg atccagcgac tgacaccatt   7500
gcatcatcta agggcctcaa aactacctcg gaactgctgc gctgatctgg acaccacaga   7560
ggttccgagc actttaggtt gcaccaaatg tcccaccagg tgcaggcaga aaacgctgga   7620
acagcgtgta cagtttgtct taacaaaaag tgagggcgct gaggtcgagc agggtggtgt   7680
gacttgttat agcctttaga gctgcgaaag cgcgtatgga tttggctcat caggccagat   7740
tgagggtctg tggacacatg tcatgttagt gtacttcaat cgccccctgg atatagcccc   7800
gacaataggc cgtggcctca tttttttgcc ttccgcacat ttccattgct cggtacccac   7860
accttgcttc tcctgcactt gccaacctta atactggttt acattgacca acatcttaca   7920
agcgggggc ttgtctaggg tatatataaa cagtggctct cccaatcggt tgccagtctc   7980
ttttttcctt tctttcccca cagattcgaa atctaaacta cacatcacac catggtcgga   8040
tacaccatct cctcgaagcc cgtgtccgtc gaggttggcc ccgccaagcc tggcgagact   8100
gctccccgac ggaacgtcat tgccaaggac gctcctgtgg tcttccccga caacgattcg   8160
tccctcacca ctgtctacaa gctgttcaaa aagtacgccg agatcaactc cgaacgaaag   8220
gctatgggat ggcgagacac catcgacatt cacgtggaga ccaagcaggt cacaaaggtg   8280
gtcgacggcg tggagaagaa agtgcccaag gaatggaagt acttcgagat gggtccttac   8340
aagtggctgt cctacaagga ggccctcaag ctggttcacg attatggagc tggtcttcga   8400
catctcggca tcaagcccaa agagaagatg cacatttacg cacagacctc tcaccgatgg   8460
atgctttccg gactggcctc tctctcgcag ggcattccca tcgtcactgc ctacgacacc   8520
cttggagagg aaggtctcac acgatctctg caggagacca actccgtcat catgttcacg   8580
gacaaggctc ttctgtcgtc tctcaaggtg tccctcaaaa agggcaccga tctgcgaatc   8640
attatctacg gaggcgacct gactcccgat gacaagaaag ccggaaacac cgagatcgac   8700
gccatcaagg agattgttcc agacatgaag atctacacta tggacgaggt tgtcgctctc   8760
ggtcgagagc atcctcaccc cgtggaagag gtcgactacg aggatctggc cttcatcatg   8820
tacacctctg gctccacagg agttcccaag ggtgtcgtgc tgcagcacaa gcagatcctc   8880
gcctctgtgg ccggtgtcac caagattatc gacagatcca ttatcggcaa tacagatcga   8940
ctgctcaact ttcttcccct cgcacacatc ttcgagtttg tgttcgagat ggtcaccttc   9000
tggtggggtg cctctctggg ctacggaact gtcaagacca tttccgacct gtcgatgaag   9060
aactgcaagg gagacatccg agagctcaag cccaccatca tggtcggcgt tccagctgtc   9120
tgggaaccca tgcggaaggg tattcttggc aaaatcaagg agctgtctcc tctcatgcag   9180
cgagtcttct gggcctcctt tgctgccaag caacgtctcg acgagaacgg acttcccggt   9240
ggctctattc tggattcgct catcttcaag aaagtcaagg acgccactgg aggctgtctc   9300
cgatacgtgt gcaacggagg tgctccagtt tccgtcgaca cccagaagtt cattactacc   9360
cttatctgtc ccatgctcat tggatgcggt ctgaccgaga ctacagccaa caccactatc   9420
atgtctccca agtcctatgc ctttggcacc attggagagc ctactgcagc cgtcaccctc   9480
```

aagcttatcg acgtgcccga agctggctac ttcgccgaga acaatcaggg agagctgtgc 9540
atcaagggca acgtggtcat gaaggagtat tacaagaacg aggaagagac caagaaagcg 9600
ttctccgacg atggctactt tctcaccgga gacattgccg agtggactgc caatggtcag 9660
cttcgaatta tcgacagacg aaagaacctc gtcaagaccc agaacggaga gtacattgct 9720
ctggagaagc tcgaaacaca gtaccgatcg tcttcctacg ttgccaacct gtgcgtctac 9780
gccgaccaga accgagtcaa gcccatcgct ctggtcattc ccaacgaggg tcctaccaaa 9840
aagcttgccc agagcttggg cgtggattcc gacgactggg atgccgtctg ttccaacaag 9900
aaagtggtca aggctgttct caaggacatg ctggataccg gacgatctct cggtctgtcc 9960
ggcatcgagc tgctgcaagg aatcgtgttg ctgcctggcg agtggactcc ccagaacagc 10020
tacctcaccg ctgcccagaa gctcaaccga aagaagattg tcgatgacaa caaaaaggag 10080
atcgacgagt gctacgagca gtcctaagc 10109

<210> SEQ ID NO 68
<211> LENGTH: 9037
<212> TYPE: DNA
<213> ORGANISM: artificial sequence
<220> FEATURE:
<223> OTHER INFORMATION: Plasmid pZP2-YlACoS-5PS3s

<400> SEQUENCE: 68
ggccgcaagt gtggatgggg aagtgagtgc ccggttctgt gtgcacaatt ggcaatccaa 60
gatggatgga ttcaacacag ggatatagcg agctacgtgg tggtgcgagg atatagcaac 120
ggatatttat gtttgacact tgagaatgta cgatacaagc actgtccaag tacaatacta 180
aacatactgt acatactcat actcgtaccc gggcaacggt ttcacttgag tgcagtggct 240
agtgctctta ctcgtacagt gtgcaatact gcgtatcata gtctttgatg tatatcgtat 300
tcattcatgt tagttgcgta cgggcgtcgt tgcttgtgtg atttttgagg acccatccct 360
ttggtatata agtatactct ggggttaagg ttgcccgtgt agtctaggtt atagttttca 420
tgtgaaatac cgagagccga gggagaataa acgggggtat ttggacttgt ttttttcgcg 480
gaaaagcgtc gaatcaaccc tgcgggcctt gcaccatgtc cacgacgtgt ttctcgcccc 540
aattcgcccc ttgcacgtca aaattaggcc tccatctaga cccctccata acatgtgact 600
gtggggaaaa gtataaggga aaccatgcaa ccatagacga cgtgaaagac ggggaggaac 660
caatggaggc caaagaaatg gggtagcaac agtccaggag acagacaagg agacaaggag 720
agggcgcccg aaagatcgga aaaacaaaca tgtccaattg gggcagtgac ggaaacgaca 780
cggacacttc agtacaatgg accgaccatc tccaagccag ggttattccg gtatcacctt 840
ggccgtaacc tcccgctggt acctgatatt gtacacgttc acattcaata tactttcagc 900
tacaataaga gaggctgttt gtcgggcatg tgtgtccgtc gtatggggtg atgtccgagg 960
gcgaaattcg ctacaagctt aactctggcg cttgtccagt atgaatagac aagtcaagac 1020
cagtggtgcc atgattgaca gggaggtaca agacttcgat actcgagcat tactcggact 1080
tgtggcgatt gaacagacgg gcgatcgctt ctccccccgta ttgccggcgc gccagctgca 1140
ttaatgaatc ggccaacgcg cggggagagg cggtttgcgt attgggcgct cttccgcttc 1200
ctcgctcact gactcgctgc gctcggtcgt tcggctgcgg cgagcggtat cagctcactc 1260
aaaggcggta atacggttat ccacagaatc aggggataac gcaggaaaga acatgtgagc 1320
aaaaggccag caaaaggcca ggaaccgtaa aaaggccgcg ttgctggcgt ttttccatag 1380

-continued

```
gctccgcccc cctgacgagc atcacaaaaa tcgacgctca agtcagaggt ggcgaaaccc   1440
gacaggacta taaagatacc aggcgtttcc ccctggaagc tccctcgtgc gctctcctgt   1500
tccgaccctg ccgcttaccg gatacctgtc cgcctttctc ccttcgggaa gcgtggcgct   1560
ttctcatagc tcacgctgta ggtatctcag ttcggtgtag gtcgttcgct ccaagctggg   1620
ctgtgtgcac gaaccccccg ttcagcccga ccgctgcgcc ttatccggta actatcgtct   1680
tgagtccaac ccggtaagac acgacttatc gccactggca gcagccactg gtaacaggat   1740
tagcagagcg aggtatgtag gcggtgctac agagttcttg aagtggtggc ctaactacgg   1800
ctacactaga agaacagtat ttggtatctg cgctctgctg aagccagtta ccttcggaaa   1860
aagagttggt agctcttgat ccggcaaaca aaccaccgct ggtagcggtg gtttttttgt   1920
ttgcaagcag cagattacgc gcagaaaaaa aggatctcaa gaagatcctt tgatcttttc   1980
tacggggtct gacgctcagt ggaacgaaaa ctcacgttaa gggattttgg tcatgagatt   2040
atcaaaaagg atcttcacct agatcctttt aaattaaaaa tgaagtttta aatcaatcta   2100
aagtatatat gagtaaactt ggtctgacag ttaccaatgc ttaatcagtg aggcacctat   2160
ctcagcgatc tgtctatttc gttcatccat agttgcctga ctccccgtcg tgtagataac   2220
tacgatacgg gagggcttac catctggccc cagtgctgca atgataccgc gagacccacg   2280
ctcaccggct ccagatttat cagcaataaa ccagccagcc ggaagggccg agcgcagaag   2340
tggtcctgca actttatccg cctccatcca gtctattaat tgttgccggg aagctagagt   2400
aagtagttcg ccagttaata gtttgcgcaa cgttgttgcc attgctacag gcatcgtggt   2460
gtcacgctcg tcgtttggta tggcttcatt cagctccggt tcccaacgat caaggcgagt   2520
tacatgatcc cccatgttgt gcaaaaaagc ggttagctcc ttcggtcctc cgatcgttgt   2580
cagaagtaag ttggccgcag tgttatcact catggttatg gcagcactgc ataattctct   2640
tactgtcatg ccatccgtaa gatgcttttc tgtgactggt gagtactcaa ccaagtcatt   2700
ctgagaatag tgtatgcggc gaccgagttg ctcttgcccg gcgtcaatac gggataatac   2760
cgcgccacat agcagaactt taaaagtgct catcattgga aaacgttctt cggggcgaaa   2820
actctcaagg atcttaccgc tgttgagatc cagttcgatg taacccactc gtgcacccaa   2880
ctgatcttca gcatctttta ctttcaccag cgtttctggg tgagcaaaaa caggaaggca   2940
aaatgccgca aaaaagggaa taagggcgac acggaaatgt tgaatactca tactcttcct   3000
ttttcaatat tattgaagca tttatcaggg ttattgtctc atgagcggat acatatttga   3060
atgtatttag aaaaataaac aaataggggt tccgcgcaca tttccccgaa aagtgccacc   3120
tgatgcggtg tgaaataccg cacagatgcg taaggagaaa ataccgcatc aggaaattgt   3180
aagcgttaat attttgttaa aattcgcgtt aaatttttgt taaatcagct cattttttaa   3240
ccaataggcc gaaatcggca aaatccctta taaatcaaaa gaatagaccg agatagggtt   3300
gagtgttgtt ccagtttgga acaagagtcc actattaaag aacgtggact ccaacgtcaa   3360
agggcgaaaa accgtctatc agggcgatgg cccactacgt gaaccatcac cctaatcaag   3420
ttttttgggg tcgaggtgcc gtaaagcact aaatcggaac cctaaaggga gcccccgatt   3480
tagagcttga cggggaaagc cggcgaacgt ggcgagaaag gaagggaaga aagcgaaagg   3540
agcgggcgct agggcgctgg caagtgtagc ggtcacgctg cgcgtaacca ccacacccgc   3600
cgcgcttaat gcgccgctac agggcgcgtc cattcgccat tcaggctgcg caactgttgg   3660
gaagggcgat cggtgcgggc ctcttcgcta ttacgccagc tggcgaaagg gggatgtgct   3720
gcaaggcgat taagttgggt aacgccaggg ttttcccagt cacgacgttg taaaacgacg   3780
```

-continued

```
gccagtgaat tgtaatacga ctcactatag ggcgaattgg gcccgacgtc gcatgcgctg   3840
atgacacttt ggtctgaaag agatgcattt tgaatcccaa acttgcagtg cccaagtgac   3900
atacatctcc gcgttttgga aaatgttcag aaacagttga ttgtgttgga atggggaatg   3960
gggaatggaa aaatgactca agtatcaatt ccaaaaactt ctctggctgg cagtacctac   4020
tgtccatact actgcatttt ctccagtcag gccactctat actcgacgac acagtagtaa   4080
aacccagata atttcgacat aaacaagaaa acagacccaa taatatttat atatagtcag   4140
ccgtttgtcc agttcagact gtaatagccg aaaaaaaatc caaagtttct attctaggaa   4200
aatatattcc aatattttta attcttaatc tcatttattt tattctagcg aaatacattt   4260
cagctacttg agacatgtga tacccacaaa tcggattcgg actcggttgt tcagaagagc   4320
atatggcatt cgtgctcgct tgttcacgta ttcttcctgt tccatctctt ggccgacaat   4380
cacacaaaaa tggggttttt tttttaattc taatgattca ttacagcaaa attgagatat   4440
agcagaccac gtattccata atcaccaagg aagttcttgg gcgtcttaat taagtcatac   4500
acaagtcagc tttcttcgag cctcatataa gtataagtag ttcaacgtat tagcactgta   4560
cccagcatct ccgtatcgag aaacacaaca acatgcccca ttggacagat catgcggata   4620
cacaggttgt gcagtatcat acatactcga tcagacaggt cgtctgacca tcatacaagc   4680
tgaacaagcg ctccatactt gcacgctctc tatatacaca gttaaattac atatccatag   4740
tctaacctct aacagttaat cttctggtaa gcctcccagc cagccttctg gtatcgcttg   4800
gcctcctcaa taggatctcg gttctggccg tacagacctc ggccgacaat tatgatatcc   4860
gttccggtag acatgacatc ctcaacagtt cggtactgct gtccgagagc gtctcccttg   4920
tcgtcaagac ccaccccggg ggtcagaata agccagtcct cagagtcgcc cttaggtcgg   4980
ttctgggcaa tgaagccaac cacaaactcg gggtcggatc gggcaagctc aatggtctgc   5040
ttggagtact cgccagtggc cagagagccc ttgcaagaca gctcggccag catgagcaga   5100
cctctggcca gcttctcgtt gggagagggg actaggaact ccttgtactg ggagttctcg   5160
tagtcagaga cgtcctcctt cttctgttca gagacagttt cctcggcacc agctcgcagg   5220
ccagcaatga ttccggttcc gggtacaccg tgggcgttgg tgatatcgga ccactcggcg   5280
attcggtgac accggtactg gtgcttgaca gtgttgccaa tatctgcgaa ctttctgtcc   5340
tcgaacagga agaaaccgtg cttaagagca agttccttga gggggagcac agtgccggcg   5400
taggtgaagt cgtcaatgat gtcgatatgg gttttgatca tgcacacata aggtccgacc   5460
ttatcggcaa gctcaatgag ctccttggtg gtggtaacat ccagagaagc acacaggttg   5520
gttttcttgg ctgccacgag cttgagcact cgagcggcaa aggcggactt gtggacgtta   5580
gctcgagctt cgtaggaggg cattttggtg gtgaagagga gactgaaata aatttagtct   5640
gcagaacttt ttatcggaac cttatctggg gcagtgaagt atatgttatg gtaatagtta   5700
cgagttagtt gaacttatag atagactgga ctatacggct atcggtccaa attagaaaga   5760
acgtcaatgg ctctctgggc gtcgcctttg ccgacaaaaa tgtgatcatg atgaaagcca   5820
gcaatgacgt tgcagctgat attgttgtcg gccaaccgcg ccgaaaacgc agctgtcaga   5880
cccacagcct ccaacgaaga atgtatcgtc aaagtgatcc aagcacactc atagttggag   5940
tcgtactcca aaggcggcaa tgacgagtca gacagatact cgtcaaacgg taggttagtg   6000
cttggtatat gagttgtagg catgacaatt tggaaagggg tggactttgg gaatattgtg   6060
ggatttcaat accttagttt gtacagggta attgttacaa atgatacaaa gaactgtatt   6120
```

tcttttcatt tgttttaatt ggttgtatat caagtccgtt agacgagctc agtgccttgg 6180
cttttggcac tgtatttcat ttttagaggt acactacatt cagtgaggta tggtaaggtt 6240
gagggcataa tgaaggcacc ttgtactgac agtcacagac ctctcaccga gaattttatg 6300
agatatactc gggttcattt taggctcatc gattgccccg gagaagacgg ccaggccgcc 6360
tagatgacaa attcaacaac tcacagctga ctttctgcca ttgccactag gggggggcct 6420
ttttatatgg ccaagccaag ctctccacgt cggttgggct gcacccaaca ataaatgggt 6480
agggttgcac caacaaaggg atgggatggg gggtagaaga tacgaggata acggggctca 6540
atggcacaaa taagaacgaa tactgccatt aagactcgtg atccagcgac tgacaccatt 6600
gcatcatcta agggcctcaa aactacctcg gaactgctgc gctgatctgg acaccacaga 6660
ggttccgagc actttaggtt gcaccaaatg tcccaccagg tgcaggcaga aaacgctgga 6720
acagcgtgta cagtttgtct taacaaaaag tgagggcgct gaggtcgagc agggtggtgt 6780
gacttgttat agcctttaga gctgcgaaag cgcgtatgga tttggctcat caggccagat 6840
tgagggtctg tggacacatg tcatgttagt gtacttcaat cgccccctgg atatagcccc 6900
gacaataggc cgtggcctca tttttttgcc ttccgcacat ttccattgct cggtacccac 6960
accttgcttc tcctgcactt gccaacctta atactggttt acattgacca acatcttaca 7020
agcggggggc ttgtctaggg tatatataaa cagtggctct cccaatcggt tgccagtctc 7080
ttttttcctt tctttcccca cagattcgaa atctaaacta cacatcacag aattccgagc 7140
cgtgagtatc cacgacaaga tcagtgtcga gacgacgcgt tttgtgtaat gacacaatcc 7200
gaaagtcgct agcaacacac actctctaca caaactaacc cagctctggt accatggcct 7260
caatcattca caagtctcct gtgcccgacg ttcagctgtt ctacggttcc tggccagatc 7320
tcatgcgaac ctctcctcat gcccacaacg actccaaacc cgtggtcttt gacttcgata 7380
ccaagcagca acttacttgg aagcaggtct ggcaactcag cgctcgactc agagcccagc 7440
tgtaccacaa gtacggaatc ggcaaacccg gtgctcttgc acctttccac aacgatccct 7500
ctctcggaga cgtggtcatc ttctacactc ccaacaccta cagctcgttg ccctatcatc 7560
tggctcttca cgatctcgga gccaccattt ctcctgcctc cacatcttac gacgtcaagg 7620
acatttgcca tcagatcgtt actaccgatg cggtcgtggt tgtcgctgca gccgagaaat 7680
ccgagattgc tcgagaggcc gttcagctgt ctggtcgaga cgtcagagtt gtggtcatgg 7740
aggacctcat caacaatgct cccaccgttg cgcagaacga tatcgactcg gcacctcatg 7800
tgtccctgtc tcgggaccag gctcgagcca agattgcata cctgggcatg tcttccggta 7860
cgtctggcgg acttcccaag gctgttcgtc tcactcactt caacgttacc tcgaactgtc 7920
tgcaggtctc cgctgccgca cccaaccttg cccagaacgt ggttgccagc gccgtcattc 7980
caaccactca catctacggt ctcaccatgt ttctgtcggt tcttccctac aacggttccg 8040
tggtcattca tcacaagcaa ttcaacttgc gagatctgct cgaggctcag aagacataca 8100
aggtctctct gtggattctc gttcctcccg tcatcgtgca gcttgccaag aaccctatgg 8160
tcgacgagta cctggactcc attcgagccc atgtgcggtg catcgtctct ggagctgctc 8220
ctctcggtgg caatgtcgtg gatcaggttt cggttcgtct taccggcaac aaggaaggca 8280
ttctgcccaa cggagacaag ctcgtcattc atcaagccta cggtcttacc gagtcctctc 8340
ccatcgttgg aatgctcgat cctctgtcgg accacatcga cgtcatgact gtgggctgtc 8400
tcatgcccaa taccgaggct cgaattgtcg acgaagaggg aaacgatcag ccagcagtcc 8460
acgttaccga cacacgaggc atcggtgccg ctgtcaagcg aggcgagaag attccctccg 8520

```
gagaactctg gattcgaggt cctcagatca tggacggata ccacaagaac cccgagtcgt   8580

ctcgtgagtc cctggaaccc agcacagaga cctacggtct gcaacatttc caggacagat   8640

ggcttcgaac tggagacgtt gctgtcatcg acaccttcgg acgagtcatg gttgtggatc   8700

gaaccaagga gctcatcaag tccatgtctc gacaggttgc tcctgccgag ctcgaagctc   8760

ttctgctcaa ccatccttcc gtcaacgatg tggctgtcgt tggcgtccac aacgacgata   8820

atggcacaga gtcagcacga gcgtttgtcg ttcttcaacc aggcgacgcc tgtgatccta   8880

ctaccatcaa gcactggatg gaccagcaag ttccctccta caagcggctg tacggaggca   8940

ttgtggtcat cgacactgtt cccaagaatg cctctggcaa gattctgcga agactgcttc   9000

gacagcggag agacgatcga gtctggggtc tgtaagc                            9037
```

<210> SEQ ID NO 69
<211> LENGTH: 3663
<212> TYPE: DNA
<213> ORGANISM: artificial sequence
<220> FEATURE:
<223> OTHER INFORMATION: pET23d plasmid

<400> SEQUENCE: 69

```
atccggatat agttcctcct ttcagcaaaa aacccctcaa gacccgttta gaggccccaa     60

ggggttatgc tagttattgc tcagcggtgg cagcagccaa ctcagcttcc tttcgggctt    120

tgttagcagc cggatctcag tggtggtggt ggtggtgctc gagtgcggcc gcaagcttgt    180

cgacggagct cgaattcgga tccgacccat ttgctgtcca ccagtcatgc tagccatggt    240

atatctcctt cttaaagtta aacaaaatta tttctagagg gaaaccgttg tggtctccct    300

atagtgagtc gtattaattt cgcgggatcg agatctcggg cagcgttggg tcctggccac    360

gggtgcgcat gatcgtgctc ctgtcgttga ggacccggct aggctggcgg ggttgcctta    420

ctggttagca gaatgaatca ccgatacgcg agcgaacgtg aagcgactgc tgctgcaaaa    480

cgtctgcgac ctgagcaaca acatgaatgg tcttcggttt ccgtgtttcg taaagtctgg    540

aaacgcggaa gtcagcgccc tgcaccatta tgttccggat ctgcatcgca ggatgctgct    600

ggctaccctg tggaacacct acatctgtat taacgaagcg ctggcattga ccctgagtga    660

tttttctctg gtcccgccgc atccataccg ccagttgttt accctcacaa cgttccagta    720

accgggcatg ttcatcatca gtaacccgta tcgtgagcat cctctctcgt ttcatcggta    780

tcattacccc catgaacaga aatccccctt acacggaggc atcagtgacc aaacaggaaa    840

aaaccgccct taacatggcc cgctttatca gaagccagac attaacgctt ctggagaaac    900

tcaacgagct ggacgcggat gaacaggcag acatctgtga atcgcttcac gaccacgctg    960

atgagcttta ccgcagctgc ctcgcgcgtt tcggtgatga cggtgaaaac ctctgacaca   1020

tgcagctccc ggagacggtc acagcttgtc tgtaagcgga tgccgggagc agacaagccc   1080

gtcagggcgc gtcagcgggt gttggcgggt gtcggggcgc agccatgacc cagtcacgta   1140

gcgatagcgg agtgtatact ggcttaacta tgcggcatca gagcagattg tactgagagt   1200

gcaccatata tgcggtgtga aataccgcac agatgcgtaa ggagaaaata ccgcatcagg   1260

cgctcttccg cttcctcgct cactgactcg ctgcgctcgg tcgttcggct gcggcgagcg   1320

gtatcagctc actcaaaggc ggtaatacgg ttatccacag aatcagggga taacgcagga   1380

aagaacatgt gagcaaaagg ccagcaaaag gccaggaacc gtaaaaaggc cgcgttgctg   1440

gcgtttttcc ataggctccg cccccctgac gagcatcaca aaaatcgacg ctcaagtcag   1500
```

-continued

```
aggtggcgaa acccgacagg actataaaga taccaggcgt ttccccctgg aagctccctc   1560
gtgcgctctc ctgttccgac cctgccgctt accggatacc tgtccgcctt tctcccttcg   1620
ggaagcgtgg cgctttctca tagctcacgc tgtaggtatc tcagttcggt gtaggtcgtt   1680
cgctccaagc tgggctgtgt gcacgaaccc cccgttcagc ccgaccgctg cgccttatcc   1740
ggtaactatc gtcttgagtc caacccggta agacacgact tatcgccact ggcagcagcc   1800
actggtaaca ggattagcag agcgaggtat gtaggcggtg ctacagagtt cttgaagtgg   1860
tggcctaact acggctacac tagaaggaca gtatttggta tctgcgctct gctgaagcca   1920
gttaccttcg gaaaaagagt tggtagctct tgatccggca aacaaaccac cgctggtagc   1980
ggtggttttt ttgtttgcaa gcagcagatt acgcgcagaa aaaaaggatc tcaagaagat   2040
cctttgatct tttctacggg gtctgacgct cagtggaacg aaaactcacg ttaagggatt   2100
ttggtcatga gattatcaaa aaggatcttc acctagatcc ttttaaatta aaaatgaagt   2160
tttaaatcaa tctaaagtat atatgagtaa acttggtctg acagttacca atgcttaatc   2220
agtgaggcac ctatctcagc gatctgtcta tttcgttcat ccatagttgc ctgactcccc   2280
gtcgtgtaga taactacgat acgggagggc ttaccatctg gccccagtgc tgcaatgata   2340
ccgcgagacc cacgctcacc ggctccagat ttatcagcaa taaaccagcc agccggaagg   2400
gccgagcgca gaagtggtcc tgcaacttta tccgcctcca tccagtctat taattgttgc   2460
cgggaagcta gagtaagtag ttcgccagtt aatagtttgc gcaacgttgt tgccattgct   2520
gcaggcatcg tggtgtcacg ctcgtcgttt ggtatggctt cattcagctc cggttcccaa   2580
cgatcaaggc gagttacatg atcccccatg ttgtgcaaaa aagcggttag ctccttcggt   2640
cctccgatcg ttgtcagaag taagttggcc gcagtgttat cactcatggt tatggcagca   2700
ctgcataatt ctcttactgt catgccatcc gtaagatgct tttctgtgac tggtgagtac   2760
tcaaccaagt cattctgaga atagtgtatg cggcgaccga gttgctcttg cccggcgtca   2820
atacgggata ataccgcgcc acatagcaga actttaaaag tgctcatcat tggaaaacgt   2880
tcttcggggc gaaaactctc aaggatctta ccgctgttga gatccagttc gatgtaaccc   2940
actcgtgcac ccaactgatc ttcagcatct tttactttca ccagcgtttc tgggtgagca   3000
aaaacaggaa ggcaaaatgc cgcaaaaaag ggaataaggg cgacacggaa atgttgaata   3060
ctcatactct tcctttttca atattattga agcatttatc agggttattg tctcatgagc   3120
ggatacatat ttgaatgtat ttagaaaaat aaacaaatag gggttccgcg cacatttccc   3180
cgaaaagtgc cacctgaaat tgtaaacgtt aatattttgt taaaattcgc gttaaatttt   3240
tgttaaatca gctcattttt taaccaatag gccgaaatcg gcaaaatccc ttataaatca   3300
aaagaataga ccgagatagg gttgagtgtt gttccagttt ggaacaagag tccactatta   3360
aagaacgtgg actccaacgt caaagggcga aaaaccgtct atcagggcga tggcccacta   3420
cgtgaaccat caccctaatc aagttttttg gggtcgaggt gccgtaaagc actaaatcgg   3480
aaccctaaag ggagcccccg atttagagct tgacggggaa agccggcgaa cgtggcgaga   3540
aaggaaggga agaaagcgaa aggagcgggc gctagggcgc tggcaagtgt agcggtcacg   3600
ctgcgcgtaa ccaccacacc cgccgcgctt aatgcgccgc tacagggcgc gtcccattcg   3660
cca                                                                 3663
```

<210> SEQ ID NO 70
<211> LENGTH: 12712
<212> TYPE: DNA
<213> ORGANISM: artificial sequence
<220> FEATURE:
<223> OTHER INFORMATION: pY157 plasmid

<400> SEQUENCE: 70

```
ttgagaagcc cattgtatat tattaggatc gtagcattat tgtggcaaaa aatattcaag     60
tgctcatgtg aattgacacg atcacgtaaa tacctggtga aattgctagt attcgtgatg    120
ttctaataca actctgttca atatttccgg cgctctcttg tatacaagag cacaagacat    180
gcaccccaca ttaaccgagg tcaagtgttt atgtatgaaa agtgacataa atcgtccaaa    240
aaaaagtagc acatagttgt atggctgtaa gttatgtgat tgtcagttct tcggccttcc    300
aactcctatg caccgtcttc aatcatctac ccccgtgccc cacaccccgc actattagag    360
tttatcacag tcagctaaac tgcttgcaca tctacacctc tgactacacc accatggatt    420
tcttcagacg gcaccagaaa aaggtgctgg cactggtagg tgtggcgctg agttcctacc    480
tgtttatcga ctatgtgaag aaaaagttct tcgagatcca gggtcgtttg agctcggagc    540
gaaccgctaa acagaatctc cggcgccgat ttgaacagaa ccagcaggat gcagatttta    600
caatcatggc tctgctatcc agcttgacga caccggtaat ggagcgttac cccgtcgacc    660
agatcaaggc agagttacag agcaagagac gccccacaga ccgggttttg gctctcgaga    720
gctccacctc gtcctcagct accgcacaaa ccgtgcccac catgacaagt ggcgccacag    780
aggagggcga gaagttaatt aactttggcc ggcctttacc tgcaggataa cttcgtataa    840
tgtatgctat acgaagttat gaattctctc tcttgagctt ttccataaca agttcttctg    900
cctccaggaa gtccatgggt ggtttgatca tggttttggt gtagtggtag tgcagtggtg    960
gtattgtgac tggggatgta gttgagaata agtcatacac aagtcagctt tcttcgagcc   1020
tcatataagt ataagtagtt caacgtatta gcactgtacc cagcatctcc gtatcgagaa   1080
acacaacaac atgccccatt ggacagatca tgcggataca caggttgtgc agtatcatac   1140
atactcgatc agacaggtcg tctgaccatc atacaagctg aacaagcgct ccatacttgc   1200
acgctctcta tatacacagt taaattacat atccatagtc taacctctaa cagttaatct   1260
tctggtaagc ctcccagcca gccttctggt atcgcttggc ctcctcaata ggatctcggt   1320
tctggccgta cagacctcgg ccgacaatta tgatatccgt tccggtagac atgacatcct   1380
caacagttcg gtactgctgt ccgagagcgt ctcccttgtc gtcaagaccc accccggggg   1440
tcagaataag ccagtcctca gagtcgccct taggtcggtt ctgggcaatg aagccaacca   1500
caaactcggg gtcggatcgg gcaagctcaa tggtctgctt ggagtactcg ccagtggcca   1560
gagagccctt gcaagacagc tcggccagca tgagcagacc tctggccagc ttctcgttgg   1620
gagaggggac taggaactcc ttgtactggg agttctcgta gtcagagacg tcctccttct   1680
tctgttcaga gacagtttcc tcggcaccag ctcgcaggcc agcaatgatt ccggttccgg   1740
gtacaccgtg ggcgttggtg atatcggacc actcggcgat tcggtgacac cggtactggt   1800
gcttgacagt gttgccaata tctgcgaact ttctgtcctc gaacaggaag aaaccgtgct   1860
taagagcaag ttccttgagg gggagcacag tgccggcgta ggtgaagtcg tcaatgatgt   1920
cgatatgggt tttgatcatg cacacataag gtccgacctt atcggcaagc tcaatgagct   1980
ccttggtggt ggtaacatcc agagaagcac acaggttggt tttcttggct gccacgagct   2040
tgagcactcg agcggcaaag gcggacttgt ggacgttagc tcgagcttcg taggagggca   2100
ttttggtggt gaagaggaga ctgaaataaa tttagtctgc agaacttttt atcggaacct   2160
tatctggggc agtgaagtat atgttatggt aatagttacg agttagttga acttatagat   2220
```

-continued agactggact atacggctat cggtccaaat tagaaagaac gtcaatggct ctctgggcgt 2280
cgcctttgcc gacaaaaatg tgatcatgat gaaagccagc aatgacgttg cagctgatat 2340
tgttgtcggc caaccgcgcc gaaaacgcag ctgtcagacc cacagcctcc aacgaagaat 2400
gtatcgtcaa agtgatccaa gcacactcat agttggagtc gtactccaaa ggcggcaatg 2460
acgagtcaga cagatactcg tcgactcatc gatataactt cgtataatgt atgctatacg 2520
aagttatcct aggtatagat cttgcacttc ttattttctt cacgcgtttg cagctcaaca 2580
ttctaggacg acgaaactac gtcaacagtg ttgtcgctct ggcgcagcag ggccgagagg 2640
gtaatgccga gggtcgagtg gcgccctcgt ttggtgatct tgcagatatg ggctatttcg 2700
gcgacctttc aggctcgtcc agcttcggag aaactattgt cgatcccgat ctggacgaac 2760
agtaccttac cttttcgtgg tggctgctga acgagggatg ggtgtcgctg agcgagcgag 2820
tggaggaagc ggttcgtcga gtgtgggacc ccgtgtcacc caaggccgaa cttggatttg 2880
acgagttgtc ggaactcatt ggacgaacac agatgctcat tgatcgacct ctcaatccct 2940
cgtcgccact caactttctg agccagctgc tgccaccacg ggagcaggag gagtacgtgc 3000
ttgcccagaa ccccagcgat actgctgccc ccattgtagg acctaccctc cgacggcttc 3060
tggacgagac tgccgacttc atcgagtccc ctaatgccgc agaggtgatt gagcgacttg 3120
ttcactccgg tctctctgtg ttcatggaca agctggctgt cacgtttgga gccacacctg 3180
ctgattcggg ttcgccttat cctgtggtgc tgcctactgc aaaggtcaag ctgccctcca 3240
ttcttgccaa catggctcga caggctggag gcatggccca gggatcgccg ggcgtggaaa 3300
acgagtacat tgacgtgatg aaccaagtgc aggagctgac ctcctttagt gctgtggtct 3360
attcatcttt tgattgggct ctctagaggc tcattcacga aagacacgaa gaacgaagat 3420
ggggactgaa tacagcgctc tcatttgtac acaaatgatt tatgacagag taacttgtac 3480
atcatgtaga gcatacatac tgaaggtgtg atctcacggg atatcttgaa gaccactcgt 3540
agctggaggc ataggtagtg ctagtacgga tacttgcacc gtatccaaca taagtagagg 3600
agcctcctag tggctattgg tacaccgata aagatacaca tacatggcgc gccagctgca 3660
ttaatgaatc ggccaacgcg cggggagagg cggtttgcgt attgggcgct cttccgcttc 3720
ctcgctcact gactcgctgc gctcggtcgt tcggctgcgg cgagcggtat cagctcactc 3780
aaaggcggta atacggttat ccacagaatc aggggataac gcaggaaaga acatgtgagc 3840
aaaaggccag caaaaggcca ggaaccgtaa aaaggccgcg ttgctggcgt ttttccatag 3900
gctccgcccc cctgacgagc atcacaaaaa tcgacgctca agtcagaggt ggcgaaaccc 3960
gacaggacta taaagatacc aggcgtttcc ccctggaagc tccctcgtgc gctctcctgt 4020
tccgaccctg ccgcttaccg gatacctgtc cgcctttctc ccttcgggaa gcgtggcgct 4080
ttctcatagc tcacgctgta ggtatctcag ttcggtgtag gtcgttcgct ccaagctggg 4140
ctgtgtgcac gaaccccccg ttcagcccga ccgctgcgcc ttatccggta actatcgtct 4200
tgagtccaac ccggtaagac acgacttatc gccactggca gcagccactg gtaacaggat 4260
tagcagagcg aggtatgtag gcggtgctac agagttcttg aagtggtggc ctaactacgg 4320
ctacactaga agaacagtat ttggtatctg cgctctgctg aagccagtta ccttcggaaa 4380
aagagttggt agctcttgat ccggcaaaca aaccaccgct ggtagcggtg gtttttttgt 4440
ttgcaagcag cagattacgc gcagaaaaaa aggatctcaa gaagatcctt tgatcttttc 4500
tacggggtct gacgctcagt ggaacgaaaa ctcacgttaa gggattttgg tcatgagatt 4560
atcaaaaagg atcttcacct agatcctttt aaattaaaaa tgaagtttta aatcaatcta 4620

```
aagtatatat gagtaaactt ggtctgacag ttaccaatgc ttaatcagtg aggcacctat   4680
ctcagcgatc tgtctatttc gttcatccat agttgcctga ctccccgtcg tgtagataac   4740
tacgatacgg gagggcttac catctggccc cagtgctgca atgataccgc gagacccacg   4800
ctcaccggct ccagatttat cagcaataaa ccagccagcc ggaagggccg agcgcagaag   4860
tggtcctgca actttatccg cctccatcca gtctattaat tgttgccggg aagctagagt   4920
aagtagttcg ccagttaata gtttgcgcaa cgttgttgcc attgctacag gcatcgtggt   4980
gtcacgctcg tcgtttggta tggcttcatt cagctccggt tcccaacgat caaggcgagt   5040
tacatgatcc cccatgttgt gcaaaaaagc ggttagctcc ttcggtcctc cgatcgttgt   5100
cagaagtaag ttggccgcag tgttatcact catggttatg gcagcactgc ataattctct   5160
tactgtcatg ccatccgtaa gatgcttttc tgtgactggt gagtactcaa ccaagtcatt   5220
ctgagaatag tgtatgcggc gaccgagttg ctcttgcccg gcgtcaatac gggataatac   5280
cgcgccacat agcagaactt taaaagtgct catcattgga aaacgttctt cggggcgaaa   5340
actctcaagg atcttaccgc tgttgagatc cagttcgatg taacccactc gtgcacccaa   5400
ctgatcttca gcatctttta ctttcaccag cgtttctggg tgagcaaaaa caggaaggca   5460
aaatgccgca aaaaagggaa taagggcgac acggaaatgt tgaatactca tactcttcct   5520
ttttcaatat tattgaagca tttatcaggg ttattgtctc atgagcggat acatatttga   5580
atgtatttag aaaaataaac aaataggggt tccgcgcaca tttccccgaa aagtgccacc   5640
tgatgcggtg tgaaataccg cacagatgcg taaggagaaa ataccgcatc aggaaattgt   5700
aagcgttaat attttgttaa aattcgcgtt aaatttttgt taaatcagct cattttttaa   5760
ccaataggcc gaaatcggca aaatccctta taaatcaaaa gaatagaccg agatagggtt   5820
gagtgttgtt ccagtttgga acaagagtcc actattaaag aacgtggact ccaacgtcaa   5880
agggcgaaaa accgtctatc agggcgatgg cccactacgt gaaccatcac cctaatcaag   5940
ttttttgggg tcgaggtgcc gtaaagcact aaatcggaac cctaaaggga gcccccgatt   6000
tagagcttga cggggaaagc cggcgaacgt ggcgagaaag gaagggaaga aagcgaaagg   6060
agcgggcgct agggcgctgg caagtgtagc ggtcacgctg cgcgtaacca ccacacccgc   6120
cgcgcttaat gcgccgctac agggcgcgtc cattcgccat tcaggctgcg caactgttgg   6180
gaagggcgat cggtgcgggc ctcttcgcta ttacgccagc tggcgaaagg gggatgtgct   6240
gcaaggcgat taagttgggt aacgccaggg ttttcccagt cacgacgttg taaaacgacg   6300
gccagtgaat tgtaatacga ctcactatag ggcgaattgg gcccgacgtc gcatgcttga   6360
gaagcccatt gtatattatt aggatcgtag cattattgtg gcaaaaaata ttcaagtgct   6420
catgtgaatt gacacgatca cgtaaatacc tggtgaaatt gctagtattc gtgatgttct   6480
aatacaactc tgttcaatat ttccggcgct ctcttgtata caagagcaca agacatgcac   6540
cccacattaa ccgaggtcaa gtgtttatgt atgaaaagtg acataaatcg tccaaaaaaa   6600
agtagcacat agttgtatgg ctgtaagtta tgtgattgtc agttcttcgg ccttccaact   6660
cctatgcacc gtcttcaatc atctaccccc gtgccccaca ccccgcacta ttagagttta   6720
tcacagtcag ctaaactgct tgcacatcta cacctctgac tacaccacca tggatttctt   6780
cagacggcac cagaaaaagg tgctggcact ggtaggtgtg gcgctgagtt cctacctgtt   6840
tatcgactat gtgaagaaaa agttcttcga gatccagggt cgtttgagct cggagcgaac   6900
cgctaaacag aatctccggc gccgatttga acagaaccag caggatgcag atttacaat   6960
```

-continued

```
catggctctg ctatccagct tgacgacacc ggtaatggag cgttaccccg tcgaccagat   7020
caaggcagag ttacagagca agagacgccc cacagaccgg gttttggctc tcgagagctc   7080
cacctcgtcc tcagctaccg cacaaaccgt gcccaccatg acaagtggcg ccacagagga   7140
gggcgagaag ttaattaact ttggccggcc tttacctgca ggataacttc gtataatgta   7200
tgctatacga agttatgaat tctctctctt gagcttttcc ataacaagtt cttctgcctc   7260
caggaagtcc atgggtggtt tgatcatggt tttggtgtag tggtagtgca gtggtggtat   7320
tgtgactggg gatgtagttg agaataagtc atacacaagt cagctttctt cgagcctcat   7380
ataagtataa gtagttcaac gtattagcac tgtacccagc atctccgtat cgagaaacac   7440
aacaacatgc cccattggac agatcatgcg gatacacagg ttgtgcagta tcatacatac   7500
tcgatcagac aggtcgtctg accatcatac aagctgaaca agcgctccat acttgcacgc   7560
tctctatata cacagttaaa ttacatatcc atagtctaac ctctaacagt taatcttctg   7620
gtaagcctcc cagccagcct tctggtatcg cttggcctcc tcaataggat ctcggttctg   7680
gccgtacaga cctcggccga caattatgat atccgttccg gtagacatga catcctcaac   7740
agttcggtac tgctgtccga gagcgtctcc cttgtcgtca agacccaccc cgggggtcag   7800
aataagccag tcctcagagt cgcccttagg tcggttctgg gcaatgaagc caaccacaaa   7860
ctcggggtcg gatcgggcaa gctcaatggt ctgcttggag tactcgccag tggccagaga   7920
gcccttgcaa gacagctcgg ccagcatgag cagacctctg gccagcttct cgttgggaga   7980
ggggactagg aactccttgt actgggagtt ctcgtagtca gagacgtcct ccttcttctg   8040
ttcagagaca gtttcctcgg caccagctcg caggccagca atgattccgg ttccgggtac   8100
accgtgggcg ttggtgatat cggaccactc ggcgattcgg tgacaccggt actggtgctt   8160
gacagtgttg ccaatatctg cgaactttct gtcctcgaac aggaagaaac cgtgcttaag   8220
agcaagttcc ttgaggggga gcacagtgcc ggcgtaggtg aagtcgtcaa tgatgtcgat   8280
atgggttttg atcatgcaca cataaggtcc gaccttatcg gcaagctcaa tgagctcctt   8340
ggtggtggta acatccagag aagcacacag gttggttttc ttggctgcca cgagcttgag   8400
cactcgagcg gcaaaggcgg acttgtggac gttagctcga gcttcgtagg agggcatttt   8460
ggtggtgaag aggagactga aataaattta gtctgcagaa ctttttatcg gaaccttatc   8520
tggggcagtg aagtatatgt tatggtaata gttacgagtt agttgaactt atagatagac   8580
tggactatac ggctatcggt ccaaattaga aagaacgtca atggctctct gggcgtcgcc   8640
tttgccgaca aaaatgtgat catgatgaaa gccagcaatg acgttgcagc tgatattgtt   8700
gtcggccaac cgcgccgaaa acgcagctgt cagacccaca gcctccaacg aagaatgtat   8760
cgtcaaagtg atccaagcac actcatagtt ggagtcgtac tccaaaggcg gcaatgacga   8820
gtcagacaga tactcgtcga ctcatcgata taacttcgta taatgtatgc tatacgaagt   8880
tatcctaggt atagatcttg cacttcttat tttcttcacg cgtttgcagc tcaacattct   8940
aggacgacga aactacgtca acagtgttgt cgctctggcg cagcagggcc gagagggtaa   9000
tgccgagggt cgagtggcgc cctcgtttgg tgatcttgca gatatgggct atttcggcga   9060
cctttcaggc tcgtccagct tcggagaaac tattgtcgat cccgatctgg acgaacagta   9120
ccttaccttt tcgtggtggc tgctgaacga gggatgggtg tcgctgagcg agcgagtgga   9180
ggaagcggtt cgtcgagtgt gggaccccgt gtcacccaag gccgaacttg gatttgacga   9240
gttgtcggaa ctcattggac gaacacagat gctcattgat cgacctctca atccctcgtc   9300
gccactcaac tttctgagcc agctgctgcc accacgggag caggaggagt acgtgcttgc   9360
```

```
ccagaacccc agcgatactg ctgcccccat tgtaggacct accctccgac ggcttctgga    9420
cgagactgcc gacttcatcg agtcccctaa tgccgcagag gtgattgagc gacttgttca    9480
ctccggtctc tctgtgttca tggacaagct ggctgtcacg tttggagcca cacctgctga    9540
ttcgggttcg ccttatcctg tggtgctgcc tactgcaaag gtcaagctgc cctccattct    9600
tgccaacatg gctcgacagg ctggaggcat ggcccaggga tcgccgggcg tggaaaacga    9660
gtacattgac gtgatgaacc aagtgcagga gctgacctcc tttagtgctg tggtctattc    9720
atcttttgat tgggctctct agaggctcat tcacgaaaga cacgaagaac gaagatgggg    9780
actgaataca gcgctctcat ttgtacacaa atgatttatg acagagtaac ttgtacatca    9840
tgtagagcat acatactgaa ggtgtgatct cacgggatat cttgaagacc actcgtagct    9900
ggaggcatag gtagtgctag tacggatact tgcaccgtat ccaacataag tagaggagcc    9960
tcctagtggc tattggtaca ccgataaaga tacacataca tggcgcgcca gctgcattaa   10020
tgaatcggcc aacgcgcggg gagaggcggt ttgcgtattg ggcgctcttc cgcttcctcg   10080
ctcactgact cgctgcgctc ggtcgttcgg ctgcggcgag cggtatcagc tcactcaaag   10140
gcggtaatac ggttatccac agaatcaggg gataacgcag gaaagaacat gtgagcaaaa   10200
ggccagcaaa aggccaggaa ccgtaaaaag gccgcgttgc tggcgttttt ccataggctc   10260
cgcccccctg acgagcatca caaaaatcga cgctcaagtc agaggtggcg aaacccgaca   10320
ggactataaa gataccaggc gtttccccct ggaagctccc tcgtgcgctc tcctgttccg   10380
accctgccgc ttaccggata cctgtccgcc tttctccctt cgggaagcgt ggcgctttct   10440
catagctcac gctgtaggta tctcagttcg gtgtaggtcg ttcgctccaa gctgggctgt   10500
gtgcacgaac cccccgttca gcccgaccgc tgcgccttat ccggtaacta tcgtcttgag   10560
tccaacccgg taagacacga cttatcgcca ctggcagcag ccactggtaa caggattagc   10620
agagcgaggt atgtaggcgg tgctacagag ttcttgaagt ggtggcctaa ctacggctac   10680
actagaagaa cagtatttgg tatctgcgct ctgctgaagc cagttacctt cggaaaaaga   10740
gttggtagct cttgatccgg caaacaaacc accgctggta gcggtggttt ttttgtttgc   10800
aagcagcaga ttacgcgcag aaaaaaagga tctcaagaag atcctttgat cttttctacg   10860
gggtctgacg ctcagtggaa cgaaaactca cgttaaggga ttttggtcat gagattatca   10920
aaaaggatct tcacctagat ccttttaaat taaaaatgaa gttttaaatc aatctaaagt   10980
atatatgagt aaacttggtc tgacagttac caatgcttaa tcagtgaggc acctatctca   11040
gcgatctgtc tatttcgttc atccatagtt gcctgactcc ccgtcgtgta gataactacg   11100
atacgggagg gcttaccatc tggccccagt gctgcaatga taccgcgaga cccacgctca   11160
ccggctccag atttatcagc aataaaccag ccagccggaa gggccgagcg cagaagtggt   11220
cctgcaactt tatccgcctc catccagtct attaattgtt gccgggaagc tagagtaagt   11280
agttcgccag ttaatagttt gcgcaacgtt gttgccattg ctacaggcat cgtggtgtca   11340
cgctcgtcgt ttggtatggc ttcattcagc tccggttccc aacgatcaag gcgagttaca   11400
tgatccccca tgttgtgcaa aaaagcggtt agctccttcg gtcctccgat cgttgtcaga   11460
agtaagttgg ccgcagtgtt atcactcatg gttatggcag cactgcataa ttctcttact   11520
gtcatgccat ccgtaagatg cttttctgtg actggtgagt actcaaccaa gtcattctga   11580
gaatagtgta tgcggcgacc gagttgctct tgcccggcgt caatacggga taataccgcg   11640
ccacatagca gaactttaaa agtgctcatc attggaaaac gttcttcggg gcgaaaactc   11700
```

-continued

```
tcaaggatct taccgctgtt gagatccagt tcgatgtaac ccactcgtgc acccaactga  11760

tcttcagcat cttttacttt caccagcgtt tctgggtgag caaaaacagg aaggcaaaat  11820

gccgcaaaaa agggaataag ggcgacacgg aaatgttgaa tactcatact cttccttttt  11880

caatattatt gaagcattta tcagggttat tgtctcatga gcggatacat atttgaatgt  11940

atttagaaaa ataaacaaat aggggttccg cgcacatttc cccgaaaagt gccacctgat  12000

gcggtgtgaa ataccgcaca gatgcgtaag gagaaaatac cgcatcagga aattgtaagc  12060

gttaatattt tgttaaaatt cgcgttaaat ttttgttaaa tcagctcatt ttttaaccaa  12120

taggccgaaa tcggcaaaat cccttataaa tcaaaagaat agaccgagat agggttgagt  12180

gttgttccag tttggaacaa gagtccacta ttaaagaacg tggactccaa cgtcaaaggg  12240

cgaaaaaccg tctatcaggg cgatggccca ctacgtgaac catcacccta atcaagtttt  12300

ttggggtcga ggtgccgtaa agcactaaat cggaacccta aagggagccc ccgatttaga  12360

gcttgacggg gaaagccggc gaacgtggcg agaaaggaag ggaagaaagc gaaaggagcg  12420

ggcgctaggg cgctggcaag tgtagcggtc acgctgcgcg taaccaccac acccgccgcg  12480

cttaatgcgc cgctacaggg cgcgtccatt cgccattcag gctgcgcaac tgttgggaag  12540

ggcgatcggt gcgggcctct tcgctattac gccagctggc gaaaggggga tgtgctgcaa  12600

ggcgattaag ttgggtaacg ccagggtttt cccagtcacg acgttgtaaa acgacggcca  12660

gtgaattgta atacgactca ctatagggcg aattgggccc gacgtcgcat gc          12712
```

<210> SEQ ID NO 71
<211> LENGTH: 1947
<212> TYPE: DNA
<213> ORGANISM: artificial sequence
<220> FEATURE:
<223> OTHER INFORMATION: PEX3 knockout site, including LoxP-flanked URA3

<400> SEQUENCE: 71

```
acagaccggg ttttggctct cgagagctcc acctcgtcct cagctaccgc acaaaccgtg     60

cccaccatga caagtggcgc cacagaggag ggcgagaagt taattaactt tggccggcct    120

ttacctgcag gataacttcg tataatgtat gctatacgaa gttatgaatt ctctctcttg    180

agcttttcca taacaagttc ttctgcctcc aggaagtcca tgggtggttt gatcatggtt    240

ttggtgtagt ggtagtgcag tggtggtatt gtgactgggg atgtagttga gaataagtca    300

tacacaagtc agctttcttc gagcctcata taagtataag tagttcaacg tattagcact    360

gtacccagca tctccgtatc gagaaacaca acaacatgcc ccattggaca gatcatgcgg    420

atacacaggt tgtgcagtat catacatact cgatcagaca ggtcgtctga ccatcataca    480

agctgaacaa gcgctccata cttgcacgct ctctatatac acagttaaat tacatatcca    540

tagtctaacc tctaacagtt aatcttctgg taagcctccc agccagcctt ctggtatcgc    600

ttggcctcct caataggatc tcggttctgg ccgtacagac ctcggccgac aattatgata    660

tccgttccgg tagacatgac atcctcaaca gttcggtact gctgtccgag agcgtctccc    720

ttgtcgtcaa gacccacccc gggggtcaga ataagccagt cctcagagtc gcccttaggt    780

cggttctggg caatgaagcc aaccacaaac tcggggtcgg atcgggcaag ctcaatggtc    840

tgcttggagt actcgccagt ggccagagag cccttgcaag acagctcggc cagcatgagc    900

agacctctgg ccagcttctc gttgggagag gggactagga actccttgta ctgggagttc    960

tcgtagtcag agacgtcctc cttcttctgt tcagagacag tttcctcggc accagctcgc   1020

aggccagcaa tgattccggt tccgggtaca ccgtgggcgt tggtgatatc ggaccactcg   1080
```

```
gcgattcggt gacaccggta ctggtgcttg acagtgttgc caatatctgc gaactttctg   1140

tcctcgaaca ggaagaaacc gtgcttaaga gcaagttcct tgagggggag cacagtgccg   1200

gcgtaggtga agtcgtcaat gatgtcgata tgggttttga tcatgcacac ataaggtccg   1260

accttatcgg caagctcaat gagctccttg gtggtggtaa catccagaga agcacacagg   1320

ttggttttct tggctgccac gagcttgagc actcgagcgg caaaggcgga cttgtggacg   1380

ttagctcgag cttcgtagga gggcattttg gtggtgaaga ggagactgaa ataaatttag   1440

tctgcagaac tttttatcgg aaccttatct ggggcagtga agtatatgtt atggtaatag   1500

ttacgagtta gttgaactta tagatagact ggactatacg gctatcggtc caaattagaa   1560

agaacgtcaa tggctctctg ggcgtcgcct ttgccgacaa aaatgtgatc atgatgaaag   1620

ccagcaatga cgttgcagct gatattgttg tcggccaacc gcgccgaaaa cgcagctgtc   1680

agacccacag cctccaacga agaatgtatc gtcaaagtga tccaagcaca ctcatagttg   1740

gagtcgtact ccaaaggcgg caatgacgag tcagacagat actcgtcgac tcatcgatat   1800

aacttcgtat aatgtatgct atacgaagtt atcctaggta tagatcttgc acttcttatt   1860

ttcttcacgc gtttgcagct caacattcta ggacgacgaa actacgtcaa cagtgttgtc   1920

gctctggcgc agcagggccg agagggt                                       1947
```

<210> SEQ ID NO 72
<211> LENGTH: 280
<212> TYPE: DNA
<213> ORGANISM: artificial sequence
<220> FEATURE:
<223> OTHER INFORMATION: PEX3 knockout site, including single LoxP (URA3 removed)

<400> SEQUENCE: 72

```
acagaccggg ttttggctct cgagagctcc acctcgtcct cagctaccgc acaaaccgtg     60

cccaccatga caagtggcgc cacagaggag ggcgagaagt taattaactt tggccggcct    120

ttacctgcag gataacttcg tataatgtat gctatacgaa gttatcctag gtatagatct    180

tgcacttctt attttcttca cgcgtttgca gctcaacatt ctaggacgac gaaactacgt    240

caacagtgtt gtcgctctgg cgcagcaggg ccgagagggt                         280
```

<210> SEQ ID NO 73
<211> LENGTH: 5164
<212> TYPE: DNA
<213> ORGANISM: artificial sequence
<220> FEATURE:
<223> OTHER INFORMATION: pYRH146-Pox4KO plasmid

<400> SEQUENCE: 73

```
cgcgccagct gcattaatga atcggccaac gcgcggggag aggcggtttg cgtattgggc     60

gctcttccgc ttcctcgctc actgactcgc tgcgctcggt cgttcggctg cggcgagcgg    120

tatcagctca ctcaaaggcg gtaatacggt tatccacaga atcaggggat aacgcaggaa    180

agaacatgtg agcaaaaggc cagcaaaagg ccaggaaccg taaaaaggcc gcgttgctgg    240

cgtttttcca taggctccgc ccccctgacg agcatcacaa aaatcgacgc tcaagtcaga    300

ggtggcgaaa cccgacagga ctataaagat accaggcgtt tccccctgga agctccctcg    360

tgcgctctcc tgttccgacc ctgccgctta ccggatacct gtccgccttt ctcccttcgg    420

gaagcgtggc gctttctcat agctcacgct gtaggtatct cagttcggtg taggtcgttc    480

gctccaagct gggctgtgtg cacgaacccc ccgttcagcc cgaccgctgc gccttatccg    540
```

```
gtaactatcg tcttgagtcc aacccggtaa gacacgactt atcgccactg gcagcagcca    600
ctggtaacag gattagcaga gcgaggtatg taggcggtgc tacagagttc ttgaagtggt    660
ggcctaacta cggctacact agaagaacag tatttggtat ctgcgctctg ctgaagccag    720
ttaccttcgg aaaaagagtt ggtagctctt gatccggcaa acaaaccacc gctggtagcg    780
gtggtttttt tgtttgcaag cagcagatta cgcgcagaaa aaaaggatct caagaagatc    840
ctttgatctt ttctacgggg tctgacgctc agtggaacga aaactcacgt taagggattt    900
tggtcatgag attatcaaaa aggatcttca cctagatcct tttaaattaa aaatgaagtt    960
ttaaatcaat ctaaagtata tatgagtaaa cttggtctga cagttaccaa tgcttaatca   1020
gtgaggcacc tatctcagcg atctgtctat ttcgttcatc catagttgcc tgactccccg   1080
tcgtgtagat aactacgata cgggagggct taccatctgg ccccagtgct gcaatgatac   1140
cgcgagaccc acgctcaccg gctccagatt tatcagcaat aaaccagcca gccggaaggg   1200
ccgagcgcag aagtggtcct gcaactttat ccgcctccat ccagtctatt aattgttgcc   1260
gggaagctag agtaagtagt tcgccagtta atagtttgcg caacgttgtt gccattgcta   1320
caggcatcgt ggtgtcacgc tcgtcgtttg gtatggcttc attcagctcc ggttcccaac   1380
gatcaaggcg agttacatga tcccccatgt tgtgcaaaaa agcggttagc tccttcggtc   1440
ctccgatcgt tgtcagaagt aagttggccg cagtgttatc actcatggtt atggcagcac   1500
tgcataattc tcttactgtc atgccatccg taagatgctt ttctgtgact ggtgagtact   1560
caaccaagtc attctgagaa tagtgtatgc ggcgaccgag ttgctcttgc ccggcgtcaa   1620
tacgggataa taccgcgcca catagcagaa ctttaaaagt gctcatcatt ggaaaacgtt   1680
cttcggggcg aaaactctca aggatcttac cgctgttgag atccagttcg atgtaaccca   1740
ctcgtgcacc caactgatct tcagcatctt ttactttcac cagcgtttct gggtgagcaa   1800
aaacaggaag gcaaaatgcc gcaaaaaagg gaataagggc gacacggaaa tgttgaatac   1860
tcatactctt cctttttcaa tattattgaa gcatttatca gggttattgt ctcatgagcg   1920
gatacatatt tgaatgtatt tagaaaaata aacaaatagg ggttccgcgc acatttcccc   1980
gaaaagtgcc acctgatgcg gtgtgaaata ccgcacagat gcgtaaggag aaaataccgc   2040
atcaggaaat tgtaagcgtt aatattttgt taaaattcgc gttaaatttt tgttaaatca   2100
gctcattttt taaccaatag gccgaaatcg gcaaaatccc ttataaatca aaagaataga   2160
ccgagatagg gttgagtgtt gttccagttt ggaacaagag tccactatta aagaacgtgg   2220
actccaacgt caaagggcga aaaaccgtct atcagggcga tggcccacta cgtgaaccat   2280
caccctaatc aagttttttg gggtcgaggt gccgtaaagc actaaatcgg aaccctaaag   2340
ggagcccccg atttagagct tgacggggaa agccggcgaa cgtggcgaga aaggaaggga   2400
agaaagcgaa aggagcgggc gctagggcgc tggcaagtgt agcggtcacg ctgcgcgtaa   2460
ccaccacacc cgccgcgctt aatgcgccgc tacagggcgc gtccattcgc cattcaggct   2520
gcgcaactgt tgggaagggc gatcggtgcg ggcctcttcg ctattacgcc agctggcgaa   2580
agggggatgt gctgcaaggc gattaagttg ggtaacgcca gggttttccc agtcacgacg   2640
ttgtaaaacg acggccagtg aattgtaata cgactcacta tagggcgaat tgggcccgac   2700
gtcgcgatcg cgagtatctg tctgactcgt cattgccgcc tttggagtac gactccaact   2760
atgagtgtgc ttggatcact ttgacgatac attcttcgtt ggaggctgtg ggtctgacag   2820
ctgcgttttc ggcgcggttg gccgacaaca atatcagctg caacgtcatt gctggctttc   2880
```

-continued

```
atcatgatca catttttgtc ggcaaaggcg acgcccagag agccattgac gttctttcta   2940
atttggaccg atagccgtat agtccagtct atctataagt tcaactaact cgtaactatt   3000
accataacat atacttcact gccccagata aggttccgat aaaaagttct gcagactaaa   3060
tttatttcag tctcctcttc accaccaaaa tgccctccta cgaagctcga gctaacgtcc   3120
acaagtccgc ctttgccgct cgagtgctca agctcgtggc agccaagaaa accaacctgt   3180
gtgcttctct ggatgttacc accaccaagg agctcattga gcttgccgat aaggtcggac   3240
cttatgtgtg catgatcaaa acccatatcg acatcattga cgacttcacc tacgccggca   3300
ctgtgctccc cctcaaggaa cttgctctta agcacggttt cttcctgttc gaggacagaa   3360
agttcgcaga tattggcaac actgtcaagc accagtaccg gtgtcaccga atcgccgagt   3420
ggtccgatat caccaacgcc cacggtgtac ccggaaccgg aatcattgct ggcctgcgag   3480
ctggtgccga ggaaactgtc tctgaacaga agaaggagga cgtctctgac tacgagaact   3540
cccagtacaa ggagttccta gtcccctctc ccaacgagaa gctggccaga ggtctgctca   3600
tgctggccga gctgtcttgc aagggctctc tggccactgg cgagtactcc aagcagacca   3660
ttgagcttgc ccgatccgac cccgagtttg tggttggctt cattgcccag aaccgaccta   3720
agggcgactc tgaggactgg cttattctga cccccggggt gggtcttgac gacaagggag   3780
acgctctcgg acagcagtac cgaactgttg aggatgtcat gtctaccgga acggatatca   3840
taattgtcgg ccgaggtctg tacggccaga accgagatcc tattgaggag gccaagcgat   3900
accagaaggc tggctgggag gcttaccaga agattaactg ttagaggtta gactatggat   3960
atgtaattta actgtgtata tagagagcgt gcaagtatgg agcgcttgtt cagcttgtat   4020
gatggtcaga cgacctgtct gatcgagtat gtatgatact gcacaacctg tgtatccgca   4080
tgatctgtcc aatggggcat gttgttgtgt ttctcgatac ggagatgctg ggtacagtgc   4140
taatacgttg aactacttat acttatatga ggctcgaaga aagctgactt gtgtatgacg   4200
catgcttgag cgattgggag agttggttgt gtacaattat tttaatacct cttctgattg   4260
ttttctattg ccttccattt ctatctttac ctgccatctc acgtcgtgtg taccatcccc   4320
acatacggaa ccagtaggtc ttttaggctc tgaacgtgca aatgagtttg gtggggtagg   4380
cagagatcgc atagagacgg gtagaatgag cagttaaaag ctgtgttgag tggtaaaaat   4440
ttacaataag tgttcctcaa ggcatcaagg agacgaaata agccattatg gacacgaacc   4500
aacagtccca ccacgttcta aacacattcc tccactgcca ctcccaaaca ccacgtccca   4560
cataaacttc taccccacat tttgacaagc ctattcgttt aataatcacc ccgaggagac   4620
agaaagccta acagctggag ccactatata gttgcagtgg ttaattaagg agttgtgtgt   4680
aacttgtaca ggtacaccta catactgtac tgtaggtcca aagataggta cactgtggca   4740
ataattatgc gagtacttgt accgtcatcg tagctgctgt aaagagatca gacacaggca   4800
cttttcccca ccatgagatc accactcgtc gtccgagtac ttctatggca cagccacaat   4860
cacatgtact tgtgcatgcc aatgtgtgac atcatcatct agagctatca tcatattccc   4920
gctgcaaatg gtctacgtat tactattaag caggggggggg ggaggaatta tgacgacatt   4980
gtacgtgtac tcgtaccggt acttgtagca cgccgaactg cggtattact gtgcactgta   5040
atttcggacc cctcttatag ccccaagttg gtctatacat ctgaaccggt gcagactcac   5100
tattaaaagt gcggcagcta attttgctga cacagccttg tcgataaaag tagctacttg   5160
tagg                                                                5164
```

<210> SEQ ID NO 74
<211> LENGTH: 957
<212> TYPE: DNA
<213> ORGANISM: artificial sequence
<220> FEATURE:
<223> OTHER INFORMATION: POX4 knockout site

<400> SEQUENCE: 74
ttgagcgatt gggagagttg gttgtgtaca attattttaa tacctcttct gattgttttc 60
tattgccttc catttctatc tttacctgcc atctcacgtc gtgtgtacca tccccacata 120
cggaaccagt aggtctttta ggctctgaac gtgcaaatga gtttggtggg gtaggcagag 180
atcgcataga gacgggtaga atgagcagtt aaaagctgtg ttgagtggta aaaatttaca 240
ataagtgttc ctcaaggcat caaggagacg aaataagcca ttatggacac gaaccaacag 300
tcccaccacg ttctaaacac attcctccac tgccactccc aaacaccacg tcccacataa 360
acttctaccc cacattttga caagcctatt cgtttaataa tcaccccgag gagacagaaa 420
gcctaacagc tggagccact atatagttgc agtggttaat taaggagttg tgtgtaactt 480
gtacaggtac acctacatac tgtactgtag gtccaaagat aggtacactg tggcaataat 540
tatgcgagta cttgtaccgt catcgtagct gctgtaaaga gatcagacac aggcactttt 600
ccccaccatg agatcaccac tcgtcgtccg agtacttcta tggcacagcc acaatcacat 660
gtacttgtgc atgccaatgt gtgacatcat catctagagc tatcatcata ttcccgctgc 720
aaatggtcta cgtattacta ttaagcaggg ggggggaggg aattatgacg acattgtacg 780
tgtactcgta ccggtacttg tagcacgccg aactgcggta ttactgtgca ctgtaatttc 840
ggacccctct tatagcccca agttggtcta tacatctgaa ccggtgcaga ctcactatta 900
aaagtgcggc agctaatttt gctgacacag ccttgtcgat aaaagtagct acttgta 957

<210> SEQ ID NO 75
<211> LENGTH: 6853
<212> TYPE: DNA
<213> ORGANISM: artificial sequence
<220> FEATURE:
<223> OTHER INFORMATION: pYRH72 plasmid

<400> SEQUENCE: 75
gcatgcgacg tcgggcccaa ttcgccctat agtgagtcgt attacaattc actggccgtc 60
gttttacaac gtcgtgactg ggaaaaccct ggcgttaccc aacttaatcg ccttgcagca 120
catccccctt tcgccagctg gcgtaatagc gaagaggccc gcaccgatcg cccttcccaa 180
cagttgcgca gcctgaatgg cgaatggacg cgccctgtag cggcgcatta agcgcggcgg 240
gtgtggtggt tacgcgcagc gtgaccgcta cacttgccag cgccctagcg cccgctcctt 300
tcgctttctt cccttccttt ctcgccacgt tcgccggctt tccccgtcaa gctctaaatc 360
gggggctccc tttagggttc cgatttagtg ctttacggca cctcgacccc aaaaaacttg 420
attagggtga tggttcacgt agtgggccat cgccctgata gacggttttt cgccctttga 480
cgttggagtc cacgttcttt aatagtggac tcttgttcca aactggaaca acactcaacc 540
ctatctcggt ctattctttt gatttataag ggattttgcc gatttcggcc tattggttaa 600
aaaatgagct gatttaacaa aaatttaacg cgaattttaa caaaatatta acgcttacaa 660
tttcctgatg cggtattttc tccttacgca tctgtgcggt atttcacacc gcatcaggtg 720
gcacttttcg gggaaatgtg cgcggaaccc ctatttgttt atttttctaa atacattcaa 780
atatgtatcc gctcatgaga caataaccct gataaatgct tcaataatat tgaaaaagga 840

-continued agagtatgag tattcaacat ttccgtgtcg cccttattcc cttttttgcg gcattttgcc 900
ttcctgtttt tgctcaccca gaaacgctgg tgaaagtaaa agatgctgaa gatcagttgg 960
gtgcacgagt gggttacatc gaactggatc tcaacagcgg taagatcctt gagagttttc 1020
gccccgaaga acgttttcca atgatgagca cttttaaagt tctgctatgt ggcgcggtat 1080
tatcccgtat tgacgccggg caagagcaac tcggtcgccg catacactat tctcagaatg 1140
acttggttga gtactcacca gtcacagaaa agcatcttac ggatggcatg acagtaagag 1200
aattatgcag tgctgccata accatgagtg ataacactgc ggccaactta cttctgacaa 1260
cgatcggagg accgaaggag ctaaccgctt ttttgcacaa catgggggat catgtaactc 1320
gccttgatcg ttgggaaccg gagctgaatg aagccatacc aaacgacgag cgtgacacca 1380
cgatgcctgt agcaatggca acaacgttgc gcaaactatt aactggcgaa ctacttactc 1440
tagcttcccg gcaacaatta atagactgga tggaggcgga taaagttgca ggaccacttc 1500
tgcgctcggc ccttccggct ggctggttta ttgctgataa atctggagcc ggtgagcgtg 1560
ggtctcgcgg tatcattgca gcactggggc cagatggtaa gccctcccgt atcgtagtta 1620
tctacacgac ggggagtcag gcaactatgg atgaacgaaa tagacagatc gctgagatag 1680
gtgcctcact gattaagcat tggtaactgt cagaccaagt ttactcatat atactttaga 1740
ttgatttaaa acttcatttt taatttaaaa ggatctaggt gaagatcctt tttgataatc 1800
tcatgaccaa aatcccttaa cgtgagtttt cgttccactg agcgtcagac cccgtagaaa 1860
agatcaaagg atcttcttga gatccttttt ttctgcgcgt aatctgctgc ttgcaaacaa 1920
aaaaaccacc gctaccagcg gtggtttgtt tgccggatca agagctacca actctttttc 1980
cgaaggtaac tggcttcagc agagcgcaga taccaaatac tgttcttcta gtgtagccgt 2040
agttaggcca ccacttcaag aactctgtag caccgcctac atacctcgct ctgctaatcc 2100
tgttaccagt ggctgctgcc agtggcgata agtcgtgtct taccgggttg gactcaagac 2160
gatagttacc ggataaggcg cagcggtcgg gctgaacggg gggttcgtgc acacagccca 2220
gcttggagcg aacgacctac accgaactga gatacctaca gcgtgagcta tgagaaagcg 2280
ccacgcttcc cgaagggaga aaggcggaca ggtatccggt aagcggcagg gtcggaacag 2340
gagagcgcac gagggagctt ccagggggaa acgcctggta tctttatagt cctgtcgggt 2400
ttcgccacct ctgacttgag cgtcgatttt tgtgatgctc gtcagggggg cggagcctat 2460
ggaaaaacgc cagcaacgcg gcctttttac ggttcctggc cttttgctgg ccttttgctc 2520
acatgttctt tcctgcgtta tcccctgatt ctgtggataa ccgtattacc gcctttgagt 2580
gagctgatac cgctcgccgc agccgaacga ccgagcgcag cgagtcagtg agcgaggaag 2640
cggaagagcg cccaatacgc aaaccgcctc tccccgcgcg ttggccgatt cattaatgca 2700
gctggcgcgc caccatcatt gagaacctca gtaagctcaa gtgggataag accgccatcc 2760
acatccgtgc caccaaacag gcccatgctg gtgccattgt gcgtcatcca gacccgtcct 2820
tctatgaagg taagaccgtt gtcaagcact ggattgacaa caaggcccgt ctttgagagc 2880
agcctgactc ggcctttgta gagcaaggcc attattgatt tatagacatt ataccgggaa 2940
atactaaaca caagaacctt cggcgtgatt atctgcactt gtaccacgct gcagtaagtt 3000
agtaatcgga attcaactgc cattagacat tatttacctg cagacccaat tcgtccagca 3060
acggaggaat gaacgttggg ggttcgggtc taaagatgcg tcctgtaagt gggggcgttg 3120
gtctacgagt agggtcctgc tttagtgtgg aaaatttatc tctttatgtg tttccattgg 3180
ctggtgcgtt ttgttgtttt cctttattca gccaatcaga atgcgtgaga atacctgtta 3240

-continued

```
tgttttcctc acaatatttt tttccaccgc cattttggag agccgccgga aaccagagtg   3300
ccgaaaggct atcttttggg ctggaattat atatcctaag ccagacacaa tcctgactca   3360
ctaaccttgg agtagataga gaaagagcaa gaagctctgt gagtcagaga ggaagaggga   3420
ggcacataat gtgggagtta taggggtatc gtacgttgtg tggaagcttg tgagcggata   3480
acaatttcac acaggaaaca gctatgacca tgattacgcc aagctcgaaa ttaaccctca   3540
ctaaagggaa caaaagctgg agctccaccg cggacacaat atctggtcaa atttcagttt   3600
cgttacattt aaacggtagg ttagtgcttg gtatatgagt tgtaggcatg acaatttgga   3660
aaggggtgga ctttgggaat attgtgggat ttcaatacct tagtttgtac agggtaattg   3720
ttacaaatga tacaaagaac tgtatttctt ttcatttgtt ttaattggtt gtatatcaag   3780
tccgttagac gagctcagtg ccttggcttt tggcactgta tttcattttt agaggtacac   3840
tacattcagt gaggtatggt aaggttgagg gcataatgaa ggcaccttgt actgacagtc   3900
acagacctct caccgagaat tttatgagat atactcgggt tcattttagg ctcatcgata   3960
cgctctcatc aagaatactt cttgagaacc gtggagaccg gggttcgatt ccccgtatcg   4020
gagtgtttat tttttgctca accataccct ggggtgtgtt ctgtggagca ttctcacttt   4080
tggtaaacga cattgcttca agtgcagcgg aatcaaaaag tataaagtgg gcagcgagta   4140
tacctgtaca gactgtaggc gataactcaa tccaattacc ccccacaaca tgactggcca   4200
aactgatctc aagactttat tgaaatcagc aacaccgatt ctcaatgaag gcacatactt   4260
cttctgcaac attcacttga cgcctaaagt tggtgagaaa tggaccgaca agacatattc   4320
tgctatccac ggactgttgc ctgtgtcggt ggctacaata cgtgagtcag aagggctgac   4380
ggtggtggtt cccaaggaaa aggtcgacga gtatctgtct gactcgtcat tgccgccttt   4440
ggagtacgac tccaactatg agtgtgcttg gatcactttg acgatacatt cttcgttgga   4500
ggctgtgggt ctgacagctg cgttttcggc gcggttggcc gacaacaata tcagctgcaa   4560
cgtcattgct ggctttcatc atgatcacat ttttgtcggc aaaggcgacg cccagagagc   4620
cattgacgtt ctttctaatt tggaccgata gccgtatagt ccagtctatc tataagttca   4680
actaactcgt aactattacc ataacatata cttcactgcc ccagataagg ttccgataaa   4740
aagttctgca gactaaattt atttcagtct cctcttcacc accaaaatgc cctcctacga   4800
agctcgagct aacgtccaca agtccgcctt tgccgctcga gtgctcaagc tcgtggcagc   4860
caagaaaacc aacctgtgtg cttctctgga tgttaccacc accaaggagc tcattgagct   4920
tgccgataag gtcggacctt atgtgtgcat gatcaaaacc catatcgaca tcattgacga   4980
cttcacctac gccggcactg tgctccccct caaggaactt gctcttaagc acggtttctt   5040
cctgttcgag gacagaaagt tcgcagatat tggcaacact gtcaagcacc agtaccggtg   5100
tcaccgaatc gccgagtggt ccgatatcac caacgcccac ggtgtacccg gaaccggaat   5160
cattgctggc ctgcgagctg gtgccgagga aactgtctct gaacagaaga aggaggacgt   5220
ctctgactac gagaactccc agtacaagga gttcctagtc cctctcccca acgagaagct   5280
ggccagaggt ctgctcatgc tggccgagct gtcttgcaag ggctctctgg ccactggcga   5340
gtactccaag cagaccattg agcttgcccg atccgacccc gagtttgtgg ttggcttcat   5400
tgcccagaac cgacctaagg gcgactctga ggactggctt attctgaccc ccggggtggg   5460
tcttgacgac aagggagacg ctctcggaca gcagtaccga actgttgagg atgtcatgtc   5520
taccggaacg gatatcataa ttgtcggccg aggtctgtac ggccagaacc gagatcctat   5580
```

-continued

```
tgaggaggcc aagcgatacc agaaggctgg ctgggaggct taccagaaga ttaactgtta   5640

gaggttagac tatggatatg taatttaact gtgtatatag agagcgtgca agtatggagc   5700

gcttgttcag cttgtatgat ggtcagacga cctgtctgat cgagtatgta tgatactgca   5760

caacctgtgt atccgcatga tctgtccaat ggggcatgtt gttgtgtttc tcgatacgga   5820

gatgctgggt acagtgctaa tacgttgaac tacttatact tatatgaggc tcgaagaaag   5880

ctgacttgtg tatgacttat tctcaactac atccccagtc acaataccac cactgcacta   5940

ccactacacc aaaaccatga tcaaaccacc catggacttc ctggaggcag aagaacttgt   6000

tatggaaaag ctcaagagag agaattcaag atactatcaa gacatgtgtc gcaacttaat   6060

taatgtatct atacctaatc gacatggact gcaccgcatt cgttatctta tcgtagtcct   6120

gcttactttg atccgtatca cattcgtgta tcgcgataag aagtaaacat tgctgcaagt   6180

ataaatcagg tctcaaatct cttcttgaag atagttttaa gctcaccgtg aactgaacgt   6240

gaacactacg agtacgattt tcaatattat taccgtcgat ataacaacca tgcaatttct   6300

atatacatat atacattccc tcattcgtct gtgctgtttg gttcactgca gcaaatcaaa   6360

cagcttttcg tactttctgt gctgcgaatg tttgttacta tccgcgtgca ttctttgcag   6420

cttttgagat cccgtatagt ccttccacac gttggcactc gcctttttcg tcgtcgattg   6480

cagcttcata atcaacttgt cattgtccag cttggccccc tggacctcca tcatcacaat   6540

cttgtctctg tggtgtttga tagacgagtc gttcacttca caggtagcca caacgccgat   6600

gcaagcagct tttgtgcgct gatcatccac aatacgtgct ggtaacatgg gatttgccat   6660

gactccgtta cgagatgtgt gtagcgatcc cttggggaag taggacggtc cagccacggg   6720

tttcgtggat attgagtccc acggaccgaa tttttgtgtt gcagcgtact ctttggcaag   6780

ctggatgaga tactcgccgt ccagagcgct gcgcttgacg cctcggtcgt tgcaccactt   6840

gatgaaggcg taa                                                      6853
```

<210> SEQ ID NO 76
<211> LENGTH: 6512
<212> TYPE: DNA
<213> ORGANISM: artificial sequence
<220> FEATURE:
<223> OTHER INFORMATION: p12_3-B-Pex3del1 plasmid

<400> SEQUENCE: 76

```
gtacgataac ttcgtatagc atacattata cgaagttatc gcgtcgacga gtatctgtct     60

gactcgtcat tgccgccttt ggagtacgac tccaactatg agtgtgcttg gatcactttg    120

acgatacatt cttcgttgga ggctgtgggt ctgacagctg cgttttcggc gcggttggcc    180

gacaacaata tcagctgcaa cgtcattgct ggctttcatc atgatcacat ttttgtcggc    240

aaaggcgacg cccagagagc cattgacgtt ctttctaatt tggaccgata gccgtatagt    300

ccagtctatc tataagttca actaactcgt aactattacc ataacatata cttcactgcc    360

ccagataagg ttccgataaa aagttctgca gactaaattt atttcagtct cctcttcacc    420

accaaaatgc cctcctacga agctcgagct aacgtccaca agtccgcctt tgccgctcga    480

gtgctcaagc tcgtggcagc caagaaaacc aacctgtgtg cttctctgga tgttaccacc    540

accaaggagc tcattgagct tgccgataag gtcggacctt atgtgtgcat gatcaaaacc    600

catatcgaca tcattgacga cttcacctac gccggcactg tgctccccct caaggaactt    660

gctcttaagc acggtttctt cctgttcgag gacagaaagt tcgcagatat tggcaacact    720

gtcaagcacc agtaccggtg tcaccgaatc gccgagtggt ccgatatcac caacgcccac    780
```

-continued

```
ggtgtacccg gaaccggaat cattgctggc ctgcgagctg gtgccgagga aactgtctct    840
gaacagaaga aggaggacgt ctctgactac gagaactccc agtacaagga gttcctagtc    900
ccctctccca acgagaagct ggccagaggt ctgctcatgc tggccgagct gtcttgcaag    960
ggctctctgg ccactggcga gtactccaag cagaccattg agcttgcccg atccgacccc   1020
gagtttgtgg ttggcttcat tgcccagaac cgacctaagg gcgactctga ggactggctt   1080
attctgaccc ccggggtggg tcttgacgac aagggagacg ctctcggaca gcagtaccga   1140
actgttgagg atgtcatgtc taccggaacg gatatcataa ttgtcggccg aggtctgtac   1200
ggccagaacc gagatcctat tgaggaggcc aagcgatacc agaaggctgg ctgggaggct   1260
taccagaaga ttaactgtta gaggttagac tatggatatg taatttaact gtgtatatag   1320
agagcgtgca agtatggagc gcttgttcag cttgtatgat ggtcagacga cctgtctgat   1380
cgagtatgta tgatactgca caacctgtgt atccgcatga tctgtccaat ggggcatgtt   1440
gttgtgtttc tcgatacgga gatgctgggt acagtgctaa tacgttgaac tacttatact   1500
tatatgaggc tcgaagaaag ctgacttgtg tatgacttat tctcaactac atccccagtc   1560
acaataccac cactgcacta ccactacacc aaaaccatga tcaaaccacc catggacttc   1620
ctggaggcag aagaacttgt tatggaaaag ctcaagagag agatcataac ttcgtatagc   1680
atacattata cgaagttatc ctgcaggtaa aggaattcag gagagaccgg gttggcggcg   1740
tatttgtgtc ccaaaaaaca gccccaattg ccccaattga ccccaaattg acccagtagc   1800
gggcccaacc ccggcgagag cccccttcac cccacatatc aaacctcccc cggttcccac   1860
acttgccgtt aagggcgtag ggtactgcag tctggaatct acgcttgttc agactttgta   1920
ctagtttctt tgtctggcca tccgggtaac ccatgccgga cgcaaaatag actactgaaa   1980
atttttttgc tttgtggttg ggactttagc caagggtata aaagaccacc gtccccgaat   2040
tacctttcct cttcttttct ctctctcctt gtcaactcac acccgaaatc gttaagcatt   2100
tccttctgag tataagaatc attcaccatg gacttcctgg aggcagaaga acttgttatg   2160
gaaaagctca agagagagaa gccaagatac tatcaagaca tgtgtcgcaa cttaattaag   2220
atgacgacat ttgcgagctg gacgaggaat agatggagcg tgtgttctga gtcgatgttt   2280
tctatggagt tgtgagtgtt agtagacatg atgggtttat atatgatgaa tgaatagatg   2340
tgattttgat ttgcacgatg gaattgagaa ctttgtaaac gtacatggga atgtatgaat   2400
gtgggggttt tgtgactgga taactgacgg tcagtggacg ccgttgttca aatatccaag   2460
agatgcgaga aactttgggt caagtgaaca tgtcctctct gttcaagtaa accatcaact   2520
atgggtagta tatttagtaa ggacaagagt tgagattctt tggagtccta gaaacgtatt   2580
ttcgcgttcc aagatcaaat tagtagagta atacgggcac gggaatccat tcatagtctc   2640
aattttccca taggtgtgct acaaggtgtt gagatgtggt acagtaccac catgattcga   2700
ggtaaagagc ccagaagtca ttgatgaggt caagaaatac acagatctac agctcaatac   2760
aatgaatatc ttctttcata ttcttcaggt gacaccaagg gtgtctattt tccccagaaa   2820
tgcgtgaaaa ggcgcgtgtg tagcgtggag tatgggttcg gttggcgtat ccttcatata   2880
tcgacgaaat agtagggcaa gagatgacaa aaagtatcta tatgtagaca gcgtagaata   2940
tggatttgat tggtataaat tcatttattg cgtgtctcac aaatactctc gataagttgg   3000
ggttaaactg gagatggaac aatgtcgata tctcgacgca tgcgacgtcg ggcccaattc   3060
gccctatagt gagtcgtatt acaattcact ggccgtcgtt ttacaacgtc gtgactggga   3120
```

-continued aaaccctggc gttacccaac ttaatcgcct tgcagcacat ccccctttcg ccagctggcg 3180
taatagcgaa gaggcccgca ccgatcgccc ttcccaacag ttgcgcagcc tgaatggcga 3240
atggacgcgc cctgtagcgg cgcattaagc gcggcgggtg tggtggttac gcgcagcgtg 3300
accgctacac ttgccagcgc cctagcgccc gctcctttcg ctttcttccc ttcctttctc 3360
gccacgttcg ccggctttcc ccgtcaagct ctaaatcggg ggctcccttt agggttccga 3420
tttagtgctt tacggcacct cgaccccaaa aaacttgatt agggtgatgg ttcacgtagt 3480
gggccatcgc cctgatagac ggtttttcgc cctttgacgt tggagtccac gttctttaat 3540
agtggactct tgttccaaac tggaacaaca ctcaacccta tctcggtcta ttcttttgat 3600
ttataaggga ttttgccgat ttcggcctat tggttaaaaa atgagctgat ttaacaaaaa 3660
tttaacgcga attttaacaa aatattaacg cttacaattt cctgatgcgg tattttctcc 3720
ttacgcatct gtgcggtatt tcacaccgca tcaggtggca cttttcgggg aaatgtgcgc 3780
ggaaccccta tttgtttatt tttctaaata cattcaaata tgtatccgct catgagacaa 3840
taaccctgat aaatgcttca ataatattga aaaaggaaga gtatgagtat tcaacatttc 3900
cgtgtcgccc ttattccctt ttttgcggca ttttgccttc ctgtttttgc tcacccagaa 3960
acgctggtga aagtaaaaga tgctgaagat cagttgggtg cacgagtggg ttacatcgaa 4020
ctggatctca acagcggtaa gatccttgag agttttcgcc ccgaagaacg ttttccaatg 4080
atgagcactt ttaaagttct gctatgtggc gcggtattat cccgtattga cgccgggcaa 4140
gagcaactcg gtcgccgcat acactattct cagaatgact tggttgagta ctcaccagtc 4200
acagaaaagc atcttacgga tggcatgaca gtaagagaat tatgcagtgc tgccataacc 4260
atgagtgata acactgcggc caacttactt ctgacaacga tcggaggacc gaaggagcta 4320
accgcttttt tgcacaacat gggggatcat gtaactcgcc ttgatcgttg ggaaccggag 4380
ctgaatgaag ccataccaaa cgacgagcgt gacaccacga tgcctgtagc aatggcaaca 4440
acgttgcgca aactattaac tggcgaacta cttactctag cttcccggca acaattaata 4500
gactggatgg aggcggataa agttgcagga ccacttctgc gctcggccct tccggctggc 4560
tggtttattg ctgataaatc tggagccggt gagcgtgggt ctcgcggtat cattgcagca 4620
ctggggccag atggtaagcc ctcccgtatc gtagttatct acacgacggg gagtcaggca 4680
actatggatg aacgaaatag acagatcgct gagataggtg cctcactgat taagcattgg 4740
taactgtcag accaagttta ctcatatata ctttagattg atttaaaact tcatttttaa 4800
tttaaaagga tctaggtgaa gatccttttt gataatctca tgaccaaaat cccttaacgt 4860
gagttttcgt tccactgagc gtcagacccc gtagaaaaga tcaaaggatc ttcttgagat 4920
cctttttttc tgcgcgtaat ctgctgcttg caaacaaaaa aaccaccgct accagcggtg 4980
gtttgtttgc cggatcaaga gctaccaact ctttttccga aggtaactgg cttcagcaga 5040
gcgcagatac caaatactgt tcttctagtg tagccgtagt taggccacca cttcaagaac 5100
tctgtagcac cgcctacata cctcgctctg ctaatcctgt taccagtggc tgctgccagt 5160
ggcgataagt cgtgtcttac cgggttggac tcaagacgat agttaccgga taaggcgcag 5220
cggtcgggct gaacgggggg ttcgtgcaca cagcccagct tggagcgaac gacctacacc 5280
gaactgagat acctacagcg tgagctatga gaaagcgcca cgcttcccga agggagaaag 5340
gcggacaggt atccggtaag cggcagggtc ggaacaggag agcgcacgag ggagcttcca 5400
gggggaaacg cctggtatct ttatagtcct gtcgggtttc gccacctctg acttgagcgt 5460
cgatttttgt gatgctcgtc aggggggcgg agcctatgga aaaacgccag caacgcggcc 5520

-continued tttttacggt tcctggcctt ttgctggcct tttgctcaca tgttctttcc tgcgttatcc 5580
cctgattctg tggataaccg tattaccgcc tttgagtgag ctgataccgc tcgccgcagc 5640
cgaacgaccg agcgcagcga gtcagtgagc gaggaagcgg aagagcgccc aatacgcaaa 5700
ccgcctctcc ccgcgcgttg gccgattcat taatgcagct ggcgcgccac caatcacaat 5760
tctgaaaagc acatcttgat ctcctcattg cggggagtcc aacggtggtc ttattccccc 5820
gaatttcccg ctcaatctcg ttccagaccg acccggacac agtgcttaac gccgttccga 5880
aactctaccg cagatatgct ccaacggact gggctgcata gatgtgatcc tcggcttgga 5940
gaaatggata aaagccggcc aaaaaaaaag cggaaaaaag cggaaaaaaa gagaaaaaaa 6000
atcgcaaaat ttgaaaaata gggggaaaag acgcaaaaac gcaaggaggg gggagtatat 6060
gacactgata agcaagctca caacggttcc tcttattttt ttcctcatct tctgcctagg 6120
ttcccaaaat cccagatgct tctctccagt gccaaaagta agtaccccac aggttttcgg 6180
ccgaaaattc cacgtgcagc aacgtcgtgt ggggtgttaa aatgtggggg gggggaacca 6240
ggacaagagg ctcttgtggg agccgaatga gagcacaaag cgggcgggtg tgataagggc 6300
atttttgccc attttccctt ctcctgtctc tccgacggtg atggcgttgt gcgtcctcta 6360
tttcttttta tttcttttg ttttatttct ctgactaccg atttggtttg atttcctcaa 6420
ccccacacaa ataagctcgg gccgaggaat atatatatac acggacacag tcgccctgtg 6480
gacaacacgt cactacctct acgatacaca cc 6512

<210> SEQ ID NO 77
<211> LENGTH: 6906
<212> TYPE: DNA
<213> ORGANISM: artificial sequence
<220> FEATURE:
<223> OTHER INFORMATION: p70_Pox2::Leu2 plasmid

<400> SEQUENCE: 77
cgatagttgg agcaagggag aaatgtttgt acgggcgtcg ttgcttgtgt gatttttgag 60
gacccatccc tttggtatat aagtatactc tggggttaag gttgcccgtg tagtctaggt 120
tatagttttc atgtgaaata ccgagagccg agggagaata aacgggggta tttggacttg 180 ttttttcgc ggaaaagcgt cgaatcaacc ctgcgggcct tgcaccatgt ccacgacgtg 240
tttctcgccc caattcgccc cttgcacgtc aaaattaggc ctccatctag acccctccat 300
aacatgtgac tgtggggaaa agtataaggg aaaccatgca accatagacg acgtgaaaga 360
cggggaggaa ccaatggagg ccaaagaaat ggggtagcaa cagtccagga gacagacaag 420
gagacaagga gagggcgccc gaaagatcgg aaaaacaaac atgtccaatt ggggcagtga 480
cggaaacgac acggacactt cagtacaatg gaccgaccat ctccaagcca gggttattcc 540
ggtatcacct tggccgtaac ctcccgctgg tacctgatat tgtacacgtt cacattcaat 600
atactttcag ctacaataag agaggctgtt tgtcgggcat gtgtgtccgt cgtatggggt 660
gatgtccgag ggcgaaattc gctacaagct taactctggc gcttgtccag tatgaataga 720
caagtcaaga ccagtggtgc catgattgac agggaggtac aagacttcga tactcgagca 780
ttactcggac ttgtggcgat tgaacagacg ggcgatcgct tctcccccgt attgccggcg 840
cgccagctgc attaatgaat cggccaacgc gcggggagag gcggtttgcg tattgggcgc 900
tcttccgctt cctcgctcac tgactcgctg cgctcggtcg ttcggctgcg gcgagcggta 960
tcagctcact caaaggcggt aatacggtta tccacagaat caggggataa cgcaggaaag 1020

-continued

```
aacatgtgag caaaaggcca gcaaaaggcc aggaaccgta aaaaggccgc gttgctggcg   1080
tttttccata ggctccgccc ccctgacgag catcacaaaa atcgacgctc aagtcagagg   1140
tggcgaaacc cgacaggact ataaagatac caggcgtttc cccctggaag ctccctcgtg   1200
cgctctcctg ttccgaccct gccgcttacc ggatacctgt ccgcctttct cccttcggga   1260
agcgtggcgc tttctcatag ctcacgctgt aggtatctca gttcggtgta ggtcgttcgc   1320
tccaagctgg gctgtgtgca cgaacccccc gttcagcccg accgctgcgc cttatccggt   1380
aactatcgtc ttgagtccaa cccggtaaga cacgacttat cgccactggc agcagccact   1440
ggtaacagga ttagcagagc gaggtatgta ggcggtgcta cagagttctt gaagtggtgg   1500
cctaactacg gctacactag aagaacagta tttggtatct gcgctctgct gaagccagtt   1560
accttcggaa aaagagttgg tagctcttga tccggcaaac aaaccaccgc tggtagcggt   1620
ggtttttttg tttgcaagca gcagattacg cgcagaaaaa aaggatctca agaagatcct   1680
ttgatctttt ctacggggtc tgacgctcag tggaacgaaa actcacgtta agggattttg   1740
gtcatgagat tatcaaaaag gatcttcacc tagatccttt taaattaaaa atgaagtttt   1800
aaatcaatct aaagtatata tgagtaaact tggtctgaca gttaccaatg cttaatcagt   1860
gaggcaccta tctcagcgat ctgtctattt cgttcatcca tagttgcctg actccccgtc   1920
gtgtagataa ctacgatacg ggagggctta ccatctggcc ccagtgctgc aatgataccg   1980
cgagacccac gctcaccggc tccagattta tcagcaataa accagccagc cggaagggcc   2040
gagcgcagaa gtggtcctgc aactttatcc gcctccatcc agtctattaa ttgttgccgg   2100
gaagctagag taagtagttc gccagttaat agtttgcgca acgttgttgc cattgctaca   2160
ggcatcgtgg tgtcacgctc gtcgtttggt atggcttcat tcagctccgg ttcccaacga   2220
tcaaggcgag ttacatgatc ccccatgttg tgcaaaaaag cggttagctc cttcggtcct   2280
ccgatcgttg tcagaagtaa gttggccgca gtgttatcac tcatggttat ggcagcactg   2340
cataattctc ttactgtcat gccatccgta agatgctttt ctgtgactgg tgagtactca   2400
accaagtcat tctgagaata gtgtatgcgg cgaccgagtt gctcttgccc ggcgtcaata   2460
cgggataata ccgcgccaca tagcagaact ttaaaagtgc tcatcattgg aaaacgttct   2520
tcggggcgaa aactctcaag gatcttaccg ctgttgagat ccagttcgat gtaacccact   2580
cgtgcaccca actgatcttc agcatctttt actttcacca gcgtttctgg gtgagcaaaa   2640
acaggaaggc aaaatgccgc aaaaaaggga ataagggcga cacggaaatg ttgaatactc   2700
atactcttcc tttttcaata ttattgaagc atttatcagg gttattgtct catgagcgga   2760
tacatatttg aatgtattta gaaaaataaa caaatagggg ttccgcgcac atttccccga   2820
aaagtgccac ctgatgcggt gtgaaatacc gcacagatgc gtaaggagaa aataccgcat   2880
caggaaattg taagcgttaa tattttgtta aaattcgcgt taaatttttg ttaaatcagc   2940
tcatttttta accaataggc cgaaatcggc aaaatccctt ataaatcaaa agaatagacc   3000
gagatagggt tgagtgttgt tccagtttgg aacaagagtc cactattaaa gaacgtggac   3060
tccaacgtca aagggcgaaa aaccgtctat cagggcgatg gcccactacg tgaaccatca   3120
ccctaatcaa gttttttggg gtcgaggtgc cgtaaagcac taaatcggaa ccctaaaggg   3180
agcccccgat ttagagcttg acggggaaag ccggcgaacg tggcgagaaa ggaagggaag   3240
aaagcgaaag gagcgggcgc tagggcgctg gcaagtgtag cggtcacgct gcgcgtaacc   3300
accacacccg ccgcgcttaa tgcgccgcta cagggcgcgt ccattcgcca ttcaggctgc   3360
gcaactgttg ggaagggcga tcggtgcggg cctcttcgct attacgccag ctggcgaaag   3420
```

```
ggggatgtgc tgcaaggcga ttaagttggg taacgccagg gttttcccag tcacgacgtt   3480
gtaaaacgac ggccagtgaa ttgtaatacg actcactata gggcgaattg ggcccgacgt   3540
cgcatgcgct gatgacactt tggtctgaaa gagatgcatt ttgaatccca aacttgcagt   3600
gcccaagtga catacatctc cgcgttttgg aaaatgttca gaaacagttg attgtgttgg   3660
aatggggaat ggggaatgga aaaatgactc aagtatcaat tccaaaaact tctctggctg   3720
gcagtaccta ctgtccatac tactgcattt tctccagtca ggccactcta tactcgacga   3780
cacagtagta aaacccagat aatttcgaca taaacaagaa aacagaccca ataatattta   3840
tatatagtca gccgtttgtc cagttcagac tgtaatagcc gaaaaaaaat ccaaagtttc   3900
tattctagga aaatatattc caatattttt aattcttaat ctcatttatt ttattctagc   3960
gaaatacatt tcagctactt gagacatgtg atacccacaa atcggattcg gactcggttg   4020
ttcagaagag catatggcat tcgtgctcgc ttgttcacgt attcttcctg ttccatctct   4080
tggccgacaa tcacacaaaa atggggtttt ttttttaatt ctaatgattc attacagcaa   4140
aattgagata tagcagacca cgtattccat aatcaccaag gaagttcttg ggcgtcttaa   4200
ttaagttgcg acacatgtct tgatagtatc ttggcttctc tctcttgagc ttttccataa   4260
caagttcttc tgcctccagg aagtccatgg tgaatgattc ttatactcag aaggaaatgc   4320
ttaacgattt cgggtgtgag ttgacaagga gagagagaaa agaagaggaa aggtaattcg   4380
gggacggtgg tcttttatac ccttggctaa agtcccaacc acaaagcaaa aaaatttcca   4440
gtagtctatt ttgcgtccgg catgggttac ccggatggcc agacaaagaa actagtacaa   4500
agtctgaaca agcgtagatt ccagactgca gtaccctacg cccttaacgg caagtgtggg   4560
aaccggggga ggtttgatat gtggggtgaa gggggctctc gccggggttg ggcccgctac   4620
tgggtcaatt tggggtcaat tggggcaatt ggggctgttt tttgggacac aaatacgccg   4680
ccaacccggt ctctcctgaa ttctgcagat gggctgcagg aattccgtcg tcgcctgagt   4740
cgacatcatt tatttaccag ttggccacaa acccttgacg atctcgtatg tcccctccga   4800
catactcccg gccggctggg gtacgttcga tagcgctatc ggcatcgaca aggtttgggt   4860
ccctagccga taccgcacta cctgagtcac aatcttcgga ggtttagtct tccacatagc   4920
acgggcaaaa gtgcgtatat atacaagagc gtttgccagc cacagatttt cactccacac   4980
accacatcac acatacaacc acacacatcc acaatggaac ccgaaactaa gaagaccaag   5040
actgactcca agaagattgt tcttctcggc ggcgacttct gtggccccga ggtgattgcc   5100
gaggccgtca aggtgctcaa gtctgttgct gaggcctccg gcaccgagtt tgtgtttgag   5160
gaccgactca ttggaggagc tgccattgag aaggagggcg agcccatcac cgacgctact   5220
ctcgacatct gccgaaaggc tgactctatt atgctcggtg ctgtcggagg cgctgccaac   5280
accgtatgga ccactcccga cggacgaacc gacgtgcgac ccgagcaggg tctcctcaag   5340
ctgcgaaagg acctgaacct gtacgccaac ctgcgaccct gccagctgct gtcgcccaag   5400
ctcgccgatc tctcccccat ccgaaacgtt gagggcaccg acttcatcat tgtccgagag   5460
ctcgtcggag gtatctactt tggagagcga aaggaggatg acggatctgg cgtcgcttcc   5520
gacaccgaga cctactccgt tcctgaggtt gagcgaattg cccgaatggc cgccttcctg   5580
gcccttcagc acaacccccc tcttcccgtg tggtctcttg acaaggccaa cgtgctggcc   5640
tcctctcgac tttggcgaaa gactgtcact cgagtcctca aggacgaatt cccccagctc   5700
gagctcaacc accagctgat cgactcggcc gccatgatcc tcatcaagca gccctccaag   5760
```

-continued atgaatggta tcatcatcac caccaacatg tttggcgata tcatctccga cgaggcctcc 5820
gtcatccccg gttctctggg tctgctgccc tccgcctctc tggcttctct gcccgacacc 5880
aacgaggcgt tcggtctgta cgagccctgt cacggatctg cccccgatct cggcaagcag 5940
aaggtcaacc ccattgccac cattctgtct gccgccatga tgctcaagtt ctctcttaac 6000
atgaagcccg ccggtgacgc tgttgaggct gccgtcaagg agtccgtcga ggctggtatc 6060
actaccgccg atatcggagg ctcttcctcc acctccgagg tcggagactt gttgccaaca 6120
aggtcaagga gctgctcaag aaggagtaag tcgtttctac gacgcattga tggaaggagc 6180
aaactgacgc gcctgcgggt tggtctaccg gcagggtccg ctagtgtata agactctata 6240
aaaagggccc tgccctgcta atgaaatgat gatttataat ttaccggtgt agcaaccttg 6300
actagaagaa gcagattggg tgtgtttgta gtggaggaca gtggtacgtt ttggaaacag 6360
tcttcttgaa agtgtcttgt ctacagtata ttcactcata acctcaatag ccaagggtgt 6420
agtcggttta ttaaaggaag ggagttgtgg ctgatgtgga tagatatctt taagctggcg 6480
actgcaccca acgagtgtgg tggtagcttg ttagatctgt atattcggta agatatattt 6540
tgtggggttt tagtggtgtt taaacggtag gttagtgctt ggtatatgag ttgtaggcat 6600
gacaatttgg aaaggggtgg actttgggaa tattgtggga tttcaatacc ttagtttgta 6660
cagggtaatt gttacaaatg atacaaagaa ctgtatttct tttcatttgt tttaattggt 6720
tgtatatcaa gtccgttaga cgagctcagt gccttggctt ttggcactgt atttcatttt 6780
tagaggtaca ctacattcag tgaggtatgg taaggttgag ggcataatga aggcaccttg 6840
tactgacagt cacagacctc tcaccgagaa ttttatgaga tatactcggg ttcattttag 6900
gctcat 6906

<210> SEQ ID NO 78
<211> LENGTH: 2103
<212> TYPE: DNA
<213> ORGANISM: Yarrowia lipolytica

<400> SEQUENCE: 78
atgaacccca acaacactgg caccattgaa atcaacggta aggagtacaa caccttcacc 60
gagccccccg tggccatggc tcaggagcga gccaagacct ccttccccgt gcgagagatg 120
acctacttcc tcgacggtgg cgagaagaac accctcaaaa acgagcagat catggaggag 180
attgagcgag accctctttt caacaacgac aactactacg atctcaacaa ggagcagatc 240
cgagagctca ccatggagcg agtcgccaag ctgtctctgt ttgtgcgtga tcagcccgag 300
gacgacatca agaagcgatt tgctctcatt ggtatcgccg atatgggaac ctacacccga 360
cttggtgtcc actacggcct cttctttggc gccgtccgag gtaccggaac tgccgagcag 420
tttggccact ggatctccaa gggagccgga gacctgcgaa agttctacgg atgtttctcc 480
atgaccgagc tgggccatgg ctccaacctg gctggtctcg agaccaccgc catctacgat 540
gaggagaccg acgagttcat catcaacacc cctcacattg ccgccaccaa gtggtggatt 600
ggaggagccg cccacaccgc cacccacact gtcgtgttcg cccgactcat tgtcaagggc 660
aaggactacg gtgtcaagac ctttgttgtc cagctgcgaa acatcaacga ccacagcctc 720
aaggtcggta tctctattgg tgatatcgga aagaagatgg gccgagacgg tatcgataac 780
ggatggatcc agttcaccaa cgtgcgaatc ccccgacaga acctgctcat gaagtacaca 840
aaggtcgacc gagagggtaa cgtgacccag cctcctctgg ctcagcttac ctacggttct 900
cttatcactg gtcgagtctc catggcctct gattctcacc aggtcggaaa gcgattcatc 960

```
accattgctc tgcgatacgc ctgcattcga cgacagttct ccaccacccc cggccagccc   1020

gagaccaaga tcatcgacta cccctaccat cagcgacgac ttctgcctct tctggcctat   1080

gtctatgctc ttaagatgac tgccgatgag gttggagctc tcttctcccg aaccatgctt   1140

aagatggacg acctcaagcc cgacgacaag gccggcctca atgaggttgt ttccgacgtc   1200

aaggagctct tctccgtctc cgccggtctc aaggccttct ccacctgggc ttgtgccgac   1260

gtcattgaca agacccgaca ggcttgcggt ggccacggtt actctggata caacggtttc   1320

ggccaggcct acgccgactg ggttgtccag tgcacctggg agggtgacaa caacattctc   1380

accctttctg ccggccgagc tcttatccag tctgccgttg ctctgcgaaa gggcgagcct   1440

gttggtaacg ccgtttctta cctgaagcga tacaaggatc tggccaacgc taagctcaat   1500

ggccgatctc tcaccgaccc caaggtcctc gtcgaggcct gggaggttgc tgccggtaac   1560

atcatcaacc gagccaccga ccagtacgag aagctcattg gcgagggtct taacgccgac   1620

caggcctttg aggttctgtc tcagcagcga ttccaggccg ccaaggtcca cacacgacga   1680

cacctcattg ccgctttctt ctcccgaatt gacaccgagg ctggcgaggc catcaagcag   1740

cccctgctta acctggctct gctgtttgcc ctgtggtcca tcgaagagga ctctggtctg   1800

ttcctgcgag agggcttcct cgagcccaag gatatcgaca ccgtcaccga gctcgtcaac   1860

aagtactgca ccactgtgcg agaggaggtc attggctaca ccgatgcctt caacctgtcc   1920

gactacttca tcaacgctcc tattggatgc tacgatggtg acgcttaccg acactacttc   1980

cagaaggtca acgagcagaa ccctgcccga gacccccgac ctccttacta cgcctctact   2040

ctcaagccct tccttttccg agaggaggag gatgatgaca tttgcgagct tgatgaggaa   2100

tag                                                                 2103
```

<210> SEQ ID NO 79
<211> LENGTH: 700
<212> TYPE: PRT
<213> ORGANISM: Yarrowia lipolytica

<400> SEQUENCE: 79

```
Met Asn Pro Asn Asn Thr Gly Thr Ile Glu Ile Asn Gly Lys Glu Tyr
1               5                   10                  15

Asn Thr Phe Thr Glu Pro Pro Val Ala Met Ala Gln Glu Arg Ala Lys
            20                  25                  30

Thr Ser Phe Pro Val Arg Glu Met Thr Tyr Phe Leu Asp Gly Gly Glu
        35                  40                  45

Lys Asn Thr Leu Lys Asn Glu Gln Ile Met Glu Glu Ile Glu Arg Asp
    50                  55                  60

Pro Leu Phe Asn Asn Asp Asn Tyr Tyr Asp Leu Asn Lys Glu Gln Ile
65                  70                  75                  80

Arg Glu Leu Thr Met Glu Arg Val Ala Lys Leu Ser Leu Phe Val Arg
                85                  90                  95

Asp Gln Pro Glu Asp Asp Ile Lys Lys Arg Phe Ala Leu Ile Gly Ile
            100                 105                 110

Ala Asp Met Gly Thr Tyr Thr Arg Leu Gly Val His Tyr Gly Leu Phe
        115                 120                 125

Phe Gly Ala Val Arg Gly Thr Gly Thr Ala Glu Gln Phe Gly His Trp
    130                 135                 140

Ile Ser Lys Gly Ala Gly Asp Leu Arg Lys Phe Tyr Gly Cys Phe Ser
145                 150                 155                 160
```

-continued

```
Met Thr Glu Leu Gly His Gly Ser Asn Leu Ala Gly Leu Glu Thr Thr
                165                 170                 175

Ala Ile Tyr Asp Glu Glu Thr Asp Glu Phe Ile Ile Asn Thr Pro His
            180                 185                 190

Ile Ala Ala Thr Lys Trp Trp Ile Gly Gly Ala Ala His Thr Ala Thr
        195                 200                 205

His Thr Val Val Phe Ala Arg Leu Ile Val Lys Gly Lys Asp Tyr Gly
    210                 215                 220

Val Lys Thr Phe Val Val Gln Leu Arg Asn Ile Asn Asp His Ser Leu
225                 230                 235                 240

Lys Val Gly Ile Ser Ile Gly Asp Ile Gly Lys Lys Met Gly Arg Asp
                245                 250                 255

Gly Ile Asp Asn Gly Trp Ile Gln Phe Thr Asn Val Arg Ile Pro Arg
            260                 265                 270

Gln Asn Leu Leu Met Lys Tyr Thr Lys Val Asp Arg Glu Gly Asn Val
        275                 280                 285

Thr Gln Pro Pro Leu Ala Gln Leu Thr Tyr Gly Ser Leu Ile Thr Gly
    290                 295                 300

Arg Val Ser Met Ala Ser Asp Ser His Gln Val Gly Lys Arg Phe Ile
305                 310                 315                 320

Thr Ile Ala Leu Arg Tyr Ala Cys Ile Arg Arg Gln Phe Ser Thr Thr
                325                 330                 335

Pro Gly Gln Pro Glu Thr Lys Ile Ile Asp Tyr Pro Tyr His Gln Arg
            340                 345                 350

Arg Leu Leu Pro Leu Leu Ala Tyr Val Tyr Ala Leu Lys Met Thr Ala
        355                 360                 365

Asp Glu Val Gly Ala Leu Phe Ser Arg Thr Met Leu Lys Met Asp Asp
    370                 375                 380

Leu Lys Pro Asp Asp Lys Ala Gly Leu Asn Glu Val Val Ser Asp Val
385                 390                 395                 400

Lys Glu Leu Phe Ser Val Ser Ala Gly Leu Lys Ala Phe Ser Thr Trp
                405                 410                 415

Ala Cys Ala Asp Val Ile Asp Lys Thr Arg Gln Ala Cys Gly Gly His
            420                 425                 430

Gly Tyr Ser Gly Tyr Asn Gly Phe Gly Gln Ala Tyr Ala Asp Trp Val
        435                 440                 445

Val Gln Cys Thr Trp Glu Gly Asp Asn Asn Ile Leu Thr Leu Ser Ala
    450                 455                 460

Gly Arg Ala Leu Ile Gln Ser Ala Val Ala Leu Arg Lys Gly Glu Pro
465                 470                 475                 480

Val Gly Asn Ala Val Ser Tyr Leu Lys Arg Tyr Lys Asp Leu Ala Asn
                485                 490                 495

Ala Lys Leu Asn Gly Arg Ser Leu Thr Asp Pro Lys Val Leu Val Glu
            500                 505                 510

Ala Trp Glu Val Ala Ala Gly Asn Ile Ile Asn Arg Ala Thr Asp Gln
        515                 520                 525

Tyr Glu Lys Leu Ile Gly Glu Gly Leu Asn Ala Asp Gln Ala Phe Glu
    530                 535                 540

Val Leu Ser Gln Gln Arg Phe Gln Ala Ala Lys Val His Thr Arg Arg
545                 550                 555                 560

His Leu Ile Ala Ala Phe Phe Ser Arg Ile Asp Thr Glu Ala Gly Glu
                565                 570                 575

Ala Ile Lys Gln Pro Leu Leu Asn Leu Ala Leu Leu Phe Ala Leu Trp
```

-continued

```
            580                 585                 590

Ser Ile Glu Glu Asp Ser Gly Leu Phe Leu Arg Glu Gly Phe Leu Glu
        595                 600                 605

Pro Lys Asp Ile Asp Thr Val Thr Glu Leu Val Asn Lys Tyr Cys Thr
    610                 615                 620

Thr Val Arg Glu Glu Val Ile Gly Tyr Thr Asp Ala Phe Asn Leu Ser
625                 630                 635                 640

Asp Tyr Phe Ile Asn Ala Pro Ile Gly Cys Tyr Asp Gly Asp Ala Tyr
                645                 650                 655

Arg His Tyr Phe Gln Lys Val Asn Glu Gln Asn Pro Ala Arg Asp Pro
            660                 665                 670

Arg Pro Pro Tyr Tyr Ala Ser Thr Leu Lys Pro Phe Leu Phe Arg Glu
        675                 680                 685

Glu Glu Asp Asp Asp Ile Cys Glu Leu Asp Glu Glu
    690                 695                 700
```

```
<210> SEQ ID NO 80
<211> LENGTH: 2103
<212> TYPE: DNA
<213> ORGANISM: Yarrowia lipolytica

<400> SEQUENCE: 80

atgatctccc ccaacctcac agctaacgtc gagattgacg gcaagcagta caacaccttc     60

acagagccac ccaaggcgct cgccggcgag cgagccaagg tcaagttccc catcaaggac    120

atgacggagt ttctgcacgg tggcgaggag aacgtgacca tgatcgagcg actgatgacg    180

gagctcgagc gagaccccgt gctcaacgtg tcgggcgact acgacatgcc caaggagcag    240

ctgcgagaga cggccgtggc gcgaattgcg gcgctgtccg gccactggaa gaaggacaca    300

gaaaaggagg cgctgctgcg gtcccagctg cacggcattg tggacatggg cacccgaatc    360

cgactcggtg tgcacacggg cctgttcatg ggcgccatcc ggggttccgg caccaaggag    420

cagtacgact actgggtgcg aaagggcgcc gcggacgtca agggcttcta cggctgcttt    480

gctatgaccg agctgggcca tggctccaac gtggccggtc ttgagaccac cgccacctac    540

atccaggaca cggacgagtt catcatcaac acccccaaca ctggagccac caagtggtgg    600

attggaggag ccgcccactc ggccacccac accgcctgct ttgctcgtct gcttgtcgac    660

ggcaaggact acggcgtcaa gatctttgtt gtccagctgc gagacgtctc ttctcactct    720

ctcatgcccg gcatcgctct cggcgacatt ggaaagaaga tgggccgaga cgccatcgac    780

aacggctgga tccagttcac caatgtgcga atcccccgac agaacatgct catgaagtac    840

gccaaggtct cgtctaccgg caaggtgtcg cagcctcctc tggcccagct cacctacggc    900

gctctcattg gcggccgagt caccatgatt gccgactcct tctttgtctc ccagcgattc    960

atcaccattg ctctgcgata cgcctgtgtg cgacgacagt ttggcaccac ccccggccag   1020

cccgagacta agatcatcga ctacccctac catcagcgac gtctgctgcc tcttctggcc   1080

ttcacctacg ccatgaagat ggccgccgac cagtcccaga ttcagtacga tcagaccacc   1140

gatctgctgc agaccatcga ccctaaggac aagggcgctc tgggcaaggc cattgtcgac   1200

ctcaaggagc tgtttgcctc ttctgctggt ctcaaggcct tcaccacctg gacctgtgcc   1260

aacatcattg accagtgccg acaggcctgc ggtggccacg gctactctgg ctacaacggc   1320

tttggccagg cctacgccga ctgggttgtc cagtgcacct gggagggtga caacaacgtc   1380

ctgtgtctgt ccatgggccg aggtctcatc cagtcgtgtc tgggccaccg aaagggtaag   1440
```

```
cctctgggct cttctgtcgg ctacctggct aacaagggtc ttgagcaggc tactctgagc   1500

ggccgagacc tcaaggaccc caaggttctc atcgaggcct gggagaaggt cgccaacggc   1560

gccatccagc gggccactga caaatttgtc gagctcacca agggcggcct ctctcctgac   1620

caggcctttg aggagctgtc gcagcagcga ttccagtgtg ccaagatcca cacccgaaag   1680

cacctggtga ctgccttcta cgagcgaatc aacgcctctg cgaaggccga cgtcaagcct   1740

tacctcatca acctcgccaa cctcttcact ctgtggtcca ttgaggagga ctctggtctc   1800

ttcctgcgag agggtttcct gcagcccaag gacattgacc aggtgactga gctggtgaac   1860

cactactgca aggaggttcg agaccaggtt gccggctaca ccgatgcctt tggtctgtct   1920

gactggttca tcaacgctcc cattggaaac tacgatggtg acgtttacaa gcattacttt   1980

gccaaggtta accagcagaa ccctgctcag aacccccgac ctccttacta tgagagcact   2040

cttcgacctt tcctgttccg agaggatgag gatgacgaca tttgcgagct ggacgaggaa   2100

tag                                                                 2103
```

```
<210> SEQ ID NO 81
<211> LENGTH: 700
<212> TYPE: PRT
<213> ORGANISM: Yarrowia lipolytica

<400> SEQUENCE: 81

Met Ile Ser Pro Asn Leu Thr Ala Asn Val Glu Ile Asp Gly Lys Gln
1               5                   10                  15

Tyr Asn Thr Phe Thr Glu Pro Pro Lys Ala Leu Ala Gly Glu Arg Ala
            20                  25                  30

Lys Val Lys Phe Pro Ile Lys Asp Met Thr Glu Phe Leu His Gly Gly
        35                  40                  45

Glu Glu Asn Val Thr Met Ile Glu Arg Leu Met Thr Glu Leu Glu Arg
    50                  55                  60

Asp Pro Val Leu Asn Val Ser Gly Asp Tyr Asp Met Pro Lys Glu Gln
65                  70                  75                  80

Leu Arg Glu Thr Ala Val Ala Arg Ile Ala Ala Leu Ser Gly His Trp
                85                  90                  95

Lys Lys Asp Thr Glu Lys Glu Ala Leu Leu Arg Ser Gln Leu His Gly
            100                 105                 110

Ile Val Asp Met Gly Thr Arg Ile Arg Leu Gly Val His Thr Gly Leu
        115                 120                 125

Phe Met Gly Ala Ile Arg Gly Ser Gly Thr Lys Glu Gln Tyr Asp Tyr
    130                 135                 140

Trp Val Arg Lys Gly Ala Ala Asp Val Lys Gly Phe Tyr Gly Cys Phe
145                 150                 155                 160

Ala Met Thr Glu Leu Gly His Gly Ser Asn Val Ala Gly Leu Glu Thr
                165                 170                 175

Thr Ala Thr Tyr Ile Gln Asp Thr Asp Glu Phe Ile Ile Asn Thr Pro
            180                 185                 190

Asn Thr Gly Ala Thr Lys Trp Trp Ile Gly Gly Ala Ala His Ser Ala
        195                 200                 205

Thr His Thr Ala Cys Phe Ala Arg Leu Leu Val Asp Gly Lys Asp Tyr
    210                 215                 220

Gly Val Lys Ile Phe Val Val Gln Leu Arg Asp Val Ser Ser His Ser
225                 230                 235                 240

Leu Met Pro Gly Ile Ala Leu Gly Asp Ile Gly Lys Lys Met Gly Arg
                245                 250                 255
```

-continued

```
Asp Ala Ile Asp Asn Gly Trp Ile Gln Phe Thr Asn Val Arg Ile Pro
            260                 265                 270

Arg Gln Asn Met Leu Met Lys Tyr Ala Lys Val Ser Ser Thr Gly Lys
        275                 280                 285

Val Ser Gln Pro Pro Leu Ala Gln Leu Thr Tyr Gly Ala Leu Ile Gly
    290                 295                 300

Gly Arg Val Thr Met Ile Ala Asp Ser Phe Phe Val Ser Gln Arg Phe
305                 310                 315                 320

Ile Thr Ile Ala Leu Arg Tyr Ala Cys Val Arg Arg Gln Phe Gly Thr
            325                 330                 335

Thr Pro Gly Gln Pro Glu Thr Lys Ile Ile Asp Tyr Pro Tyr His Gln
            340                 345                 350

Arg Arg Leu Leu Pro Leu Leu Ala Phe Thr Tyr Ala Met Lys Met Ala
        355                 360                 365

Ala Asp Gln Ser Gln Ile Gln Tyr Asp Gln Thr Thr Asp Leu Leu Gln
    370                 375                 380

Thr Ile Asp Pro Lys Asp Lys Gly Ala Leu Gly Lys Ala Ile Val Asp
385                 390                 395                 400

Leu Lys Glu Leu Phe Ala Ser Ser Ala Gly Leu Lys Ala Phe Thr Thr
            405                 410                 415

Trp Thr Cys Ala Asn Ile Ile Asp Gln Cys Arg Gln Ala Cys Gly Gly
            420                 425                 430

His Gly Tyr Ser Gly Tyr Asn Gly Phe Gly Gln Ala Tyr Ala Asp Trp
        435                 440                 445

Val Val Gln Cys Thr Trp Glu Gly Asp Asn Asn Val Leu Cys Leu Ser
    450                 455                 460

Met Gly Arg Gly Leu Ile Gln Ser Cys Leu Gly His Arg Lys Gly Lys
465                 470                 475                 480

Pro Leu Gly Ser Ser Val Gly Tyr Leu Ala Asn Lys Gly Leu Glu Gln
            485                 490                 495

Ala Thr Leu Ser Gly Arg Asp Leu Lys Asp Pro Lys Val Leu Ile Glu
            500                 505                 510

Ala Trp Glu Lys Val Ala Asn Gly Ala Ile Gln Arg Ala Thr Asp Lys
        515                 520                 525

Phe Val Glu Leu Thr Lys Gly Gly Leu Ser Pro Asp Gln Ala Phe Glu
    530                 535                 540

Glu Leu Ser Gln Gln Arg Phe Gln Cys Ala Lys Ile His Thr Arg Lys
545                 550                 555                 560

His Leu Val Thr Ala Phe Tyr Glu Arg Ile Asn Ala Ser Ala Lys Ala
            565                 570                 575

Asp Val Lys Pro Tyr Leu Ile Asn Leu Ala Asn Leu Phe Thr Leu Trp
            580                 585                 590

Ser Ile Glu Glu Asp Ser Gly Leu Phe Leu Arg Glu Gly Phe Leu Gln
        595                 600                 605

Pro Lys Asp Ile Asp Gln Val Thr Glu Leu Val Asn His Tyr Cys Lys
    610                 615                 620

Glu Val Arg Asp Gln Val Ala Gly Tyr Thr Asp Ala Phe Gly Leu Ser
625                 630                 635                 640

Asp Trp Phe Ile Asn Ala Pro Ile Gly Asn Tyr Asp Gly Asp Val Tyr
            645                 650                 655

Lys His Tyr Phe Ala Lys Val Asn Gln Gln Asn Pro Ala Gln Asn Pro
            660                 665                 670
```

```
Arg Pro Pro Tyr Tyr Glu Ser Thr Leu Arg Pro Phe Leu Phe Arg Glu
        675                 680                 685

Asp Glu Asp Asp Asp Ile Cys Glu Leu Asp Glu Glu
    690                 695                 700


<210> SEQ ID NO 82
<211> LENGTH: 12355
<212> TYPE: DNA
<213> ORGANISM: artificial sequence
<220> FEATURE:
<223> OTHER INFORMATION: pZKLY-FCtR17U plasmid

<400> SEQUENCE: 82

cgatgagcct aaaatgaacc cgagtatatc tcataaaatt ctcggtgaga ggtctgtgac     60

tgtcagtaca aggtgccttc attatgccct caaccttacc atacctcact gaatgtagtg    120

tacctctaaa aatgaaatac agtgccaaaa gccaaggcac tgagctcgtc taacggactt    180

gatatacaac caattaaaac aaatgaaaag aaatacagtt ctttgtatca tttgtaacaa    240

ttaccctgta caaactaagg tattgaaatc ccacaatatt cccaaagtcc accccttttcc   300

aaattgtcat gcctacaact catataccaa gcactaacct accgtttaaa cagtgtacgc    360

agtactatag aggaacaatt gccccggaga agacggccag gccgcctaga tgacaaattc    420

aacaactcac agctgacttt ctgccattgc cactaggggg gggccttttt atatggccaa    480

gccaagctct ccacgtcggt tggctgcac ccaacaataa atgggtaggg ttgcaccaac     540

aaagggatgg gatggggggt agaagatacg aggataacgg ggctcaatgg cacaaataag    600

aacgaatact gccattaaga ctcgtgatcc agcgactgac accattgcat catctaaggg    660

cctcaaaact acctcggaac tgctgcgctg atctggacac cacagaggtt ccgagcactt    720

taggttgcac caaatgtccc accaggtgca ggcagaaaac gctggaacag cgtgtacagt    780

ttgtcttaac aaaaagtgag ggcgctgagg tcgagcaggg tggtgtgact tgttatagcc    840

tttagagctg cgaaagcgcg tatggatttg gctcatcagg ccagattgag ggtctgtgga    900

cacatgtcat gttagtgtac ttcaatcgcc ccctggatat agccccgaca ataggccgtg    960

gcctcatttt tttgccttcc gcacatttcc attgctcggt acccacacct tgcttctcct   1020

gcacttgcca accttaatac tggtttacat tgaccaacat cttacaagcg gggggcttgt   1080

ctagggtata tataaacagt ggctctccca atcggttgcc agtctctttt ttcctttctt   1140

tccccacaga ttcgaaatct aaactacaca tcacacaatt ccgagccgtg agtatccacg   1200

acaagatcag tgtcgagacg acgcgttttg tgtaatgaca caatccgaaa gtcgctagca   1260

acacacactc tctacacaaa ctaacccagc tctccatggc catcgagcag ctgctcgagt   1320

actggtacgt cgttgtgccc gtcctgtaca ttatcaagca gctccttgcc tacaccaaga   1380

ctcgagtgct gatgaaaaag ctcggagccg ctcccgtcac caacaagctg tacgacaacg   1440

ccttcggtat cgtcaacggc tggaaggctc ttcagttcaa gaaagagggc cgagctcagg   1500

aatacaacga ctacaagttc gatcactcca agaatccttc tgtgggaacc tacgtctcca   1560

ttctgtttgg cactcgaatc gtggttacca aggatcccga gaacatcaag gccattctcg   1620

caacccagtt cggagacttt tcgctgggca agcgacacac tctcttcaag cccttgctgg   1680

gagacggtat cttcacactc gatggagaag gctggaagca ttccagagct atgctgcgac   1740

ctcagtttgc ccgagagcaa gttgctcacg tcaccagcct cgaaccacac ttccagctgc   1800

tcaagaaaca tatcctcaag cacaagggcg agtacttcga cattcaggag ctgttctttc   1860

gattcaccgt ggactctgcc acggagtttc tgttcggcga gtccgttcac tctctcaagg   1920
```

-continued

```
acgagtcgat tggaatcaac caggacgata tcgacttcgc tggtcggaag gactttgccg   1980
agtccttcaa caaggcacag gaatacttgg ccattcgaac tctggtgcag accttctact   2040
ggctcgtcaa caacaaggag tttcgagact gcaccaagct ggttcacaag ttcaccaact   2100
actatgtcca gaaggctctc gatgcatctc ccgaggaact tgagaagcaa agcggctacg   2160
tgttcctgta cgagcttgtc aagcagacca gagatcccaa cgtgctgcga gaccagtccc   2220
tcaacatctt gctggccgga cgagacacca ctgctggcct cctgtcgttt gcagtcttcg   2280
agttggctcg tcatcccgag atctgggcca agctgcgaga ggaaatcgag caacagttcg   2340
gacttggcga ggactctcgt gtcgaagaga ttaccttcga gagcctcaag cgatgcgagt   2400
acctcaaggc ctttctcaac gaaaccctgc ggatctaccc ttccgttcct cgaaacttca   2460
gaatcgctac caagaacaca acccttcccc gaggcggtgg atcggacggt acttctccaa   2520
tcctcattca gaagggcgag gccgtgtcct acggtatcaa ttctactcat ctggatcctg   2580
tctattacgg acccgacgct gccgagtttc gacccgagcg atggttcgaa ccttcgacca   2640
aaaagctcgg ctgggcctac cttcccttca acggaggtcc acgaatctgt ctgggccaac   2700
agtttgccct caccgaggct ggctacgtgc tggtcagact cgttcaggag ttctcccacg   2760
tccgatccga tcccgacgag gtgtaccctc ccaagcgact tacaaacctg accatgtgtc   2820
tccaggacgg tgccattgtc aagttcgact aagcggccgc aagtgtggat ggggaagtga   2880
gtgcccggtt ctgtgtgcac aattggcaat ccaagatgga tggattcaac acagggatat   2940
agcgagctac gtggtggtgc gaggatatag caacggatat ttatgtttga cacttgagaa   3000
tgtacgatac aagcactgtc caagtacaat actaaacata ctgtacatac tcatactcgt   3060
acccgggcaa cggtttcact tgagtgcagt ggctagtgct cttactcgta cagtgtgcaa   3120
tactgcgtat catagtcttt gatgtatatc gtattcattc atgttagttg atttaaacca   3180
tcatctaagg gcctcaaaac tacctcggaa ctgctgcgct gatctggaca ccacagaggt   3240
tccgagcact ttaggttgca ccaaatgtcc caccaggtgc aggcagaaaa cgctggaaca   3300
gcgtgtacag tttgtcttaa caaaaagtga gggcgctgag gtcgagcagg gtggtgtgac   3360
ttgttatagc ctttagagct gcgaaagcgc gtatggattt ggctcatcag gccagattga   3420
gggtctgtgg acacatgtca tgttagtgta cttcaatcgc cccctggata tagccccgac   3480
aataggccgt ggcctcattt ttttgccttc cgcacatttc cattgctcgg tacccacacc   3540
ttgcttctcc tgcacttgcc aaccttaata ctggtttaca ttgaccaaca tcttacaagc   3600
ggggggcttg tctagggtat atataaacag tggctctccc aatcggttgc cagtctcttt   3660
tttcctttct ttccccacag attcgaaatc taaactacac atcacaccat ggccctggac   3720
aagctcgacc tgtacgtcat cattaccctc gtggttgcta tcgccgctta cttcgccaag   3780
aaccagttcc tggatcagca acaggacact ggctttctca acaccgactc cggagatggc   3840
aactctcgag acatccttca ggctctcaag aaaaacaata agaacaccct gcttctcttc   3900
ggttcccaga ctggcacagc cgaggactac gccaacaagt tgtcgcgaga gctgcactcc   3960
cgatttggct tgaagactat ggtcgcagat ttcgccgatt acgacttcga gaactttgga   4020
gacattaccg aggacatcct cgtgttcttt atcgttgcta cctacggcga aggcgagccc   4080
accgacaatg ccgacgagtt tcacacttgg ctgaccgagg aagcagatac cctgtctaca   4140
ctcaagtata ccgtcttcgg tctgggtaac tccacctacg agtttttcaa cgccatcggt   4200
cgaaagttcg acagactgct cggagagaag ggtggcgacc gatttgccga gtacggcgaa   4260
```

-continued

```
ggagacgatg gtactggcac tctcgacgag gatttcctgg cttggaagga caacgtgttc   4320
gattctctca agaacgacct gaatttcgaa gagaaggagc tcaaatacga acccaacgtc   4380
aagttgaccg agcgggacga tctgtctggc aacgatcccg acgtttcgct gggcgagcca   4440
aacgtcaagt acatcaagtc cgagggtgtt gaccttacca agggaccttt cgatcacact   4500
catccctttc tggcccgaat cgtcaagacc aaagagctct ttacttccga ggacagacac   4560
tgcgtgcacg tcgagttcga cattagcgag tccaacctca agtatactac cggagatcat   4620
cttgctatct ggccctccaa ttcggacgag aacatcaagc agtttgccaa gtgctttggc   4680
ctggaggaca agctcgatac cgtcatcgag ctgaaggctc tcgattccac ttactccatt   4740
ccatttccca atccaatcac ctacggagcc gtcattcgtc accatttgga gatctctggt   4800
cctgtgtcgc gacagttctt tctgtccatt gccggatttg ctcccgacga agagaccaaa   4860
aagtccttca ctcgaatcgg tggcgacaag caagagttcg ccagcaaggt cacccgtcga   4920
aagttcaaca ttgccgatgc tcttctgttt gcctccaaca atcgaccctg gtccgacgtt   4980
cccttcgagt tccttatcga gaacgtccag catctcactc ctcggtacta ttccatttct   5040
tcgtcctctc tcagcgagaa gcagaccatc aacgttactg ctgtggtcga agccgaggaa   5100
gaggccgatg gacgacccgt tactggtgtc gttaccaacc tgctcaagaa catcgagatt   5160
gaacagaaca agactggcga gacaccaatg gtccactacg acctcaatgg tcccagaggc   5220
aagttctcca agtttcgact gcccgtgcac gtcagacgat ccaacttcaa acttcccaag   5280
aactctacta cccctgtcat cctgattggt ccaggcaccg gtgttgctcc cctgcgaggc   5340
tttgtccggg agcgagtgca gcaagtcaag aacggagtca acgttggtaa gactgtgctg   5400
ttctacggct gtcgaaattc cgaacaggac tttctctaca aacaggagtg gagcgagtat   5460
gcctccgtcc tgggagagaa cttcgaaatg ttcaacgcct tttctcgaca ggaccctacc   5520
aagaaagtgt acgttcaaga caagatcctc gagaactctg ctcttgtcga cgagctcctg   5580
tccagcggtg caattatcta cgtttgcgga gatgcctctc gaatggctcg agacgtgcag   5640
gctgcaattg ccaagatcgt tgccaagtcc cgagacatcc acgaggacaa ggctgccgag   5700
ctggtcaagt cttggaaggt gcagaaccga taccaggagg atgtctggta agcggccgca   5760
tgagaagata aatatataaa tacattgaga tattaaatgc gctagattag agagcctcat   5820
actgctcgga gagaagccaa gacgagtact caaaggggat tacaccatcc atatccacag   5880
acacaagctg gggaaaggtt ctatatacac tttccggaat accgtagttt ccgatgttat   5940
caatgggggc agccaggatt tcaggcactt cggtgtctcg ggtgaaatg gcgttcttgg   6000
cctccatcaa gtcgtaccat gtcttcattt gcctgtcaaa gtaaaacaga agcagatgaa   6060
gaatgaactt gaagtgaagg aatttaaatg taacgaaact gaaatttgac cagatattgt   6120
gtccgcggtg gagctccagc ttttgttccc tttagtgagg gttaatttcg agcttggcgt   6180
aatcatggtc atagctgttt cctgtgtgaa attgttatcc gctcacaagc ttccacacaa   6240
cgtacgttga ttgaggtgga gccagatggg ctattgtttc atatatagac tggcagccac   6300
ctctttggcc cagcatgttt gtatacctgg aagggaaaac taaagaagct ggctagttta   6360
gtttgattat tatagtagat gtcctaatca ctagagatta gaatgtcttg gcgatgatta   6420
gtcgtcgtcc cctgtatcat gtctagacca actgtgtcat gaagttggtg ctggtgtttt   6480
acctgtgtac tacaagtagg tgtcctagat ctagtgtaca gagccgttta gacccatgtg   6540
gacttcacca ttaacgatgg aaaatgttca ttatatgaca gtatattaca atggacttgc   6600
tccatttctt ccttgcatca catgttctcc acctccatag ttgatcaaca catcatagta   6660
```

```
gctaaggctg ctgctctccc actacagtcc accacaagtt aagtagcacc gtcagtacag   6720
ctaaaagtac acgtctagta cgtttcataa ctagtcaagt agcccctatt acagatatca   6780
gcactatcac gcacgagttt ttctctgtgc tatctaatca acttgccaag tattcggaga   6840
agatacactt tcttggcatc aggtatacga gggagcctat cagatgaaaa agggtatatt   6900
ggatccattc atatccacct acacgttgtc ataatctcct cattcacgtg attcatttcg   6960
tgacactagt ttctcacttt cccccccgca cctatagtca acttggcgga cacgctactt   7020
gtagctgacg ttgatttata gacccaatca aagcgggtta tcggtcaggt agcacttatc   7080
attcatcgtt catactacga tgagcaatct cgggcatgtc cggaaaagtg tcgggcgcgc   7140
cagctgcatt aatgaatcgg ccaacgcgcg gggagaggcg gtttgcgtat tgggcgctct   7200
tccgcttcct cgctcactga ctcgctgcgc tcggtcgttc ggctgcggcg agcggtatca   7260
gctcactcaa aggcggtaat acggttatcc acagaatcag gggataacgc aggaaagaac   7320
atgtgagcaa aaggccagca aaaggccagg aaccgtaaaa aggccgcgtt gctggcgttt   7380
ttccataggc tccgcccccc tgacgagcat cacaaaaatc gacgctcaag tcagaggtgg   7440
cgaaacccga caggactata aagataccag gcgtttcccc ctggaagctc cctcgtgcgc   7500
tctcctgttc cgaccctgcc gcttaccgga tacctgtccg cctttctccc ttcgggaagc   7560
gtggcgcttt ctcatagctc acgctgtagg tatctcagtt cggtgtaggt cgttcgctcc   7620
aagctgggct gtgtgcacga accccccgtt cagcccgacc gctgcgcctt atccggtaac   7680
tatcgtcttg agtccaaccc ggtaagacac gacttatcgc cactggcagc agccactggt   7740
aacaggatta gcagagcgag gtatgtaggc ggtgctacag agttcttgaa gtggtggcct   7800
aactacggct acactagaag aacagtattt ggtatctgcg ctctgctgaa gccagttacc   7860
ttcggaaaaa gagttggtag ctcttgatcc ggcaaacaaa ccaccgctgg tagcggtggt   7920
tttttgtttg caagcagcag attacgcgca gaaaaaaagg atctcaagaa gatcctttga   7980
atcttttcta cggggtctga cgctcagtgg aacgaaaact cacgttaagg gattttggtc   8040
atgagattat caaaaaggat cttcacctag atccttttaa attaaaaatg aagttttaaa   8100
tcaatctaaa gtatatatga gtaaacttgg tctgacagtt accaatgctt aatcagtgag   8160
gcacctatct cagcgatctg tctatttcgt tcatccatag ttgcctgact ccccgtcgtg   8220
tagataacta cgatacggga gggcttacca tctggcccca gtgctgcaat gataccgcga   8280
gacccacgct caccggctcc agatttatca gcaataaacc agccagccgg aagggccgag   8340
cgcagaagtg gtcctgcaac tttatccgcc tccatccagt ctattaattg ttgccgggaa   8400
gctagagtaa gtagttcgcc agttaatagt ttgcgcaacg ttgttgccat tgctacaggc   8460
atcgtggtgt cacgctcgtc gtttggtatg gcttcattca gctccggttc ccaacgatca   8520
aggcgagtta catgatcccc catgttgtgc aaaaaagcgg ttagctcctt cggtcctccg   8580
atcgttgtca gaagtaagtt ggccgcagtg ttatcactca tggttatggc agcactgcat   8640
aattctctta ctgtcatgcc atccgtaaga tgcttttctg tgactggtga gtactcaacc   8700
aagtcattct gagaatagtg tatgcggcga ccgagttgct cttgcccggc gtcaatacgg   8760
gataataccg cgccacatag cagaacttta aaagtgctca tcattggaaa acgttcttcg   8820
gggcgaaaac tctcaaggat cttaccgctg ttgagatcca gttcgatgta acccactcgt   8880
gcacccaact gatcttcagc atcttttact ttcaccagcg tttctgggtg agcaaaaaca   8940
ggaaggcaaa atgccgcaaa aaagggaata agggcgacac ggaaatgttg aatactcata   9000
```

-continued

```
ctcttccttt ttcaatatta ttgaagcatt tatcagggtt attgtctcat gagcggatac   9060
atatttgaat gtatttagaa aaataaacaa ataggggttc cgcgcacatt tccccgaaaa   9120
gtgccacctg atgcggtgtg aaataccgca cagatgcgta aggagaaaat accgcatcag   9180
gaaattgtaa gcgttaatat tttgttaaaa ttcgcgttaa atttttgtta aatcagctca   9240
ttttttaacc aataggccga aatcggcaaa atcccttata aatcaaaaga atagaccgag   9300
atagggttga gtgttgttcc agtttggaac aagagtccac tattaaagaa cgtggactcc   9360
aacgtcaaag ggcgaaaaac cgtctatcag ggcgatggcc cactacgtga accatcaccc   9420
taatcaagtt ttttggggtc gaggtgccgt aaagcactaa atcggaaccc taaagggagc   9480
ccccgattta gagcttgacg gggaaagccg gcgaacgtgg cgagaaagga agggaagaaa   9540
gcgaaaggag cgggcgctag ggcgctggca agtgtagcgg tcacgctgcg cgtaaccacc   9600
acacccgccg cgcttaatgc gccgctacag ggcgcgtcca ttcgccattc aggctgcgca   9660
actgttggga agggcgatcg gtgcgggcct cttcgctatt acgccagctg gcgaaagggg   9720
gatgtgctgc aaggcgatta agttgggtaa cgccagggtt ttcccagtca cgacgttgta   9780
aaacgacggc cagtgaattg taatacgact cactataggg cgaattgggc ccgacgtcgc   9840
atgcattccg acagcagcga ctgggcacca tgatcaagcg aaacaccttc ccccagctgc   9900
cctggcaaac catcaagaac cctactttca tcaagtgcaa gaacggttct actcttctca   9960
cctccggtgt ctacggctgg tgccgaaagc ctaactacac cgctgatttc atcatgtgcc  10020
tcacctgggc tctcatgtgc ggtgttgctt ctcccctgcc ttacttctac ccggtcttct  10080
tcttcctggt gctcatccac cgagcttacc gagactttga gcgactggag cgaaagtacg  10140
gtgaggacta ccaggagttc aagcgacagg tcccttggat cttcatccct tatgttttct  10200
aaacgataag cttagtgagc gaatggtgag gttacttaat tgagtggcca gcctatggga  10260
ttgtataaca gacagtcaat atattactga aaagactgaa cagccagacg gagtgaggtt  10320
gtgagtgaat cgtagagggc ggctattaca gcaagtctac tctacagtgt actaacacag  10380
cagagaacaa atacaggtgt gcattcggct atctgagaat tagttggaga gctcgagacc  10440
ctcggcgata aactgctcct cggttttgtg tccatacttg tacggaccat tgtaatgggg  10500
caagtcgttg agttctcgtc gtccgacgtt cagagcacag aaaccaatgt aatcaatgta  10560
gcagagatgg ttctgcaaaa gattgatttg tgcgagcagg ttaattaact ttggccggaa  10620
ttcctttacc tgcaggataa cttcgtataa tgtatgctat acgaagttat gatctctctc  10680
ttgagctttt ccataacaag ttcttctgcc tccaggaagt ccatgggtgg tttgatcatg  10740
gttttggtgt agtggtagtg cagtggtggt attgtgactg gggatgtagt tgagaataag  10800
tcatacacaa gtcagctttc ttcgagcctc atataagtat aagtagttca acgtattagc  10860
actgtaccca gcatctccgt atcgagaaac acaacaacat gccccattgg acagatcatg  10920
cggatacaca ggttgtgcag tatcatacat actcgatcag acaggtcgtc tgaccatcat  10980
acaagctgaa caagcgctcc atacttgcac gctctctata tacacagtta aattacatat  11040
ccatagtcta acctctaaca gttaatcttc tggtaagcct cccagccagc cttctggtat  11100
cgcttggcct cctcaatagg atctcggttc tggccgtaca gacctcggcc gacaattatg  11160
atatccgttc cggtagacat gacatcctca acagttcggt actgctgtcc gagagcgtct  11220
cccttgtcgt caagacccac cccgggggtc agaataagcc agtcctcaga gtcgccctta  11280
ggtcggttct gggcaatgaa gccaaccaca aactcggggt cggatcgggc aagctcaatg  11340
gtctgcttgg agtactcgcc agtggccaga gagcccttgc aagacagctc ggccagcatg  11400
```

agcagacctc tggccagctt ctcgttggga gaggggacta ggaactcctt gtactgggag 11460
ttctcgtagt cagagacgtc ctccttcttc tgttcagaga cagtttcctc ggcaccagct 11520
cgcaggccag caatgattcc ggttccgggt acaccgtggg cgttggtgat atcggaccac 11580
tcggcgattc ggtgacaccg gtactggtgc ttgacagtgt tgccaatatc tgcgaacttt 11640
ctgtcctcga acaggaagaa accgtgctta agagcaagtt ccttgagggg gagcacagtg 11700
ccggcgtagg tgaagtcgtc aatgatgtcg atatgggttt tgatcatgca cacataaggt 11760
ccgaccttat cggcaagctc aatgagctcc ttggtggtgg taacatccag agaagcacac 11820
aggttggttt tcttggctgc cacgagcttg agcactcgag cggcaaaggc ggacttgtgg 11880
acgttagctc gagcttcgta ggagggcatt ttggtggtga agaggagact gaaataaatt 11940
tagtctgcag aactttttat cggaacctta tctggggcag tgaagtatat gttatggtaa 12000
tagttacgag ttagttgaac ttatagatag actggactat acggctatcg gtccaaatta 12060
gaaagaacgt caatggctct ctgggcgtcg cctttgccga caaaaatgtg atcatgatga 12120
aagccagcaa tgacgttgca gctgatattg ttgtcggcca accgcgccga aaacgcagct 12180
gtcagaccca cagcctccaa cgaagaatgt atcgtcaaag tgatccaagc acactcatag 12240
ttggagtcgt actccaaagg cggcaatgac gagtcagaca gatactcgtc gacgcgataa 12300
cttcgtataa tgtatgctat acgaagttat cgtacgatag ttagtagaca acaat 12355

<210> SEQ ID NO 83
<211> LENGTH: 1557
<212> TYPE: DNA
<213> ORGANISM: artificial sequence
<220> FEATURE:
<223> OTHER INFORMATION: CtCYPs(52A17)

<400> SEQUENCE: 83
atggccatcg agcagctgct cgagtactgg tacgtcgttg tgcccgtcct gtacattatc 60
aagcagctcc ttgcctacac caagactcga gtgctgatga aaaagctcgg agccgctccc 120
gtcaccaaca agctgtacga caacgccttc ggtatcgtca acggctggaa ggctcttcag 180
ttcaagaaag agggccgagc tcaggaatac aacgactaca agttcgatca ctccaagaat 240
ccttctgtgg gaacctacgt ctccattctg tttggcactc gaatcgtggt taccaaggat 300
cccgagaaca tcaaggccat tctcgcaacc cagttcggag acttttcgct gggcaagcga 360
cacactctct tcaagccctt gctgggagac ggtatcttca cactcgatgg agaaggctgg 420
aagcattcca gagctatgct gcgacctcag tttgcccgag agcaagttgc tcacgtcacc 480
agcctcgaac cacacttcca gctgctcaag aaacatatcc tcaagcacaa gggcgagtac 540
ttcgacattc aggagctgtt ctttcgattc accgtggact ctgccacgga gtttctgttc 600
ggcgagtccg ttcactctct caaggacgag tcgattggaa tcaaccagga cgatatcgac 660
ttcgctggtc ggaaggactt tgccgagtcc ttcaacaagg cacaggaata cttggccatt 720
cgaactctgg tgcagacctt ctactggctc gtcaacaaca aggagtttcg agactgcacc 780
aagctggttc acaagttcac caactactat gtccagaagg ctctcgatgc atctcccgag 840
gaacttgaga agcaaagcgg ctacgtgttc ctgtacgagc ttgtcaagca gaccagagat 900
cccaacgtgc tgcgagacca gtccctcaac atcttgctgg ccggacgaga caccactgct 960
ggcctcctgt cgtttgcagt cttcgagttg gctcgtcatc ccgagatctg ggccaagctg 1020
cgagaggaaa tcgagcaaca gttcggactt ggcgaggact ctcgtgtcga agagattacc 1080

-continued

```
ttcgagagcc tcaagcgatg cgagtacctc aaggcctttc tcaacgaaac cctgcggatc   1140

tacccttccg ttcctcgaaa cttcagaatc gctaccaaga acacaaccct tccccgaggc   1200

ggtggatcgg acggtacttc tccaatcctc attcagaagg gcgaggccgt gtcctacggt   1260

atcaattcta ctcatctgga tcctgtctat tacggacccg acgctgccga gtttcgaccc   1320

gagcgatggt tcgaaccttc gaccaaaaag ctcggctggg cctaccttcc cttcaacgga   1380

ggtccacgaa tctgtctggg ccaacagttt gccctcaccg aggctggcta cgtgctggtc   1440

agactcgttc aggagttctc ccacgtccga tccgatcccg acgaggtgta ccctcccaag   1500

cgacttacaa acctgaccat gtgtctccag gacggtgcca ttgtcaagtt cgactaa      1557


<210> SEQ ID NO 84
<211> LENGTH: 518
<212> TYPE: PRT
<213> ORGANISM: artificial sequence
<220> FEATURE:
<223> OTHER INFORMATION: CtCYPs(52A17) protein

<400> SEQUENCE: 84

Met Ala Ile Glu Gln Leu Leu Glu Tyr Trp Tyr Val Val Val Pro Val
1               5                   10                  15

Leu Tyr Ile Ile Lys Gln Leu Leu Ala Tyr Thr Lys Thr Arg Val Leu
            20                  25                  30

Met Lys Lys Leu Gly Ala Ala Pro Val Thr Asn Lys Leu Tyr Asp Asn
        35                  40                  45

Ala Phe Gly Ile Val Asn Gly Trp Lys Ala Leu Gln Phe Lys Lys Glu
    50                  55                  60

Gly Arg Ala Gln Glu Tyr Asn Asp Tyr Lys Phe Asp His Ser Lys Asn
65                  70                  75                  80

Pro Ser Val Gly Thr Tyr Val Ser Ile Leu Phe Gly Thr Arg Ile Val
                85                  90                  95

Val Thr Lys Asp Pro Glu Asn Ile Lys Ala Ile Leu Ala Thr Gln Phe
            100                 105                 110

Gly Asp Phe Ser Leu Gly Lys Arg His Thr Leu Phe Lys Pro Leu Leu
        115                 120                 125

Gly Asp Gly Ile Phe Thr Leu Asp Gly Glu Gly Trp Lys His Ser Arg
    130                 135                 140

Ala Met Leu Arg Pro Gln Phe Ala Arg Glu Gln Val Ala His Val Thr
145                 150                 155                 160

Ser Leu Glu Pro His Phe Gln Leu Leu Lys Lys His Ile Leu Lys His
                165                 170                 175

Lys Gly Glu Tyr Phe Asp Ile Gln Glu Leu Phe Phe Arg Phe Thr Val
            180                 185                 190

Asp Ser Ala Thr Glu Phe Leu Phe Gly Glu Ser Val His Ser Leu Lys
        195                 200                 205

Asp Glu Ser Ile Gly Ile Asn Gln Asp Asp Ile Asp Phe Ala Gly Arg
    210                 215                 220

Lys Asp Phe Ala Glu Ser Phe Asn Lys Ala Gln Glu Tyr Leu Ala Ile
225                 230                 235                 240

Arg Thr Leu Val Gln Thr Phe Tyr Trp Leu Val Asn Asn Lys Glu Phe
                245                 250                 255

Arg Asp Cys Thr Lys Leu Val His Lys Phe Thr Asn Tyr Tyr Val Gln
            260                 265                 270

Lys Ala Leu Asp Ala Ser Pro Glu Glu Leu Glu Lys Gln Ser Gly Tyr
        275                 280                 285
```

```
Val Phe Leu Tyr Glu Leu Val Lys Gln Thr Arg Asp Pro Asn Val Leu
    290                 295                 300

Arg Asp Gln Ser Leu Asn Ile Leu Leu Ala Gly Arg Asp Thr Thr Ala
305                 310                 315                 320

Gly Leu Leu Ser Phe Ala Val Phe Glu Leu Ala Arg His Pro Glu Ile
                325                 330                 335

Trp Ala Lys Leu Arg Glu Glu Ile Glu Gln Gln Phe Gly Leu Gly Glu
            340                 345                 350

Asp Ser Arg Val Glu Glu Ile Thr Phe Glu Ser Leu Lys Arg Cys Glu
        355                 360                 365

Tyr Leu Lys Ala Phe Leu Asn Glu Thr Leu Arg Ile Tyr Pro Ser Val
    370                 375                 380

Pro Arg Asn Phe Arg Ile Ala Thr Lys Asn Thr Thr Leu Pro Arg Gly
385                 390                 395                 400

Gly Gly Ser Asp Gly Thr Ser Pro Ile Leu Ile Gln Lys Gly Glu Ala
                405                 410                 415

Val Ser Tyr Gly Ile Asn Ser Thr His Leu Asp Pro Val Tyr Tyr Gly
            420                 425                 430

Pro Asp Ala Ala Glu Phe Arg Pro Glu Arg Trp Phe Glu Pro Ser Thr
        435                 440                 445

Lys Lys Leu Gly Trp Ala Tyr Leu Pro Phe Asn Gly Gly Pro Arg Ile
    450                 455                 460

Cys Leu Gly Gln Gln Phe Ala Leu Thr Glu Ala Gly Tyr Val Leu Val
465                 470                 475                 480

Arg Leu Val Gln Glu Phe Ser His Val Arg Ser Asp Pro Asp Glu Val
                485                 490                 495

Tyr Pro Pro Lys Arg Leu Thr Asn Leu Thr Met Cys Leu Gln Asp Gly
            500                 505                 510

Ala Ile Val Lys Phe Asp
        515
```

<210> SEQ ID NO 85
<211> LENGTH: 2043
<212> TYPE: DNA
<213> ORGANISM: artificial sequence
<220> FEATURE:
<223> OTHER INFORMATION: CtCPRs (CPR)

<400> SEQUENCE: 85

```
atggccctgg acaagctcga cctgtacgtc atcattaccc tcgtggttgc tatcgccgct      60

tacttcgcca agaaccagtt cctggatcag caacaggaca ctggctttct caacaccgac     120

tccggagatg gcaactctcg agacatcctt caggctctca agaaaaacaa taagaacacc     180

ctgcttctct tcggttccca gactggcaca gccgaggact acgccaacaa gttgtcgcga     240

gagctgcact cccgatttgg cttgaagact atggtcgcag atttcgccga ttacgacttc     300

gagaactttg gagacattac cgaggacatc ctcgtgttct ttatcgttgc tacctacggc     360

gaaggcgagc ccaccgacaa tgccgacgag tttcacactt ggctgaccga ggaagcagat     420

accctgtcta cactcaagta taccgtcttc ggtctgggta actccaccta cgagtttttc     480

aacgccatcg gtcgaaagtt cgacagactg ctcggagaga agggtggcga ccgatttgcc     540

gagtacggcg aaggagacga tggtactggc actctcgacg aggatttcct ggcttggaag     600

gacaacgtgt tcgattctct caagaacgac ctgaatttcg aagagaagga gctcaaatac     660

gaacccaacg tcaagttgac cgagcgggac gatctgtctg gcaacgatcc cgacgtttcg     720
```

-continued

```
ctgggcgagc caaacgtcaa gtacatcaag tccgagggtg ttgaccttac caagggacct    780

ttcgatcaca ctcatccctt tctggcccga atcgtcaaga ccaaagagct ctttacttcc    840

gaggacagac actgcgtgca cgtcgagttc gacattagcg agtccaacct caagtatact    900

accggagatc atcttgctat ctggccctcc aattcggacg agaacatcaa gcagtttgcc    960

aagtgctttg gcctggagga caagctcgat accgtcatcg agctgaaggc tctcgattcc   1020

acttactcca ttccatttcc caatccaatc acctacggag ccgtcattcg tcaccatttg   1080

gagatctctg gtcctgtgtc gcgacagttc tttctgtcca ttgccggatt tgctcccgac   1140

gaagagacca aaaagtcctt cactcgaatc ggtggcgaca agcaagagtt cgccagcaag   1200

gtcacccgtc gaaagttcaa cattgccgat gctcttctgt ttgcctccaa caatcgaccc   1260

tggtccgacg ttcccttcga gttccttatc gagaacgtcc agcatctcac tcctcggtac   1320

tattccattt cttcgtcctc tctcagcgag aagcagacca tcaacgttac tgctgtggtc   1380

gaagccgagg aagaggccga tggacgaccc gttactggtg tcgttaccaa cctgctcaag   1440

aacatcgaga ttgaacagaa caagactggc gagacaccaa tggtccacta cgacctcaat   1500

ggtcccagag gcaagttctc caagtttcga ctgcccgtgc acgtcagacg atccaacttc   1560

aaacttccca agaactctac taccccctgtc atcctgattg gtccaggcac cggtgttgct   1620

cccctgcgag gctttgtccg ggagcgagtg cagcaagtca agaacggagt caacgttggt   1680

aagactgtgc tgttctacgg ctgtcgaaat tccgaacagg actttctcta caaacaggag   1740

tggagcgagt atgcctccgt cctgggagag aacttcgaaa tgttcaacgc cttttctcga   1800

caggacccta ccaagaaagt gtacgttcaa gacaagatcc tcgagaactc tgctcttgtc   1860

gacgagctcc tgtccagcgg tgcaattatc tacgtttgcg gagatgcctc tcgaatggct   1920

cgagacgtgc aggctgcaat tgccaagatc gttgccaagt cccgagacat ccacgaggac   1980

aaggctgccg agctggtcaa gtcttggaag gtgcagaacc gataccagga ggatgtctgg   2040

taa                                                                 2043
```

<210> SEQ ID NO 86
<211> LENGTH: 680
<212> TYPE: PRT
<213> ORGANISM: Candida tropicalis

<400> SEQUENCE: 86

```
Met Ala Leu Asp Lys Leu Asp Leu Tyr Val Ile Ile Thr Leu Val Val
1               5                   10                  15

Ala Ile Ala Ala Tyr Phe Ala Lys Asn Gln Phe Leu Asp Gln Gln Gln
            20                  25                  30

Asp Thr Gly Phe Leu Asn Thr Asp Ser Gly Asp Gly Asn Ser Arg Asp
        35                  40                  45

Ile Leu Gln Ala Leu Lys Lys Asn Asn Lys Asn Thr Leu Leu Leu Phe
    50                  55                  60

Gly Ser Gln Thr Gly Thr Ala Glu Asp Tyr Ala Asn Lys Leu Ser Arg
65                  70                  75                  80

Glu Leu His Ser Arg Phe Gly Leu Lys Thr Met Val Ala Asp Phe Ala
                85                  90                  95

Asp Tyr Asp Phe Glu Asn Phe Gly Asp Ile Thr Glu Asp Ile Leu Val
            100                 105                 110

Phe Phe Ile Val Ala Thr Tyr Gly Glu Gly Glu Pro Thr Asp Asn Ala
        115                 120                 125
```

-continued

```
Asp Glu Phe His Thr Trp Leu Thr Glu Glu Ala Asp Thr Leu Ser Thr
    130                 135                 140

Leu Lys Tyr Thr Val Phe Gly Leu Gly Asn Ser Thr Tyr Glu Phe Phe
145                 150                 155                 160

Asn Ala Ile Gly Arg Lys Phe Asp Arg Leu Leu Gly Glu Lys Gly Gly
                165                 170                 175

Asp Arg Phe Ala Glu Tyr Gly Glu Gly Asp Asp Gly Thr Gly Thr Leu
            180                 185                 190

Asp Glu Asp Phe Leu Ala Trp Lys Asp Asn Val Phe Asp Ser Leu Lys
        195                 200                 205

Asn Asp Leu Asn Phe Glu Glu Lys Glu Leu Lys Tyr Glu Pro Asn Val
    210                 215                 220

Lys Leu Thr Glu Arg Asp Asp Leu Ser Gly Asn Asp Pro Asp Val Ser
225                 230                 235                 240

Leu Gly Glu Pro Asn Val Lys Tyr Ile Lys Ser Glu Gly Val Asp Leu
                245                 250                 255

Thr Lys Gly Pro Phe Asp His Thr His Pro Phe Leu Ala Arg Ile Val
            260                 265                 270

Lys Thr Lys Glu Leu Phe Thr Ser Glu Asp Arg His Cys Val His Val
        275                 280                 285

Glu Phe Asp Ile Ser Glu Ser Asn Leu Lys Tyr Thr Thr Gly Asp His
    290                 295                 300

Leu Ala Ile Trp Pro Ser Asn Ser Asp Glu Asn Ile Lys Gln Phe Ala
305                 310                 315                 320

Lys Cys Phe Gly Leu Glu Asp Lys Leu Asp Thr Val Ile Glu Leu Lys
                325                 330                 335

Ala Leu Asp Ser Thr Tyr Ser Ile Pro Phe Pro Asn Pro Ile Thr Tyr
            340                 345                 350

Gly Ala Val Ile Arg His His Leu Glu Ile Ser Gly Pro Val Ser Arg
        355                 360                 365

Gln Phe Phe Leu Ser Ile Ala Gly Phe Ala Pro Asp Glu Glu Thr Lys
    370                 375                 380

Lys Ser Phe Thr Arg Ile Gly Gly Asp Lys Gln Glu Phe Ala Ser Lys
385                 390                 395                 400

Val Thr Arg Arg Lys Phe Asn Ile Ala Asp Ala Leu Leu Phe Ala Ser
                405                 410                 415

Asn Asn Arg Pro Trp Ser Asp Val Pro Phe Glu Phe Leu Ile Glu Asn
            420                 425                 430

Val Gln His Leu Thr Pro Arg Tyr Tyr Ser Ile Ser Ser Ser Ser Leu
        435                 440                 445

Ser Glu Lys Gln Thr Ile Asn Val Thr Ala Val Val Glu Ala Glu Glu
    450                 455                 460

Glu Ala Asp Gly Arg Pro Val Thr Gly Val Val Thr Asn Leu Leu Lys
465                 470                 475                 480

Asn Ile Glu Ile Glu Gln Asn Lys Thr Gly Glu Thr Pro Met Val His
                485                 490                 495

Tyr Asp Leu Asn Gly Pro Arg Gly Lys Phe Ser Lys Phe Arg Leu Pro
            500                 505                 510

Val His Val Arg Arg Ser Asn Phe Lys Leu Pro Lys Asn Ser Thr Thr
        515                 520                 525

Pro Val Ile Leu Ile Gly Pro Gly Thr Gly Val Ala Pro Leu Arg Gly
    530                 535                 540

Phe Val Arg Glu Arg Val Gln Gln Val Lys Asn Gly Val Asn Val Gly
```

```
545                 550                 555                 560

Lys Thr Val Leu Phe Tyr Gly Cys Arg Asn Ser Glu Gln Asp Phe Leu
                565                 570                 575

Tyr Lys Gln Glu Trp Ser Glu Tyr Ala Ser Val Leu Gly Glu Asn Phe
            580                 585                 590

Glu Met Phe Asn Ala Phe Ser Arg Gln Asp Pro Thr Lys Lys Val Tyr
        595                 600                 605

Val Gln Asp Lys Ile Leu Glu Asn Ser Ala Leu Val Asp Glu Leu Leu
    610                 615                 620

Ser Ser Gly Ala Ile Ile Tyr Val Cys Gly Asp Ala Ser Arg Met Ala
625                 630                 635                 640

Arg Asp Val Gln Ala Ala Ile Ala Lys Ile Val Ala Lys Ser Arg Asp
                645                 650                 655

Ile His Glu Asp Lys Ala Ala Glu Leu Val Lys Ser Trp Lys Val Gln
            660                 665                 670

Asn Arg Tyr Gln Glu Asp Val Trp
        675                 680


<210> SEQ ID NO 87
<211> LENGTH: 12573
<212> TYPE: DNA
<213> ORGANISM: artificial sequence
<220> FEATURE:
<223> OTHER INFORMATION: pZKADn-C2F1U plasmid

<400> SEQUENCE: 87

cgatagtgta cgcagtacta tagaggaaca attgccccgg agaagacggc caggccgcct      60

agatgacaaa ttcaacaact cacagctgac tttctgccat tgccactagg ggggggcctt     120

tttatatggc caagccaagc tctccacgtc ggttgggctg cacccaacaa taaatgggta     180

gggttgcacc aacaaaggga tgggatgggg ggtagaagat acgaggataa cggggctcaa     240

tggcacaaat aagaacgaat actgccatta agactcgtga tccagcgact gacaccattg     300

catcatctaa gggcctcaaa actacctcgg aactgctgcg ctgatctgga caccacagag     360

gttccgagca ctttaggttg caccaaatgt cccaccaggt gcaggcagaa aacgctggaa     420

cagcgtgtac agtttgtctt aacaaaaagt gagggcgctg aggtcgagca gggtggtgtg     480

acttgttata gcctttagag ctgcgaaagc gcgtatggat ttggctcatc aggccagatt     540

gagggtctgt ggacacatgt catgttagtg tacttcaatc gccccctgga tatagccccg     600

acaataggcc gtggcctcat ttttttgcct tccgcacatt tccattgctc ggtacccaca     660

ccttgcttct cctgcacttg ccaaccttaa tactggttta cattgaccaa catcttacaa     720

gcggggggct tgtctagggt atatataaac agtggctctc ccaatcggtt gccagtctct     780

tttttccttt ctttccccac agattcgaaa tctaaactac acatcacacc atggcctccc     840

accaggtcga ggaccacgat ctggacgtgt tctgcctcct ggccgacgct gttctccacg     900

agattcctcc ctccgaaatc gtcgagtacc ttcatcccga tttccccaag gacaagatcg     960

aagagtacct gaccggcttt tctcgaccct ccgccgttcc tcagttccga cagtgtgcca    1020

agaaactcat caaccgaggt tccgagctgt cgatcaagct cttcctttac ttgaccactg    1080

ctctggactc tcgaatcctt gcaccagccc tgaccaactc gctcactctg atcagagaca    1140

tggatctttc ccagcgagag gaactgttgc ggtcctggcg agattctcca ctgactgcca    1200

agcgaagact ctttcgagtc tacgcctcct ttaccctgtc tacattcaac aagctcggaa    1260

ccgacttgca cttcaaggcc ctgggctacc ctggtcgaga gctccggacc cagattcaag    1320
```

-continued

```
actacgaggt cgatcccttt cgatactcgt tcatggagaa gctcaaacac gagggacatg   1380
aactgttcct tcccgatatc gacgttctga tcattggctc tggatccggt gcaggcgtgg   1440
tcgctcagac tcttaccgag agcggactca agtctctggt tctcgagaag ggcaagtact   1500
ttgcctccga agagctgtgc atgaccgatc tcgacggaaa cgaggccctg ttcgaaagcg   1560
gtggcactat tccttccacc aatcaacagt tgttcatgat cgctggatct acttttggtg   1620
gaggctccac cgtcaactgg tctgcctgtc tcaagactcc cttcaaggtt cgaaaggagt   1680
ggtacgacga tttcggactg gactttgtgg ctacccagca atacgacgat tgcatggact   1740
acgtgtggaa gaaaatgggt gcctcgaccg agcacatcga gcattctgct gcaaatgccg   1800
tcatcatgga cggagctgcc aagcttggct acgctcaccg agccctcgag cagaacaccg   1860
gtggccatgt tcacgactgt ggaatgtgcc acctgggctg tcgattcggt atcaagcagg   1920
gaggcgtcaa ctgctggttt cgagaaccct ccgagaaggg ttccaagttc atggagcagg   1980
tcgttgtcga gaagattctg cagcacaagg gcaaggccac tggaattctc tgcagagata   2040
ccgagtctgg catcaagttc aagattactg gacccaagaa atacgtcgtg tccggtggct   2100
ctttgcagac ccctgttctc cttcagaagt ctggcttcaa gaacaagcac attggagcca   2160
acctcaagct gcatcccgtc tcggttgctc ttggcgactt tggtaacgag gtggacttcg   2220
aagcctacaa gcgacccctc atgaccgcag tctgcaatgc cgtggacgat ctggacggca   2280
aggctcacgg aacacgaatc gaggccattc tgcacgctcc ttacgtcact gctcccttct   2340
atccctggca gtccggtgcc caggctcgga agaacttgct caaatacaag cagaccgtgc   2400
ctctgctcct tctgtctcga gacacctcct cgggtaccgt tacatacgac aaacagaagc   2460
cagatgtctt ggtggtcgac tacactgtca acaagttcga tcgaaactcc atcctgcagg   2520
gatttctcgt tgcttccgac attttgtaca tcgagggtgc caaggagatt ctgtctcccc   2580
aggcttgggt gcccaccttc aagagcaaca agcccaagca cgccagatcc atcaaggacg   2640
aggactacgt caagtggcga gaaaccgtgg ccaagattcc ctttgattcc tacggctcgc   2700
cttacggttc tgctcatcag atgtcctcgt gtcgaatgtc tggcaaggga cccggatacg   2760
gtgcctgcga taccaaggga cgactcttcg agtgcaacaa tgtgtacgtt gcagacgcct   2820
ccgtcatgcc tactgcttct ggagtcaacc ccatgattac cacaatggcc tttgcacgac   2880
acgttgctct ctgtctggcc aaggaccttc aaccccagac caagctgtaa gcggccgcat   2940
ggagcgtgtg ttctgagtcg atgttttcta tggagttgtg agtgttagta gacatgatgg   3000
gtttatatat gatgaatgaa tagatgtgat tttgatttgc acgatggaat tgagaacttt   3060
gtaaacgtac atgggaatgt atgaatgtgg gggttttgtg actggataac tgacggtcag   3120
tggacgccgt tgttcaaata tccaagagat gcgagaaact ttgggtcaag tgaacatgtc   3180
ctctctgttc aagtaaacca tcaactatgg gtagtatatt tagtaaggac aagagttgag   3240
attctttgga gtcctagaaa cgtattttcg cgttccaaga tcaaattagt agagtaatac   3300
gggcacggga atccattcat agtctcaagt ttaaaccacg ccaactgata tccccttacg   3360
ttacccccctc atcacctggt gaggcaaaac tgtaaggtga aagctaaaaa tgacatctca   3420
gctgcacgaa ggaccggggc ttaaaagacg ggctggtgct tgtgatttaa aactggacaa   3480
atctcagctt gcttgaaatt ttggtctcca actgtttccg agcgaatcgc acacaaaccg   3540
ggcttctctc tgcagaccac gcccccgaaa ctctttctcc caccaccacc aacactccct   3600
ttccattccc acaccgttcc tctctcatcc ttgcgcaatc atcttcgtct gcgacatatt   3660
```

```
gtacgacata cagtaccacg gaacgtttca gaccgtcgac gtgaacacat cttaggaaca   3720
gcaacctgag ctacagaaat ctatctatag gcggataaaa aaacgcaccc actgctcgtc   3780
ctccttgctc ctcgaaaccg actcctctac acacgtcaaa tccgaggttg aaatcttccc   3840
cacatttggc agccaaacca gcacatccca gcaacctcgc acagcgccga aatcgacctg   3900
tcgacttggc cacaaaaaaa agcaccggct ctgcaacagt tctcacgacc aattacgtac   3960
aagtacgaaa tcgttcgtgg accgtgactg ataagctccc actttttctt ctaacaacag   4020
gcaacagaca agtcacacaa aacaaaagcc atggccaagt cctacaagct gcccaagcct   4080
tccaagatcg ctcccatcat tcgaggcaag acctctgcca agaccaaagg ctccactcag   4140
cctcccgagt ctccacctgc ctcggctaag atcacagctc cccagctcga acccgtcgag   4200
cccaccagcg actccgagat tccttctacc aaggtctccg ttcgacgtac atcgaccact   4260
tccagcaaga ccatcacgga cgattccatc tctgccactt ccaccgacca gatgaagtcg   4320
agcaccaacg aagccgagat tccaaacccc aagccagagt ccgtggttgc ccctatgacc   4380
aagcccgtcg aggacgataa actcgaggac cacaccaagc tggagactgc cgaatcgtac   4440
atcaacgttc agaaggaagc tgcaattcct ggcgagacca agagcgtcgt ttcctcgaag   4500
actgcttctg tgctcgagta cacacctctt tccgagatct ctggcggagt caagaaagtg   4560
gtcgacggtt tccacaccgg caagacgcat cccctggagt tcagactcaa gcagcttcga   4620
aacctgtact ttgctatgaa ggacaatcag gaggccatct gcgaagcgct tgccaaggac   4680
tttcaccgag ccccttccga gactcgaaac tacgagctgg tcacaggtct caacgagctg   4740
ctctacacca tgactcaact gcacaagtgg tccaagcccc ttcctgtgga cgcgctgccc   4800
atcaacctca agaccaatcc cgtctacatc gagcggattc cagtcggaac cgttctcgtc   4860
atttctgcct tcaactatcc cttctttgtc tccgtgtctc ccatcgcagg tgctattgcc   4920
gcaggcaact ccgtcgtgtt caagccgtcg gagcttacac cccactttac caagctgttc   4980
acagagttgc tcaccaaggc tctggatccc gagatcttct acgtggtcaa cggtgccgtt   5040
tccgagacta ccgaactgct caaccagaag ttcgacaaga tcgtctacac tggcagcgac   5100
attgtcggca agatcattgc caagaaagca gcggagaccc ttactccagt catcttggag   5160
ctcggtggca agtctcctgc tttcgtgctg gacgatgtct cggacaagga tcttcccgtc   5220
atcgctcgac gtatcgcctg gggacgatac gccaacgctg gtcaaacctg cattggcgtc   5280
gactacgttc tcgtggccga gtccaagcac gagaagttca ttcaggctct gcggaatgtc   5340
atcgaaaacg agttctttcc caacatcgac cagaactcca actttaccca catgatccac   5400
gagcgagcct tcctcaagat gaaaaagatc ctggatacca ctgccggaga gatcattatc   5460
ggtggcaagc tcgacagcga gtccaactac gtgtctccca ccgtcatcga caatgcttcg   5520
tgggacgatt cctcgatgaa ggaggaaatc ttcggtccta ttcttcccat cattacttac   5580
accgacctca agcaggcctg caacgaggtc atttctcatc atgacactcc ccttgctcag   5640
tacatcttca cgtctggctc cacctcgcga aagtacaact ctcagatcaa cacaatctcc   5700
accatgattc gatcgggtgg actggtcatc aacgacgttc tcatgcatat ctcccttcat   5760
aacgctccct tcggtggcgt gggaaagtcc ggctacggtg cctatcacgg agagttctcc   5820
tacagagcct ttacccacga gcgaaccgtc ctcgagcagc atctgtggaa cgattggatt   5880
atcaactctc ggtatcctcc ctactccaac aagaaagaac gactggtggc ctccagccag   5940
tccaactacg gtggcagagt ctggtttggt cgaaagggcg acgttcgaat cgagggaccc   6000
actaccttct tcagcgcctg gaccaacgtg ctcggcgttg ctgccgtcgt tcgagacttc   6060
```

atcggtgctt ccatgtaagc ggccgcatga gaagataaat atataaatac attgagatat 6120
taaatgcgct agattagaga gcctcatact gctcggagag aagccaagac gagtactcaa 6180
aggggattac accatccata tccacagaca caagctgggg aaaggttcta tatacacttt 6240
ccggaatacc gtagtttccg atgttatcaa tgggggcagc caggatttca ggcacttcgg 6300
tgtctcgggg tgaaatggcg ttcttggcct ccatcaagtc gtaccatgtc ttcatttgcc 6360
tgtcaaagta aaacagaagc agatgaagaa tgaacttgaa gtgaaggaat ttaaatgtaa 6420
cgaaactgaa atttgaccag atattgtgtc cgcggtggag ctccagcttt tgttcccttt 6480
agtgagggtt aatttcgagc ttggcgtaat catggtcata gctgtttcct gtgtgaaatt 6540
gttatccgct cacaagcttc cacacaacgt acgaacgcac ggtatcggag catcggatac 6600
cccacattga gccaacctac tttgtagtgt acatactgta gagaagaggg acgcttcgac 6660
atgattggcc gatgtgggca tgtagaaaca cgatatatgg tgcttactaa tggacacttg 6720
cacaaccatt tctcttctag ggtaacctcg acagtgacag ccgtttttc tgcgctagcg 6780 tgtcgtcgta tttttggttt cgacatgtta agatttgtgg ggcaatcgag cgacattaag 6840
gtgcatcgga tcatcggccc aagggagagt cactggagtc tcgtagggtg gaggaaaaga 6900
gcaatttggg acgatttggg gcgatttgaa gacggattgg ggcaggtgtt tgtcacgtga 6960
ctgtggtatt actattacta atcgtcattg ttcgaaagtc ctgtcaattg tatcactttg 7020
gtgggtctac caaaacactg gtcaaatcta cgccacatga aaatataaag tttcacatta 7080
gccacattga ggggtaccct tagttggaat ctacaaggag ggatgcagtg aaaaatgttc 7140
ctttgatcct tcagagatga aaatgccatt gaccaatcac agcgggttta aagagtggcg 7200
aaaagagccc ctttttgca ccggttggcc cagcagccac gtgactggcc ccttccccat 7260
cccactcaac tgttgaggag gtgggatgcc aagatgcacc gtcaatgtac ttccgtgtat 7320
ccttctgcaa ttgatccgag ataggcgcgc cagctgcatt aatgaatcgg ccaacgcgcg 7380
gggagaggcg gtttgcgtat tgggcgctct tccgcttcct cgctcactga ctcgctgcgc 7440
tcggtcgttc ggctgcggcg agcggtatca gctcactcaa aggcggtaat acggttatcc 7500
acagaatcag gggataacgc aggaaagaac atgtgagcaa aaggccagca aaaggccagg 7560
aaccgtaaaa aggccgcgtt gctggcgttt ttccataggc tccgcccccc tgacgagcat 7620
cacaaaaatc gacgctcaag tcagaggtgg cgaaacccga caggactata aagataccag 7680
gcgtttcccc ctggaagctc cctcgtgcgc tctcctgttc cgaccctgcc gcttaccgga 7740
tacctgtccg cctttctccc ttcgggaagc gtggcgcttt ctcatagctc acgctgtagg 7800
tatctcagtt cggtgtaggt cgttcgctcc aagctgggct gtgtgcacga accccccgtt 7860
cagcccgacc gctgcgcctt atccggtaac tatcgtcttg agtccaaccc ggtaagacac 7920
gacttatcgc cactggcagc agccactggt aacaggatta gcagagcgag gtatgtaggc 7980
ggtgctacag agttcttgaa gtggtggcct aactacggct acactagaag aacagtattt 8040
ggtatctgcg ctctgctgaa gccagttacc ttcggaaaaa gagttggtag ctcttgatcc 8100
ggcaaacaaa ccaccgctgg tagcggtggt ttttttgttt gcaagcagca gattacgcgc 8160
agaaaaaaag gatctcaaga agatcctttg atcttttcta cggggtctga cgctcagtgg 8220
aacgaaaact cacgttaagg gattttggtc atgagattat caaaaaggat cttcacctag 8280
atccttttaa attaaaaatg aagttttaaa tcaatctaaa gtatatatga gtaaacttgg 8340
tctgacagtt accaatgctt aatcagtgag gcacctatct cagcgatctg tctatttcgt 8400

-continued tcatccatag ttgcctgact ccccgtcgtg tagataacta cgatacggga gggcttacca 8460
tctggcccca gtgctgcaat gataccgcga gacccacgct caccggctcc agatttatca 8520
gcaataaacc agccagccgg aagggccgag cgcagaagtg gtcctgcaac tttatccgcc 8580
tccatccagt ctattaattg ttgccgggaa gctagagtaa gtagttcgcc agttaatagt 8640
ttgcgcaacg ttgttgccat tgctacaggc atcgtggtgt cacgctcgtc gtttggtatg 8700
gcttcattca gctccggttc ccaacgatca aggcgagtta catgatcccc catgttgtgc 8760
aaaaaagcgg ttagctcctt cggtcctccg atcgttgtca gaagtaagtt ggccgcagtg 8820
ttatcactca tggttatggc agcactgcat aattctctta ctgtcatgcc atccgtaaga 8880
tgcttttctg tgactggtga gtactcaacc aagtcattct gagaatagtg tatgcggcga 8940
ccgagttgct cttgcccggc gtcaatacgg gataataccg cgccacatag cagaacttta 9000
aaagtgctca tcattggaaa acgttcttcg gggcgaaaac tctcaaggat cttaccgctg 9060
ttgagatcca gttcgatgta acccactcgt gcacccaact gatcttcagc atcttttact 9120
ttcaccagcg tttctgggtg agcaaaaaca ggaaggcaaa atgccgcaaa aaagggaata 9180
agggcgacac ggaaatgttg aatactcata ctcttccttt ttcaatatta ttgaagcatt 9240
tatcagggtt attgtctcat gagcggatac atatttgaat gtatttagaa aaataaacaa 9300
ataggggttc cgcgcacatt tccccgaaaa gtgccacctg atgcggtgtg aaataccgca 9360
cagatgcgta aggagaaaat accgcatcag gaaattgtaa gcgttaatat tttgttaaaa 9420
ttcgcgttaa atttttgtta aatcagctca ttttttaacc aataggccga aatcggcaaa 9480
atcccttata aatcaaaaga atagaccgag atagggttga gtgttgttcc agtttggaac 9540
aagagtccac tattaaagaa cgtggactcc aacgtcaaag ggcgaaaaac cgtctatcag 9600
ggcgatggcc cactacgtga accatcaccc taatcaagtt ttttggggtc gaggtgccgt 9660
aaagcactaa atcggaaccc taaagggagc ccccgattta gagcttgacg gggaaagccg 9720
gcgaacgtgg cgagaaagga agggaagaaa gcgaaaggag cgggcgctag ggcgctggca 9780
agtgtagcgg tcacgctgcg cgtaaccacc acacccgccg cgcttaatgc gccgctacag 9840
ggcgcgtcca ttcgccattc aggctgcgca actgttggga agggcgatcg gtgcgggcct 9900
cttcgctatt acgccagctg gcgaaagggg gatgtgctgc aaggcgatta agttgggtaa 9960
cgccagggtt ttcccagtca cgacgttgta aaacgacggc cagtgaattg taatacgact 10020
cactataggg cgaattgggc ccgacgtcgc atgctacaag tatcgcacca tacttttgct 10080
gacggcgcgc cttcttgcag tgatataatc ggtttcttgg agctgatggg gtgagcatca 10140
tacaagtatg agtacgagaa gtcgcacttg tactccaagt acaaatgccc ggaatggcag 10200
acacacaagt cctacgggtg ttcagagact actgactgga gattgcaact acaagtactg 10260
tacacacagt acaacacaca agttaactca tcattcataa ttatcataaa ctagacggcc 10320
aaaaagtcgt ggccgctcct cagcgtcaat agccgcgctt acttggagca gtccagaacg 10380
tatcgaccgg caatcttgcc ctcctccatg agcttgtaga cggattcgag ctcggagaga 10440
ccaacaataa tgatggggga cttgaccagt cctcgggcaa agaactcaat ggcctcctgg 10500
gagtcggctc ggtttccgac gtaagagccc ttgatctgaa tagatcgagc aacctgctgg 10560
aagatgggcg acttgcagac ggcaccggcg ggcagaccga ccagaacaac ggttcccagg 10620
gttcgcacgt actcaacaga ctggttgacg gcaaactcgg agacagacac gttgatgacg 10680
gcgtggggtc cgcccttggt ggcctcctgg acgtccttga ccagatcctt ggacttggca 10740
aagtcgatga agacctcggc gccgagctcc ttgcacatct tctccttgtc agcgccagtg 10800

```
tcaatggcca gcactcggtt aattaacttt ggccggaatt cctttacctg caggataact  10860

tcgtataatg tatgctatac gaagttatga tctctctctt gagcttttcc ataacaagtt  10920

cttctgcctc caggaagtcc atgggtggtt tgatcatggt tttggtgtag tggtagtgca  10980

gtggtggtat tgtgactggg gatgtagttg agaataagtc atacacaagt cagctttctt  11040

cgagcctcat ataagtataa gtagttcaac gtattagcac tgtacccagc atctccgtat  11100

cgagaaacac aacaacatgc cccattggac agatcatgcg gatacacagg ttgtgcagta  11160

tcatacatac tcgatcagac aggtcgtctg accatcatac aagctgaaca agcgctccat  11220

acttgcacgc tctctatata cacagttaaa ttacatatcc atagtctaac ctctaacagt  11280

taatcttctg gtaagcctcc cagccagcct tctggtatcg cttggcctcc tcaataggat  11340

ctcggttctg gccgtacaga cctcggccga caattatgat atccgttccg gtagacatga  11400

catcctcaac agttcggtac tgctgtccga gagcgtctcc cttgtcgtca agacccaccc  11460

cgggggtcag aataagccag tcctcagagt cgcccttagg tcggttctgg gcaatgaagc  11520

caaccacaaa ctcggggtcg gatcgggcaa gctcaatggt ctgcttggag tactcgccag  11580

tggccagaga gcccttgcaa gacagctcgg ccagcatgag cagacctctg gccagcttct  11640

cgttgggaga ggggactagg aactccttgt actgggagtt ctcgtagtca gagacgtcct  11700

ccttcttctg ttcagagaca gtttcctcgg caccagctcg caggccagca atgattccgg  11760

ttccgggtac accgtgggcg ttggtgatat cggaccactc ggcgattcgg tgacaccggt  11820

actggtgctt gacagtgttg ccaatatctg cgaactttct gtcctcgaac aggaagaaac  11880

cgtgcttaag agcaagttcc ttgaggggga gcacagtgcc ggcgtaggtg aagtcgtcaa  11940

tgatgtcgat atgggttttg atcatgcaca cataaggtcc gaccttatcg gcaagctcaa  12000

tgagctcctt ggtggtggta acatccagag aagcacacag gttggttttc ttggctgcca  12060

cgagcttgag cactcgagcg gcaaaggcgg acttgtggac gttagctcga gcttcgtagg  12120

agggcatttt ggtggtgaag aggagactga aataaattta gtctgcagaa ctttttatcg  12180

gaaccttatc tggggcagtg aagtatatgt tatggtaata gttacgagtt agttgaactt  12240

atagatagac tggactatac ggctatcggt ccaaattaga aagaacgtca atggctctct  12300

gggcgtcgcc tttgccgaca aaaatgtgat catgatgaaa gccagcaatg acgttgcagc  12360

tgatattgtt gtcggccaac cgcgccgaaa acgcagctgt cagacccaca gcctccaacg  12420

aagaatgtat cgtcaaagtg atccaagcac actcatagtt ggagtcgtac tccaaaggcg  12480

gcaatgacga gtcagacaga tactcgtcga cgcgataact tcgtataatg tatgctatac  12540

gaagttatcg tacgatagtt agtagacaac aat                               12573
```

```
<210> SEQ ID NO 88
<211> LENGTH: 2100
<212> TYPE: DNA
<213> ORGANISM: artificial sequence
<220> FEATURE:
<223> OTHER INFORMATION: CcFAO1s (FAO)

<400> SEQUENCE: 88

atggcctccc accaggtcga ggaccacgat ctggacgtgt tctgcctcct ggccgacgct     60

gttctccacg agattcctcc ctccgaaatc gtcgagtacc ttcatcccga tttccccaag    120

gacaagatcg aagagtacct gaccggcttt tctcgaccct ccgccgttcc tcagttccga    180

cagtgtgcca agaaactcat caaccgaggt tccgagctgt cgatcaagct cttcctttac    240
```

-continued

```
ttgaccactg ctctggactc tcgaatcctt gcaccagccc tgaccaactc gctcactctg    300

atcagagaca tggatctttc ccagcgagag gaactgttgc ggtcctggcg agattctcca    360

ctgactgcca agcgaagact ctttcgagtc tacgcctcct ttaccctgtc tacattcaac    420

aagctcggaa ccgacttgca cttcaaggcc ctgggctacc ctggtcgaga gctccggacc    480

cagattcaag actacgaggt cgatcccttt cgatactcgt tcatggagaa gctcaaacac    540

gagggacatg aactgttcct tcccgatatc gacgttctga tcattggctc tggatccggt    600

gcaggcgtgg tcgctcagac tcttaccgag agcggactca agtctctggt tctcgagaag    660

ggcaagtact ttgcctccga agagctgtgc atgaccgatc tcgacggaaa cgaggccctg    720

ttcgaaagcg gtggcactat tccttccacc aatcaacagt tgttcatgat cgctggatct    780

acttttggtg gaggctccac cgtcaactgg tctgcctgtc tcaagactcc cttcaaggtt    840

cgaaaggagt ggtacgacga tttcggactg gactttgtgg ctacccagca atacgacgat    900

tgcatggact acgtgtggaa gaaaatgggt gcctcgaccg agcacatcga gcattctgct    960

gcaaatgccg tcatcatgga cggagctgcc aagcttggct acgctcaccg agccctcgag   1020

cagaacaccg gtggccatgt tcacgactgt ggaatgtgcc acctgggctg tcgattcggt   1080

atcaagcagg gaggcgtcaa ctgctggttt cgagaaccct ccgagaaggg ttccaagttc   1140

atggagcagg tcgttgtcga gaagattctg cagcacaagg gcaaggccac tggaattctc   1200

tgcagagata ccgagtctgg catcaagttc aagattactg gacccaagaa atacgtcgtg   1260

tccggtggct ctttgcagac ccctgttctc cttcagaagt ctggcttcaa gaacaagcac   1320

attggagcca acctcaagct gcatcccgtc tcggttgctc ttggcgactt tggtaacgag   1380

gtggacttcg aagcctacaa gcgacccctc atgaccgcag tctgcaatgc cgtggacgat   1440

ctggacggca aggctcacgg aacacgaatc gaggccattc tgcacgctcc ttacgtcact   1500

gctcccttct atccctggca gtccggtgcc caggctcgga agaacttgct caaatacaag   1560

cagaccgtgc ctctgctcct tctgtctcga gacacctcct cgggtaccgt tacatacgac   1620

aaacagaagc cagatgtctt ggtggtcgac tacactgtca acaagttcga tcgaaactcc   1680

atcctgcagg gatttctcgt tgcttccgac attttgtaca tcgagggtgc caaggagatt   1740

ctgtctcccc aggcttgggt gcccaccttc aagagcaaca agcccaagca cgccagatcc   1800

atcaaggacg aggactacgt caagtggcga gaaaccgtgg ccaagattcc ctttgattcc   1860

tacggctcgc cttacggttc tgctcatcag atgtcctcgt gtcgaatgtc tggcaaggga   1920

cccggatacg gtgcctgcga taccaaggga cgactcttcg agtgcaacaa tgtgtacgtt   1980

gcagacgcct ccgtcatgcc tactgcttct ggagtcaacc ccatgattac cacaatggcc   2040

tttgcacgac acgttgctct ctgtctggcc aaggaccttc aaccccagac caagctgtaa   2100
```

<210> SEQ ID NO 89
<211> LENGTH: 699
<212> TYPE: PRT
<213> ORGANISM: artificial sequence
<220> FEATURE:
<223> OTHER INFORMATION: CcFAO1s (FAO) protein

<400> SEQUENCE: 89

```
Met Ala Ser His Gln Val Glu Asp His Asp Leu Asp Val Phe Cys Leu
1               5                   10                  15

Leu Ala Asp Ala Val Leu His Glu Ile Pro Pro Ser Glu Ile Val Glu
            20                  25                  30

Tyr Leu His Pro Asp Phe Pro Lys Asp Lys Ile Glu Glu Tyr Leu Thr
```

-continued

```
        35                  40                  45

Gly Phe Ser Arg Pro Ser Ala Val Pro Gln Phe Arg Gln Cys Ala Lys
    50                  55                  60

Lys Leu Ile Asn Arg Gly Ser Glu Leu Ser Ile Lys Leu Phe Leu Tyr
65                  70                  75                  80

Leu Thr Thr Ala Leu Asp Ser Arg Ile Leu Ala Pro Ala Leu Thr Asn
                85                  90                  95

Ser Leu Thr Leu Ile Arg Asp Met Asp Leu Ser Gln Arg Glu Glu Leu
            100                 105                 110

Leu Arg Ser Trp Arg Asp Ser Pro Leu Thr Ala Lys Arg Arg Leu Phe
        115                 120                 125

Arg Val Tyr Ala Ser Phe Thr Leu Ser Thr Phe Asn Lys Leu Gly Thr
    130                 135                 140

Asp Leu His Phe Lys Ala Leu Gly Tyr Pro Gly Arg Glu Leu Arg Thr
145                 150                 155                 160

Gln Ile Gln Asp Tyr Glu Val Asp Pro Phe Arg Tyr Ser Phe Met Glu
                165                 170                 175

Lys Leu Lys His Glu Gly His Glu Leu Phe Leu Pro Asp Ile Asp Val
            180                 185                 190

Leu Ile Ile Gly Ser Gly Ser Gly Ala Gly Val Val Ala Gln Thr Leu
        195                 200                 205

Thr Glu Ser Gly Leu Lys Ser Leu Val Leu Glu Lys Gly Lys Tyr Phe
    210                 215                 220

Ala Ser Glu Glu Leu Cys Met Thr Asp Leu Asp Gly Asn Glu Ala Leu
225                 230                 235                 240

Phe Glu Ser Gly Gly Thr Ile Pro Ser Thr Asn Gln Gln Leu Phe Met
                245                 250                 255

Ile Ala Gly Ser Thr Phe Gly Gly Gly Ser Thr Val Asn Trp Ser Ala
            260                 265                 270

Cys Leu Lys Thr Pro Phe Lys Val Arg Lys Glu Trp Tyr Asp Asp Phe
        275                 280                 285

Gly Leu Asp Phe Val Ala Thr Gln Gln Tyr Asp Asp Cys Met Asp Tyr
    290                 295                 300

Val Trp Lys Lys Met Gly Ala Ser Thr Glu His Ile Glu His Ser Ala
305                 310                 315                 320

Ala Asn Ala Val Ile Met Asp Gly Ala Ala Lys Leu Gly Tyr Ala His
                325                 330                 335

Arg Ala Leu Glu Gln Asn Thr Gly Gly His Val His Asp Cys Gly Met
            340                 345                 350

Cys His Leu Gly Cys Arg Phe Gly Ile Lys Gln Gly Gly Val Asn Cys
        355                 360                 365

Trp Phe Arg Glu Pro Ser Glu Lys Gly Ser Lys Phe Met Glu Gln Val
    370                 375                 380

Val Val Glu Lys Ile Leu Gln His Lys Gly Lys Ala Thr Gly Ile Leu
385                 390                 395                 400

Cys Arg Asp Thr Glu Ser Gly Ile Lys Phe Lys Ile Thr Gly Pro Lys
                405                 410                 415

Lys Tyr Val Val Ser Gly Gly Ser Leu Gln Thr Pro Val Leu Leu Gln
            420                 425                 430

Lys Ser Gly Phe Lys Asn Lys His Ile Gly Ala Asn Leu Lys Leu His
        435                 440                 445

Pro Val Ser Val Ala Leu Gly Asp Phe Gly Asn Glu Val Asp Phe Glu
    450                 455                 460
```

```
Ala Tyr Lys Arg Pro Leu Met Thr Ala Val Cys Asn Ala Val Asp Asp
465                 470                 475                 480

Leu Asp Gly Lys Ala His Gly Thr Arg Ile Glu Ala Ile Leu His Ala
                485                 490                 495

Pro Tyr Val Thr Ala Pro Phe Tyr Pro Trp Gln Ser Gly Ala Gln Ala
            500                 505                 510

Arg Lys Asn Leu Leu Lys Tyr Lys Gln Thr Val Pro Leu Leu Leu Leu
        515                 520                 525

Ser Arg Asp Thr Ser Ser Gly Thr Val Thr Tyr Asp Lys Gln Lys Pro
    530                 535                 540

Asp Val Leu Val Val Asp Tyr Thr Val Asn Lys Phe Asp Arg Asn Ser
545                 550                 555                 560

Ile Leu Gln Gly Phe Leu Val Ala Ser Asp Ile Leu Tyr Ile Glu Gly
                565                 570                 575

Ala Lys Glu Ile Leu Ser Pro Gln Ala Trp Val Pro Thr Phe Lys Ser
            580                 585                 590

Asn Lys Pro Lys His Ala Arg Ser Ile Lys Asp Glu Asp Tyr Val Lys
        595                 600                 605

Trp Arg Glu Thr Val Ala Lys Ile Pro Phe Asp Ser Tyr Gly Ser Pro
    610                 615                 620

Tyr Gly Ser Ala His Gln Met Ser Ser Cys Arg Met Ser Gly Lys Gly
625                 630                 635                 640

Pro Gly Tyr Gly Ala Cys Asp Thr Lys Gly Arg Leu Phe Glu Cys Asn
                645                 650                 655

Asn Val Tyr Val Ala Asp Ala Ser Val Met Pro Thr Ala Ser Gly Val
            660                 665                 670

Asn Pro Met Ile Thr Thr Met Ala Phe Ala Arg His Val Ala Leu Cys
        675                 680                 685

Leu Ala Lys Asp Leu Gln Pro Gln Thr Lys Leu
    690                 695


<210> SEQ ID NO 90
<211> LENGTH: 2028
<212> TYPE: DNA
<213> ORGANISM: artificial sequence
<220> FEATURE:
<223> OTHER INFORMATION: CtFALDH2s (FALDH)

<400> SEQUENCE: 90

atggccaagt cctacaagct gcccaagcct tccaagatcg ctcccatcat tcgaggcaag     60

acctctgcca agaccaaagg ctccactcag cctcccgagt ctccacctgc ctcggctaag    120

atcacagctc cccagctcga acccgtcgag cccaccagcg actccgagat tccttctacc    180

aaggtctccg ttcgacgtac atcgaccact tccagcaaga ccatcacgga cgattccatc    240

tctgccactt ccaccgacca gatgaagtcg agcaccaacg aagccgagat tccaaacccc    300

aagccagagt ccgtggttgc ccctatgacc aagcccgtcg aggacgataa actcgaggac    360

cacaccaagc tggagactgc cgaatcgtac atcaacgttc agaaggaagc tgcaattcct    420

ggcgagacca agagcgtcgt ttcctcgaag actgcttctg tgctcgagta cacacctctt    480

tccgagatct ctggcggagt caagaaagtg gtcgacggtt tccacaccgg caagacgcat    540

cccctggagt tcagactcaa gcagcttcga aacctgtact ttgctatgaa ggacaatcag    600

gaggccatct gcgaagcgct tgccaaggac tttcaccgag ccccttccga gactcgaaac    660

tacgagctgg tcacaggtct caacgagctg ctctacacca tgactcaact gcacaagtgg    720
```

-continued

```
tccaagcccc ttcctgtgga cgcgctgccc atcaacctca agaccaatcc cgtctacatc    780

gagcggattc cagtcggaac cgttctcgtc atttctgcct tcaactatcc cttctttgtc    840

tccgtgtctc ccatcgcagg tgctattgcc gcaggcaact ccgtcgtgtt caagccgtcg    900

gagcttacac cccactttac caagctgttc acagagttgc tcaccaaggc tctggatccc    960

gagatcttct acgtggtcaa cggtgccgtt tccgagacta ccgaactgct caaccagaag   1020

ttcgacaaga tcgtctacac tggcagcgac attgtcggca agatcattgc caagaaagca   1080

gcggagaccc ttactccagt catcttggag ctcggtggca agtctcctgc tttcgtgctg   1140

gacgatgtct cggacaagga tcttcccgtc atcgctcgac gtatcgcctg ggacgatac    1200

gccaacgctg gtcaaacctg cattggcgtc gactacgttc tcgtggccga gtccaagcac   1260

gagaagttca ttcaggctct gcggaatgtc atcgaaaacg agttctttcc caacatcgac   1320

cagaactcca actttaccca catgatccac gagcgagcct tcctcaagat gaaaaagatc   1380

ctggatacca ctgccggaga gatcattatc ggtggcaagc tcgacagcga gtccaactac   1440

gtgtctccca ccgtcatcga caatgcttcg tgggacgatt cctcgatgaa ggaggaaatc   1500

ttcggtccta ttcttcccat cattacttac accgacctca agcaggcctg caacgaggtc   1560

atttctcatc atgacactcc ccttgctcag tacatcttca cgtctggctc cacctcgcga   1620

aagtacaact ctcagatcaa cacaatctcc accatgattc gatcgggtgg actggtcatc   1680

aacgacgttc tcatgcatat ctcccttcat aacgctccct tcggtggcgt gggaaagtcc   1740

ggctacggtg cctatcacgg agagttctcc tacagagcct ttacccacga gcgaaccgtc   1800

ctcgagcagc atctgtggaa cgattggatt atcaactctc ggtatcctcc ctactccaac   1860

aagaaagaac gactggtggc ctccagccag tccaactacg gtggcagagt ctggtttggt   1920

cgaaagggcg acgttcgaat cgagggaccc actaccttct tcagcgcctg gaccaacgtg   1980

ctcggcgttg ctgccgtcgt tcgagacttc atcggtgctt ccatgtaa                2028
```

<210> SEQ ID NO 91
<211> LENGTH: 675
<212> TYPE: PRT
<213> ORGANISM: Candida tropicalis

<400> SEQUENCE: 91

```
Met Ala Lys Ser Tyr Lys Leu Pro Lys Pro Ser Lys Ile Ala Pro Ile
1               5                   10                  15

Ile Arg Gly Lys Thr Ser Ala Lys Thr Lys Gly Ser Thr Gln Pro Pro
            20                  25                  30

Glu Ser Pro Pro Ala Ser Ala Lys Ile Thr Ala Pro Gln Leu Glu Pro
        35                  40                  45

Val Glu Pro Thr Ser Asp Ser Glu Ile Pro Ser Thr Lys Val Ser Val
    50                  55                  60

Arg Arg Thr Ser Thr Thr Ser Ser Lys Thr Ile Thr Asp Asp Ser Ile
65                  70                  75                  80

Ser Ala Thr Ser Thr Asp Gln Met Lys Ser Ser Thr Asn Glu Ala Glu
                85                  90                  95

Ile Pro Asn Pro Lys Pro Glu Ser Val Val Ala Pro Met Thr Lys Pro
            100                 105                 110

Val Glu Asp Asp Lys Leu Glu Asp His Thr Lys Leu Glu Thr Ala Glu
        115                 120                 125

Ser Tyr Ile Asn Val Gln Lys Glu Ala Ala Ile Pro Gly Glu Thr Lys
    130                 135                 140
```

```
Ser Val Val Ser Ser Lys Thr Ala Ser Val Leu Glu Tyr Thr Pro Leu
145                 150                 155                 160

Ser Glu Ile Ser Gly Gly Val Lys Lys Val Val Asp Gly Phe His Thr
                165                 170                 175

Gly Lys Thr His Pro Leu Glu Phe Arg Leu Lys Gln Leu Arg Asn Leu
            180                 185                 190

Tyr Phe Ala Met Lys Asp Asn Gln Glu Ala Ile Cys Glu Ala Leu Ala
        195                 200                 205

Lys Asp Phe His Arg Ala Pro Ser Glu Thr Arg Asn Tyr Glu Leu Val
    210                 215                 220

Thr Gly Leu Asn Glu Leu Leu Tyr Thr Met Thr Gln Leu His Lys Trp
225                 230                 235                 240

Ser Lys Pro Leu Pro Val Asp Ala Leu Pro Ile Asn Leu Lys Thr Asn
                245                 250                 255

Pro Val Tyr Ile Glu Arg Ile Pro Val Gly Thr Val Leu Val Ile Ser
            260                 265                 270

Ala Phe Asn Tyr Pro Phe Phe Val Ser Val Ser Pro Ile Ala Gly Ala
        275                 280                 285

Ile Ala Ala Gly Asn Ser Val Val Phe Lys Pro Ser Glu Leu Thr Pro
    290                 295                 300

His Phe Thr Lys Leu Phe Thr Glu Leu Leu Thr Lys Ala Leu Asp Pro
305                 310                 315                 320

Glu Ile Phe Tyr Val Val Asn Gly Ala Val Ser Glu Thr Thr Glu Leu
                325                 330                 335

Leu Asn Gln Lys Phe Asp Lys Ile Val Tyr Thr Gly Ser Asp Ile Val
            340                 345                 350

Gly Lys Ile Ile Ala Lys Lys Ala Ala Glu Thr Leu Thr Pro Val Ile
        355                 360                 365

Leu Glu Leu Gly Gly Lys Ser Pro Ala Phe Val Leu Asp Asp Val Ser
    370                 375                 380

Asp Lys Asp Leu Pro Val Ile Ala Arg Arg Ile Ala Trp Gly Arg Tyr
385                 390                 395                 400

Ala Asn Ala Gly Gln Thr Cys Ile Gly Val Asp Tyr Val Leu Val Ala
                405                 410                 415

Glu Ser Lys His Glu Lys Phe Ile Gln Ala Leu Arg Asn Val Ile Glu
            420                 425                 430

Asn Glu Phe Phe Pro Asn Ile Asp Gln Asn Ser Asn Phe Thr His Met
        435                 440                 445

Ile His Glu Arg Ala Phe Leu Lys Met Lys Lys Ile Leu Asp Thr Thr
    450                 455                 460

Ala Gly Glu Ile Ile Ile Gly Gly Lys Leu Asp Ser Glu Ser Asn Tyr
465                 470                 475                 480

Val Ser Pro Thr Val Ile Asp Asn Ala Ser Trp Asp Asp Ser Ser Met
                485                 490                 495

Lys Glu Glu Ile Phe Gly Pro Ile Leu Pro Ile Ile Thr Tyr Thr Asp
            500                 505                 510

Leu Lys Gln Ala Cys Asn Glu Val Ile Ser His His Asp Thr Pro Leu
        515                 520                 525

Ala Gln Tyr Ile Phe Thr Ser Gly Ser Thr Ser Arg Lys Tyr Asn Ser
    530                 535                 540

Gln Ile Asn Thr Ile Ser Thr Met Ile Arg Ser Gly Gly Leu Val Ile
545                 550                 555                 560
```

-continued

```
Asn Asp Val Leu Met His Ile Ser Leu His Asn Ala Pro Phe Gly Gly
                565                 570                 575

Val Gly Lys Ser Gly Tyr Gly Ala Tyr His Gly Glu Phe Ser Tyr Arg
            580                 585                 590

Ala Phe Thr His Glu Arg Thr Val Leu Glu Gln His Leu Trp Asn Asp
        595                 600                 605

Trp Ile Ile Asn Ser Arg Tyr Pro Pro Tyr Ser Asn Lys Lys Glu Arg
    610                 615                 620

Leu Val Ala Ser Ser Gln Ser Asn Tyr Gly Gly Arg Val Trp Phe Gly
625                 630                 635                 640

Arg Lys Gly Asp Val Arg Ile Glu Gly Pro Thr Thr Phe Phe Ser Ala
                645                 650                 655

Trp Thr Asn Val Leu Gly Val Ala Ala Val Val Arg Asp Phe Ile Gly
            660                 665                 670

Ala Ser Met
        675


<210> SEQ ID NO 92
<211> LENGTH: 12572
<212> TYPE: DNA
<213> ORGANISM: artificial sequence
<220> FEATURE:
<223> OTHER INFORMATION: pYRH213 plasmid

<400> SEQUENCE: 92

aaaccatcat ctaagggcct caaaactacc tcggaactgc tgcgctgatc tggacaccac      60

agaggttccg agcactttag gttgcaccaa atgtcccacc aggtgcaggc agaaaacgct     120

ggaacagcgt gtacagtttg tcttaacaaa aagtgagggc gctgaggtcg agcagggtgg     180

tgtgacttgt tatagccttt agagctgcga aagcgcgtat ggatttggct catcaggcca     240

gattgagggt ctgtggacac atgtcatgtt agtgtacttc aatcgccccc tggatatagc     300

cccgacaata ggccgtggcc tcattttttt gccttccgca catttccatt gctcggtacc     360

cacaccttgc ttctcctgca cttgccaacc ttaatactgg tttacattga ccaacatctt     420

acaagcgggg ggcttgtcta gggtatatat aaacagtggc tctcccaatc ggttgccagt     480

ctcttttttc ctttctttcc ccacagattc gaaatctaaa ctacacatca caccatggcc     540

acctcctcta actccgacct ggtccgaacc atcgagtccg ccctcggcat ttctctcggc     600

gacagcgtgt ccgattctgt cgttatcatt gccaccactt ctgctgccgt catcattgga     660

cttctggtct tcctctggcg aaagtctccc gacagatcgc gagagctgcg tcctgtcatt     720

gtgcccaagt ttaccgttaa gcacgaggac gatgaagtcg aggtggaccg aggcaaaacc     780

aaggttacag ttttctacgg aactcagacc ggtactgccg agggctttgc aaaggccctt     840

gcggaggaaa tcaaggccag atacgagaag gccgttgtca aggtggttga catggatgac     900

tacgctattg acgatgacca gtacgaggaa aagctcaaaa aggagaccct ggtcttcttt     960

atgcttgcca cctatggaga cggcgaaccc accgataacg ctgcacgatt ctacaagtgg    1020

tttaccgagg gcaaggagga acgaggaacc tggctgcagc aactcactta cggtgtgttc    1080

gccttgggca accgacagta cgagcatttc aacaagatcg gcaagattgt cgacgaggat    1140

cttaccgagc agggagccaa gcgtctggtt cccgtcggtc tcggcgacga tgaccagtcc    1200

atcgaggacg atttcaacgc ttggaaggaa accttgtggc cagagctgga ccaacttctc    1260

cgagacgagg atgacgtcaa cactgcttcg accccttaca ctgccgctat ctccgagtat    1320

cgtgtcgtta tccacgatcc taccgtgtct ccctcctacg agaaccattt caatgttgcc    1380
```

-continued

```
aacggtggag cagtgttcga cattcaccat ccctgtcgag tcaacgttgc cgtgcgacgg   1440
gaacttcaca agccccagtc cgaccgatct tgcattcacc tggagtttga tctctccggt   1500
actggcgtta catacgagac tggcgaccac gtcggagtgt acgccgagaa ctgcgacgaa   1560
actgtcgagg aagctggcaa gctgctcggt cagtcgctgg atcttctctt ttctctgcat   1620
accgacaagg aggatggcac aagccttggt ggatctctgc tccctccatt tcctggaccc   1680
tgtaccgttc gaactgccct cgcttgctac gccgaccttc ttaatcctcc acggaaagcc   1740
gctatcgtgg cacttgctgc ccatgcttcc gagcccagcg aggccgaacg actcaagttt   1800
ctttcttcgc ctcagggcaa ggacgagtac tccaagtggg tcgttggatc tcagcgatcg   1860
ctgctcgaag tcatggccga ttttccctcc gccaagcctc cactgggagt gttctttgct   1920
gccattgcac ctcgactgca gcctcgatac tattctatct cctcttcgcc cagaccagct   1980
ccccagcgag tgcacgttac ctgtgccctt gtcgagggac ccactcctac cggtcggatt   2040
cacaagggtg tgtgctccac ctggatgaag tctgctactc ccttggagaa gtctcacgac   2100
tgttcccgag cacctatctt cattcgaccc tccaacttca agcttcctgc cgaccattcg   2160
attcccatta tcatggtcgg acctggtaca ggtctggctc cctttcgagg attcctccag   2220
gaacgacttg ccctcaagga ggatggagtt cagcttggac ctgccctgct cttctttggt   2280
tgccgaaaca gacagatgga cttcatctac gaggacgaac tcaacaattt cgttcagcaa   2340
ggtgccattt ccgagctcat cgttgcgttt tctcgagagg gcccagaaaa ggagtacgtg   2400
cagcacaaga tgatggacaa ggccgagtat ctgtggtctc tcatttcgca gggaggctac   2460
ctgtacgtct gtggtgatgc caaaggcatg gctcgagacg tgcaccgatc ccttcatacc   2520
attgttcagc aacaggagaa cgcagattct tcgaaggctg aggccactgt caagaaactc   2580
cagatggacg gaagatacct gcgagacgtg tggtaagcgg ccgcatgaga agataaatat   2640
ataaatacat tgagatatta aatgcgctag attagagagc ctcatactgc tcggagagaa   2700
gccaagacga gtactcaaag ggattacac catccatatc cacagacaca agctggggaa   2760
aggttctata tacactttcc ggaataccgt agtttccgat gttatcaatg ggggcagcca   2820
ggatttcagg cacttcggtg tctcggggtg aaatggcgtt cttggcctcc atcaagtcgt   2880
accatgtctt catttgcctg tcaaagtaaa acagaagcag atgaagaatg aacttgaagt   2940
gaaggaattt aaatgtaacg aaactgaaat ttgaccagat attgtgtccg cggtggagct   3000
ccagcttttg ttccctttag tgagggttaa tttcgagctt ggcgtaatca tggtcatagc   3060
tgtttcctgt gtgaaattgt tatccgctca caagcttcca cacaacgtac gttgattgag   3120
gtggagccag atgggctatt gtttcatata tagactggca gccacctctt tggcccagca   3180
tgtttgtata cctggaaggg aaaactaaag aagctggcta gtttagtttg attattatag   3240
tagatgtcct aatcactaga gattagaatg tcttggcgat gattagtcgt cgtcccctgt   3300
atcatgtcta gaccaactgt gtcatgaagt tggtgctggt gttttacctg tgtactacaa   3360
gtaggtgtcc tagatctagt gtacagagcc gtttagaccc atgtggactt caccattaac   3420
gatggaaaat gttcattata tgacagtata ttacaatgga cttgctccat ttcttccttg   3480
catcacatgt tctccacctc catagttgat caacacatca tagtagctaa ggctgctgct   3540
ctcccactac agtccaccac aagttaagta gcaccgtcag tacagctaaa agtacacgtc   3600
tagtacgttt cataactagt caagtagccc ctattacaga tatcagcact atcacgcacg   3660
agtttttctc tgtgctatct aatcaacttg ccaagtattc ggagaagata cactttcttg   3720
```

-continued

```
gcatcaggta tacgagggag cctatcagat gaaaaagggt atattggatc cattcatatc   3780
cacctacacg ttgtcataat ctcctcattc acgtgattca tttcgtgaca ctagtttctc   3840
actttccccc ccgcacctat agtcaacttg gcggacacgc tacttgtagc tgacgttgat   3900
ttatagaccc aatcaaagcg ggttatcggt caggtagcac ttatcattca tcgttcatac   3960
tacgatgagc aatctcgggc atgtccggaa aagtgtcggg cgcgccagct gcattaatga   4020
atcggccaac gcgcggggag aggcggtttg cgtattgggc gctcttccgc ttcctcgctc   4080
actgactcgc tgcgctcggt cgttcggctg cggcgagcgg tatcagctca ctcaaaggcg   4140
gtaatacggt tatccacaga atcaggggat aacgcaggaa agaacatgtg agcaaaaggc   4200
cagcaaaagg ccaggaaccg taaaaaggcc gcgttgctgg cgtttttcca taggctccgc   4260
cccctgacg agcatcacaa aaatcgacgc tcaagtcaga ggtggcgaaa cccgacagga    4320
ctataaagat accaggcgtt tccccctgga agctccctcg tgcgctctcc tgttccgacc   4380
ctgccgctta ccggatacct gtccgccttt ctcccttcgg gaagcgtggc gctttctcat   4440
agctcacgct gtaggtatct cagttcggtg taggtcgttc gctccaagct gggctgtgtg   4500
cacgaacccc ccgttcagcc cgaccgctgc gccttatccg gtaactatcg tcttgagtcc   4560
aacccggtaa gacacgactt atcgccactg gcagcagcca ctggtaacag gattagcaga   4620
gcgaggtatg taggcggtgc tacagagttc ttgaagtggt ggcctaacta cggctacact   4680
agaagaacag tatttggtat ctgcgctctg ctgaagccag ttaccttcgg aaaaagagtt   4740
ggtagctctt gatccggcaa acaaaccacc gctggtagcg gtggtttttt tgtttgcaag   4800
cagcagatta cgcgcagaaa aaaaggatct caagaagatc ctttgatctt ttctacgggg   4860
tctgacgctc agtggaacga aaactcacgt taagggattt tggtcatgag attatcaaaa   4920
aggatcttca cctagatcct tttaaattaa aaatgaagtt ttaaatcaat ctaaagtata   4980
tatgagtaaa cttggtctga cagttaccaa tgcttaatca gtgaggcacc tatctcagcg   5040
atctgtctat ttcgttcatc catagttgcc tgactccccg tcgtgtagat aactacgata   5100
cgggagggct taccatctgg ccccagtgct gcaatgatac cgcgagaccc acgctcaccg   5160
gctccagatt tatcagcaat aaaccagcca gccggaaggg ccgagcgcag aagtggtcct   5220
gcaactttat ccgcctccat ccagtctatt aattgttgcc gggaagctag agtaagtagt   5280
tcgccagtta atagtttgcg caacgttgtt gccattgcta caggcatcgt ggtgtcacgc   5340
tcgtcgtttg gtatggcttc attcagctcc ggttcccaac gatcaaggcg agttacatga   5400
tcccccatgt tgtgcaaaaa agcggttagc tccttcggtc ctccgatcgt tgtcagaagt   5460
aagttggccg cagtgttatc actcatggtt atggcagcac tgcataattc tcttactgtc   5520
atgccatccg taagatgctt ttctgtgact ggtgagtact caaccaagtc attctgagaa   5580
tagtgtatgc ggcgaccgag ttgctcttgc ccggcgtcaa tacgggataa taccgcgcca   5640
catagcagaa ctttaaaagt gctcatcatt ggaaaacgtt cttcggggcg aaaactctca   5700
aggatcttac cgctgttgag atccagttcg atgtaaccca ctcgtgcacc caactgatct   5760
tcagcatctt ttactttcac cagcgtttct gggtgagcaa aaacaggaag gcaaaatgcc   5820
gcaaaaaagg gaataagggc gacacggaaa tgttgaatac tcatactctt cctttttcaa   5880
tattattgaa gcatttatca gggttattgt ctcatgagcg gatacatatt tgaatgtatt   5940
tagaaaaata aacaaatagg ggttccgcgc acatttcccc gaaaagtgcc acctgatgcg   6000
gtgtgaaata ccgcacagat gcgtaaggag aaaataccgc atcaggaaat tgtaagcgtt   6060
aatattttgt taaaattcgc gttaaatttt tgttaaatca gctcattttt taaccaatag   6120
```

```
gccgaaatcg gcaaaatccc ttataaatca aaagaataga ccgagatagg gttgagtgtt   6180
gttccagttt ggaacaagag tccactatta aagaacgtgg actccaacgt caaagggcga   6240
aaaaccgtct atcagggcga tggcccacta cgtgaaccat caccctaatc aagttttttg   6300
gggtcgaggt gccgtaaagc actaaatcgg aaccctaaag ggagcccccg atttagagct   6360
tgacggggaa agccggcgaa cgtggcgaga aaggaaggga agaaagcgaa aggagcgggc   6420
gctagggcgc tggcaagtgt agcggtcacg ctgcgcgtaa ccaccacacc cgccgcgctt   6480
aatgcgccgc tacagggcgc gtccattcgc cattcaggct gcgcaactgt tgggaagggc   6540
gatcggtgcg ggcctcttcg ctattacgcc agctggcgaa agggggatgt gctgcaaggc   6600
gattaagttg ggtaacgcca gggttttccc agtcacgacg ttgtaaaacg acggccagtg   6660
aattgtaata cgactcacta tagggcgaat tgggcccgac gtcgcatgca ttccgacagc   6720
agcgactggg caccatgatc aagcgaaaca ccttccccca gctgccctgg caaaccatca   6780
agaaccctac tttcatcaag tgcaagaacg gttctactct tctcacctcc ggtgtctacg   6840
gctggtgccg aaagcctaac tacaccgctg atttcatcat gtgcctcacc tgggctctca   6900
tgtgcggtgt tgcttctccc ctgccttact tctacccggt cttcttcttc ctggtgctca   6960
tccaccgagc ttaccgagac tttgagcgac tggagcgaaa gtacggtgag gactaccagg   7020
agttcaagcg acaggtccct tggatcttca tcccttatgt tttctaaacg ataagcttag   7080
tgagcgaatg gtgaggttac ttaattgagt ggccagccta tgggattgta taacagacag   7140
tcaatatatt actgaaaaga ctgaacagcc agacggagtg aggttgtgag tgaatcgtag   7200
agggcggcta ttacagcaag tctactctac agtgtactaa cacagcagag aacaaataca   7260
ggtgtgcatt cggctatctg agaattagtt ggagagctcg agaccctcgg cgataaactg   7320
ctcctcggtt ttgtgtccat acttgtacgg accattgtaa tggggcaagt cgttgagttc   7380
tcgtcgtccg acgttcagag cacagaaacc aatgtaatca atgtagcaga gatggttctg   7440
caaaagattg atttgtgcga gcaggttaat taagttgcga cacatgtctt gatagtatct   7500
tgaattctct ctcttgagct tttccataac aagttcttct gcctccagga agtccatggg   7560
tggtttgatc atggttttgg tgtagtggta gtgcagtggt ggtattgtga ctggggatgt   7620
agttgagaat aagtcataca caagtcagct ttcttcgagc ctcatataag tataagtagt   7680
tcaacgtatt agcactgtac ccagcatctc cgtatcgaga aacacaacaa catgccccat   7740
tggacagatc atgcggatac acaggttgtg cagtatcata catactcgat cagacaggtc   7800
gtctgaccat catacaagct gaacaagcgc tccatacttg cacgctctct atatacacag   7860
ttaaattaca tatccatagt ctaacctcta acagttaatc ttctggtaag cctcccagcc   7920
agccttctgg tatcgcttgg cctcctcaat aggatctcgg ttctggccgt acagacctcg   7980
gccgacaatt atgatatccg ttccggtaga catgacatcc tcaacagttc ggtactgctg   8040
tccgagagcg tctcccttgt cgtcaagacc caccccgggg gtcagaataa gccagtcctc   8100
agagtcgccc ttaggtcggt tctgggcaat gaagccaacc acaaactcgg ggtcggatcg   8160
ggcaagctca atggtctgct tggagtactc gccagtggcc agagagccct tgcaagacag   8220
ctcggccagc atgagcagac ctctggccag cttctcgttg ggagagggga ctaggaactc   8280
cttgtactgg gagttctcgt agtcagagac gtcctccttc ttctgttcag agacagtttc   8340
ctcggcacca gctcgcaggc cagcaatgat tccggttccg ggtacaccgt gggcgttggt   8400
gatatcggac cactcggcga ttcggtgaca ccggtactgg tgcttgacag tgttgccaat   8460
```

-continued

```
atctgcgaac tttctgtcct cgaacaggaa gaaaccgtgc ttaagagcaa gttccttgag   8520
ggggagcaca gtgccggcgt aggtgaagtc gtcaatgatg tcgatatggg ttttgatcat   8580
gcacacataa ggtccgacct tatcggcaag ctcaatgagc tccttggtgg tggtaacatc   8640
cagagaagca cacaggttgg ttttcttggc tgccacgagc ttgagcactc gagcggcaaa   8700
ggcggacttg tggacgttag ctcgagcttc gtaggagggc attttggtgg tgaagaggag   8760
actgaaataa atttagtctg cagaactttt tatcggaacc ttatctgggg cagtgaagta   8820
tatgttatgg taatagttac gagttagttg aacttataga tagactggac tatacggcta   8880
tcggtccaaa ttagaaagaa cgtcaatggc tctctgggcg tcgcctttgc cgacaaaaat   8940
gtgatcatga tgaaagccag caatgacgtt gcagctgata ttgttgtcgg ccaaccgcgc   9000
cgaaaacgca gctgtcagac ccacagcctc caacgaagaa tgtatcgtca aagtgatcca   9060
agcacactca tagttggagt cgtactccaa aggcggcaat gacgagtcag acagatactc   9120
gtcgaccttt tccttgggaa ccaccaccgt cagcccttct gactcacgta ttgtagccac   9180
cgacacaggc aacagtccgt ggatagcaga atatgtcttg tcggtccatt tctcaccaac   9240
tttaggcgtc aagtgaatgt tgcagaagaa gtatgtgcct tcattgagaa tcggtgttgc   9300
tgatttcaat aaagtcttga gatcagtttg gccagtcatg ttgtgggggg taattggatt   9360
gagttatcgc ctacagtctg tacaggtata ctcgctgccc actttatact ttttgattcc   9420
gctgcacttg aagcaatgtc gtttaccaaa agtgagaatg ctccacagaa cacaccccag   9480
ggtatggttg agcaaaaaat aaacactccg atacggggaa tcgaaccccg gtctccacgg   9540
ttctcaagaa gtattcttga tgagagcgta tcgatgagcc taaaatgaac ccgagtatat   9600
ctcataaaat tctcggtgag aggtctgtga ctgtcagtac aaggtgcctt cattatgccc   9660
tcaaccttac catacctcac tgaatgtagt gtacctctaa aaatgaaata cagtgccaaa   9720
agccaaggca ctgagctcgt ctaacggact tgatatacaa ccaattaaaa caaatgaaaa   9780
gaaatacagt tctttgtatc atttgtaaca attaccctgt acaaactaag gtattgaaat   9840
cccacaatat tcccaaagtc caccccttc caaattgtca tgcctacaac tcatatacca   9900
agcactaacc taccgtttaa acgagaatcg tacagagttg tttctgaacc atttcgaagc   9960
cgttcagagt cgtttaaccg cagtttgagt cgtttcagag cggttctcag tcgtttttga  10020
tccatctctg aatgattcag agccgcctaa ctccttgtga gccgttaaat cgcgaattga  10080
gccactctga gccgttgatt cttccatttg tggccccttc accatctcct catctccttc  10140
ctctcgtcgc catctccttt tctcctctcg cacctcgcac tactccaaac caactcactg  10200
actacatccc aacagcgatc taaccaacgc cgcgcaagca aacagacaca aaaacaacgt  10260
ccgcgccgcc gaccacgtca gcagatcccg ctctcctggg ttttgtcgtc gtttgccgcc  10320
ttttgccgcc gctatttgca acgccgccac actcaatggc cgagccatga tgccgtcgtc  10380
gtgtcttttc ccaaatagga aaccgggcac caaccctagc cccacaactg gagtactcaa  10440
ctcggcgaaa aatgggccaa tcgccgcggg agaaacgaca atcggcttgt tttgactcaa  10500
ttacctcacc aagcgcccct tcgtcgccgc catacctccg caacaccccc tcaccgtccc  10560
tccctccgcc cctctggaaa ctcatagaac cccaaacctt atttccgatg accgcaaact  10620
ttagactata caggcgaatc tgggtggtgg caccaaccct tcctcttctc catcaccccc  10680
ccctcaatct ctttttctca ccatggcctt ccagtttcac ctggaggtcc tcctgcccta  10740
cctccttcct ctgcttctgc tcatcctgcc caccactatc ttctttctca ccaagcccaa  10800
caataaggtg tcctctactt ccaccaacaa taacatcatt acactgccca agtcgtaccc  10860
```

tctcattggc tcctaccttt cgttccgaaa gaacctgcat cgacggatcc agtggctctc 10920
cgacattgtt cagatctctc cctccgctac cttccagctc gacggaaccc tgggcaagcg 10980
acagatcatt actggcaacc cttctaccgt ccagcacatt ctcaagaacc agttctccaa 11040
ctatcagaag ggcaccacat tcaccaacac tctgtccgac tttctcggaa caggcatctt 11100
caacaccaac ggtcccaact ggaagtttca acgacaggtt gcctctcacg agttcaacac 11160
caagtccatt cggaacttcg tcgagcacat cgtggatacc gaactcacca accgattgat 11220
tcccatcctc acttcgagca cccagacaaa caatatcctg gacttccagg atattctgca 11280
gcgatttacc ttcgacaaca tctgcaacat tgccttcgga tacgatcccg agtacctcac 11340
tccctcgacc aatcgttcca agttcgcgga ggcctacgaa gacgctaccg agatctccag 11400
caagcgattc agactgcctc ttcccatcat ttggaagatc aaaaagtact tcaacattgg 11460
ctccgagaag cgactcaagg aagccgtcac cgaggtccga tcctttgcca agaaactggt 11520
ccgagagaag aaacgggagc tcgaagagaa gtcttcgctg gagaccgaag acatgctttc 11580
tcgatttctg tccagcggtc actcggacga ggatttcgtt gccgacattg tcatctcctt 11640
cattctcgca ggcaaggaca ctacctctgc cgctcttacc tggtttttct ggctgctctg 11700
gaagaaccct cgagtggagg aagagatcgt caacgagctg tccaagaaat cggagcttat 11760
ggtgtacgac gaggtcaagg aaatggtcta cacccatgct gcgctgtccg agtcgatgag 11820
actctaccct cccgttccaa tggattccaa ggaggccgtc aacgacgatg tgctgcccga 11880
cggctgggtg gtcaagaaag gtacaatcgt cacctaccat gtctacgcta tgggtcgaat 11940
gaagtctctc tggggagacg attgggcaga gtttcgacca gaacggtggc tcgagaagga 12000
cgaggtcaac ggcaagtggg tgttcgtcgg acgagacagc tactcctatc ctgtgttcca 12060
ggctggtccc agagtctgcc tgggaaagga gatggccttc atgcagatga agcgaattgt 12120
ggctggcatc gtcggaaagt tcaaggtggt tcccgaagcc cacttggctc aggagccagg 12180
attcatttcc tttctgtcgt ctcagatgga gggtggattt cccgtcacta tccagaagcg 12240
agactcctaa gcggccgcaa gtgtggatgg ggaagtgagt gcccggttct gtgtgcacaa 12300
ttggcaatcc aagatggatg gattcaacac agggatatag cgagctacgt ggtggtgcga 12360
ggatatagca acggatattt atgtttgaca cttgagaatg tacgatacaa gcactgtcca 12420
agtacaatac taaacatact gtacatactc atactcgtac ccgggcaacg gtttcacttg 12480
agtgcagtgg ctagtgctct tactcgtaca gtgtgcaata ctgcgtatca tagtctttga 12540
tgtatatcgt attcattcat gttagttgat tt 12572

<210> SEQ ID NO 93
<211> LENGTH: 1548
<212> TYPE: DNA
<213> ORGANISM: artificial sequence
<220> FEATURE:
<223> OTHER INFORMATION: VsCYP94A1s (CYP)

<400> SEQUENCE: 93
atggccttcc agtttcacct ggaggtcctc ctgccctacc tccttcctct gcttctgctc 60
atcctgccca ccactatctt ctttctcacc aagcccaaca ataaggtgtc ctctacttcc 120
accaacaata acatcattac actgcccaag tcgtaccctc tcattggctc ctacctttcg 180
ttccgaaaga acctgcatcg acggatccag tggctctccg acattgttca gatctctccc 240
tccgctacct tccagctcga cggaaccctg ggcaagcgac agatcattac tggcaaccct 300

-continued

```
tctaccgtcc agcacattct caagaaccag ttctccaact atcagaaggg caccacattc    360

accaacactc tgtccgactt tctcggaaca ggcatcttca acaccaacgg tcccaactgg    420

aagtttcaac gacaggttgc ctctcacgag ttcaacacca agtccattcg gaacttcgtc    480

gagcacatcg tggataccga actcaccaac cgattgattc ccatcctcac ttcgagcacc    540

cagacaaaca atatcctgga cttccaggat attctgcagc gatttacctt cgacaacatc    600

tgcaacattg ccttcggata cgatcccgag tacctcactc cctcgaccaa tcgttccaag    660

ttcgcggagg cctacgaaga cgctaccgag atctccagca agcgattcag actgcctctt    720

cccatcattt ggaagatcaa aaagtacttc aacattggct ccgagaagcg actcaaggaa    780

gccgtcaccg aggtccgatc ctttgccaag aaactggtcc gagagaagaa acgggagctc    840

gaagagaagt cttcgctgga gaccgaagac atgctttctc gatttctgtc cagcggtcac    900

tcggacgagg atttcgttgc cgacattgtc atctccttca ttctcgcagg caaggacact    960

acctctgccg ctcttacctg gtttttctgg ctgctctgga agaaccctcg agtggaggaa   1020

gagatcgtca acgagctgtc caagaaatcg gagcttatgg tgtacgacga ggtcaaggaa   1080

atggtctaca cccatgctgc gctgtccgag tcgatgagac tctaccctcc cgttccaatg   1140

gattccaagg aggccgtcaa cgacgatgtg ctgcccgacg gctgggtggt caagaaaggt   1200

acaatcgtca cctaccatgt ctacgctatg ggtcgaatga agtctctctg gggagacgat   1260

tgggcagagt ttcgaccaga acggtggctc gagaaggacg aggtcaacgg caagtgggtg   1320

ttcgtcggac gagacagcta ctcctatcct gtgttccagg ctggtcccag agtctgcctg   1380

ggaaaggaga tggccttcat gcagatgaag cgaattgtgg ctggcatcgt cggaaagttc   1440

aaggtggttc ccgaagccca cttggctcag gagccaggat tcatttcctt tctgtcgtct   1500

cagatggagg gtggatttcc cgtcactatc cagaagcgag actcctaa                1548
```

```
<210> SEQ ID NO 94
<211> LENGTH: 515
<212> TYPE: PRT
<213> ORGANISM: artificial sequence
<220> FEATURE:
<223> OTHER INFORMATION: VsCYP94A1s (CYP) protein

<400> SEQUENCE: 94

Met Ala Phe Gln Phe His Leu Glu Val Leu Leu Pro Tyr Leu Leu Pro
1               5                   10                  15

Leu Leu Leu Leu Ile Leu Pro Thr Thr Ile Phe Phe Leu Thr Lys Pro
            20                  25                  30

Asn Asn Lys Val Ser Ser Thr Ser Thr Asn Asn Asn Ile Ile Thr Leu
        35                  40                  45

Pro Lys Ser Tyr Pro Leu Ile Gly Ser Tyr Leu Ser Phe Arg Lys Asn
    50                  55                  60

Leu His Arg Arg Ile Gln Trp Leu Ser Asp Ile Val Gln Ile Ser Pro
65                  70                  75                  80

Ser Ala Thr Phe Gln Leu Asp Gly Thr Leu Gly Lys Arg Gln Ile Ile
                85                  90                  95

Thr Gly Asn Pro Ser Thr Val Gln His Ile Leu Lys Asn Gln Phe Ser
            100                 105                 110

Asn Tyr Gln Lys Gly Thr Thr Phe Thr Asn Thr Leu Ser Asp Phe Leu
        115                 120                 125

Gly Thr Gly Ile Phe Asn Thr Asn Gly Pro Asn Trp Lys Phe Gln Arg
    130                 135                 140
```

-continued

```
Gln Val Ala Ser His Glu Phe Asn Thr Lys Ser Ile Arg Asn Phe Val
145                 150                 155                 160

Glu His Ile Val Asp Thr Glu Leu Thr Asn Arg Leu Ile Pro Ile Leu
                165                 170                 175

Thr Ser Ser Thr Gln Thr Asn Asn Ile Leu Asp Phe Gln Asp Ile Leu
            180                 185                 190

Gln Arg Phe Thr Phe Asp Asn Ile Cys Asn Ile Ala Phe Gly Tyr Asp
        195                 200                 205

Pro Glu Tyr Leu Thr Pro Ser Thr Asn Arg Ser Lys Phe Ala Glu Ala
    210                 215                 220

Tyr Glu Asp Ala Thr Glu Ile Ser Ser Lys Arg Phe Arg Leu Pro Leu
225                 230                 235                 240

Pro Ile Ile Trp Lys Ile Lys Lys Tyr Phe Asn Ile Gly Ser Glu Lys
                245                 250                 255

Arg Leu Lys Glu Ala Val Thr Glu Val Arg Ser Phe Ala Lys Lys Leu
            260                 265                 270

Val Arg Glu Lys Lys Arg Glu Leu Glu Glu Lys Ser Ser Leu Glu Thr
        275                 280                 285

Glu Asp Met Leu Ser Arg Phe Leu Ser Ser Gly His Ser Asp Glu Asp
    290                 295                 300

Phe Val Ala Asp Ile Val Ile Ser Phe Ile Leu Ala Gly Lys Asp Thr
305                 310                 315                 320

Thr Ser Ala Ala Leu Thr Trp Phe Phe Trp Leu Leu Trp Lys Asn Pro
                325                 330                 335

Arg Val Glu Glu Glu Ile Val Asn Glu Leu Ser Lys Lys Ser Glu Leu
            340                 345                 350

Met Val Tyr Asp Glu Val Lys Glu Met Val Tyr Thr His Ala Ala Leu
        355                 360                 365

Ser Glu Ser Met Arg Leu Tyr Pro Pro Val Pro Met Asp Ser Lys Glu
    370                 375                 380

Ala Val Asn Asp Asp Val Leu Pro Asp Gly Trp Val Val Lys Lys Gly
385                 390                 395                 400

Thr Ile Val Thr Tyr His Val Tyr Ala Met Gly Arg Met Lys Ser Leu
                405                 410                 415

Trp Gly Asp Asp Trp Ala Glu Phe Arg Pro Glu Arg Trp Leu Glu Lys
            420                 425                 430

Asp Glu Val Asn Gly Lys Trp Val Phe Val Gly Arg Asp Ser Tyr Ser
        435                 440                 445

Tyr Pro Val Phe Gln Ala Gly Pro Arg Val Cys Leu Gly Lys Glu Met
    450                 455                 460

Ala Phe Met Gln Met Lys Arg Ile Val Ala Gly Ile Val Gly Lys Phe
465                 470                 475                 480

Lys Val Val Pro Glu Ala His Leu Ala Gln Glu Pro Gly Phe Ile Ser
                485                 490                 495

Phe Leu Ser Ser Gln Met Glu Gly Gly Phe Pro Val Thr Ile Gln Lys
            500                 505                 510

Arg Asp Ser
        515
```

<210> SEQ ID NO 95
<211> LENGTH: 2082
<212> TYPE: DNA
<213> ORGANISM: artificial sequence
<220> FEATURE:
<223> OTHER INFORMATION: VsCPRs (CPR)

<400> SEQUENCE: 95
atggccacct cctctaactc cgacctggtc cgaaccatcg agtccgccct cggcatttct 60
ctcggcgaca gcgtgtccga ttctgtcgtt atcattgcca ccacttctgc tgccgtcatc 120
attggacttc tggtcttcct ctggcgaaag tctcccgaca gatcgcgaga gctgcgtcct 180
gtcattgtgc ccaagtttac cgttaagcac gaggacgatg aagtcgaggt ggaccgaggc 240
aaaaccaagg ttacagtttt ctacggaact cagaccggta ctgccgaggg ctttgcaaag 300
gcccttgcgg aggaaatcaa ggccagatac gagaaggccg ttgtcaaggt ggttgacatg 360
gatgactacg ctattgacga tgaccagtac gaggaaaagc tcaaaaagga gaccctggtc 420
ttctttatgc ttgccaccta tggagacggc gaacccaccg ataacgctgc acgattctac 480
aagtggttta ccgagggcaa ggaggaacga ggaacctggc tgcagcaact cacttacggt 540
gtgttcgcct tgggcaaccg acagtacgag catttcaaca agatcggcaa gattgtcgac 600
gaggatctta ccgagcaggg agccaagcgt ctggttcccg tcggtctcgg cgacgatgac 660
cagtccatcg aggacgattt caacgcttgg aaggaaacct tgtggccaga gctggaccaa 720
cttctccgag acgaggatga cgtcaacact gcttcgaccc cttacactgc cgctatctcc 780
gagtatcgtg tcgttatcca cgatcctacc gtgtctccct cctacgagaa ccatttcaat 840
gttgccaacg gtggagcagt gttcgacatt caccatccct gtcgagtcaa cgttgccgtg 900
cgacgggaac ttcacaagcc ccagtccgac cgatcttgca ttcacctgga gtttgatctc 960
tccggtactg gcgttacata cgagactggc gaccacgtcg gagtgtacgc cgagaactgc 1020
gacgaaactg tcgaggaagc tggcaagctg ctcggtcagt cgctggatct tctcttttct 1080
ctgcataccg acaaggagga tggcacaagc cttggtggat ctctgctccc tccatttcct 1140
ggaccctgta ccgttcgaac tgccctcgct tgctacgccg accttcttaa tcctccacgg 1200
aaagccgcta tcgtggcact tgctgcccat gcttccgagc ccagcgaggc cgaacgactc 1260
aagtttcttt cttcgcctca gggcaaggac gagtactcca agtgggtcgt tggatctcag 1320
cgatcgctgc tcgaagtcat ggccgatttt ccctccgcca agcctccact gggagtgttc 1380
tttgctgcca ttgcacctcg actgcagcct cgatactatt ctatctcctc ttcgcccaga 1440
ccagctcccc agcgagtgca cgttacctgt gcccttgtcg agggacccac tcctaccggt 1500
cggattcaca agggtgtgtg ctccacctgg atgaagtctg ctactccctt ggagaagtct 1560
cacgactgtt cccgagcacc tatcttcatt cgaccctcca acttcaagct tcctgccgac 1620
cattcgattc ccattatcat ggtcggacct ggtacaggtc tggctccctt tcgaggattc 1680
ctccaggaac gacttgccct caaggaggat ggagttcagc ttggacctgc cctgctcttc 1740
tttggttgcc gaaacagaca gatggacttc atctacgagg acgaactcaa caatttcgtt 1800
cagcaaggtg ccatttccga gctcatcgtt gcgttttctc gagagggccc agaaaaggag 1860
tacgtgcagc acaagatgat ggacaaggcc gagtatctgt ggtctctcat ttcgcaggga 1920
ggctacctgt acgtctgtgg tgatgccaaa ggcatggctc gagacgtgca ccgatccctt 1980
cataccattg ttcagcaaca ggagaacgca gattcttcga aggctgaggc cactgtcaag 2040
aaactccaga tggacggaag atacctgcga gacgtgtggt aa 2082

<210> SEQ ID NO 96
<211> LENGTH: 693
<212> TYPE: PRT
<213> ORGANISM: artificial sequence
<220> FEATURE:

<223> OTHER INFORMATION: VsCPRs (CPR) protein

<400> SEQUENCE: 96

```
Met Ala Thr Ser Ser Asn Ser Asp Leu Val Arg Thr Ile Glu Ser Ala
1               5                   10                  15

Leu Gly Ile Ser Leu Gly Asp Ser Val Ser Asp Ser Val Val Ile Ile
            20                  25                  30

Ala Thr Thr Ser Ala Ala Val Ile Ile Gly Leu Leu Val Phe Leu Trp
        35                  40                  45

Arg Lys Ser Pro Asp Arg Ser Arg Glu Leu Arg Pro Val Ile Val Pro
    50                  55                  60

Lys Phe Thr Val Lys His Glu Asp Asp Glu Val Glu Val Asp Arg Gly
65                  70                  75                  80

Lys Thr Lys Val Thr Val Phe Tyr Gly Thr Gln Thr Gly Thr Ala Glu
                85                  90                  95

Gly Phe Ala Lys Ala Leu Ala Glu Glu Ile Lys Ala Arg Tyr Glu Lys
            100                 105                 110

Ala Val Val Lys Val Val Asp Met Asp Asp Tyr Ala Ile Asp Asp Asp
        115                 120                 125

Gln Tyr Glu Glu Lys Leu Lys Lys Glu Thr Leu Val Phe Phe Met Leu
    130                 135                 140

Ala Thr Tyr Gly Asp Gly Glu Pro Thr Asp Asn Ala Ala Arg Phe Tyr
145                 150                 155                 160

Lys Trp Phe Thr Glu Gly Lys Glu Glu Arg Gly Thr Trp Leu Gln Gln
                165                 170                 175

Leu Thr Tyr Gly Val Phe Ala Leu Gly Asn Arg Gln Tyr Glu His Phe
            180                 185                 190

Asn Lys Ile Gly Lys Ile Val Asp Glu Asp Leu Thr Glu Gln Gly Ala
        195                 200                 205

Lys Arg Leu Val Pro Val Gly Leu Gly Asp Asp Asp Gln Ser Ile Glu
    210                 215                 220

Asp Asp Phe Asn Ala Trp Lys Glu Thr Leu Trp Pro Glu Leu Asp Gln
225                 230                 235                 240

Leu Leu Arg Asp Glu Asp Asp Val Asn Thr Ala Ser Thr Pro Tyr Thr
                245                 250                 255

Ala Ala Ile Ser Glu Tyr Arg Val Val Ile His Asp Pro Thr Val Ser
            260                 265                 270

Pro Ser Tyr Glu Asn His Phe Asn Val Ala Asn Gly Gly Ala Val Phe
        275                 280                 285

Asp Ile His His Pro Cys Arg Val Asn Val Ala Val Arg Arg Glu Leu
    290                 295                 300

His Lys Pro Gln Ser Asp Arg Ser Cys Ile His Leu Glu Phe Asp Leu
305                 310                 315                 320

Ser Gly Thr Gly Val Thr Tyr Glu Thr Gly Asp His Val Gly Val Tyr
                325                 330                 335

Ala Glu Asn Cys Asp Glu Thr Val Glu Glu Ala Gly Lys Leu Leu Gly
            340                 345                 350

Gln Ser Leu Asp Leu Leu Phe Ser Leu His Thr Asp Lys Glu Asp Gly
        355                 360                 365

Thr Ser Leu Gly Gly Ser Leu Leu Pro Pro Phe Pro Gly Pro Cys Thr
    370                 375                 380

Val Arg Thr Ala Leu Ala Cys Tyr Ala Asp Leu Leu Asn Pro Pro Arg
385                 390                 395                 400
```

```
Lys Ala Ala Ile Val Ala Leu Ala Ala His Ala Ser Glu Pro Ser Glu
                405                 410                 415

Ala Glu Arg Leu Lys Phe Leu Ser Ser Pro Gln Gly Lys Asp Glu Tyr
            420                 425                 430

Ser Lys Trp Val Val Gly Ser Gln Arg Ser Leu Leu Glu Val Met Ala
        435                 440                 445

Asp Phe Pro Ser Ala Lys Pro Pro Leu Gly Val Phe Phe Ala Ala Ile
    450                 455                 460

Ala Pro Arg Leu Gln Pro Arg Tyr Tyr Ser Ile Ser Ser Ser Pro Arg
465                 470                 475                 480

Pro Ala Pro Gln Arg Val His Val Thr Cys Ala Leu Val Glu Gly Pro
                485                 490                 495

Thr Pro Thr Gly Arg Ile His Lys Gly Val Cys Ser Thr Trp Met Lys
            500                 505                 510

Ser Ala Thr Pro Leu Glu Lys Ser His Asp Cys Ser Arg Ala Pro Ile
        515                 520                 525

Phe Ile Arg Pro Ser Asn Phe Lys Leu Pro Ala Asp His Ser Ile Pro
    530                 535                 540

Ile Ile Met Val Gly Pro Gly Thr Gly Leu Ala Pro Phe Arg Gly Phe
545                 550                 555                 560

Leu Gln Glu Arg Leu Ala Leu Lys Glu Asp Gly Val Gln Leu Gly Pro
                565                 570                 575

Ala Leu Leu Phe Phe Gly Cys Arg Asn Arg Gln Met Asp Phe Ile Tyr
            580                 585                 590

Glu Asp Glu Leu Asn Asn Phe Val Gln Gln Gly Ala Ile Ser Glu Leu
        595                 600                 605

Ile Val Ala Phe Ser Arg Glu Gly Pro Glu Lys Glu Tyr Val Gln His
    610                 615                 620

Lys Met Met Asp Lys Ala Glu Tyr Leu Trp Ser Leu Ile Ser Gln Gly
625                 630                 635                 640

Gly Tyr Leu Tyr Val Cys Gly Asp Ala Lys Gly Met Ala Arg Asp Val
                645                 650                 655

His Arg Ser Leu His Thr Ile Val Gln Gln Gln Glu Asn Ala Asp Ser
            660                 665                 670

Ser Lys Ala Glu Ala Thr Val Lys Lys Leu Gln Met Asp Gly Arg Tyr
        675                 680                 685

Leu Arg Asp Val Trp
    690
```

<210> SEQ ID NO 97
<211> LENGTH: 783
<212> TYPE: DNA
<213> ORGANISM: Yarrowia lipolytica

<400> SEQUENCE: 97

```
aaacgagaat cgtacagagt tgtttctgaa ccatttcgaa gccgttcaga gtcgtttaac      60

cgcagtttga gtcgtttcag agcggttctc agtcgttttt gatccatctc tgaatgattc     120

agagccgcct aactccttgt gagccgttaa atcgcgaatt gagccactct gagccgttga     180

ttcttccatt tgtggcccct tcaccatctc ctcatctcct tcctctcgtc gccatctcct     240

tttctcctct cgcacctcgc actactccaa accaactcac tgactacatc ccaacagcga     300

tctaaccaac gccgcgcaag caaacagaca caaaaacaac gtccgcgccg ccgaccacgt     360

cagcagatcc cgctctcctg ggttttgtcg tcgtttgccg ccttttgccg ccgctatttg     420
```

caacgccgcc acactcaatg gccgagccat gatgccgtcg tcgtgtcttt tcccaaatag 480
gaaaccgggc accaacccta gccccacaac tggagtactc aactcggcga aaaatgggcc 540
aatcgccgcg ggagaaacga caatcggctt gttttgactc aattacctca ccaagcgccc 600
cttcgtcgcc gccatacctc cgcaacaccc cctcaccgtc cctccctccg cccctctgga 660
aactcataga accccaaacc ttatttccga tgaccgcaaa ctttagacta tacaggcgaa 720
tctgggtggt ggcaccaacc cttcctcttc tccatcaccc ccccctcaat ctctttttct 780
cac 783

<210> SEQ ID NO 98
<211> LENGTH: 17083
<212> TYPE: DNA
<213> ORGANISM: artificial sequence
<220> FEATURE:
<223> OTHER INFORMATION: pZSCPn-3FAOBU plasmid

<400> SEQUENCE: 98
cgattcgaga ttttacagat atttctcgca gtttttcacg tccccttgtc cttgtcctat 60
tgtttcaaat aaactctcgt ctactgattt cacatggaac ctttgctatt tcggggataa 120
ccccctttgc cattgcacga tggacgtggc aaaagaaaga tcgccctgcg ggatacttta 180
tcatgtggtc acatgctgtg attagaaata aagaaaaagg tgcttttttg gcgctgtgat 240
taacatctcg tctgccgtgc tctactagtc gcaatagcaa aaactcgctt aatagtgtgc 300
atagtgcggg gtagcaggat actgaactac agtacgattt gcttgctact gcttgtagca 360
attaccttta ctgtagggac cacacctcct ggtttcaatg tctttcctcg cctcgacaaa 420
gcaaaactgt cacccaatca caccttgttc atattcatta gtgcatccgt taaccttgac 480
atgacacttc tcatactagt gatagggctg tagttgagac aagttgattc acacggatac 540
atacaaagcc tcagagagca aatgttatat actcagggac cgaccaatca aaaaaacaca 600
ctcctaataa ccaccatttc catctacgcg tactcactct gtcagctgcc ccacattgcc 660
caatgcacaa tgcacaatga tgtgtgcaaa caacgcaatc aaaagtctat ggatgctgac 720
caaactctga tcaccaagtt gcgaacatga aaaagaagac ctgtgtatat ataagtaagg 780
gggagagccc taactagatc tttcgaaaac cccccgacct tcaccttcca caaccatggc 840
caaccccgtc gtggaggact cccatctgga cgtcttctgc ctccttgccg atgctgtggt 900
tcacgagatt cctccctccg agatcgtcga gtacctgcat cctgactttc ccaaggacaa 960
ggtcgaagag taccttgccg agttctctca tccctccgct attccagagt tccgagaggt 1020
tgccaagcga atcattaaca agggcaccgt gctgtcgatc aagctctttc tgctcttggc 1080
cactgctctg gattctcgaa tccttgctcc tgccttgacc aactccacta cactcatccg 1140
agacatggat ctttctcagc gggaggaact cctgagatcc tggcgagact ctcccttcac 1200
taccaaacga aagctgttcc gagtctacaa ctcgtttacc ctcaacgcct tcagcaagac 1260
tgctaccgac cttcacttca aggccctggg ataccctggt cgagagctcc gtactcagat 1320
tcaggactac gaggtcgatc cctttcgata cacgttcctg gagaagcctc agcaagacgg 1380
acaggagctc cactttcccg acattgatgt gctcattatc ggatctggct ccggtgcagg 1440
cgtcgttgct cagactcttt cggagaacgg actcaagtct ctggtgctcg agaagggcaa 1500
atacttttcc aacgacgagc tgaccatgaa cgacctcgaa ggttccgagg ccctgttcga 1560
aaacggaggt gctctctcct ctaccaatca acagatcttt atcattgccg gatcgacttt 1620
cggtggcgga tccacagtca actggtctgc ctgtctcaag actcccttca aggtgcgaaa 1680
ggagtggtac gacaactttg gactggattt cgttgctacc cagtattacg aggactgtat 1740
ggactacgtc tggaagaaaa tgggtgcctc caacgagaat atcgaccatt ctggagccaa 1800
ctcggtcatt ctggaaggtt ccaagaaact tggctaccct caccgtgccg tggaacagaa 1860
caatggaggc aagattcacg actgtggtat gtgccacctc ggatgtcgat ttggcatcaa 1920
gcagggatcg gtcaactgct ggtttcgtgg tccctccgag aacggctcga agttcatgca 1980
gcaagttctc gtggacaaga tcctgcagcg agatggcaag gctgtcggtg ttctctgtag 2040
agacgtggtt accggagtca agttcaagat cactggaccc aagaaaatcg tcgtgttctg 2100
gtggttcttt gccaactccg gatttgttac caagtctggt ttcaagaaca agcacatcgg 2160
tgcaaacctc aagctgcatc ccgtcagcct tacgctcggc gactttggta acaatgtgga 2220
tttcgaggcc taccgaaagc caatcatgac ctccatttgt aacaaggtcg aggacctgga 2280
tggaaaggct cacggcactc gaatcgaggc catgctcaat gctccctacg gtgttgctcc 2340
attctttccc tggaagtctg gcgcagagtc ccgaaaggac ctcctgcgat acaagcagac 2400
tgtgcccatt ctcctgcttt ccagagacac cacttctgga tccgtcacct acgacaaaca 2460
gaagcccgat gccttggtga tcgactacct gctcaacaag ttcgaccgaa actccatcct 2520
gcagggcttt ctcattgctt cggatcttct gtacatcgag ggtgccagcc gagaccatgt 2580
tacctacaag cttggatacc agtggttcaa gtcttccaag cccaagcacg ctcgatccat 2640
cgaagacgag gactacgtca actggagagc caaggttgca aagattccct ttgattccta 2700
tggatctcct tacggttcgg ctcaccagat gtccacttgc agaatgtctg gcaagggacc 2760
aggctacgga gcctgcgaca ccaagggcaa actcttcgag tgcagcaacg tgtacgtcgc 2820
cgatgcttcc actctgccca ccgcatctgg tgccaaccct atggtctcta ccatgtcctt 2880
tgcccgacac gtgtcgcttg gcatcgtcaa ggagctgcag caatccaagc tctaagcggc 2940
cgcatggagc gtgtgttctg agtcgatgtt ttctatggag ttgtgagtgt tagtagacat 3000
gatgggttta tatatgatga atgaatagat gtgattttga tttgcacgat ggaattgaga 3060
actttgtaaa cgtacatggg aatgtatgaa tgtgggggtt ttgtgactgg ataactgacg 3120
gtcagtggac gccgttgttc aaatatccaa gagatgcgag aaactttggg tcaagtgaac 3180
atgtcctctc tgttcaagta aaccatcaac tatgggtagt atatttagta aggacaagag 3240
ttgagattct ttggagtcct agaaacgtat tttcgcgttc caagatcaaa ttagtagagt 3300
aatacgggca cgggaatcca ttcatagtct caagtttaaa ccatcatcta agggcctcaa 3360
aactacctcg gaactgctgc gctgatctgg acaccacaga ggttccgagc actttaggtt 3420
gcaccaaatg tcccaccagg tgcaggcaga aaacgctgga acagcgtgta cagtttgtct 3480
taacaaaaag tgagggcgct gaggtcgagc agggtggtgt gacttgttat agcctttaga 3540
gctgcgaaag cgcgtatgga tttggctcat caggccagat tgagggtctg tggacacatg 3600
tcatgttagt gtacttcaat cgccccctgg atatagcccc gacaataggc cgtggcctca 3660
ttttttttgcc ttccgcacat ttccattgct cggtacccac accttgcttc tcctgcactt 3720
gccaacctta atactggttt acattgacca acatcttaca agcgggggc ttgtctaggg 3780
tatatataaa cagtggctct cccaatcggt tgccagtctc ttttttcctt tctttcccca 3840
cagattcgaa atctaaacta cacatcacac catggcctcc caccaggtcg aggaccacga 3900
tctggacgtg ttctgcctcc tggccgacgc tgttctccac gagattcctc cctccgaaat 3960
cgtcgagtac cttcatcccg atttccccaa ggacaagatc gaagagtacc tgaccggctt 4020

-continued

```
ttctcgaccc tccgccgttc ctcagttccg acagtgtgcc aagaaactca tcaaccgagg   4080
ttccgagctg tcgatcaagc tcttccttta cttgaccact gctctggact ctcgaatcct   4140
tgcaccagcc ctgaccaact cgctcactct gatcagagac atggatcttt cccagcgaga   4200
ggaactgttg cggtcctggc gagattctcc actgactgcc aagcgaagac tctttcgagt   4260
ctacgcctcc tttaccctgt ctacattcaa caagctcgga accgacttgc acttcaaggc   4320
cctgggctac cctggtcgag agctccggac ccagattcaa gactacgagg tcgatccctt   4380
tcgatactcg ttcatggaga agctcaaaca cgagggacat gaactgttcc ttcccgatat   4440
cgacgttctg atcattggct ctggatccgg tgcaggcgtg gtcgctcaga ctcttaccga   4500
gagcggactc aagtctctgg ttctcgagaa gggcaagtac tttgcctccg aagagctgtg   4560
catgaccgat ctcgacggaa acgaggccct gttcgaaagc ggtggcacta ttccttccac   4620
caatcaacag ttgttcatga tcgctggatc tacttttggt ggaggctcca ccgtcaactg   4680
gtctgcctgt ctcaagactc ccttcaaggt tcgaaaggag tggtacgacg atttcggact   4740
ggactttgtg gctacccagc aatacgacga ttgcatggac tacgtgtgga agaaaatggg   4800
tgcctcgacc gagcacatcg agcattctgc tgcaaatgcc gtcatcatgg acggagctgc   4860
caagcttggc tacgctcacc gagccctcga gcagaacacc ggtggccatg ttcacgactg   4920
tggaatgtgc cacctgggct gtcgattcgg tatcaagcag ggaggcgtca actgctggtt   4980
tcgagaaccc tccgagaagg gttccaagtt catggagcag gtcgttgtcg agaagattct   5040
gcagcacaag ggcaaggcca ctggaattct ctgcagagat accgagtctg gcatcaagtt   5100
caagattact ggacccaaga aatacgtcgt gtccggtggc tctttgcaga cccctgttct   5160
ccttcagaag tctggcttca agaacaagca cattggagcc aacctcaagc tgcatcccgt   5220
ctcggttgct cttggcgact ttggtaacga ggtggacttc gaagcctaca agcgacccct   5280
catgaccgca gtctgcaatg ccgtggacga tctggacggc aaggctcacg gaacacgaat   5340
cgaggccatt ctgcacgctc cttacgtcac tgctcccttc tatccctggc agtccggtgc   5400
ccaggctcgg aagaacttgc tcaaatacaa gcagaccgtg cctctgctcc ttctgtctcg   5460
agacacctcc tcgggtaccg ttacatacga caaacagaag ccagatgtct tggtggtcga   5520
ctacactgtc aacaagttcg atcgaaactc catcctgcag ggatttctcg ttgcttccga   5580
cattttgtac atcgagggtg ccaaggagat tctgtctccc caggcttggg tgcccacctt   5640
caagagcaac aagcccaagc acgccagatc catcaaggac gaggactacg tcaagtggcg   5700
agaaaccgtg gccaagattc cctttgattc ctacggctcg ccttacggtt ctgctcatca   5760
gatgtcctcg tgtcgaatgt ctggcaaggg acccggatac ggtgcctgcg ataccaaggg   5820
acgactcttc gagtgcaaca atgtgtacgt tgcagacgcc tccgtcatgc ctactgcttc   5880
tggagtcaac cccatgatta ccacaatggc ctttgcacga cacgttgctc tctgtctggc   5940
caaggacctt caaccccaga ccaagctgta agcggccgca tgagaagata aatatataaa   6000
tacattgaga tattaaatgc gctagattag agagcctcat actgctcgga gagaagccaa   6060
gacgagtact caaaggggat tacaccatcc atatccacag acacaagctg gggaaaggtt   6120
ctatatacac tttccggaat accgtagttt ccgatgttat caatgggggc agccaggatt   6180
tcaggcactt cggtgtctcg gggtgaaatg gcgttcttgg cctccatcaa gtcgtaccat   6240
gtcttcattt gcctgtcaaa gtaaaacaga agcagatgaa gaatgaactt gaagtgaagg   6300
aatttaaata agtttgcaaa aagatcgtat tatagttgga gcaagggaga aatgtagagt   6360
gtgaaagact cactatggtc cgggcttatc tcgaccaata gccaaagtct ggagtttctg   6420
```

-continued agagaaaaag gcaagatacg tatgtaacaa agcgacgcat ggtacaataa taccggaggc 6480
atgtatcata gagagttagt ggttcgatga tggcactggt gcctggtatg actttatacg 6540
gctgactaca tatttgtcct cagacataca attacagtca agcacttacc cttggacatc 6600
tgtaggtacc ccccggccaa gacgatctca gcgtgtcgta tgtcggattg gcgtagctcc 6660
ctcgctcgtc aattggctcc catctacttt cttctgcttg gctacaccca gcatgtctgc 6720
tatggctcgt tttcgtgcct tatctatcct cccagtatta ccaactctaa atgacatgat 6780
gtgattgggt ctacactttc atatcagaga taaggagtag cacagttgca taaaaagccc 6840
aactctaatc agcttcttcc tttcttgtaa ttagtacaaa ggtgattagc gaaatctgga 6900
agcttagttg gccctaaaaa aatcaaaaaa agcaaaaaac gaaaaacgaa aaaccacagt 6960
tttgagaaca gggaggtaac gaaggatcgt atatatatat atatatatat atacccacgg 7020
atcccgagac cggcctttga ttcttcccta caaccaacca ttctcaccac cctaattcac 7080
aaccatggct cccttcctgc ccgaccaggt cgactacaag cacgtcgata ccctcatgct 7140
gctgtgcgac ggcatcattc acgagactac cgtggacgag atcaaggatg tcattgctcc 7200
tgactttcca gccgacaagt acgaggaata cgttcgaacc ttcacaaagc cctccgagac 7260
tcccggtttc cgagagaccg tgtacaacac cgtcaatgcc aacactatgg atgccatcca 7320
tcagttcatt atcctgacca acgttctcgg atctcgagtc cttgctcctg ccctgaccaa 7380
ctccttgact cccatcaagg acatgtctct cgaagaccgg gagaagctgc ttgcctcgtg 7440
gcgagattct cccattgctg ccaagcggaa gctgttcaga ctcgtgtcca cgcttactct 7500
ggtcaccttt acacgacttg ccaacgagtt gcatctcaag gccattcact atccaggacg 7560
agaagaccga gagaaggctt acgagaccca ggagatcgac cccttcaagt accagtttct 7620
ggagaaaccc aagttctacg gcgcagagct gtacctccca gacattgatg tcatcattat 7680
cggatctggt gccggagctg gtgtcgttgc ccatactctc accaacgacg gcttcaagtc 7740
cctggttctc gaaaagggca gatactttag caactccgag ctcaacttcg acgataagga 7800
cggtgttcag gagctgtacc aatctggagg taccttgact accgtcaatc agcaactctt 7860
cgtgcttgct ggttccactt ttggaggtgg cactaccgtc aactggtctg cctgtctcaa 7920
gacgcccttc aaggtgcgga aggagtggta cgacgagttc ggcgtcgatt ttgctgccga 7980
cgaagcctac gacaaggcac aggattacgt gtggcagcaa atgggagcct cgaccgaagg 8040
catcactcac tccttggcca acgagatcat tatcgaaggt ggcaagaaac tcggatacaa 8100
ggccaaggtc ctggaccaga actctggtgg acatcctcat caccgatgcg gcttctgtca 8160
cctcggttgc aagcacggaa tcaagcaggg ctccgtcaac aattggtttc gagacgcagc 8220
tgcccacgga tcgcagttca tgcaacaggt gcgagttctg cagattctca acaagaaagg 8280
catcgcctac ggtatcttgt gcgaggatgt cgttaccgga gccaagttta ccattactgg 8340
tcccaaaaag ttcgtggtcg ctgcaggagc cctcaacact cccagcgtgc tggtcaactc 8400
cggattcaag aacaaaaaca ttggcaagaa ccttaccttg catcccgttt ctgtcgtgtt 8460
tggcgacttc ggaaaggacg tgcaggccga tcactttcac aattccatca tgactgctct 8520
gtgttcggaa gccgctgacc tcgacggcaa gggtcatgga tgccgaattg agaccatcct 8580
gaacgcaccc ttcattcagg cttcctttct tccttggcga ggttccaacg aggccagacg 8640
agacctcctg cgatacaaca atatggtcgc gatgctgctt ctctctcgag atacaacctc 8700
gggttccgtg tcttcccatc ccaccaaacc agaagccctg gttgtcgagt acgacgtcaa 8760

-continued

```
caagtttgat cgaaactcca tcttgcaggc cctgcttgtc actgcagacc tgctctacat   8820
tcagggagcc aagcgaatcc tttctcctca gccctgggtg ccaatcttcg agtccgacaa   8880
gcccaaggac aagcgatcta tcaaggacga ggattacgtc gaatggcgag ccaaggttgc   8940
caagattccc ttcgacacct acggctctcc ttatggttcg gctcaccaga tgtcttcctg   9000
tcgtatgagc ggcaagggtc ccaagtacgg agccgtcgat accgacggtc gactgtttga   9060
gtgctcgaac gtgtacgttg ccgacgcttc ccttctgccc actgctagcg gtgccaaccc   9120
tatggtcaca accatgactc tcgctcgaca cgttgccctc ggcttggcag actccctgaa   9180
gaccaaagcc aagctctaag cggccgcaag tgtggatggg gaagtgagtg cccggttctg   9240
tgtgcacaat tggcaatcca agatggatgg attcaacaca gggatatagc gagctacgtg   9300
gtggtgcgag gatatagcaa cggatattta tgtttgacac ttgagaatgt acgatacaag   9360
cactgtccaa gtacaatact aaacatactg tacatactca tactcgtacc cgggcaacgg   9420
tttcacttga gtgcagtggc tagtgctctt actcgtacag tgtgcaatac tgcgtatcat   9480
agtctttgat gtatatcgta ttcattcatg ttagttgcgt acgacccctc tcaggccaag   9540
cagaaggctg agtccatcaa gaaggccaac gctatcattg tcttcaacct caagaacaag   9600
gctggcaaga ccgagtcttg gtaccttgac ctcaagaacg acggtgacgt cggcaagggc   9660
aacaagtccc ccaagggtga tgctgacatc cagctcactc tctctgacga ccacttccag   9720
cagctcgttg agggtaaggc taacgcccag cgactcttca tgaccggcaa gctcaaggtt   9780
aagggcaacg tcatgaaggc tgccgccatt gagggtatcc tcaagaacgc tcagaacaac   9840
ctctaagcgc atcatttatt gattaattga tgatttacta tattgatttc gcaactgtag   9900
tgtgattgta tgtgatctgg ctcgtaggct tcagtaaata ctagacgggt atcctacgta   9960
gttgtatcat acatcgagcc tgtggttact tgtacaataa ttcgtaatgt agagataccc  10020
cttgatccat tgcctgtttc taacatacaa tgatctccac gcaataatcc cactcttgac  10080
taaaagttgc tactcttgca cggttacctc ggcatagtca cgcctctctt gtctcgtctc  10140
gaacgcacaa agtcaattga caacgccact cactcgagtg tgccccaaca gggcaccata  10200
tcgactaatt tgaggccaac tagggtgatt ttggatggaa tttgatcgga aaaaatagct  10260
gcagaaattc ctggagagaa aaattgaccg catccacatg gtttgaccaa aaaatcgtct  10320
ccatctctgt gctcaactct cctgacgaga tatgcgcgcg cacccccaca tgatgtgatt  10380
gatctcaaca aacttcaccc agacccttat ctttccggga aacttactgt ataagtggtc  10440
gtgcgaacag aaagtgtgcg cactttaggt gtctagatcc gattgttctc gttctgataa  10500
tgagccagcc ccgcgaggca atgtttttta caattgaaaa cttcgttaac cactcacatt  10560
accgtttttg ccccatattt accctctggt acactccctc ttgcatacac acacactgca  10620
gtgaaaatgc actccgttag caccgttgtg attggttcag ggcacgagtt tggtggttta  10680
aggcgcaact acatcaatat gaaaacagga gacgctgaaa aggggtaata tcggactgct  10740
gctatgttgt atgtactgca tgacgaattg gtgttattca agaccgtggc acaggttgct  10800
gcggtacgag acctggtagc ttctctaaac ggcatgtcta ggtggcgcgc cagctgcatt  10860
aatgaatcgg ccaacgcgcg gggagaggcg gtttgcgtat tgggcgctct tccgcttcct  10920
cgctcactga ctcgctgcgc tcggtcgttc ggctgcggcg agcggtatca gctcactcaa  10980
aggcggtaat acggttatcc acagaatcag gggataacgc aggaaagaac atgtgagcaa  11040
aaggccagca aaaggccagg aaccgtaaaa aggccgcgtt gctggcgttt ttccataggc  11100
tccgcccccc tgacgagcat cacaaaaatc gacgctcaag tcagaggtgg cgaaacccga  11160
```

-continued

```
caggactata aagataccag gcgtttcccc ctggaagctc cctcgtgcgc tctcctgttc  11220
cgaccctgcc gcttaccgga tacctgtccg cctttctccc ttcgggaagc gtggcgcttt  11280
ctcatagctc acgctgtagg tatctcagtt cggtgtaggt cgttcgctcc aagctgggct  11340
gtgtgcacga accccccgtt cagcccgacc gctgcgcctt atccggtaac tatcgtcttg  11400
agtccaaccc ggtaagacac gacttatcgc cactggcagc agccactggt aacaggatta  11460
gcagagcgag gtatgtaggc ggtgctacag agttcttgaa gtggtggcct aactacggct  11520
acactagaag aacagtattt ggtatctgcg ctctgctgaa gccagttacc ttcggaaaaa  11580
gagttggtag ctcttgatcc ggcaaacaaa ccaccgctgg tagcggtggt ttttttgttt  11640
gcaagcagca gattacgcgc agaaaaaaag gatctcaaga agatcctttg atcttttcta  11700
cggggtctga cgctcagtgg aacgaaaact cacgttaagg gattttggtc atgagattat  11760
caaaaaggat cttcacctag atccttttaa attaaaaatg aagttttaaa tcaatctaaa  11820
gtatatatga gtaaacttgg tctgacagtt accaatgctt aatcagtgag gcacctatct  11880
cagcgatctg tctatttcgt tcatccatag ttgcctgact ccccgtcgtg tagataacta  11940
cgatacggga gggcttacca tctggcccca gtgctgcaat gataccgcga gacccacgct  12000
caccggctcc agatttatca gcaataaacc agccagccgg aagggccgag cgcagaagtg  12060
gtcctgcaac tttatccgcc tccatccagt ctattaattg ttgccgggaa gctagagtaa  12120
gtagttcgcc agttaatagt ttgcgcaacg ttgttgccat tgctacaggc atcgtggtgt  12180
cacgctcgtc gtttggtatg gcttcattca gctccggttc ccaacgatca aggcgagtta  12240
catgatcccc catgttgtgc aaaaaagcgg ttagctcctt cggtcctccg atcgttgtca  12300
gaagtaagtt ggccgcagtg ttatcactca tggttatggc agcactgcat aattctctta  12360
ctgtcatgcc atccgtaaga tgcttttctg tgactggtga gtactcaacc aagtcattct  12420
gagaatagtg tatgcggcga ccgagttgct cttgcccggc gtcaatacgg gataataccg  12480
cgccacatag cagaacttta aaagtgctca tcattggaaa acgttcttcg gggcgaaaac  12540
tctcaaggat cttaccgctg ttgagatcca gttcgatgta acccactcgt gcacccaact  12600
gatcttcagc atcttttact ttcaccagcg tttctgggtg agcaaaaaca ggaaggcaaa  12660
atgccgcaaa aaagggaata agggcgacac ggaaatgttg aatactcata ctcttccttt  12720
ttcaatatta ttgaagcatt tatcagggtt attgtctcat gagcggatac atatttgaat  12780
gtatttagaa aaataaacaa ataggggttc cgcgcacatt tccccgaaaa gtgccacctg  12840
atgcggtgtg aaataccgca cagatgcgta aggagaaaat accgcatcag gaaattgtaa  12900
gcgttaatat tttgttaaaa ttcgcgttaa atttttgtta aatcagctca ttttttaacc  12960
aataggccga aatcggcaaa atcccttata aatcaaaaga atagaccgag atagggttga  13020
gtgttgttcc agtttggaac aagagtccac tattaaagaa cgtggactcc aacgtcaaag  13080
ggcgaaaaac cgtctatcag ggcgatggcc cactacgtga accatcaccc taatcaagtt  13140
ttttggggtc gaggtgccgt aaagcactaa atcggaaccc taaagggagc ccccgattta  13200
gagcttgacg gggaaagccg gcgaacgtgg cgagaaagga agggaagaaa gcgaaaggag  13260
cgggcgctag ggcgctggca agtgtagcgg tcacgctgcg cgtaaccacc acacccgccg  13320
cgcttaatgc gccgctacag ggcgcgtcca ttcgccattc aggctgcgca actgttggga  13380
agggcgatcg gtgcgggcct cttcgctatt acgccagctg gcgaaagggg gatgtgctgc  13440
aaggcgatta agttgggtaa cgccagggtt ttcccagtca cgacgttgta aaacgacggc  13500
```

-continued

```
cagtgaattg taatacgact cactataggg cgaattgggc ccgacgtcgc atgcgtcact  13560
aatcaaggat acctaccatg ccactatgat gtttgcagga ggtgtacctc ggcagtcatc  13620
aaaaaatgga actactggct ttagatcttg ttgtatggca tcgcgcctaa aaaagaaacc  13680
cccttccagc gagctactac aagtagttgt agttgcgggc gttggatacc gaaagtcaca  13740
agcacatgtc gaagctctca tctgaaacac cgacagtcgt ctgcaccccg caagtctcgg  13800
ttcgtaccag caccaatgtt aggcagaact atacacaaga gggcggacga tcacttcggc  13860
gttaggcaac tgaaggctat tttcggctgg tactgtaggg gacagaggaa acgcaagtga  13920
ttagtaaatc ggataatagg cctgttagtt taccgaaatg gtgggggagg ggttccgtgg  13980
atatcttgaa gttatggagg ctgatcgtta tttgtgggga tggatatcat tgtatggaca  14040
tactgtagct actgtataaa caacggatct tacacctgcc tcttgtatgc ccattgcttg  14100
atcatctatc gtgttactgt acatatacaa tagatatagg gaagaaaagc cggaagtaga  14160
gaccatagtc tggcagaagt aacggcctcg ggtcgagaga actataacaa agtccaacgg  14220
cgggtcttag aatagcccca aggatcacac agttccgcaa tccagtttca catgttccgt  14280
tgcatggact tttgcatgtc tactgttgct acgattcccc cattgcaacc acagtttggg  14340
gttaccccgc attatattag catgattacg aaagagataa gtatcatatg gaacatgtga  14400
agggtagtat gcaggtccgg cggagaaaga gaatgacgtt ttcattaagc gattcgcttg  14460
gcggcttgtg gggatgtga cgatacttac ggtaaagacc ctgtgtgaga gctggtactc  14520
gctcgttact tcgctgatct gttgggccgt caatcgaatc tcgtggaact tgcattcttc  14580
ttaactgtgt ctatacaaga cacctaatga aacatacaag ctaccgaaat cattttactc  14640
gtactgaccg gtacggtact tgcacaagta gtgaaacttc cgaaaatagc cagcctcatg  14700
catcatcgct tcacccccttc tgttgacctc aaaagcattc caacggtaaa aaattataac  14760
gccgccaact ggatggttgt gacggcgttg accaccaatg tgtgggggct ggcggtagga  14820
ccgagcttat tcgtcccaat aagctctttg gatttgattc tttggggtgt gtggtaaaat  14880
tcacatgggg aagaacacgg tggcagtttg aggcagaggc ccagcgtgta gttcctaggg  14940
catgaatata ccgaactcat ggcgcagaat tgagctgaat gcgcaaaaag ctacaggatc  15000
aaccgcgtta gaaatgccgc aaatgtccac taattccccg gactgttcca aatgattctg  15060
tggggataaa tctcaaactg ggttaggctt tgtcacgttt ctttgtgtcg tgtcggttcg  15120
tccggggcaa tgtgcccacg cttggctgtc tccctacacc tcggtaaaaa ctatcacatg  15180
ctgcccctct cgagcaagca ttaaatgcat atagtcaatc taacgacata tatataggta  15240
gggtgcatcc tccggtttag ctccccagaa tatctcttat tcattacaca aaaacaacaa  15300
tgtctctcaa ggtcgacggc ttcacttctt aattaacttt ggccggaatt cctttacctg  15360
caggataact tcgtataatg tatgctatac gaagttatga tctctctctt gagcttttcc  15420
ataacaagtt cttctgcctc caggaagtcc atgggtggtt tgatcatggt tttggtgtag  15480
tggtagtgca gtggtggtat tgtgactggg gatgtagttg agaataagtc atacacaagt  15540
cagctttctt cgagcctcat ataagtataa gtagttcaac gtattagcac tgtacccagc  15600
atctccgtat cgagaaacac aacaacatgc cccattggac agatcatgcg gatacacagg  15660
ttgtgcagta tcatacatac tcgatcagac aggtcgtctg accatcatac aagctgaaca  15720
agcgctccat acttgcacgc tctctatata cacagttaaa ttacatatcc atagtctaac  15780
ctctaacagt taatcttctg gtaagcctcc cagccagcct tctggtatcg cttggcctcc  15840
tcaataggat ctcggttctg gccgtacaga cctcggccga caattatgat atccgttccg  15900
```

gtagacatga catcctcaac agttcggtac tgctgtccga gagcgtctcc cttgtcgtca 15960
agacccaccc cgggggtcag aataagccag tcctcagagt cgcccttagg tcggttctgg 16020
gcaatgaagc caaccacaaa ctcggggtcg gatcgggcaa gctcaatggt ctgcttggag 16080
tactcgccag tggccagaga gcccttgcaa gacagctcgg ccagcatgag cagacctctg 16140
gccagcttct cgttgggaga ggggactagg aactccttgt actgggagtt ctcgtagtca 16200
gagacgtcct ccttcttctg ttcagagaca gtttcctcgg caccagctcg caggccagca 16260
atgattccgg ttccgggtac accgtgggcg ttggtgatat cggaccactc ggcgattcgg 16320
tgacaccggt actggtgctt gacagtgttg ccaatatctg cgaactttct gtcctcgaac 16380
aggaagaaac cgtgcttaag agcaagttcc ttgaggggga gcacagtgcc ggcgtaggtg 16440
aagtcgtcaa tgatgtcgat atgggttttg atcatgcaca cataaggtcc gaccttatcg 16500
gcaagctcaa tgagctcctt ggtggtggta acatccagag aagcacacag gttggttttc 16560
ttggctgcca cgagcttgag cactcgagcg gcaaaggcgg acttgtggac gttagctcga 16620
gcttcgtagg agggcatttt ggtggtgaag aggagactga aataaattta gtctgcagaa 16680
ctttttatcg gaaccttatc tggggcagtg aagtatatgt tatggtaata gttacgagtt 16740
agttgaactt atagatagac tggactatac ggctatcggt ccaaattaga aagaacgtca 16800
atggctctct gggcgtcgcc tttgccgaca aaaatgtgat catgatgaaa gccagcaatg 16860
acgttgcagc tgatattgtt gtcggccaac cgcgccgaaa acgcagctgt cagacccaca 16920
gcctccaacg aagaatgtat cgtcaaagtg atccaagcac actcatagtt ggagtcgtac 16980
tccaaaggcg gcaatgacga gtcagacaga tactcgtcga cgcgataact tcgtataatg 17040
tatgctatac gaagttatcg tacgatagtt agtagacaac aat 17083

<210> SEQ ID NO 99
<211> LENGTH: 2115
<212> TYPE: DNA
<213> ORGANISM: artificial sequence
<220> FEATURE:
<223> OTHER INFORMATION: CtFAO1M (FAO)

<400> SEQUENCE: 99
atggctccct tcctgcccga ccaggtcgac tacaagcacg tcgataccct catgctgctg 60
tgcgacggca tcattcacga gactaccgtg gacgagatca aggatgtcat tgctcctgac 120
tttccagccg acaagtacga ggaatacgtt cgaaccttca caaagccctc cgagactccc 180
ggtttccgag agaccgtgta caacaccgtc aatgccaaca ctatggatgc catccatcag 240
ttcattatcc tgaccaacgt tctcggatct cgagtccttg ctcctgccct gaccaactcc 300
ttgactccca tcaaggacat gtctctcgaa gaccgggaga agctgcttgc ctcgtggcga 360
gattctccca ttgctgccaa gcggaagctg ttcagactcg tgtccacgct tactctggtc 420
acctttacac gacttgccaa cgagttgcat ctcaaggcca ttcactatcc aggacgagaa 480
gaccgagaga aggcttacga gacccaggag atcgacccct tcaagtacca gtttctggag 540
aaacccaagt tctacggcgc agagctgtac ctcccagaca ttgatgtcat cattatcgga 600
tctggtgccg gagctggtgt cgttgcccat actctcacca acgacggctt caagtccctg 660
gttctcgaaa agggcagata ctttagcaac tccgagctca acttcgacga taaggacggt 720
gttcaggagc tgtaccaatc tggaggtacc ttgactaccg tcaatcagca actcttcgtg 780
cttgctggtt ccacttttgg aggtggcact accgtcaact ggtctgcctg tctcaagacg 840

-continued

```
cccttcaagg tgcggaagga gtggtacgac gagttcggcg tcgattttgc tgccgacgaa    900

gcctacgaca aggcacagga ttacgtgtgg cagcaaatgg gagcctcgac cgaaggcatc    960

actcactcct tggccaacga gatcattatc gaaggtggca agaaactcgg atacaaggcc   1020

aaggtcctgg accagaactc tggtggacat cctcatcacc gatgcggctt ctgtcacctc   1080

ggttgcaagc acggaatcaa gcagggctcc gtcaacaatt ggtttcgaga cgcagctgcc   1140

cacggatcgc agttcatgca acaggtgcga gttctgcaga ttctcaacaa gaaaggcatc   1200

gcctacggta tcttgtgcga ggatgtcgtt accggagcca agtttaccat tactggtccc   1260

aaaaagttcg tggtcgctgc aggagccctc aacactccca gcgtgctggt caactccgga   1320

ttcaagaaca aaaacattgg caagaacctt accttgcatc ccgtttctgt cgtgtttggc   1380

gacttcggaa aggacgtgca ggccgatcac tttcacaatt ccatcatgac tgctctgtgt   1440

tcggaagccg ctgacctcga cggcaagggt catggatgcc gaattgagac catcctgaac   1500

gcacccttca ttcaggcttc ctttcttcct tggcgaggtt ccaacgaggc cagacgagac   1560

ctcctgcgat acaacaatat ggtcgcgatg ctgcttctct ctcgagatac aacctcgggt   1620

tccgtgtctt cccatcccac caaaccagaa gccctggttg tcgagtacga cgtcaacaag   1680

tttgatcgaa actccatctt gcaggccctg cttgtcactg cagacctgct ctacattcag   1740

ggagccaagc gaatcctttc tcctcagccc tgggtgccaa tcttcgagtc cgacaagccc   1800

aaggacaagc gatctatcaa ggacgaggat tacgtcgaat ggcgagccaa ggttgccaag   1860

attcccttcg acacctacgg ctctccttat ggttcggctc accagatgtc ttcctgtcgt   1920

atgagcggca agggtcccaa gtacggagcc gtcgataccg acggtcgact gtttgagtgc   1980

tcgaacgtgt acgttgccga cgcttccctt ctgcccactg ctagcggtgc caaccctatg   2040

gtcacaacca tgactctcgc tcgacacgtt gccctcggct tggcagactc cctgaagacc   2100

aaagccaagc tctaa                                                     2115
```

```
<210> SEQ ID NO 100
<211> LENGTH: 704
<212> TYPE: PRT
<213> ORGANISM: artificial sequence
<220> FEATURE:
<223> OTHER INFORMATION: CtFAO1M (FAO) protein

<400> SEQUENCE: 100

Met Ala Pro Phe Leu Pro Asp Gln Val Asp Tyr Lys His Val Asp Thr
1               5                   10                  15

Leu Met Leu Leu Cys Asp Gly Ile Ile His Glu Thr Thr Val Asp Glu
            20                  25                  30

Ile Lys Asp Val Ile Ala Pro Asp Phe Pro Ala Asp Lys Tyr Glu Glu
        35                  40                  45

Tyr Val Arg Thr Phe Thr Lys Pro Ser Glu Thr Pro Gly Phe Arg Glu
    50                  55                  60

Thr Val Tyr Asn Thr Val Asn Ala Asn Thr Met Asp Ala Ile His Gln
65                  70                  75                  80

Phe Ile Ile Leu Thr Asn Val Leu Gly Ser Arg Val Leu Ala Pro Ala
                85                  90                  95

Leu Thr Asn Ser Leu Thr Pro Ile Lys Asp Met Ser Leu Glu Asp Arg
            100                 105                 110

Glu Lys Leu Leu Ala Ser Trp Arg Asp Ser Pro Ile Ala Ala Lys Arg
        115                 120                 125

Lys Leu Phe Arg Leu Val Ser Thr Leu Thr Leu Val Thr Phe Thr Arg
```

-continued

```
    130                 135                 140

Leu Ala Asn Glu Leu His Leu Lys Ala Ile His Tyr Pro Gly Arg Glu
145                 150                 155                 160

Asp Arg Glu Lys Ala Tyr Glu Thr Gln Glu Ile Asp Pro Phe Lys Tyr
                165                 170                 175

Gln Phe Leu Glu Lys Pro Lys Phe Tyr Gly Ala Glu Leu Tyr Leu Pro
            180                 185                 190

Asp Ile Asp Val Ile Ile Ile Gly Ser Gly Ala Gly Ala Gly Val Val
        195                 200                 205

Ala His Thr Leu Thr Asn Asp Gly Phe Lys Ser Leu Val Leu Glu Lys
    210                 215                 220

Gly Arg Tyr Phe Ser Asn Ser Glu Leu Asn Phe Asp Asp Lys Asp Gly
225                 230                 235                 240

Val Gln Glu Leu Tyr Gln Ser Gly Gly Thr Leu Thr Thr Val Asn Gln
                245                 250                 255

Gln Leu Phe Val Leu Ala Gly Ser Thr Phe Gly Gly Gly Thr Thr Val
            260                 265                 270

Asn Trp Ser Ala Cys Leu Lys Thr Pro Phe Lys Val Arg Lys Glu Trp
        275                 280                 285

Tyr Asp Glu Phe Gly Val Asp Phe Ala Ala Asp Glu Ala Tyr Asp Lys
    290                 295                 300

Ala Gln Asp Tyr Val Trp Gln Gln Met Gly Ala Ser Thr Glu Gly Ile
305                 310                 315                 320

Thr His Ser Leu Ala Asn Glu Ile Ile Ile Glu Gly Gly Lys Lys Leu
                325                 330                 335

Gly Tyr Lys Ala Lys Val Leu Asp Gln Asn Ser Gly Gly His Pro His
            340                 345                 350

His Arg Cys Gly Phe Cys His Leu Gly Cys Lys His Gly Ile Lys Gln
        355                 360                 365

Gly Ser Val Asn Asn Trp Phe Arg Asp Ala Ala Ala His Gly Ser Gln
    370                 375                 380

Phe Met Gln Gln Val Arg Val Leu Gln Ile Leu Asn Lys Lys Gly Ile
385                 390                 395                 400

Ala Tyr Gly Ile Leu Cys Glu Asp Val Val Thr Gly Ala Lys Phe Thr
                405                 410                 415

Ile Thr Gly Pro Lys Lys Phe Val Val Ala Ala Gly Ala Leu Asn Thr
            420                 425                 430

Pro Ser Val Leu Val Asn Ser Gly Phe Lys Asn Lys Asn Ile Gly Lys
        435                 440                 445

Asn Leu Thr Leu His Pro Val Ser Val Val Phe Gly Asp Phe Gly Lys
    450                 455                 460

Asp Val Gln Ala Asp His Phe His Asn Ser Ile Met Thr Ala Leu Cys
465                 470                 475                 480

Ser Glu Ala Ala Asp Leu Asp Gly Lys Gly His Gly Cys Arg Ile Glu
                485                 490                 495

Thr Ile Leu Asn Ala Pro Phe Ile Gln Ala Ser Phe Leu Pro Trp Arg
            500                 505                 510

Gly Ser Asn Glu Ala Arg Arg Asp Leu Leu Arg Tyr Asn Asn Met Val
        515                 520                 525

Ala Met Leu Leu Leu Ser Arg Asp Thr Thr Ser Gly Ser Val Ser Ser
    530                 535                 540

His Pro Thr Lys Pro Glu Ala Leu Val Val Glu Tyr Asp Val Asn Lys
545                 550                 555                 560
```

```
Phe Asp Arg Asn Ser Ile Leu Gln Ala Leu Leu Val Thr Ala Asp Leu
                565                 570                 575

Leu Tyr Ile Gln Gly Ala Lys Arg Ile Leu Ser Pro Gln Pro Trp Val
            580                 585                 590

Pro Ile Phe Glu Ser Asp Lys Pro Lys Asp Lys Arg Ser Ile Lys Asp
        595                 600                 605

Glu Asp Tyr Val Glu Trp Arg Ala Lys Val Ala Lys Ile Pro Phe Asp
    610                 615                 620

Thr Tyr Gly Ser Pro Tyr Gly Ser Ala His Gln Met Ser Ser Cys Arg
625                 630                 635                 640

Met Ser Gly Lys Gly Pro Lys Tyr Gly Ala Val Asp Thr Asp Gly Arg
                645                 650                 655

Leu Phe Glu Cys Ser Asn Val Tyr Val Ala Asp Ala Ser Leu Leu Pro
            660                 665                 670

Thr Ala Ser Gly Ala Asn Pro Met Val Thr Thr Met Thr Leu Ala Arg
        675                 680                 685

His Val Ala Leu Gly Leu Ala Asp Ser Leu Lys Thr Lys Ala Lys Leu
    690                 695                 700
```

<210> SEQ ID NO 101
<211> LENGTH: 2100
<212> TYPE: DNA
<213> ORGANISM: artificial sequence
<220> FEATURE:
<223> OTHER INFORMATION: CcFAO1 (FAO)

<400> SEQUENCE: 101

```
atggcctccc accaggtcga ggaccacgat ctggacgtgt tctgcctcct ggccgacgct     60

gttctccacg agattcctcc ctccgaaatc gtcgagtacc ttcatcccga tttccccaag    120

gacaagatcg aagagtacct gaccggcttt tctcgaccct ccgccgttcc tcagttccga    180

cagtgtgcca agaaactcat caaccgaggt tccgagctgt cgatcaagct cttcctttac    240

ttgaccactg ctctggactc tcgaatcctt gcaccagccc tgaccaactc gctcactctg    300

atcagagaca tggatctttc ccagcgagag gaactgttgc ggtcctggcg agattctcca    360

ctgactgcca agcgaagact ctttcgagtc tacgcctcct ttaccctgtc tacattcaac    420

aagctcggaa ccgacttgca cttcaaggcc ctgggctacc ctggtcgaga gctccggacc    480

cagattcaag actacgaggt cgatcccttt cgatactcgt tcatggagaa gctcaaacac    540

gagggacatg aactgttcct tcccgatatc gacgttctga tcattggctc tggatccggt    600

gcaggcgtgg tcgctcagac tcttaccgag agcggactca agtctctggt tctcgagaag    660

ggcaagtact ttgcctccga agagctgtgc atgaccgatc tcgacggaaa cgaggccctg    720

ttcgaaagcg gtggcactat tccttccacc aatcaacagt tgttcatgat cgctggatct    780

acttttggtg gaggctccac cgtcaactgg tctgcctgtc tcaagactcc cttcaaggtt    840

cgaaaggagt ggtacgacga tttcggactg gactttgtgg ctacccagca atacgacgat    900

tgcatggact acgtgtggaa gaaaatgggt gcctcgaccg agcacatcga gcattctgct    960

gcaaatgccg tcatcatgga cggagctgcc aagcttggct acgctcaccg agccctcgag   1020

cagaacaccg gtggccatgt tcacgactgt ggaatgtgcc acctgggctg tcgattcggt   1080

atcaagcagg gaggcgtcaa ctgctggttt cgagaaccct ccgagaaggg ttccaagttc   1140

atggagcagg tcgttgtcga gaagattctg cagcacaagg gcaaggccac tggaattctc   1200

tgcagagata ccgagtctgg catcaagttc aagattactg gacccaagaa atacgtcgtg   1260
```

```
tccggtggct ctttgcagac ccctgttctc cttcagaagt ctggcttcaa gaacaagcac   1320

attggagcca acctcaagct gcatcccgtc tcggttgctc ttggcgactt tggtaacgag   1380

gtggacttcg aagcctacaa gcgacccctc atgaccgcag tctgcaatgc cgtggacgat   1440

ctggacggca aggctcacgg aacacgaatc gaggccattc tgcacgctcc ttacgtcact   1500

gctcccttct atccctggca gtccggtgcc caggctcgga agaacttgct caaatacaag   1560

cagaccgtgc ctctgctcct tctgtctcga gacacctcct cgggtaccgt tacatacgac   1620

aaacagaagc cagatgtctt ggtggtcgac tacactgtca acaagttcga tcgaaactcc   1680

atcctgcagg gatttctcgt tgcttccgac attttgtaca tcgagggtgc caaggagatt   1740

ctgtctcccc aggcttgggt gcccaccttc aagagcaaca agcccaagca cgccagatcc   1800

atcaaggacg aggactacgt caagtggcga gaaaccgtgg ccaagattcc ctttgattcc   1860

tacggctcgc cttacggttc tgctcatcag atgtcctcgt gtcgaatgtc tggcaaggga   1920

cccggatacg gtgcctgcga taccaaggga cgactcttcg agtgcaacaa tgtgtacgtt   1980

gcagacgcct ccgtcatgcc tactgcttct ggagtcaacc ccatgattac cacaatggcc   2040

tttgcacgac acgttgctct ctgtctggcc aaggaccttc aaccccagac caagctgtaa   2100
```

```
<210> SEQ ID NO 102
<211> LENGTH: 699
<212> TYPE: PRT
<213> ORGANISM: artificial sequence
<220> FEATURE:
<223> OTHER INFORMATION: CcFAO1 (FAO) protein

<400> SEQUENCE: 102

Met Ala Ser His Gln Val Glu Asp His Asp Leu Asp Val Phe Cys Leu
1               5                   10                  15

Leu Ala Asp Ala Val Leu His Glu Ile Pro Pro Ser Glu Ile Val Glu
            20                  25                  30

Tyr Leu His Pro Asp Phe Pro Lys Asp Lys Ile Glu Glu Tyr Leu Thr
        35                  40                  45

Gly Phe Ser Arg Pro Ser Ala Val Pro Gln Phe Arg Gln Cys Ala Lys
    50                  55                  60

Lys Leu Ile Asn Arg Gly Ser Glu Leu Ser Ile Lys Leu Phe Leu Tyr
65                  70                  75                  80

Leu Thr Thr Ala Leu Asp Ser Arg Ile Leu Ala Pro Ala Leu Thr Asn
                85                  90                  95

Ser Leu Thr Leu Ile Arg Asp Met Asp Leu Ser Gln Arg Glu Glu Leu
            100                 105                 110

Leu Arg Ser Trp Arg Asp Ser Pro Leu Thr Ala Lys Arg Arg Leu Phe
        115                 120                 125

Arg Val Tyr Ala Ser Phe Thr Leu Ser Thr Phe Asn Lys Leu Gly Thr
    130                 135                 140

Asp Leu His Phe Lys Ala Leu Gly Tyr Pro Gly Arg Glu Leu Arg Thr
145                 150                 155                 160

Gln Ile Gln Asp Tyr Glu Val Asp Pro Phe Arg Tyr Ser Phe Met Glu
                165                 170                 175

Lys Leu Lys His Glu Gly His Glu Leu Phe Leu Pro Asp Ile Asp Val
            180                 185                 190

Leu Ile Ile Gly Ser Gly Ser Gly Ala Gly Val Val Ala Gln Thr Leu
        195                 200                 205

Thr Glu Ser Gly Leu Lys Ser Leu Val Leu Glu Lys Gly Lys Tyr Phe
```

-continued

```
    210                 215                 220

Ala Ser Glu Glu Leu Cys Met Thr Asp Leu Asp Gly Asn Glu Ala Leu
225                 230                 235                 240

Phe Glu Ser Gly Gly Thr Ile Pro Ser Thr Asn Gln Gln Leu Phe Met
                245                 250                 255

Ile Ala Gly Ser Thr Phe Gly Gly Gly Ser Thr Val Asn Trp Ser Ala
            260                 265                 270

Cys Leu Lys Thr Pro Phe Lys Val Arg Lys Glu Trp Tyr Asp Asp Phe
        275                 280                 285

Gly Leu Asp Phe Val Ala Thr Gln Gln Tyr Asp Asp Cys Met Asp Tyr
    290                 295                 300

Val Trp Lys Lys Met Gly Ala Ser Thr Glu His Ile Glu His Ser Ala
305                 310                 315                 320

Ala Asn Ala Val Ile Met Asp Gly Ala Ala Lys Leu Gly Tyr Ala His
                325                 330                 335

Arg Ala Leu Glu Gln Asn Thr Gly Gly His Val His Asp Cys Gly Met
            340                 345                 350

Cys His Leu Gly Cys Arg Phe Gly Ile Lys Gln Gly Gly Val Asn Cys
        355                 360                 365

Trp Phe Arg Glu Pro Ser Glu Lys Gly Ser Lys Phe Met Glu Gln Val
    370                 375                 380

Val Val Glu Lys Ile Leu Gln His Lys Gly Lys Ala Thr Gly Ile Leu
385                 390                 395                 400

Cys Arg Asp Thr Glu Ser Gly Ile Lys Phe Lys Ile Thr Gly Pro Lys
                405                 410                 415

Lys Tyr Val Val Ser Gly Gly Ser Leu Gln Thr Pro Val Leu Leu Gln
            420                 425                 430

Lys Ser Gly Phe Lys Asn Lys His Ile Gly Ala Asn Leu Lys Leu His
        435                 440                 445

Pro Val Ser Val Ala Leu Gly Asp Phe Gly Asn Glu Val Asp Phe Glu
    450                 455                 460

Ala Tyr Lys Arg Pro Leu Met Thr Ala Val Cys Asn Ala Val Asp Asp
465                 470                 475                 480

Leu Asp Gly Lys Ala His Gly Thr Arg Ile Glu Ala Ile Leu His Ala
                485                 490                 495

Pro Tyr Val Thr Ala Pro Phe Tyr Pro Trp Gln Ser Gly Ala Gln Ala
            500                 505                 510

Arg Lys Asn Leu Leu Lys Tyr Lys Gln Thr Val Pro Leu Leu Leu Leu
        515                 520                 525

Ser Arg Asp Thr Ser Ser Gly Thr Val Thr Tyr Asp Lys Gln Lys Pro
    530                 535                 540

Asp Val Leu Val Val Asp Tyr Thr Val Asn Lys Phe Asp Arg Asn Ser
545                 550                 555                 560

Ile Leu Gln Gly Phe Leu Val Ala Ser Asp Ile Leu Tyr Ile Glu Gly
                565                 570                 575

Ala Lys Glu Ile Leu Ser Pro Gln Ala Trp Val Pro Thr Phe Lys Ser
            580                 585                 590

Asn Lys Pro Lys His Ala Arg Ser Ile Lys Asp Glu Asp Tyr Val Lys
        595                 600                 605

Trp Arg Glu Thr Val Ala Lys Ile Pro Phe Asp Ser Tyr Gly Ser Pro
    610                 615                 620

Tyr Gly Ser Ala His Gln Met Ser Ser Cys Arg Met Ser Gly Lys Gly
625                 630                 635                 640
```

-continued

```
Pro Gly Tyr Gly Ala Cys Asp Thr Lys Gly Arg Leu Phe Glu Cys Asn
                645                 650                 655

Asn Val Tyr Val Ala Asp Ala Ser Val Met Pro Thr Ala Ser Gly Val
            660                 665                 670

Asn Pro Met Ile Thr Thr Met Ala Phe Ala Arg His Val Ala Leu Cys
        675                 680                 685

Leu Ala Lys Asp Leu Gln Pro Gln Thr Lys Leu
    690                 695
```

<210> SEQ ID NO 103
<211> LENGTH: 2100
<212> TYPE: DNA
<213> ORGANISM: artificial sequence
<220> FEATURE:
<223> OTHER INFORMATION: CcFAO2 (FAO)

<400> SEQUENCE: 103

```
atggccaacc ccgtcgtgga ggactcccat ctggacgtct tctgcctcct tgccgatgct     60

gtggttcacg agattcctcc ctccgagatc gtcgagtacc tgcatcctga ctttcccaag    120

gacaaggtcg aagagtacct tgccgagttc tctcatccct ccgctattcc agagttccga    180

gaggttgcca agcgaatcat taacaagggc accgtgctgt cgatcaagct ctttctgctc    240

ttggccactg ctctggattc tcgaatcctt gctcctgcct tgaccaactc cactacactc    300

atccgagaca tggatctttc tcagcgggag gaactcctga gatcctggcg agactctccc    360

ttcactacca aacgaaagct gttccgagtc tacaactcgt ttaccctcaa cgccttcagc    420

aagactgcta ccgaccttca cttcaaggcc ctgggatacc ctggtcgaga gctccgtact    480

cagattcagg actacgaggt cgatcccttt cgatacacgt tcctggagaa gcctcagcaa    540

gacggacagg agctccactt tcccgacatt gatgtgctca ttatcggatc tggctccggt    600

gcaggcgtcg ttgctcagac tctttcggag aacggactca agtctctggt gctcgagaag    660

ggcaaatact tttccaacga cgagctgacc atgaacgacc tcgaaggttc cgaggccctg    720

ttcgaaaacg gaggtgctct ctcctctacc aatcaacaga tctttatcat tgccggatcg    780

actttcggtg gcggatccac agtcaactgg tctgcctgtc tcaagactcc cttcaaggtg    840

cgaaaggagt ggtacgacaa ctttggactg gatttcgttg ctacccagta ttacgaggac    900

tgtatggact acgtctggaa gaaaatgggt gcctccaacg agaatatcga ccattctgga    960

gccaactcgg tcattctgga aggttccaag aaacttggct accctcaccg tgccgtggaa   1020

cagaacaatg gaggcaagat tcacgactgt ggtatgtgcc acctcggatg tcgatttggc   1080

atcaagcagg gatcggtcaa ctgctggttt cgtggtccct ccgagaacgg ctcgaagttc   1140

atgcagcaag ttctcgtgga caagatcctg cagcgagatg gcaaggctgt cggtgttctc   1200

tgtagagacg tggttaccgg agtcaagttc aagatcactg gacccaagaa aatcgtcgtg   1260

ttctggtggt tctttgccaa ctccggattt gttaccaagt ctggtttcaa gaacaagcac   1320

atcggtgcaa acctcaagct gcatcccgtc agccttacgc tcggcgactt tggtaacaat   1380

gtggatttcg aggcctaccg aaagccaatc atgacctcca tttgtaacaa ggtcgaggac   1440

ctggatggaa aggctcacgg cactcgaatc gaggccatgc tcaatgctcc ctacggtgtt   1500

gctccattct ttccctggaa gtctggcgca gagtcccgaa aggacctcct gcgatacaag   1560

cagactgtgc ccattctcct gctttccaga gacaccactt ctggatccgt cacctacgac   1620

aaacagaagc ccgatgcctt ggtgatcgac tacctgctca acaagttcga ccgaaactcc   1680
```

-continued

```
atcctgcagg gctttctcat tgcttcggat cttctgtaca tcgagggtgc cagccgagac   1740

catgttacct acaagcttgg ataccagtgg ttcaagtctt ccaagcccaa gcacgctcga   1800

tccatcgaag acgaggacta cgtcaactgg agagccaagg ttgcaaagat tccctttgat   1860

tcctatggat ctccttacgg ttcggctcac cagatgtcca cttgcagaat gtctggcaag   1920

ggaccaggct acggagcctg cgacaccaag ggcaaactct tcgagtgcag caacgtgtac   1980

gtcgccgatg cttccactct gcccaccgca tctggtgcca accctatggt ctctaccatg   2040

tcctttgccc gacacgtgtc gcttggcatc gtcaaggagc tgcagcaatc caagctctaa   2100
```

<210> SEQ ID NO 104
<211> LENGTH: 699
<212> TYPE: PRT
<213> ORGANISM: artificial sequence
<220> FEATURE:
<223> OTHER INFORMATION: CcFAO2 (FAO) protein

<400> SEQUENCE: 104

```
Met Ala Asn Pro Val Val Glu Asp Ser His Leu Asp Val Phe Cys Leu
1               5                   10                  15

Leu Ala Asp Ala Val Val His Glu Ile Pro Pro Ser Glu Ile Val Glu
            20                  25                  30

Tyr Leu His Pro Asp Phe Pro Lys Asp Lys Val Glu Glu Tyr Leu Ala
        35                  40                  45

Glu Phe Ser His Pro Ser Ala Ile Pro Glu Phe Arg Glu Val Ala Lys
    50                  55                  60

Arg Ile Ile Asn Lys Gly Thr Val Leu Ser Ile Lys Leu Phe Leu Leu
65                  70                  75                  80

Leu Ala Thr Ala Leu Asp Ser Arg Ile Leu Ala Pro Ala Leu Thr Asn
                85                  90                  95

Ser Thr Thr Leu Ile Arg Asp Met Asp Leu Ser Gln Arg Glu Glu Leu
            100                 105                 110

Leu Arg Ser Trp Arg Asp Ser Pro Phe Thr Thr Lys Arg Lys Leu Phe
        115                 120                 125

Arg Val Tyr Asn Ser Phe Thr Leu Asn Ala Phe Ser Lys Thr Ala Thr
    130                 135                 140

Asp Leu His Phe Lys Ala Leu Gly Tyr Pro Gly Arg Glu Leu Arg Thr
145                 150                 155                 160

Gln Ile Gln Asp Tyr Glu Val Asp Pro Phe Arg Tyr Thr Phe Leu Glu
                165                 170                 175

Lys Pro Gln Gln Asp Gly Gln Glu Leu His Phe Pro Asp Ile Asp Val
            180                 185                 190

Leu Ile Ile Gly Ser Gly Ser Gly Ala Gly Val Val Ala Gln Thr Leu
        195                 200                 205

Ser Glu Asn Gly Leu Lys Ser Leu Val Leu Glu Lys Gly Lys Tyr Phe
    210                 215                 220

Ser Asn Asp Glu Leu Thr Met Asn Asp Leu Glu Gly Ser Glu Ala Leu
225                 230                 235                 240

Phe Glu Asn Gly Gly Ala Leu Ser Ser Thr Asn Gln Gln Ile Phe Ile
                245                 250                 255

Ile Ala Gly Ser Thr Phe Gly Gly Gly Ser Thr Val Asn Trp Ser Ala
            260                 265                 270

Cys Leu Lys Thr Pro Phe Lys Val Arg Lys Glu Trp Tyr Asp Asn Phe
        275                 280                 285

Gly Leu Asp Phe Val Ala Thr Gln Tyr Tyr Glu Asp Cys Met Asp Tyr
```

```
    290                 295                 300

Val Trp Lys Lys Met Gly Ala Ser Asn Glu Asn Ile Asp His Ser Gly
305                 310                 315                 320

Ala Asn Ser Val Ile Leu Glu Gly Ser Lys Lys Leu Gly Tyr Pro His
                325                 330                 335

Arg Ala Val Glu Gln Asn Asn Gly Gly Lys Ile His Asp Cys Gly Met
            340                 345                 350

Cys His Leu Gly Cys Arg Phe Gly Ile Lys Gln Gly Ser Val Asn Cys
        355                 360                 365

Trp Phe Arg Gly Pro Ser Glu Asn Gly Ser Lys Phe Met Gln Gln Val
    370                 375                 380

Leu Val Asp Lys Ile Leu Gln Arg Asp Gly Lys Ala Val Gly Val Leu
385                 390                 395                 400

Cys Arg Asp Val Val Thr Gly Val Lys Phe Lys Ile Thr Gly Pro Lys
                405                 410                 415

Lys Ile Val Val Phe Trp Trp Phe Phe Ala Asn Ser Gly Phe Val Thr
            420                 425                 430

Lys Ser Gly Phe Lys Asn Lys His Ile Gly Ala Asn Leu Lys Leu His
        435                 440                 445

Pro Val Ser Leu Thr Leu Gly Asp Phe Gly Asn Asn Val Asp Phe Glu
    450                 455                 460

Ala Tyr Arg Lys Pro Ile Met Thr Ser Ile Cys Asn Lys Val Glu Asp
465                 470                 475                 480

Leu Asp Gly Lys Ala His Gly Thr Arg Ile Glu Ala Met Leu Asn Ala
                485                 490                 495

Pro Tyr Gly Val Ala Pro Phe Phe Pro Trp Lys Ser Gly Ala Glu Ser
            500                 505                 510

Arg Lys Asp Leu Leu Arg Tyr Lys Gln Thr Val Pro Ile Leu Leu Leu
        515                 520                 525

Ser Arg Asp Thr Thr Ser Gly Ser Val Thr Tyr Asp Lys Gln Lys Pro
    530                 535                 540

Asp Ala Leu Val Ile Asp Tyr Leu Leu Asn Lys Phe Asp Arg Asn Ser
545                 550                 555                 560

Ile Leu Gln Gly Phe Leu Ile Ala Ser Asp Leu Leu Tyr Ile Glu Gly
                565                 570                 575

Ala Ser Arg Asp His Val Thr Tyr Lys Leu Gly Tyr Gln Trp Phe Lys
            580                 585                 590

Ser Ser Lys Pro Lys His Ala Arg Ser Ile Glu Asp Glu Asp Tyr Val
        595                 600                 605

Asn Trp Arg Ala Lys Val Ala Lys Ile Pro Phe Asp Ser Tyr Gly Ser
    610                 615                 620

Pro Tyr Gly Ser Ala His Gln Met Ser Thr Cys Arg Met Ser Gly Lys
625                 630                 635                 640

Gly Pro Gly Tyr Gly Ala Cys Asp Thr Lys Gly Lys Leu Phe Glu Cys
                645                 650                 655

Ser Asn Val Tyr Val Ala Asp Ala Ser Thr Leu Pro Thr Ala Ser Gly
            660                 665                 670

Ala Asn Pro Met Val Ser Thr Met Ser Phe Ala Arg His Val Ser Leu
        675                 680                 685

Gly Ile Val Lys Glu Leu Gln Gln Ser Lys Leu
    690                 695

<210> SEQ ID NO 105
```

<211> LENGTH: 12358
<212> TYPE: DNA
<213> ORGANISM: artificial sequence
<220> FEATURE:
<223> OTHER INFORMATION: pZKLY-VsCPR&CYP plasmid

<400> SEQUENCE: 105
aaaccatcat ctaagggcct caaaactacc tcggaactgc tgcgctgatc tggacaccac 60
agaggttccg agcactttag gttgcaccaa atgtcccacc aggtgcaggc agaaaacgct 120
ggaacagcgt gtacagtttg tcttaacaaa aagtgagggc gctgaggtcg agcagggtgg 180
tgtgacttgt tatagccttt agagctgcga aagcgcgtat ggatttggct catcaggcca 240
gattgagggt ctgtggacac atgtcatgtt agtgtacttc aatcgccccc tggatatagc 300
cccgacaata ggccgtggcc tcattttttt gccttccgca catttccatt gctcggtacc 360
cacaccttgc ttctcctgca cttgccaacc ttaatactgg tttacattga ccaacatctt 420
acaagcgggg ggcttgtcta gggtatatat aaacagtggc tctcccaatc ggttgccagt 480
ctcttttttc ctttctttcc ccacagattc gaaatctaaa ctacacatca caccatggcc 540
acctcctcta actccgacct ggtccgaacc atcgagtccg ccctcggcat ttctctcggc 600
gacagcgtgt ccgattctgt cgttatcatt gccaccactt ctgctgccgt catcattgga 660
cttctggtct tcctctggcg aaagtctccc gacagatcgc gagagctgcg tcctgtcatt 720
gtgcccaagt ttaccgttaa gcacgaggac gatgaagtcg aggtggaccg aggcaaaacc 780
aaggttacag ttttctacgg aactcagacc ggtactgccg agggctttgc aaaggccctt 840
gcggaggaaa tcaaggccag atacgagaag gccgttgtca aggtggttga catggatgac 900
tacgctattg acgatgacca gtacgaggaa aagctcaaaa aggagaccct ggtcttcttt 960
atgcttgcca cctatggaga cggcgaaccc accgataacg ctgcacgatt ctacaagtgg 1020
tttaccgagg gcaaggagga acgaggaacc tggctgcagc aactcactta cggtgtgttc 1080
gccttgggca accgacagta cgagcatttc aacaagatcg gcaagattgt cgacgaggat 1140
cttaccgagc agggagccaa gcgtctggtt cccgtcggtc tcggcgacga tgaccagtcc 1200
atcgaggacg atttcaacgc ttggaaggaa accttgtggc cagagctgga ccaacttctc 1260
cgagacgagg atgacgtcaa cactgcttcg accccttaca ctgccgctat ctccgagtat 1320
cgtgtcgtta tccacgatcc taccgtgtct ccctcctacg agaaccattt caatgttgcc 1380
aacggtggag cagtgttcga cattcaccat ccctgtcgag tcaacgttgc cgtgcgacgg 1440
gaacttcaca agccccagtc cgaccgatct tgcattcacc tggagtttga tctctccggt 1500
actggcgtta catacgagac tggcgaccac gtcggagtgt acgccgagaa ctgcgacgaa 1560
actgtcgagg aagctggcaa gctgctcggt cagtcgctgg atcttctctt ttctctgcat 1620
accgacaagg aggatggcac aagccttggt ggatctctgc tccctccatt tcctggaccc 1680
tgtaccgttc gaactgccct cgcttgctac gccgaccttc ttaatcctcc acggaaagcc 1740
gctatcgtgg cacttgctgc ccatgcttcc gagcccagcg aggccgaacg actcaagttt 1800
ctttcttcgc ctcagggcaa ggacgagtac tccaagtggg tcgttggatc tcagcgatcg 1860
ctgctcgaag tcatggccga ttttccctcc gccaagcctc cactgggagt gttctttgct 1920
gccattgcac ctcgactgca gcctcgatac tattctatct cctcttcgcc cagaccagct 1980
ccccagcgag tgcacgttac ctgtgccctt gtcgagggac ccactcctac cggtcggatt 2040
cacaagggtg tgtgctccac ctggatgaag tctgctactc ccttggagaa gtctcacgac 2100
tgttcccgag cacctatctt cattcgaccc tccaacttca agcttcctgc cgaccattcg 2160

-continued

```
attcccatta tcatggtcgg acctggtaca ggtctggctc cctttcgagg attcctccag   2220
gaacgacttg ccctcaagga ggatggagtt cagcttggac ctgccctgct cttctttggt   2280
tgccgaaaca gacagatgga cttcatctac gaggacgaac tcaacaattt cgttcagcaa   2340
ggtgccattt ccgagctcat cgttgcgttt tctcgagagg gcccagaaaa ggagtacgtg   2400
cagcacaaga tgatggacaa ggccgagtat ctgtggtctc tcatttcgca gggaggctac   2460
ctgtacgtct gtggtgatgc caaaggcatg gctcgagacg tgcaccgatc ccttcatacc   2520
attgttcagc aacaggagaa cgcagattct tcgaaggctg aggccactgt caagaaactc   2580
cagatggacg gaagatacct gcgagacgtg tggtaagcgg ccgcatgaga agataaatat   2640
ataaatacat tgagatatta aatgcgctag attagagagc ctcatactgc tcggagagaa   2700
gccaagacga gtactcaaag ggattacac catccatatc cacagacaca agctggggaa    2760
aggttctata tacactttcc ggaataccgt agtttccgat gttatcaatg ggggcagcca   2820
ggatttcagg cacttcggtg tctcggggtg aaatggcgtt cttggcctcc atcaagtcgt   2880
accatgtctt catttgcctg tcaaagtaaa acagaagcag atgaagaatg aacttgaagt   2940
gaaggaattt aaatgtaacg aaactgaaat ttgaccagat attgtgtccg cggtggagct   3000
ccagcttttg ttccctttag tgagggttaa tttcgagctt ggcgtaatca tggtcatagc   3060
tgtttcctgt gtgaaattgt tatccgctca caagcttcca cacaacgtac gttgattgag   3120
gtggagccag atgggctatt gtttcatata tagactggca gccacctctt tggcccagca   3180
tgtttgtata cctggaaggg aaaactaaag aagctggcta gtttagtttg attattatag   3240
tagatgtcct aatcactaga gattagaatg tcttggcgat gattagtcgt cgtcccctgt   3300
atcatgtcta gaccaactgt gtcatgaagt tggtgctggt gttttacctg tgtactacaa   3360
gtaggtgtcc tagatctagt gtacagagcc gtttagaccc atgtggactt caccattaac   3420
gatggaaaat gttcattata tgacagtata ttacaatgga cttgctccat ttcttccttg   3480
catcacatgt tctccacctc catagttgat caacacatca tagtagctaa ggctgctgct   3540
ctcccactac agtccaccac aagttaagta gcaccgtcag tacagctaaa agtacacgtc   3600
tagtacgttt cataactagt caagtagccc ctattacaga tatcagcact atcacgcacg   3660
agtttttctc tgtgctatct aatcaacttg ccaagtattc ggagaagata cactttcttg   3720
gcatcaggta tacgagggag cctatcagat gaaaaagggt atattggatc cattcatatc   3780
cacctacacg ttgtcataat ctcctcattc acgtgattca tttcgtgaca ctagtttctc   3840
actttccccc ccgcacctat agtcaacttg gcggacacgc tacttgtagc tgacgttgat   3900
ttatagaccc aatcaaagcg ggttatcggt caggtagcac ttatcattca tcgttcatac   3960
tacgatgagc aatctcgggc atgtccggaa aagtgtcggg cgcgccagct gcattaatga   4020
atcggccaac gcgcggggag aggcggtttg cgtattgggc gctcttccgc ttcctcgctc   4080
actgactcgc tgcgctcggt cgttcggctg cggcgagcgg tatcagctca ctcaaaggcg   4140
gtaatacggt tatccacaga atcaggggat aacgcaggaa agaacatgtg agcaaaaggc   4200
cagcaaaagg ccaggaaccg taaaaaggcc gcgttgctgg cgtttttcca taggctccgc   4260
cccccctgacg agcatcacaa aaatcgacgc tcaagtcaga ggtggcgaaa cccgacagga   4320
ctataaagat accaggcgtt tccccctgga agctccctcg tgcgctctcc tgttccgacc   4380
ctgccgctta ccggatacct gtccgccttt ctcccttcgg gaagcgtggc gctttctcat   4440
agctcacgct gtaggtatct cagttcggtg taggtcgttc gctccaagct gggctgtgtg   4500
```

-continued

```
cacgaacccc ccgttcagcc cgaccgctgc gccttatccg gtaactatcg tcttgagtcc   4560
aacccggtaa gacacgactt atcgccactg gcagcagcca ctggtaacag gattagcaga   4620
gcgaggtatg taggcggtgc tacagagttc ttgaagtggt ggcctaacta cggctacact   4680
agaagaacag tatttggtat ctgcgctctg ctgaagccag ttaccttcgg aaaaagagtt   4740
ggtagctctt gatccggcaa acaaaccacc gctggtagcg gtggtttttt tgtttgcaag   4800
cagcagatta cgcgcagaaa aaaaggatct caagaagatc ctttgatctt ttctacgggg   4860
tctgacgctc agtggaacga aaactcacgt taagggattt tggtcatgag attatcaaaa   4920
aggatcttca cctagatcct tttaaattaa aaatgaagtt ttaaatcaat ctaaagtata   4980
tatgagtaaa cttggtctga cagttaccaa tgcttaatca gtgaggcacc tatctcagcg   5040
atctgtctat ttcgttcatc catagttgcc tgactccccg tcgtgtagat aactacgata   5100
cgggagggct taccatctgg ccccagtgct gcaatgatac cgcgagaccc acgctcaccg   5160
gctccagatt tatcagcaat aaaccagcca gccggaaggg ccgagcgcag aagtggtcct   5220
gcaactttat ccgcctccat ccagtctatt aattgttgcc gggaagctag agtaagtagt   5280
tcgccagtta atagtttgcg caacgttgtt gccattgcta caggcatcgt ggtgtcacgc   5340
tcgtcgtttg gtatggcttc attcagctcc ggttcccaac gatcaaggcg agttacatga   5400
tcccccatgt tgtgcaaaaa agcggttagc tccttcggtc ctccgatcgt tgtcagaagt   5460
aagttggccg cagtgttatc actcatggtt atggcagcac tgcataattc tcttactgtc   5520
atgccatccg taagatgctt ttctgtgact ggtgagtact caaccaagtc attctgagaa   5580
tagtgtatgc ggcgaccgag ttgctcttgc ccggcgtcaa tacgggataa taccgcgcca   5640
catagcagaa ctttaaaagt gctcatcatt ggaaaacgtt cttcggggcg aaaactctca   5700
aggatcttac cgctgttgag atccagttcg atgtaaccca ctcgtgcacc caactgatct   5760
tcagcatctt ttactttcac cagcgtttct gggtgagcaa aaacaggaag gcaaaatgcc   5820
gcaaaaaagg gaataagggc gacacggaaa tgttgaatac tcatactctt cctttttcaa   5880
tattattgaa gcatttatca gggttattgt ctcatgagcg gatacatatt tgaatgtatt   5940
tagaaaaata aacaaatagg ggttccgcgc acatttcccc gaaaagtgcc acctgatgcg   6000
gtgtgaaata ccgcacagat gcgtaaggag aaaataccgc atcaggaaat tgtaagcgtt   6060
aatattttgt taaaattcgc gttaaatttt tgttaaatca gctcattttt taaccaatag   6120
gccgaaatcg gcaaaatccc ttataaatca aaagaataga ccgagatagg gttgagtgtt   6180
gttccagttt ggaacaagag tccactatta aagaacgtgg actccaacgt caaagggcga   6240
aaaaccgtct atcagggcga tggcccacta cgtgaaccat caccctaatc aagttttttg   6300
gggtcgaggt gccgtaaagc actaaatcgg aaccctaaag ggagcccccg atttagagct   6360
tgacggggaa agccggcgaa cgtggcgaga aaggaaggga agaaagcgaa aggagcgggc   6420
gctagggcgc tggcaagtgt agcggtcacg ctgcgcgtaa ccaccacacc cgccgcgctt   6480
aatgcgccgc tacagggcgc gtccattcgc cattcaggct gcgcaactgt tgggaagggc   6540
gatcggtgcg ggcctcttcg ctattacgcc agctggcgaa agggggatgt gctgcaaggc   6600
gattaagttg ggtaacgcca gggttttccc agtcacgacg ttgtaaaacg acggccagtg   6660
aattgtaata cgactcacta tagggcgaat tgggcccgac gtcgcatgca ttccgacagc   6720
agcgactggg caccatgatc aagcgaaaca ccttccccca gctgccctgg caaaccatca   6780
agaaccctac tttcatcaag tgcaagaacg gttctactct tctcacctcc ggtgtctacg   6840
gctggtgccg aaagcctaac tacaccgctg atttcatcat gtgcctcacc tgggctctca   6900
```

-continued

```
tgtgcggtgt tgcttctccc ctgccttact tctacccggt cttcttcttc ctggtgctca   6960
tccaccgagc ttaccgagac tttgagcgac tggagcgaaa gtacggtgag gactaccagg   7020
agttcaagcg acaggtccct tggatcttca tcccttatgt tttctaaacg ataagcttag   7080
tgagcgaatg gtgaggttac ttaattgagt ggccagccta tgggattgta taacagacag   7140
tcaatatatt actgaaaaga ctgaacagcc agacggagtg aggttgtgag tgaatcgtag   7200
agggcggcta ttacagcaag tctactctac agtgtactaa cacagcagag aacaaataca   7260
ggtgtgcatt cggctatctg agaattagtt ggagagctcg agaccctcgg cgataaactg   7320
ctcctcggtt ttgtgtccat acttgtacgg accattgtaa tggggcaagt cgttgagttc   7380
tcgtcgtccg acgttcagag cacagaaacc aatgtaatca atgtagcaga gatggttctg   7440
caaaagattg atttgtgcga gcaggttaat taagttgcga cacatgtctt gatagtatct   7500
tgaattctct ctcttgagct tttccataac aagttcttct gcctccagga agtccatggg   7560
tggtttgatc atggttttgg tgtagtggta gtgcagtggt ggtattgtga ctggggatgt   7620
agttgagaat aagtcataca caagtcagct ttcttcgagc ctcatataag tataagtagt   7680
tcaacgtatt agcactgtac ccagcatctc cgtatcgaga aacacaacaa catgccccat   7740
tggacagatc atgcggatac acaggttgtg cagtatcata catactcgat cagacaggtc   7800
gtctgaccat catacaagct gaacaagcgc tccatacttg cacgctctct atatacacag   7860
ttaaattaca tatccatagt ctaacctcta acagttaatc ttctggtaag cctcccagcc   7920
agccttctgg tatcgcttgg cctcctcaat aggatctcgg ttctggccgt acagacctcg   7980
gccgacaatt atgatatccg ttccggtaga catgacatcc tcaacagttc ggtactgctg   8040
tccgagagcg tctcccttgt cgtcaagacc caccccgggg gtcagaataa gccagtcctc   8100
agagtcgccc ttaggtcggt tctgggcaat gaagccaacc acaaactcgg ggtcggatcg   8160
ggcaagctca atggtctgct tggagtactc gccagtggcc agagagccct tgcaagacag   8220
ctcggccagc atgagcagac ctctggccag cttctcgttg ggagagggga ctaggaactc   8280
cttgtactgg gagttctcgt agtcagagac gtcctccttc ttctgttcag agacagtttc   8340
ctcggcacca gctcgcaggc cagcaatgat tccggttccg ggtacaccgt gggcgttggt   8400
gatatcggac cactcggcga ttcggtgaca ccggtactgg tgcttgacag tgttgccaat   8460
atctgcgaac tttctgtcct cgaacaggaa gaaaccgtgc ttaagagcaa gttccttgag   8520
ggggagcaca gtgccggcgt aggtgaagtc gtcaatgatg tcgatatggg ttttgatcat   8580
gcacacataa ggtccgacct tatcggcaag ctcaatgagc tccttggtgg tggtaacatc   8640
cagagaagca cacaggttgg ttttcttggc tgccacgagc ttgagcactc gagcggcaaa   8700
ggcggacttg tggacgttag ctcgagcttc gtaggagggc attttggtgg tgaagaggag   8760
actgaaataa atttagtctg cagaactttt tatcggaacc ttatctgggg cagtgaagta   8820
tatgttatgg taatagttac gagttagttg aacttataga tagactggac tatacggcta   8880
tcggtccaaa ttagaaagaa cgtcaatggc tctctgggcg tcgcctttgc cgacaaaaat   8940
gtgatcatga tgaaagccag caatgacgtt gcagctgata ttgttgtcgg ccaaccgcgc   9000
cgaaaacgca gctgtcagac ccacagcctc caacgaagaa tgtatcgtca aagtgatcca   9060
agcacactca tagttggagt cgtactccaa aggcggcaat gacgagtcag acagatactc   9120
gtcgaccttt tccttgggaa ccaccaccgt cagcccttct gactcacgta ttgtagccac   9180
cgacacaggc aacagtccgt ggatagcaga atatgtcttg tcggtccatt tctcaccaac   9240
```

-continued

```
tttaggcgtc aagtgaatgt tgcagaagaa gtatgtgcct tcattgagaa tcggtgttgc   9300
tgatttcaat aaagtcttga gatcagtttg gccagtcatg ttgtgggggg taattggatt   9360
gagttatcgc ctacagtctg tacaggtata ctcgctgccc actttatact tttgattcc    9420
gctgcacttg aagcaatgtc gtttaccaaa agtgagaatg ctccacagaa cacaccccag   9480
ggtatggttg agcaaaaaat aaacactccg atacggggaa tcgaaccccg gtctccacgg   9540
ttctcaagaa gtattcttga tgagagcgta tcgattgccc cggagaagac ggccaggccg   9600
cctagatgac aaattcaaca actcacagct gactttctgc cattgccact agggggggc    9660
ctttttatat ggccaagcca agctctccac gtcggttggg ctgcacccaa caataaatgg   9720
gtagggttgc accaacaaag ggatgggatg gggggtagaa gatacgagga taacggggct   9780
caatggcaca aataagaacg aatactgcca ttaagactcg tgatccagcg actgacacca   9840
ttgcatcatc taagggcctc aaaactacct cggaactgct gcgctgatct ggacaccaca   9900
gaggttccga gcactttagg ttgcaccaaa tgtcccacca ggtgcaggca gaaaacgctg   9960
gaacagcgtg tacagtttgt cttaacaaaa agtgagggcg ctgaggtcga gcagggtggt  10020
gtgacttgtt atagccttta gagctgcgaa agcgcgtatg gatttggctc atcaggccag  10080
attgagggtc tgtggacaca tgtcatgtta gtgtacttca atcgccccct ggatatagcc  10140
ccgacaatag gccgtggcct cattttttg ccttccgcac atttccattg ctcggtaccc   10200
acaccttgct tctcctgcac ttgccaacct taatactggt ttacattgac caacatctta  10260
caagcggggg gcttgtctag ggtatatata aacagtggct ctcccaatcg gttgccagtc  10320
tctttttcc tttctttccc cacagattcg aaatctaaac tacacatcac agaattccga   10380
gccgtgagta tccacgacaa gatcagtgtc gagacgacgc gttttgtgta atgacacaat  10440
ccgaaagtcg ctagcaacac acactctcta cacaaactaa cccagctctc catggccttc  10500
cagtttcacc tggaggtcct cctgccctac ctccttcctc tgcttctgct catcctgccc  10560
accactatct tctttctcac caagcccaac aataaggtgt cctctacttc caccaacaat  10620
aacatcatta cactgcccaa gtcgtaccct ctcattggct cctacctttc gttccgaaag  10680
aacctgcatc gacggatcca gtggctctcc gacattgttc agatctctcc ctccgctacc  10740
ttccagctcg acggaaccct gggcaagcga cagatcatta ctggcaaccc ttctaccgtc  10800
cagcacattc tcaagaacca gttctccaac tatcagaagg gcaccacatt caccaacact  10860
ctgtccgact ttctcggaac aggcatcttc aacaccaacg gtcccaactg gaagtttcaa  10920
cgacaggttg cctctcacga gttcaacacc aagtccattc ggaacttcgt cgagcacatc  10980
gtggataccg aactcaccaa ccgattgatt cccatcctca cttcgagcac ccagacaaac  11040
aatatcctgg acttccagga tattctgcag cgatttacct tcgacaacat ctgcaacatt  11100
gccttcggat acgatcccga gtacctcact ccctcgacca atcgttccaa gttcgcggag  11160
gcctacgaag acgctaccga gatctccagc aagcgattca gactgcctct tcccatcatt  11220
tggaagatca aaaagtactt caacattggc tccgagaagc gactcaagga agccgtcacc  11280
gaggtccgat cctttgccaa gaaactggtc cgagagaaga aacgggagct cgaagagaag  11340
tcttcgctgg agaccgaaga catgctttct cgatttctgt ccagcggtca ctcggacgag  11400
gatttcgttg ccgacattgt catctccttc attctcgcag gcaaggacac tacctctgcc  11460
gctcttacct ggtttttctg gctgctctgg aagaaccctc gagtggagga agagatcgtc  11520
aacgagctgt ccaagaaatc ggagcttatg gtgtacgacg aggtcaagga aatggtctac  11580
acccatgctg cgctgtccga gtcgatgaga ctctaccctc ccgttccaat ggattccaag  11640
```

```
gaggccgtca acgacgatgt gctgcccgac ggctgggtgg tcaagaaagg tacaatcgtc  11700

acctaccatg tctacgctat gggtcgaatg aagtctctct ggggagacga ttgggcagag  11760

tttcgaccag aacggtggct cgagaaggac gaggtcaacg gcaagtgggt gttcgtcgga  11820

cgagacagct actcctatcc tgtgttccag gctggtccca gagtctgcct gggaaaggag  11880

atggccttca tgcagatgaa gcgaattgtg gctggcatcg tcggaaagtt caaggtggtt  11940

cccgaagccc acttggctca ggagccagga ttcatttcct ttctgtcgtc tcagatggag  12000

ggtggatttc ccgtcactat ccagaagcga gactcctaag cggccgcatt gatgattgga  12060

aacacacaca tgggttatat ctaggtgaga gttagttgga cagttatata ttaaatcagc  12120

tatgccaacg gtaacttcat tcatgtcaac gaggaaccag tgactgcaag taatatagaa  12180

tttgaccacc ttgccattct cttgcactcc tttactatat ctcatttatt tcttatatac  12240

aaatcacttc ttcttcccag catcgagctc ggaaacctca tgagcaataa catcgtggat  12300

ctcgtcaata gagggctttt tggactcctt gctgttggcc accttgtcct tgctgttt    12358
```

<210> SEQ ID NO 106
<211> LENGTH: 1296
<212> TYPE: DNA
<213> ORGANISM: Yarrowia lipolytica

<400> SEQUENCE: 106

```
atggatttct tcagacggca ccagaaaaag gtgctggcac tggtaggtgt ggcgctgagt     60

tcctacctgt ttatcgacta tgtgaagaaa aagttcttcg agatccaggg tcgtttgagc    120

tcggagcgaa ccgctaaaca gaatctccgg cgccgatttg aacagaacca gcaggatgca    180

gattttacaa tcatggctct gctatccagc ttgacgacac cggtaatgga gcgttacccc    240

gtcgaccaga tcaaggcaga gttacagagc aagagacgcc ccacagaccg ggttttggct    300

ctcgagagct ccacctcgtc ctcagctacc gcacaaaccg tgcccaccat gacaagtggc    360

gccacagagg agggcgagaa gtcgaaaaca cagttgtggc aggatctcaa gcgaacgacc    420

atttcccgag cgttttctct tgtctatgca gatgcacttc ttattttctt cacgcgtttg    480

cagctcaaca ttctaggacg acgaaactac gtcaacagtg ttgtcgctct ggcgcagcag    540

ggccgagagg gtaatgccga gggtcgagtg gcgccctcgt ttggtgatct tgcagatatg    600

ggctatttcg gcgacctttc aggctcgtcc agcttcggag aaactattgt cgatcccgat    660

ctggacgaac agtaccttac cttttcgtgg tggctgctga acgagggatg ggtgtcgctg    720

agcgagcgag tggaggaagc ggttcgtcga gtgtgggacc ccgtgtcacc caaggccgaa    780

cttggatttg acgagttgtc ggaactcatt ggacgaacac agatgctcat tgatcgacct    840

ctcaatccct cgtcgccact caactttctg agccagctgc tgccaccacg ggagcaggag    900

gagtacgtgc ttgcccagaa ccccagcgat actgctgccc ccattgtagg acctaccctc    960

cgacggcttc tggacgagac tgccgacttc atcgagtccc ctaatgccgc agaggtgatt   1020

gagcgacttg ttcactccgg tctctctgtg ttcatggaca agctggctgt cacgtttgga   1080

gccacacctg ctgattcggg ttcgccttat cctgtggtgc tgcctactgc aaaggtcaag   1140

ctgccctcca ttcttgccaa catggctcga caggctggag gcatggccca gggatcgccg   1200

ggcgtggaaa acgagtacat tgacgtgatg aaccaagtgc aggagctgac ctcctttagt   1260

gctgtggtct attcatcttt tgattgggct ctctag                             1296
```

<210> SEQ ID NO 107

<211> LENGTH: 431
<212> TYPE: PRT
<213> ORGANISM: Yarrowia lipolytica

<400> SEQUENCE: 107

```
Met Asp Phe Phe Arg Arg His Gln Lys Lys Val Leu Ala Leu Val Gly
1               5                   10                  15

Val Ala Leu Ser Ser Tyr Leu Phe Ile Asp Tyr Val Lys Lys Lys Phe
            20                  25                  30

Phe Glu Ile Gln Gly Arg Leu Ser Ser Glu Arg Thr Ala Lys Gln Asn
        35                  40                  45

Leu Arg Arg Arg Phe Glu Gln Asn Gln Gln Asp Ala Asp Phe Thr Ile
    50                  55                  60

Met Ala Leu Leu Ser Ser Leu Thr Thr Pro Val Met Glu Arg Tyr Pro
65                  70                  75                  80

Val Asp Gln Ile Lys Ala Glu Leu Gln Ser Lys Arg Arg Pro Thr Asp
                85                  90                  95

Arg Val Leu Ala Leu Glu Ser Ser Thr Ser Ser Ser Ala Thr Ala Gln
            100                 105                 110

Thr Val Pro Thr Met Thr Ser Gly Ala Thr Glu Glu Gly Glu Lys Ser
        115                 120                 125

Lys Thr Gln Leu Trp Gln Asp Leu Lys Arg Thr Thr Ile Ser Arg Ala
    130                 135                 140

Phe Ser Leu Val Tyr Ala Asp Ala Leu Leu Ile Phe Phe Thr Arg Leu
145                 150                 155                 160

Gln Leu Asn Ile Leu Gly Arg Arg Asn Tyr Val Asn Ser Val Val Ala
                165                 170                 175

Leu Ala Gln Gln Gly Arg Glu Gly Asn Ala Glu Gly Arg Val Ala Pro
            180                 185                 190

Ser Phe Gly Asp Leu Ala Asp Met Gly Tyr Phe Gly Asp Leu Ser Gly
        195                 200                 205

Ser Ser Ser Phe Gly Glu Thr Ile Val Asp Pro Asp Leu Asp Glu Gln
    210                 215                 220

Tyr Leu Thr Phe Ser Trp Trp Leu Leu Asn Glu Gly Trp Val Ser Leu
225                 230                 235                 240

Ser Glu Arg Val Glu Glu Ala Val Arg Arg Val Trp Asp Pro Val Ser
                245                 250                 255

Pro Lys Ala Glu Leu Gly Phe Asp Glu Leu Ser Glu Leu Ile Gly Arg
            260                 265                 270

Thr Gln Met Leu Ile Asp Arg Pro Leu Asn Pro Ser Ser Pro Leu Asn
        275                 280                 285

Phe Leu Ser Gln Leu Leu Pro Pro Arg Glu Gln Glu Glu Tyr Val Leu
    290                 295                 300

Ala Gln Asn Pro Ser Asp Thr Ala Ala Pro Ile Val Gly Pro Thr Leu
305                 310                 315                 320

Arg Arg Leu Leu Asp Glu Thr Ala Asp Phe Ile Glu Ser Pro Asn Ala
                325                 330                 335

Ala Glu Val Ile Glu Arg Leu Val His Ser Gly Leu Ser Val Phe Met
            340                 345                 350

Asp Lys Leu Ala Val Thr Phe Gly Ala Thr Pro Ala Asp Ser Gly Ser
        355                 360                 365

Pro Tyr Pro Val Val Leu Pro Thr Ala Lys Val Lys Leu Pro Ser Ile
    370                 375                 380

Leu Ala Asn Met Ala Arg Gln Ala Gly Gly Met Ala Gln Gly Ser Pro
```

```
385                 390                 395                 400

Gly Val Glu Asn Glu Tyr Ile Asp Val Met Asn Gln Val Gln Glu Leu
                405                 410                 415

Thr Ser Phe Ser Ala Val Val Tyr Ser Ser Phe Asp Trp Ala Leu
            420                 425                 430


<210> SEQ ID NO 108
<211> LENGTH: 377
<212> TYPE: PRT
<213> ORGANISM: Yarrowia lipolytica

<400> SEQUENCE: 108

Met Trp Gly Ser Ser His Ala Phe Ala Gly Glu Ser Asp Leu Thr Leu
1               5                   10                  15

Gln Leu His Thr Arg Ser Asn Met Ser Asp Asn Thr Thr Ile Lys Lys
            20                  25                  30

Pro Ile Arg Pro Lys Pro Ile Arg Thr Glu Arg Leu Pro Tyr Ala Gly
        35                  40                  45

Ala Ala Glu Ile Ile Arg Ala Asn Gln Lys Asp His Tyr Phe Glu Ser
    50                  55                  60

Val Leu Glu Gln His Leu Val Thr Phe Leu Gln Lys Trp Lys Gly Val
65                  70                  75                  80

Arg Phe Ile His Gln Tyr Lys Glu Glu Leu Glu Thr Ala Ser Lys Phe
                85                  90                  95

Ala Tyr Leu Gly Leu Cys Thr Leu Val Gly Ser Lys Thr Leu Gly Glu
            100                 105                 110

Glu Tyr Thr Asn Leu Met Tyr Thr Ile Arg Asp Arg Thr Ala Leu Pro
        115                 120                 125

Gly Val Val Arg Arg Phe Gly Tyr Val Leu Ser Asn Thr Leu Phe Pro
    130                 135                 140

Tyr Leu Phe Val Arg Tyr Met Gly Lys Leu Arg Ala Lys Leu Met Arg
145                 150                 155                 160

Glu Tyr Pro His Leu Val Glu Tyr Asp Glu Asp Glu Pro Val Pro Ser
                165                 170                 175

Pro Glu Thr Trp Lys Glu Arg Val Ile Lys Thr Phe Val Asn Lys Phe
            180                 185                 190

Asp Lys Phe Thr Ala Leu Glu Gly Phe Thr Ala Ile His Leu Ala Ile
        195                 200                 205

Phe Tyr Val Tyr Gly Ser Tyr Tyr Gln Leu Ser Lys Arg Ile Trp Gly
    210                 215                 220

Met Arg Tyr Val Phe Gly His Arg Leu Asp Lys Asn Glu Pro Arg Ile
225                 230                 235                 240

Gly Tyr Glu Met Leu Gly Leu Leu Ile Phe Ala Arg Phe Ala Thr Ser
                245                 250                 255

Phe Val Gln Thr Gly Arg Glu Tyr Leu Gly Ala Leu Leu Glu Lys Ser
            260                 265                 270

Val Glu Lys Glu Ala Gly Glu Lys Glu Asp Glu Lys Glu Ala Val Val
        275                 280                 285

Pro Lys Lys Lys Ser Ser Ile Pro Phe Ile Glu Asp Thr Glu Gly Glu
    290                 295                 300

Thr Glu Asp Lys Ile Asp Leu Glu Asp Pro Arg Gln Leu Lys Phe Ile
305                 310                 315                 320

Pro Glu Ala Ser Arg Ala Cys Thr Leu Cys Leu Ser Tyr Ile Ser Ala
                325                 330                 335
```

Pro Ala Cys Thr Pro Cys Gly His Phe Phe Cys Trp Asp Cys Ile Ser
340 345 350

Glu Trp Val Arg Glu Lys Pro Glu Cys Pro Leu Cys Arg Gln Gly Val
355 360 365

Arg Glu Gln Asn Leu Leu Pro Ile Arg
370 375

<210> SEQ ID NO 109
<211> LENGTH: 391
<212> TYPE: PRT
<213> ORGANISM: Yarrowia lipolytica

<400> SEQUENCE: 109

Met Thr Asp Lys Leu Val Lys Val Met Gln Lys Lys Lys Ser Ala Pro
1 5 10 15

Gln Thr Trp Leu Asp Ser Tyr Asp Lys Phe Leu Val Arg Asn Ala Ala
20 25 30

Ser Ile Gly Ser Ile Glu Ser Thr Leu Arg Thr Val Ser Tyr Val Leu
35 40 45

Pro Gly Arg Phe Asn Asp Val Glu Ile Ala Thr Glu Thr Leu Tyr Ala
50 55 60

Val Leu Asn Val Leu Gly Leu Tyr His Asp Thr Ile Ile Ala Arg Ala
65 70 75 80

Val Ala Ala Ser Pro Asn Ala Ala Ala Val Tyr Arg Pro Ser Pro His
85 90 95

Asn Arg Tyr Thr Asp Trp Phe Ile Lys Asn Arg Lys Gly Tyr Lys Tyr
100 105 110

Ala Ser Arg Ala Val Thr Phe Val Lys Phe Gly Glu Leu Val Ala Glu
115 120 125

Met Val Ala Lys Lys Asn Gly Gly Glu Met Ala Arg Trp Lys Cys Ile
130 135 140

Ile Gly Ile Glu Gly Ile Lys Ala Gly Leu Arg Ile Tyr Met Leu Gly
145 150 155 160

Ser Thr Leu Tyr Gln Pro Leu Cys Thr Thr Pro Tyr Pro Asp Arg Glu
165 170 175

Val Thr Gly Glu Leu Leu Glu Thr Ile Cys Arg Asp Glu Gly Glu Leu
180 185 190

Asp Ile Glu Lys Gly Leu Met Asp Pro Gln Trp Lys Met Pro Arg Thr
195 200 205

Gly Arg Thr Ile Pro Glu Ile Ala Pro Thr Asn Val Glu Gly Tyr Leu
210 215 220

Leu Thr Lys Val Leu Arg Ser Glu Asp Val Asp Arg Pro Tyr Asn Leu
225 230 235 240

Leu Ser Arg Leu Asp Asn Trp Gly Val Val Ala Glu Leu Leu Ser Ile
245 250 255

Leu Arg Pro Leu Ile Tyr Ala Cys Leu Leu Phe Arg Gln His Val Asn
260 265 270

Lys Thr Val Pro Ala Ser Thr Lys Ser Lys Phe Pro Phe Leu Asn Ser
275 280 285

Pro Trp Ala Pro Trp Ile Ile Gly Leu Val Ile Glu Ala Leu Ser Arg
290 295 300

Lys Met Met Gly Ser Trp Leu Leu Arg Gln Arg Gln Ser Gly Lys Thr
305 310 315 320

Pro Thr Ala Leu Asp Gln Met Glu Val Lys Gly Arg Thr Asn Leu Leu
325 330 335

```
Gly Trp Trp Leu Phe Arg Gly Glu Phe Tyr Gln Ala Tyr Thr Arg Pro
            340                 345                 350

Leu Leu Tyr Ser Ile Val Ala Arg Leu Glu Lys Ile Pro Gly Leu Gly
        355                 360                 365

Leu Phe Gly Ala Leu Ile Ser Asp Tyr Leu Tyr Leu Phe Asp Arg Tyr
    370                 375                 380

Tyr Phe Thr Ala Ser Thr Leu
385                 390


<210> SEQ ID NO 110
<211> LENGTH: 2106
<212> TYPE: DNA
<213> ORGANISM: Yarrowia lipolytica

<400> SEQUENCE: 110

atgatcaccc caaaccccgc taacgacatt gtccatgacg gcaagctcta cgacaccttc     60

actgagcccc ccaagctgat ggctcaggag cgagctcagc tggacttcga ccctagagac    120

atcacctact ttctggatgg ctctaaggag gagaccgagc tgctggagtc gctcatgctc    180

atgtacgagc gagaccctct cttcaacaac cagaacgagt acgatgaatc gtttgaaaca    240

ctgcgagagc gatctgtgaa gcgaattttc cagctgtcca agtccatcgc catggacccc    300

gagcccatgt ctttccgaaa gattgggttc ctgggtattc ttgacatggg aacgtatgct    360

cgactgggag tccactacgc gctcttctgt aactccatcc ggggccaggg aaccccccgat    420

cagctcatgt actggctgga ccagggagcc atggtcatca agggcttcta cggctgtttt    480

gccatgaccg aaatgggcca tggatctaac ctgtcgcgtc tggaaaccat cgccactttc    540

gacaaagaga ccgacgaatt tatcattaac acgccccacg ttggagccac aaagtggtgg    600

attggaggag ccgcccacac tgctactcac acacttgcct ttgcccgtct tcaagtagac    660

ggaaaggact acggtgtgaa atcgtttgtc gtacctctcc gaaacctgga cgaccattcg    720

ctgcgtcctg gaatcgccac aggtgatatt ggtaagaaga tgggtcgaga tgccgttgac    780

aacggctgga ttcagttcac caacgtccga gtgccccgaa actacatgct catgaagcat    840

accaaggttc ttcgagacgg taccgtcaag cagccgcctt tggcccaact gacttacgga    900

tctctcatca ctggacgagt ccagatgacc actgactctc acaatgtgtc caaaaagttc    960

ctcaccattg ccctgagata cgccaccatc cgacgacagt tctcgtcaac tccaggagag   1020

cccgaaaccc gactaattga ctacctgtac caccaaagac gactcctgcc tcttatggct   1080

tactcttacg ccatgaaact agctggagat cacgtccgag agctgttctt tgcatcccag   1140

gagaaggctg agagcctcaa ggaggacgac aaagccggag ttgagtctta cgtccaggat   1200

atcaaggagc tcttctctgt ttctgctggt ctcaaggctg ccactacatg ggcttgtgct   1260

gacatcattg acaaggcccg acaggcgtgt ggaggccacg gatactctgc ctacaacggc   1320

tttggacagg ccttccagga ctgggttgtc cagtgcactt gggagggtga caatactgtt   1380

ctgactctat ctgccggccg agctctgatc caatctgctc tcgtctaccg aaaggagggc   1440

aaactaggta acgccacgaa gtacctctct cggtccaagg agcttgccaa cgccaagaga   1500

aacggacgat ccctggaaga ccccaagctg ctcgtggagg catgggaggc tgtctctgcc   1560

ggtgctatca acgctgctac tgacgcttac gaggagctct ccaagcaggg agtttctgtt   1620

gacgagtgct ttgagcaggt gtcccaggag cgattccagg ctgcccgaat ccacactcga   1680

cgagctctta tcgaggcctt ctactcacga atcgccactg ctgatgagaa ggtgaagcct   1740

catctgatcc ctctggccaa cctgtttgcc ctgtggtcca ttgaggagga ctctgctctg   1800
```

ttcctggctg agggctactt tgagcctgag gatatcattg aggtgacttc tcttgtcaac 1860
aagtactgcg gaattgttcg aaagaacgtt attggataca ccgatgcctt caacctgtcc 1920
gactacttca tcaacgctgc cattggacga tacgacggag acgtgtacaa gaactacttt 1980
gagaaggtca aacagcagta ccctcctgag ggtggcaagc ctcactacta cgaggatgtc 2040
atgaagccct tcctgcatcg agagcgaatt cccgatgtcc ccatggagcc cgaggatatt 2100
cagtaa 2106

<210> SEQ ID NO 111
<211> LENGTH: 701
<212> TYPE: PRT
<213> ORGANISM: Yarrowia lipolytica

<400> SEQUENCE: 111

Met Ile Thr Pro Asn Pro Ala Asn Asp Ile Val His Asp Gly Lys Leu
1 5 10 15

Tyr Asp Thr Phe Thr Glu Pro Pro Lys Leu Met Ala Gln Glu Arg Ala
20 25 30

Gln Leu Asp Phe Asp Pro Arg Asp Ile Thr Tyr Phe Leu Asp Gly Ser
35 40 45

Lys Glu Glu Thr Glu Leu Leu Glu Ser Leu Met Leu Met Tyr Glu Arg
50 55 60

Asp Pro Leu Phe Asn Asn Gln Asn Glu Tyr Asp Glu Ser Phe Glu Thr
65 70 75 80

Leu Arg Glu Arg Ser Val Lys Arg Ile Phe Gln Leu Ser Lys Ser Ile
85 90 95

Ala Met Asp Pro Glu Pro Met Ser Phe Arg Lys Ile Gly Phe Leu Gly
100 105 110

Ile Leu Asp Met Gly Thr Tyr Ala Arg Leu Gly Val His Tyr Ala Leu
115 120 125

Phe Cys Asn Ser Ile Arg Gly Gln Gly Thr Pro Asp Gln Leu Met Tyr
130 135 140

Trp Leu Asp Gln Gly Ala Met Val Ile Lys Gly Phe Tyr Gly Cys Phe
145 150 155 160

Ala Met Thr Glu Met Gly His Gly Ser Asn Leu Ser Arg Leu Glu Thr
165 170 175

Ile Ala Thr Phe Asp Lys Glu Thr Asp Glu Phe Ile Ile Asn Thr Pro
180 185 190

His Val Gly Ala Thr Lys Trp Trp Ile Gly Gly Ala Ala His Thr Ala
195 200 205

Thr His Thr Leu Ala Phe Ala Arg Leu Gln Val Asp Gly Lys Asp Tyr
210 215 220

Gly Val Lys Ser Phe Val Val Pro Leu Arg Asn Leu Asp Asp His Ser
225 230 235 240

Leu Arg Pro Gly Ile Ala Thr Gly Asp Ile Gly Lys Lys Met Gly Arg
245 250 255

Asp Ala Val Asp Asn Gly Trp Ile Gln Phe Thr Asn Val Arg Val Pro
260 265 270

Arg Asn Tyr Met Leu Met Lys His Thr Lys Val Leu Arg Asp Gly Thr
275 280 285

Val Lys Gln Pro Pro Leu Ala Gln Leu Thr Tyr Gly Ser Leu Ile Thr
290 295 300

Gly Arg Val Gln Met Thr Thr Asp Ser His Asn Val Ser Lys Lys Phe
305 310 315 320

-continued

```
Leu Thr Ile Ala Leu Arg Tyr Ala Thr Ile Arg Arg Gln Phe Ser Ser
                325                 330                 335

Thr Pro Gly Glu Pro Glu Thr Arg Leu Ile Asp Tyr Leu Tyr His Gln
            340                 345                 350

Arg Arg Leu Leu Pro Leu Met Ala Tyr Ser Tyr Ala Met Lys Leu Ala
        355                 360                 365

Gly Asp His Val Arg Glu Leu Phe Phe Ala Ser Gln Glu Lys Ala Glu
    370                 375                 380

Ser Leu Lys Glu Asp Asp Lys Ala Gly Val Glu Ser Tyr Val Gln Asp
385                 390                 395                 400

Ile Lys Glu Leu Phe Ser Val Ser Ala Gly Leu Lys Ala Ala Thr Thr
                405                 410                 415

Trp Ala Cys Ala Asp Ile Ile Asp Lys Ala Arg Gln Ala Cys Gly Gly
            420                 425                 430

His Gly Tyr Ser Ala Tyr Asn Gly Phe Gly Gln Ala Phe Gln Asp Trp
        435                 440                 445

Val Val Gln Cys Thr Trp Glu Gly Asp Asn Thr Val Leu Thr Leu Ser
    450                 455                 460

Ala Gly Arg Ala Leu Ile Gln Ser Ala Leu Val Tyr Arg Lys Glu Gly
465                 470                 475                 480

Lys Leu Gly Asn Ala Thr Lys Tyr Leu Ser Arg Ser Lys Glu Leu Ala
                485                 490                 495

Asn Ala Lys Arg Asn Gly Arg Ser Leu Glu Asp Pro Lys Leu Leu Val
            500                 505                 510

Glu Ala Trp Glu Ala Val Ser Ala Gly Ala Ile Asn Ala Ala Thr Asp
        515                 520                 525

Ala Tyr Glu Glu Leu Ser Lys Gln Gly Val Ser Val Asp Glu Cys Phe
    530                 535                 540

Glu Gln Val Ser Gln Glu Arg Phe Gln Ala Ala Arg Ile His Thr Arg
545                 550                 555                 560

Arg Ala Leu Ile Glu Ala Phe Tyr Ser Arg Ile Ala Thr Ala Asp Glu
                565                 570                 575

Lys Val Lys Pro His Leu Ile Pro Leu Ala Asn Leu Phe Ala Leu Trp
            580                 585                 590

Ser Ile Glu Glu Asp Ser Ala Leu Phe Leu Ala Glu Gly Tyr Phe Glu
        595                 600                 605

Pro Glu Asp Ile Ile Glu Val Thr Ser Leu Val Asn Lys Tyr Cys Gly
    610                 615                 620

Ile Val Arg Lys Asn Val Ile Gly Tyr Thr Asp Ala Phe Asn Leu Ser
625                 630                 635                 640

Asp Tyr Phe Ile Asn Ala Ala Ile Gly Arg Tyr Asp Gly Asp Val Tyr
                645                 650                 655

Lys Asn Tyr Phe Glu Lys Val Lys Gln Gln Tyr Pro Pro Glu Gly Gly
            660                 665                 670

Lys Pro His Tyr Tyr Glu Asp Val Met Lys Pro Phe Leu His Arg Glu
        675                 680                 685

Arg Ile Pro Asp Val Pro Met Glu Pro Glu Asp Ile Gln
    690                 695                 700
```

<210> SEQ ID NO 112
<211> LENGTH: 1581
<212> TYPE: DNA
<213> ORGANISM: Yarrowia lipolytica

<400> SEQUENCE: 112

```
atggaagtcc gacgacgaaa aatcgacgtg ctcaaggccc agaaaaacgg ctacgaatcg      60
ggcccaccat ctcgacaatc gtcgcagccc tcctcaagag catcgtccag aacccgcaac     120
aaacactcct cgtccaccct gtcgctcagc ggactgacca tgaaagtcca gaagaaacct     180
gcgggacccc cggcgaactc caaaacgcca ttcctacaca tcaagcccgt gcacacgtgc     240
tgctccacat caatgctttc gcgcgattat gacggctcca accccagctt caagggcttc     300
aaaaacatcg gcatgatcat tctcattgtg ggaaatctac ggctcgcatt cgaaaactac     360
ctcaaatacg gcatttccaa cccgttcttc gaccccaaaa ttactccttc cgagtggcag     420
ctctcaggct tgctcatagt cgtggcctac gcacatatcc tcatggccta cgctattgag     480
agcgctgcca agctgctgtt cctctctagc aaacaccact acatggccgt ggggcttctg     540
cataccatga acactttgtc gtccatctcg ttgctgtcct acgtcgtcta ctactacctg     600
cccaaccccg tggcaggcac aatagtcgag tttgtggccg ttattctgtc tctcaaactc     660
gcctcatacg ccctcactaa ctcggatctc cgaaaagccg caattcatgc ccagaagctc     720
gacaagacgc aagacgataa cgaaaaggaa tccacctcgt cttcctcttc ttcagatgac     780
gcagagactt tggcagacat tgacgtcatt cctgcatact acgcacagct gccctacccc     840
cagaatgtga cgctgtcgaa cctgctgtac ttctggtttg ctcccacact ggtctaccag     900
cccgtgtacc ccaagacgga gcgtattcga cccaagcacg tgatccgaaa cctgtttgag     960
ctcgtctctc tgtgcatgct tattcagttt ctcatcttcc agtacgccta ccccatcatg    1020
cagtcgtgtc tggctctgtt cttccagccc aagctcgatt atgccaacat ctccgagcgc    1080
ctcatgaagt tggcctccgt gtctatgatg gtctggctca ttggattcta cgctttcttc    1140
cagaacggtc tcaatcttat tgccgagctc acctgttttg gaaacagaac cttctaccag    1200
cagtggtgga attcccgctc cattggccag tactggactc tatggaacaa gccagtcaac    1260
cagtacttta gacaccacgt ctacgtgcct cttctcgctc ggggcatgtc gcggttcaat    1320
gcgtcggtgg tggttttctt tttctccgcc gtcatccatg aactgcttgt cggcatcccc    1380
actcacaaca tcatcggagc cgccttcttc ggcatgatgt cgcaggtgcc tctgatcatg    1440
gctactgaga accttcagca tattaactcc tctctgggcc ccttccttgg caactgtgca    1500
ttctggttca cctttttcct gggacaaccc acttgtgcat tcctttatta tctggcttac    1560
aactacaagc agaaccagta g                                              1581
```

<210> SEQ ID NO 113
<211> LENGTH: 526
<212> TYPE: PRT
<213> ORGANISM: Yarrowia lipolytica

<400> SEQUENCE: 113

```
Met Glu Val Arg Arg Arg Lys Ile Asp Val Leu Lys Ala Gln Lys Asn
1               5                   10                  15

Gly Tyr Glu Ser Gly Pro Pro Ser Arg Gln Ser Ser Gln Pro Ser Ser
            20                  25                  30

Arg Ala Ser Ser Arg Thr Arg Asn Lys His Ser Ser Ser Thr Leu Ser
        35                  40                  45

Leu Ser Gly Leu Thr Met Lys Val Gln Lys Lys Pro Ala Gly Pro Pro
    50                  55                  60

Ala Asn Ser Lys Thr Pro Phe Leu His Ile Lys Pro Val His Thr Cys
65                  70                  75                  80
```

-continued

```
Cys Ser Thr Ser Met Leu Ser Arg Asp Tyr Asp Gly Ser Asn Pro Ser
                85                  90                  95

Phe Lys Gly Phe Lys Asn Ile Gly Met Ile Ile Leu Ile Val Gly Asn
            100                 105                 110

Leu Arg Leu Ala Phe Glu Asn Tyr Leu Lys Tyr Gly Ile Ser Asn Pro
        115                 120                 125

Phe Phe Asp Pro Lys Ile Thr Pro Ser Glu Trp Gln Leu Ser Gly Leu
    130                 135                 140

Leu Ile Val Val Ala Tyr Ala His Ile Leu Met Ala Tyr Ala Ile Glu
145                 150                 155                 160

Ser Ala Ala Lys Leu Leu Phe Leu Ser Ser Lys His His Tyr Met Ala
                165                 170                 175

Val Gly Leu Leu His Thr Met Asn Thr Leu Ser Ser Ile Ser Leu Leu
            180                 185                 190

Ser Tyr Val Val Tyr Tyr Tyr Leu Pro Asn Pro Val Ala Gly Thr Ile
        195                 200                 205

Val Glu Phe Val Ala Val Ile Leu Ser Leu Lys Leu Ala Ser Tyr Ala
    210                 215                 220

Leu Thr Asn Ser Asp Leu Arg Lys Ala Ala Ile His Ala Gln Lys Leu
225                 230                 235                 240

Asp Lys Thr Gln Asp Asp Asn Glu Lys Glu Ser Thr Ser Ser Ser Ser
                245                 250                 255

Ser Ser Asp Asp Ala Glu Thr Leu Ala Asp Ile Asp Val Ile Pro Ala
            260                 265                 270

Tyr Tyr Ala Gln Leu Pro Tyr Pro Gln Asn Val Thr Leu Ser Asn Leu
        275                 280                 285

Leu Tyr Phe Trp Phe Ala Pro Thr Leu Val Tyr Gln Pro Val Tyr Pro
    290                 295                 300

Lys Thr Glu Arg Ile Arg Pro Lys His Val Ile Arg Asn Leu Phe Glu
305                 310                 315                 320

Leu Val Ser Leu Cys Met Leu Ile Gln Phe Leu Ile Phe Gln Tyr Ala
                325                 330                 335

Tyr Pro Ile Met Gln Ser Cys Leu Ala Leu Phe Phe Gln Pro Lys Leu
            340                 345                 350

Asp Tyr Ala Asn Ile Ser Glu Arg Leu Met Lys Leu Ala Ser Val Ser
        355                 360                 365

Met Met Val Trp Leu Ile Gly Phe Tyr Ala Phe Phe Gln Asn Gly Leu
    370                 375                 380

Asn Leu Ile Ala Glu Leu Thr Cys Phe Gly Asn Arg Thr Phe Tyr Gln
385                 390                 395                 400

Gln Trp Trp Asn Ser Arg Ser Ile Gly Gln Tyr Trp Thr Leu Trp Asn
                405                 410                 415

Lys Pro Val Asn Gln Tyr Phe Arg His His Val Tyr Val Pro Leu Leu
            420                 425                 430

Ala Arg Gly Met Ser Arg Phe Asn Ala Ser Val Val Val Phe Phe Phe
        435                 440                 445

Ser Ala Val Ile His Glu Leu Leu Val Gly Ile Pro Thr His Asn Ile
    450                 455                 460

Ile Gly Ala Ala Phe Phe Gly Met Met Ser Gln Val Pro Leu Ile Met
465                 470                 475                 480

Ala Thr Glu Asn Leu Gln His Ile Asn Ser Ser Leu Gly Pro Phe Leu
                485                 490                 495
```

```
Gly Asn Cys Ala Phe Trp Phe Thr Phe Phe Leu Gly Gln Pro Thr Cys
            500                 505                 510

Ala Phe Leu Tyr Tyr Leu Ala Tyr Asn Tyr Lys Gln Asn Gln
        515                 520                 525


<210> SEQ ID NO 114
<211> LENGTH: 1545
<212> TYPE: DNA
<213> ORGANISM: Yarrowia lipolytica

<400> SEQUENCE: 114

atgactatcg actcacaata ctacaagtcg cgagacaaaa acgacacggc acccaaaatc     60

gcgggaatcc gatatgcccc gctatcgaca ccattactca accgatgtga gaccttctct    120

ctggtctggc acattttcag cattcccact ttcctcacaa ttttcatgct atgctgcgca    180

attccactgc tctggccatt tgtgattgcg tatgtagtgt acgctgttaa agacgactcc    240

ccgtccaacg gaggagtggt caagcgatac tcgcctattt caagaaactt cttcatctgg    300

aagctctttg gccgctactt ccccataact ctgcacaaga cggtggatct ggagcccacg    360

cacacatact accctctgga cgtccaggag tatcacctga ttgctgagag atactggccg    420

cagaacaagt acctccgagc aatcatctcc accatcgagt actttctgcc cgccttcatg    480

aaacggtctc tttctatcaa cgagcaggag cagcctgccg agcgagatcc tctcctgtct    540

cccgtttctc ccagctctcc gggttctcaa cctgacaagt ggattaacca cgacagcaga    600

tatagccgtg gagaatcatc tggctccaac ggccacgcct cgggctccga acttaacggc    660

aacggcaaca atggcaccac taaccgacga cctttgtcgt ccgcctctgc tggctccact    720

gcatctgatt ccacgcttct taacgggtcc ctcaactcct acgccaacca gatcattggc    780

gaaaacgacc cacagctgtc gcccacaaaa ctcaagccca ctggcagaaa atacatcttc    840

ggctaccacc cccacggcat tatcggcatg ggagcctttg gtggaattgc caccgaggga    900

gctggatggt ccaagctctt tccgggcatc cctgtttctc ttatgactct caccaacaac    960

ttccgagtgc ctctctacag agagtacctc atgagtctgg gagtcgcttc tgtctccaag   1020

aagtcctgca aggccctcct caagcgaaac cagtctatct gcattgtcgt tggtggagca   1080

caggaaagtc ttctggccag acccggtgtc atggacctgg tgctactcaa gcgaaagggt   1140

tttgttcgac ttggtatgga ggtcggaaat gtcgcccttg ttcccatcat ggcctttggt   1200

gagaacgacc tctatgacca ggttagcaac gacaagtcgt ccaagctgta ccgattccag   1260

cagtttgtca agaacttcct tggattcacc cttcctttga tgcatgcccg aggcgtcttc   1320

aactacgatg tcggtcttgt cccctacagg cgacccgtca acattgtggt tggttccccc   1380

attgacttgc cttatctccc acaccccacc gacgaagaag tgtccgaata ccacgaccga   1440

tacatcgccg agctgcagcg aatctacaac gagcacaagg atgaatattt catcgattgg   1500

accgaggagg gcaaaggagc cccagagttc cgaatgattg agtaa                    1545


<210> SEQ ID NO 115
<211> LENGTH: 514
<212> TYPE: PRT
<213> ORGANISM: Yarrowia lipolytica

<400> SEQUENCE: 115

Met Thr Ile Asp Ser Gln Tyr Tyr Lys Ser Arg Asp Lys Asn Asp Thr
1               5                   10                  15

Ala Pro Lys Ile Ala Gly Ile Arg Tyr Ala Pro Leu Ser Thr Pro Leu
            20                  25                  30
```

```
Leu Asn Arg Cys Glu Thr Phe Ser Leu Val Trp His Ile Phe Ser Ile
        35                  40                  45

Pro Thr Phe Leu Thr Ile Phe Met Leu Cys Cys Ala Ile Pro Leu Leu
    50                  55                  60

Trp Pro Phe Val Ile Ala Tyr Val Val Tyr Ala Val Lys Asp Asp Ser
65                  70                  75                  80

Pro Ser Asn Gly Gly Val Val Lys Arg Tyr Ser Pro Ile Ser Arg Asn
                85                  90                  95

Phe Phe Ile Trp Lys Leu Phe Gly Arg Tyr Phe Pro Ile Thr Leu His
            100                 105                 110

Lys Thr Val Asp Leu Glu Pro Thr His Thr Tyr Tyr Pro Leu Asp Val
        115                 120                 125

Gln Glu Tyr His Leu Ile Ala Glu Arg Tyr Trp Pro Gln Asn Lys Tyr
    130                 135                 140

Leu Arg Ala Ile Ile Ser Thr Ile Glu Tyr Phe Leu Pro Ala Phe Met
145                 150                 155                 160

Lys Arg Ser Leu Ser Ile Asn Glu Gln Glu Gln Pro Ala Glu Arg Asp
                165                 170                 175

Pro Leu Leu Ser Pro Val Ser Pro Ser Ser Pro Gly Ser Gln Pro Asp
            180                 185                 190

Lys Trp Ile Asn His Asp Ser Arg Tyr Ser Arg Gly Glu Ser Ser Gly
        195                 200                 205

Ser Asn Gly His Ala Ser Gly Ser Glu Leu Asn Gly Asn Gly Asn Asn
    210                 215                 220

Gly Thr Thr Asn Arg Arg Pro Leu Ser Ser Ala Ser Ala Gly Ser Thr
225                 230                 235                 240

Ala Ser Asp Ser Thr Leu Leu Asn Gly Ser Leu Asn Ser Tyr Ala Asn
                245                 250                 255

Gln Ile Ile Gly Glu Asn Asp Pro Gln Leu Ser Pro Thr Lys Leu Lys
            260                 265                 270

Pro Thr Gly Arg Lys Tyr Ile Phe Gly Tyr His Pro His Gly Ile Ile
        275                 280                 285

Gly Met Gly Ala Phe Gly Gly Ile Ala Thr Glu Gly Ala Gly Trp Ser
    290                 295                 300

Lys Leu Phe Pro Gly Ile Pro Val Ser Leu Met Thr Leu Thr Asn Asn
305                 310                 315                 320

Phe Arg Val Pro Leu Tyr Arg Glu Tyr Leu Met Ser Leu Gly Val Ala
                325                 330                 335

Ser Val Ser Lys Lys Ser Cys Lys Ala Leu Leu Lys Arg Asn Gln Ser
            340                 345                 350

Ile Cys Ile Val Val Gly Gly Ala Gln Glu Ser Leu Leu Ala Arg Pro
        355                 360                 365

Gly Val Met Asp Leu Val Leu Leu Lys Arg Lys Gly Phe Val Arg Leu
    370                 375                 380

Gly Met Glu Val Gly Asn Val Ala Leu Val Pro Ile Met Ala Phe Gly
385                 390                 395                 400

Glu Asn Asp Leu Tyr Asp Gln Val Ser Asn Asp Lys Ser Ser Lys Leu
                405                 410                 415

Tyr Arg Phe Gln Gln Phe Val Lys Asn Phe Leu Gly Phe Thr Leu Pro
            420                 425                 430

Leu Met His Ala Arg Gly Val Phe Asn Tyr Asp Val Gly Leu Val Pro
        435                 440                 445
```

-continued

```
Tyr Arg Arg Pro Val Asn Ile Val Val Gly Ser Pro Ile Asp Leu Pro
    450                 455                 460

Tyr Leu Pro His Pro Thr Asp Glu Glu Val Ser Glu Tyr His Asp Arg
465                 470                 475                 480

Tyr Ile Ala Glu Leu Gln Arg Ile Tyr Asn Glu His Lys Asp Glu Tyr
                485                 490                 495

Phe Ile Asp Trp Thr Glu Glu Gly Lys Gly Ala Pro Glu Phe Arg Met
            500                 505                 510

Ile Glu
```

HIGH LEVEL PRODUCTION OF LONG-CHAIN DICARBOXYLIC ACIDS WITH MICROBES

This application is the National Stage application of International Application No. PCT/US2016/043133 (filed Jul. 20, 2016), which claims the benefit of U.S. Provisional Application Nos. 62/195,340 (filed Jul. 22, 2015) and 62/195,338 (filed Jul. 22, 2015), which prior applications are incorporated herein by reference in their entirety.

FIELD OF INVENTION

The present disclosure is in the field of molecular biology. For example, the disclosure pertains to microbes, such as yeast, genetically engineered to produce long-chain dicarboxylic acids (LCDA) from fatty acid-comprising substrates.

REFERENCE TO SEQUENCE LISTING SUBMITTED ELECTRONICALLY

The official copy of the sequence listing is submitted electronically via EFS-Web as an ASCII formatted sequence listing with a file named CL6467WOPCT_Sequence Listing_ST25 created on Jul. 18, 2016, and having a size of 480 kilobytes and is filed concurrently with the specification. The sequence listing contained in this ASCII-formatted document is part of the specification and is herein incorporated by reference in its entirety.

BACKGROUND

Dicarboxylic acids comprising ten or more carbon atoms can be referred to as long-chain dicarboxylic acids (LCDAs). LCDAs are useful as constituent monomers for various synthetic materials such as polyamides (nylons), polyurethanes, and polyesters. Other uses of LCDAs include, for example, production of certain polycarbonates, powder coatings, fragrances, personal care items, food additives, solvents, cleaning additives, hot-melt adhesives, lubricants, insecticides and fungicides. LCDAs can also be used as plasticizers for engineering plastics and as corrosion inhibitors in metal processing technology, for example.

Quantities of LCDAs suitable for carrying out commercial applications such as described above are generally not found in nature. Certain LCDAs, such as dodecanedioic acid (DDDA), can be prepared via various synthetic processes. However, biological processes such as microbial fermentation could also be useful for producing LCDAs. Feedstocks containing oil or free fatty acids, for example, may be suitable as substrates for fermenting LCDA products. Efforts to ferment LCDAs with yeast biocatalysts have been undertaken (U.S. Pat. Appl. Publ. Nos. 2004/0146999, 2010/0041115, 2013/0267012, 2014/0228586).

Fatty acids can be activated in yeast for use in beta-oxidation and other downstream pathways, thereby drawing fatty acids away from pathways of omega-oxidation. Thus, some yeast biocatalysts have been modified to exhibit reduced fatty acid activation, such as by down-regulating expression of long-chain fatty acyl-CoA synthetase, to augment fermentation of LCDA products via omega-oxidation (e.g., see U.S. Pat. Appl. Publ. Nos. 2014/0228586 and 2013/0267012).

The above disclosures notwithstanding, it has now surprisingly been found that increasing fatty acid activation in yeast by up-regulating long-chain fatty acyl-CoA synthetase allows for high LCDA production. Thus, microbial biocatalysts engineered for high levels of LCDA production are disclosed herein.

SUMMARY OF INVENTION

In one embodiment, the disclosure concerns a recombinant microbial cell comprising an engineered LCDA production pathway that comprises up-regulation of a polynucleotide sequence encoding a long-chain acyl-CoA synthetase (ACoS enzyme), wherein the microbial cell is capable of producing one or more long-chain dicarboxylic acid (LCDA) products from a long-chain fatty acid-comprising substrate.

Another embodiment concerns a recombinant microbial cell, comprising:

(i) up-regulation of a polynucleotide sequence encoding a cytochrome P450 monooxygenase (CYP enzyme) and/or up-regulation of a polynucleotide sequence encoding a cytochrome P450 reductase (CPR enzyme), (ii) up-regulation of a polynucleotide sequence encoding a long-chain acyl-CoA synthetase (ACoS enzyme), and (iii) down-regulation of an endogenous polynucleotide sequence encoding a peroxisome biogenesis factor-3, wherein the microbial cell is capable of producing one or more long-chain dicarboxylic acid (LCDA) products from a long-chain fatty acid-comprising substrate.

Another embodiment concerns a method of producing a long-chain dicarboxylic acid (LCDA). This method comprises: a) contacting a recombinant microbial cell as disclosed herein with a long-chain fatty acid-comprising substrate, wherein the microbial cell synthesizes an LCDA from the substrate; and b) optionally recovering the LCDA of step (a).

BRIEF DESCRIPTION OF THE DRAWINGS AND SEQUENCES

FIG. 1: Lipid metabolic pathways, including fatty acid beta-oxidation and omega-oxidation aspects of lipid metabolism, are depicted. Dashed lines/arrows indicate low or weak activity in *Y. lipolytica.*

Figure 2:
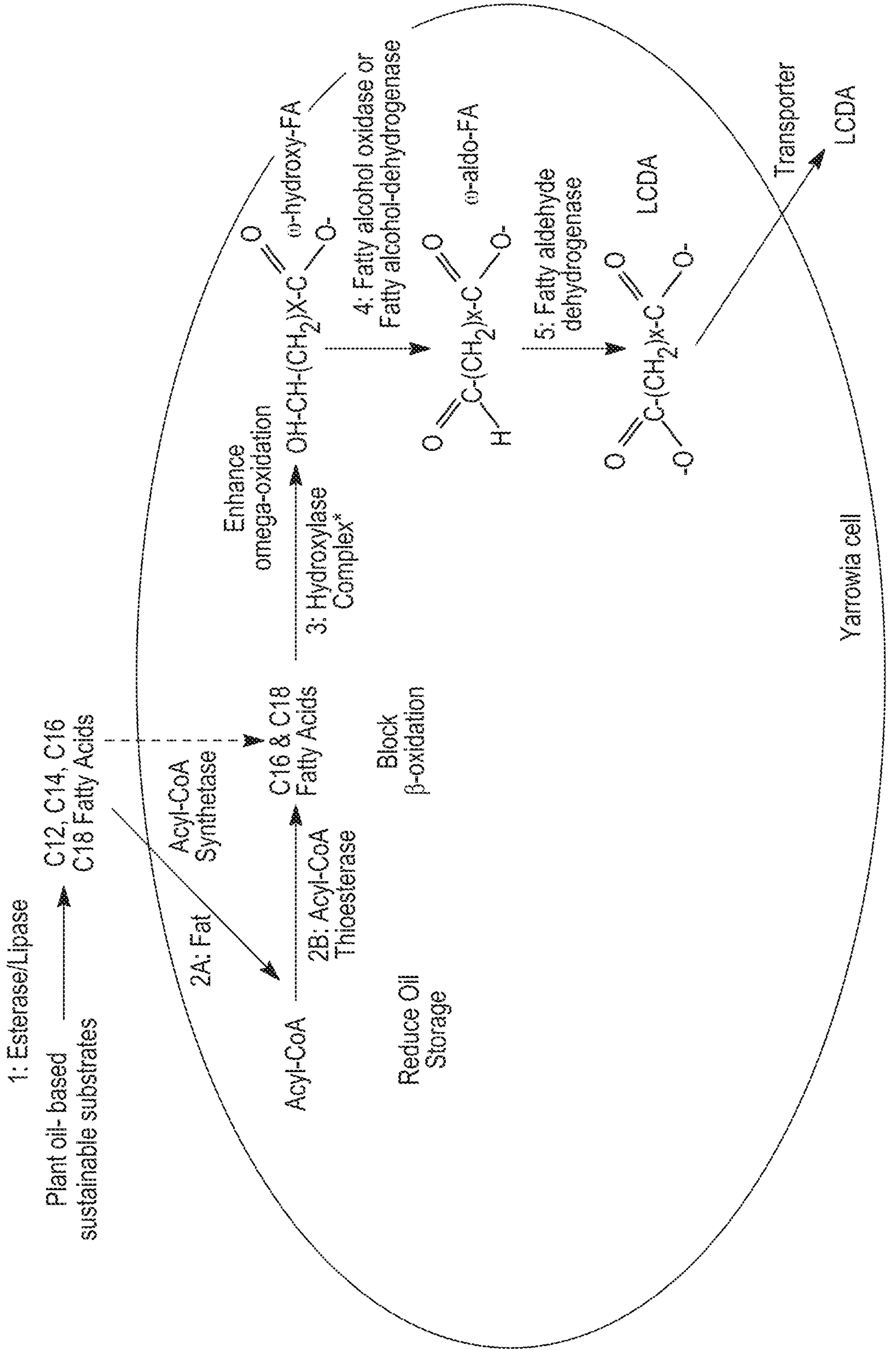

FIG. 2: Strategies are shown for engineering *Y. lipolytica* to produce LCDA from oil, oil-derived fatty acids, and/or fatty acid esters.

Figure 3:
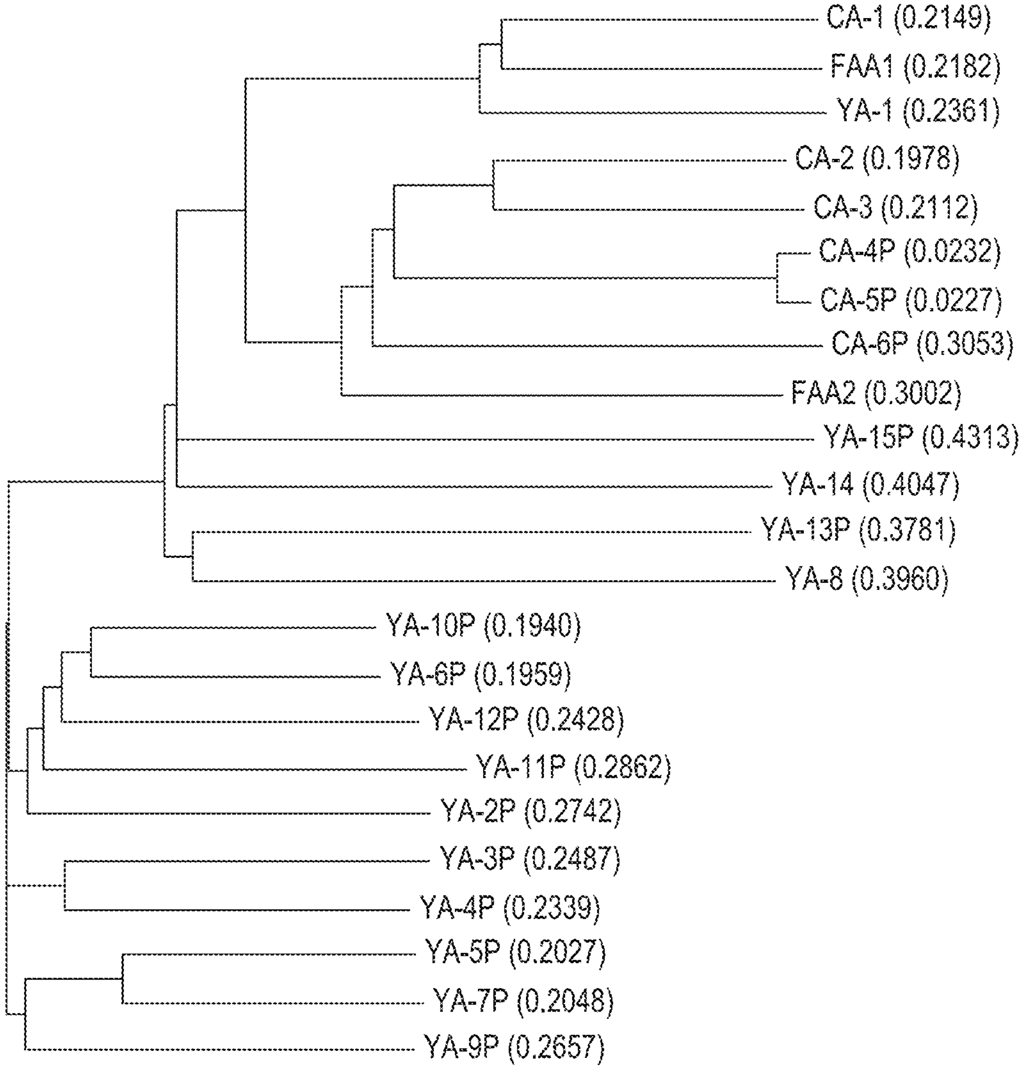

FIG. 3: Phylogenetic tree of candidate acyl-CoA synthetases from *S. cerevisiae, Y. lipolytica* and *C. tropicalis*. Certain abbreviations used in this figure: FAA1 and FAA2 denote *S. cerevisiae* Faa1p and Faa2p, respectively. YA-1 denotes YlFaa1p. "YA-" denotes "YlACoS-". Refer to Example 1.

Figure 4:
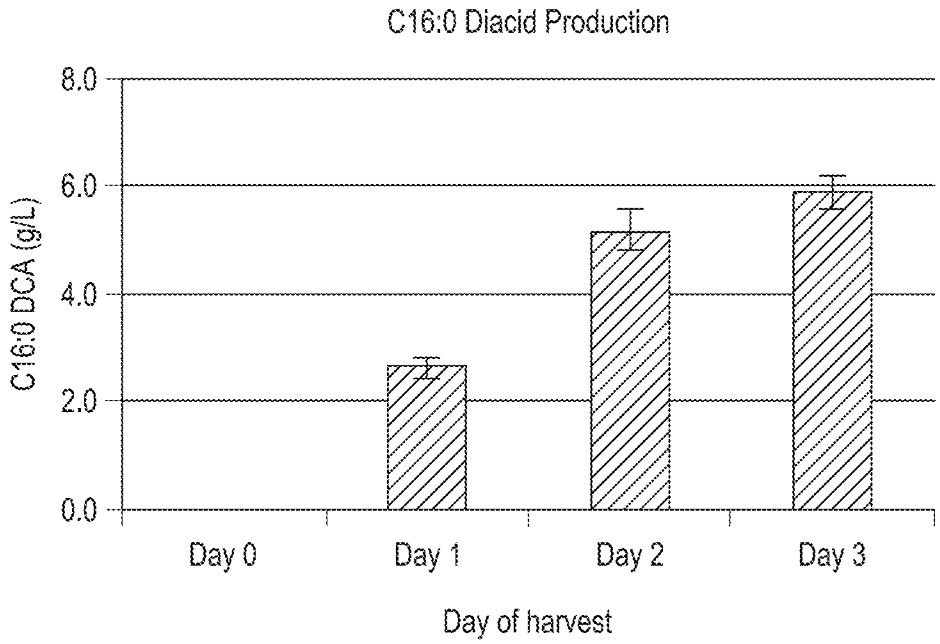

FIG. 4: LCDA production by strain D0145 in flask assay. DCA, dicarboxylic acid. Refer to Example 2.

Figure 5A:
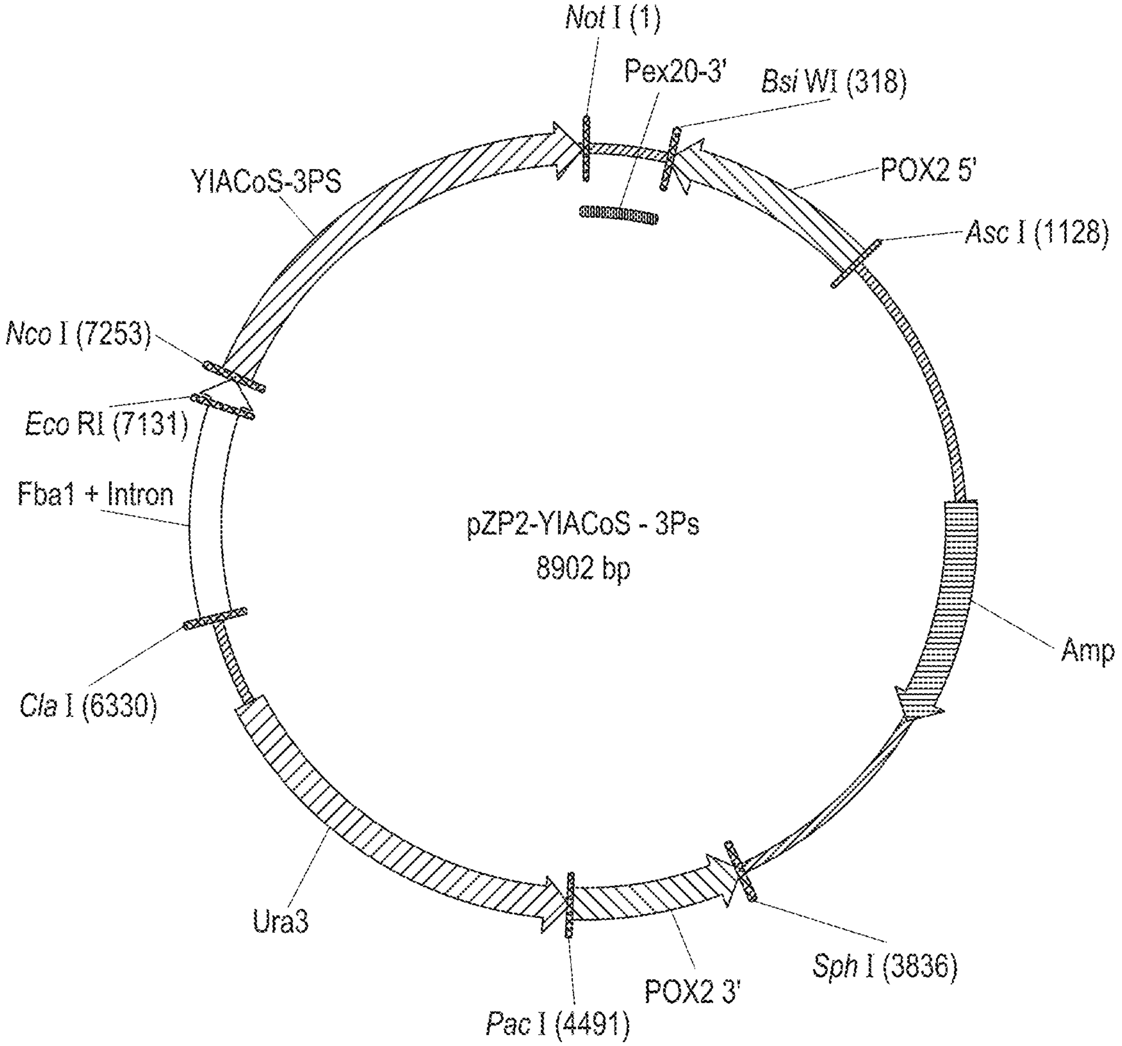

FIG. 5A: Plasmid construct pZP2-YlACoS-3Ps (SEQ ID NO:63).

Figure 5B:
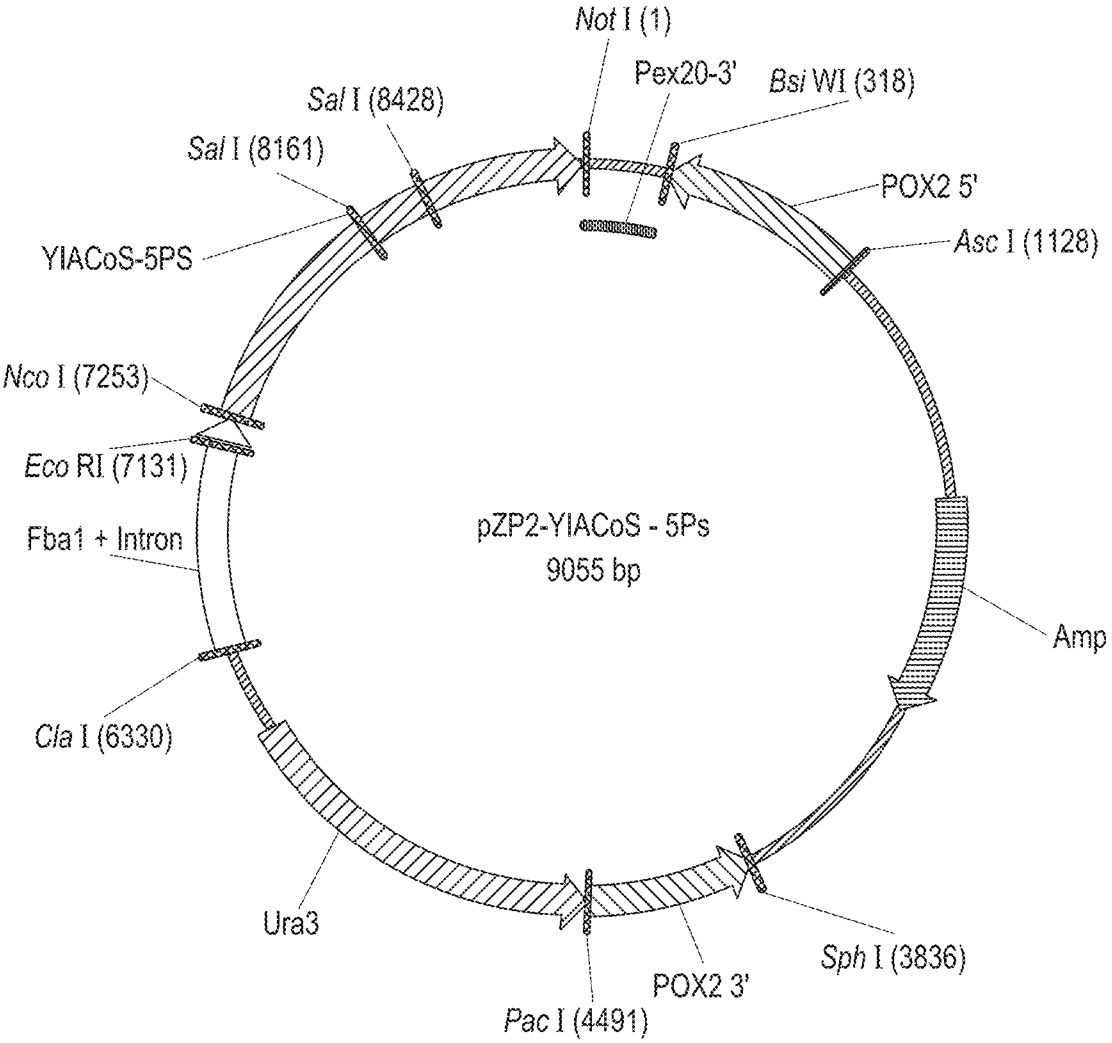

FIG. 5B: Plasmid construct pZP2-YlACoS-5Ps (SEQ ID NO:64).

Figure 5C:
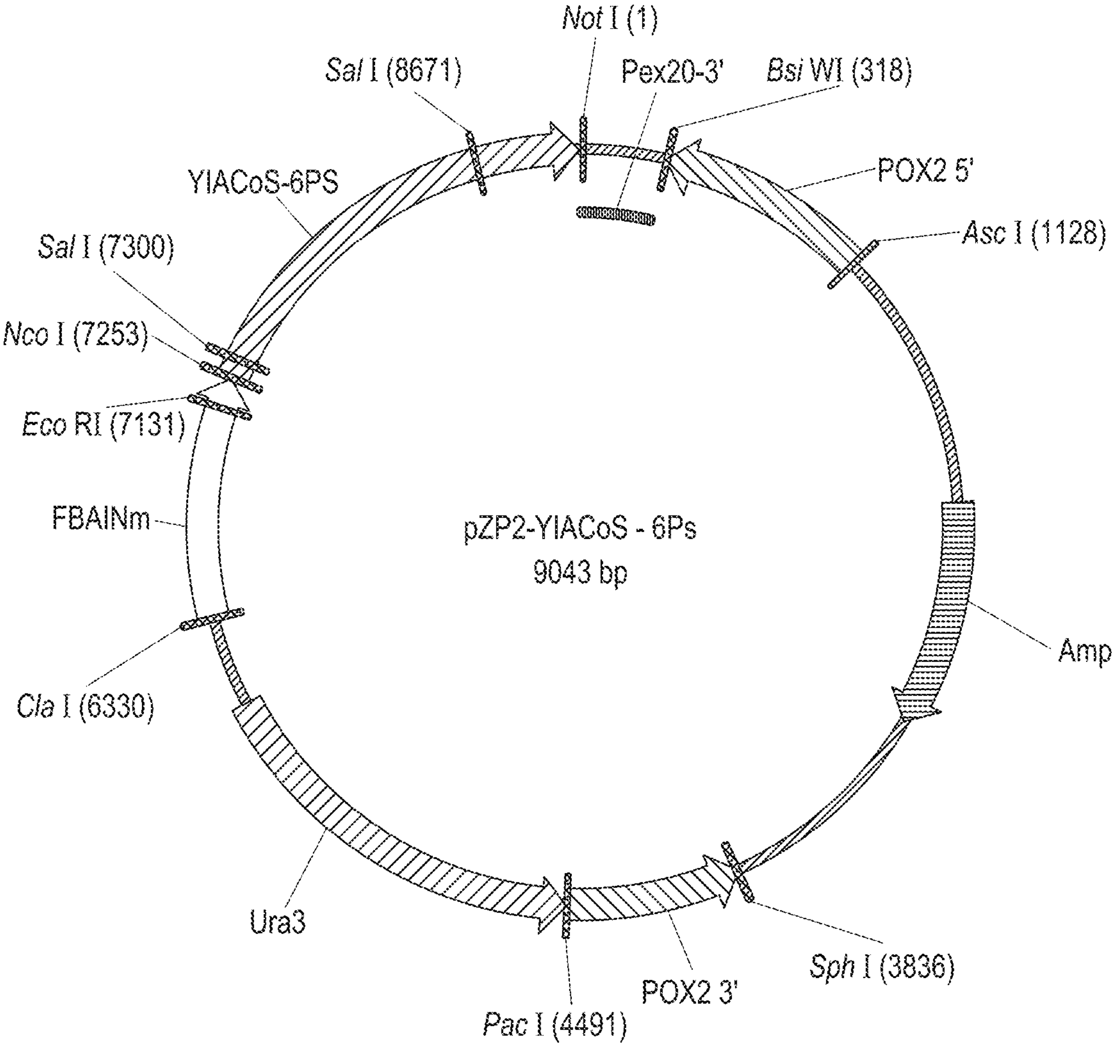

FIG. 5C: Plasmid construct pZP2-YlACoS-6Ps (SEQ ID N0:65).

Figure 5D:
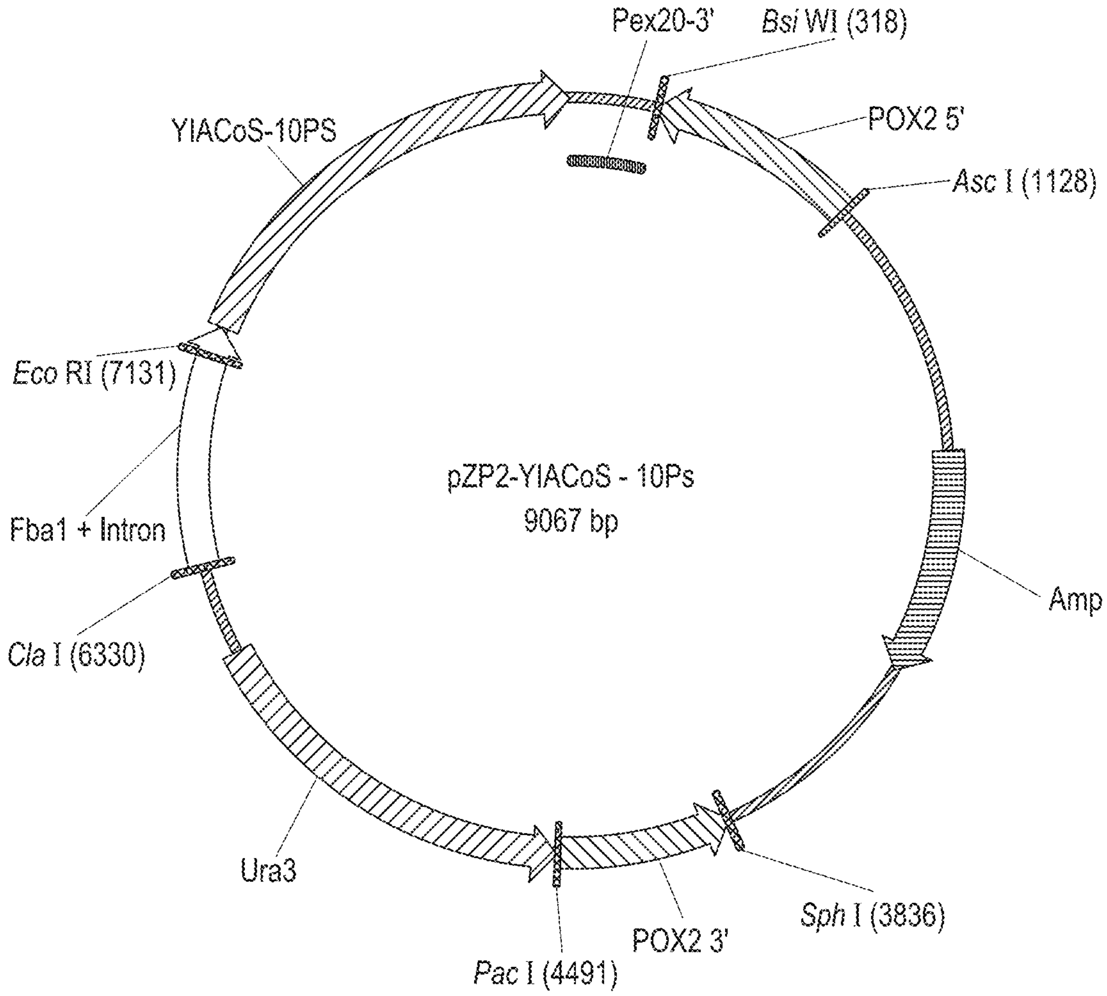

FIG. 5D: Plasmid construct pZP2-YlACoS-10Ps (SEQ ID NO:66).

Figure 5E:
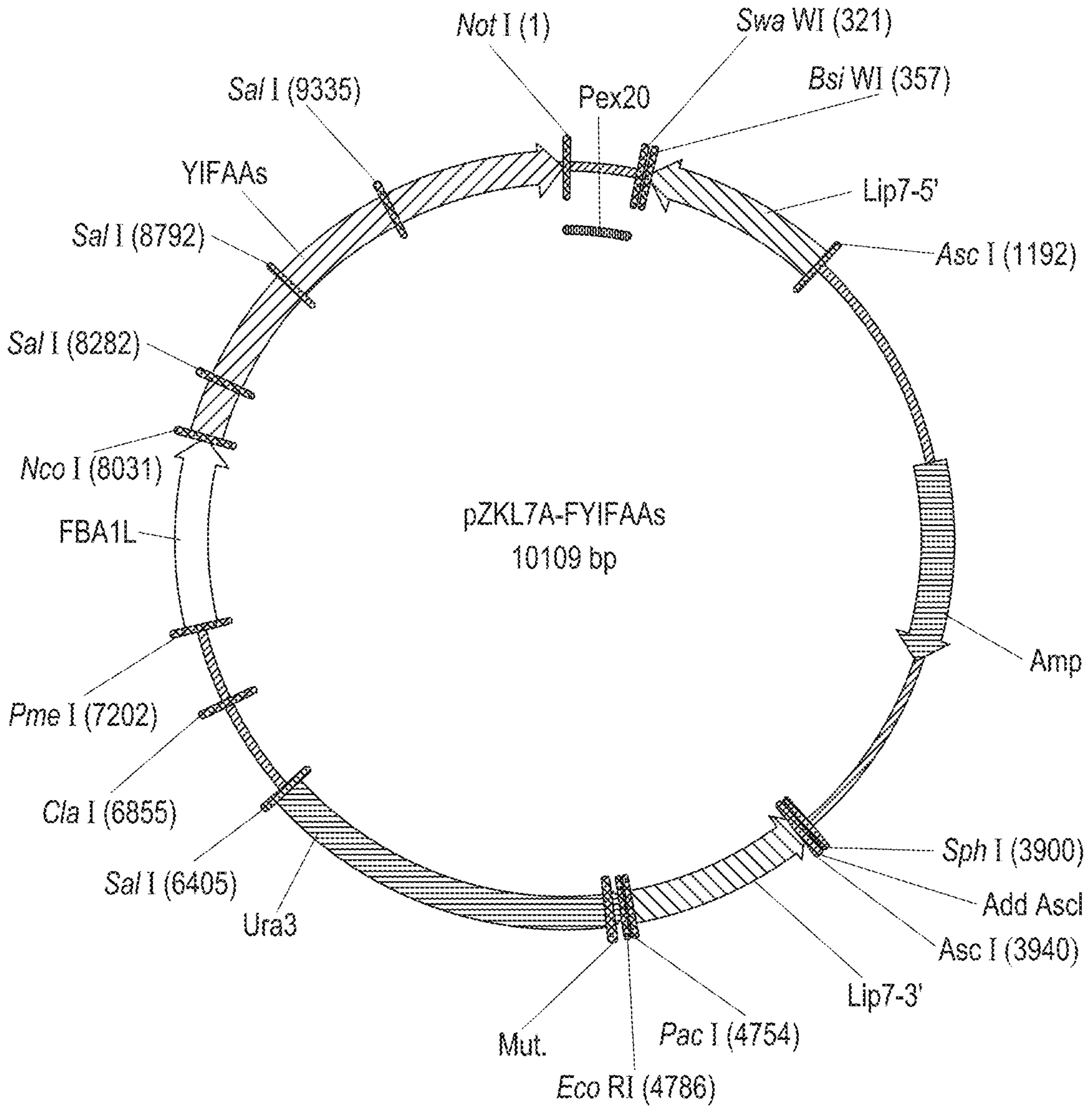

FIG. 5E: Plasmid construct pZKL7A-FYlFAAs (SEQ ID NO:67).

Figure 5F:
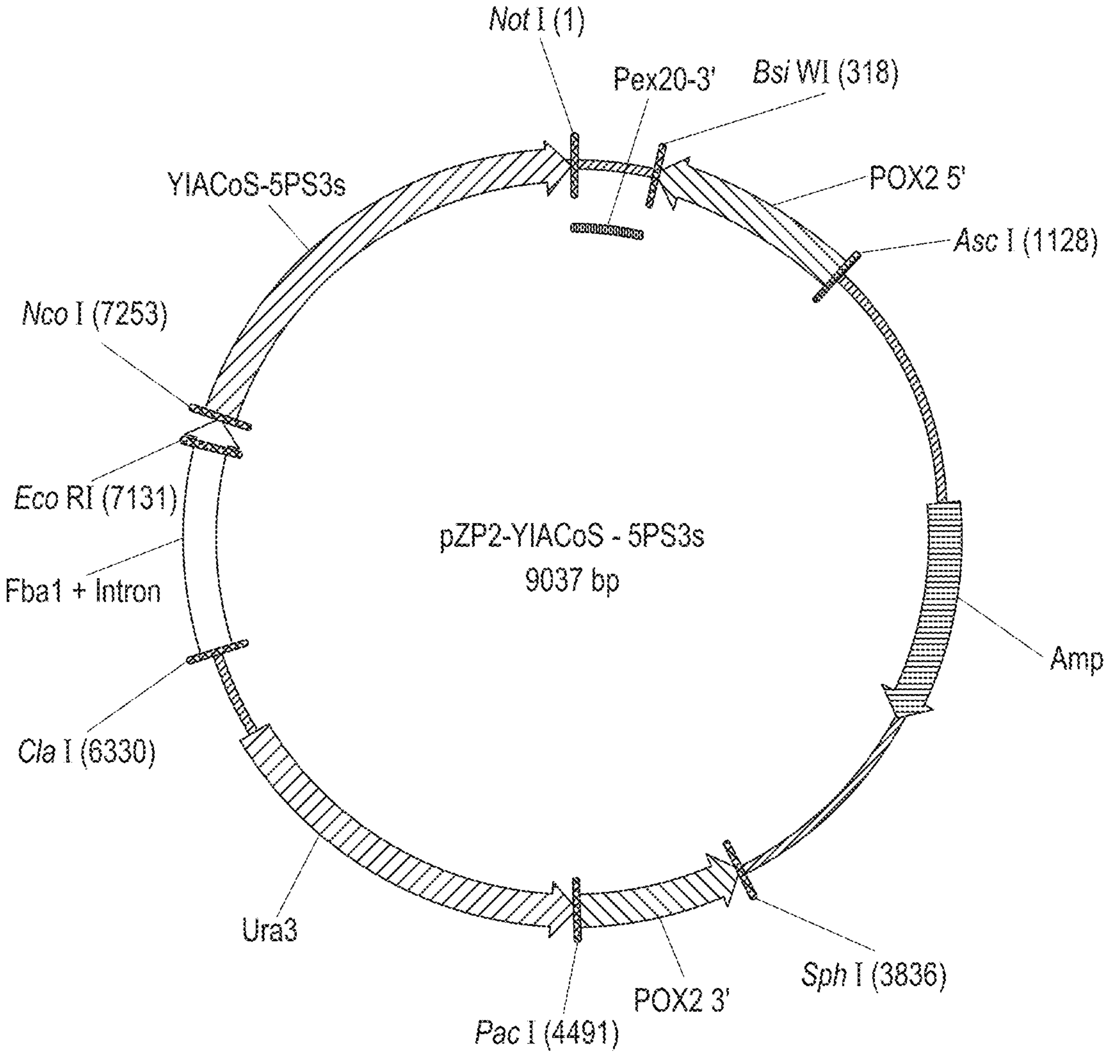

FIG. 5F: Plasmid construct pZP2-YlACoS-5PS3s (SEQ ID NO:68).

Figure 6A:
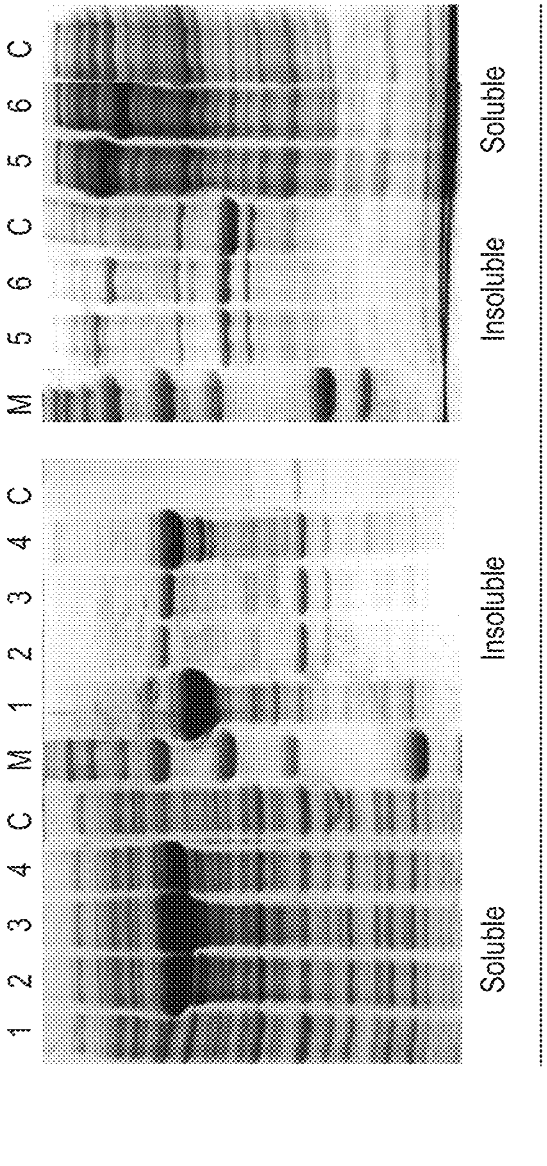

FIG. 6A: SDS-PAGE analysis of soluble and insoluble fractions of *E. coli* cells transformed to over-express putative fatty acyl CoA synthetases. Lanes 1, 2, 3, 4, 5, 6: samples from *E. coli* cells over-expressing YlACoS-3P (SEQ ID NO:39), YlACoS-5P (SEQ ID NO:42), YlACoS-6P (SEQ ID NO:44), YlACoS-10P (SEQ ID NO:49), YlFAA (SEQ ID NO:36), or YlACoS-5PS3 (SEQ ID NO:56), respectively. Lane C: sample from *E. coli* cells transformed with the pET23d vector alone (negative control). Lane M: protein markers. Refer to Example 5.

Figure 6B:
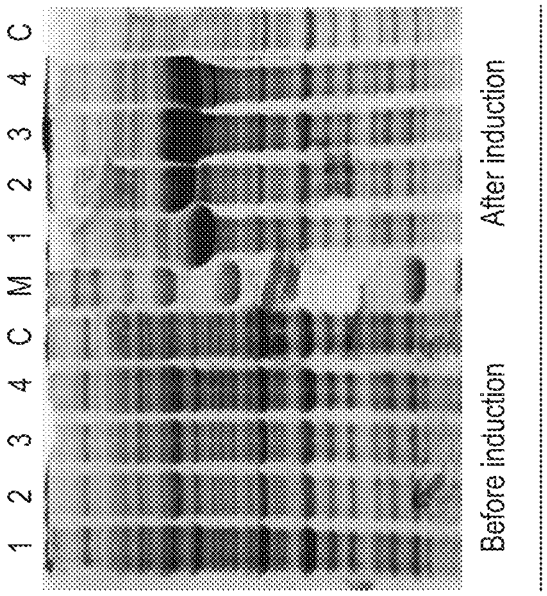

FIG. 6B: SDS-PAGE of lysates of *E. coli* cells before and after IPTG-induced over-expression of putative fatty acyl CoA synthetases. Lanes 1, 2, 3, 4: samples from *E. coli* cells over-expressing YlACoS-3P (SEQ ID NO:39), YlACoS-5P (SEQ ID NO:42), YlACoS-6P (SEQ ID NO:44), or YlACoS-10P (SEQ ID NO:49), respectively. Lane C: sample from *E. coli* cells transformed with the pET23d vector alone (negative control). Lane M: protein markers. Refer to Example 5.

Figure 7A:
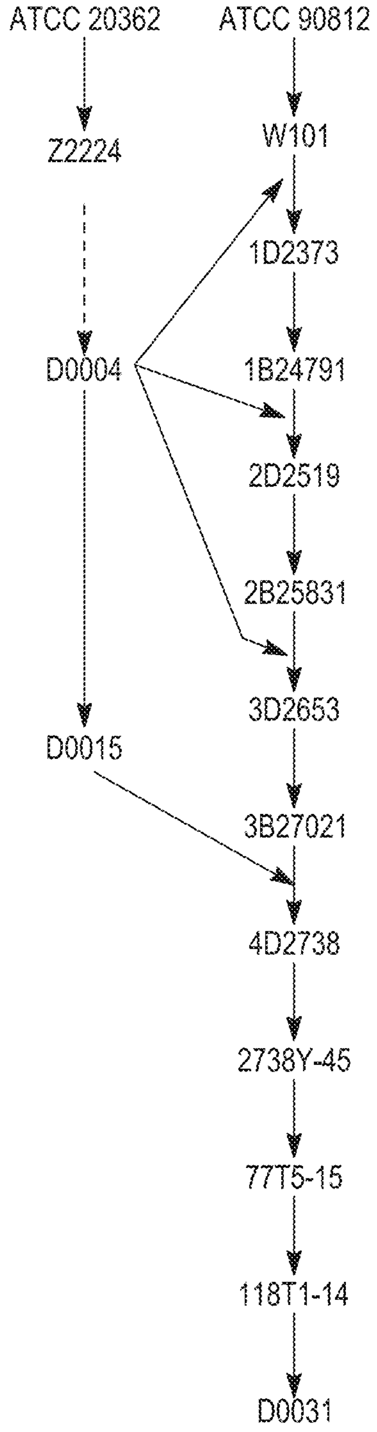

FIG. 7A: A diagram is shown depicting the lineage of certain strains listed in Table 7. Refer to Example 6.

Figure 7B:
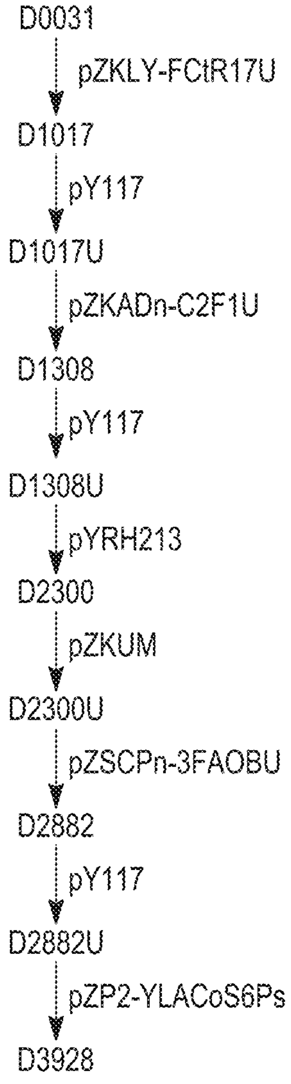

FIG. 7B: A diagram is shown depicting the lineage of certain strains disclosed herein.

Figure 8A:
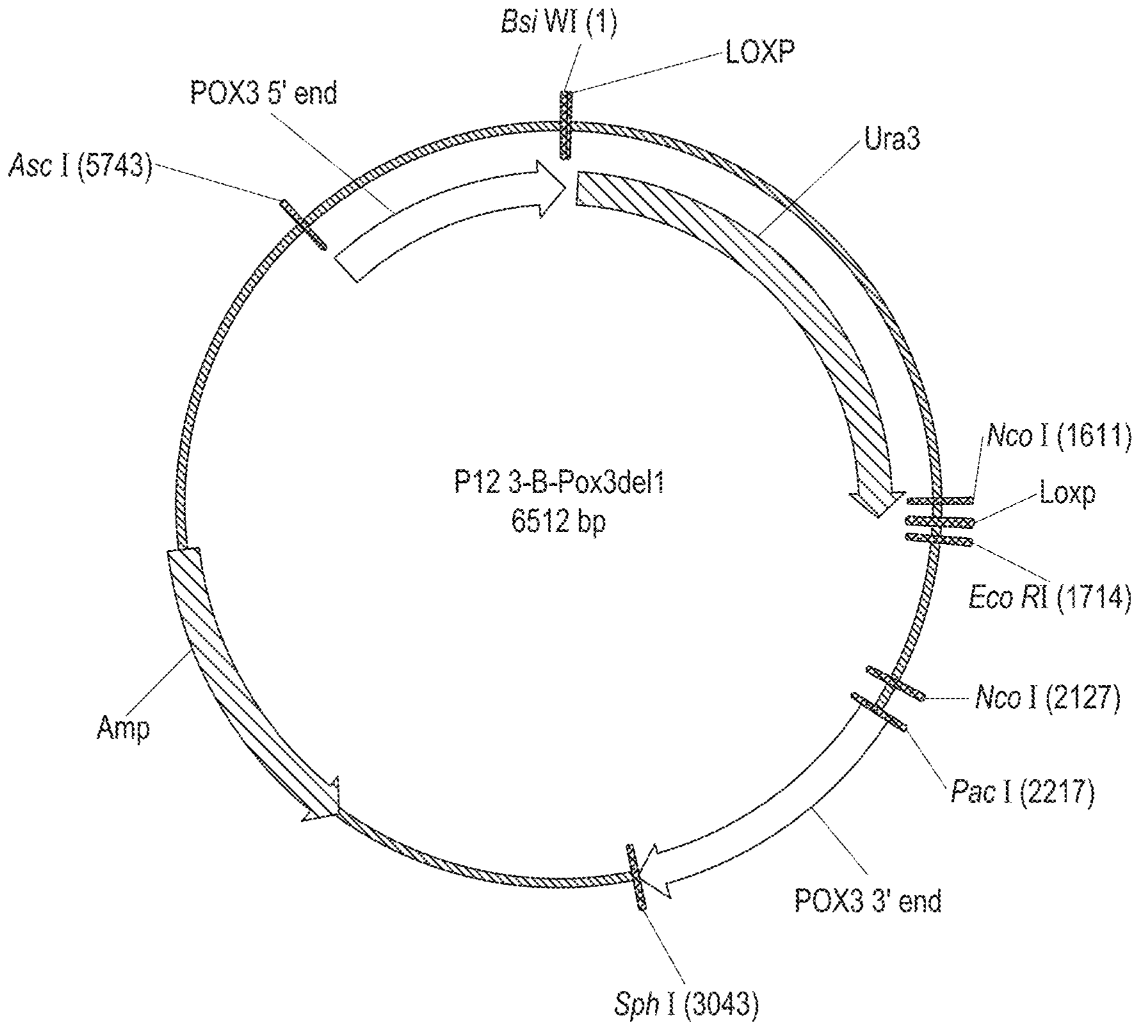

FIG. 8A: Plasmid construct p12_3-B-Pex3del1 (SEQ ID NO:76).

Figure 8B:
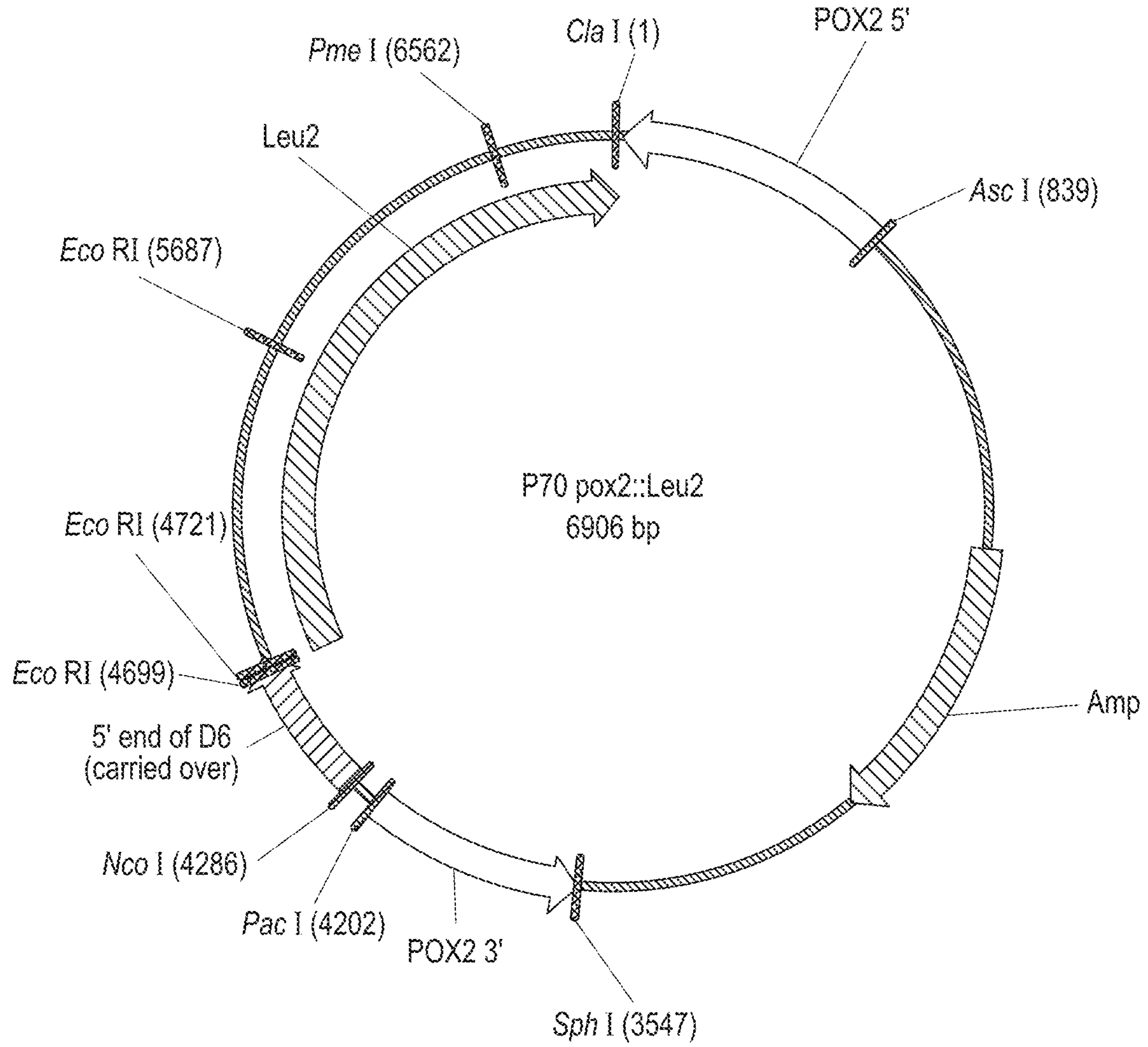

FIG. 8B: Plasmid construct p70_Pox2::Leu2 (SEQ ID NO:77).

Figure 9A:
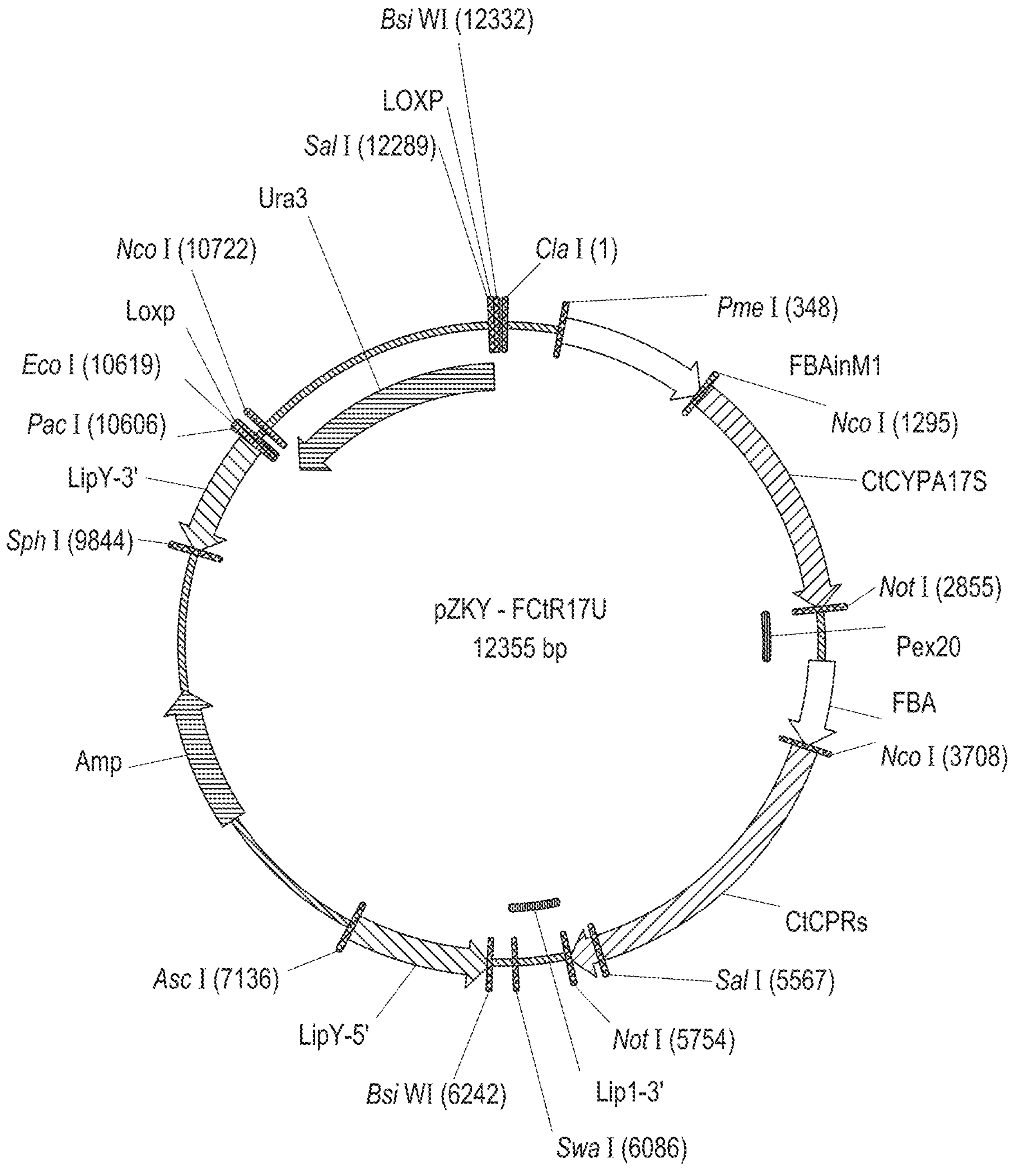

FIG. 9A: Plasmid construct pZKLY-FCtR17U (SEQ ID NO:82).

Figure 9B:
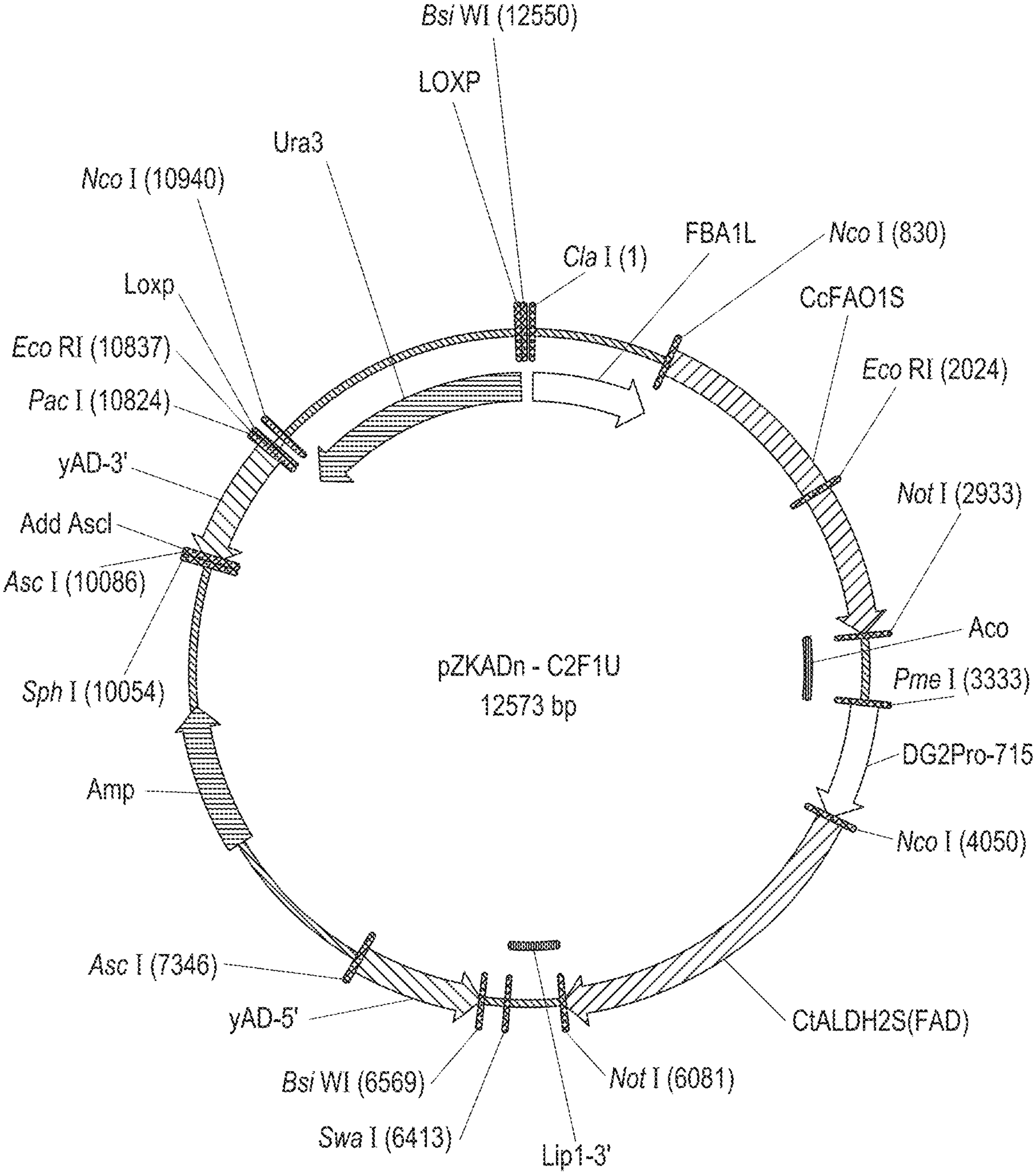

FIG. 9B: Plasmid construct pZKADn-C2F1U (SEQ ID NO:87).

Figure 10:
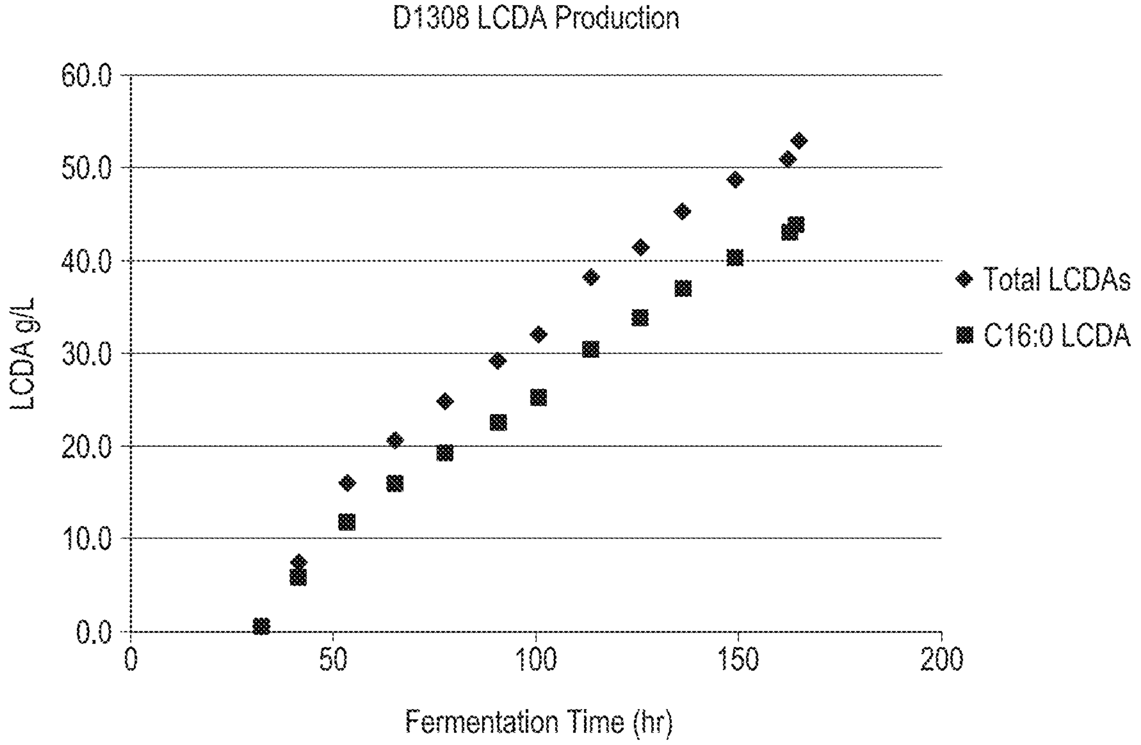

FIG. 10: Time course of LCDA production by *Yarrowia* strain D1308 in a 2-L fermentation experiment. Ethyl palmitate was used as substrate for LCDA production. Diamonds indicate total LCDA amount, and squares indicate amount of C16:0 LCDA, measured during the time course. Refer to Example 8.

Figure 11A:
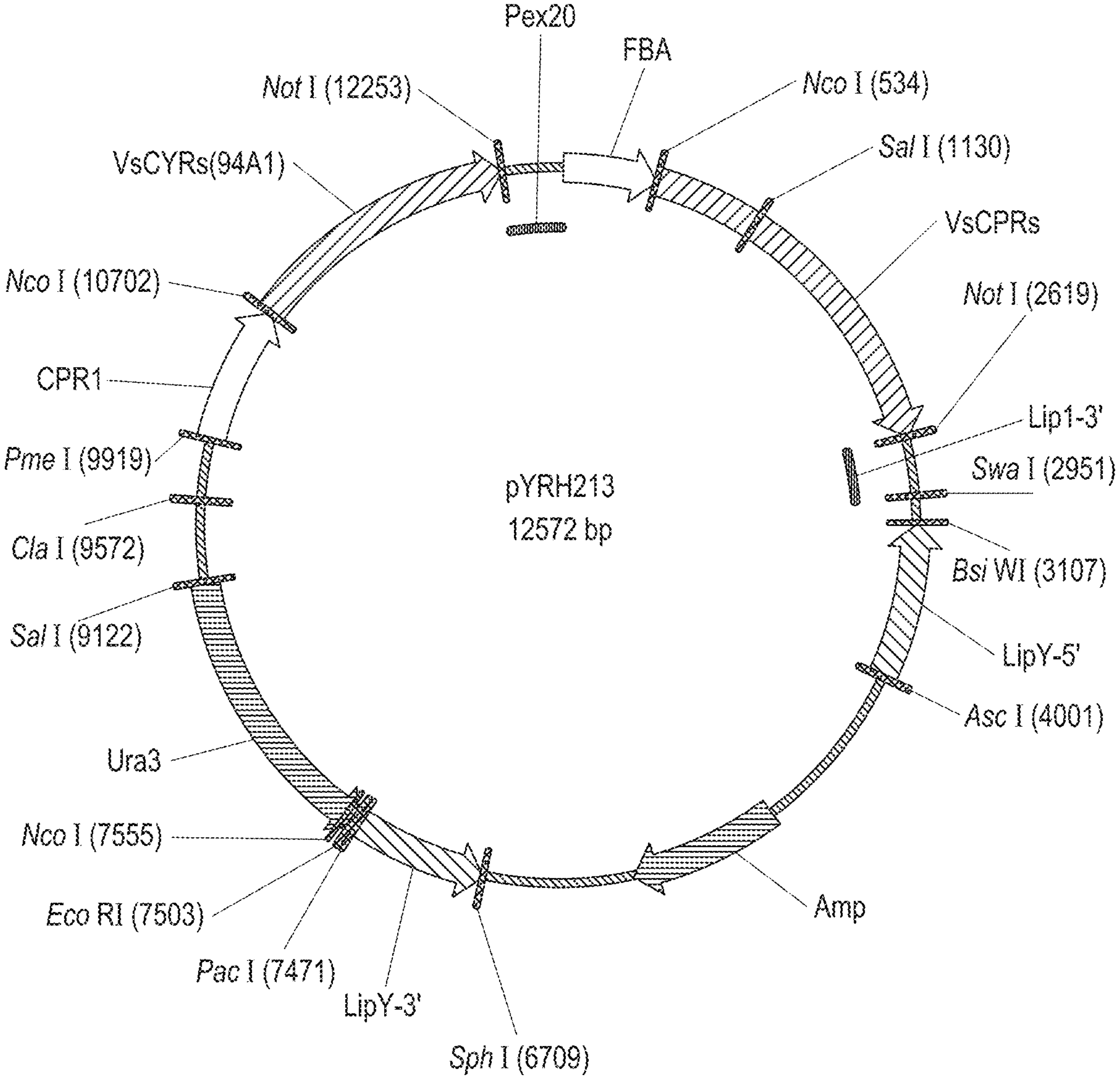

FIG. 11A: Plasmid construct pYRH213 (SEQ ID NO:92).

Figure 11B:
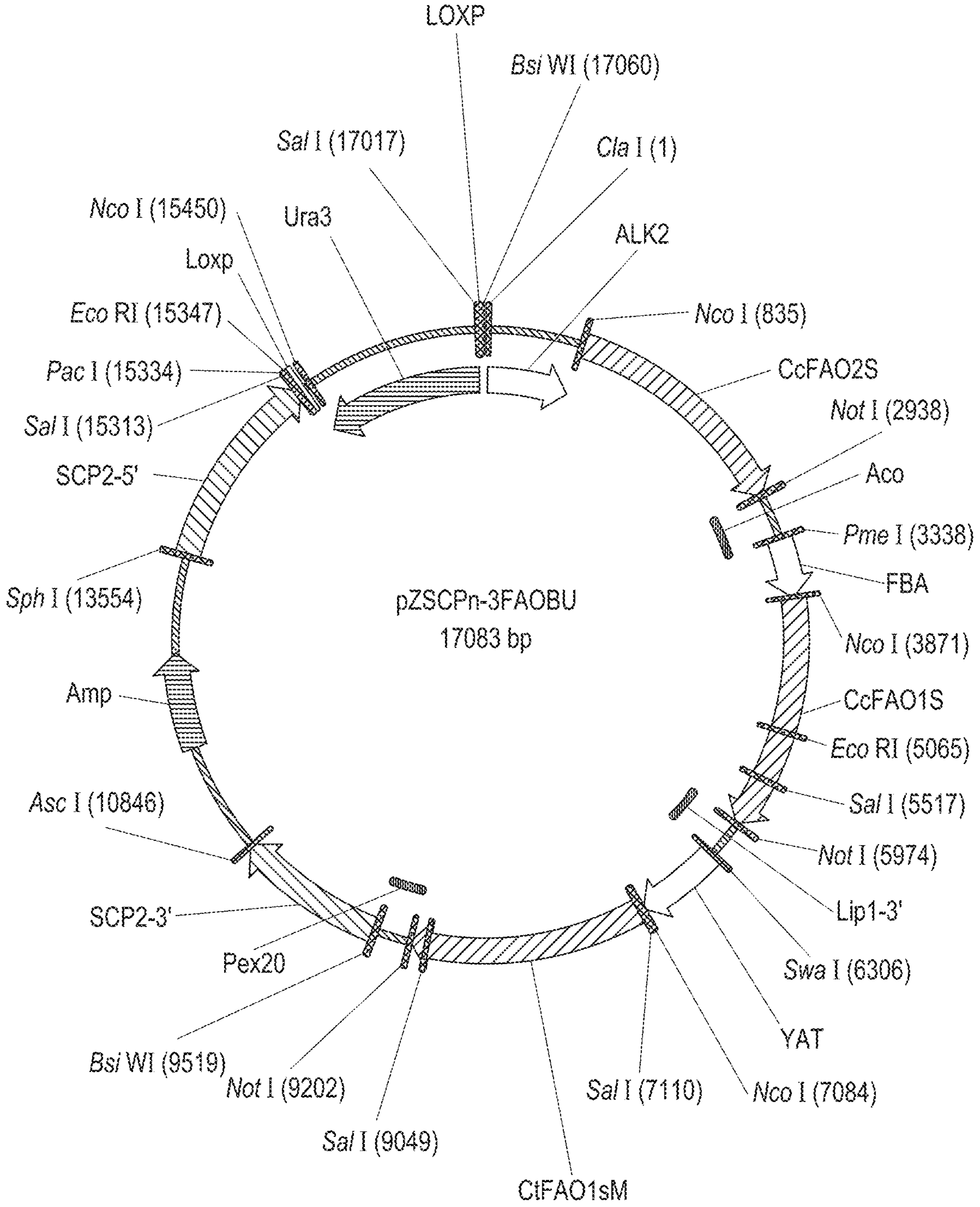

FIG. 11B: Plasmid construct pZSCPn-3FAOBU (SEQ ID NO:98).

Figure 12:
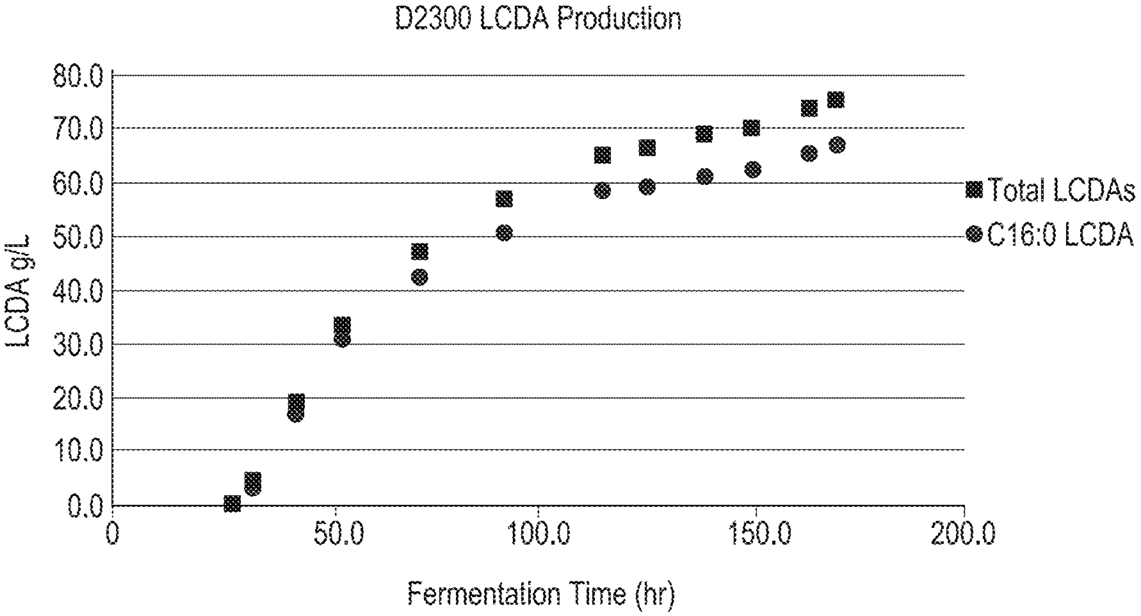

FIG. 12: Time course of LCDA production by *Yarrowia* strain D2300 in a 2-L fermentation experiment. Ethyl palmitate was used as substrate for LCDA production. Squares indicate total LCDA amount, and circles indicate amount of C16:0 LCDA, measured during the time course. Refer to Example 9.

Figure 13:
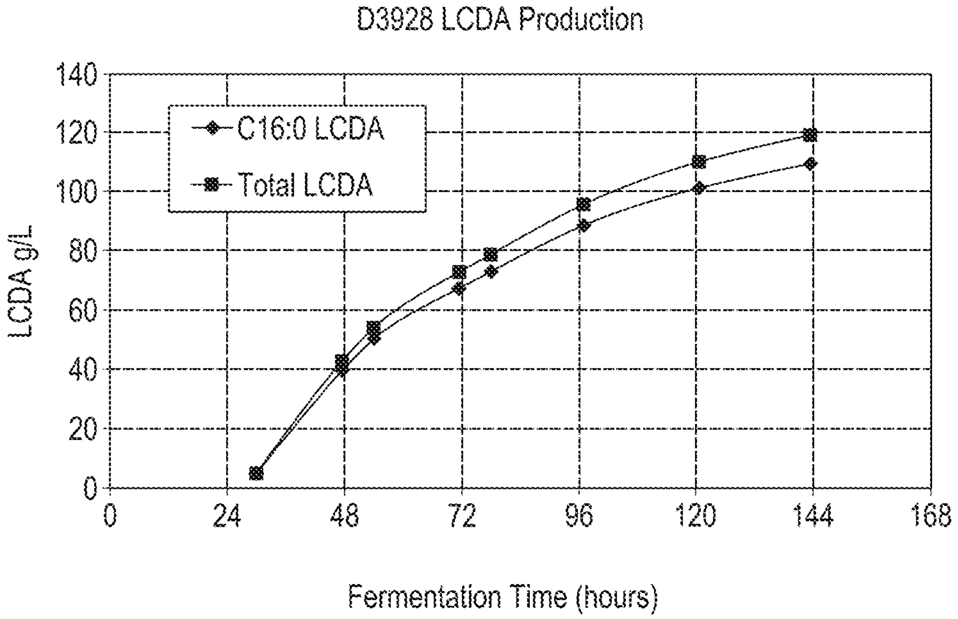

FIG. 13. Time course of LCDA production by *Yarrowia* strain D3928 in a 5-L fed-batch fermentation experiment. Ethyl palmitate was used as substrate for LCDA production. Squares indicate total LCDA amount, and diamonds indicate amount of C16:0 LCDA, measured during the time course. Refer to Example 12.

TABLE 1

Summary of Nucleic Acid and Protein SEQ ID Numbers

| Description | Nucleic acid SEQ ID NO. | Protein SEQ ID NO. |
|---|---|---|
| Primer 17864-900F (see Table 4) | 1 | |
| Primer 17864-967R (see Table 4) | 2 | |
| Primer 5885-1034F (see Table 4) | 3 | |
| Primer 5885-1097R (see Table 4) | 4 | |
| Primer 14234-1341F (see Table 4) | 5 | |
| Primer 14234-1404R (see Table 4) | 6 | |
| Primer 11979-1248F (see Table 4) | 7 | |
| Primer 11979-1315R (see Table 4) | 8 | |
| Primer 7755-282F (see Table 4) | 9 | |
| Primer 7755-343R (see Table 4) | 10 | |
| Primer 12419-1677F (see Table 4) | 11 | |
| Primer 12419-1744R (see Table 4) | 12 | |
| Primer 20405-626F (see Table 4) | 13 | |
| Primer 20405-691R (see Table 4) | 14 | |
| Primer 5456-1758F (see Table 4) | 15 | |
| Primer 5456-1825R (see Table 4) | 16 | |
| Primer 15103-516F (see Table 4) | 17 | |
| Primer 15103-588R (see Table 4) | 18 | |
| Primer 5951-327F (see Table 4) | 19 | |
| Primer 5951-399R (see Table 4) | 20 | |
| Primer 17314-47F (see Table 4) | 21 | |
| Primer 17314-112R (see Table 4) | 22 | |
| Primer 6556-1321F (see Table 4) | 23 | |
| Primer 6556-1384R (see Table 4) | 24 | |
| Primer 12859-1002 (see Table 4) | 25 | |
| Primer 12859-1071 (see Table 4) | 26 | |
| Primer 9284-924F (see Table 4) | 27 | |
| Primer 9284-995R (see Table 4) | 28 | |
| Primer 16016-1393F (see Table 4) | 29 | |
| Primer 16016-1422T (see Table 4) | 30 | |
| Primer YL-18S-329F (see Table 4) | 31 | |
| Primer YL-18S-395R (see Table 4) | 32 | |
| ScFaa1, *S. cerevisiae* long-chain fatty acyl-CoA synthetase | | 33 (700 aa) |
| ScFaa2, *S. cerevisiae* long-chain fatty acyl-CoA synthetase | | 34 (744 aa) |
| YlFaa1 (YALI0D17864p), *Y. lipolytica* long-chain fatty acyl-CoA synthetase, DNA sequence is codon-optimized for expression in *Yarrowia* | 35 (2076 bases) | 36 (691 aa) |

TABLE 1-continued

Summary of Nucleic Acid and Protein SEQ ID Numbers

| Description | Nucleic acid SEQ ID NO. | Protein SEQ ID NO. |
|---|---|---|
| YlACoS-2P (YALI0C05885p), *Y. lipolytica* | | 37 (574 aa) |
| YlACoS-3P (YALI0A14234p), *Y. lipolytica*, DNA sequence is codon-optimized for expression in *Yarrowia*, amino acid sequence varies from GENBANK Acc. No. XP_500052.1 | 38 (1647 bases) | 39 (550 aa) |
| YlACoS-4P (YALI0E11979p), *Y. lipolytica* | | 40 (616 aa) |
| YlACoS-5P (YALI0B07755p), *Y. lipolytica*, DNA sequence is codon-optimized for expression in *Yarrowia*, amino acid sequence varies from GENBANK Acc. No. XP_500618.1 | 41 (1800 bases) | 42 (599 aa) |
| YlACoS-6P (YALI0E12419p), *Y. lipolytica* long-chain fatty acyl-CoA synthetase, DNA sequence is codon-optimized for expression in *Yarrowia*, amino acid sequence varies from GENBANK Acc. No. XP_503862.1 | 43 (1788 bases) | 44 (595 aa) |
| YlACoS-7P (YALI0E20405p), *Y. lipolytica* | | 45 (598 aa) |
| YlACoS-8 (YALI0B05456p), *Y. lipolytica* | | 46 (741 aa) |
| YlACoS-9P (YALI0A15103p), *Y. lipolytica* | | 47 (554 aa) |
| YlACoS-10P (YALI0E05951p), *Y. lipolytica* long-chain fatty acyl-CoA synthetase, DNA sequence is codon-optimized for expression in *Yarrowia*, amino acid sequence varies from GENBANK Acc. No. XP_503608.1 | 48 (1812 bases) | 49 (603 aa) |
| YlACoS-11P (YALI0D17314p), *Y. lipolytica* | | 50 (627 aa) |
| YlACoS-12P (YALI0F06556p), *Y. lipolytica* | | 51 (593 aa) |
| YlACoS-13P (YALI0E12859p), *Y. lipolytica* | | 52 (583 aa) |
| YlACoS-14 (YALI0C09284p), *Y. lipolytica* | | 53 (585 aa) |
| YlACoS-15P (YALI0E16016p), *Y. lipolytica* | | 54 (712 aa) |
| YlACoS-5PS3, DNA sequence is codon-optimized for expression in *Yarrowia* | 55 (1782 bases) | 56 (593 aa) |
| CA-1 (CTRG_05829), *C. tropicalis* | | 57 (696 aa) |
| CA-2 (CTRG_02563), *C. tropicalis* | | 58 (718 aa) |
| CA-3 (CTRG_01503), *C. tropicalis* | | 59 (718 aa) |
| CA-4P (CTRG_05500), *C. tropicalis* | | 60 (741 aa) |
| CA-5P (CTRG_04022), *C. tropicalis* | | 61 (741 aa) |
| CA-6P (CTRG_02265), *C. tropicalis* | | 62 (749 aa) |
| pZP2-YlACoS-3Ps plasmid | 63 (8902 bases) | |
| pZP2-YlACoS-5Ps plasmid | 64 (9055 bases) | |
| pZP2-YlACoS-6Ps plasmid | 65 (9043 bases) | |
| pZP2-YlACoS-10Ps plasmid | 66 (9067 bases) | |
| pZKL7A-FYIFAAs plasmid | 67 (10109 bases) | |
| pZP2-YlACoS-5PS3s plasmid | 68 (9037 bases) | |
| pET23d plasmid | 69 (3663 bases) | |
| pY157 plasmid | 70 (6356 bases) | |
| Initial PEX3 knockout site in *Yarrowia*, with 100-bp 5'- and 3'-PEX3 sequences (corresponding to respective portions of homology arms in pY157) flanking a LoxP-flanked URA3 cassette (and certain other pY157-borne sequences) | 71 (1947 bases) | |

TABLE 1-continued

Summary of Nucleic Acid and Protein SEQ ID Numbers

| Description | Nucleic acid SEQ ID NO. | Protein SEQ ID NO. |
|---|---|---|
| PEX3 knockout site in *Yarrowia*, with 100-bp 5'- and 3'-PEX3 sequences (corresponding to respective portions of homology arms in pY157) flanking a LoxP site (and certain other pY157-borne sequences) | 72 (280 bases) | |
| pYRH146-Pox4KO plasmid | 73 (5164 bases) | |
| PDX4 knockout site in *Yarrowia*, with 5'- and 3'-PDX4 sequences (corresponding to respective portions of homology arms in pYRH146-Pox4KO) | 74 (957 bases) | |
| pYRH72 plasmid | 75 (6853 bases) | |
| p12_3-B-Pex3del1 plasmid | 76 (6512 bases) | |
| p70_Pox2::Leu2 plasmid | 77 (6906 bases) | |
| Pox2 enzyme, *Y. lipolytica*, "YlPox2", Gen Bank Acc. No. O74935.1. DNA sequence is ORF from GenBank Acc. No. NC_006072.1 | 78 (2103 bases) | 79 (700 aa) |
| Pox3 enzyme, *Y. lipolytica*, "YlPox3", Gen Bank Acc. No. O74936.1. DNA sequence is ORF from GenBank Acc. No. NC_006070.1 | 80 (2103 bases) | 81 (700 aa) |
| pZKLY-FCtR17U plasmid | 82 (12335 bases) | |
| CtCYP52A17s, cytochrome P450 monooxygenase, derived from *C. tropicalis*, DNA sequence is codon-optimized for expression in *Yarrowia* | 83 (1557 bases) | 84 (518 aa) |
| CtCPRs, cytochrome P450 reductase (CPR), derived from *C. tropicalis*, DNA sequence is codon-optimized for expression in *Yarrowia* | 85 (2043 bases) | 86 (680 aa) |
| pZKADn-C2F1U plasmid | 87 (12573 bases) | |
| CcFAO1s, *Candida cloacae* FAO1 enzyme, DNA sequence is codon-optimized for expression in *Yarrowia* | 88 (2100 bases) | 89 (699 aa) |
| CtFALDH2s, *C. tropicalis* FALDH enzyme, DNA sequence is codon-optimized for expression in *Yarrowia* | 90 (2028 bases) | 91 (675 aa) |
| pYRH213 plasmid | 92 (12572 bases) | |
| VsCYP94A1s, cytochrome P450 monooxygenase, derived from *V. sativa*, DNA sequence is codon-optimized for expression in *Yarrowia* | 93 (1548 bases) | 94 (515 aa) |
| VsCPRs, cytochrome P450 reductase, derived from *V. sativa*, DNA sequence is codon-optimized for expression in *Yarrowia* | 95 (2082 bases) | 96 (693 aa) |
| CPR1 promoter region, *Y. lipolytica* | 97 (783 bases) | |
| pZSCPn-3FAOBU plasmid | 98 (17083 bases) | |
| CtFAO1Ms, mutant form of *C. tropicalis* FAO1 enzyme (comprising Y359H substitution), DNA sequence is codon-optimized for expression in *Yarrowia* | 99 (2115 bases) | 100 (704 aa) |
| CcFAO1s, *C. cloacae* FAO1 enzyme, DNA sequence is codon-optimized for expression in Yarrowia | 101 (2100 bases) | 102 (699 aa) |
| CcFAO2s, *C. cloacae* FAO2 enzyme, DNA sequence is codon-optimized for expression in *Yarrowia* | 103 (2100 bases) | 104 (699 aa) |
| pZKLY-VsCPR&CYP plasmid | 105 (12358 bases) | |
| Pex3 protein, *Y. lipolytica*, "YlPex3p", GenBank Acc. No. CAG78565. DNA sequence is ORF from GenBank Acc. No. NC_006072 | 106 (1296 bases) | 107 (431 aa) |
| Pex10 protein, *Y. lipolytica*, "YlPex10p", GenBank Acc. No. BAA99413 | | 108 (377 aa) |
| Pex16 protein, *Y. lipolytica*, "YlPex16p", GenBank Acc. No. AAB41724 | | 109 (391 aa) |
| Pox4 enzyme, *Y. lipolytica*, "YlPox4", GenBank Acc. No. CAG80078. DNA sequence is ORF from GenBank Acc. No. NC_006071 | 110 (2106 bases) | 111 (701 aa) |

TABLE 1-continued

| Summary of Nucleic Acid and Protein SEQ ID Numbers | | |
|---|---|---|
| Description | Nucleic acid SEQ ID NO. | Protein SEQ ID NO. |
| DGAT1, *Y. lipolytica*, "YlDGAT1", GenBank Acc. No. CAG80745. DNA sequence is ORF from GenBank Acc. No. NC_006070 | 112 (1581 bases) | 113 (526 aa) |
| DGAT2, *Yarrowia lipolytica*, "YlDGAT2", GenBank Acc. No. XP 504700 | 114 (1545 bases) | 115 (514 aa) |

DETAILED DESCRIPTION

The disclosures of all patent and non-patent literature cited herein are incorporated herein by reference in their entirety.

Unless otherwise disclosed, the terms "a" and "an" as used herein are intended to encompass one or more (i.e., at least one) of a referenced feature.

Where present, all ranges are inclusive and combinable, except as otherwise noted. For example, when a range of "1 to 5" is recited, the recited range should be construed as including ranges "1 to 4", "1 to 3", "1-2", "1-2 & 4-5", "1-3 & 5", and the like. The terms "long-chain acyl-CoA synthetase", "long-chain fatty acyl-CoA synthetase", "long-chain fatty acid CoA ligase" and the like are used interchangeably herein, and can be abbreviated as "ACoS". An ACoS enzyme herein, which has the EC entry 6.2.1.3, can catalyze the activation of a long fatty acid chain to a fatty acyl-CoA using energy provided by ATP. In particular, a reaction catalyzed by an ACoS enzyme is as follows ("ACoS activity"): ATP+long-chain carboxylate+CoA (coenzyme A)→AMP+diphosphate (PR)+acyl-CoA. In general, ACoS enzymes are peroxisomal proteins in eukaryotic cells. Up-regulation of a polynucleotide sequence encoding an ACoS enzyme herein leads to expression of an elevated amount of ACoS enzyme, which in turn is available for activating an elevated amount to long-chain fatty acids to long-chain acyl-CoA's. An ACoS enzyme herein is not a "fatty-acyl-CoA synthase" enzyme, which has EC entry 2.3.1.86.

The terms "cytochrome P450 monooxygenase", "CYP enzyme" and the like are used interchangeably herein. A CYP enzyme herein can catalyze the transfer of an atom of diatomic oxygen ($O_2$) onto an organic substrate (typically yielding an alcohol group), while the other oxygen atom is reduced to water. CYP enzymes have the Enzyme Commission (EC) entry 1.14.14.1. A CYP enzyme can be comprised within an omega-hydroxylase complex (below). A CYP enzyme herein is generally classified as a class II P450 enzyme, which utilizes a CPR enzyme for electron transfer. In general, a CYP enzyme is membrane-bound. CYP enzymes are generally described in Urlacher and Girhard (*Cell* 30:26-36) and van Bogaert et al. (*FEBS Journal* 278:206-221), which are incorporated herein by reference. Up-regulation of a polynucleotide sequence encoding a CYP enzyme herein leads to expression of an elevated amount of CYP enzyme, which in turn is available for forming an elevated amount of an omega-hydroxylase complex.

The terms "cytochrome P450 reductase", "NADPH-cytochrome P450 reductase" "CPR enzyme", "NADPH-ferrihemoprotein reductase" and the like are used interchangeably herein. A CPR enzyme, via FAD (flavin adenine dinucleotide) and FMN (flavin mononucleotide) redox cofactors, can catalyze the reduction of the heme-thiolate moiety in cytochrome P450 monooxygenase by transferring an electron thereto. CPR enzymes have the EC entry 1.6.2.4. A CPR enzyme can be comprised within an omega-hydroxylase complex (below). In general, a CPR enzyme is membrane-bound. CPR enzyme function is generally described in Porter and Kasper (Biochemistry 25:1682-1687) and Elmore and Porter (*J. Biol. Chem.* 277:48960-48964), which are incorporated herein by reference. Up-regulation of a polynucleotide sequence encoding a CPR enzyme herein leads to expression of an elevated amount of CPR enzyme, which in turn is available for forming an elevated amount of an omega-hydroxylase complex.

The terms "omega-hydroxylase complex", "hydroxylase complex", "hydroxylase enzyme complex", "CPR-P450 system" and the like are used interchangeably herein. An omega-hydroxylase complex herein comprises a CYP enzyme and a CPR enzyme, and can carry out omega-hydroxylation of certain organic substrates such as alkanes, fatty alcohols, fatty aldehydes, and fatty acids. In general, an omega-hydroxylase complex is membrane-bound. Omega-hydroxylation, which occurs in the endoplasmic reticulum (ER) membrane of yeast, is typically the first step of omega-oxidation.

The terms "fatty alcohol oxidase" (FAO), "long-chain fatty acid oxidase", "long-chain alcohol oxidase", "FAO enzyme" and the like are used interchangeably herein. FAO enzymes have the EC entry 1.1.3.20. An FAO enzyme herein can catalyze the following reaction: fatty alcohol+$O_2$→fatty aldehyde+$H_2O_2$, where a fatty alcohol is preferably an omega-hydroxy long-chain fatty acid, and a fatty aldehyde is preferably an omega-aldo long-chain fatty acid, each having a carbon chain length of at least 10 (e.g., 10-24 carbons). In general, FAO enzymes are peroxisomal proteins in yeast cells.

The terms "fatty alcohol dehydrogenase" (FADH), "long-chain fatty acid dehydrogenase", "ADH enzyme", "FADH enzyme" and the like are used interchangeably herein. FADH enzymes have the EC entry 1.1.1.1. An FADH enzyme herein can catalyze the following reaction: fatty alcohol+$NAD^+$→fatty aldehyde+NADH, where a fatty alcohol is preferably an omega-hydroxy long-chain fatty acid, and a fatty aldehyde is preferably an omega-aldo long-chain fatty acid, each having a carbon chain length of at least 10 (e.g., 10-24 carbons). In general, FADH enzymes are endoplasmic reticulum membrane proteins in yeast cells. FADH enzymes typically use $Zn^{2+}$ or Fe cation as cofactors.

The terms "fatty aldehyde dehydrogenase" (FALDH), "long-chain aldehyde dehydrogenase", "FALDH enzyme" and the like are used interchangeably herein. FALDH enzymes have the EC entry 1.2.1.48. An FALDH enzyme herein can catalyze the following reaction: fatty aldehyde+$NAD^+$+$H_2O$→LCDA+NADH+$2H^+$, where a fatty aldehyde is preferably an omega-aldo long-chain fatty acid having a carbon chain length of at least 10 (e.g., 10-24 carbons) (preferred LCDAs are disclosed further herein). In general, FALDH enzymes are peroxisomal proteins and/or endoplasmic reticulum membrane proteins in yeast cells.

An "engineered LCDA production pathway" herein can comprise, for example:

(i) up-regulation of a polynucleotide sequence encoding an ACoS enzyme, and (ii) up-regulation of a polynucleotide sequence encoding a CYP enzyme and/or CPR enzyme (i.e., up-regulation of omega-hydroxylase). Such a pathway can produce an LCDA product from a long-chain fatty acid-comprising substrate, for example.

The term "omega-oxidation" as used herein refers to a fatty acid metabolic pathway in which the omega carbon (the carbon most distant from the carboxyl group of a fatty acid) is oxidized to a carboxylic group (refer to FIG. 1). The first step of omega-oxidation is performed by an omega-hydroxylase complex, which catalyzes the addition of a hydroxyl (OH) group to the omega carbon, resulting in an omega-hydroxy fatty acid. The next step of omega-oxidation comprises oxidation of the omega-hydroxyl group to an aldehyde (C═O) group by a fatty alcohol oxidase (e.g., EC entry 1.1.3.20), or fatty alcohol dehydrogenase (e.g., EC entries 1.1.1.66, 1.1.1.192), resulting in an omega-aldo-fatty acid. The final step of omega-oxidation comprises oxidation of the aldehyde group to a carboxylic (COOH) group (carboxylic acid group) by a fatty aldehyde dehydrogenase (e.g., EC entries 1.2.1.3, 1.2.1.48), resulting in a dicarboxylic acid. The product of omega-oxidation of a long-chain fatty acid is a long-chain dicarboxylic acid (LCDA).

The term "beta-oxidation" herein refers to a process in which a fatty acid is catabolized by removal of two carbons at a time from the carboxyl end of the fatty acid. Beta-oxidation typically occurs exclusively in peroxisomes in yeast. Peroxisomes are membrane-enclosed, cytoplasmic organelles that contain a variety of oxidoreductases. Blocking beta-oxidation of fatty acids herein can be accomplished, for example, by disrupting peroxisome development and/or down-regulating expression of one or more beta-oxidation pathway enzymes.

The terms "peroxisomal protein", "peroxisome-associated protein" and the like are used interchangeably herein. A peroxisomal protein is a protein that is involved in peroxisome development and/or is located in peroxisomes where the protein is involved in maintaining peroxisome structure and/or metabolic function (e.g., beta-oxidation pathway). Examples of peroxisomal proteins herein include Pex proteins and Pox proteins.

The terms "peroxisome biogenesis factor", "peroxisome biogenesis factor protein", "peroxin", "Pex protein" and the like are used interchangeably herein and refer to proteins involved in peroxisome biogenesis and/or that participate in processes of importing cellular proteins into peroxisomes. The abbreviation of a polynucleotide sequence such as a gene or open reading frame that encodes a Pex protein can be referred to as "PEX" or "PEX polynucleotide" or PEX gene", for example. A system for nomenclature of PEX sequences is described by Distel et al. (*J. Cell Biol.* 135:1-3). At least 32 different PEX sequences have been identified so far in various eukaryotic organisms. The following fungal Pex proteins were identified by Kiel et al. (*Traffic* 7:1291-1303): Pex1p, Pex2p, Pex3p, Pex3Bp, Pex4p, Pex5p, Pex5Bp, Pex5Cp, Pex5/20p, Pex6p, Pex7p, Pex8p, Pex10p, Pex12p, Pex13p, Pex14p, Pex15p, Pex16p, Pex17p, Pex14/17p, Pex18p, Pex19p, Pex20p, Pex21p, Pex21Bp, Pex22p, Pex22p-like and Pex26p. Hong et al. (U.S. Pat. Appl. Publ. No. 2009/0117253) disclosed that down-regulation of certain PEX sequences in yeast enhances lipid and fatty acid accumulation.

The term "PEX3" herein refers to a polynucleotide sequence encoding peroxisome biogenesis factor-3 (Pex3 protein ["Pex3p"]). Pex3 protein is a peroxisomal integral membrane protein believed to play a role in peroxisomal membrane formation during peroxisome biogenesis (e.g., Baerends et al., *J. Biol. Chem.* 271:8887-8894; Bascom et al., *Mol. Biol. Cell* 14:939-957).

The terms "peroxisomal acyl-CoA oxidase", "Pox protein", "Aox protein" and the like are used interchangeably herein and refer to proteins comprised in the beta-oxidation pathway occurring in peroxisomes. Pox proteins herein, which are of EC entry EC:1.3.3.6, typically catalyze the following reaction: fatty acyl-CoA+$O_2$→trans-2,3-dehydroacyl-CoA+$H_2O_2$. The abbreviation of a polynucleotide sequence such as a gene or open reading frame that encodes a Pox protein can be referred to as "POX", "POX polynucleotide", or "POX gene", for example (e.g., POX4). Examples of Pox proteins are Pox-1, -2, -3, -4, -5 and -6.

The terms "diacylglycerol acyltransferase", "acyl-CoA: diacylglycerol acyltransferase", "diacylglycerol O-acyltransferase", "DGAT", "DAGAT" and the like are used interchangeably herein. A DGAT enzyme has the EC entry 2.3.1.20 and converts acyl-CoA and 1,2-diacylglycerol (DAG) to triacylglycerol (TAG) and CoA (thereby involved in the terminal step of TAG biosynthesis). DGAT1 and DGAT2 are examples of DGATS herein. DGAT1 enzymes share homology with acyl-CoA: cholesterol acyltransferase enzymes (Lardizabal et al., *J. Biol. Chem.* 276:38862-38869).

The terms "coumaroyl-CoA synthetase", "4-coumaroyl-CoA synthetase", "4-coumarate-CoA ligase" and the like are used interchangeably herein. A coumaroyl-CoA synthetase enzyme herein, which has the EC entry 6.2.1.12, can catalyze the following reaction ("coumaroyl-CoA synthetase activity"): ATP+4-coumarate+CoA→AMP+diphosphate+4-coumaroyl-CoA.

The term "long-chain" as used herein refers to a linear chain of at least 10 carbon atoms, and typically up to 24 carbon atoms. A "long-chain fatty acid" can have a chain of 10 to 24 carbon atoms in length, for example. The number of carbon atoms in the carbon chain of a long-chain fatty acid consists of its aliphatic carbons ($CH_3$—, —$CH_2$—, and ═CH— if present) and carboxylic group carbon (COOH).

The terms "long-chain dicarboxylic acid" (LCDA), "long-chain diacid", "long-chain dibasic acid", "long-chain α,ω-dicarboxylic acid", "long-chain fatty dicarboxylic acid" and the like are used interchangeably herein. An LCDA results from the complete omega-oxidation of a long-chain fatty acid, and thus has alpha and omega carboxylic acid groups (i.e., COOH at each terminus of carbon chain). An LCDA herein can have a chain of 10 to 24 carbon atoms in length, for example. The number of carbon atoms in the carbon chain of an LCDA consists of its aliphatic carbons (—$CH_2$—, and ═CH— if present) and carbons of both carboxylic groups. To illustrate, a C18:0 LCDA (18 carbon chain length, no double-bonds) has 16 $CH_2$ and 2 carboxyl groups; and a C18:1 LCDA (18 carbon chain length, 1 double-bond) has 14 $CH_2$, 2 CH, and 2 carboxyl groups. An LCDA herein is preferably linear with no organic side-chain off of any of the aliphatic carbons.

A "long-chain acyl-CoA" or "long-chain fatty acyl-CoA" herein refers to a compound in which a long-chain fatty acid is in thioester linkage with coenzyme A (CoA). A long-chain acyl-CoA is a product of long-chain acyl-CoA synthetase activity on a long-chain fatty acid substrate. "Long-chain fatty acid activation" herein refers to the process by which long-chain fatty acids are converted to long-chain acyl-CoA in a cell via long-chain acyl-CoA synthetase activity.

The terms "long-chain fatty acid-comprising substrate", "substrate comprising a long-chain fatty acid", "long-chain fatty acid-comprising feedstock", and the like are used interchangeably herein. Any long-chain fatty acid-comprising substrate herein that is obtained from a biological or biologically derived source can be characterized as "renewable" or "biorenewable", if desired. A long-chain fatty acid-comprising substrate can comprise a "free long-chain fatty acid" (e.g., non-esterified or non-amide-linked long-chain fatty acid) or "linked long-chain fatty acid" (e.g., esterified or amide-linked long-chain fatty acid), for example.

The COOH group of a free long-chain fatty acid herein is not involved in a linkage such as an ester bond (i.e., a free long-chain fatty acid is non-esterified) or amide bond (i.e., a free long-chain fatty acid is not amide-linked).

A linked long-chain fatty acid can be an "esterified long-chain fatty acid" or an "amide-linked long-chain fatty acid", for example.

The structure of a long-chain fatty acid can be represented by a simple notation system of "X:Y", where X is the total number of carbon (C) atoms in the fatty acid and Y is the number of double bonds (if any). Additional information concerning the differentiation between "saturated fatty acids" versus "unsaturated fatty acids", "monounsaturated fatty acids" versus "polyunsaturated fatty acids" (PUFAs), and "omega-6 fatty acids" versus "omega-3 fatty acids" are provided in U.S. Pat. No. 7,238,482, for example, which is incorporated herein by reference.

A "glyceride molecule" or "glyceride" herein refers to mono-, di- and/or triglycerides which contain one, two, or three fatty acids, respectively, esterified to glycerol (can alternatively be referred to as monoacylglycerol, diacylglycerol, and/or triacylglycerol, respectively). Glyceride molecules are examples of neutral lipids.

A "fatty acid alkyl ester" herein refers to an ester formed by ester linkage between the carboxylic group of a fatty acid and the hydroxyl group of an alkyl alcohol. To illustrate, a fatty acid alkyl ester herein can be a fatty acid methyl ester, for example, which is produced by esterification of a fatty acid to methanol. A fatty acid alkyl ester is an example of a fatty ester.

An "ester group" as used herein refers to an organic moiety having a carbonyl group (C═O) adjacent to an ether linkage. The general formula of an ester group is:

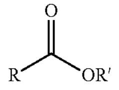

With respect to an esterified long-chain fatty acid, the R in the above ester formula comprises the linear chain of aliphatic carbon atoms of the esterified fatty acid. The R' group refers to an alkyl group, aryl group, or other organic group, for example. Examples of ester groups are found in mono-, di- and triglycerides which contain one, two, or three fatty acids, respectively, esterified to glycerol. With reference to the above formula, the R' group of a monoglyceride would refer to the glycerol portion of the molecule; the R' group of a diglyceride or triglyceride would refer to the glycerol portion further ester-linked to one or two, respectively, other fatty acids.

The term "lipid" as used herein refers to a fat-soluble (i.e., lipophilic) molecule. A general overview of lipids is provided in U.S. Pat. Appl. Publ. No. 2009/0093543 (see Table 2 therein), which is incorporated herein by reference. Examples of lipids useful herein as long-chain fatty acid-comprising substrates include glycerolipids (e.g., mono-, di- and triacylglycerols), fatty acyls (e.g., fatty esters, fatty amides), glycerophospholipids (e.g., phosphatidylcholines, phosphatidylethanolamines, phosphatidylserines, phosphatidylinositols, phosphatidic acids), sphingolipids (e.g., ceram ides, phospho-sphingolipids such as sphingomyelins, glycosphingolipids such as gangliosides and cerebrosides), and saccharolipids (compounds in which fatty acids are linked directly to a sugar backbone) (e.g., acylamino-sugars, acylamino-glycans, acyltrehaloses). A fatty acid-comprising substrate herein can be characterized, if desired, as a fatty-acid-comprising lipid.

The term "oil" as used herein refers to a lipid that is liquid at 25° C.; oil is hydrophobic and soluble in organic solvents. Oil is typically composed primarily of triacylglycerols, but may also contain other neutral lipids, as well as phospholipids and free fatty acids.

The terms "fatty acid distillate", "fatty acid distillate of an oil" and the like as used herein refer to a composition comprising the fatty acids of a particular type of oil. For example, a palm fatty acid distillate comprises fatty acids that are present in palm oil. Fatty acid distillates commonly are byproducts of plant oil refining processes.

The term "cell" herein refers to any type of cell such as a prokaryotic or eukaryotic cell. A eukaryotic cell has a nucleus and other membrane-enclosed structures (organelles), whereas a prokaryotic cell lacks a nucleus. A "microbial cell" (microbe) herein can refer to a fungal cell (e.g., yeast cell), prokaryotic cell, protist cell (e.g., algal cell), euglenoid cell, stramenopile cell, or oomycete cell, for example. A prokaryotic cell herein typically refers to a bacterial cell.

The term "yeast" herein refers to fungal species that predominantly exist in unicellular form. Yeast can alternatively be referred to as "yeast cells". A yeast herein can be characterized as either a conventional yeast or non-conventional yeast, for example.

The term "conventional yeast" ("model yeast") herein generally refers to *Saccharomyces* or *Schizosaccharomyces* yeast species. Conventional yeast in certain embodiments are yeast that favor homologous recombination (HR) DNA repair processes over repair processes mediated by non-homologous end-joining (NHEJ). The term "non-conventional yeast" herein refers to any yeast that is not a *Saccharomyces* or *Schizosaccharomyces* yeast species. Non-conventional yeast are described in *Non-Conventional Yeasts in Genetics, Biochemistry and Biotechnology: Practical Protocols* (K. Wolf, K. D. Breunig, G. Barth, Eds., Springer-Verlag, Berlin, Germany, 2003) and Spencer et al. (Appl. Microbiol. Biotechnol. 58:147-156), which are incorporated herein by reference. Some strains of non-conventional yeast may additionally (or alternatively) be yeast that favor NHEJ DNA repair processes over repair processes mediated by HR. Definition of a non-conventional yeast along these lines—preference of NHEJ over HR—is further disclosed by Chen et al. (*PLoS ONE* 8:e57952), which is incorporated herein by reference. Preferred non-conventional yeast herein are those of the genus *Yarrowia* (e.g., *Yarrowia lipolytica*).

When used to describe the expression of a gene or polynucleotide sequence, the terms "down-regulated", "down-regulation", "disruption", "inhibition", "inactivation", "silencing" and the like are used interchangeably herein to refer to instances when the transcription of the polynucleotide sequence is reduced or eliminated. This results in the reduction or elimination of RNA transcripts from the polynucleotide sequence, which results in a reduction or elimination of protein expression derived from the polynucleotide sequence (if the gene comprised an ORF). Alternatively, down-regulation can refer to instances where protein translation from transcripts produced by the polynucleotide sequence is reduced or eliminated. Alternatively still, down-regulation can refer to instances where a protein expressed by the polynucleotide sequence has reduced activity. The reduction in any of the above processes (transcription, translation, protein activity) in a cell can be by at least about 20%, 30%, 40%, 50%, 60%, 70%, 80%, 90%, 95%, or 100% relative to a corresponding process in a suitable control cell. Down-regulation can result from a targeting event (e.g., indel, knock-out, knock-in) or from using antisense or RNAi technology, for example.

The terms "targeting", "gene targeting", "DNA targeting", "editing", "gene editing", "DNA editing" and the like are used interchangeably herein. DNA targeting herein may be the introduction of an indel, knock-out, or knock-in at a particular DNA sequence, such as in a chromosome of a cell. Means for targeting in microbial cells, such as homologous recombination (HR), are known in the art and can be applied accordingly. Various HR procedures that can be performed in a yeast cell, for example, are disclosed in *DNA Recombination: Methods and Protocols: 1st Edition* (H. Tsubouchi, Ed., Springer-Verlag, New York, 2011), which is incorporated herein by reference. An HR process can be used to introduce an indel, knock-out, or knock-in at a DNA target site, for example.

The terms "knock-out", "gene knock-out", "genetic knock-out", "disrupted" and the like are used interchangeably herein. A knock-out represents a DNA sequence of a cell herein that has been rendered partially or completely inoperative by DNA targeting; such a DNA sequence prior to its knock-out could have encoded an amino acid sequence, or could have had a regulatory function (e.g., promoter), for example. A knock-out represents a particular way for providing a DNA sequence deletion, for example. A knock-out may be produced by a mutagenic process (e.g., leading to indel formation) or by specific removal of sequence (e.g., by HR), for example, and reduces or completely destroys the function of a DNA sequence such as a polynucleotide encoding a protein and/or a regulatory sequence thereof. A knocked out DNA polynucleotide sequence herein can also be characterized as being partially or totally disrupted or being partially or totally down-regulated.

The terms "knock-in", "gene knock-in", "genetic knock-in" and the like are used interchangeably herein. A knock-in represents the replacement or insertion of a DNA sequence at a specific DNA sequence in a cell by DNA targeting. Examples of knock-ins include a specific insertion of a heterologous amino acid coding sequence into a protein-coding region of a polynucleotide sequence and/or a regulatory sequence thereof. Such insertion can result in down-regulation of the targeted sequence, for example. A knock-in may be produced by a specific insertion of sequence (e.g., by HR), for example.

The term "indel" herein refers to an insertion or deletion of a nucleotide base or bases in a target DNA sequence. Such an insertion or deletion may be of 1, 2, 3, 4, 5, 6, 7, 8, 9, 10, or more bases, for example. An indel in certain embodiments can be even larger, at least about 20, 30, 40, 50, 60, 70, 80, 90, or 100 bases. If an indel is introduced within an open reading frame (ORF) of a gene, oftentimes the indel disrupts wild type expression of protein encoded by the ORF by creating a frameshift mutation. An indel can be created using a mutagenic process, for example.

The terms "percent by volume", "volume percent", "vol %", "v/v %" and the like are used interchangeably herein. The percent by volume of a solute in a solution can be determined using the formula: [(volume of solute)/(volume of solution)]×100%.

The terms "percent by weight", "weight percentage (wt %)", "weight-weight percentage (% w/w)" and the like are used interchangeably herein. Percent by weight refers to the percentage of a material on a mass basis as it is comprised in a composition, mixture, or solution.

The terms "polynucleotide", "polynucleotide sequence", "nucleic acid sequence" and the like are used interchangeably herein. These terms encompass nucleotide sequences and the like. A polynucleotide may be a polymer of DNA or RNA that is single- or double-stranded, that optionally contains synthetic, non-natural or altered nucleotide bases. A polynucleotide may be comprised of one or more segments of cDNA, genomic DNA, synthetic DNA, or mixtures thereof. Nucleotides (ribonucleotides or deoxyribonucleotides) can be referred to by a single letter designation as follows: "A" for adenylate or deoxyadenylate (for RNA or DNA, respectively), "C" for cytidylate or deoxycytidylate (for RNA or DNA, respectively), "G" for guanylate or deoxyguanylate (for RNA or DNA, respectively), "U" for uridylate (for RNA), "T" for deoxythymidylate (for DNA), "R" for purines (A or G), "Y" for pyrimidines (C or T), "K" for G or T, "H" for A or C or T, "I" for inosine, "W" for A or T, and "N" for any nucleotide (e.g., N can be A, C, T, or G, if referring to a DNA sequence; N can be A, C, U, or G, if referring to an RNA sequence).

The term "gene" as used herein refers to a DNA polynucleotide sequence that expresses an RNA (RNA is transcribed from the DNA polynucleotide sequence) from a coding region, which RNA can be a messenger RNA (encoding a protein) or a non-protein-coding RNA. A gene may refer to the coding region alone, or may include regulatory sequences upstream and/or downstream to the coding region (e.g., promoters, 5'-untranslated regions, 3'-transcription terminator regions). A coding region encoding a protein can alternatively be referred to herein as an "open reading frame" (ORF). A gene that is "native" or "endogenous" refers to a gene as found in nature with its own regulatory sequences; such a gene is located in its natural location in the genome of a host cell. A "chimeric" gene refers to any gene that is not a native gene, comprising regulatory and coding sequences that are not found together in nature (i.e., the regulatory and coding regions are heterologous with each other). Accordingly, a chimeric gene may comprise regulatory sequences and coding sequences that are derived from different sources, or regulatory sequences and coding sequences derived from the same source, but arranged in a manner different than that found in nature. A "foreign" or "heterologous" gene refers to a gene that is introduced into the host organism by gene transfer. Foreign/heterologous genes can comprise native genes inserted into a non-native organism, native genes introduced into a new location within the native host, or chimeric genes. The polynucleotide sequences in certain embodiments disclosed herein are heterologous. A "transgene" is a gene that has been introduced into the genome by a gene delivery procedure (e.g., transformation). A "codon-optimized" open reading frame has its frequency of codon usage designed to mimic the frequency of preferred codon usage of the host cell.

A "non-native" amino acid sequence or polynucleotide sequence comprised in a cell or organism herein does not occur in a native (natural) counterpart of such cell or organism.

"Regulatory sequences" as used herein refer to nucleotide sequences located upstream of a gene's transcription start site (e.g., promoter), 5' untranslated regions, introns, and 3' non-coding regions, and which may influence the transcription, processing or stability, and/or translation of an RNA transcribed from the gene. Regulatory sequences herein may include promoters, enhancers, silencers, 5' untranslated leader sequences, introns, polyadenylation recognition sequences, RNA processing sites, effector binding sites, stem-loop structures, and other elements involved in regulation of gene expression. One or more regulatory elements herein may be heterologous to a coding region herein.

A "promoter" as used herein refers to a DNA sequence capable of controlling the transcription of RNA from a gene. In general, a promoter sequence is upstream of the transcription start site of a gene. Promoters may be derived in their entirety from a native gene, or be composed of different elements derived from different promoters found in nature, or even comprise synthetic DNA segments. Promoters that cause a gene to be expressed in a cell at most times under all circumstances are commonly referred to as "constitutive promoters". One or more promoters herein may be heterologous to a coding region herein.

An "inducible promoter" as used herein refers to a promoter capable of controlling the transcription of RNA from a gene under certain specific conditions (i.e., by the presence or absence of biotic or abiotic factors). These types of promoters typically have no, or very low, activity under conditions in which inducing conditions are not present.

A "strong promoter" as used herein refers to a promoter that can direct a relatively large number of productive initiations per unit time, and/or is a promoter driving a higher level of gene transcription than the average transcription level of the genes in a cell.

The terms "3' non-coding sequence", "transcription terminator" and "terminator" as used herein refer to DNA sequences located downstream of a coding sequence. This includes polyadenylation recognition sequences and other sequences encoding regulatory signals capable of affecting mRNA processing or gene expression.

The terms "cassette", "expression cassette", "gene cassette" and the like are used interchangeably herein. A cassette can refer to a promoter operably linked to a DNA sequence encoding a protein-coding RNA or non-protein-coding RNA. A cassette may optionally be operably linked to a 3' non-coding sequence. The structure of a cassette herein can optionally be represented by the simple notation system of "X::Y::Z". Specifically, X describes a promoter, Y describes a coding sequence, and Z describes a terminator (optional); X is operably linked to Y, and Y is operably linked to Z.

The term "expression" as used herein refers to (i) transcription of RNA (e.g., mRNA or a non-protein-coding RNA) from a coding region, and/or (ii) translation of a polypeptide from mRNA. Expression of a coding region of a polynucleotide sequence can be up-regulated or down-regulated in certain embodiments.

The term "operably linked" as used herein refers to the association of two or more nucleic acid sequences such that the function of one is affected by the other. For example, a promoter is operably linked with a coding sequence when it is capable of affecting the expression of that coding sequence. That is, the coding sequence is under the transcriptional control of the promoter. A coding sequence can be operably linked to one (e.g., promoter) or more (e.g., promoter and terminator) regulatory sequences, for example.

The term "recombinant" when used herein to characterize a DNA sequence such as a plasmid, vector, or construct refers to an artificial combination of two otherwise separated segments of sequence, e.g., by chemical synthesis and/or by manipulation of isolated segments of nucleic acids by genetic engineering techniques. Methods for preparing recombinant constructs/vectors herein can follow standard recombinant DNA and molecular cloning techniques as described by J. Sambrook and D. Russell (*Molecular Cloning: A Laboratory Manual,* 3rd Edition, Cold Spring Harbor Laboratory Press, Cold Spring Harbor, N.Y., 2001); T. J. Silhavy et al. (*Experiments with Gene Fusions*, Cold Spring Harbor Laboratory Press, Cold Spring Harbor, N.Y., 1984); and F. M. Ausubel et al. (*Short Protocols in Molecular Biology,* 5th Ed. Current Protocols, John Wiley and Sons, Inc., NY, 2002), for example.

The term "transformation" as used herein refers to the transfer of a nucleic acid molecule into a host organism or host cell by any method. A nucleic acid molecule that has been transformed into an organism/cell may be one that replicates autonomously in the organism/cell, or that integrates into the genome of the organism/cell, or that exists transiently in the cell without replicating or integrating. Non-limiting examples of nucleic acid molecules suitable for transformation are disclosed herein, such as plasmids and linear DNA molecules. Host organisms/cells herein containing a transforming nucleic acid sequence can be referred to as "transgenic", "recombinant", "transformed", "engineered", as a "transformant", and/or as being "modified for exogenous gene expression", for example.

Constructs or vectors comprising polynucleotides described herein may be introduced into a cell by any standard technique. These techniques include transformation (e.g., lithium acetate transformation [*Methods in Enzymology,* 194:186-187 (1991)]), biolistic impact, electroporation, and microinjection, for example. As an example, U.S. Pat. Nos. 4,880,741 and 5,071,764, and Chen et al. (1997, *Appl. Microbiol. Biotechnol.* 48:232-235), disclose integration techniques for *Y. lipolytica*, based on linearized fragments of DNA.

The terms "control cell" and "suitable control cell" are used interchangeably herein and may be referenced with respect to a cell in which a particular modification (e.g., over-expression of a polynucleotide, down-regulation of a polynucleotide) has been made (i.e., an "experimental cell"). A control cell may be any cell that does not have or does not express the particular modification of the experimental cell. Thus, a control cell may be an untransformed wild type cell or may be genetically transformed but does not express the particular modification. For example, a control cell may be a direct parent of the experimental cell, which direct parent cell does not have the particular modification that is in the experimental cell. Alternatively, a control cell may be a parent of the experimental cell that is removed by one or more generations. Alternatively still, a control cell may be a sibling of the experimental cell, which sibling does not comprise the particular modification that is present in the experimental cell. A control cell can optionally be characterized as a cell as it existed before being modified to be an experimental cell.

The terms "sequence identity" or "identity" as used herein with respect to polynucleotide or polypeptide sequences refer to the nucleic acid bases or amino acid residues in two sequences that are the same when aligned for maximum correspondence over a specified comparison window. Thus, "percentage of sequence identity" or "percent identity" refers to the value determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the results by 100 to yield the percentage of sequence identity. It would be understood that, when calculating sequence identity between a DNA sequence and an RNA sequence, T residues of the DNA sequence align with, and can be considered "identical" with, U residues of the RNA sequence. For purposes of determining "percent complementarity" of first and second polynucleotides, one can obtain this by determining (i) the percent identity between the first polynucleotide and the complement sequence of the second polynucleotide (or vice versa), for example, and/or (ii) the percentage of bases between the first and second polynucleotides that would create canonical Watson and Crick base pairs.

The Basic Local Alignment Search Tool (BLAST) algorithm, which is available online at the National Center for Biotechnology Information (NCBI) website, may be used, for example, to measure percent identity between or among two or more of the polynucleotide sequences (BLASTN algorithm) or polypeptide sequences (BLASTP algorithm) disclosed herein. Alternatively, percent identity between sequences may be performed using a Clustal algorithm (e.g., ClustalW, ClustalV, or Clustal-Omega). For multiple alignments using a Clustal method of alignment, the default values may correspond to GAP PENALTY=10 and GAP LENGTH PENALTY=10. Default parameters for pairwise alignments and calculation of percent identity of protein sequences using a Clustal method may be KTUPLE=1, GAP PENALTY=3, WINDOW=5 and DIAGONALS SAVED=5. For nucleic acids, these parameters may be KTUPLE=2, GAP PENALTY=5, WINDOW=4 and DIAGONALS SAVED=4. Alternatively still, percent identity between sequences may be performed using an EMBOSS algorithm (e.g., needle) with parameters such as GAP OPEN=10, GAP EXTEND=0.5, END GAP PENALTY=false, END GAP OPEN=10, END GAP EXTEND=0.5 using a BLOSUM matrix (e.g., BLOSUM62).

Herein, a first sequence that is "complementary" to a second sequence can alternatively be referred to as being in the "antisense" orientation with the second sequence.

Various polypeptide amino acid sequences and polynucleotide sequences are disclosed herein as features of certain embodiments. Variants of these sequences that are at least about 70-85%, 85-90%, or 90%-95% identical to the sequences disclosed herein can be used or referenced. Alternatively, a variant amino acid sequence or polynucleotide sequence can have at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% identity with a sequence disclosed herein. The variant amino acid sequence or polynucleotide sequence has the same function/activity of the disclosed sequence, or at least about 80%, 81%, 82%, 83%, 84%, 85%, 86%, 87%, 88%, 89%, 90%, 91%, 92%, 93%, 94%, 95%, 96%, 97%, 98%, or 99% of the function/activity of the disclosed sequence. Any polypeptide amino acid sequence disclosed herein not beginning with a methionine can typically further comprise at least a start-methionine at the N-terminus of the amino acid sequence.

All the amino acid residues at each amino acid position of the proteins disclosed herein are examples. Given that certain amino acids share similar structural and/or charge features with each other (i.e., conserved), the amino acid at each position of a protein herein can be as provided in the disclosed sequences or substituted with a conserved amino acid residue ("conservative amino acid substitution") as follows:

1. The following small aliphatic, nonpolar or slightly polar residues can substitute for each other: Ala (A), Ser (S), Thr (T), Pro (P), Gly (G);
2. The following polar, negatively charged residues and their amides can substitute for each other: Asp (D), Asn (N), Glu (E), Gln (Q);
3. The following polar, positively charged residues can substitute for each other: His (H), Arg (R), Lys (K);
4. The following aliphatic, nonpolar residues can substitute for each other: Ala (A), Leu (L), Ile (I), Val (V), Cys (C), Met (M); and
5. The following large aromatic residues can substitute for each other: Phe (F), Tyr (Y), Trp (W).

The term "isolated" as used herein refers to a polynucleotide or polypeptide molecule that has been completely or partially purified from its native source. In some instances, the isolated polynucleotide or polypeptide molecule is part of a greater composition, buffer system or reagent mix. For example, the isolated polynucleotide or polypeptide molecule can be comprised within a cell or organism in a heterologous manner. Such a cell or organism containing heterologous components and/or one or more genetic deletions does not occur in nature. "Isolated" herein can also characterize embodiments that are synthetic/man-made, and/or have properties that are not naturally occurring.

The term "increased" as used herein can refer to a quantity or activity that is at least about 1%, 2%, 3%, 4%, 5%, 6%, 7%, 8%, 9%, 10%, 11%, 12%, 13%, 14%, 15%, 16%, 17%, 18%, 19%, 20%, 50%, 100%, or 200% more than the quantity or activity for which the increased quantity or activity is being compared. The terms "increased", "elevated", "enhanced", "greater than", "improved" and the like are used interchangeably herein. These terms can be used to characterize the "over-expression" or "up-regulation" of a polynucleotide encoding a protein, for example.

New microbial biocatalysts with enhanced LCDA fermentation capabilities are desired. Thus, some embodiments disclosed herein concern a recombinant microbial cell comprising an engineered LCDA production pathway that comprises up-regulation of a polynucleotide sequence encoding a long-chain acyl-CoA synthetase (ACoS enzyme). Significantly, such a microbial cell can produce one or more long-chain dicarboxylic acid (LCDA) products from a long-chain fatty acid-comprising substrate.

Some embodiments disclosed herein concern a recombinant microbial cell, such as yeast cell, comprising:

(i) up-regulation of a polynucleotide sequence encoding a cytochrome P450 monooxygenase (CYP enzyme) and/or up-regulation of a polynucleotide sequence encoding a cytochrome P450 reductase (CPR enzyme), (ii) up-regulation of a polynucleotide sequence encoding a long-chain acyl-CoA synthetase (ACoS enzyme), and (iii) down-regulation of an endogenous polynucleotide sequence encoding a peroxisome biogenesis factor-3.

Significantly, such a microbial cell can produce one or more long-chain dicarboxylic acid (LCDA) products from a long-chain fatty acid-comprising substrate.

Up-regulation of an ACoS enzyme in a recombinant cell herein by up-regulating a polynucleotide encoding this enzyme is believed to result in an increased level of long-chain acyl-CoA in the cell. Such an increase of this metabolite reflects an increased level of long-chain fatty acid activation in the cell.

Up-regulation of an ACoS enzyme in certain aspects herein can be through up-regulation of a polynucleotide sequence encoding an ACoS enzyme. Such up-regulation, which leads to over-expression of an ACoS enzyme, can be done by one or more of a variety of methods. For example, an ACoS-encoding polynucleotide can be provided in multi-copy to a cell, either transiently or stably (such a polynucleotide sequence is operably linked to a promoter sequence [e.g., heterologous promoter]). Providing a polynucleotide sequence in multi-copy may be accomplished by providing one or more copies of the polynucleotide (e.g., at least 1, 2, 3, 4, 5, 6, 7, 8, 9, 10, 15, 20, 25, or 50 copies) to a cell. It would be understood that a polynucleotide sequence provided in a stable manner typically has a lower copy number compared to that of a polynucleotide sequence provided in a transient manner. As another example, an ACoS-encoding polynucleotide sequence can be up-regulated by operable linkage to a constitutive promoter, strong promoter, or inducible promoter, any of which can be heterologous.

Up-regulation (e.g., over-expression) of an ACoS enzyme in a cell herein may optionally be considered with respect to a suitable control cell. For example, the increased level of an ACoS enzyme in a cell herein may be characterized to be at least about 5%, 10%, 20%, 30%, 40%, 50%, 60%, 75%, 80%, 90%, 100%, 150%, 200%, 500%, or 1000% above the expression of the ACoS enzyme in a suitable control cell. An example of a suitable control cell is a cell as it existed before it was modified to have up-regulated ACoS enzyme expression (e.g., parent cell).

An ACoS enzyme herein can be heterologous to a cell, for example. An example of a heterologous ACoS enzyme can be one that is derived from a species or strain that is different from the species or strain of the cell in which the ACoS enzyme is up-regulated.

Alternatively, an ACoS enzyme that is up-regulated in a cell may be native to the cell. A native ACoS enzyme can be up-regulated, for example, using any of the means disclosed above regarding polynucleotide sequence up-regulation. For example, a polynucleotide sequence encoding this enzyme (operably linked to a promoter sequence [e.g., heterologous promoter]) that is native to a cell may be provided to the cell in a stable or transient manner (but the location of the polynucleotide sequences would be located in a non-native site [i.e., heterologous site]). As another example, a polynucleotide sequence encoding an ACoS enzyme, as naturally existing in the genome of a cell, can be modified such that the native polynucleotide sequence(s) is over-expressed. This can be accomplished, for example, by modifying one or more regulatory elements (e.g., promoter) of a gene containing a polynucleotide sequence encoding an ACoS enzyme.

One, two, three, four, or more ACoS enzymes can optionally be up-regulated in a cell herein by providing two, three, four, or more sets (copies) of polynucleotide sequences encoding ACoS enzyme(s). ACoS enzymes can be provided to a cell, for example, by introducing (i) copies of a polynucleotide sequence encoding the same ACoS enzyme, and/or (ii) polynucleotide sequences encoding different ACoS enzymes (e.g., over-expression of both a *Saccharomyces* ACoS and a *Yarrowia* ACoS).

An ACoS enzyme herein can be derived from a eukaryote, for example, such as any eukaryote disclosed as follows: A eukaryote herein can be an animal, plant, fungus, or protist. An animal herein can be a mammal, bird, amphibian, reptile, fish, or invertebrate (e.g., insect, crustacean, mollusc, nematode), for example. A mammal herein can be a human or rodent (e.g., mouse, rat), for example. A plant herein can be a monocot or a dicot, for example. Examples of monocot plants herein include corn, rice, rye, sorghum, millet, wheat, sugarcane, oats, barley, and switchgrass. Examples of dicot plants herein include soybean, canola, alfalfa, tobacco, *Arabidopsis* (e.g., *A. thaliana, A. lyrata*), sunflower, cotton, peanut, tomato, potato and common vetch (e.g., *Vicia sativa*). A fungus herein can be a Basidiomycetes, Zygomycetes, Chytridiomycetes, or Ascomycetes fungus, for example. A fungus may be a yeast or a filamentous fungus in certain embodiments. Yeast examples include any of those species disclosed below (e.g., *Yarrowia* species such as *Y. lipolytica, Candida* species such as *C. tropicalis, Saccharomyces* species such as *S. cerevisiae*) that can be used for preparing a recombinant yeast cell in certain aspects herein. Examples of filamentous fungi herein include those species of the genera *Acremonium, Aspergillus, Aureobasidium, Chrysosporium, Cryphonectria, Cryptococcus, Filibasidium, Fusarium, Gibberella, Humicola, Mucor, Myceliophthora, Neurospora, Penicillium, Piromyces, Scytalidium, Schizophyllum, Sporotrichum, Thielavia, Tolypocladium*, and *Trichoderma*. Examples of protists herein include algal cells (e.g., green algae, brown algae, red algae) and protists of the class *Ciliata*, the subphylum Mastigophora (*flagellates*), the class Phytomastigophorea, the class Zoomastigophorea, the superclass Rhizopoda, the class Lobosea, and the class Eumycetozoea.

An ACoS enzyme in certain embodiments can be derived from a prokaryote, for example, such as any prokaryote disclosed as follows: A prokaryote herein can be a bacteria or archaea, for example. Examples of bacteria include those that are Gram-negative and Gram-positive. Still other examples of bacteria include those of the genera *Achromobacter, Acidaminococcus, Acinetobacter, Actinobacillus, Actinomadura, Actinomyces, Aerococcus, Aeromonas, Afipia, Agrobacterium, Alcaligenes*, Arcanobacterium, Arcobacter, *Bacillus* (e.g., *B. subtilis, B. megaterium*), *Bacteroides, Bartonella, Bifidobacterium, Bilophila, Bordetella, Borrelia, Brucella, Calymmatobacterium, Campylobacter, Cardiobacterium, Chlamydiae, Chryseomonas, Citrobacter, Clostridium, Comamonas, Coprococcus, Coxiella, Corynebacterium, Edwardsiella, Ehrlichia, Eikenella, Enterobacter, Enterococcus, Erysipelothrix, Escherichia* (e.g., *E. coli*), *Eubacterium, Ewingella, Flavimonas, Flavobacterium, Franciesella, Fusobacterium, Gardnerella, Gemella, Haemophilus, Hafnia, Helicobacter* (e.g., *H. pylori*), *Klebsiella, Kluyvera, Lactobacillus, Lactococcus, Legionella, Leptospira, Leptotrichia, Leuconostoc, Listeria, Megasphaera, Mycobacterium, Micrococcus, Micropolysporas, Mobi-*

*luncus, Moraxella, Morganella, Mycoplasma, Neisseria, Norcardia, Norcardiopsis, Oligella, Pasteurella, Pedicoccus, Peptococcus, Peptostreptococcus, Planococcus, Plessiomonas, Porphyromonas, Prevotella, Proteus, Providencia, Propionibacterium, Pseudomonas, Rhodococcus, Rickettsia, Rochalimaea, Rothia, Ruminococcus, Sarcinia, Salmonella, Shewanella, Shigella, Serratia, Spirillum, Staphylococcus, Stomatococcus, Streptobacillus, Streptococcus, Streptomyces, Thermoactinomycetes, Treponema, Ureaplasma, Veilonella, Vibrio, Weeksella, Wolinella, Xanthomonas*, or *Yersinia*.

In some embodiments, an ACoS enzyme can be characterized as being microbial (i.e., being derived from: a bacterial cell; protist cell such as an algal cell; fungal cell such as a yeast cell; euglenoid cell; stramenopile cell; or oomycete cell).

The amino acid sequence of an ACoS enzyme herein can comprise, for example, any of the amino acid sequences disclosed in GenBank Acc. Nos. XP_503862.1, XP_503608.1, XP_502959.1, AJT71734.1, NP_014962.3, AJU13255.1, NP_010931.3, EWG91402.1, EJT42092.1, NP_001153101.1, NP_001273637.1, XP_001146361.1, XP_003829365.1, XP_004033324.1, NP_001125625.1, XP_003266954.1, XP_001363547.2, XP_007422758.1, XP_002880290.1, NP_631034.1, 014975.2, CAH21295.1, CAL20709.1, AEV18827.1, CEM58466.1, CBA20954.1, BAK25224.1, AIU33175.1, CBJ51928.1, CAL93650.1, CAL09544.1, CEE01548.1, GAE33988.1, AAY81441.1, BAH81064.1, CCA89166.1, KJX89569.1, WP_023306469.1, EAZ59428.1, EFH75916.1, EFG64803.1, EFF13066.1, AIE60968.1, KJF31148.1, WP_023290211.1, AGC43083.1, GAL05408.1, KGM65079.1, CEE01549.1, KDL77549.1, BA070678.1, EPY53810.1, EEB08740.1, GAF10677.1, CCG43904.1, WP_042268578.1, KGG85769.1, CNO88241.1, KKE73357.1, WP_001055160.1, WP_003239466.1, WP_028742371.1, WP_027325346.1, and KBA42642.1, which are incorporated herein by reference. A variant of any of these ACoS amino acid sequences may be used, but should have some of (e.g., at least 30%, 40%, 50%, 60%, 70%, 80%, or 90% of), or all of, the enzymatic activity (refer to above definitions) of the corresponding non-variant ACoS enzyme reference. Such a variant ACoS enzyme may comprise an amino acid sequence that is at least about 80%, 81%, 82%, 83%, 84%, 85%, 86%, 87%, 88%, 89%, 90%, 91%, 92%, 93%, 94%, 95%, 96%, 97%, 98%, or 99% identical to the amino acid sequence of the corresponding non-variant ACoS enzyme reference.

In certain aspects herein, an ACoS enzyme can comprise the amino acid sequence of SEQ ID NO:44 (a *Y. lipolytica* ACoS), SEQ ID NO:49 (a *Y. lipolytica* ACoS), SEQ ID NO:36 (a *Y. lipolytica* ACoS), SEQ ID NO:33 (an *S. cerevisiae* ACoS), or SEQ ID NO:34 (an *S. cerevisiae* ACoS). It is believed that a protein comprising any of the amino acid sequences listed in Tables 2 and 3 (below) may be useful as an ACoS enzyme in some other aspects. Alternatively, an ACoS enzyme herein can comprise an amino acid sequence that is at least about 80%, 81%, 82%, 83%, 84%, 85%, 86%, 87%, 88%, 89%, 90%, 91%, 92%, 93%, 94%, 95%, 96%, 97%, 98%, or 99% identical to any of the foregoing ACoS enzyme amino acid sequences, for example. Such a variant ACoS enzyme should have some of (e.g., at least about 30%, 40%, 50%, 60%, 70%, 80%, or 90% of), or all of, the enzymatic activity (refer to above definitions) of the corresponding non-variant ACoS enzyme reference. Methods of measuring ACoS enzyme activity available in the art (e.g., Galton and Fraser, *Analytical Biochemistry* 28:59-64, incorporated herein by reference), or as disclosed in Example 5 below, can be applied accordingly herein.

In certain embodiments, an ACoS enzyme herein has both long-chain acyl-CoA synthetase activity and coumaroyl-CoA synthetase activity. Examples of such an ACoS enzyme as presently disclosed comprise an amino acid sequence that is at least 90% identical with SEQ ID NO:44 or 49.

A recombinant cell herein can optionally be characterized as comprising an engineered LCDA production pathway that comprises at least one up-regulated ACoS enzyme. An engineered LCDA production pathway in some aspects further comprises: (i) up-regulation of a polynucleotide sequence encoding a cytochrome P450 monooxygenase (CYP enzyme), and/or (ii) up-regulation of a polynucleotide sequence encoding a cytochrome P450 reductase (CPR enzyme). It is expected that either or both these up-regulations ([i] and/or [ii]) lead to omega-hydroxylase up-regulation. In some other embodiments, an engineered LCDA production pathway further comprises (optionally in addition to up-regulations [i] and/or [ii]) at least one of: (iii) up-regulation of a polynucleotide sequence encoding a fatty alcohol oxidase (FAO enzyme), (iv) up-regulation of a polynucleotide sequence encoding a fatty alcohol dehydrogenase (FADH enzyme), and/or (v) up-regulation of a polynucleotide sequence encoding a fatty aldehyde dehydrogenase (FALDH enzyme).

A recombinant cell in certain embodiment can have both a CYP enzyme and a CPR enzyme up-regulated, for example. Alternatively, a CYP enzyme can be up-regulated, or a CPR enzyme can be up-regulated. In embodiments in which a CYP enzyme is up-regulated, but a CPR enzyme is expressed at a wild type level, an up-regulated omega-hydroxylase complex may result by virtue of the CYP enzyme up-regulation. In embodiments in which a CPR enzyme is up-regulated, but a CYP enzyme is expressed at a wild type level, an up-regulated omega-hydroxylase complex may result by virtue of the CPR enzyme up-regulation.

Up-regulation of a CYP enzyme and/or CPR enzyme in certain aspects herein can be through up-regulation of a polynucleotide sequence encoding a CYP enzyme and/or up-regulation of a polynucleotide sequence encoding a CPR enzyme. Such up-regulation, which leads to over-expression of a CYP enzyme and/or CPR enzyme, can be done by one or more of a variety of methods. For example, a CYP-encoding polynucleotide and/or a CYP enzyme-encoding polynucleotide can be provided in multi-copy to a cell, either transiently or stably (such a polynucleotide sequence is operably linked to a promoter sequence [e.g., heterologous promoter]). Providing a polynucleotide sequence in multi-copy may be accomplished by providing one or more copies of the polynucleotide (e.g., at least 1, 2, 3, 4, 5, 6, 7, 8, 9, 10, 15, 20, 25, or 50 copies) to a cell. It would be understood that a polynucleotide sequence provided in a stable manner typically has a lower copy number compared to that of a polynucleotide sequence provided in a transient manner. As another example, a CYP enzyme-encoding polynucleotide sequence and/or a CPR enzyme-encoding polynucleotide can be up-regulated by operable linkage to a constitutive promoter, strong promoter, or inducible promoter, any of which can be heterologous.

Both a CYP enzyme-encoding polynucleotide sequence and a CPR enzyme-encoding polynucleotide sequence are up-regulated in certain embodiments; this up-regulation can be performed, for example, following one or a combination of the over-expression strategies disclosed herein. Individual polynucleotides (e.g., vectors such as plasmids)—one encoding a CYP enzyme and the other encoding a CPR enzyme—may be employed, for example. As another example, a single polynucleotide (e.g., a vector such as a plasmid) comprising each CYP and CPR coding sequence may be used; each coding sequence may be comprised in its own expression cassette (e.g., promoter—coding sequence—terminator) or within a bi-cistronic expression cassette, for example.

Up-regulation (e.g., over-expression) of a CYP enzyme and/or a CPR enzyme in a cell may optionally be considered with respect to a suitable control cell. For example, the increased level of a CYP enzyme and/or a CPR enzyme in a cell herein may be characterized to be at least about 5%, 10%, 20%, 30%, 40%, 50%, 60%, 75%, 80%, 90%, 100%, 150%, 200%, 500%, or 1000% above the expression of the CYP enzyme and/or CPR enzyme in a suitable control cell. An example of a suitable control cell is a cell as it existed before it was modified to have up-regulated CYP enzyme and/or CPR enzyme expression (e.g., parent cell).

A CYP enzyme and/or CPR enzyme can be heterologous to a cell, for example. An example of a heterologous CYP enzyme (and/or CPR enzyme) can be one that is derived from a species or strain that is different from the species or strain of the cell in which the CYP enzyme (and/or CPR enzyme) is up-regulated. Both a CYP enzyme and CPR enzyme are heterologous to a cell in certain aspects. Heterologous expression of a CYP enzyme and/or CPR enzyme in a cell can optionally be characterized as providing a heterologous omega-hydroxylase complex to the cell. A heterologous omega-hydroxylase complex comprises one of, or both of, a heterologous CYP enzyme or CPR enzyme.

Alternatively, a CYP enzyme and/or CPR enzyme that is up-regulated in a cell may be native to the cell. A native CYP enzyme and/or CPR enzyme can be up-regulated, for example, using any of the means disclosed above regarding polynucleotide sequence up-regulation. For example, respective polynucleotide sequences encoding these enzymes (operably linked to a promoter sequence) that are native to a cell may be provided to the cell in a stable or transient manner (but the location of the polynucleotide sequences[s] would be located in a non-native site [i.e., heterologous site]). As another example, respective polynucleotide sequences encoding a CYP enzyme and/or CPR enzyme, as they naturally exist in the genome of a cell, can be modified such that the native polynucleotide sequence(s) is/are over-expressed. This can be accomplished, for example, by modifying one or more regulatory elements (e.g., promoter) of gene(s) containing a polynucleotide sequence encoding a CYP enzyme or CPR enzyme.

Two, three, four, or more omega-hydroxylase complexes can optionally be up-regulated in a cell herein by providing two, three, four, or more sets (e.g., copies), respectively, of polynucleotide sequences encoding CYP and/or CPR enzymes. Multiple omega-hydroxylases can be provided to a cell, for example, by introducing (i) copies of polynucleotide sequences encoding CYP and/or CPR enzymes (e.g., yeast cell transformed with two copies of CYP/CPR-encoding sequences) to over-express the same omega-hydroxylase, and/or (ii) sets of polynucleotide sequences encoding CYP and/or CPR enzymes of different omega-hydroxylases (e.g., over-expression of both a murine and a plant omega-hydroxylase). In some embodiments, a cell herein comprises two, or at least two, up-regulated CYP- and CPR-encoding polynucleotide sequences (e.g., VsCYP and VsCPR).

In embodiments in which both a CYP enzyme and a CPR enzyme are up-regulated in a cell herein, polynucleotide sequences encoding these enzymes may be derived from the same species/source. Alternatively, polynucleotide sequences encoding these enzymes may be derived from different species/sources. An example is an embodiment in which a CYP enzyme is encoded by a mammalian sequence, and a CPR enzyme encoded by a plant sequence. Another example is an embodiment in which one of these enzymes (e.g., CYP) is heterologous to a cell, and the other enzyme (e.g., CPR) is native to the cell. In these latter embodiment types in which polynucleotide sequences encoding CYP and CPR enzymes are derived from different species/sources, the resulting omega-hydroxylase (containing differentially sourced CYP and CPR enzyme components) can optionally be characterized as being a chimeric omega-hydroxylase complex.

A CYP enzyme and/or a CPR enzyme herein can be derived from a eukaryote or prokaryote, for example. Examples of such eukaryotes and prokaryotes are disclosed above with regard to the derivation of an ACoS enzyme. A CYP enzyme having both CYP and CPR activities useful herein can be derived from a prokaryote in some aspects. A CYP enzyme and/or a CPR enzyme in some embodiments can be characterized as being microbial (i.e., being derived from: a bacterial cell; protist cell such as an algal cell; fungal cell such as a yeast cell; euglenoid cell; stramenopile cell; or oomycete cell).

In those embodiments in which the omega-hydroxylase complex has CYP and CPR enzyme components derived from the same species or strain (e.g., any of the species/strains disclosed herein such as mouse, rat, human, plant, *Arabidopsis*, common vetch, yeast, *Candida*), such omega-hydroxylase complex can optionally be characterized as being from that species or strain. For example, an omega-hydroxylase complex comprising mouse CYP and CPR enzyme components can optionally be characterized as a mouse omega-hydroxylase complex. Likewise, certain omega-hydroxylase complexes herein can be characterized, respectively, as being a rat, human, plant, *Arabidopsis*, common vetch, yeast, or *Candida* omega-hydroxylase complex, for example.

A CYP enzyme in certain embodiments can be from a particular CYP enzyme subfamily. For example, a CYP enzyme can be from the subfamily CYP4 (e.g., mammalian CYP4 such as CYP4A1 and CYP4A10), CYP86 (e.g., plant CYP86), CYP94 (e.g., plant CYP94 such as CYP94A1), CYP96 (e.g., plant CYP96 such as CYP96A4), CYP52 (e.g., yeast CYP52 such as CYP52A4 and CYP52A1), or CYP102 (e.g., bacterial CYP102).

The amino acid sequence of a CYP enzyme herein can comprise, for example, any of the CYP amino acid sequences disclosed in GenBank Acc. Nos. BAA31435, BAA31437, BAA31439, P16496, P16141, Q12586, EEQ43763, P10615, P30609, P30610, AAO73952, AAO73953, AAO73954, AAO73955, AAO73958, AAO73959, NP_200694, NM_100042, NP_182121, DQ099538, AAD10204, P98188, Q9FMV7, Q9SMP5, Q9ZUX1, NP_200045, XP_002865907, NM_175837, P20816, NP_786936, AAH81771, NP_034141, and Q02928, which are incorporated herein by reference. A variant of any of these CYP amino acid sequences may be used, but should have some of (e.g., at least 30%, 40%, 50%, 60%, 70%, 80%, or 90% of), or all of, the enzymatic activity (refer to above definitions) of the corresponding non-variant CYP enzyme reference. Such a variant CYP enzyme may comprise an amino acid sequence that is at least about 80%, 81%, 82%, 83%, 84%, 85%, 86%, 87%, 88%, 89%, 90%, 91%, 92%, 93%, 94%, 95%, 96%, 97%, 98%, or 99% identical to the amino acid sequence of the corresponding non-variant CYP enzyme reference.

In certain aspects herein, a CYP enzyme can comprise the amino acid sequence of SEQ ID NO:84 (a *C. tropicalis* CYP) or SEQ ID NO:94 (a *V. sativa* CYP). Alternatively, a CYP enzyme herein can comprise an amino acid sequence that is at least about 80%, 81%, 82%, 83%, 84%, 85%, 86%, 87%, 88%, 89%, 90%, 91%, 92%, 93%, 94%, 95%, 96%, 97%, 98%, or 99% identical to any of the foregoing CYP enzyme amino acid sequences, for example. Such a variant CYP enzyme should have some of (e.g., at least about 30%, 40%, 50%, 60%, 70%, 80%, or 90% of), or all of, the enzymatic activity (refer to above definitions) of the corresponding non-variant CYP enzyme reference.

The amino acid sequence of a CPR enzyme herein can comprise, for example, any of the CPR amino acid sequences disclosed in GenBank Acc. Nos. X76226, P37201, X66016, X66017, NM_008898, M12516, and Z26252, which are incorporated herein by reference. A variant of any of these CPR amino acid sequences may be used, but should have some of (e.g., at least 30%, 40%, 50%, 60%, 70%, 80%, or 90% of), or all of, the enzymatic activity (refer to above definitions) of the corresponding non-variant CPR enzyme reference. Such a variant CPR enzyme may comprise an amino acid sequence that is at least about 80%, 81%, 82%, 83%, 84%, 85%, 86%, 87%, 88%, 89%, 90%, 91%, 92%, 93%, 94%, 95%, 96%, 97%, 98%, or 99% identical to the amino acid sequence of the corresponding non-variant CPR enzyme reference.

In certain aspects herein, a CPR enzyme can comprise the amino acid sequence of SEQ ID NO:86 (a *C. tropicalis* CPR) or SEQ ID NO: 96 (a *V. sativa* CPR). Alternatively, a CPR enzyme herein can comprise an amino acid sequence that is at least about 80%, 81%, 82%, 83%, 84%, 85%, 86%, 87%, 88%, 89%, 90%, 91%, 92%, 93%, 94%, 95%, 96%, 97%, 98%, or 99% identical to any of the foregoing CPR enzyme amino acid sequences, for example. Such a variant CPR enzyme should have some of (e.g., at least 30%, 40%, 50%, 60%, 70%, 80%, or 90% of), or all of, the enzymatic activity (refer to above definitions) of the corresponding non-variant CPR enzyme reference.

A recombinant cell in some aspects herein can comprise up-regulation of (1) a fatty alcohol oxidase (FAO enzyme), and/or (2) up-regulation of a fatty alcohol dehydrogenase (FADH enzyme), and/or (3) up-regulation of a fatty aldehyde dehydrogenase (FALDH enzyme). Up-regulation of an FAO and/or FADH provides up-regulated conversion of omega-hydroxy fatty acid to omega-aldo fatty acid in a pathway of long-chain fatty acid omega-oxidation (FIGS. 1 and 2). Up-regulation of an FALDH provides up-regulated conversion of omega-aldo fatty acid to LCDA in a pathway of long-chain fatty acid omega-oxidation (FIGS. 1 and 2).

Up-regulation of FAO, FADH, and/or FALDH enzymes in a recombinant cell herein can be as follows, for example:

(i) at least one FAO enzyme is up-regulated, (ii) at least one FADH enzyme is up-regulated, (iii) at least one FALDH enzyme is up-regulated, (iv) at least one FAO and at least one FADH enzyme are up-regulated, (v) at least one FAO and at least one FALDH enzyme are up-regulated, (vi) at least one FADH and at least one FALDH enzyme are up-regulated, or (vii) at least one FAO, at least one FADH, and at least one FALDH enzyme are up-regulated.

Up-regulation of an FAO, FADH, and/or FALDH enzyme in certain aspects herein can be through up-regulation of (1) a polynucleotide sequence encoding an FAO enzyme, (2) up-regulation of a polynucleotide sequence encoding an FADH enzyme, and/or (3) up-regulation of a polynucleotide sequence encoding an FALDH enzyme. Such up-regulation, which leads to over-expression of an FAO, FADH, and/or FALDH enzyme, can be done by one or more of a variety of methods. For example, an FAO-, FADH-, and/or FALDH-encoding polynucleotide can be provided in multi-copy to a cell, either transiently or stably (such a polynucleotide sequence is operably linked to a promoter sequence [e.g., heterologous promoter]). Providing a polynucleotide sequence in multi-copy may be accomplished by providing one or more copies of the polynucleotide (e.g., at least 1, 2, 3, 4, 5, 6, 7, 8, 9, 10, 15, 20, 25, or 50 copies) to a cell. As another example, an FAO-, FADH-, and/or FALDH-encoding polynucleotide sequence can be up-regulated by operable linkage to a constitutive promoter or strong promoter, either of which can be heterologous. Any of the FAO, FADH and/or FALDH enzyme up-regulations listed in (i)-(vii) above can be via polynucleotide sequence(s) up-regulation.

Polynucleotide sequence up-regulation can be performed, for example, following one or a combination of the over-expression strategies disclosed herein. An individual polynucleotide (e.g., a vector such as a plasmid) encoding an FAO, FADH, or FALDH enzyme may be employed, for example. As another example, a single polynucleotide (e.g., a vector such as a plasmid) comprising two or more FAO, FADH, or FALDH coding sequences may be used; each coding sequence may be comprised in its own expression cassette (e.g., promoter—coding sequence—terminator) or within a bi-cistronic expression cassette, for example.

Up-regulation (e.g., over-expression) of an FAO, FADH, and/or FALDH enzyme in a cell herein may optionally be considered with respect to a suitable control cell. For example, the increased level of an FAO, FADH, and/or FALDH enzyme in a cell herein may be characterized to be at least about 5%, 10%, 20%, 30%, 40%, 50%, 60%, 75%, 80%, 90%, 100%, 150%, 200%, 500%, or 1000% above the expression of the FAO, FADH, and/or FALDH enzyme in a suitable control cell. An example of a suitable control cell is a cell as it existed before it was modified to have up-regulated FAO, FADH, and/or FALDH enzyme expression (e.g., parent cell).

An FAO, FADH, and/or FALDH enzyme can be heterologous to a cell, for example. An example of a heterologous FAO, FADH, or FALDH enzyme can be one that is derived from a species or strain that is different from the species or strain of the cell in which the FAO, FADH, and/or FALDH enzyme is up-regulated. At least one of, two of, or all of an FAO, FADH, and FALDH enzyme are heterologous to a cell in certain aspects (e.g., any of the up-regulations listed in (i)-(vii) above).

Alternatively, an FAO, FADH, and FALDH enzyme that is up-regulated in a cell may be native to the cell. A native FAO, FADH, and FALDH enzyme can be up-regulated, for example, using any of the means disclosed above regarding polynucleotide sequence up-regulation. For example, respective polynucleotide sequences encoding these enzymes (operably linked to a promoter sequence [e.g., heterologous promoter]) that are native to a cell may be provided to the cell in a stable or transient manner (but the location of the polynucleotide sequences[s] would be located in a non-native site [i.e., heterologous site]). As another example, respective polynucleotide sequences encoding FAO, FADH, and/or FALDH enzymes, as naturally existing in the genome of a cell, can be modified such that the native polynucleotide sequence(s) is/are over-expressed. This can be accomplished, for example, by modifying one or more regulatory elements (e.g., promoter) of gene(s) containing a polynucleotide sequence encoding an FAO, FADH, and/or FALDH enzyme.

One, two, three, four, or more FAO, FADH, and/or FALDH enzymes can optionally be up-regulated in a cell herein by providing one, two, three, four, or more sets (e.g., copies), respectively, of polynucleotide sequences encoding FAO, FADH, and/or FALDH enzymes. Multiple FAO, FADH, and/or FALDH enzymes can be provided to a cell, for example, by introducing (i) copies of polynucleotide sequences encoding FAO, FADH, and/or FALDH enzymes (e.g., cell transformed with two copies of FAO-, FADH-, and/or FALDH-encoding sequences) to over-express the same FAO, FADH, and/or FALDH enzyme, and/or (ii) sets of polynucleotide sequences encoding different FAO, FADH, and/or FALDH enzymes (e.g., over-expression of both a murine FAO and a plant FAO). In some embodiments, a cell herein comprises three, or at least three, different up-regulated FAO-encoding polynucleotide sequences (e.g., CtFAO1M, CcFAO1, and CcFAO2).

An FAO, FADH, and/or FALDH enzyme herein can be derived from a eukaryote or prokaryote, for example. Examples of such eukaryotes and prokaryotes are disclosed above with regard to the derivation of an ACoS enzyme. An FAO, FADH, and/or FALDH enzyme in some embodiments can be characterized as being microbial (i.e., being derived from: a bacterial cell; protist cell such as an algal cell; fungal cell such as a yeast cell; euglenoid cell; stramenopile cell; or oomycete cell).

An FAO, FADH, and/or FALDH enzyme can be from a particular enzyme family or subfamily. For example, an FAO enzyme can be an FAO1, FAO2, FAO3, or FAO4 enzyme. An FADH enzyme can be an ADH, ADH1, ADH2, ADH3, FADH1, FADH2, or FADH3 enzyme, for example. An FALDH enzyme can be an FALDH1, FALDH2, FALDH3, or FALDH4 enzyme, for example.

The amino acid sequence of an FAO enzyme herein can comprise, for example, any of the amino acid sequences disclosed in GenBank Acc. Nos. XP_001389382, XP_002867943, Q9ZWB9, CAA18625, AEE76762.1, AEE84174, AEE85508, XP_007158083, XP_007132926, XP_003540021, XP_003554295, XP_003534338, XP_009102621, EAK93199, CAB75351, CAB75352, XP_002422236, CCG23291, CCG23293, CCE42799, CCE42800, AAS46878, AAS46879, AAS46880, CAB75353, EGV61357, XP_459506, EFX04185, JX879776, XP_001525361, CAP15762.1, KEH23950, EGW33941, and XP_001386087, which are incorporated herein by reference. A variant of any of these FAO amino acid sequences may be used, but should have some of (e.g., at least 30%, 40%, 50%, 60%, 70%, 80%, or 90% of), or all of, the enzymatic activity (refer to above definitions) of the corresponding non-variant FAO enzyme reference. Such a variant FAO enzyme may comprise an amino acid sequence that is at least about 80%, 81%, 82%, 83%, 84%, 85%, 86%, 87%, 88%, 89%, 90%, 91%, 92%, 93%, 94%, 95%, 96%, 97%, 98%, or 99% identical to the amino acid sequence of the corresponding non-variant FAO enzyme reference.

In certain aspects herein, an FAO enzyme can comprise the amino acid sequence of SEQ ID NO:100 (a *C. tropicalis* FAO), SEQ ID NO:102 (a *C. cloacae* FAO), or SEQ ID NO:104 (a *C. cloacae* FAO). Alternatively, an FAO enzyme herein can comprise an amino acid sequence that is at least about 80%, 81%, 82%, 83%, 84%, 85%, 86%, 87%, 88%, 89%, 90%, 91%, 92%, 93%, 94%, 95%, 96%, 97%, 98%, or 99% identical to any of the foregoing FAO enzyme amino acid sequences, for example. Such a variant FAO enzyme should have some of (e.g., at least about 30%, 40%, 50%, 60%, 70%, 80%, or 90% of), or all of, the enzymatic activity (refer to above definitions) of the corresponding non-variant FAO enzyme reference.

The amino acid sequence of an FADH (ADH) enzyme herein can comprise, for example, any of the amino acid sequences disclosed in GenBank Acc. Nos. NP_982625, EEQ46516, EEQ42383, XM_712556, BAD12482, CD36_07850, ABD60084, ABD60084, XP_002619012, ADM08005, ADM08008, XP_003870523, AFD29185, XP_006683745, XP_002546635, XP-002550829, GU056282, GU056283, GU056286, GU056287, XP_460537, WP_024173607, AHC53987, AAP51040, XP_001524974, AAP51047, AAP51048, AAP51049, XP_001485610, ESW95881, AFH35136, KGK40277, EJS44121, AAP51043, EHN00693, EJT43588, XP_007377163, AGO10074, CAA73690, XP_001382922, XP_003686595, XP_001642939, CCH41227, XP_503282, F2Z678, XP_500127, XP_500087, and XP_503672, which are incorporated herein by reference. A variant of any of these amino acid sequences may be used, but should have some of (e.g., at least 30%, 40%, 50%, 60%, 70%, 80%, or 90% of), or all of, the enzymatic activity (refer to above definitions) of the corresponding non-variant FADH (ADH) enzyme reference. Such a variant FADH (ADH) enzyme may comprise an amino acid sequence that is at least about 80%, 81%, 82%, 83%, 84%, 85%, 86%, 87%, 88%, 89%, 90%, 91%, 92%, 93%, 94%, 95%, 96%, 97%, 98%, or 99% identical to the amino acid sequence of the corresponding non-variant FADH (ADH) enzyme reference.

The amino acid sequence of an FALDH enzyme herein can comprise, for example, any of the amino acid sequences disclosed in GenBank Acc. Nos. XP_719028, KGQ84508, KGQ98444, XP_002421401, EMG46594, EMG47675, XP_003868193, XP_002550173, XP_002550712, XP_505802, XP_500380, XP_503981, BAP82457, XP_500179, and CCH41136, which are incorporated herein by reference. A variant of any of these FALDH amino acid sequences may be used, but should have some of (e.g., at least 30%, 40%, 50%, 60%, 70%, 80%, or 90% of), or all of, the enzymatic activity (refer to above definitions) of the corresponding non-variant FALDH enzyme reference. Such a variant FALDH enzyme may comprise an amino acid sequence that is at least about 80%, 81%, 82%, 83%, 84%, 85%, 86%, 87%, 88%, 89%, 90%, 91%, 92%, 93%, 94%, 95%, 96%, 97%, 98%, or 99% identical to the amino acid sequence of the corresponding non-variant FALDH enzyme reference.

In certain aspects herein, an FALDH enzyme can comprise the amino acid sequence of SEQ ID NO:91 (a *C. tropicalis* FALDH), or an amino acid sequence that is at least about 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO:91. Such a variant FALDH enzyme should have some of (e.g., at least about 30%, 40%, 50%, 60%, 70%, 80%, or 90% of), or all of, the enzymatic activity (refer to above definitions) of the FALDH enzyme of SEQ ID NO:91.

In some embodiments, a recombinant cell can comprise down-regulation of a peroxisome biogenesis factor (Pex protein). For example, a recombinant cell can comprise down-regulation of an endogenous polynucleotide sequence encoding a peroxisome biogenesis factor-3 (Pex3 protein). Though not intending to be held to any particular theory or mechanism, it is contemplated that Pex protein down-regulation results in a blocked or reduced level of beta-oxidation in a recombinant cell by virtue of impairing normal peroxisome function (e.g., peroxisome membrane function). A blocked or reduced level of beta-oxidation is contemplated to result in re-directing fatty acids to an omega-oxidation pathway, in which the fatty acids serve as substrate for LCDA synthesis (refer to FIGS. 1 and 2). Expression of one or more of the following Pex proteins can be down-regulated in certain embodiments: Pex1p, Pex2p, Pex3p, Pex3Bp, Pex4p, Pex5p, Pex5Bp, Pex5Cp, Pex5/20p, Pex6p, Pex7p, Pex8p, Pex10p, Pex12p, Pex13p, Pex14p, Pex15p, Pex16p, Pex17p, Pex14/17p, Pex18p, Pex19p, Pex20p, Pex21p, Pex21Bp, Pex22p, Pex22p-like and Pex26p.

Examples of Pex3 proteins that can be down-regulated, such as by down-regulating a polynucleotide sequence encoding such protein, are disclosed in GenBank Acc. Nos. CAG78565 (*Y. lipolytica*, also disclosed herein as SEQ ID NO:107), NP_010616.3 (*S. cerevisiae* S288), AHY75303.1 (*S. cerevisiae* YJM993), EWH19033.1 (*S. cerevisiae* P283), EWG96624.1 (*S. cerevisiae* R103), EWG87344.1 (*S. cerevisiae* R008), EGA75546.1 (*S. cerevisiae* AWRI796), CAB10141 (*S. pombe*), EKD00377.1 (*Trichosporon asahii*), AAC49471 (*Hansenula polymorpha*), XP_569751.1 (*Cryptococcus neoformans*), XP_003193133.1 (*Cryptococcus gattii*), XP_713871.1 (*Candida albicans*), CCG21168.1 (*Candida orthopsilosis*), CAX44998.1 (*Candida dubliniensis*), CCA39066.1 (*Komagataella pastoris*), Q6BK00.1 (*Debaryomyces hansenii*), 094227.1 (*Kluyveromyces lactis*), Q01497.1 (*Ogataea angusta*), ABN67699.2 (*Scheffersomyces stipitis*), AAS52217.1 (*Ashbya gossypii*), and CCH44061.1 (*Wickerhamomyces ciferrii*), which are incorporated herein by reference. It would be understood that each of these Pex3 proteins would be targeted for down-regulation in the respective cell that expresses the Pex3 protein (for instance, an *S. cerevisiae* Pex3 protein would be down-regulated in *S. cerevisiae*).

A Pex3 protein comprising an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to any of the foregoing Pex3 proteins, for example, can be down-regulated in a cell in other embodiments. For example, a *Yarrowia* cell, or any other type of yeast cell herein, that expresses a Pex3 protein comprising an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO:107 can be modified to have down-regulated expression of such a Pex3 protein.

In some embodiments, such as with a *Yarrowia* cell, a down-regulated endogenous polynucleotide sequence may encode a Pex3 protein that comprises an amino acid sequence that is at least 90%, 91%, 92%, 93%, 94%, 95%, 96%, 97%, 98%, or 99% identical to SEQ ID NO:107. In certain other embodiments, a down-regulated endogenous polynucleotide sequence encoding a Pex3 protein comprises a nucleotide sequence that is at least 90%, 91%, 92%, 93%, 94%, 95%, 96%, 97%, 98%, or 99% identical to SEQ ID NO:106.

Down-regulation of an endogenous polynucleotide sequence encoding a Pex protein such as Pex3 can be due to a mutation of the polynucleotide sequence in certain aspects herein. Such a mutation can be a substitution, deletion, or insertion, for instance.

A deletion can remove (i) one or more nucleotides from an open reading frame encoding a Pex protein (i.e., a PEX open reading frame), and/or (ii) one or more nucleotides of a non-protein-coding sequence located within 500, or 1000, base pairs of the 5'-end of an open reading frame encoding a Pex protein, for example. An insertion in certain embodiments can occur within (i) an open reading frame encoding a Pex protein, or (ii) a non-protein-coding sequence located within 500, or 1000, base pairs of the 5'-end of an open reading frame encoding a Pex protein. Other types of mutations can also be used to down-regulate an endogenous polynucleotide sequence encoding a Pex protein, if desired. For example, one or more point mutations, which exchange a single nucleotide for another (i.e., a nucleotide substitution), may be used accordingly.

Example 6 discloses deleting an endogenous polynucleotide sequence in *Y. lipolytica* encoding a Pex3 protein. In one aspect of this work, the PEX3 open reading frame was removed by homologous recombination-based targeting, and replaced with a URA3 cassette using an appropriate donor DNA. This replacement rendered a down-regulated (disrupted, or knocked-out) sequence comprising SEQ ID NO:71, which comprises portions of 5'- and 3'-non-coding PEX3 homology arm sequences (100-bp of each) flanking a LoxP-flanked URA3 cassette. Another aspect of this work involved removing the URA3 cassette by expressing Cre recombinase (stimulated recombination between the LoxP sequences, leaving one LoxP sequence) to render a down-regulated (disrupted, or knocked-out) sequence comprising SEQ ID NO:72. SEQ ID NO:72 comprises portions of 5'- and 3'-non-coding PEX3 homology arm sequences (100-bp of each) flanking one LoxP sequence. Thus, certain embodiments herein are drawn to a recombinant *Yarrowia* yeast cell comprising a down-regulated endogenous polynucleotide sequence encoding a Pex3 protein, wherein this down-regulation is due to a disruption (knock-out) of the endogenous polynucleotide sequence encoding the Pex3 protein; this disruption (knock-out) comprises SEQ ID NO:71 or 72, or a nucleotide sequence that is at least about 90%, 91%, 92%, 93%, 94%, 95%, 96%, 97%, 98%, or 99% identical to SEQ ID NO:71 or 72.

A mutation in a codon of a PEX open reading frame that does not change the amino acid encoded by the codon (i.e., a silent mutation) typically is not a mutation as described herein that down-regulates a PEX polynucleotide. Nor, typically, is it a mutation that changes the amino acid encoded by a codon to a related amino acid that does not alter the wild type function of a Pex protein (e.g., conservative mutation). Related amino acids in certain embodiments have side groups that share structure and/or charge, and can be grouped as follows: aliphatic (glycine, alanine, valine, leucine, isoleucine), aromatic (phenylalanine, tyrosine, tryptophan), hydroxyl group-containing (serine, threonine), sulfur group-containing (cysteine, methionine), carboxylic acid group-containing (aspartate, glutamate), amide group-containing (asparagine, glutamine), and amino group-containing (histidine, lysine, arginine). However, any of such mutations (silent mutation or conservative mutation) that down-regulate transcription and/or translation of a PEX polynucleotide (e.g., by inhibiting trans-activating transcription and/or translation factors) typically are considered herein as mutations that down-regulate a PEX polynucleotide.

It would be understood by one of ordinary skill in the art that any of the disclosed mutations to an endogenous polynucleotide sequence encoding a Pex protein can be determined to constitute a down-regulating mutation by referring to the corresponding endogenous Pex protein-encoding sequence in a suitable control cell. For example, a PEX polynucleotide sequence in a modified cell can be compared to the endogenous corresponding PEX polynucleotide sequence of a counterpart cell from which the modified cell was derived (e.g., parent cell).

Down-regulation of an endogenous polynucleotide sequence encoding a Pex protein in certain embodiments is a reduction in the transcription and/or translation of the endogenous polynucleotide sequence by at least about 20%, 30%, 40%, 50%, 60%, 70%, 80%, 90%, 95%, or 100% relative to the transcription and/or translation of a corresponding Pex protein-encoding polynucleotide sequence in a suitable control cell (e.g., parent cell). In other embodiments, down-regulation of an endogenous polynucleotide sequence encoding a Pex protein is reflected by a reduction of at least about 20%, 30%, 40%, 50%, 60%, 70%, 80%, 90%, 95%, or 100% in the function (e.g., protein localization and/or activity) of the encoded Pex protein relative to the function of a corresponding Pex protein in a suitable control cell (e.g., parent cell).

Though not intending to be held to any particular theory or mechanism, it is contemplated that down-regulating a polynucleotide sequence encoding a Pex protein in a recombinant cell herein leads to a blocked or reduced level of beta-oxidation in the recombinant cell by virtue of impairing normal peroxisome function (e.g., peroxisome membrane function). Beta-oxidation can be reduced by at least about 40%, 50%, 60%, 70%, 80%, 90%, 95%, or 100%, for example, in a cell comprising a down-regulated Pex protein-encoding polynucleotide sequence (compared to a suitable control cell, such as a parent cell without the subject down-regulation.

In certain aspects herein, down-regulating a polynucleotide encoding a Pex3 protein (e.g., SEQ ID NO:107), but not one encoding a Pex10 protein (e.g., SEQ ID NO:108) or a Pex16 protein (e.g., SEQ ID NO:109), is suitable for preparing a recombinant yeast cell (e.g., *Y. lipolytica*, refer to Example 14) that can produce one or more LCDA products from a long-chain fatty acid-comprising substrate. Thus, a yeast cell in some embodiments does not comprise a down-regulated Pex10 protein-encoding polynucleotide, Pex16 protein-encoding polynucleotide, and/or a down-regulated polynucleotide encoding a Pex-1, -2, -4, -5, -6, -7, -8, -12, -13, -14, -15, -17, -18, -19, -20, -21, -22, or -26 protein. Examples herein of a Pex10 protein ora Pex16 protein comprise SEQ ID NO:108 or SEQ ID NO:109, respectively, or an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO:108 or SEQ ID NO:109.

Down-regulation of a polynucleotide sequence encoding a Pex3 protein can be, in some embodiments, the only modification to a peroxisomal protein-encoding polynucleotide sequence necessary for a recombinant yeast cell to produce an LCDA product. Indeed, Example 14 below demonstrates that recombinant yeast having only a down-regulated PEX3 polynucleotide, but no down-regulation of any other protein directly involved in peroxisome function (e.g., peroxisome development and/or maintenance; metabolic pathways such as beta-oxidation occurring in peroxisomes), are able to produce LCDA from a fatty acid-comprising substrate. Thus, certain embodiments disclosed herein are drawn to recombinant yeast cells in which a down-regulated PEX3 polynucleotide is the only modification to a polynucleotide encoding a peroxisomal protein.

A peroxisomal protein in certain aspects can be one that plays a role in developing and/or maintaining peroxisome structure/function, such as a Pex protein (e.g., Pex-1, -2, -3, -4, -5, -6, -7, -8, -12, -13, -14, -15, -16, -17, -18, -19, -20, -21, -22, and/or -26 protein). Another example of a peroxisomal protein herein is one that plays a role in a metabolic activity carried out in peroxisomes, such as beta-oxidation. Examples of peroxisomal proteins involved in beta-oxidation include Pox proteins (e.g., Pox-1, -2, -3, -4, -5, -6). A yeast cell in some aspects herein does not have down-regulated expression of a Pex protein other than Pex3, and/or down-regulated expression of a Pox protein. In some other aspects, a yeast cell does not have down-regulated expression of (i) Pox-1, -2, -3, -4, -5 and -6 proteins; (ii) Pox-1, -2, -3, -4 and -5 proteins; (iii) Pox-2, -3, -4 and -5 proteins; (iv) Pox-2, -3 and -5 proteins; or (v) Pox-4 and -5 proteins.

Though it is contemplated that a Pex3 protein is the only Pex protein for down-regulation in a recombinant yeast cell herein, one or more additional Pex proteins may optionally be down-regulated. Any of the Pex-proteins listed herein, for example, can be down-regulated; particular examples of such other Pex proteins are listed in Table 4 of U.S. Pat. Appl. Publ. No. 2009/0117253, which is incorporated herein by reference. For instance, a Pex10 and/or Pex16 protein can be down-regulated in addition to down-regulating a Pex3 protein.

A recombinant cell as presently disclosed can, in some embodiments, comprise down-regulation of an endogenous polynucleotide sequence encoding a peroxisomal acyl-CoA oxidase (Pox protein). For example, one or more of Pox-1, -2, -3, -4, -5, or -6 may be suitable for down-regulation. Down-regulating any one, two, three, four, five, or six of these Pox proteins, or any combination thereof can be employed, as desired. Examples of combinations of Pox proteins for down-regulation herein include: (i) Pox-2, -3, -4; (ii) Pox-2, -3, -4, -5; (iii) Pox-1, -2, -3, -4, -5; (iv) Pox-1, -2, -3, -4, -5, -6; (v) Pox-1, -2, -3, -4; and (vi) Pox-2, -3, -4, -5, -6. As an additional example, a recombinant cell can comprise down-regulation of acyl-CoA oxidase-2, -3, and/or -4 enzymes. Down-regulation of a one or more Pox proteins herein can be performed using any of the strategies presently disclosed that are useful for down-regulating Pex3 protein expression, for example (e.g., deletion, insertion, other type of mutation). Also, the level of such down-regulation and the manner in which down-regulation is determined can follow those relevant embodiments disclosed above regarding down-regulation of Pex3 protein expression. A recombinant cell optionally does not comprise down-regulation of a Pox protein in some aspects.

Any of the aforementioned Pox proteins can be down-regulated herein, for instance, by down-regulating one or more endogenous Pox protein-encoding polynucleotide sequences. Down-regulation of an endogenous polynucleotide sequence encoding a Pox protein in certain embodiments is a reduction in the transcription and/or translation of the endogenous polynucleotide sequence by at least about 20%, 30%, 40%, 50%, 60%, 70%, 80%, 90%, 95%, or 100% relative to the transcription and/or translation of a corresponding Pox protein-encoding polynucleotide sequence in a suitable control cell (e.g., parent cell). In other embodiments, down-regulation of an endogenous polynucleotide sequence encoding a Pox protein is reflected by a reduction of at least about 20%, 30%, 40%, 50%, 60%, 70%, 80%, 90%, 95%, or 100% in the function (e.g., protein localization and/or activity) of the encoded Pox protein relative to the function of a corresponding Pox protein in a suitable control cell (e.g., parent cell).

Examples of Pox4 proteins that can be down-regulated herein, such as by down-regulating a polynucleotide sequence encoding such protein, are disclosed in GenBank Acc. Nos. CAG80078 (*Y. lipolytica*, also disclosed herein as SEQ ID NO:111), P06598 (*Candida tropicalis*), P05335

(*Candida maltose*), KHC52040 (*Candida albicans*), EIF46613 (*Brettanomyces bruxellensis*), XP_007376225 (*Spathaspora passalidarum*), XP_001526373 (*Lodderomyces elongisporus*), XP_001387042 (*Scheffersomyces stipitis*), XP_011276972 (*Wickerhamomyces ciferrii*), and ENH66703 (*Fusarium oxysporum*), which are incorporated herein by reference. It would be understood that each of these Pox4 proteins would be targeted for down-regulation in the respective cell that expresses the Pox4 protein (for instance, a *C. tropicalis* Pox4 protein would be down-regulated in *C. tropicalis*).

A Pox4 protein comprising an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to any of the foregoing Pox4 proteins, and which has Pox4 activity, can be down-regulated in a cell in certain embodiments. For example, a *Yarrowia* cell, or any other type of cell herein, that expresses a Pox4 protein comprising an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO:111 can be modified to have down-regulated expression of such a Pox4 protein.

Example 6 discloses deleting an endogenous polynucleotide sequence in *Y. lipolytica* encoding a Pox4 protein. In one aspect of this work, the POX4 open reading frame was removed by homologous recombination-based targeting. This targeting rendered a down-regulated (disrupted, or knocked-out) sequence comprising SEQ ID NO:74, which comprises certain portions of 5' and 3' POX4 homology arm sequences. Specifically, base positions 1-455 and 464-957 of SEQ ID NO:74 correspond, respectively, with certain 5' and 3' POX4 gene sequences. Thus, certain embodiments herein are drawn to a recombinant *Yarrowia* yeast cell comprising a down-regulated endogenous polynucleotide sequence encoding a Pox4 protein, wherein this down-regulation is due to a disruption (knock-out) of the endogenous polynucleotide sequence encoding the Pox4 protein; this disruption (knock-out) comprises SEQ ID NO:74, or a nucleotide sequence that is at least about 90%, 91%, 92%, 93%, 94%, 95%, 96%, 97%, 98%, or 99% identical to SEQ ID NO:74.

Examples of Pox2 proteins that can be down-regulated herein, such as by down-regulating a polynucleotide sequence encoding such protein, are disclosed in GenBank Acc. Nos. Q00468.1 (*Candida maltose*), P11356.3 (*Candida tropicalis*), 074935.1 (*Y. lipolytica*, also disclosed herein as SEQ ID NO:79), CCA37459.1 (*Komagataella pastoris*), CAX42707.1 (*Candida dubliniensis*), and XP_721613.1 (*Candida albicans*), which are incorporated herein by reference. It would be understood that each of these Pox2 proteins would be targeted for down-regulation in the respective cell that expresses the Pox2 protein.

A Pox2 protein comprising an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to any of the foregoing Pox2 proteins, and which has Pox2 activity, can be down-regulated in a cell in certain embodiments. For example, a *Yarrowia* cell, or any other type of cell herein, that expresses a Pox2 protein comprising an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO:79 can be modified to have down-regulated expression of such a Pox2 protein.

Examples of Pox3 proteins that can be down-regulated herein, such as by down-regulating a polynucleotide sequence encoding such protein, comprise an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO:81.

A recombinant cell can have reduced lipid (oil) synthesis and/or storage capability in certain aspects of the present disclosure. Lipid synthesis and/or storage capability can be reduced by at least about 40%, 50%, 60%, 70%, 80%, 90%, 91%,92%, 93%, 94%, 95%, 96%, 97%, 98%, 99%, or 100%, for example (compared to a suitable control cell, such as a parent cell). Reduced lipid synthesis and/or storage in a cell can be determined using any number of means known in the art such as chromatographic analysis of cell lipid content (e.g., gas chromatography) and/or certain visual analyses (e.g., microscopic assessment of lipid bodies).

A recombinant cell with reduced lipid synthesis and/or storage capability can have, for example, less than about 50%, 25%, 10%, 5%, 4%, 3%, 2.5%, 2.0%, 1.5%, or 1.0%, total lipids measured as a percent of dry cell weight (DCW).

An endogenous activity that converts diacylglycerol (DAG) into triacylglycerol (TAG) can be reduced in some embodiments to effect a reduction in lipid synthesis and/or storage capability. This reflects that TAG generally represents a major lipid storage molecule in cells. An example of reducing TAG synthesis can be by down-regulating at least one endogenous polynucleotide sequence encoding a diacylglycerol acyltransferase (DGAT). Examples of DGATs herein for down-regulation include DGAT1 and DGAT2. Either or both DGAT1 and DGAT2 can be down-regulated in some aspects herein. Down-regulation of DGAT1 and/or DGAT2 can be performed using any of the strategies disclosed herein useful for down-regulating Pex3 protein expression, for example (e.g., deletion, insertion, other type of mutation). Also, the level of such down-regulation and the manner in which down-regulation is determined can follow those relevant embodiments disclosed above regarding down-regulation of Pex3 protein expression.

An example of a DGAT1 enzyme that can be down-regulated herein is SEQ ID NO:113, which represents a *Y. lipolytica* DGAT1 enzyme. A *Yarrowia* cell, or any other cell herein, that expresses a DGAT1 enzyme comprising an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% A identical to SEQ ID NO:113 can be modified to have down-regulated expression of such a DGAT1 enzyme. As another example, a *Yarrowia* cell, or any other cell herein, that expresses an enzyme having at least 80%, 90%, 95%, or 100% the activity of the DGAT1 of SEQ ID NO:113 can be modified to have down-regulated expression of such a DGAT1 enzyme.

An example of a DGAT2 enzyme that can be down-regulated herein is SEQ ID NO:115, which represents a *Y. lipolytica* DGAT2 enzyme. A *Yarrowia* cell, or any other cell herein, that expresses a DGAT2 enzyme comprising an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% A identical to SEQ ID NO:115 can be modified to have down-regulated expression of such a DGAT2 enzyme. As another example, a *Yarrowia* cell, or any other cell herein, that expresses an enzyme having at least 80%, 90%, 95%, or 100% the activity of the DGAT2 of SEQ ID NO:115 can be modified to have down-regulated expression of such a DGAT2 enzyme.

A DGAT enzyme herein can be down-regulated, for instance, by down-regulating one or more endogenous DGAT-encoding polynucleotide sequences. Down-regulation of an endogenous polynucleotide sequence encoding a DGAT in certain embodiments is a reduction in the transcription and/or translation of the endogenous polynucleotide sequence by at least about 20%, 30%, 40%, 50%, 60%, 70%, 80%, 90%, 95%, or 100% relative to the transcription and/or translation of a corresponding DGAT-encoding polynucleotide sequence in a suitable control cell (e.g., parent cell). In other embodiments, down-regulation of an endogenous polynucleotide sequence encoding a DGAT is reflected by a reduction of at least about 20%, 30%, 40%, 50%, 60%, 70%, 80%, 90%, 95%, or 100% in the function (e.g., protein localization and/or activity) of the encoded DGAT relative to the function of a corresponding DGAT in a suitable control cell (e.g., parent cell).

Other types of acyltransferases can be down-regulated in a recombinant cell herein to effect a reduction in lipid synthesis and/or storage capability, if desired. Such down-regulation can be independent of, or in addition to, down-regulating a DGAT1 and/or DGAT2 enzyme. Other acyltransferases that may optionally be targeted for down-regulation include lecithin-cholesterol acyltransferase (EC 2.3.1.43; also referred to as phosphatidylcholine-sterol O-acyltransferase) and phospholipid:diacylglycerol acyltransferase (PDAT, EC 2.3.1.158), both of which can catalyze, in general, the conversion of phospholipid and DAG to lysophospholipid and TAG.

A recombinant microbial cell herein can refer to a fungal cell (e.g., yeast cell), prokaryotic cell, protist cell (e.g., algal cell), euglenoid cell, stramenopile cell, or oomycete cell, for example. A prokaryotic cell herein can refer to a bacterial cell or archaeal cell, for example. A yeast cell can be any yeast as presently disclosed. For example, a yeast can be a *Yarrowia* (e.g., *Y. lipolytica*), *Candida* (e.g., *C. tropicalis*), *Debaryomyces* (e.g., *D. hansenii*), *Saccharomyces* (e.g., *S. cerevisiae*), *Schizosaccharomyces* (e.g., *S. pombe*), or *Pichia* (e.g., *P. pastoris*) yeast species.

A fungal cell herein can be a yeast (e.g., below) or of any other fungal type such as a filamentous fungus. For instance, a fungus herein can be a Basidiomycetes, Zygomycetes, Chytridiomycetes, or Ascomycetes fungus. Examples of filamentous fungi herein include those of the genera *Trichoderma* (e.g., *T. reesei*), *Chrysosporium, Thielavia, Neurospora* (e.g., *N. crassa, N. sitophila*), *Cryphonectria* (e.g., *C. parasitica*), *Aureobasidium* (e.g., *A. pullulans*), *Filibasidium, Piromyces, Cryptococcus, Acremonium, Tolypocladium, Scytalidium, Schizophyllum, Sporotrichum, Penicillium* (e.g., *P. bilaiae, P. camemberti, P. candidum, P. chrysogenum, P. expansum, P. funiculosum, P. glaucum, P. marneffei, P. roqueforti, P. verrucosum, P. viridicatum*), *Gibberella* (e.g., *G. acuminata, G. avenacea, G. baccata, G. circinata, G. cyanogena, G. fujikuroi, G. intricans, G. pulicaris, G. stilboides, G. tricincta, G. zeae*), *Myceliophthora, Mucor* (e.g., *M. rouxii, M. circinelloides*), *Aspergillus* (e.g., *A. niger, A. oryzae, A. nidulans, A. flavus, A. lentulus, A. terreus, A. clavatus, A. fumigatus*), *Fusarium* (e.g., *F. graminearum, F. oxysporum, F. bubigenum, F. solani, F. oxysporum, F. verticillioides, F. proliferatum, F. venenatum*), and *Humicola*, and anamorphs and teleomorphs thereof. The genus and species of fungi herein can be defined, if desired, by morphology as disclosed in Barnett and Hunter (*Illustrated Genera of Imperfect Fungi, 3rd Edition*, Burgess Publishing Company, 1972).

A yeast in certain aspects herein can be one that reproduces asexually (anamorphic) or sexually (teleomorphic). While yeast herein typically exist in unicellular form, certain types of these yeast may optionally be able to form pseudohyphae (strings of connected budding cells). In still further aspects, a yeast may be haploid or diploid, and/or may have the ability to exist in either of these ploidy forms.

Examples of yeast herein include conventional yeast and non-conventional yeast. Conventional yeast herein include species of the genera *Saccharomyces* (e.g., *S. cerevisiae*, which is also known as budding yeast, baker's yeast, and/or brewer's yeast; *S. bayanus; S. boulardii; S. bulderi; S. cariocanus; S. cariocus; S. chevalieri; S. dairenensis; S. ellipsoideus; S. eubayanus; S. exiguus; S. florentinus; S. kluyveri; S. martiniae; S. monacensis; S. norbensis; S. paradoxus; S. pastorianus; S. spencerorum; S. turicensis; S. unisporus; S. uvarum; S. zonatus*) and *Schizosaccharomyces* (e.g., *S. pombe*, which is also known as fission yeast; *S. cryophilus; S. japonicus; S. octosporus*), for example.

A non-conventional yeast herein is not a conventional yeast such as a *Saccharomyces* (e.g., *S. cerevisiae*) or *Schizosaccharomyces* (e.g., *S. pombe*) species. A non-conventional yeast herein can be cultivated following any means known in the art, such as described in *Non-Conventional Yeasts in Genetics, Biochemistry and Biotechnology: Practical Protocols* (K. Wolf, K. D. Breunig, G. Barth, Eds., Springer-Verlag, Berlin, Germany, 2003), *Yeasts in Natural and Artificial Habitats* (J. F. T. Spencer, D. M. Spencer, Eds., Springer-Verlag, Berlin, Germany, 1997), and/or *Yeast Biotechnology: Diversity and Applications* (T. Satyanarayana, G. Kunze, Eds., Springer, 2009), all of which are incorporated herein by reference.

Non-limiting examples of non-conventional yeast herein include yeasts of the following genera: *Yarrowia, Pichia, Schwanniomyces, Kluyveromyces, Arxula, Trichosporon, Candida, Ustilago, Torulopsis, Zygosaccharomyces, Trigonopsis, Cryptococcus, Rhodotorula, Phaffia, Sporobolomyces, Pachysolen*, and *Moniliella*. A suitable example of a *Yarrowia* species is *Y. lipolytica*. Suitable examples of *Pichia* species include *P. pastoris* (also known as *Komagataella pastoris*), *P. methanolica, P. stipitis, P. anomala* and *P. angusta* (also known as *Hansenula polymorpha*). Suitable examples of *Schwanniomyces* species include *S. casteffii, S. alluvius, S. hominis, S. occidentalis, S. capriottii, S. etchellsii, S. polymorphus, S. pseudopolymorphus, S. vanrijiae* and *S. yamadae*. Suitable examples of *Kluyveromyces* species include *K. lactis, K. marxianus, K. fragilis, K. drosophilarum, K. thermotolerans, K. phaseolosporus, K. vanudenii, K. waltii, K. africanus* and *K. polysporus*. Suitable examples of *Arxula* species include *A. adeninivorans* and *A. terrestre*. Suitable examples of *Trichosporon* species include *T. cutaneum, T. capitatum, T. inkin* and *T. beemeri*. Suitable examples of *Candida* species include *C. albicans, C. ascalaphidarum, C. amphixiae, C. antarctica, C. apicola, C. argentea, C. atlantica, C. atmosphaerica, C. blattae, C. bromeliacearum, C. carpophila, C. carvajalis, C. cerambycidarum, C. chauliodes, C. corydali, C. dosseyi, C. dubliniensis, C. ergatensis, C. fructus, C. glabrata, C. fermentati, C. guilliermondii, C. haemulonii, C. insectamens, C. insectorum, C. intermedia, C. jeffresii, C. kefyr, C. keroseneae, C. krusei, C. lusitaniae, C. lyxosophila, C. maltosa, C. marina, C. membranifaciens, C. milleri, C. mogii, C. oleophila, C. oregonensis, C. parapsilosis, C. quercitrusa, C. rugosa, C. sake, C. shehatea, C. temnochilae, C. tenuis, C. theae, C. tolerans, C. tropicalis, C. tsuchiyae, C. sinolaborantium, C. sojae, C. subhashii, C. viswanathii, C. utilis, C. ubatubensis* and *C. zemplinina*. Suitable examples of *Ustilago* species include *U. avenae, U. esculenta, U. hordei, U. maydis, U. nuda* and *U. tritici*. Suitable examples of *Torulopsis* species include *T. geochares, T. azyma, T. glabrata* and *T. candida*. Suitable examples of *Zygosaccharomyces* species include *Z. bailii, Z. bisporus, Z. cidri, Z. fermentati, Z. florentinus, Z. kombuchaensis, Z. lentus, Z. mellis, Z. microellipsoides, Z. mrakii, Z. pseudorouxii* and *Z. rouxii*. Suitable examples of

*Trigonopsis* species include *T. variabilis*. Suitable examples of *Cryptococcus* species include *C. laurentii, C. albidus, C. neoformans, C. gattii, C. uniguttulatus, C. adeliensis, C. aerius, C. albidosimilis, C. antarcticus, C. aquaticus, C. ater, C. bhutanensis, C. consortionis, C. curvatus, C. phenolicus, C. skinneri, C. terreus* and *C. vishniacci*. Suitable examples of *Rhodotorula* species include *R. acheniorum, R. tula, R. acuta, R. americana, R. araucariae, R. arctica, R. armeniaca, R. aurantiaca, R. auriculariae, R. bacarum, R. benthica, R. biourgei, R. bogoriensis, R. bronchialis, R. buffonii, R. calyptogenae, R. chungnamensis, R. cladiensis, R. corallina, R. cresolica, R. crocea, R. cycloclastica, R. dairenensis, R. diffluens, R. evergladiensis, R. ferulica, R. foliorum, R. fragaria, R. fujisanensis, R. futronensis, R. gelatinosa, R. glacialis, R. glutinis, R. gracilis, R. graminis, R. grinbergsii, R. himalayensis, R. hinnulea, R. histolytica, R. hylophila, R. incarnata, R. ingeniosa, R. javanica, R. koishikawensis, R. lactosa, R. lamellibrachiae, R. laryngis, R. lignophila, R. lini, R. longissima, R. ludwigii, R. lysinophila, R. marina, R. martyniae-fragantis, R. matritensis, R. meli, R. minuta, R. mucilaginosa, R. nitens, R. nothofagi, R. oryzae, R. pacifica, R. paffida, R. peneaus, R. philyla, R. phylloplana, R. pilatii, R. pilimanae, R. pinicola, R. plicata, R. polymorpha, R. psychrophenolica, R. psychrophila, R. pustula, R. retinophila, R. rosacea, R. rosulata, R. rubefaciens, R. rubella, R. rubescens, R. rubra, R. rubrorugosa, R. rufula, R. rutila, R. sanguinea, R. sanniei, R. sartoryi, R. silvestris, R. simplex, R. sinensis, R. slooffiae, R. sonckii, R. straminea, R. subericola, R. suganii, R. taiwanensis, R. taiwaniana, R. terpenoidalis, R. terrea, R. texensis, R. tokyoensis, R. ulzamae, R. vaniffica, R. vuilleminii, R. yarrowii, R. yunnanensis* and *R. zsoltii*. Suitable examples of *Phaffia* species include *P. rhodozyma*. Suitable examples of *Sporobolomyces* species include *S. alborubescens, S. bannaensis, S. beijingensis, S. bischofiae, S. clavatus, S. coprosmae, S. coprosmicola, S. coraffinus, S. dimmenae, S. dracophyffi, S. elongatus, S. gracilis, S. inositophilus, S. johnsonii, S. koalae, S. magnisporus, S. novozealandicus, S. odorus, S. patagonicus, S. productus, S. roseus, S. sasicola, S. shibatanus, S. singularis, S. subbrunneus, S. symmetricus, S. syzygii, S. taupoensis, S. tsugae, S. xanthus* and *S. yunnanensis*. Suitable examples of *Pachysolen* and *Moniliella* species include *P. tannophilus* and *M. poffinis*, respectively. Still other examples of non-conventional yeasts herein include *Pseudozyma* species (*e.g., S. antarctica*), *Thodotorula* species (*e.g., T. bogoriensis*), *Wickerhamiella* species (e.g., *W. domercqiae*), *Starmerella* species (e.g., *S. bombicola*), *Debaryomyces* species (e.g., *D. hansenii*), *Ogataea* species (e.g., *O. angusta*), and *Ashbya* species (e.g., *A. gossypii*).

A yeast in certain embodiments is a *Yarrowia* yeast, such as *Yarrowia lipolytica*. Examples of suitable *Y. lipolytica* include the following isolates available from the American Type Culture Collection (ATCC, Manassas, Va.): strain designations ATCC #20362, #8862, #8661, #8662, #9773, #15586, #16617, #16618, #18942, #18943, #18944, #18945, #20114, #20177, #20182, #20225, #20226, #20228, #20327, #20255, #20287, #20297, #20315, #20320, #20324, #20336, #20341, #20346, #20348, #20363, #20364, #20372, #20373, #20383, #20390, #20400, #20460, #20461, #20462, #20496, #20510, #20628, #20688, #20774, #20775, #20776, #20777, #20778, #20779, #20780, #20781, #20794, #20795, #20875, #20241, #20422, #20423, #32338, #32339, #32340, #32341, #34342, #32343, #32935, #34017, #34018, #34088, #34922, #34922, #38295, #42281, #44601, #46025, #46026, #46027, #46028, #46067, #46068, #46069, #46070, #46330, #46482, #46483, #46484, #46436, #60594, #62385, #64042, #74234, #76598, #76861, #76862, #76982, #90716, #90811, #90812, #90813, #90814, #90903, #90904, #90905, #96028, #201241, #201242, #201243, #201244, #201245, #201246, #201247, #201249, and/or #201847.

A microbial cell in certain embodiments is an algal cell. For example, an algal cell can be from any of the following: Chlorophyta (green algae), Rhodophyta (red algae), Phaeophyceae (brown algae), Bacillariophycaeae (diatoms), and Dinoflagellata (dinoflagellates). An algal cell can be of a microalgae (e.g., phytoplankton, microphytes, or planktonic algae) or macroalgae (kelp, seaweed) in other aspects. As further examples, an algal cell herein can be a species of *Chlamydomonas* (e.g., *C. reinhardtii*), *Porphyra* (purple laver), *Palmaria* (e.g., *P. palmata* [dulse]), *Arthrospira* (e.g., *A. platensis* [*spirulina*]), *Chlorella* (e.g., *C. protothecoides, C. vulgaris*), *Chondrus* (e.g., *C. crispus* [Irish moss]), *Aphanizomenon, Sargassum, Cochayuyo, Botryococcus* (e.g., *B. braunii*), *Dunaliella* (e.g., *D. tertiolecta, D. salina*), *Gracilaria, Pleurochrysis* (e.g., *P. carterae*), *Ankistrodesmus, Cyclotella, Hantzschia, Nannochloris, Nannochloropsis, Nitzschia, Phaeodactylum* (e.g., *P. tricornutum*), *Scenedesmus* (e.g., *S. obliquus*), *Stichococcus, Tetraselmis* (e.g., *T. suecica*), *Thalassiosira* (e.g., *T. pseudonana*), *Crypthecodinium* (e.g., *C. cohnii*), *Neochloris* (e.g., *N. oleoabundans*), or *Schiochytrium*. An algal species herein can be cultivated and/or manipulated as described in Thompson (*Algal Cell Culture. Encyclopedia of Life Support System* (*EOLSS*), *Biotechnology Vol* 1, available at eolss.net/sample-chapters internet site), for example, which is incorporated herein by reference.

A bacterial cell in certain embodiments can be those in the form of cocci, bacilli, spirochetes, spheroplasts, protoplasts, etc. Still other non-limiting examples of bacteria include those of the genera *Salmonella* (e.g., *S. typhi, S. enteritidis*), *Shigella* (e.g., *S. dysenteriae*), *Escherichia* (e.g., *E. coli*), *Enterobacter, Serratia, Proteus, Citrobacter, Edwardsiella, Providencia, Klebsiella, Hafnia, Ewingella, Kluyvera, Morganella, Planococcus, Stomatococcus, Micrococcus, Staphylococcus* (e.g., *S. aureus*), *Vibrio* (e.g., *V. cholerae*), *Aeromonas, Plessiomonas, Actinobacillus, Pasteurella, Ureaplasma, Coxiella, Rochalimaea, Ehrlichia, Streptococcus* (e.g., *S. pyogenes, S. mutans, S. pneumoniae*), *Enterococcus* (e.g., *E. faecalis*), *Aerococcus, Gemella, Lactococcus* (e.g., *L. lactis*), *Leuconostoc* (e.g., *L. mesenteroides*), *Pedicoccus, Bacillus* (e.g., *B. cereus, B. subtilis, B. thuringiensis*), *Corynebacterium* (e.g., *C. diphtheriae*), *Arcanobacterium, Actinomyces, Rhodococcus, Listeria* (e.g., *L. monocytogenes*), *Erysipelothrix, Gardnerella, Campylobacter, Arcobacter, Wolinella, Achromobacter, Acinetobacter, Agrobacterium* (e.g., *A. tumefaciens*), *Alcaligenes, Chryseomonas, Comamonas, Eikenella, Flavimonas, Flavobacterium, Moraxella, Oligella, Pseudomonas* (e.g., *P. aeruginosa*), *Shewanella, Weeksella, Xanthomonas, Franciesella, Afipia, Bartonella, Calymmatobacterium, Cardiobacterium, Streptobacillus, Spirillum, Peptostreptococcus, Peptococcus, Sarcinia, Coprococcus, Ruminococcus, Propionibacterium, Mobiluncus, Bifidobacterium, Eubacterium, Lactobacillus* (e.g., *L. lactis, L. acidophilus*), *Rothia, Clostridium* (e.g., *C. botulinum, C. perfringens*), *Bacteroides, Porphyromonas, Prevotella, Fusobacterium, Bilophila, Leptotrichia, Wolinella, Acidaminococcus, Megasphaera, Veilonella, Norcardia, Actinomadura, Norcardiopsis, Streptomyces, Micropolysporas, Thermoactinomycetes, Treponema, Leptospira*, and *Chlamydiae*.

A recombinant cell herein can produce one or more LCDA products from a long-chain fatty acid-comprising substrate. The total amount of LCDA that can be produced in a volume of culture medium by a cell as presently disclosed can be about, or at least about, 10, 20, 30, 40, 50, 60, 70, 80, 90, 100, 110, or 120 g/L (or any integer between 5 to 120 g/L), for example. Examples of a recombinant cell of the present disclosure can exhibit at least a 10-fold to 1000-fold increase in LCDA production, as compared to a suitable control cell (e.g., parent cell), when grown under identical fermentation conditions, Such an increase can be about, or at least about, 10-fold, 25-fold, 50-fold, 75-fold, 100-fold, 150-fold, 200-fold, 250-fold, 300-fold, 400-fold, 500-fold, 750-fold, or 1000-fold, for example.

The degree of homogeneity or heterogeneity of LCDAs produced by a cell herein typically depends on the nature of the long-chain fatty acid-comprising substrate fed to the cell. For example, a cell grown with a substrate comprising one type of long-chain fatty acid (a homogeneous fatty acid-comprising substrate) can typically produce LCDA products comprising mostly (e.g., at least 50, 55, 60, 65, 70, or 75 wt %) LCDAs with the same carbon chain length as the fatty acid in the substrate. To illustrate, a cell in some aspects grown in a culture medium with a substrate comprising only palmitic acid (C16:0) or oleic acid (C18:1) typically can produce LCDAs comprising at least 50 wt % LCDA products with carbon chain lengths of 16 or 18, respectively.

A cell in some aspects grown with a substrate comprising more than one type of long-chain fatty acid (a heterogeneous fatty acid-comprising substrate) can typically produce a profile of LCDA products with carbon chain lengths generally proportional to the corresponding carbon chain lengths of the fatty acids in the substrate. For example, a cell herein grown with soybean oil, which typically comprises ~7% alpha-linolenic acid (C18:3), ~55% linoleic acid (C18:2), ~23% oleic acid (C18:1), ~4% stearic acid (C18:0), and ~11% palmitic acid (C16:0) of the fatty acids (thus, ~89% of the fatty acids are C18 and ~11% are C16) can produce LCDAs comprising mostly (e.g., at least 50, 55, 60, 65, 70, or 75 wt %) LCDA products with carbon chain lengths of 18.

An LCDA herein can have a carbon chain length of 10 to 24, for example. An LCDA can be a C10, C11, C12, C13, C14, C15, C16, C17, C18, C19, C20, C21, C22, C23, or C24 LCDA, for instance. An LCDA can have a chain length of 10-22, 12-22, 14-22, 16-22, 18-22, 20-22, 16-18, 16-20, or 16-22 carbon atoms in some embodiments. Examples of LCDA products in certain aspects are saturated (carbon chain thereof does not comprise any double-bonds) and are listed in Table A.

TABLE A

Examples of LCDA Products

| Shorthand Notation (common name) | Systematic Name | Formula |
|---|---|---|
| C10:0 (sebacic acid) | decanedioic acid | HOOC—$(CH_2)_8$—COOH |
| C11:0 | undecanedioic acid | HOOC—$(CH_2)_9$—COOH |
| C12:0 | dodecanedioic acid | HOOC—$(CH_2)_{10}$—COOH |
| C13:0 (brassylic acid) | tridecanedioic acid | HOOC—$(CH_2)_{11}$—COOH |
| C14:0 | tetradecanedioic acid | HOOC—$(CH_2)_{12}$—COOH |
| C15:0 | pentadecanedioic acid | HOOC—$(CH_2)_{13}$—COOH |
| C16:0 (thapsic acid) | hexadecanedioic acid | HOOC—$(CH_2)_{14}$—COOH |
| C17:0 | heptadecanedioic acid | HOOC—$(CH_2)_{15}$—COOH |
| C18:0 | octadecanedioic acid | HOOC—$(CH_2)_{16}$—COOH |
| C19:0 | nonadecanedioic acid | HOOC—$(CH_2)_{17}$—COOH |
| C20:0 | eicosanedioic acid | HOOC—$(CH_2)_{18}$—COOH |
| C21:0 | | HOOC—$(CH_2)_{19}$—COOH |

TABLE A-continued

Examples of LCDA Products

| Shorthand Notation (common name) | Systematic Name | Formula |
|---|---|---|
| C22:0 | | HOOC—$(CH_2)_{20}$—COOH |
| C24:0 | | HOOC—$(CH_2)_{22}$—COOH |

Still other examples of LCDA products herein are unsaturated. An unsaturated LCDA can comprise an aliphatic carbon chain having 1, 2, 3, 4, 5, or 6 double-bonds, for instance. Examples of unsaturated LCDAs herein include C16:1, C16:2, C18:1, C18:2, C18:3, C18:4, C20:1, C20:2, C20:3, C20:4, C20:5, C22:1, C22:2, C22:3, C22:4, C22:5 and C22:6. Any of the aforementioned LCDAs can be produced, for example, by growing a recombinant cell as presently disclosed with a substrate comprising a fatty acid having a corresponding chain length and saturation/unsaturation profile. Position(s) of unsaturation in the carbon chain of an LCDA product can correspond, for example, to the position(s) of unsaturation in a fatty acid-comprising substrate used to prepare the LCDA.

A long-chain fatty acid, as provided in a long-chain fatty acid-comprising substrate herein, can have a carbon chain length of at least 10, or a length of 10 to 24 carbon atoms, for example. A long-chain fatty acid can be a C10, C11, C12, C13, C14, C15, C16, C17, C18, C19, C20, C21, C22, C23, or C24 long-chain fatty acid, for instance. A long-chain fatty acid can have a chain length of 10-24, 12-24, 14-24, 16-24, 18-24, 20-24, 10-22, 12-22, 14-22, 16-22, 18-22, 20-22, 16-18, 16-20, or 16-22 carbon atoms in some embodiments. Although the presently disclosed substrates comprise fatty acids with a carbon chain length of at least 10, or a range of 10 to 24 carbon atoms, additional types of fatty acids can also be present in the substrate, if desired. For example, a substrate can further comprise one or more types of fatty acids with carbon chain lengths of less than 10.

A long-chain fatty acid herein can be saturated or unsaturated. Examples of unsaturated long-chain fatty acids are monounsaturated fatty acids (MUFA) if only one double-bond is present in the fatty acid carbon chain, and polyunsaturated fatty acids (PUFA) if the fatty acid carbon chain has two or more double-bonds. Examples of long-chain fatty acids herein are provided in Table B.

TABLE B

Examples of Long-Chain Fatty Acids that Can Be Comprised in a Substrate

| Common Name | Systematic Name | Shorthand Notation |
|---|---|---|
| capric acid | decanoic acid | C10:0 |
| undecylic acid | undecanoic acid | C11:0 |
| lauric acid | dodecanoic acid | C12:0 |
| tridecylic acid | tridecanoic acid | C13:0 |
| myristic acid | tetradecanoic acid | C14:0 |
| myristoleic acid | tetradecenoic acid | C14:1 |
| pentadecylic acid | pentadecanoic acid | C15:0 |
| palmitic acid | hexadecanoic acid | C16:0 |
| palmitoleic acid | 9-hexadecenoic acid | C16:1 |
| | hexadecadienoic acid | C16:2 |
| margaric acid | heptadecanoic acid | C17:0 |
| stearic acid | octadecanoic acid | C18:0 |
| oleic acid | cis-9-octadecenoic acid | C18:1 |
| linoleic acid | cis-9, 12-octadecadienoic acid | C18:2 omega-6 |

TABLE B-continued

| Examples of Long-Chain Fatty Acids that Can Be Comprised in a Substrate | | |
|---|---|---|
| Common Name | Systematic Name | Shorthand Notation |
| gamma-linolenic acid | cis-6, 9, 12-octadecatrienoic acid | C18:3 omega-6 |
| alpha-linolenic acid | cis-9, 12, 15-octadecatrienoic acid | C18:3 omega-3 |
| stearidonic acid | cis-6, 9, 12, 15-octadecatetraenoic acid | C18:4 omega-3 |
| nonadecylic acid | nonadecanoic acid | C19:0 |
| arachidic acid | eicosanoic acid | C20:0 |
| eicosatrienoic | cis-11, 14, 17-eicosatrienoic | 20:3 omega-3 |
| eicosatetraenoic | cis-8, 11, 14, 17-eicosatetraenoic | 20:4 omega-3 |
| eicosapentaenoic | cis-5, 8, 11, 14, 17-eicosapentaenoic | 20:5 omega-3 |
| heneicosylic acid | heneicosanoic acid | C21:0 |
| behenic acid | docosanoic acid | C22:0 |
| tricosylic acid | tricosanoic acid | C23:0 |
| lignoceric acid | tetracosanoic acid | C24:0 |

A long-chain fatty acid can be a substituted fatty acid in some cases, so long as that it is non-toxic or only exhibits low toxicity to a cell. One or more hydrogens in the aliphatic chain of a fatty acid can optionally be substituted with a halogen, acetyl, OR, $NR_2$, or SR group, where R is independently an H or C1-C8 alkyl group, for example. Certain examples of substituted fatty acids herein include fatty acids with an omega-alcohol or omega-aldehyde group.

A long-chain fatty acid-comprising substrate as presently disclosed can comprise a free long-chain fatty acid in some aspects herein. Such a fatty acid can optionally be characterized as a non-esterified long-chain fatty acid or non-linked long-chain fatty acid. Any long-chain fatty acid disclosed herein (e.g., as listed in Table B) can be comprised in such a substrate, for example. Other examples of substrates comprising free long-chain fatty acids include fatty acid distillates of an oil. A fatty acid distillate can be of any oil disclosed herein, such as a plant oil (e.g., palm oil fatty acid distillate [PFAD]).

A long-chain fatty acid-comprising substrate as presently disclosed can comprise an esterified long-chain fatty acid in some aspects. Any long-chain fatty acid disclosed herein (e.g., as listed in Table B) can be comprised in such a substrate, for example. Some examples of esterified long-chain fatty acids herein include long-chain fatty acids that are comprised within a glyceride molecule or a fatty acid alkyl ester.

A glyceride molecule herein can be a mono-, di-, or triglyceride, or a mixture thereof. In those embodiments in which a long-chain fatty acid-comprising substrate comprises a di- and/or triglyceride, not all the esterified fatty acids thereof need be long-chain fatty acids. A glyceride molecule herein is typically provided as an oil, although it can also be provided as a fat in some embodiments. Thus, a long-chain fatty acid-comprising substrate can optionally be characterized as comprising one or more types of oil and/or fat.

Examples of oil (or fat) suitable for use herein can be derived from plants, microbes, yeast, fungi, bacteria, algae, euglenoids, stramenopiles, animals, poultry, and fish. Examples of plant oils (vegetable oil) include canola oil, corn oil, palm kernel oil, cheru seed oil, wild apricot seed oil, sesame oil, sorghum oil, soy oil, rapeseed oil, soybean oil, colza oil, tall oil, sunflower oil, hempseed oil, olive oil, linseed oil, coconut oil, castor oil, peanut oil, palm oil, mustard oil, cottonseed oil, camelina oil, jatropha oil and *crambe* oil. Other examples of oils and fats herein include rendered fats and oil; restaurant grease; yellow and brown greases; waste industrial frying oil; tallow; lard; train oil; fats in milk; fish oil; algal oil; yeast oil; microbial oil; oil/fat from yeast biomass, microbial biomass, sewage sludge; and phospholipids (e.g., as provided in soap stock). Still other examples of oil useful herein include (i) fossil fuel-derived oil such as oil from petroleum-based products, spent motor oils and industrial lubricants, coal-derived liquids; (ii) synthetic oils generated as byproducts from petrochemical and chemical processes; and (iii) oils from industrial waste and/or agricultural waste.

A fatty acid alkyl ester herein can comprise a $C_1$-$C_{10}$ alkyl group such as, respectively, a methyl, ethyl, propyl, butyl, pentyl, hexyl, heptyl, octyl, nonyl, or decyl group, for example. Examples include fatty acid methyl ester and fatty acid ethyl ester. While any long-chain fatty acid disclosed herein can be comprised in a fatty acid alkyl ester, some examples include C16 (e.g., palmitic) and C18 (e.g., oleic) fatty acids. One of, or a mixture of, fatty acid alkyl esters can be used with a cell herein for LCDA production. A mixture of a fatty acid alkyl esters can be provided in some aspects by chemically reacting any oil or fat (i.e., lipid) disclosed herein with an alcohol (e.g., methanol or ethanol) to produce fatty acid esters, using any appropriate method known in the art. An example of such a mixture is biodiesel, which is typically derived from vegetable oil or animal fat (e.g., tallow).

A long-chain fatty acid-comprising substrate as presently disclosed can comprise an amide-linked long-chain fatty acid in some aspects. Examples of amide-linked long-chain fatty acids herein include fatty amides, acylamino-sugars and acylamino-glycans. Any long-chain fatty acid disclosed herein (e.g., as listed in Table B) can be provided as an amide-linked long-chain fatty acid, for example.

It is believed that a cell herein, though described as producing LCDA from long-chain fatty acid comprising substrates, is also capable of producing LCDA from other organic substrates such as alkanes, fatty alcohols, and/or fatty aldehydes. Such other substrates can be of the same carbon chain length as disclosed herein for long-chain fatty acid comprising substrates.

The instant disclosure also concerns a method of producing one or more long-chain dicarboxylic acids (LCDA). This method comprises contacting a recombinant cell (e.g., microbial cell such as a yeast cell) as disclosed herein with a long-chain fatty acid-comprising substrate, wherein the cell synthesizes an LCDA from the substrate. This method further comprises an optional step of recovering the LCDA synthesized by the cell.

This method can be practiced using any feature(s) of the above-disclosed embodiments or below Examples (e.g., features related to cell type; ACoS enzyme sequences; CYP and/or CPR enzyme sequences; FAO, FADH, and/or FALDH enzyme sequences; Pex3 protein sequence, etc.), for example. Thus, any of the features disclosed above or in the Examples, or any combination of these features, can be used appropriately to characterize embodiments of an LCDA production method herein. The following method features are further examples.

An LCDA production method as currently disclosed includes a step of contacting a recombinant cell with a long-chain fatty acid-comprising substrate, wherein the cell synthesizes an LCDA from the substrate. Such a contacting step can optionally be characterized as incubating, culturing, and/or growing a recombinant cell in a medium comprising a fatty acid-comprising substrate. This contacting step can also be characterized as a fermentation step (e.g., fermentation of an LCDA from a long-chain fatty acid-comprising substrate) (e.g., LCDA fermentation method), if desired.

A suitable pH for fermenting an LCDA herein (e.g., pH of media in which a cell is contacted with a long-chain fatty acid-comprising substrate) is between about pH 4.0 to 9.0, for example. Suitable pH's in this range can be, for instance, about 4.0, 4.5, 5.0, 5.5, 6.0, 6.5, 7.0, 7.5, 8.0, 8.5, or 9.0. A pH in the range of about pH 7.5 to 8.5 can be employed in some other aspects. A pH of about 5.5 to 7.5 can sometimes be useful for initial growth conditions.

A suitable temperature for fermenting an LCDA herein (e.g., temperature of media in which a cell is contacted with a long-chain fatty acid-comprising substrate) can be one in which a recombinant cell herein exhibits optimal growth. Examples of suitable temperatures include about 15, 16, 17, 18, 19, 20, 21, 22, 23, 24, 25, 26, 27, 28, 29, 30, 31, 32, 33, 34, or 35° C. Suitable temperature ranges that can be employed in some cases include 25-32° C., 28-32° C., and 28-30° C.

The amount of time for growing a recombinant cell with long-chain fatty acid-comprising substrate(s) for fermenting one or more LCDAs can be about, or at least about, 36, 48, 60, 72, 84, 96, 108, 120, 132, 144, 156, 168, 180, 192, 204, 216, 228, or 240 hours. The fermenting time period can be about 3-7, 4-6, or 5 days in certain other embodiments. A cell can optionally be grown for about 12-24 hours before initiating contact with long-chain fatty acid-comprising substrate(s).

The concentration of long-chain fatty acid-comprising substrate(s) in a medium in which a recombinant microbial cell herein is contacted with such substrate(s) can be about, or at least about, 1, 3, 5, 10, 15, 20, 25, 30, 35, 40, 45, 50, 55, 60, 65, 70, 75, 80, 85, 90, 95, or 100 g/L (or any integer between 1 to 100 g/L), for example. Such a concentration can be about 3-30 or 5-20 g/L in certain other embodiments. Any of these concentrations can be an initial concentration (starting concentration), which is the concentration of substrate present just after it is added to a medium for fermenting LCDA with a microbial cell. An initial long-chain fatty acid-comprising substrate concentration can optionally characterize the concentration at the start of pulse-feeding or continuous feeding, for example.

An LCDA fermentation method in some embodiments can be conducted using a batch, fed-batch, or continuous fermentation process. A batch fermentation method typically comprises a closed system in which the media (comprising long-chain fatty acid-comprising substrate) is fixed at the beginning of the process and not subject to further additions/modifications beyond those that may be required for maintaining pH and/or oxygen levels during the fermentation. A fed-batch process herein is similar to a batch process, except that the process is subject to one or more additions/modifications beyond those that may be required for maintaining pH and/or oxygen levels during the fermentation. For example, a long-chain fatty acid-comprising substrate may be added to the system during the process; such addition can be staggered/periodic or continuous. Batch and fed-batch culturing methods are known in the art (e.g., Brock, *Biotechnology: A Textbook of Industrial Microbiology, 2nd Edition*, Sinauer Associates, Sunderland, Mass., 1989; Deshpande, *Appl. Biochem. Biotechnol.* 36:227-234). A continuous fermentation process herein typically can be performed by continuously adding a defined medium to a fermentation vessel while simultaneously removing an equal amount of culture volume for LCDA product recovery. Brock discloses continuous fermentation methodology.

Still other culture conditions can optionally be applied for carrying out an LCDA production method herein. For example, a recombinant cell can be cultured under aerobic (e.g., microaerobic) or anaerobic conditions, where the former is preferred in some instances. Agitation in the form of shaking or rotating can optionally be applied to a culture, such as at a rate of about 100, 150, 200, 300, 500, 800, 1000, 1200, 1500, 1800, or 2000 rpm. In another example, a two-stage process may be employed in which a first stage promotes cell proliferation and a second stage promotes LCDA production. Two, three, four or more different types of recombinant cells (preferably of the same species, genus, or family) as presently disclosed can be used in yet other examples.

The total amount of LCDA(s) produced in an LCDA production method as currently disclosed can be about, or at least about, 10, 20, 30, 40, 50, 60, 70, 80, 90, 100, 110, or 120 g/L (or any integer between 5 to 120 g/L), for example. These concentrations can be as measured in a medium in which a microbial cell herein is contacted with a long-chain fatty acid-comprising substrate, and at any of the above-disclosed growth periods. The rate of LCDA production in certain LCDA production methods herein can be about, or at least about, 0.10, 0.15, 0.20, 0.25, 0.30, 0.35, 0.40, 0.45, 0.50, 0.55, 0.60, 0.65, 0.70, 0.75, 0.80, 0.85, 0.90, 0.95, 1.00, 1.05, 1.10, 1.15, or 1.20 g/L/hour. The starting amount of microbial cells leading to any of these measures of LCDA output can, in certain aspects, be any of those amounts tested in the below Examples.

LCDA product(s) synthesized by a cell in an LCDA production method herein can optionally be isolated. Any method known in the art for isolating LCDAs from a fermentation broth can be applied, for example, such as disclosed in U.S. Pat. Appl. Publ. Nos. 2014/0228587 and 2012/0253069, which are incorporated herein by reference. Also, any LCDA isolation method disclosed in the following Examples can be employed, for example.

One or more omega-hydroxy long-chain fatty acids and/or omega-aldo long-chain fatty acids are produced as intermediates during an LCDA synthesis method herein (refer to FIGS. 1 and 2). Thus, in certain alternative embodiments of the present disclosure, a method of synthesizing LCDA can be optionally be characterized as a method of producing an omega-hydroxy long-chain fatty acid and/or an omega-aldo long-chain fatty acid. Such an LCDA metabolite(s) can have a carbon number corresponding to any of the LCDAs and long-chain fatty acids presently disclosed, for example.

Non-limiting examples of compositions and methods disclosed herein include:

1. A recombinant microbial cell comprising an engineered LCDA production pathway that comprises up-regulation of a polynucleotide sequence encoding a long-chain acyl-CoA synthetase (ACoS enzyme), wherein the microbial cell can produce one or more long-chain dicarboxylic acid (LCDA) products from a long-chain fatty acid-comprising substrate.
2. The recombinant microbial cell of embodiment 1, wherein the ACoS enzyme comprises an amino acid sequence that is at least 90% identical to SEQ ID NO:44, 49, 36, 33, or 34.
3. The recombinant microbial cell of embodiment 1 or 2, wherein the ACoS enzyme has both long-chain acyl-CoA synthetase activity and coumaroyl-CoA synthetase activity.
4. The recombinant microbial cell of embodiment 3, wherein the ACoS enzyme comprises an amino acid sequence that is at least 90% identical to SEQ ID NO:44 or 49.

5. The recombinant microbial cell of embodiment 1, 2, 3, or 4, wherein the engineered LCDA production pathway further comprises one or more of the following features:

(i) up-regulation of a polynucleotide sequence encoding a cytochrome P450 monooxygenase (CYP enzyme)

(ii) up-regulation of a polynucleotide sequence encoding a cytochrome P450 reductase (CPR enzyme), (iii) up-regulation of a polynucleotide sequence encoding a fatty alcohol oxidase (FAO enzyme), (iv) up-regulation of a polynucleotide sequence encoding a fatty alcohol dehydrogenase (FADH enzyme), and/or (v) up-regulation of a polynucleotide sequence encoding a fatty aldehyde dehydrogenase (FALDH enzyme).

6. The recombinant microbial cell of embodiment 5, wherein either or both the polynucleotide sequence encoding the CYP enzyme and the polynucleotide sequence encoding the CPR enzyme are up-regulated.

7. The recombinant microbial cell of embodiment 1, 2, 3, 4, 5, or 6, wherein the microbial cell further comprises down-regulation of an endogenous polynucleotide sequence encoding a peroxisome biogenesis factor.

8. The recombinant microbial cell of embodiment 7, wherein the peroxisome biogenesis factor is peroxisome biogenesis factor-3.

9. The recombinant microbial cell of embodiment 1, 2, 3, 4, 5, 6, 7, or 8, wherein the microbial cell further comprises down-regulation of an endogenous polynucleotide sequence encoding a peroxisomal acyl-CoA oxidase.

10. The recombinant microbial cell of embodiment 9, wherein the peroxisomal acyl-CoA oxidase is peroxisomal acyl-CoA oxidase-2, -3, and/or -4.

11. The recombinant microbial cell of embodiment 1, 2, 3, 4, 5, 6, 7, 8, 9, or 10, wherein the microbial cell has reduced lipid synthesis and/or storage capability.

12. The recombinant microbial cell of embodiment 11, wherein the reduced lipid synthesis and storage capability is due to a down-regulation of at least one endogenous polynucleotide sequence encoding a diacylglycerol acyltransferase (DGAT enzyme).

13. The recombinant microbial cell of embodiment 1, 2, 3, 4, 5, 6, 7, 8, 9, 10, 11, or 12, wherein the microbial cell is a yeast cell.

14. The recombinant microbial cell of embodiment 13, wherein the yeast cell is a *Yarrowia* cell.

15. The recombinant microbial cell of embodiment 1, 2, 3, 4, 5, 6, 7, 8, 9, 10, 11, 12, 13, or 14, wherein the LCDA product has a chain length of 10 to 24 carbon atoms, and/or the long-chain fatty acid-comprising substrate comprises a free long-chain fatty acid or an esterified long-chain fatty acid.

16. A method of producing a long-chain dicarboxylic acid (LCDA), the method comprising: a) contacting the recombinant microbial cell of embodiment 1, 2, 3, 4, 5, 6, 7, 8, 9, 10, 11, 12, 13, 14, or 15 with a long-chain fatty acid-comprising substrate, wherein the microbial cell synthesizes an LCDA from the substrate; and b) optionally recovering the LCDA of step (a).

17. The method of embodiment 16, wherein the microbial cell is a yeast cell, and optionally wherein the yeast cell is a *Yarrowia* cell.

EXAMPLES

The present disclosure is further exemplified in the following Examples. It should be understood that these Examples, while indicating certain preferred aspects herein, are given by way of illustration only. From the above discussion and these Examples, one skilled in the art can ascertain the essential characteristics of the disclosed embodiments, and without departing from the spirit and scope thereof, can make various changes and modifications to adapt the disclosed embodiments to various uses and conditions.

General Methods

Standard recombinant DNA and molecular cloning techniques used in the Examples are well known in the art and described by, for example: 1) J. Sambrook and D. Russell (*Molecular Cloning: A Laboratory Manual,* 3rd Edition, Cold Spring Harbor Laboratory Press, Cold Spring Harbor, N.Y., 2001); 2) T. J. Silhavy et al. (*Experiments with Gene Fusions*, Cold Spring Harbor Laboratory Press, Cold Spring Harbor, N.Y., 1984); and 3) F. M. Ausubel et al. (*Short Protocols in Molecular Biology,* 5th Ed. Current Protocols, John Wiley and Sons, Inc., NY, 2002).

Materials and methods suitable for the maintenance and growth of microbial cultures are well known in the art. Techniques suitable for use in the following examples may be found as set out in, for example, *Manual of Methods for General Bacteriology* (P. Gerhardt, R. G. E. Murray, R. N. Costilow, E. W. Nester, W. A. Wood, N. R. Krieg and G. B. Phillips, Eds., American Society for Microbiology: Washington, D.C., 1994); and/or Thomas D. Brock in *Biotechnology: A Textbook of Industrial Microbiology, 2nd Ed.* (Sinauer Associates: Sunderland, Mass., 1989). All reagents, restriction enzymes and cell growth materials were obtained from DIFCO Laboratories (Detroit, Mich.), New England Biolabs, Inc. (Beverly, Mass.), GIBCO/BRL (Gaithersburg, Md.), or Sigma-Aldrich (St. Louis, Mo.), unless otherwise specified. *E. coli* strains were typically grown at 37° C. on Luria Bertani (LB) plates.

General molecular cloning was performed according to standard methods (e.g., Sambrook and Russell). Oligonucleotides were synthesized by Sigma-Genosys (Spring, Tex.). Individual PCR amplification reactions were carried out in a 50-μl total volume, comprising: PCR buffer (containing 10 mM KCl, 10 mM $(NH_4)_2SO_4$, 20 mM Tris-HCl (pH 8.75), 2 mM $MgSO_4$, 0.1% Triton X-100), 100 μg/mL BSA, 200 μM each deoxyribonucleotide triphosphate, 10 pmole of each primer, and 1 μl of Pfu DNA polymerase (Agilent Technologies, Santa Clara, Calif.), unless otherwise specified. Site-directed mutagenesis was performed using Agilent's Site-Directed Mutagenesis kit, per the manufacturer's instructions. When PCR or site-directed mutagenesis was involved in subcloning, the constructs were sequenced to confirm that no errors had been introduced to the sequence. PCR products were cloned into pGEM®-T Easy Vector (Promega, Madison, Wis.) and/or pCR®4-TOPO® vector (Invitrogen, Carlsbad, Calif.). All codon-optimized genes were synthesized by GenScript (Piscataway, N.J.).

DNA sequence was generated on an ABI Automatic sequencer using dye terminator technology using a combination of vector- and insert-specific primers. Sequence editing and analysis were performed using SEQUENCHER software (Gene Codes Corporation, Ann Arbor, Mich.). Comparisons of genetic sequences were accomplished using DNASTAR software (DNA Star, Inc.). Alternatively, manipulations of genetic sequences were accomplished using the Vector NTI Advance® 10 programs available from Life Technologies (Grand Island, N.Y.).

The results of alignment comparisons summarizing a sequence to which a query sequence had the most similarity are reported according to percent identity, percent similarity, and/or Expectation (E) value. "Expectation value" estimates the statistical significance of the match, specifying the number of matches, with a given score, that are expected in a search of a database of this size absolutely by chance.

The meanings of certain abbreviations used herein are as follows: "sec" means second(s), "min" means minute(s), "h" means hour(s), "d" means day(s), "μL" means microliter(s), "mL" means milliliter(s), "L" means liter(s), "μM" means micromolar, "mM" means millimolar, "M" means molar, "mmol" means millimole(s), "pmole" means micromole(s), "g" means gram(s), "μg" means microgram(s), "ng" means nanogram(s), "U" means unit(s), "bp" means base pair(s), "kB" means kilobase(s), "DCW" means dry cell weight, and "TFAs" means total fatty acids.

Cultivation and Transformation of *Yarrowia lipolytica*

*Y. lipolytica* strains ATCC #20362 and # ATCC 90812 were purchased from the American Type Culture Collection (Rockville, Md.). *Y. lipolytica* strains were routinely grown at 28-30° C. in several media, according to the recipes shown below. Agar plates were prepared by addition of 20 g/L agar to each liquid media.

YPD agar medium (per liter): 10 g of yeast extract (DIFCO), 20 g of Bacto™ Peptone (DIFCO), 20 g of glucose.

Basic Minimal Media (MM) (per liter): 20 g glucose, 1.7 g yeast nitrogen base without amino acids, 1.0 g proline, pH 6.1 (not adjusted).

Minimal Media+Uracil (MM+uracil or MMU) (per liter): Prepare MM media as above and add 0.1 g uracil and 0.1 g uridine.

Minimal Media+Uracil+Sulfonylurea (MMU+SU) (per liter): Prepare MMU media as above and add 280 mg sulfonylurea.

Minimal Media+Leucine+Lysine (MMLeuLys) (per liter): Prepare MM media as above and add 0.1 g leucine and 0.1 g lysine.

Minimal Media+5-Fluoroorotic Acid (MM+5-FOA) (per liter): 20 g glucose, 6.7 g Yeast Nitrogen base, 75 mg uracil, 75 mg uridine and appropriate amount of FOA (Zymo Research Corp., Orange, Calif.), based on FOA activity testing against a range of concentrations from 100 mg/L to 1000 mg/L (since variation occurs within each batch received from the supplier).

MF Media (per liter): 14.3 g yeast extract, 7.15 g Peptone, 0.82 g $KH_2PO_4$, 16.37 g $K_2HPO_4$, 20 g Glucose, 1.2 mL Trace metals (100×), 3 mL $MgSO_4$ (1M), 0.6 mL Thiamine. HCl (1.5 g/L).

MF Buffer 1 Media (per liter): 150 q Glucose, 100.12 q $KHCO_3$, 4.29 q Urea.

YM Medium: 0.5% peptone, 0.3% yeast extract, 0.3% *maltose* extract.

YNB Medium (per liter): 20 g glucose, 1.7 g yeast nitrogen base without amino acids, 20 g agar, pH 6.1 (not adjusted).

YPD2-B Media: 10 g Yeast Extract, 10 g Peptone, 20 g Glucose, 94 mL $K_2HPO_4$ (1 M), 6 mL $KH_2PO_4$ (1 M), 2004 Trace metals (100×), 1 mL Thiamine-HCl (75 mg/ml), 1 mL $MgSO_4$-$7H_2O$ (12.5 g/100 mL).

YPD4-B Media: 10 g Yeast Extract, 10 g Peptone, 40 g Glucose, 94 ml $K_2HPO_4$ (1 M), 6 mL $KH_2PO_4$ (1 M), 2004 Trace metals (100×), 1 mL Thiamine-HCl (75 mg/mL), 1 mL $MgSO_4$-$7H_2O$ (12.5 g/100 mL).

Y2P1D2-B Media: 20 g Yeast Extract, 10 g Peptone, 20 g Glucose, 94 ml $K_2HPO_4$ (1 M), 6 mL $KH_2PO_4$ (1 M), 2004 Trace metals (100×), 1 mL Thiamine-HCl (75 mg/mL), 1 mL $MgSO_4$-$7H_2O$ (12.5 g/100 mL).

Trace Metals Recipe (100×): 10.0 g/L Citric Acid, 1.5 g/L $CaCl_2.2H_2O$, 10.0 g/L $FeSO_4.7H_2O$, 0.39 g/L $ZnSO_4.7H_2O$, 0.38 g/L $CuSO_4.5H_2O$, 0.20 g/L $CoCl_2.6H_2O$, 0.30 g/L $MnCl_2.4H_2O$.

*Yarrowia* transformation:

Transformation of *Y. lipolytica* was performed according to the method of Chen et al. (*Appl. Microbiol. Biotechnol.* 48:232-235), unless otherwise noted. Briefly, *Yarrowia* was streaked onto a YPD plate and grown at 30° C. for approximately 18 h. Several large loopfuls of cells were scraped from the plate and resuspended in 1 mL of transformation buffer containing 2.25 mL of 50% PEG (average MW 3350), 0.125 mL of 2 M Li Acetate, pH 6.0, and 0.125 mL of 2 M DTT. Then, approximately 500 ng of linearized plasmid DNA was incubated in 100 μL of resuspended cells, and maintained at 39° C. for 1 h with vortex-mixing at 15 min intervals. The cells were plated onto selection media plates and maintained at 30° C. for 2 to 3 days.

Flask Cultures for Long-Chain Dicarboxylic Acid (LCDA) Production:

One loop of freshly streaked *Yarrowia* cells was inoculated into 3 mL MM medium in 15-mL Falcon™ culture tubes and grown overnight (~20 hours) at 30° C. with shaking (250 rpm). The overnight cultured cells were used to inoculate 50 mL of liquid Y2P1D2-B media in a 250-mL baffled flask and shaken at 250 rpm at 30° C. After 24 hours, the cultures were adjusted to pH 8.0 by adding 2.0 mL of 1 M $NaHCO_3$ and 1.0 mL of glucose solution (200 g/L). Then, 1.5 mL ethyl palmitate (substrate) was added directly to the culture media to a final concentration of 23 mg $mL^{-1}$, and the cultures were shaken for 4 days at 250 rpm at 30° C. Whole broth samples from each flask culture were subjected to LCDA analysis.

Microfermentation for LCDA Production:

Strains for microfermenter analysis were grown to single colonies on YPD agar plates from frozen stock. A single colony was inoculated into 3 mL of minimal media in 15-mL FALCON culture tubes and grown overnight at 30° C., 250 rpm. From these cultures, fermentation vials were created with 1 mL of seed culture and 1 mL of 50% glycerol stock and stored at −80° C. The fermentation vials were thawed and 200 μL of culture was used to inoculate 4 mL MF media per well in a 24-well cassette. The microfermenter was operated at 30° C., 700 rpm, with a DO of 20 for the first 24 hours and a DO of 75 for the remaining 72 hours of the run. MF Buffer 1 media was added to each well at 24 hours (200 μL), 32 hours (150 μL), 48 hours (150 μL), 56 hours (150 μL), and 72 hours (50 μL). Ethyl palmitate substrate was added to each well at 24 hours (20 μL), 32 hours (30 μL), 48 hours (20 μL), 56 hours (30 μL), 72 hours (20 μL), and 80 hours (30 μL). The microfermenter cultures were harvested at 96 hours and aliquots were taken for LCDA analyses.

LCDA Extraction and Analysis from 250-mL Flask Cultures:

Whole broth samples (1.0 mL) were harvested in screw-top glass vials with TEFLON septa. Samples were acidified to a pH of 3.0 by addition of 1 M HCl, and then extracted once with 1.0 mL tert-butylmethyl ether (MTBE, Sigma-Aldrich) containing 5.0 mg/mL myristic acid internal standard. The samples were vortexed, after which the aqueous and organic phases were separated by a 5-min. centrifugation at 4500 rpm. Aliquots (0.5 mL) of the organic, MTBE phase (containing LCDAs) were transferred to new vials, and derivatization of LCDA product with methyl groups was performed by addition of 0.5 mL of methanolic $H_2SO_4$ (5% v/v) and heating at 80° C. for 1 hour. Following derivatization, 1 M NaCl in water (0.5 mL) was added, samples were vortexed, and phase-separated upon rest. The upper MTBE organic layer containing methyl-derivatized LCDA product was collected for analysis by gas chromatography (GC) with flame ionization detector (FID). Compound retention times and mass spectral data were compared to those measured for methyl esters from commercial standards (Ultra Scientific, North Kingstown, R.I.). GC analysis was carried out using a 7890 GC (Agilent Technologies, Santa Clara, Calif.) fitted with an Omegawax® 320 fused silica capillary column, 30 m×0.32 mm×0.25 μm (Supelco Inc., Bellefonte, Pa.). Hydrogen was used as carrier gas at 5.5 mL $min^{-1}$ constant flow with a split ratio of 10:1 and an inlet pressure of 18.0 psi. The oven temperature was initially programmed at 200° C., and then increased immediately at 25° C. $min^{-1}$ to 240° C.; the detector was at 260° C.

LCDA Extraction and Analysis from 2-L Fermentation Samples:

The method involved transferring 100 μL whole broth sample to a reaction vial. The sample weight was measured and recorded to ±0.1 mg using an analytical balance. Immediately after transfer, derivatization of LCDA product with methyl groups was performed by adding 100 μL of 20 mg/mL myristic acid internal standard (provided in toluene) and 2.0 mL of methanolic $H_2SO_4$ (5% v/v) and heating the reaction vial at 80° C. for 1 hour. Following derivatization, solvent extraction was performed by adding 2.0 mL of 1 M NaCl in water and 2.0 mL of hexane to the reaction mixture. The upper hexane organic layer containing the derivatized products was collected for analysis by GC with FID. Compound retention times and mass spectral data were compared to those for methyl esters from commercial standards (Ultra Scientific, North Kingstown, R.I.). The concentration of LCDA product in the sample was calculated in relation to the myristic acid internal standard. GC analysis was carried out using a 6890 GC (Agilent Technologies) fitted with an Omegawax® 320 fused silica capillary column, 30 m×0.32 mm×0.25 μm (Supelco Inc.). Helium was used as carrier gas at 2.8 mL $min^{-1}$ constant flow with a split ratio of 20:1 and an inlet pressure of 18.0 psi. The oven temperature was initially programmed at 160° C., and then increased immediately at 5° C. $min^{-1}$ to 200° C., increased at 10° C. $min^{-1}$ to 240° C. and held for 4 min. The detector was at 260° C.

Strategies to Engineer *Yarrowia* Yeast to Produce LCDA from Plant Oil-Based Substrates

*Y. lipolytica* is a non-conventional oleaginous yeast that produces lipids at more than 25% dry cell weight (DCW) when grown under nitrogen-limited conditions with glucose as a carbon source. Since *Y. lipolytica* has strong beta-oxidation capability, this yeast can readily use hydrophobic substrates such as n-alkanes, oils, fats, and fatty acids as sole carbon sources. When *Y. lipolytica* is fed fatty acids, or fatty acid esters, it can produce lipids at more than 40% DCW. Most of the fatty acids and/or fatty acid esters fed to *Yarrowia* are stored in the form of triacylglycerol.

FIG. 1 depicts lipid metabolic pathways, including fatty acid beta-oxidation and omega-oxidation aspects. *Y. lipolytica* has very weak omega-oxidation capability (represented with dashed lines in FIG. 1). Because of this low activity, there is no detectable LCDA produced when this yeast (wild type) is fed with plant oil, plant oil-derived fatty acids, or fatty acid esters. Strategies for engineering *Y. lipolytica* to convert plant oil, plant oil-derived fatty acids, and/or fatty acid esters, to LCDA are illustrated in FIG. 2 and include: (1) Reducing storage lipids by knocking out genes encoding diacylglycerol acyltransferase 1 (DGAT1), diacylglycerol acyltransferase 2 (DGAT2), and phospholipid diacylglycerol acyltransferase (PDAT); (2) Reducing or eliminating beta-oxidation in peroxisomes by knocking out genes encoding peroxisome biogenesis factor protein(s) (PEX); (3) Enhancing omega-oxidation by over-expressing cytochrome P450 monooxygenase (CYP) and cytochrome P450 reductase (CPR) genes.

Additionally, as depicted in FIGS. 1 and 2, it is believed that that the speed and degree of fatty acid transport across the cell membrane into the cytoplasm, by virtue of fatty acid transporter and long-chain fatty acyl-CoA synthetase activities, affects the production of LCDA in engineered *Y. lipolytica* cells. Indeed, as disclosed below, long-chain fatty acyl-CoA synthetase up-regulation was found to increase LCDA production in engineered *Yarrowia* cells.

Example 1

Genes Encoding Putative Long-Chain Fatty Acyl-CoA Synthetases from *Yarrowia Lipolytica*

This example describes identification of candidate sequences of long-chain acyl-CoA synthetases in *Yarrowia lipolytica* for production of long-chain acyl-CoA metabolites in microbes.

Fatty acids have to be activated by esterification to be transported into the cells. Long-chain fatty acyl-CoA synthetase enzymes catalyze this activation step by conjugating fatty acid to co-enzyme A, forming fatty acyl-CoA. There are four genes in *S. cerevisiae* (FAA-1, -2, -3, -4) encoding acyl-CoA synthetases having specificity to medium- and long-chain fatty acids. For example, FAA1 encodes acyl-CoA synthetase ScFaa1p (SEQ ID NO:33) preferring fatty acids with a chain length of C12 to C16, and FAA2 encodes enzyme ScFaa2p (SEQ ID NO:34) preferring fatty acids with a chain length of C9 to C13 (*J. Cell Biol.* 127:751-762; *Biochim. Biophys. Acta* 1486:18-27).

To identify FAA homologs in *Y. lipolytica*, the amino acid sequences encoded by the predicted open reading frame (ORF) sequences in the *Y. lipolytica* genome database (www.genolevures.org/yali.html) were aligned against the predicted amino acid sequences of *S. cerevisiae* Faa1p (SEQ ID NO:33) and Faa2p (SEQ ID NO:34). Fifteen *Y. lipolytica* ORFs were identified by these BLAST analyses (Table 2). Of the fifteen Faa1p and Faa2p homologs encoded by these ORFs, twelve were predicted to be peroxisomal (containing a peroxisomal localization signal), while three had unknown cellular localization information.

TABLE 2

Long-Chain Fatty Acyl-CoA Synthetase Candidates in *Y. lipolytica*

| Sys. name | Designation | Predicted cellular location | E value compared to Faa1p | E value compared to Faa2p | GENBANK Accession no. | SEQ ID NO. |
|---|---|---|---|---|---|---|
| YALI0D17864g | YlFAA1 | unknown | 0.0 | 4E−49 | XP_502959.1 | 36 |
| YALI0C05885g | YlACoS-2P | peroxisome | 1E−18 | 5E−19 | XP_501493.1 | 37 |

TABLE 2-continued

| Long-Chain Fatty Acyl-CoA Synthetase Candidates in *Y. lipolytica* | | | | | | |
|---|---|---|---|---|---|---|
| Sys. name | Designation | Predicted cellular location | E value compared to Faa1p | E value compared to Faa2p | GENBANK Accession no. | SEQ ID NO. |
| YALI0A14234g | YlACoS-3P | peroxisome | 8E−16 | 3E−17 | XP_500052.1 | 39 |
| YALI0E11979g | YlACoS-4P | peroxisome | 2E−15 | 1E−18 | XP_503842.1 | 40 |
| YALI0B07755g | YlACoS-5P | peroxisome | 4E−13 | 2E−15 | XP_500618.1 | 42 |
| YALI0E12419g | YlACoS-6P | peroxisome | 1E−12 | 7E−17 | XP_503862.1 | 44 |
| YALI0E20405g | YlACoS-7P | peroxisome | 4E−12 | 6E−19 | XP_504185.1 | 45 |
| YALI0B05456g | YlACoS-8 | unknown | 2E−11 | 4E−8 | XP_500530.1 | 46 |
| YALI0A15103g | YlACoS-9P | peroxisome | 2E−11 | 2E14 | XP_500085.1 | 47 |
| YALI0E05951g | YlACoS-10P | peroxisome | 2E−10 | 5E−15 | XP_503608.1 | 49 |
| YALI0D17314g | YlACoS-11P | peroxisome | 5E−10 | 3E−15 | XP_502936.1 | 50 |
| YALI0F06556g | YlACoS-12P | peroxisome | 9E−10 | 1E−11 | XP_505085.1 | 51 |
| YALI0E12859g | YlACoS-13P | peroxisome | 6E−9 | 1E−10 | XP_503878.1 | 52 |
| YALI0C09284g | YlACoS-14 | unknown | 6E−7 | 8E−12 | XP_501636.1 | 53 |
| YALI0E16016g | YlACoS-15P | peroxisome | 0.16 | | XP_504004.1 | 54 |

Separately, the *S. cerevisiae* Faa1p (SEQ ID NO:33) and Faa2p (SEQ ID NO:34) amino acid sequences were aligned against the amino acid sequences encoded by the genome of *Candida tropicalis* (www.candidagenome.org/cgi-bin/compute/blast_clade.pl#Select_Target_Organisms). A total of six candidate ORFs were identified. Three of these ORFs encoded amino acid sequences containing a putative peroxisome localization signal, and thus were predicted to encode peroxisomal proteins. Table 3 lists each of these candidate sequences.

TABLE 3

| Long-Chain Fatty Acyl-CoA Synthetase Candidates in *Candida tropicalis* | | | | | | |
|---|---|---|---|---|---|---|
| Sys. name | Designation | Predicted cellular location | E value compared to Faa1p | E value compared to Faa2p | GENBANK Accession no. | SEQ ID NO. |
| CTRG_05829 | CA-1 | unknown | 0.0 | 1E−41 | XP_002546351.1 | 57 |
| CTRG_02563 | CA-2 | unknown | 4E−47 | 1E−157 | XP_002548266.1 | 58 |
| CTRG_01503 | CA-3 | unknown | 8E−16 | 3E−17 | XP_002547197.1 | 59 |
| CTRG_05500 | CA-4P | peroxisome | 5E−48 | 4E−132 | XP_002551202.1 | 60 |
| CTRG_04022 | CA-5P | peroxisome | 2E−48 | 3E−133 | XP_002549725.1 | 61 |
| CTRG_02265 | CA-6P | peroxisome | 2E−33 | 8E−123 | XP_002547968.1 | 62 |

The amino acid sequences of *S. cerevisiae* Faa1p (SEQ ID NO:33) and Faa2p (SEQ ID NO:34), the fifteen *Y. lipolytica* long-chain acyl-CoA synthetase candidates, and the six *C. tropicalis* long-chain acyl-CoA synthetase candidates were aligned using VECTOR NTI software. A phylogenetic tree resulting from this alignment is shown in FIG. 3. The *Yarrowia* candidates YlAcoS-2P (SEQ ID NO:37), -3P (SEQ ID NO:39), -4P (SEQ ID NO:40), -5P (SEQ ID NO:42), -6P (SEQ ID NO:44), -7P (SEQ ID NO:45), -9P (SEQ ID NO:47), -10P (SEQ ID NO:49), -11P (SEQ ID NO:50) and -12P (SEQ ID NO:51) clustered together forming a group. All of these sequences are predicted to be peroxisomal proteins. The six *Candida* long-chain acyl-CoA synthetase candidates, and *Yarrowia* long-chain acyl-CoA synthetase candidates YlFaa1 (SEQ ID NO:36), YlAcoS-8 (SEQ ID NO:46), -13P (SEQ ID NO:52), -14 (SEQ ID NO:53), -15P (SEQ ID NO:54) clustered together with the two *S. cerevisiae* acyl-CoA synthetases. ScFaa1 (SEQ ID NO:33) is closely related to CA-1 (SEQ ID NO:57) and YlFaa1 (SEQ ID NO:36, "YA-1" in FIG. 3). ScFaa2 (SEQ ID NO:34) and CA-2 to -6 formed a group, and YlAcoS-8 (SEQ ID NO:46), -13P (SEQ ID NO:52), -14 (SEQ ID NO:53) and -15P (SEQ ID NO:54) formed a third group.

Thus, sequences of candidate long-chain fatty acyl-CoA synthetases in *Y. lipolytica* were identified.

Example 2

Expression Pattern of Candidate Long-Chain Fatty Acyl-CoA Synthetases in Engineered *Y. lipolytica* Cells This example describes screening of *Y. lipolytica* long-chain acyl-CoA synthetase candidates identified in Example 1 by qRT-PCR to identify sequences that are induced under conditions of substrate addition to medium. Any long-chain acyl-CoA synthetase sequence whose expression is induced by a fatty acid-comprising substrate could be a candidate enzyme for facilitating substrate import.

An LCDA-producing *Y. lipolytica* strain, D0145 (Example 13 below describes construction of this strain), was grown in 50 mL cultures in 250-mL flasks with Y2P2D2 growth media (20 g/L yeast extract; 20 g/L BACTO-PEPTONE; 20 g/L glucose) in triplicate, with a starting $OD_{600}$ of 0.15 at 30° C. with a shaking speed 250 rpm. After 24 hours, 0.5 mL and 1 mL of "Day 0" culture samples were collected for RNA extraction and LCDA quantification, respectively. For the remaining culture, 1M $NaHCO_3$ was added to adjust the pH to 8.0, after which ethyl palmitate substrate was added to a final concentration of 3%. 24 hours after substrate addition, 0.5 mL and 1 mL of "Day 1" samples were collected for RNA extraction and LCDA quantification, respectively. FIG. 4 shows LCDA production by strain D0145 at different time-points. There was no LCDA production before ethyl palmitate addition to the medium, but there was such production following substrate addition, which increased at a steady rate to about Day 2 (FIG. 4).

To prepare RNA samples, 0.5-mL aliquots from each culture at Day 0 and Day 1 were harvested by centrifugation at 13,000×g for 1 min. Cell pellets were immediately frozen and stored at −80° C. Total RNA was prepared from each cell pellet using TRIzol™ reagent (Life Technologies, Carlsbad, Calif.). Cell breakage was performed using a MINI-BEADBEATER-8 (BSP, Bartlesville, Okla.). Extracted total RNA from each sample was then purified using a Qiagen RNeasy™ kit. To remove any residual genomic DNA, 3 μg of total RNA was treated with RNase-free DNase (Qiagen, Hilden, Germany). The DNase was then inactivated by adding 1 mM EDTA and heating to 75° C. for 5 minutes. 1 μg of DNase-treated RNA was then converted to complementary (cDNA) using the High Capacity cDNA Reverse Transcription kit (Applied Biosystems, Foster City, Calif.) per the manufacturer's instructions. cDNA was then diluted 1:10 in RNase-free water for quantitative PCR (qPCR) analysis.

qPCR was performed to detect expression of the target genes listed in Table 4. All primers listed in Table 4 were designed utilizing PRIMER EXPRESS v 3.0.1 software (Applied Biosystems). Primers were evaluated for specificity by BLAST analysis against the *Y. lipolytica* Genolevures database (genolevures.org/yali.html) and validated for quantitation using genomic DNA (data not shown). Primers with PCR efficiencies between 0.85-1.15 were validated for quantitation. All qPCR reactions were performed in triplicate using SYBR® Green for detection on the ABI 7900 SDS instrument (Applied Biosystems; Foster City, Calif.). Relative expression (RQ) was calculated using Data Assist Software v3.01 and the ΔΔCt method (Applied Biosystems, Foster City, Calif.). Genes encoding 18S rRNA were identified by the software as the optimal endogenous control genes and were utilized for data normalization. Relative expression of each gene on Day 1 was then calculated by comparing its expression to its Day 0 expression, which was set to 1.0.

TABLE 4

Primers Used for qPCR Analyses

| Gene | Primer Name | Direction | Sequence (5' to 3') | SEQ ID NO. |
|---|---|---|---|---|
| YIFAA1 | 17864-900F | Fwd | CACAGACCGGCTTCTCAACTT | 1 |
| YALI0D17864g | 17864-967R | Rev | AGGTGACCATCTCGAACACAAA | 2 |
| YIACoS-2P | 5885-1034F | Fwd | CTTCTCCCTGCGTCACTCTGT | 3 |
| YALI0C05885g | 5885-1097R | Rev | TTGCCACAAGCCTTGATGTG | 4 |
| YIACoS-3P | 14234-1341F | Fwd | GGCTCCGGCTGAGATTGA | 5 |
| YALI0A14234g | 14234-1404R | Rev | AATGACAGCGACATCCTTTACCA | 6 |
| YIACoS-4P | 11979-1248F | Fwd | TCAGCTCAAACTCGACGACTTG | 7 |
| YALI0E11979g | 11979-1315R | Rev | CCACAGGCAGAGGCTCATCT | 8 |
| YIACoS-5P | 7755-282F | Fwd | TTACAGCTCGTTGCCCTACCA | 9 |
| YALI0B07755g | 7755-343R | Rev | TGGCGGGCGAAATGG | 10 |
| YIACoS-6P | 12419-1677F | Fwd | TGCTGGCATCGTGGTGAT | 11 |
| YALI0E12419g | 12419-1744R | Rev | GCAACAATCGTCGCAGAATCT | 12 |
| YIACoS-7P | 20405-626F | Fwd | CCGTGGAGCTCACCCATT | 13 |
| YALI0E20405g | 20405-691R | Rev | GGTTAGGTGCATTCTTTGCTGTCT | 14 |
| YIACoS-8P | 5456-1758F | Fwd | CTCTGCTGCTATGGTTGTCGAT | 15 |
| YALI0B05456g | 5456-1825R | Rev | TGCAACCCTCATCACCAGTTC | 16 |
| YIACoS-9P | 15103-516F | Fwd | CAAGGCCGTGCGTGTCA | 17 |
| YALI0A15103g | 15103-588R | Rev | GAGATCGGGAGCCACAATTG | 18 |
| YIACoS-10P | 5951-327F | Fwd | GCATTTTGCCGCACTTGAT | 19 |
| YALI0E05951g | 5951-399R | Rev | GACGAGCTCCGCCACAGT | 20 |
| YIACoS-11P | 17314-47F | Fwd | TGTTCTGTGGCAACATTGCA | 21 |
| YALI0D17314g | 17314-112R | Rev | CACTTGTTTTGGAGCTCTTGGA | 22 |
| YIACoS-12P | 6556-1321F | Fwd | GCGTTCGAAGAGGCTTCTGA | 23 |
| YALI0F06556g | 6556-1384R | Rev | TTCGCAACCATCGTTTCTTG | 24 |
| YIACoS-13P | 12859-1002 | Fwd | CCAGATTCTGCTGAACACAAAGA | 25 |
| YALI0E12859g | 12859-1071 | Rev | CGAAGAGCACGATCGAATGA | 26 |
| YIACoS-14P | 9284-924F | Fwd | TCTGCTTGTTGACGACCGAAT | 27 |
| YALI0C09284g | 9284-995R | Rev | GGGTTGTTCACCAGCATGTTG | 28 |
| YIACoS-15P | 16016-1393F | Fwd | ATGGGCCGATACGGTAAGCT | 29 |
| YALI0E16016g | 16016-1422T | Probe | CATCCTGGCCACCCGACAGACC | 30 |
| Yarrowia | YL-18S-329F | For | CCTGAGAAACGGCTACCACATC | 31 |
| 18S | YL-18S-395R | Rev | CCCTGTGTCAGGATTGGGTAA | 32 |

Table 5 (below) shows the results of the qRT-PCR analysis. The expression measurements (SYBR) for each Day 0 (DO) and Day 1 (D1) sample are relative to the sample Day 0-1 ('D0-1') measurement, which was set to 1.00. Each data point was run by three independent PCR reactions and normalized to *Yarrowia* 18S rRNA expression. "SYBR SD" values are standard deviations for each trio of PCR reactions. Transcripts encoding YIAcoS-10P (SEQ ID NO:49), YIAcoS-6P (SEQ ID NO:44), and YIAcoS-3P (SEQ ID NO:39) long-chain acyl-CoA synthetases exhibited more than a 4-fold increase in relative expression on Day 1 compared to the expression on Day 0 (indicated with grey cells in Table 5.

TABLE 5

Results of qRT-PCR Analysis on Transcripts for Long-Chain Acyl-CoA Synthetase Candidates

| Transcripts encoding: Sample[a] | YIACoS-8 (SEQ ID NO: 46) SYBR | SYBR SD[b] | YIACoS-2P (SEQ ID NO: 37) SYBR | SYBR SD | YIACoS-10P (SEQ ID NO: 49) SYBR | SYBR SD | YIACoS-12P (SEQ ID NO: 51) SYBR | SYBR SD | YIACoS-5P (SEQ ID NO: 42) SYBR | SYBR SD |
|---|---|---|---|---|---|---|---|---|---|---|
| D 0-1 | 1.00 | 0.13 | 1.00 | 0.08 | 1.00 | 0.09 | 1.00 | 0.18 | 1.00 | 0.13 |
| D 0-2 | 1.89 | 0.23 | 0.83 | 0.10 | 1.09 | 0.33 | 1.29 | 0.49 | 0.26 | 0.04 |
| D 0-3 | 1.74 | 0.16 | 0.86 | 0.09 | 1.03 | 0.11 | 0.53 | 0.07 | 1.08 | 0.13 |
| D 1-1 | 1.70 | 0.14 | 0.58 | 0.06 | 7.11 | 0.43 | 0.20 | 0.10 | 0.85 | 0.09 |
| D 1-2 | 1.68 | 0.20 | 0.78 | 0.10 | 5.16 | 0.63 | 0.18 | 0.08 | 2.36 | 0.29 |
| D 1-3 | 2.14 | 0.07 | 1.02 | 0.12 | 6.77 | 0.32 | 0.24 | 0.14 | 1.47 | 0.11 |

| Transcripts encoding: Sample[a] | YIACoS-14 (SEQ ID NO: 53) SYBR | SYBR SD | YIACoS-4P (SEQ ID NO: 40) SYBR | SYBR SD | YIACoS-6P (SEQ ID NO: 44) SYBR | SYBR SD | YIACoS-13P (SEQ ID NO: 52) SYBR | SYBR SD | YIACoS-3P (SEQ ID NO: 39) YL-SYBR | SYBR SD |
|---|---|---|---|---|---|---|---|---|---|---|
| D 0-1 | 1.00 | 0.13 | 1.00 | 0.12 | 1.00 | 0.14 | 1.00 | 0.10 | 1.00 | 0.08 |
| D 0-2 | 0.77 | 0.10 | 0.71 | 0.10 | 2.19 | 0.28 | 1.31 | 0.14 | 1.38 | 0.54 |
| D 0-3 | 0.76 | 0.11 | 0.57 | 0.16 | 1.76 | 0.20 | 1.24 | 0.12 | 2.74 | 0.60 |
| D 1-1 | 0.76 | 0.05 | 0.44 | 0.06 | 7.01 | 0.61 | 1.00 | 0.06 | 19.51 | 2.14 |
| D 1-2 | 0.76 | 0.10 | 0.42 | 0.08 | 6.80 | 0.80 | 1.19 | 0.14 | 21.50 | 2.65 |
| D 1-3 | 0.91 | 0.09 | 0.29 | 0.01 | 8.40 | 0.37 | 1.33 | 0.06 | 27.62 | 2.25 |

| Transcripts encoding: Sample[a] | YIACoS-9P (SEQ ID NO: 47) SYBR | SYBR SD | YIACoS-15P (SEQ ID NO: 54) SYBR | SYBR SD | YIACoS-11P (SEQ ID NO: 50) SYBR | SYBR SD | YIFAA1 (SEQ ID NO: 36) SYBR | SYBR SD | YIACoS-7P (SEQ ID NO: 45) SYBR | SYBR SD |
|---|---|---|---|---|---|---|---|---|---|---|
| D 0-1 | 1.00 | 0.16 | 1.00 | 0.09 | 1.00 | 0.57 | 1.00 | 0.09 | 1.00 | 0.10 |
| D 0-2 | 0.99 | 0.17 | 1.54 | 0.21 | 0.69 | 0.50 | 1.53 | 0.18 | 1.16 | 0.12 |
| D 0-3 | 1.13 | 0.19 | 1.43 | 0.14 | 1.31 | 0.76 | 1.43 | 0.14 | 1.25 | 0.11 |
| D 1-1 | 1.32 | 0.19 | 1.28 | 0.20 | 0.68 | 0.34 | 0.93 | 0.07 | 1.34 | 0.09 |
| D 1-2 | 1.40 | 0.17 | 1.44 | 0.20 | 0.65 | 0.32 | 1.23 | 0.25 | 1.44 | 0.18 |
| D 1-3 | 1.87 | 0.12 | 2.03 | 0.12 | 0.56 | 0.31 | 1.57 | 0.37 | 1.91 | 0.07 |

[a]Day 0 (D 0) and Day 1 (D 1) samples were each analyzed in triplicate.
[b]SD, standard deviation Based on the data in Table 5, expression of YIAcoS-10P (SEQ ID NO:49), YIAcoS-6P (SEQ ID NO:44), and YIAcoS-3P (SEQ ID NO:39) putative long-chain acyl-CoA synthetases is induced in *Y. lipolytica* upon treatment with a long-chain fatty acid-comprising substrate. These long-chain acyl-CoA synthetases may therefore be useful for facilitating import of long-chain fatty acid-comprising substrates.

Example 3

Codon-Optimization of Polynucleotide Sequences Encoding Putative Long-Chain Acyl-CoA Synthetases for Expression in *Y. lipolytica*

DNA open reading frames encoding the long-chain acyl-CoA synthetase candidates YIACoS-3P (SEQ ID NO:39), YIACoS-5P (SEQ ID NO:42), YIACoS-6P (SEQ ID NO:44), YIACoS-10P (SEQ ID NO:49), and YIFAA (SEQ ID NO:36) were codon-optimized for high expression in *Y. lipolytica* according to the methodology disclosed in U.S. Pat. No. 7,125,672, which is incorporated herein by reference. Thus, polynucleotide sequences YIACoS-3Ps (SEQ ID NO:38), YIACoS-5Ps (SEQ ID NO:41), YIACoS-6Ps (SEQ ID NO:43), YIACoS-10Ps (SEQ ID NO:48), and YIFAA1s (SEQ ID NO:35) were prepared that encode, respectively, YIACoS-3P (SEQ ID NO:39), YIACoS-5P (SEQ ID NO:42), YIACoS-6P (SEQ ID NO:44), YIACoS-10P (SEQ ID NO:49), and YIFaa1 (SEQ ID NO:36). Each of the codon-optimized DNA sequences was individually synthesized and cloned into an expression vector by GenScript (Piscataway, N.J.) to generate pZP2-YIACoS-3Ps (SEQ ID NO:63), pZP2-YIACoS-5Ps (SEQ ID NO:64), pZP2-YIACoS-6Ps (SEQ ID NO:65), pZP2-YIACoS-10Ps (SEQ ID NO:66), and pZKL7A-FYIFAAs (SEQ ID NO:67) (FIG. 5A-E, respectively). Another vector, pZP2-YIACoS-5PS3s (SEQ ID NO:68, FIG. 5F), was also prepared that allows for expression of YIACoS-5PS3 (SEQ ID N0:56) which is a truncated version (six amino acid C-terminal truncation) of YIAcoS-5P (SEQ ID NO:42).

The above constructs can be used to over-express long-chain acyl-CoA synthetase candidates in *Yarrowia*.

Example 4

Expression of Long-Chain Acyl-CoA Synthetase Candidates in *E. coli*

This example discloses over-expressing the acyl-CoA synthetase candidates YlACoS-3P (SEQ ID NO:39), YlACoS-5P (SEQ ID NO:42), YlACoS-6P (SEQ ID NO:44), YlACoS-10P (SEQ ID NO:49), YlACoS-5PS3 (SEQ ID NO:56, a six amino acid C-terminus truncated version of YlACoS-5P) and YlFAA (SEQ ID NO:36) under a T7 inducible promoter in *Escherichia coli.*

First, the polynucleotide sequences of YlACoS-3Ps (SEQ ID NO:38), YlACoS-5Ps (SEQ ID NO:41), YlACoS-6Ps (SEQ ID NO:43), YlACoS-10Ps (SEQ ID NO:48), YlACoS-5PS3s (SEQ ID NO:55) and YlFAAs (SEQ ID NO:35) (each being codon-optimized for expression in *Yarrowia*) were excised, respectively, from pZP2-YlACoS-3Ps (SEQ ID NO:63), pZP2-YlACoS-5Ps (SEQ ID NO:64), pZP2-YlACoS-6Ps (SEQ ID NO:65), pZP2-YlACoS-10Ps (SEQ ID NO:66), pZP2-YlACoS-5PS3s (SEQ ID NO:68), and pZKL7A-FYlFAAs (SEQ ID NO:67) (FIGS. 5A-F) using NcoI/NotI restriction endonucleases and individually ligated into the pET23d vector (SEQ ID NO:69) (Novagen, Madison, Wis.) at NcoI/NotI endonuclease sites. Restriction analysis was used to verify each ligation (data not shown).

To over-express each putative long-chain acyl-CoA synthetase, an 8 hour culture of *E. coli* BL(DE3) transformed with the appropriate pET23d-based plasmid and grown in $LB^{AMP}$ medium (AMP: ampicillin, final concentration 100 µg/mL) was diluted 1:50 in 100 mL of the same medium in a 500-mL flask. Each culture was shaken at 37° C. until the optical density at 600 nm reached 0.8-0.9, after which the flask was placed in an 18° C. incubator for about 20 minutes before the addition of isopropylthio-β-D-galactoside (IPTG) to a final concentration of 100 µM. Each culture was then shaken for an additional 10-12 hours at 18° C. Cells (about 100 mg wet mass from 15 mL of culture) were collected by centrifugation, washed once with phosphate-buffered saline solution (PBS), pH 7.4, then resuspended in 400 µL of lysis buffer (BUGBUSTER HT, containing 25% glycerol, 0.5 mg/mL lysozyme and protease inhibitor cocktail from Pierce) and incubated at room temperature on a shaking platform for 20 minutes. Cell debris were removed by centrifugation at 12,000×g for 30 minutes at 4° C. For removal of small molecules from the supernatant that may interfere with the following enzymatic assay, the supernatant was placed in a 10-KDa molecular weight cut-off (MWCO) centrifugal device and centrifuged at 4° C. at 12,000×g for 30 minutes. The retained protein solution (about 50-100 µL) was resuspended in 400 µL (final volume) buffer (0.1 M KPi, 20% glycerol, pH 7.5) and concentrated once again by centrifugation at 4° C. at 12,000×g for 30 minutes in the MWCO device. The concentrated protein solution was resuspended in 0.1 M KPi, 20% glycerol, pH 7.5 in a final volume of about 200 µL, transferred to a new centrifuge tube, and centrifuged briefly at maximum speed to remove any precipitated protein. The clarified supernatant, which was used for SDS-PAGE analysis, determination of protein concentration, and enzymatic assays, was stored at −80° C. As shown in FIGS. 6A and B, all six acyl-CoA synthetase candidates were successfully over-expressed in *E. coli* and, with the exception of YlACoS-3P (SEQ ID NO:39), were found in the soluble fraction of *E. coli* cell lysates.

Example 5

Determination of Specific Activity of Long-Chain Acyl-CoA Synthetase Candidates

This example discloses analysis of the specific activity of long-chain acyl-CoA synthetase candidates. Specifically, acyl-CoA synthetase candidates present in soluble *E. coli* fractions (produced in Example 4) were tested for activity using either palmitic acid or p-coumaric acid as substrate.

The specific activity of each long-chain acyl-CoA synthetase candidate on palmitic acid substrate was determined as follows. The formation of adenosine monophosphate (AMP) in clarified supernatant (Example 4) by a putative acyl-CoA synthetase was coupled to oxidation of NADH by lactate dehydrogenase (monitored by absorbance at 340 nm) in the presence of phosphoenolpyruvate (PEP), NADH, myokinase and pyruvate kinase, as depicted in the following scheme (1→4):

1. RCOOH (fatty acid substrate)+CoASH+ATP↔RCOSCoA+AMP+$PP_i$ (acyl-CoA synthetase-catalyzed).

2. AMP+ATP↔2ADP (myokinase-catalyzed).

3. 2 ADP+2 PEP↔2 ATP+2 pyruvate (pyruvate kinase-catalyzed).

4. 2 pyruvate+2 NADH↔2 lactate+2 $NAD^+$ (lactate dehydrogenase-catalyzed).

Specifically, each assay (300 µL final volume) was carried out at 30° C. and contained: 1 mM palmitic acid (diluted from a 10 mM stock solution made in DMSO), 4 mM ATP, 1.5 mM CoASH, 1 mM PEP, 5 Units pyruvate kinase, 5 Units lactate dehydrogenase, 6 Units myokinase in 100 mM Tris-Cl, 50 mM NaCl, 10 mM $MgCl_2$, pH 7.2. The reaction process was initiated by adding the appropriate amount of cell lysate (Example 4) containing a candidate long-chain fatty acyl-CoA synthetase. The oxidation of NADH (to $NAD^+$) at 340 nm was monitored for 5 minutes after addition of cell extract using a Cary-100 UV-Vis spectrophotometer (Agilent). Initial slopes were calculated by subtracting the background activity observed in an enzymatic assay in which palmitic acid substrate was replaced with DMSO.

The specific activities of the putative long-chain acyl-CoA synthetases as measured above against palmitic acid substrate are summarized in Table 6 below. Specific activity measurements are provided in mU/mg, where one Unit corresponds to the amount of enzyme that produces 1.0 µmole of palmitoyl-CoA in the presence of 1 mM palmitic acid, 4 mM ATP and 1.5 mM CoA per minute at 30° C. and pH 7.2; absorbance coefficient of NADH=6,220 $M^{-1}$ $cm^{-1}$. No activity above the background level was detected (denoted as "n.d." in Table 6) in the supernatant prepared from control cells (transformed with empty pET23d vector) and in supernatants prepared from cells expressing YlACoS-3P (SEQ ID NO:39), YlACoS-5P (SEQ ID NO:42) and YlACoS-5P53 (SEQ ID NO:56).

Because sequences related to the acyl-CoA synthetase candidates YlACoS-3P (SEQ ID NO:39), YlACoS-5P (SEQ ID NO:42), and YlACoS-10P (SEQ ID NO:49) are annotated in the NCBI GENBANK database as putative 4-coumarate-CoA ligases, whereas YlFAA (SEQ ID NO:36) shows 50% identity to Faa1p (SEQ ID NO:33) (a well-characterized long-chain fatty acyl-CoA synthetase from *S. cerevisiae* with preference to C12:0-C16:0 fatty acids), the specific activities of the abovementioned enzymes were also tested using p-coumaric acid (pCA) as substrate. The specific activity of each long-chain acyl-CoA synthetase candidate on pCA substrate was determined as follows. Each assay (250 μL final volume) was carried out at 30° C. and contained: 1 mM p-coumaric acid (diluted from a 10 mM stock solution made in DMSO), 4 mM ATP, 1.5 mM CoASH, in 100 mM Tris-Cl, 50 mM NaCl, 10 mM $MgCl_2$, pH 7.2. The reaction was initiated by adding the appropriate amount of cell lysate (Example 4) containing a candidate long-chain fatty acyl-CoA synthetase. The increase in absorbance at 340 nm (due to formation of p-coumaroyl-CoA) was monitored for 10 min after the addition of cell extract using a Cary-100 UV-Vis spectrophotometer (Agilent). Initial slopes were calculated by subtracting the background activity observed in an enzymatic assay in which the pCA was replaced by DMSO.

The specific activities of the putative long-chain acyl-CoA synthetases as measured above against pCA substrate are summarized in Table 6 below. Specific activity measurements are provided in mU/mg, where one Unit corresponds to the amount of enzyme that produces 1.0 μmole of p-coumaroyl-CoA in the presence of 1 mM p-coumaric acid, 4 mM ATP and 1.5 mM CoA per minute at 30° C. and pH 7.2; absorbance coefficient of coumaroyl-CoA=21,000 $M^{-1}$ $cm^{-1}$. No activity above the background level was detected (denoted as "n.d." in Table 6) in the supernatant prepared from control cells (transformed with empty pET23d vector) and in supernatants prepared from cells expressing YlACoS-3P (SEQ ID NO:39), YlACoS-5P (SEQ ID NO:42), YlACoS-5PS3 (SEQ ID NO:56) and YlFAA (SEQ ID NO:36).

TABLE 6

Specific Activities of Long-Chain Acyl-CoA Synthetase Candidates on Different Substrates

| Enzyme | SEQ ID NO. | Specific Activity (mU/mg) Palmitic acid substrate | p-Coumaric acid substrate |
|---|---|---|---|
| Control/pET23d | | n.d.[a] | n.d. |
| YlACoS-3P | 39 | n.d. | n.d. |
| YlACoS-5P | 42 | n.d. | n.d. |
| YlACoS-6P | 44 | 452 ± 12 | 39 ± 9 |
| YlACoS-10P | 49 | 433 ± 21 | 225 ± 25 |
| YlACoS-5PS3 | 56 | n.d. | n.d. |
| YlFAA | 36 | 449 ± 15 | n.d. |

[a]n.d. (not detected).

These results support the notion that YlACoS-6P (SEQ ID NO:44) and YlACoS-10P (SEQ ID NO:49) can accept both aromatic carboxylic acids and long-chain fatty acids as substrates. In contrast, YlFAA1 (SEQ ID N0:36) appears to be specific for palmitic acid. Neither YlACoS-3P (SEQ ID NO:39) nor YlACoS-5P (SEQ ID NO:42) showed activity against the two substrates under the defined reaction conditions.

Example 6

Generating Advanced *Y. lipolytica* Parent Strains for Producing LCDA from Plant Oil-Based Substrates This example discloses *Y. lipolytica* strains that were amenable to additional genetic engineering, leading to strains that could produce high amounts of LCDA.

As described above, it is contemplated that *Y. lipolytica* likely needs to be engineered to reduce or eliminate lipid storage and beta-oxidation to effectively produce LCDA from plant oil, plant oil-derived fatty acids, or fatty acid esters. It is also likely that a diverse genetic background may be advantageous for LCDA production. As shown in Table 7, a series *Y. lipolytica* strains was generated from wild type strains ATCC Nos. 20362 and 90812. Some of these strains have reduced lipid storage capacity and reduced beta-oxidation function. FIG. 7A diagrams the lineage of some of these strains with respect to each other.

TABLE 7

*Y. lipolytica* Parent Strains for LCDA Production

| Strain Names | Genotypes | Reference[a] |
|---|---|---|
| ATCC #20362 | MATA | ATCC |
| ATCC #90812 | leu2-35, lys5-12, ura3-18, xpr2::LYS5B, MATB | ATCC |
| Y2224 | ura3−, MATA | U.S. Pat. Appl. Publ. No. 2007/0292924 |
| D0003 (L183) | dgat1−, dgat2−, ura3−, MATA | Yeast (2012) 29: 25-38 |
| D0004 | dgat1−, dgat2−, pex3−, ura3−, MATA | Instant disclosure and U.S. Pat. Appl. No. 62/082,734 |
| D0008 | dgat1−, dgat2−, pex10−, MATA | Instant disclosure and U.S. Pat. Appl. No. 62/082,734 |
| D0009 | dgat1−, dgat2−, pex10−, ura3−, MATA | Instant disclosure and U.S. Pat. Appl. No. 62/082,734 |
| D0015 | dgat1−, dgat2−, pex3−, pox4−, ura3−, MATA | Instant disclosure and U.S. Pat. Appl. No. 62/140,681 |
| W101 | leu2-35, lys5-12, ura3-18, xpr2::LYS5B, Ura3, MATB | Instant disclosure and U.S. Pat. Appl. No. 62/140,681 |
| 1D2373 | Diploid of W101 and D0004 | Instant disclosure and U.S. Pat. Appl. No. 62/140,681 |
| 1B2479I (2373U-6) | leu2−, MATB | Instant disclosure and U.S. Pat. Appl. No. 62/140,681 |
| 2D2519 | Diploid of 1B2479I and D0004 | Instant disclosure and U.S. Pat. Appl. No. 62/140,681 |

TABLE 7-continued

| *Y. lipolytica* Parent Strains for LCDA Production | | |
|---|---|---|
| Strain Names | Genotypes | Reference[a] |
| 2B2583I (2519U-1) | leu2−, MATB | Instant disclosure and U.S. Pat. Appl. No. 62/140,681 |
| 3D2653 | Diploid of 2B2583I and D0004 | Instant disclosure and U.S. Pat. Appl. No. 62/140,681 |
| 3B2702I (2653U-19) | dgat2−, leu2−, MATB | Instant disclosure and U.S. Pat. Appl. No. 62/140,681 |
| 4D2738 | Diploid of 3B2702I and D0015 | Instant disclosure and U.S. Pat. Appl. No. 62/140,681 |
| 2738Y-45 | MATA, dgat1−, dgat2−, pex3−, pox4−, ura3−, leu2− | Instant disclosure |
| 77T5-5 | MATA, dgat1−, dgat2−, leu2−, pex3−, pox3−, pox4−, Ura3+ | Instant disclosure |
| 118T1-14 | MATA, dgat1−, dgat2−, Leu2+, pex3−, pox2−, pox3− pox4−, Ura3+ | Instant disclosure |
| D0031 | MATA, dgat1−, dgat2−, Leu2+, pex3−, pox2−, pox3−, pox4−, ura3− | Instant disclosure |

[a]Each incorporated herein by reference.

Specifically, strain D0004 was generated by knocking out the PEX3 gene (encoding peroxisome biogenesis factor 3 protein [Pex3p]) in strain L183. Strain L183, designated as D0003, was transformed with the URA3-containing AscI/SphI fragment of plasmid pY157 (SEQ ID NO:70, see FIG. 4A in U.S. Pat. Appl. No. 62/140,681) to knock out the PEX3 gene by homologous recombination. One of the transformants, designated as strain T1876, was identified as being pex3− (i.e., Δpex3) by real-time PCR. The PEX3 knock-out site of strain T1876 was expected to comprise SEQ ID NO:71 (instead of wild type PEX3 locus sequence) (refer to Table 1 for description of SEQ ID NO:71). Strain T1876 was transformed with plasmid pY117 (disclosed in Table 20 of U.S. Pat. Appl. Publ. No. 2012/0142082, which is incorporated herein by reference) to express Cre recombinase to excise the LoxP-flanked URA3 gene (introduced by fragment of pY157 that knocked out PEX3). A pY117 transformant could not grow on MM, but could grow on MMU, indicating that the transformant lacked the URA3 gene; this transformant was designated as strain D0004 (dgat1−, dgat2−, pex3−, ura3−). The PEX3 knock-out site of strain D0004 was expected to comprise SEQ ID NO:72 (instead of wild type PEX3 locus sequence) (refer to Table 1 for description of SEQ ID NO:72).

Strain D0015 was generated from strain D0004 by knocking out the POX4 gene (encoding peroxisomal acyl-CoA oxidase-4 [Pox4 enzyme, GenBank Acc. No. CAG80078]) by a "pop-in/pop-out" process (see U.S. Pat. Appl. Publ. No. 2014/0220645, which is incorporated herein by reference, for more details regarding this type of knock-out strategy). Briefly, strain D0004 was transformed with XbaI-digested plasmid pYRH146-Pox4KO (SEQ ID NO:73, see FIG. 4C in U.S. Pat. Appl. No. 62/140,681). A total of 28 transformants were grown on MM plates. PCR analyses detected two transformants, #7 and #17, in which the first cross (pop-in) was between the homologous 3'-arm sequences of the native POX4 gene and construct pYRH146-Pox4KO. The #7 transformant was picked, grown in liquid YPD media, and then plated on FOA600 plates (to select for pop-out event leading to ura3-). PCR analyses detected a second cross (between respective 5'-arm homologous sequences) in 13 out of 28 strains grown on the FOA600 plates. One of these 13 strains was designated as D0015, which was determined to have a knock-out of the POX4 gene. D0015 has the following genotype: dgat1−, dgat2−, pex3−, pox4−, ura3−. The POX4 knock-out site was expected to comprise SEQ ID NO:74 (instead of wild type POX4 locus sequence) (refer to Table 1 for description of SEQ ID NO:74).

Strain W101 was generated by transforming strain ATCC No. 90812 with the URA3-containing EcoRI/ClaI fragment of plasmid pYRH72 (SEQ ID NO:75).

A diploid strain, 1D2373, was generated by crossing W101 to D0004.

Strain 1D2373 was sporulated and one of its progeny, strain 23731-6, was determined to be haploid with mating type B genotype by real-time PCR. Strain 23731-6 could not grow on SC-leu media and was renamed as strain 1B2479I.

A diploid strain, 2D2519, was generated by crossing 1B2479I to D0004.

Strain 2D2519 was sporulated and one of its progeny, strain 2519I-1, was determined to be haploid with mating type B genotype by real-time PCR. Strain 2519I-1 could not grow on SC-leu media and was renamed as strain 2B2583I.

A diploid strain, 3D2653, was generated by crossing 2B2583I to D0004.

Strain 3D2653 was sporulated and one of its progeny, strain 2B53I-19, was determined to be haploid with a genotype of dgat2-, MATB by real-time PCR. Strain 2653I-19 could not grow on SC-leu media and was renamed as strain 362702I.

Strain D0015 was crossed to strain 3B27021 to generate diploid strain 4D2738.

Strain 4D2738 was sporulated and one of its progeny, strain 2738Y-14, was determined to be haploid with a genotype of dgat1−, dgat2−, pox4−, pex3− and MATA by real-time PCR. Strain 2738Y-14 could not grow on MM media and was designated as D0017.

Strain 4D2738 was sporulated and one of its progeny, strain 2738Y-45, was determined to be haploid with a genotype of dgat1−, dgat2−, pox4−, and pex3− by real-time PCR. Strain 2738Y-45 could not grow on SC-ura or SC-leu plates. Therefore, strain 2738Y-45 has the genotype of MATA, dgat1−, dgat2−, pex3−, pox4−, ura3− and leu2-.

Strain 77T5-5 was generated by deleting the POX3 gene from 2738Y-45 via a one-step approach. Strain 2738Y-45 was transformed with the AscI/SphI fragment of plasmid p12_3-B-Pex3del1 (FIG. 8A, SEQ ID NO:76). One of the transformants was identified as pox3− by real time PCR. This transformant was designated as 77T5-5 (MATA, dgat1−, dgat2−, leu2−, pex3−, pox3−, pox4−, Ura3+).

Strain D0031 was generated by first deleting the POX2 gene from 77T5-5 via a one-step approach. Strain 77T5-5 was transformed with the AscI/SphI fragment of plasmid p70_Pox2::Leu2 (FIG. 8B, SEQ ID NO:77). One of the transformants 118T1-14 was identified as pox2− by real time PCR. Strain 118T1-14 (MATA, dgat1−, dgat2−, Leu2+, pex3−, pox2−, pox3−, pox4−, Ura3+) in turn was transformed with plasmid pY117 ((disclosed in Table 20 of U.S. Pat. Appl. Publ. No. 2012/0142082, which is incorporated herein by reference) to express Cre recombinase to excise the LoxP-flanked URA3 gene (introduced by p12_3-B-Pex3del1 in previous step). One of the transformants, 118T1-14-7-1U could not grow on MM, but could grow on MMU, indicating that the transformant lacked the URA3 gene; this transformant was designated as strain D0031 (MATA, dgat1−, dgat2−, Leu2+, pex3−, pox2−, pox3−, pox4−, ura3−).

Thus, certain *Y. lipolytica* strains were produced, including some lacking functional PEX3 (pex3−), POX2 (pox2−), POX3 (pox3−) and POX4 (pox4−) genes. These strains were amenable to additional genetic engineering, leading to strains that could produce significant amounts of LCDA (below Examples).

Example 7

Generation of *Y. lipolytica* Strain D1017 for LCDA Production by Over-Expressing CYP and CPR Enzymes This example discloses construction of *Yarrowia* strain D1017 by expressing codon-optimized sequences encoding *C. tropicalis* CYP and CPR enzymes in strain D0031. Strain D1017 was an intermediate strain used for developing strain D3928 (FIG. 7B).

Construct pZKLY-FCtR17U (FIG. 9A, SEQ ID NO:82) contains one copy each of codon-optimized CYP52A17 (CtCYPA17s, GenBank Acc. No. AAO73958, SEQ ID NO:83 encoding SEQ ID NO:84) and CPR (CtCPRs, GenBank Acc. No. P37201, SEQ ID NO:85 encoding SEQ ID NO:86) coding sequences from *C. tropicalis*. Each coding sequence was under the control of heterologous promoter and 3'-terminator sequences. NcoI and NotI endonuclease sites were added around the translation initiation codon (ATG) and after the stop codon, respectively, of each codon-optimized sequence encoding CtCYPA17 or CtCPR. Components of the pZKLY-FCtR17U plasmid (SEQ ID N0:82) are further described in Table 8.

TABLE 8

Description of Plasmid pZKLY-FCtR17U (SEQ ID NO: 82)

| RE Sites and Nucleotide Positions | Description of Chimeric Gene Components |
|---|---|
| AscI/BsiWI (7136-6242) | 887-bp 5' portion of Lipase Y locus (GenBank Acc. No. AJ549519, labeled as "LipY-5'" in Figure) |
| PacI/SphI (10606-9844) | 756-bp 3' portion of Lipase Y locus (GenBank Acc. No. AJ549519, labeled as "LipY-3'" in Figure) |
| PmeI and SwaI fusion site/SwaI (3175-6086) | FBA::CtCPRs::Lip1, comprising:<br>FBA: *Y. lipolytica* FBA promoter (U.S. Pat. No. 7,202,356);<br>CtCPRs: Codon-optimized synthetic sequence (SEQ ID NO: 85) encoding cytochrome P450 reductase (SEQ ID NO: 86), derived from *C. tropicalis* (GenBank Acc. No. P37201);<br>Lip1: Lip1 terminator sequence from *Yarrowia* Lip1 gene (GenBank Acc. No. Z50020) |
| PmeI/PmeI and SwaI fusion site (348-3175) | FBAINm1::CtCYPA17s::Pex20, comprising:<br>FBAINm1: *Y. lipolytica* FBAINm1 promoter (U.S. Pat. No. 7,202,356);<br>CtCYPA17s: Codon-optimized synthetic sequence (SEQ ID NO: 83) encoding cytochrome P450 monooxygenase (SEQ ID NO: 84), derived from *C. tropicalis* (CtCYP52A17, GenBank Acc. No. AAO73958);<br>Pex20: Pex20 terminator sequence from *Yarrowia* Pex20 gene (GenBank Acc. No. AF054613) |
| EcoRI/ClaI (10619-1) | LoxP-flanked Ura3 marker: *Yarrowia* Ura3 gene (GenBank Accession No. AJ306421) |

Plasmid pZKLY-FCtR17U (SEQ ID NO:82) was digested with AscI/SphI, and then used to transform strain D0031 according to the General Methods. Transformant cells were plated onto MM plates and maintained at 30° C. for 2 days. Individual colonies from each transformation were re-streaked onto MM plates, and then inoculated into liquid MM at 30° C. and shaken at 250 rpm for 1 day. Overnight cultured cells were used to inoculate 25 mL of liquid YPD4-B media in a 250-mL flask, which was then shaken at 180 rpm at 30° C. After 40 hours, the cultures were adjusted to pH 8.0 with addition of 2.0 mL of 1M $NaHCO_3$, after which ethyl palmitate (W245100, Sigma-Aldrich) was added directly to the culture media to a final concentration of 8 mg $mL^{-1}$. The cultures were then shaken for another 4 days at 180 rpm at 30° C., after which whole broth samples from each flask culture were subjected to LCDA analysis according to the General Methods.

GC analyses showed that there was no hexadecanedioic acid (C16:0 LCDA) detected in parent strain D0031. However, most transformants of parent strain D0031 produced more than 8 g/L C16:0 LCDA. Transformants #6, #8, #10 and #11, respectively, produced 9.5, 9.5, 12.1 and 9.1 g/L C16:0 LCDA. These four strains were designated as strains D1015, D1016, D1017 and D1018, respectively.

Subsequent flask analyses of strains D1015, D1016 and D1017 were performed. Specifically, D1015, D1016 and D1017 strains were each placed in a 50-mL culture in a 250-mL baffled flask, with ethyl palmitate added to a final concentration of 16 mg $mL^{-1}$. The cultures were shaken at 180 rpm at 30° C. for 4 days. Strains D1015, D1016 and D1017 produced C16:0 LCDA at about 7.4, 7.6 and 9.3 g/L, respectively.

Strain D1017 was also analyzed by micro-fermentation analysis. While a control strain (D0285, data not shown) produced C16:0 LCDA at 6.4 g/L, strain D1017 produced C16:0 LCDA at about 7.4 g/L.

It is noted that the pZKLY-FCtR17U (SEQ ID NO:82) DNA used to transform D0031 to yield strain D1017 and its siblings could potentially knockout the Lipase Y locus (GenBank Acc. No. AJ549519). Such a knockout in these strains was not confirmed, however. The genotype of D1017 and its siblings with respect to wild type *Y. lipolytica* ATCC #20362 was dgat1−, dgat2−, Leu2+, pex3−, pox2−, pox3−, pox4−, Ura3+, unknown 1−, FBA::CtCPRs::Lip1, FBAINm1::CtCYPA17s::Pex20.

Thus, *Yarrowia* strain D1017 was generated, which could produce greater than 5 g/L of LCDA products when fed with a long-chain fatty acid-comprising substrate in flask assays.

Example 8

Generation of *Y. lipolytica* Strain D1308 for LCDA Production by Over-Expressing Fatty Alcohol Oxidase and Fatty Aldehyde Dehydrogenase This example discloses construction of *Yarrowia* strain D1308 by expressing codon-optimized sequences encoding *Candida cloacae* fatty alcohol oxidase (FAO) and *C. tropicalis* fatty aldehyde dehydrogenase (FALDH) enzymes. Strain D1308 was an intermediate strain used for developing strain D3928 (FIG. 7B).

First, strain D1017U was developed from strain D1017. Plasmid pY117 was used for temporary expression of Cre recombinase to excise the LoxP-flanked URA3 gene within strain D1017. A pY117 transformant could not grow on MM, but could grow on MMU, indicating that the transformant lacked the URA3 gene; this transformant was designated as strain D1017U.

Next, strain D1017U was transformed with a linearized plasmid construct pZKADn-C2F1U (FIG. 9B, SEQ ID NO:87). This fragment contained two expression cassettes, one for over-expressing a codon-optimized sequence encoding an FAO enzyme (CcFAO1s, GenBank Acc. No. CAB75351, SEQ ID NO:88 encoding SEQ ID NO:89), and the other for over-expressing a codon-optimized sequence encoding an FALDH enzyme (CtFALDH2s, GenBank Acc. No. XP_002550712, SEQ ID NO:90 encoding SEQ ID NO:91). Components of the pZKADn-C2F1U plasmid (SEQ ID N0:87) are further described in Table 9.

TABLE 9

Description of plasmid pZKADn-C2F1U (SEQ ID NO: 87)

| RE Sites and Nucleotide positions | Description of Chimeric Gene Components |
|---|---|
| AscI/BsiWI (7346-6569) | 772 bp 5' portion of *Y. lipolytica* alcohol dehydrogenase 3 locus (GenBank Acc. No. AF175273, labeled as “yAD-5” in Figure) |
| PacI/AscI (10824-10086) | 738 bp 3' portion of *Y. lipolytica* alcohol dehydrogenase 3 locus (GenBank Acc. No. AF175273, labeled as “yAD-3” in Figure) |
| PmeI/SwaI (3333-6413) | DG2Pro-715::CtALDH2S::Lip1, comprising:<br>DG2pro-715: *Y. lipolytica* DGAT2 promoter (U.S. Pat. Appl. Publ. No. 2012/0252079);<br>CtALDH2s: Codon-optimized synthetic sequence (SEQ ID NO: 90) encoding fatty aldehyde dehydrogenase (SEQ ID NO: 91) derived from *C. tropicalis* (GenBank Acc. No. XP_002550712);<br>Lip1: Lip1 terminator sequence from *Yarrowia* Lip1 gene (GenBank Acc. No. Z50020) |
| ClaI/PmeI (1-3333) | FBA1L::CcFAO1s::Aco3, comprising:<br>FBA1L: *Y. lipolytica* FBA1L promoter (U.S. Pat. No. 7,202,356);<br>CcFAO1s: Codon-optimized synthetic sequence (SEQ ID NO: 88) encoding fatty alcohol oxidase (SEQ ID NO: 89), derived from *C. cloacae* (GenBank Acc. No. CAB75351);<br>Aco3: Aco3 terminator sequence from *Yarrowia* Aco3 gene (GenBank Acc. No. AJ001301) |
| EcoRI/ClaI (10837-1) | LoxP-flanked Ura3 marker: *Yarrowia* Ura3 gene (GenBank Accession No. AJ306421) |

Plasmid pZKADn-C2F1U (SEQ ID NO:87) was digested with AscI, and then used to transform strain D1017U according to the General Methods. Transformant cells were plated onto MM plates and maintained at 30° C. for 2 days. Individual colonies from each transformation were re-streaked onto MM plates, and then inoculated into liquid YPD2-B media in 24-well blocks, which were then shaken at 30° C. and 375 rpm for 20 hours. The cultures were adjusted to pH 8.0 with addition of 0.12 mL of 1M $NaHCO_3$, after which ethyl palmitate was added directly to the culture media to a final concentration of 23 mg $mL^{-1}$. The cultures were then shaken for another 4 days at 375 rpm at 30° C., after which whole broth samples from each culture were subjected to LCDA analysis according to the General Methods.

GC analyses showed that three transformants of strain D1017U produced more than 10 g/L C16:0 LCDA. Specifically, transformants #2, #5, and #10 produced, respectively, 10.2, 14.5, and 10.8 g/L C16:0 LCDA. These three strains were designated as strains D1307, D1308, and D1309, respectively.

Strains D1307 and D1308 were also analyzed by micro-fermentation analysis. While a control strain (D0285, data not shown) produced C16:0 LCDA at about 6.0 g/L, strains D1307 and D1308 produced C16:0 LCDA at about 9.7 and 10.8 g/L, respectively.

Strain D1308 was further tested using a 2-L fermentation experiment. As shown in Table 10 and FIG. 10, strain D1308 produced a total amount of LCDAs of about 50.9 g/L, among which about 42.6 g/L was C16:0 LCDA, after 162 hours of fermentation.

TABLE 10

| LCDAs Produced by Strain D1308 Grown in a 2-L Fermentation with Ethyl Palmitate as Substrate | | | | | | | | | | | |
|---|---|---|---|---|---|---|---|---|---|---|---|
| Fermentation | LCDA (g/L) | | | | | | | | | | |
| time (h) | 12:0 | 14:0 | 14:1 | 14:2 | 16:0 | 16:1 | 16:2 | 18:0 | 18:1 | 18:2 | total |
| 32.5 | 0.0 | 0.0 | 0.0 | 0.0 | 0.0 | 0.0 | 0.0 | 0.0 | 0.0 | 0.0 | 0.1 |
| 41.5 | 0.3 | 0.8 | 0.0 | 0.0 | 5.3 | 0.5 | 0.1 | 0.2 | 0.1 | 0.2 | 7.4 |
| 53.5 | 0.6 | 1.5 | 0.1 | 0.0 | 11.8 | 0.9 | 0.2 | 0.5 | 0.1 | 0.3 | 16.0 |
| 65.3 | 0.7 | 1.8 | 0.1 | 0.1 | 15.7 | 1.0 | 0.3 | 0.8 | 0.1 | 0.3 | 20.9 |
| 77.7 | 0.8 | 1.9 | 0.1 | 0.1 | 18.9 | 1.1 | 0.3 | 1.0 | 0.1 | 0.3 | 24.7 |
| 90.8 | 0.9 | 2.1 | 0.1 | 0.1 | 22.4 | 1.2 | 0.4 | 1.1 | 0.1 | 0.4 | 28.8 |
| 100.8 | 1.0 | 2.2 | 0.1 | 0.1 | 25.2 | 1.3 | 0.4 | 1.2 | 0.1 | 0.4 | 32.0 |
| 113.7 | 1.0 | 2.4 | 0.1 | 0.1 | 30.5 | 1.4 | 0.5 | 1.4 | 0.2 | 0.5 | 38.1 |
| 125.8 | 1.0 | 2.5 | 0.1 | 0.1 | 33.8 | 1.5 | 0.5 | 1.4 | 0.2 | 0.5 | 41.5 |
| 136.3 | 1.0 | 2.5 | 0.1 | 0.1 | 37.1 | 1.6 | 0.5 | 1.5 | 0.2 | 0.6 | 45.2 |
| 149.2 | 1.0 | 2.6 | 0.1 | 0.1 | 40.3 | 1.7 | 0.5 | 1.4 | 0.3 | 0.6 | 48.5 |
| 162.3 | 0.9 | 2.6 | 0.1 | 0.1 | 42.6 | 1.7 | 0.5 | 1.5 | 0.3 | 0.7 | 50.9 |
| 165 | 0.9 | 2.6 | 0.1 | 0.1 | 44.3 | 1.8 | 0.5 | 1.6 | 0.3 | 0.6 | 52.9 |

It is noted that the pZKADn-C2F1U (SEQ ID NO:87) DNA used to transform D1017U to yield strain D1308 and its siblings could potentially knockout the alcohol dehydrogenase 3 locus (GenBank Acc. No. AF175273). Such a knockout in these strains was not confirmed, however. The genotype of D1308 and its siblings with respect to wild type *Y. lipolytica* ATCC #20362 was dgat1−, dgat2−, Leu2+, pex3−, pox2-, pox3−, pox4−, Ura3+, unknown 1−, unknown 2−, FBA::CtCPRs::Lip1, FBAINm1::CtCYPA17s::Pex20, DG2Pro-715::CtALDH2s::Lip1, FBAIL::CcFAO1s::Aco.

Thus, *Yarrowia* strain D1308 was generated, which could produce greater than 50 g/L of LCDA products when fed with a long-chain fatty acid-comprising substrate.

Example 9

Generation of *Y. lipolytica* Strain D2300 for LCDA Production Over 70 q/L

This example discloses construction of *Yarrowia* strain D2300 by expressing codon-optimized sequences encoding *V. sativa* CYP and CPR enzymes in strain D1308. Strain D2300 was an intermediate strain used for developing strain D3928 (FIG. 7B).

First, strain D1308U was developed from strain D1308. Plasmid construct pY117 was used for temporary expression of Cre recombinase to excise the LoxP-flanked URA3 gene within strain D1308. A pY117 transformant could not grow on MM, but could grow on MMU, indicating that the transformant lacked the URA3 gene; this transformant was designated as strain D1308U.

Next, strain D1308U was transformed with a DNA fragment from plasmid construct pYRH213 (FIG. 11A, SEQ ID NO:92). This fragment contained two expression cassettes, one for over-expressing a codon-optimized sequence encoding a CYP enzyme (VsCYP94A1s, derived from *V. sativa*, GenBank Acc. No. AAD10204, SEQ ID NO:93 encoding SEQ ID NO:94) and the other for over-expressing a codon-optimized sequence encoding a CPR enzyme (VsCPRs, derived from *V. sativa*, GenBank Acc. No. Z26252, SEQ ID NO:95 encoding SEQ ID NO:96). Each coding sequence was under the control of heterologous promoter and 3'-terminator sequences. NcoI and NotI endonuclease sites were added around the translation initiation codon (ATG) and after the stop codon, respectively, of each codon-optimized sequence encoding VsCYP or VsCPR. Components of the pYRH213 plasmid (SEQ ID NO:92) are further described in Table 11.

TABLE 11

| Description of Plasmid pYRH213 (SEQ ID NO: 92) | |
|---|---|
| RE Sites and Nucleotide Positions | Description of Chimeric Gene Components |
| AscI/BsiWI (4001-3107) | 887-bp 5' portion of Lipase Y locus (GenBank Acc. No. AJ549519, labeled as "LipY-5'" in Figure) |
| PacI/SphI (7471-6709) | 756-bp 3' portion of Lipase Y locus (GenBank Acc. No. AJ549519, labeled as "LipY-3'" in Figure) |
| PmeI and SwaI Fusion site/SwaI (1-2951) | FBA::VsCPRs::Lip1, comprising:<br>FBA: *Y. lipolytica* FBA promoter (U.S. Pat. No. 7,202,356);<br>VsCPRs: Codon-optimized synthetic sequence (SEQ ID NO: 95) encoding cytochrome P450 reductase (SEQ ID NO: 96), derived from *V. sativa* (GenBank Acc. No. Z26252);<br>Lip1: Lip1 terminator sequence from *Yarrowia* Lip1 gene (GenBank Acc. No. Z50020) |
| PmeI/PmeI and SwaI Fusion site (9919-1) | CPR1::VsCYP94A1s::Pex20, comprising:<br>CPR1: *Y. lipolytica* CPR1 promoter region (SEQ ID NO: 97);<br>VsCYP94A1s: Codon-optimized synthetic sequence (SEQ ID NO: 93) encoding cytochrome P450 monooxygenase (SEQ ID NO: 94), derived from *V. sativa* (GenBank Acc. No. AAD10204);<br>Pex20: Pex20 terminator sequence from *Yarrowia* Pex20 gene (GenBank Acc. No. AF054613) |

TABLE 11-continued

| Description of Plasmid pYRH213 (SEQ ID NO: 92) | |
|---|---|
| RE Sites and Nucleotide Positions | Description of Chimeric Gene Components |
| SalI/EcoRI (9122-7503) | *Yarrowia* Ura3 gene (GenBank Acc. No. AJ306421) |

Plasmid pYRH213 (SEQ ID NO:92) was digested with AscI/SphI, and then used to transform strain D1308U according to the General Methods. Transformant cells were plated onto MM plates and maintained at 30° C. for 2 days. Individual colonies from each transformation were re-streaked onto MM plates. Two strains were directly analyzed for LCDA production using flask assays. Specifically, individual colonies were re-streaked onto MM plates, and then inoculated into liquid YPD2-B media in 24-well blocks, which were then shaken at 30° C. and 375 rpm for 20 hours. The cultures were adjusted to pH 8.0 with addition of 0.12 mL of 1M $NaHCO_3$, after which ethyl palmitate was added directly to the culture media to a final concentration of 23 mg $mL^{-1}$. The cultures were then shaken for another 4 days at 375 rpm at 30° C., after which whole broth samples from each culture were subjected to LCDA analysis according to the General Methods.

GC analyses showed that two transformants of strain D1308U each produced, respectively, 8.2 and 12.6 g/L C16:0 LCDA. The strain that produced 12.6 g/L C16:0 LCDA was designated as strain D2300.

Strain D2300 was further tested using a 2-L fermentation experiment. As shown in Table 12 and FIG. 12, strain D2300 produced a total amount of LCDAs of about 72.7 g/L, among which about 64.6 g/L was C16:0 LCDA, after 163 hours of fermentation.

TABLE 12

LCDAs Produced by Strain D2300 Grown in a 2-L Fermentation with Ethyl Palmitate as Substrate

| Fermentation | LCDA (g/L) | | | | | | | | | |
|---|---|---|---|---|---|---|---|---|---|---|
| time (h) | 14:0 | 14:1 | 14:2 | 16:0 | 16:1 | 16:2 | 18:0 | 18:1 | 18:2 | total |
| 28.1 | 0.0 | 0.0 | 0.0 | 0.3 | 0.0 | 0.0 | 0.0 | 0.0 | 0.0 | 0.3 |
| 33.0 | 0.1 | 0.0 | 0.0 | 3.7 | 0.2 | 0.0 | 0.1 | 0.1 | 0.1 | 4.3 |
| 43.1 | 0.3 | 0.0 | 0.0 | 16.6 | 0.8 | 0.1 | 0.4 | 0.2 | 0.3 | 18.8 |
| 54.0 | 0.6 | 0.0 | 0.0 | 30.0 | 1.1 | 0.2 | 0.8 | 0.3 | 0.5 | 33.5 |
| 72.0 | 0.9 | 0.1 | 0.0 | 42.0 | 1.4 | 0.3 | 1.2 | 0.4 | 0.6 | 46.8 |
| 91.9 | 1.1 | 0.1 | 0.0 | 50.4 | 1.6 | 0.3 | 1.6 | 0.5 | 0.7 | 56.3 |
| 115.0 | 1.2 | 0.1 | 0.0 | 57.4 | 1.9 | 0.4 | 1.9 | 0.6 | 0.8 | 64.3 |
| 125.5 | 1.2 | 0.1 | 0.0 | 58.5 | 2.0 | 0.4 | 1.9 | 0.6 | 0.8 | 65.6 |
| 139.1 | 1.3 | 0.1 | 0.0 | 60.4 | 2.2 | 0.4 | 2.0 | 0.6 | 0.9 | 67.9 |
| 150.2 | 1.3 | 0.1 | 0.0 | 61.6 | 2.3 | 0.4 | 2.1 | 0.7 | 0.9 | 69.4 |
| 163.4 | 1.4 | 0.1 | 0.0 | 64.6 | 2.4 | 0.4 | 2.2 | 0.8 | 0.9 | 72.7 |

It is noted that the pYRH213 (SEQ ID NO:92) DNA used to transform D1308U to yield strain D2300 and its siblings could potentially knockout the Lipase Y locus (GenBank Acc. No. AJ549519). Such a knockout in these strains was not confirmed, however. The genotype of strain D2300 and its siblings with respect to wild type *Y. lipolytica* ATCC #20362 was dgat1−, dgat2−, Leu2+, pex3−, pox2−, pox3−, pox4−, Ura3+, unknown 1−, unknown 2−, unknown 3−, FBA::CtCPRs::Lip1, FBA::VsCPRs::Lip1, FBAINm1::CtCYPA17s::Pex20, CPR1::VsCYP94A1s::Pex20, DG2Pro-715::CtALDH2s::Lip1, FBA1L::CcFAO1s::Aco.

Thus, *Yarrowia* strain D2300 was generated, which could produce greater than 70 g/L of LCDA products when fed with a long-chain fatty acid-comprising substrate.

Example 10

Generation of *Y. lipolytica* Strain D2882 for LCDA Production

This example discloses construction of *Yarrowia* strain D2882 by expressing three codon-optimized sequences encoding fatty alcohol oxidase (FAO) enzymes in strain D2300. Strain D2300 was an intermediate strain used for developing strain D3928 (FIG. 7B).

First, strain D2300, which was Ura3+ by virtue of being transformed with pYRH213 (SEQ ID NO:92) DNA (see Example 9), was rendered to be ura3−. Specifically, D2300 was transformed with plasmid pZKUM to integrate a ura3− mutant sequence into the intact URA3 sequence. The construction and use of plasmid pZKUM to obtain ura− *Y. lipolytica* cells has been described (U.S. Pat. Appl. Publ. No. 2009/0093543, see Table 15 therein, which is incorporated herein by reference). Briefly, plasmid pZKUM was digested with SalI/PacI, and then transformed into strain D2300 according to the General Methods. Following transformation, cells were plated onto MM+5-FOA plates and maintained at 30° C. for 2-3 days. A total of 8 transformants that grew on the MM+5-FOA plates were picked and separately re-streaked onto MM plates and MM+5-FOA plates. All these 8 transformants had a ura− phenotype (i.e., cells could grow on MM+5-FOA plates, but not on MM plates). Transformants #1, #2, and #3 were designated as D2300U1, D2300U2, and D2300U3, which were collectively designated as D2300U.

To generate strain D2882, strain D2300U1 was transformed with a DNA fragment from construct pZSCPn-3FAOBU (FIG. 11B, SEQ ID NO:98), which contained three expression cassettes to over-express codon-optimized sequences encoding FAO enzymes (CtFAO1, CcFAO1, CcFAO2). Specifically, the expression cassettes comprised the following sequences: (i) CtFAO1Ms (SEQ ID NO:99 encoding SEQ ID NO:100, which is a mutant form of CtFAO1 of GenBank Acc. No. AAS46878) (compared to wild type CtFAO1, CtFAO1M comprises a histidine residue at amino acid position 359 instead of a tyrosine residue), (ii) CcFAO1s (SEQ ID NO:101 encoding SEQ ID NO:102), and (iii) CcFAO2s (SEQ ID NO:103 encoding SEQ ID NO:104). NcoI and NotI sites were added around the translation initiation codon (ATG) and after the stop codon, respectively, of each codon-optimized sequence encoding the foregoing FAO enzymes. Components of the pZSCPn-3FAOBU plasmid (SEQ ID NO:98) are further described in Table 13.

TABLE 13

Description of Plasmid pZSCPn-3FAOBU (SEQ ID NO: 98)

| RE Sites and Nucleotide Positions | Description of Chimeric Gene Components |
|---|---|
| SphI/PacI (13554-15334) | 1780-bp 5' portion of *Y. lipolytica* SCP2 (sterol carrier protein) locus (GenBank Acc. No. AJ431362, YALI0E01298g, labeled as "SCP2-5'" in Figure) |
| AscI/BsiWI (10846-9519) | 1327-bp 3' portion of *Y. lipolytica* SCP2 locus (GenBank Acc. No. AJ431362, YALI0E01298g, labeled as "SCP2-3'" in Figure) |
| SwaI/BsiWI (6306-9519) | YAT::CtFAO1sM::Pex20, comprising:<br>YAT: Promoter of *Y. lipolytica* ammonium transporter protein (U.S. Pat. Appl. Publ. No. 2010/0068789);<br>CtFAO1sM: Codon-optimized synthetic sequence (SEQ ID NO: 99) encoding mutant fatty alcohol oxidase (SEQ ID NO: 100), derived from *C. tropicalis* (GenBank Acc. No. AAS46878);<br>Pex20: Pex20 terminator sequence from *Yarrowia* Pex20 gene (GenBank Acc. No. AF054613) |
| PmeI/SwaI (3338-6306) | FBA::CcFAO1s::Lip1, comprising:<br>FBA: *Y. lipolytica* FBA promoter (U.S. Pat. No. 7,202,356);<br>CcFAO1s: Codon-optimized synthetic sequence (SEQ ID NO: 101) encoding fatty alcohol oxidase (SEQ ID NO: 102), derived from *C. cloacae* (GenBank Acc. No. CAB75351);<br>Lip1: Lip1 terminator sequence from *Yarrowia* Lip1 gene (GenBank Acc. No. Z50020) |
| ClaI/PmeI (1-3338) | ALK2LM-C::CcFAO2s::Aco3, comprising:<br>ALK2LM-C: *Y. lipolytica* ALK2 promoter (U.S. Pat. Appl. Publ. No. 2013/0089910) (labeled as "ALK2" in Figure);<br>CcFAO2s: Codon-optimized synthetic sequence (SEQ ID NO: 103) encoding fatty alcohol oxidase (SEQ ID NO: 104), derived from *C. cloacae* (GenBank Acc. No. CAB75352);<br>Aco3: Aco3 terminator sequence from *Yarrowia* Aco3 gene (GenBank Acc. No. AJ001301) |
| ClaI/EcoRI (1-15347, reverse) | LoxP::Ura3::LoxP, comprising:<br>LoxP sequence;<br>*Yarrowia* Ura3 gene (GenBank Acc. No. AJ306421);<br>LoxP sequence |

Plasmid pZSCPn-3FAOBU (SEQ ID NO:98) was digested with AscI/SphI, and then used to transform strain D2300U1 according to the General Methods. Transformant cells were plated onto MM plates and maintained at 30° C. for 2 days. Individual colonies from each transformation were re-streaked onto MM plates, and then inoculated into liquid YPD2-B media in 24-well blocks, which were then shaken at 30° C. and 375 rpm for 20 hours. The cultures were then adjusted to pH 8.0 with addition of 0.12 mL of 1M $NaHCO_3$, after which ethyl palmitate was added directly to the culture media to a final concentration of 23 mg $mL^{-1}$. The cultures were then shaken for another 4 days at 375 rpm at 30° C., after which whole broth samples from each culture were subjected to LCDA analysis according to the General Methods.

Twenty-four strains, each resulting from transformation of strain D2300U1 with pZSCPn-3FAOBU (SEQ ID NO:98), were cultured and analyzed by GC. Five of the twenty-four transformants produced C16:0 LCDA at more than 10.6 g/L. Specifically, transformants #11, #14, #18, and #21 produced C16:0 LCDA at 12.1, 12.0, 12.4, and 10.6 g/L, respectively. These four strains were designated as strains D2882, D2883, D2884, and D2885, respectively.

Strains D2882, D2883, D2884 and D2885 were also analyzed for LCDA production by flask assay according to the General Methods. As shown in Table 14, strains D2882, D2883, D2884 and D2885 produced C16:0 LCDA at about 15.1, 13.2, 15.0 and 15.5 g/L, respectively.

TABLE 14

LCDA Production by Strain D2882 and Its Siblings in Flask Assays with Ethyl Palmitate as Substrate

| | LCDA (g/L) | | | | | | | | |
|---|---|---|---|---|---|---|---|---|---|
| Strains | 14:0 | 14:1 | 14:2 | 16:0 | 16:1 | 16:2 | 18:0 | 18:1 | 18:2 |
| D2882 | 0.2 | 0.4 | 0.3 | 15.1 | 0.9 | 0.3 | 0.3 | 0.2 | 0.2 |
| D2883 | 0.1 | 0.4 | 0.2 | 13.2 | 0.9 | 0.2 | 0.3 | 0.2 | 0.1 |
| D2884 | 0.2 | 0.4 | 0.3 | 15.0 | 0.6 | 0.3 | 0.3 | 0.3 | 0.2 |
| D2885 | 0.2 | 0.4 | 0.3 | 15.5 | 0.8 | 0.3 | 0.3 | 0.3 | 0.2 |

Strains D2882 and D2885 were further analyzed for LCDA production by micro-fermentation analysis according to the General Methods. As shown in Table 15, strains D2882 and D2885 produced C16:0 LCDA at about 23.4 and 21.0 g/L, respectively.

TABLE 15

| LCDA Production by Strains D2882 and D2885 in Micro-Fermentation Assay with Ethyl Palmitate as Substrate | | | | | | | | | | |
|---|---|---|---|---|---|---|---|---|---|---|
| | LCDA (g/L) | | | | | | | | | |
| Strains | 14:0 | 14:1 | 14:2 | 16:0 | 16:1 | 16:2 | 18:0 | 18:1 | 18:2 | total |
| D2882 | 0.3 | 0.0 | 0.0 | 23.4 | 1.2 | 0.1 | 0.2 | 0.1 | 0.0 | 25.4 |
| D2885 | 0.3 | 0.0 | 0.0 | 21.0 | 1.1 | 0.1 | 0.2 | 0.2 | 0.0 | 23.0 |

It is noted that the pZSCPn-3FAOBU (SEQ ID NO:98) DNA used to transform D2300U1 to yield strains D2882 and its siblings could potentially knockout the *Y. lipolytica* SCP2 (sterol carrier protein) locus (GenBank Acc. No. AJ431362, YALIOE01298g). Such a knockout in these strains was not confirmed, however. The genotype of strain D2882 and its siblings with respect to wild type *Y. lipolytica* ATCC #20362 was dgat1−, dgat2−, Leu2+, pex3−, pox2−, pox3−, pox4−, Ura3+, unknown 1−, unknown 2−, unknown 3−, unknown 4−, FBA::CtCPRs::Lip1, FBA::VsCPRs::Lip1, FBAINm1::CtCYPA17s::Pex20, CPR1::VsCYP94A1s::Pex20, DG2Pro-715::CtALDH2s::Lip1, FBA1L:CcFAO1s::Aco; YAT::CtFAO1sM::Pex20, FBA::CcFAO1s::Lip1, ALK2LM-C::CcFAO2s::Aco3.

Example 11

Generation of *Y. lipolytica* Strain D3928 by Over-Expressing Long-Chain Acyl-CoA Synthetase This example discloses construction of *Yarrowia* strain D3982 by expressing a codon-optimized sequence encoding a long-chain acyl-CoA synthetase (YLACoS-6P, SEQ ID NO:44, see Example 5). This strain was able to produce LCDA at more than 100 g/L, as shown in Example 12.

Strain D3928 was generated from strain D2882 (FIG. 7B), as follows.

First, D2882, which was Ura3+ by virtue of being transformed with pZSCPn-3FAOBU (SEQ ID NO:98) DNA (see Example 10), was rendered to be ura3-. Specifically, D2882 was transformed with plasmid pY117 for temporary expression of Cre recombinase to excise the LoxP-flanked URA3 gene within strain D2882. A pY117 transformant could not grow on MM, but could grow on MMU, indicating that the transformant lacked the URA3 gene; this transformant was designated as strain D2882U.

To generate strain D3928, strain D2882U was transformed with a DNA fragment from construct pZP2-YIACoS-6Ps (FIG. 5C, SEQ ID NO:65), which contained one expression cassette to over-express a codon-optimized sequence encoding YLACoS-6P enzyme (SEQ ID NO:44). Specifically, the expression cassette comprised the long-chain acyl-CoA synthetase sequence YLACoS-6Ps (SEQ ID NO:43), which encodes SEQ ID NO:44. NcoI and NotI sites were added around the translation initiation codon (ATG) and after the stop codon, respectively, of the synthetic sequence encoding YLACoS-6P (SEQ ID NO:44). Components of the pZP2-YLACoS-6Ps plasmid (SEQ ID NO:65) are further described in Table 16.

TABLE 16

| Description of Plasmid pZP2-YLACoS-6Ps (SEQ ID NO: 65) | |
|---|---|
| RE Sites and Nucleotide Positions | Description of Chimeric Gene Components |
| AscI/BsiWI (1128-318, reverse) | 810-bp 5' portion of *Yarrowia* Pox2 gene (GenBank Acc. No. AJ001300; labeled as "POX2 5'" in Figure) |
| PacI/SphI (4491-3836, reverse) | 655-bp 3' portion of *Yarrowia* Pox2 gene (GenBank Acc. No. AJ001300; labeled as "POX2 3'" in Figure) |
| ClaI/BsiWI (6330-318) | FBAINm::YIAcoS-6Ps::Pex20, comprising:<br>FBAINm: *Y. lipolytica* FBAINm promoter (U.S. Pat. No. 7,202,356);<br>YIAcoS-6Ps: Codon-optimized synthetic sequence (SEQ ID NO: 43) encoding YLACoS-6P enzyme (SEQ ID NO: 44), derived from *Y. lipolytica* (GenBank Acc. No. XP_503862, YALI0E12419g);<br>Pex20: Pex20 terminator sequence from *Yarrowia* Pex20 gene (GenBank Acc. No. AF054613) |
| 5981-4494 reverse | *Yarrowia* Ura3 gene (GenBank Acc. No. AJ306421) |

Plasmid pZP2-YLACoS-6Ps (SEQ ID NO:65) was digested with AscI/SphI, and then used to transform strain D2882U according to the General Methods. Transformant cells were plated onto MM plates and maintained at 30° C. for 2 days. Individual colonies from each transformation were re-streaked onto MM plates, and then inoculated into liquid YPD2-B media in 24-well, which were then shaken at 30° C. and 375 rpm for 20 hours. The cultures were then adjusted to pH 8.0 with addition of 0.12 mL of 1M $NaHCO_3$, after which ethyl palmitate was added directly to the culture media to a final concentration of 23 mg $mL^{-1}$. The cultures were then shaken for another 4 days at 375 rpm at 30° C., after which whole broth samples from each culture were subjected to LCDA analysis according to the General Methods.

Twenty-four strains, each resulting from transformation of strain D2882U with pZP2-YLACoS-6Ps (SEQ ID NO:65), were cultured and analyzed by GC. Nine of the twenty-four transformants produced C16:0 LCDA at more than 14.5 g/L. Specifically, transformants #6, #7, #8, #9, #10, #11, #12, #13 and #20 produced C16:0 LCDA at 14.8, 17.7, 18.7, 18.3, 20.6, 17.8, 15.4, 17.1 and 14.5 g/L, respectively. These transformants were designated as strains D3924, D3925, D3926, D3927, D3928, D3929, D3930, D3931 and D3932, respectively.

Strains D3928, D3931 and D3932 were also analyzed for LCDA production by micro-fermentation analysis according to the General Methods. As shown in Table 17, strains D3928, D3931 and D3932 produced C16:0 LCDA at about 23.0, 21.2 and 22.7 g/L, respectively.

TABLE 17

LCDA Production by Strains D3928, D3931 and D3932 in Micro-fermentation Assay with Ethyl Palmitate as Substrate

| | LCDA (g/L) | | | | | | | | |
|---|---|---|---|---|---|---|---|---|---|
| Strains | 14:0 | 14:1 | 16:0 | 16:1 | 16:2 | 18:0 | 18:1 | 18:2 | total |
| D3928 | 0.3 | 0.0 | 23.0 | 0.7 | 0.1 | 0.5 | 0.3 | 0.4 | 25.5 |
| D3931 | 0.3 | 0.0 | 21.2 | 0.7 | 0.1 | 0.5 | 0.3 | 0.4 | 23.6 |
| D3932 | 0.4 | 0.0 | 22.7 | 0.6 | 0.2 | 0.5 | 0.2 | 0.4 | 24.2 |

It is noted that the pZP2-YLACoS-6Ps (SEQ ID NO:65) DNA used to transform D2882U to yield strains D3928 and its siblings could potentially knockout the Pox2 gene (GenBank Acc. No. AJ001300). Such a knockout in these strains was not confirmed, however. The genotype of strain D3928 and its siblings with respect to wild type *Y. lipolytica* ATCC #20362 was dgat1−, dgat2−, Leu2+, pex3−, pox2−, pox3−, pox4−, Ura3+, unknown 1−, unknown 2−, unknown 3−, unknown 4−, unknown 5−, FBA::CtCPRs::Lip1, FBA::VsCPRs::Lip1, FBAINm1::CtCYPA17s::Pex20, CPR1::VsCYP94A1s::Pex20, DG2Pro-715::CtALDH2s::Lip1, FBA1L:CcFAO1s::Aco; YAT::CtFAO1sM::Pex20, FBA::CcFAO1s::Lip1, ALK2LM-C::CcFAO2s::Aco3, FBAINm::YIAcoS-6Ps::Pex20.

Thus, *Yarrowia* strains that over-express long-chain acyl-CoA synthetase were produced that can synthesize significant amounts of LCDA products when fed with a long-chain fatty acid-comprising substrate.

Example 12

LCDA Production by *Yarrowia* Over-Expressing Long-Chain Acyl-CoA Synthetase Under Fed-Batch Fermentation Conditions This example discloses that *Yarrowia* that over-expresses long-chain acyl-CoA synthetase can produce greater than 100 g/L LCDA products when grown in a fed-batch fermentation. In particular, strain D3928 was able to produce C16:0 LCDA at 109 g/L and total LCDAS at 119 g/L, after about a 143-hour fermentation (Table 18, FIG. 13).

Seed culture protocol: Engineered *Yarrowia* strain D3928 that was stored at −80° C. was streaked onto YPD plates and incubated for about 24 hours at 30° C. A single colony was inoculated into a 14-mL FALCON tube (Corning, N.Y.) containing 5 mL of complex medium (6.7 g/L yeast nitrogen base without amino acids, 5 g/L yeast extract, 20 g/L D-glucose, 6 g/L $KH_2PO_4$, 3.3 g/L $Na_2HPO_4.12H_2O$). The tube culture was grown for about 24 hours at 30° C. with shaking at about 250-300 rpm. One portion of this culture (0.2-5.0 mL) was transferred to a 250-mL shake flask containing 50 mL complex medium (above) and incubated for an additional ~20 hours at 30° C. to an $OD_{600}$ of approximately 5.0-10.0. This culture was used as seed culture to inoculate the 5-L fermenter at about 3% by volume.

5-L fermentation protocol: The shake-flask seed culture prepared above was transferred to a 5-L fermenter (Sartorius BBI, BioStat B plus) to initiate fermentation (t=0 h). The fermentation medium contained 50 g/L D-glucose, 6 g/L $KH_2PO_4$, 3.3 g/L $Na_2HPO_4.12H_2O$, 8 mL/L trace metals (100×), 40 g/L Bacto™ yeast extract, 20 g/L Bacto™ peptone, 20 mM $MgSO_4$, 6 mg/L Thiamine.HCl, and 15 g/L $(NH_4)_2SO_4$. The trace metals (100×) consisted of 10 g/L citric acid, 1.5 g/L $CaCl_2.2H_2O$, 10 g/L $FeSO_4.7H_2O$, 0.39 g/L 10 g/L $ZnSO_4.7H_2O$, 0.38 g/L $CuSO_4.5H_2O$, 0.2 g/L $CoCl_2.6H_2O$, and $MnCl_2.4H_2O$. The initial working volume was 3.0 L. For the first 26 hours, the dissolved oxygen level ($pO_2$) was controlled at about 20% of air saturation by cascading the agitation speed between 300 to 1200 rpm. After t=26 h, the agitation speed was fixed at 1200 rpm, and then the $pO_2$ was controlled at 60% of air saturation by cascading with only a pure oxygen supplement. A glucose feed was prepared comprising 700 g/L glucose and 15-25 g/L urea; glucose feeding commenced at about 18 hours when the initially charged glucose was consumed. The glucose feeding rate started as high as 20 mL/hr and then gradually decreased to 10 mL/hr at the end of the fermentation (~144 hours). The aeration rate was controlled at 1.5-2.5 L/min and temperature was maintained at 30° C. throughout the run. The pH value was controlled at 6.0 for the first 26 hours and then increased to 7.5 in the remainder of the run by feeding KOH. Starting from t=28 h, ethyl palmitate was fed into the fermenter to control its residual concentration within 1-20 g/L. Fermentation samples (about 25 mL at each time point) were taken twice a day to analyze $OD_{600}$, residual glucose, residual ethyl palmitate, and LCDAs in fermentation medium.

5-L fermentation results: After 143.4 hours of fermentation, about 119 g/L of LCDAs was produced. A majority of the LCDA products was hexadecanedioic acid (C16:0 diacid) (Table 18 and FIG. 13).

TABLE 18

LCDAs Produced by Strain D3928 in 5-L Fed-Batch Fermentation with Ethyl Palmitate as Substrate

| Time | LCDAs (g/L) | | | | | | | | |
|---|---|---|---|---|---|---|---|---|---|
| (hours) | C14:0 | C14:1 | C16:0 | C16:1 | C16:2 | C18:0 | C18:1 | C18:2 | Total |
| 30.0 | 0.1 | 0.0 | 4.5 | 0.1 | 0.0 | 0.0 | 0.1 | 0.1 | 5.0 |
| 47.5 | 0.6 | 0.0 | 39.5 | 0.6 | 0.1 | 0.9 | 0.3 | 0.4 | 42.5 |
| 54.0 | 0.7 | 0.0 | 50.2 | 0.8 | 0.1 | 1.1 | 0.4 | 0.5 | 54.0 |
| 71.5 | 1.0 | 0.0 | 67.4 | 1.3 | 0.2 | 1.6 | 0.5 | 0.6 | 72.8 |
| 78.0 | 1.1 | 0.0 | 72.9 | 1.4 | 0.2 | 1.8 | 0.6 | 0.6 | 78.7 |
| 97.1 | 1.3 | 0.0 | 88.5 | 1.8 | 0.3 | 2.2 | 0.7 | 0.8 | 95.7 |
| 120.7 | 1.5 | 0.1 | 101.3 | 2.2 | 0.3 | 2.6 | 0.9 | 0.9 | 110.0 |
| 143.4 | 1.7 | 0.1 | 109.2 | 2.6 | 0.4 | 2.8 | 1.0 | 1.0 | 119.0 |

Thus, *Yarrowia* over-expressing long-chain acyl-CoA synthetase can synthesize significant amounts of LCDA products when fed with a long-chain fatty acid-comprising substrate.

Example 13

Generation of *Yarrowia lipolytica* Strain D0145 as a Positive Control for LCDA Production This example discloses construction of various *Yarrowia* strains by expressing codon-optimized sequences encoding certain *Vicia sativa* (common vetch) CYP and CPR enzymes. Most of these strains, including strain D0145, were able to produce LCDA.

Construct pZKLY-VsCPR&CYP (SEQ ID NO:105) was generated to integrate one copy each of codon-optimized common vetch CYP (VsCYP94A1s, derived from *V. sativa*, GenBank Acc. No. AAD10204, SEQ ID NO:93 encoding SEQ ID NO:94) and CPR (VsCPRs, derived from *V. sativa*, GenBank Acc. No. Z26252, SEQ ID NO:95 encoding SEQ ID NO:96) coding sequences. Each coding sequence was under the control of heterologous promoter and 3'-terminator sequences. NcoI and NotI endonuclease sites were added around the translation initiation codon (ATG) and after the stop codon, respectively, of each codon-optimized sequence encoding VsCYP or VsCPR. Components of the pZKLY-VsCPR&CYP (SEQ ID NO:105) plasmid are further described in Table 19.

TABLE 19

Description of Plasmid pZKLY-VsCPR&CYP (SEQ ID NO: 105)

| RE Sites and Nucleotide Positions | Description of Chimeric Gene Components |
|---|---|
| AscI/BsiWI (4001-3107) | 887-bp 5' portion of Lipase Y locus (GenBank Acc. No. AJ549519, labeled as "LipY-5'" in Figure) |
| PacI/SphI (7471-6709) | 756-bp 3' portion of Lipase Y locus (GenBank Acc. No. AJ549519, labeled as "LipY-3'" in Figure) |
| PmeI/SwaI (1-2951) | FBA::VsCPRs::Lip1, comprising:<br>FBA: *Y. lipolytica* FBA promoter (U.S. Pat. No. 7,202,356);<br>VsCPRs: Codon-optimized synthetic sequence (SEQ ID NO: 95) encoding cytochrome P450 reductase (SEQ ID NO: 96), derived from *V. sativa* (GenBank Acc. No. Z26252);<br>Lip1: Lip1 terminator sequence from *Yarrowia* Lip1 gene (GenBank Acc. No. Z50020) |
| ClaI/PmeI (9572-1) | FBAINm::VsCYPs(94A1s)::Pex16, comprising:<br>FBAINm: *Y. lipolytica* FBAINm promoter (U.S. Pat. No. 7,202,356);<br>VsCYP94A1s: Codon-optimized synthetic sequence (SEQ ID NO: 93) encoding cytochrome P450 monooxygenase (SEQ ID NO: 94), derived from *V. sativa* (GenBank Acc. No. AAD10204);<br>Pex16: Pex16 terminator sequence from *Yarrowia* Pex16 gene (GenBank Acc. No. U75433) |
| SalI/PacI (9122-6709) | *Yarrowia* Ura3 gene (GenBank Acc. No. AJ306421) |

Plasmid pZKLY-VsCPR&CYP (SEQ ID NO:105) was digested with AscI/SphI, and then used to transform strain D0004 (dgat1−, dgat2−, pex3−, ura3−) (refer to Table 7) according to the General Methods. Transformant cells were plated onto MM plates and maintained at 30° C. for 2 days. Individual colonies from each transformation were re-streaked onto MM plates, and then inoculated into liquid MM at 30° C. and shaken at 250 rpm for 1 day. Overnight cultured cells were used to inoculate 50 mL liquid YPD2-B media in a 250-mL baffled flask, which was then shaken at 250 rpm at 30° C. After 24 hours, the cultures were adjusted to pH 8.0 with the addition of 2.0 mL 1M $NaHCO_3$, after which ethyl palmitate was added directly to the culture media to a final concentration of 16 mg $mL^{-1}$. The cultures were then shaken for another 4 days at 250 rpm at 30° C., after which whole broth samples from each flask culture were subjected to LCDA analysis according to the General Methods.

Forty-eight strains, each resulting from transformation of parent strain D0004 with pZKLY-VsCPR&CYP (SEQ ID NO:105), were cultured and analyzed by GC. Almost all of the 48 strains produced C16:0 LCDA at more than 3 g/L. For example, transformants #12, #15, #20, #23, #28, #29, #31, #37, #39, #44 and #48 produced C16:0 LCDA at 5.0, 5.1, 5.1, 5.0, 5.2, 4.9, 5.5, 4.8, 5.5, 5.0 and 4.8 g/L, respectively. These eleven transformants were designated as strains D0138, D0139, D0140, D0141, D0142, D0143, D0144, D0145, D0146, D0147 and D0148, respectively.

It is noted that the pZKLY-VsCPR&CYP (SEQ ID NO:105) DNA used to transform D0004 to yield strain D0145 and its siblings could potentially knockout the Lipase Y locus (GenBank Acc. No. AJ549519). Such a knockout in these strains was not confirmed, however. The genotype of strain D0145 and its siblings with respect to wild type *Yarrowia lipolytica* ATCC #20362 was Ura3+, dgat1−, dgat2−, pex3−, unknown 1−, FBA::VsCPRs::Lip1, FBAINm::VsCYP94A1s::Pex16.

Thus, yeast (e.g., *Yarrowia*) with up-regulated hydroxylase complex expression and down-regulated PEX3 expression can produce LCDA from a fatty acid-comprising substrate.

Example 14

Pex3− *Yarrowia* can Produce LCDA

This example discloses construction of *Yarrowia* strain D0101 by expressing codon-optimized sequences encoding *C. tropicalis* CYP and CPR enzymes. Also, this example discloses that pex3− strains can produce LCDA, while PEX3+ strains (e.g., strains having no PEX gene disruption, or that are pex10- or pex16-) do not have this activity.

Construct pZP2N-FCtA1R was generated to integrate one copy each of codon-optimized CYP (CtALK1s, GenBank Acc. No. P10615) and CPR (CtCPRs, GenBank Acc. No.

P37201) coding sequences from *C. tropicalis*. Each coding sequence was under the control of heterologous promoter and 3'-terminator sequences. NcoI and NotI endonuclease sites were added around the translation initiation codon (ATG) and after the stop codon, respectively, of each codon-optimized sequence encoding CtALK1 or CtCPR. Components of the pZP2N-FCtA1R plasmid are further described in Table 12.

TABLE 20

Description of Plasmid pZP2N-FCtA1R

| RE Sites and Nucleotide Positions | Description of Chimeric Gene Components |
|---|---|
| AscI/BsiWI (3299-2489) | 810-bp 5' portion of *Yarrowia* Pox2 gene (GenBank Acc. No. AJ001300) |
| PacI/SphI (6662-6007) | 655-bp 3' portion of *Yarrowia* Pox2 gene (GenBank Acc. No. AJ001300) |
| PmeI/BsiWI (1-2480) | FBA1::CtALK1s::Pex20, comprising:<br>FBA1: *Y. lipolytica* FBA1 promoter (U.S. Pat. No. 7,202,356);<br>CtALK1s: Codon-optimized synthetic sequence encoding cytochrome P450 monooxygenase, derived from *C. tropicalis* (GenBank Acc. No. P10615);<br>Pex20: Pex20 terminator sequence from *Yarrowia* Pex20 gene (GenBank Acc. No. AF054613) |
| ClaI/PmeI (8501-1) | FBAINm::CtCPRs::Pex16, comprising:<br>FBAINm: *Y. lipolytica* FBAINm promoter (U.S. Pat. No. 7,202,356);<br>CtCPRs: Codon-optimized synthetic sequence encoding cytochrome P450 reductase, derived from *C. tropicalis* (GenBank Acc. No. P37201);<br>Pex16: Pex16 terminator sequence from *Yarrowia* Pex16 gene (GenBank Acc. No. U75433) |
| 8152-6665 | *Yarrowia* Ura3 gene (GenBank Acc. No. AJ306421) |

Plasmid pZP2N-FCtA1R was digested with AscI/SphI, and then used to transform strains Y2224, D0003, D0004 and D0009 according to the General Methods. Transformant cells were plated onto MM plates and maintained at 30° C. for 2 days. Individual colonies from each transformation were re-streaked onto MM plates, and then inoculated into liquid MM at 30° C. and shaken at 250 rpm for 1 day. Overnight cultured cells were used to inoculate 25 mL of liquid YPD4-B media in a 250-mL flask, which was then shaken at 180 rpm at 30° C. After 40 hours, the cultures were adjusted to pH 8.0 with addition of 2.0 mL of 1M $NaHCO_3$, after which ethyl palmitate (W245100, Sigma-Aldrich) was added directly to the culture media to a final concentration of 8 mg $mL^{-1}$. The cultures were then shaken for another 4 days at 180 rpm at 30° C., after which whole broth samples from each flask culture were subjected to LCDA analysis according to the General Methods.

Strains resulting from transformation of each parent strain (Y2224, D0003, D0004, D0009) with pZP2N-FCtA1R were analyzed by GC. There was no hexadecanedioic acid (C16:0 LCDA) detected in transformants of parent strains Y2224, D0003, or D0009. However, transformants of parent strain D0004 produced more than 1 g/L C16:0 LCDA. One D0004-transformant that produced 1.24 g/L C16:0 LCDA was designated as strain D0101.

A subsequent flask analysis of strain D0101 was performed. Specifically, D0101 was placed in a 25-mL culture in a 250-mL baffled flask, with ethyl palmitate added to a final concentration of 16 mg $mL^{-1}$. The culture was shaken at 180 rpm at 30° C. for 4 days. The culture produced C16:0 LCDA at about 5 g/L.

It is noted that the pZP2N-FCtA1R DNA used to transform D0004 to yield strain D0101 could potentially knockout the Pox2 gene (GenBank Acc. No. AJ001300). Such a knockout in D0101 was not confirmed, however. The genotype of strain D0101 with respect to wild type *Y. lipolytica* ATCC #20362 was Ura3+, dgat1−, dgat2−, pex3−, unknown 1−, FBA1::CtALK1s::Pex20, FBAINm::CtCPRs::Pex16.

It is noteworthy that transformants (e.g., strain D0101) of parent strain D0004 (dgat1−, dgat2−, pex3−, ura3−) produced LCDA, while transformants of parent strain D0009 (dgat1−, dgat2−, pex10−, ura3−) did not have this capability. Even though both types of transformants had (i) a down-regulated PEX gene (resulting in impaired peroxisome function and blocked beta-oxidation), and (ii) otherwise same genotypes (including down-regulated DGAT genes leading to reduced oil storage), only yeast having down-regulated PEX3 were able to produce LCDA. Similar to the pex10− strain, a pex16− strain also lacked the ability to produce LCDA (data not shown). Hence, the manner in which peroxisome function and beta-oxidation are blocked has a significant effect on production of LCDA from fatty acid-comprising substrates.

Thus, yeast (e.g., *Yarrowia*) that have down-regulated PEX3 expression can produce LCDA from a fatty acid-comprising substrate.

What is claimed is:

1. A recombinant yeast cell comprising an engineered long-chain dicarboxylic acid (LCDA) production pathway that comprises up-regulation of a polynucleotide sequence encoding a long-chain acyl-CoA synthetase (ACoS enzyme) comprising the amino acid sequence of SEQ ID NO:44, wherein said upregulation of the polynucleotide sequence encoding the ACoS enzyme is by having introduced one or more copies of the polynucleotide sequence to the yeast cell, wherein the polynucleotide sequence is operably linked to a promoter, and wherein said yeast cell can produce one or more LCDA products from a long-chain fatty acid-comprising substrate.

2. The recombinant yeast cell of claim 1, wherein the ACoS enzyme has both long-chain acyl-CoA synthetase activity and coumaroyl-CoA synthetase activity.

3. The recombinant yeast cell of claim 1, wherein the engineered LCDA production pathway further comprises one or more of the following features:

(i) up-regulation of a polynucleotide sequence encoding a cytochrome P450 monooxygenase (CYP enzyme), (ii) up-regulation of a polynucleotide sequence encoding a cytochrome P450 reductase (CPR enzyme), (iii) up-regulation of a polynucleotide sequence encoding a fatty alcohol oxidase (FAO enzyme), (iv) up-regulation of a polynucleotide sequence encoding a fatty alcohol dehydrogenase (FADH enzyme), and/or (v) up-regulation of a polynucleotide sequence encoding a fatty aldehyde dehydrogenase (FALDH enzyme), wherein said up-regulation of the polynucleotide sequence of (i)-(v) is by having introduced one or more copies of the polynucleotide sequence of (i)-(v) to the yeast cell, and wherein the polynucleotide sequence of (i)-(v) is operably linked to a promoter.

4. The recombinant yeast cell of claim 3, wherein either or both the polynucleotide sequence encoding said CYP enzyme and the polynucleotide sequence encoding said CPR enzyme are up-regulated.

5. The recombinant yeast cell of claim 1, wherein the yeast cell further comprises down-regulation of an endogenous polynucleotide sequence encoding a peroxisome biogenesis factor, wherein said down-regulation is by having disrupted a gene encoding the peroxisome biogenesis factor, or by having used antisense or RNAi technology.

6. The recombinant yeast cell of claim 5, wherein the peroxisome biogenesis factor is peroxisome biogenesis factor-3.

7. The recombinant yeast cell of claim 1, wherein the yeast cell further comprises down-regulation of an endogenous polynucleotide sequence encoding a peroxisomal acyl-CoA oxidase, wherein said down-regulation is by having disrupted a gene encoding the peroxisomal acyl-CoA oxidase, or by having used antisense or RNAi technology.

8. The recombinant yeast cell of claim 7, wherein the peroxisomal acyl-CoA oxidase is peroxisomal acyl-CoA oxidase-2, -3, and/or -4.

9. The recombinant yeast cell of claim 1, wherein the yeast cell has reduced lipid synthesis and/or storage capability.

10. The recombinant yeast cell of claim 9, wherein said reduced lipid synthesis and/or storage capability is due to a down-regulation of at least one endogenous polynucleotide sequence encoding a diacylglycerol acyltransferase (DGAT enzyme), wherein said down-regulation is by having disrupted a gene encoding the DGAT enzyme, or by having used antisense or RNAi technology.

11. The recombinant yeast cell of claim 1, wherein the yeast cell is a *Yarrowia* cell.

12. The recombinant yeast cell of claim 1, wherein:

the LCDA product has a chain length of 10 to 24 carbon atoms, and/or the long-chain fatty acid-comprising substrate comprises a free long-chain fatty acid or an esterified long-chain fatty acid.

13. A method of producing a long-chain dicarboxylic acid (LCDA), said method comprising:

(a) contacting the recombinant yeast cell of claim 1 with a long-chain fatty acid-comprising substrate, wherein the yeast cell synthesizes an LCDA from said substrate; and (b) optionally recovering the LCDA of step (a).

14. The method of claim 13, wherein the yeast cell is a *Yarrowia* cell.

15. The method of claim 13, comprising step (b) of recovering the LCDA of step (a).

* * * * *